(12) United States Patent
Gurney et al.

(10) Patent No.: US 9,777,024 B2
(45) Date of Patent: *Oct. 3, 2017

(54) HETEROARYL INHIBITORS OF PDE4

(71) Applicant: Tetra Discovery Partners, LLC, Grand Rapids, MI (US)

(72) Inventors: Mark E. Gurney, Grand Rapids, MI (US); Timothy J. Hagen, Lisle, IL (US); Xuesheng Mo, Naperville, IL (US); A. Samuel Vellekoop, Altamont, NY (US); Donna L. Romero, Chesterfield, MO (US); Robert F. Campbell, Niskayuna, NY (US); Joel R. Walker, Schenectady, NY (US); Lei Zhu, Schenectady, NY (US)

(73) Assignee: Tetra Discovery Partners, LLC, Grand Rapids, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/938,544

(22) Filed: Nov. 11, 2015

(65) Prior Publication Data

US 2016/0137672 A1    May 19, 2016

Related U.S. Application Data

(62) Division of application No. 14/349,688, filed as application No. PCT/US2013/006645 on Oct. 24, 2013, now Pat. No. 9,221,843.

(Continued)

(51) Int. Cl.

| C07D 213/24 | (2006.01) |
|---|---|
| A61K 31/505 | (2006.01) |
| C07F 5/02 | (2006.01) |
| C07D 213/72 | (2006.01) |
| C07D 403/12 | (2006.01) |
| C07D 413/14 | (2006.01) |
| C07D 213/74 | (2006.01) |
| C07D 221/04 | (2006.01) |
| C07D 409/04 | (2006.01) |
| C07D 409/14 | (2006.01) |
| C07D 413/12 | (2006.01) |
| C07D 495/04 | (2006.01) |
| C07D 213/56 | (2006.01) |
| A61K 45/06 | (2006.01) |
| A61K 31/435 | (2006.01) |
| A61K 31/4418 | (2006.01) |
| A61K 31/517 | (2006.01) |
| A61K 31/53 | (2006.01) |
| A61K 31/69 | (2006.01) |
| C07D 239/26 | (2006.01) |
| C07D 239/70 | (2006.01) |
| C07D 251/22 | (2006.01) |
| C07D 401/12 | (2006.01) |
| C07D 405/04 | (2006.01) |
| A61K 31/44 | (2006.01) |
| A61K 31/496 | (2006.01) |
| A61K 31/506 | (2006.01) |
| A61K 31/519 | (2006.01) |

(Continued)

(52) U.S. Cl.
CPC ............ *C07F 5/027* (2013.01); *A61K 31/435* (2013.01); *A61K 31/44* (2013.01); *A61K 31/4418* (2013.01); *A61K 31/496* (2013.01); *A61K 31/505* (2013.01); *A61K 31/506* (2013.01); *A61K 31/517* (2013.01); *A61K 31/519* (2013.01); *A61K 31/53* (2013.01); *A61K 31/5377* (2013.01); *A61K 31/69* (2013.01); *A61K 45/06* (2013.01); *C07D 213/56* (2013.01); *C07D 213/72* (2013.01); *C07D 213/74* (2013.01); *C07D 221/04* (2013.01); *C07D 239/26* (2013.01); *C07D 239/70* (2013.01); *C07D 251/22* (2013.01); *C07D 251/30* (2013.01); *C07D 251/42* (2013.01); *C07D 401/04* (2013.01); *C07D 401/12* (2013.01); *C07D 403/12* (2013.01); *C07D 405/04* (2013.01); *C07D 409/04* (2013.01); *C07D 409/14* (2013.01); *C07D 413/12* (2013.01); *C07D 413/14* (2013.01); *C07D 495/04* (2013.01); *C07F 5/025* (2013.01)

(58) Field of Classification Search
CPC .. C07D 213/24; C07D 239/26; C07D 403/10; A61K 31/4418; A61K 31/505
USPC ..... 544/242, 335; 546/1, 341, 342; 514/258, 514/277, 256
See application file for complete search history.

(56) References Cited

U.S. PATENT DOCUMENTS

| 9,221,843 B2 | 12/2015 | Gurney et al. |
| 2006/0293343 A1 | 12/2006 | Naganuma et al. |
| 2012/0189591 A1 | 7/2012 | Van Epps et al. |

FOREIGN PATENT DOCUMENTS

| WO | 0015645 A1 | 3/2000 |
| WO | 2010027975 A1 | 3/2010 |

(Continued)

OTHER PUBLICATIONS

Garcia-Osta et al., Phosphodiesterases as Therapeutic Targets for Alzheimer's Disease, ACS Chemical Neuroscience, 3(11), pp. 832-844 (2012).*

(Continued)

*Primary Examiner* — Deepak Rao
(74) *Attorney, Agent, or Firm* — Dennis A. Bennett; Cynthia Hathaway

(57) ABSTRACT

The present invention relates to compounds and methods useful as inhibitors of phosphodiesterase 4 (PDE4) for the treatment or prevention of disease.

34 Claims, No Drawings

Related U.S. Application Data

(60) Provisional application No. 61/776,937, filed on Mar. 12, 2013, provisional application No. 61/733,675, filed on Dec. 5, 2012, provisional application No. 61/718,285, filed on Oct. 25, 2012.

(51) Int. Cl.
    *A61K 31/5377*     (2006.01)
    *C07D 251/30*     (2006.01)
    *C07D 251/42*     (2006.01)
    *C07D 401/04*     (2006.01)

(56) References Cited

FOREIGN PATENT DOCUMENTS

| | | |
|---|---|---|
| WO | 2010097334 A1 | 9/2010 |
| WO | 2014066659 A9 | 5/2014 |
| WO | 2014117948 A1 | 8/2014 |

OTHER PUBLICATIONS

Wang et al., The phosphodiesterase-4 inhibitor rolipram reverses Aβ-induced cognitive impairment and neuroinflammatory and apoptotic responses in rats, International Journal of Neuropsychopharmacology, 15(6), pp. 749-766 (2012).*
Goto T et al., "Identification of the fused bicyclic 4-amino-2-phenylpyrimidine derivatives as novel and potent PDE4 Inhibitors," Bioorganic & Medicinal Chemistry Letters 23 (2013) 3325-3328.
Naganuma K et al., "Discovery of selective PDE4B inhibitors," Bioorg Med Chem Lett. Jun. 15, 2009;19(12):3174-6.
Kato Y et al., "Identification of 2,3-disubstituted pyridines as potent, orally active PDE4 inhibitors," Bioorganic & Medicinal Chemistry 21 (2013) 5851-5854.
International Search Report, WO2014066659 (PCT/US2013/066645), mailed Mar. 25, 2014.
Written Opinion, WO2014066659 (PCT/US2013/066645), mailed Mar. 25, 2014.
International Preliminary Report on Patentability, WO2014066659 (PCT/US2013/066645), mailed Feb. 13, 2015.
Layzer, Degenerative. "Diseases of the Nervous System." Cecil Textbook of Medicine, 2 (1996): 2050-2057.
Damasio, Antonio R. "Alzheimer's disease and related dementias." Cecil Textbook of Medicine, 2 (1996): 1992-1996.
Huang et al., The next generation of PDE4 inhibitors, Current Opinion in Chemical Biology, 5, pp. 432-438 (2001).
Chen, Z et al., "Selective synthesis of poly-substituted fluorine-containing pyridines and dihydropyrimidines via cascade C—F bond cleavage protocol;" Organic & Biomolecular Chemistry (2011), vol. 9, No. 16, pp. 5682-5691, XP055245515.

* cited by examiner

HETEROARYL INHIBITORS OF PDE4

This application is a divisional application of U.S. application Ser. No. 14/349,688, filed Apr. 4, 2014, which is a national phase entry under 35 U.S.C. §371, and claims the benefit of, International Application No. PCT/US2013/066645, filed Oct. 24, 2013, which claims the benefit of U.S. Provisional Applications No. 61/718,285, filed Oct. 25, 2012, No. 61/733,675, filed Dec. 5, 2012, and No. 61/776,937, filed Mar. 12, 2013, the disclosures of which are hereby incorporated by reference as if written herein in their entireties.

Disclosed herein are new bicyclic heteroaryl compounds and compositions and their application as pharmaceuticals for the treatment of disease. Methods of inhibition of phosphodiesterase 4 (PDE4) activity in a human or animal subject are also provided for the treatment diseases such as inflammatory diseases and other diseases involving elevated levels of cytokines and proinflammatory mediators.

Chronic inflammation is a multi-factorial disease complication characterized by activation of multiple types of inflammatory cells, for example cells of lymphoid lineage (including T lymphocytes) and myeloid lineage (including granulocytes, macrophages, and monocytes). Proinflammatory mediators, including cytokines, such as tumor necrosis factor (TNF) and interleukin-1 (IL-1), are produced by these activated cells. Accordingly, an agent that suppresses the activation of these cells, or their production of proinflammatory cytokines, would be useful in the therapeutic treatment of inflammatory diseases and other diseases involving elevated levels of cytokines.

Cyclic adenosine monophosphate (cAMP) is a second messenger that mediates the biologic responses of cells to a wide range of extracellular stimuli. When the appropriate agonist binds to specific cell surface receptors, adenylate cyclase is activated to convert adenosine triphosphate (ATP) to cAMP. It is theorized that the agonist induced actions of cAMP within the cell are mediated predominately by the action of cAMP-dependent protein kinases. The intracellular actions of cAMP are terminated by either a transport of the nucleotide to the outside of the cell, or by enzymatic cleavage by cyclic nucleotide phosphodiesterases (PDEs), which hydrolyze the 3'-phosphodiester bond to form 5'-adenosine monophosphate (5'-AMP). 5'-AMP is an inactive metabolite.

The superfamily of PDEs is subdivided into two major classes, class I and class II, which have no recognizable sequence similarity. Class I includes all known mammalian PDEs and is comprised of 11 identified families that are products of separate genes. Some PDEs are highly specific for hydrolysis of cAMP (PDE4, PDE7, PDE8), some are highly cGMP-specific (PDE5, PDE6, PDE9), and some have mixed specificity (PDE1, PDE2, PDE3, PDE10, PDE11). All of the characterized mammalian PDEs are dimeric, but the importance of the dimeric structure for function in each of the PDEs is unknown.

The PDE4 subfamily is comprised of 4 members: PDE4A, PDE4B, PDE4C, and PDE4D. These enzymes possess N-terminal regulatory domains that presumably mediate dimerization, which results in optimally regulated PDE activity. In addition, activity is regulated via cAMP-dependent protein kinase phosphorylation sites in this upstream regulatory domain. PDE4 enzymes are broadly expressed and distributed.

Elevated levels of cAMP in human myeloid and lymphoid lineage cells are associated with the suppression of cell activation. The intracellular enzyme family of PDEs, therefore, regulates the level of cAMP in cells. PDE4 is a predominant PDE isotype in these cells, and is a major contributor to cAMP degradation. Accordingly, the inhibition of PDE function would prevent the conversion of cAMP to the inactive metabolite 5'-AMP and, consequently, maintain higher cAMP levels, and, accordingly, suppress cell activation.

PDE4 inhibitors have been shown to inhibit production of TNFα and partially inhibit IL-1β release by monocytes (see Semmler et al., *Int. J. Immunopharmacol.*, 15, pp. 409-413, (1993); Molnar-Kimber et al., *Mediators of Inflammation*, 1, pp. 411-417, (1992)). PDE4 inhibitors also have been shown to inhibit the production of superoxide radicals from human polymorphonuclear leukocytes (see Verghese et al., *J. Mol. Cell. Cardiol.*, 21 (Suppl. 2), S61 (1989); Nielson et al., *J. Allergy Immunol.*, 86, pp. 801-808, (1990)); to inhibit the release of vasoactive amines and prostanoids from human basophils (see Peachell et al., *J. Immunol.*, 148, pp. 2503-2510, (1992)); to inhibit respiratory bursts in eosinophils (see Dent et al., *J. Pharmacol.*, 103, pp. 1339-1346, (1991)); and to inhibit the activation of human T-lymphocytes (see Robicsek et al., *Biochem. Pharmacol.*, 42, pp. 869-877, (1991)).

Inflammatory cell activation and excessive or unregulated cytokine (e.g., TNFα and IL-1β) production are implicated in allergic, autoimmune, and inflammatory diseases and disorders, discussed herein.

Additionally, several properties of TNFα, such as stimulation of collagenases, stimulation of angiogenesis in vivo, stimulation of bone resorption, and an ability to increase the adherence of tumor cells to endothelium, are consistent with a role for TNF in the development and metastatic spread of cancer in the host. TNFα recently has been directly implicated in the promotion of growth and metastasis of tumor cells (see Orosz et al., *J. Exp. Med.*, 177, pp. 1391-1398, (1993)).

Investigators have shown considerable interest in the use of PDE4 inhibitors as anti-inflammatory agents. Early evidence indicates that PDE4 inhibition has beneficial effects on a variety of inflammatory cells such as monocytes, macrophages, T-cells of the Th-1 lineage, and granulocytes. The synthesis and/or release of many proinflammatory mediators, such as cytokines, lipid mediators, superoxide, and biogenic amines, such as histamine, have been attenuated in these cells by the action of PDE4 inhibitors. The PDE4 inhibitors also affect other cellular functions including T-cell proliferation, granulocyte transmigration in response to chemotoxic substances, and integrity of endothelial cell junctions within the vasculature.

The design, synthesis, and screening of various PDE4 inhibitors have been reported. Methylxanthines, such as caffeine and theophylline, were the first PDE inhibitors discovered, but these compounds are nonselective with respect to which PDE is inhibited. The drug rolipram, an antidepressant agent, was one of the first reported specific PDE4 inhibitors, with a reported $IC_{50}$ of about 200 nM with respect to inhibiting recombinant human PDE4.

Investigators have continued to search for PDE4 inhibitors that are more selective with respect to inhibiting PDE4, that have a lower $IC_{50}$ than rolipram, and that avoid the undesirable central nervous system (CNS) side effects, such as retching, vomiting, and sedation, associated with the administration of rolipram. In addition, several companies are now undertaking clinical trials of other PDE4 inhibitors. However, problems relating to efficacy and adverse side effects, such as emesis and central nervous system disturbances, remain unsolved.

Accordingly, compounds that selectively inhibit PDE4, isoforms PDE4B or PDE4D, or a PDE4 isoform containing a UCR1 activating mutation (such as PDE4B1 containing UCR1 activating mutation S133D, PDE4B1*; or PDE4D7 containing UCR1 activating mutation S54D, PDE4D7*), and, in certain embodiments, that reduce or eliminate the adverse side effects associated with prior PDE4 inhibitors, would be useful in the treatment of disease, including neurologic and psychological diseases, and in the enhancement of memory and cognition. In addition, selective PDE4 inhibitors would be useful in the treatment of diseases that would benefit from elevated cAMP levels or reduced PDE4 function in a particular target tissue.

Compounds and pharmaceutical compositions, certain of which have been found to inhibit PDE4 have been discovered, together with methods of synthesizing and using the compounds including methods for the treatment of PDE4-mediated diseases in a patient by administering the compounds.

Certain compounds disclosed herein may possess useful PDE4 inhibiting activity, and may be used in the treatment or prophylaxis of a disease or condition in which PDE4 plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting PDE4. Other embodiments provide methods for treating a PDE4-mediated disorder in a patient in need of such treatment, comprising administering to said patient a therapeutically effective amount of a compound or composition according to the present invention. Related embodiments disclose the use of certain compounds disclosed herein as therapeutic agents, for example, in treating inflammatory diseases and other diseases involving elevated levels of cytokines and proinflammatory mediators. Also provided is the use of certain compounds disclosed herein for use in the manufacture of a medicament for the treatment of a disease or condition ameliorated by the inhibition of PDE4.

Accordingly, provided herein are compounds of structural Formula I:

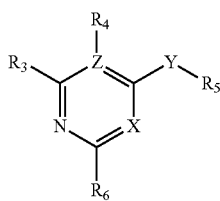

(I)

or a salt, ester, amide, or prodrug thereof, wherein:
Y is chosen from O, NH, NR$_2$, CH$_2$, C(R$_2$)$_2$, S(O)$_n$, and CO;
X is chosen from CR$_1$ and N;
Z is chosen from C and N;
n is an integer chosen from 0, 1 or 2;
R$_1$ is chosen from hydrogen, halogen, lower alkyl, hydroxyl, trifluoromethyl, OR$_2$, and N(R$_2$)$_2$;
each R$_2$ is independently chosen from hydrogen, hydroxyl, and lower alkyl;
R$_3$ is chosen from lower alkyl, lower heteroalkyl, lower haloalkyl, and lower cycloalkyl;
R$_4$ is chosen from:
  null if Z is N; and
  hydrogen, lower heteroalkyl, and lower alkyl if Z is C;

or R$_3$ and R$_4$, together with the atoms to which they are attached, join to form a 4 to 7 membered cycloalkyl or heterocycloalkyl, any of which may be optionally substituted;
R$_5$ is chosen from aryl, heteroaryl, heterocycloalkyl, cycloalkyl, and a carboxylic acid isostere, any of which may be optionally substituted; and
R$_6$ is chosen from aryl, heteroaryl, heterocycloalkyl, cycloalkyl, lower alkoxy, lower cycloalkoxy, and lower heterocycloalkoxy, any of which may be optionally substituted.

In certain embodiments of Formula I, Z is C.
In other embodiments of Formula I, Z is N.
In certain embodiments of Formula I, R$_1$ is hydrogen.
In certain embodiments of Formula I, R$_3$ and R$_4$ join to form a 4- to 7-membered cycloalkyl or heterocycloalkyl.
In certain embodiments of Formula I, R$_3$ and R$_4$ join to form a 5-membered cycloalkyl or 5- or 6-membered heterocycloalkyl.
In certain embodiments of Formula I,
R$_3$ and is chosen from lower alkyl, lower cycloalkyl, and trifluoromethyl;
R$_4$ is chosen from hydrogen and lower alkyl.
In certain embodiments of Formula I, R$_3$ and R$_4$ are each lower alkyl.
In certain embodiments of Formula I:
R$_3$ and R$_4$ are each lower alkyl; and
Z is C.
In certain embodiments of Formula I, R$_3$ and R$_4$ are each chosen from methyl and ethyl.
In certain embodiments of Formula I, R$_3$ is methyl and R$_4$ is ethyl.
In certain embodiments of Formula I, R$_3$ is ethyl and R$_4$ is hydrogen.
In certain embodiments of Formula I, R$_3$ is trifluoromethyl and R$_4$ is hydrogen.
In certain embodiments of Formula I, R$_3$ is cyclopropyl and R$_4$ is hydrogen.
In certain embodiments of Formula I, the compound has a structure chosen from:

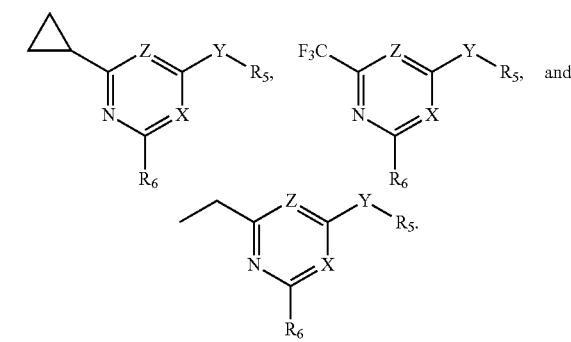

In certain embodiments of Formula I, the compound has a structure chosen from:

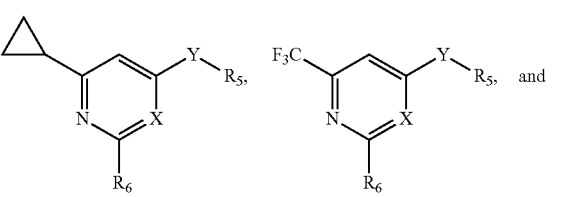

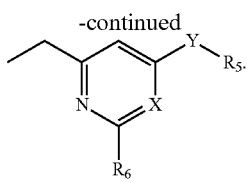

In certain embodiments of Formula I, $R_4$ is null.
In certain embodiments of Formula I, Y is NH.
In certain embodiments of Formula I, Y is $CH_2$.
In other embodiments of Formula I, Y is O.
In certain embodiments of Formula I, Y is $NR_2$.
In certain embodiments of Formula I, X is $CR_1$.
In certain embodiments of Formula I, X is N.
In certain embodiments of Formula I wherein Z is C, X is N, and $R_5$ is substituted phenyl, the phenyl is either substituted in the ortho or meta position, or, if substituted in the para position, contains at least one additional substituent.

In certain further embodiments of Formula I, $R_1$ is chosen from hydrogen, halogen, hydroxyl, and $NH_2$.

In certain embodiments of Formula I, $R_1$ is hydrogen.

In certain further embodiments of Formula I:
$R_1$ is chosen from lower alkyl, $OR_2$, and $N(R_2)_2$; and
at least one of $R_2$ is lower alkyl.

In further embodiments of Formula I, $R_2$ is chosen from methyl, ethyl, propyl, isopropyl, butyl, and t-butyl.

In certain embodiments of Formula I, $R_5$ is optionally substituted aryl.

In certain embodiments of Formula I, $R_5$ is substituted phenyl, which is either substituted in the ortho or meta position, or, if substituted in the para position, contains at least one additional substituent.

In further embodiments of Formula I, $R_5$ is substituted with between one and four substituents of the form $R_8$—$R_9$—$(R_{10})_p$, wherein:
   $R_8$ is chosen from a bond, lower alkyl, lower alkoxy, amino, lower alkylamino, and sulfonamide;
   $R_9$ is chosen from halogen, lower alkyl, lower haloalkyl, lower hydroxyalkyl, lower alkoxy, lower haloalkoxy, amino, carboxyl, carboxamido, a carboxylic acid isostere, cyano, and tetrazole;
   $R_{10}$ is chosen from null, hydrogen, and lower alkyl; and
   p is an integer chosen from 0, 1 or 2.

In further embodiments of Formula I, $R_9$ is a carboxylic acid isostere chosen from tetrazole, oxazole, isoxazole, isothiazole, —$SO_3H$, —$SO_2NHR$, —$PO_2(R)_2$, —CN, —$PO_3(R)_2$, —OR, —SR, —$N(R)_2$, —NHC(O)R, —NN$(R)_2$, —C(O)N$(R)_2$, —RC(O)N(CN)H, —N(CN)C(O)(R), —C(O)NHOR, —C(O)NHNHSO$_2$R, —C(O)NHSO$_2$R, —C(O)ONRCN, boronic acid, benzoxaborole, acyl sulfonamide, cyclobutenedione, cyclopentenedione, wherein R is hydrogen or a carbon chain or ring or a carbon-linked group, such as an alkyl, alkenyl, alkynyl, cycloalkyl, or aryl group, or a heterocycloalkyl or heteroaryl group where the bond is to a carbon, any of which may be optionally substituted.

In further embodiments of Formula I, $R_9$ is a carboxylic acid isostere chosen from boronic acid, benzoxaborole, 3,3-dimethylbenzoxaborole, 3-hydroxy-cyclopent-2-enone and cyclopentenedione.

In certain embodiments of Formula I, $R_5$ is heteroaryl.

In further embodiments of Formula I, $R_5$ is a carboxylic acid isostere.

In other embodiments of Formula I, $R_5$ is a carboxylic acid isostere chosen from tetrazole, oxazole, isoxazole, isothiazole, —$SO_3H$, —$SO_2NHR$, —$PO_2(R)_2$, —CN, —$PO_3(R)_2$, —OR, —SR, —$N(R)_2$, —NHC(O)R, —NN$(R)_2$, —C(O)N$(R)_2$, —RC(O)N(CN)H, —N(CN)C(O)(R), —C(O)NHOR, —C(O)NHNHSO$_2$R, —C(O)NHSO$_2$R, —C(O)ONRCN, boronic acid, benzoxaborole, acyl sulfonamide, cyclobutenedione, cyclopentenedione, wherein R is hydrogen or a carbon chain or ring or a carbon-linked group, such as an alkyl, alkenyl, alkynyl, cycloalkyl, or aryl group, or a heterocycloalkyl or heteroaryl group where the bond is to a carbon, any of which may be optionally substituted.

In other embodiments of Formula I, $R_5$ is chosen from benzoxaborole, 3,3-dimethylbenzoxaborole, 3-hydroxy-cyclopent-2-enone and cyclopentenedione.

In yet further embodiments of Formula I, $R_5$ is benzoxaborole.

In further embodiments of Formula I, $R_5$ has the structure

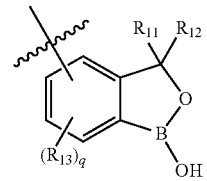

wherein
   $R_{11}$ and $R_{12}$ are independently chosen from hydrogen and lower alkyl;
   each $R_{13}$ is chosen from halogen, hydroxy, lower haloalkyl, lower alkoxy, lower haloalkoxy, lower acyl, amino, cyano, and sulfonyl; and
   q is an integer from 0 to 3.

In yet further embodiments of Formula I,
   $R_8$ is chosen from a bond, methyl, ethyl, methoxy, and ethoxy; and
   $R_9$ is chosen from methyl, ethyl, methoxy, ethoxy, fluorine, chlorine, bromine, perfluoromethyl, perfluoromethoxy, carboxyl, carboxamide, cyano, and tetrazole.

In certain embodiments of Formula I, $R_6$ is chosen from:
substituted phenyl or naphthyl;
substituted monocyclic or bicyclic heteroaryl, having between four and twelve ring atoms, of which up to six are heteroatoms chosen from O, S, and N;
optionally substituted monocyclic or bicyclic heterocycloalkyl, having between four and twelve ring atoms, of which up to six are heteroatoms chosen from O, S, and N; and
optionally substituted monocyclic or bicyclic $C_3$-$C_{10}$ cycloalkyl.

In further embodiments of Formula I, $R_6$ is substituted with between one and four substituents chosen from halogen, hydroxy, lower haloalkyl, lower alkoxy, lower haloalkoxy, lower acyl, amino, cyano, and sulfonyl.

In certain further embodiments of Formula I, $R_6$ is substituted phenyl or naphthyl.

In certain further embodiments of Formula I, $R_6$ is optionally substituted monocyclic heteroaryl, having between five and six ring atoms, of which up to four are heteroatoms chosen from O, S, and N.

In yet further embodiments of Formula I, $R_6$ is chosen from thiophene, pyrrole, pyrimidine, oxazole, isoxazole, pyrazole, imidazole, thiazole, isothiazole, pyridine, pyrazine and pyridazine, any of which may be optionally substituted with between a substituent chosen from halogen, hydroxy, trifluoromethyl, methoxy, trifluoromethoxy, acetyl, amino, cyano, and sulfonyl.

In still further embodiments of Formula I, $R_6$ is thiophene.

In certain further embodiments of Formula I, $R_6$ is optionally substituted bicyclic heteroaryl, having between eight and nine ring atoms, of which up to six are heteroatoms chosen from O, S, and N.

In yet further embodiments of Formula I, $R_6$ is chosen from indole, benzoxazole, benzisoxazole, benzothiazole, quinoline, isoquinoline, and coumarin.

In further embodiments of Formula I, $R_6$ is optionally substituted monocyclic heterocycloalkyl, having between five and seven ring atoms, of which up to six are heteroatoms chosen from O, S, and N.

In yet further embodiments of Formula I, $R_6$ is chosen from pyrrolidine, furan, morpholine, piperazine, and piperidine.

In further embodiments of Formula I, $R_6$ is optionally substituted monocyclic cycloalkyl having between five and seven ring atoms, and optionally substituted monocyclic cycloalkoxy having between five and seven ring atoms.

In further embodiments of Formula I, $R_6$ is optionally substituted cyclopentyl or optionally substituted cyclopentyloxy.

In further embodiments of Formula I, $R_6$ is optionally substituted cyclopentyloxy.

In further embodiments of Formula I, $R_6$ is chosen from 3-chlorophenyl and 5-chloro-2-thienyl.

In certain embodiments of Formula I, Z is C.

In certain embodiments of Formula I, $R_3$ and $R_4$ join to form a 4- to 7-membered cycloalkyl or heterocycloalkyl, any of which may be optionally substituted.

In certain embodiments of Formula I:
$R_3$ and $R_4$ join to form a 4- to 7-membered cycloalkyl or heterocycloalkyl, either of which may be optionally substituted; and
Z is C.

In certain embodiments of Formula I, $R_3$ and $R_4$ join to form a five-membered cycloalkyl or heterocycloalkyl, any of which may be optionally substituted.

In certain embodiments of Formula I, X is $CR_1$.

In certain embodiments of Formula I, $R_1$ is hydrogen.

Also provided are embodiments wherein any of embodiment above in paragraphs [017]-[077] above may be combined with any one or more of these embodiments, provided the combination is not mutually exclusive.

As used herein, two embodiments are "mutually exclusive" when one is defined to be something which is different than the other. For example, an embodiment wherein $R_3$ and $R_4$ combine to form a cycloalkyl is mutually exclusive with an embodiment in which $R_3$ is ethyl and $R_4$ is hydrogen. Similarly, an embodiment wherein Y is $CH_2$ is mutually exclusive with an embodiment wherein Y is NH.

In certain embodiments are provided compounds of structural Formula II:

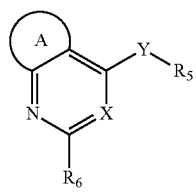

(II)

or a salt, ester, amide, or prodrug thereof, wherein:
A is a 4- to 7-membered cycloalkyl or heterocycloalkyl, any of which may be optionally substituted;
Y is chosen from O, NH, $NR_2$, $CH_2$, $C(R_2)_2$, $S(O)_n$ and CO;
X is chosen from $CR_1$ and N;
Z is chosen from C and N;

n is an integer chosen from 0, 1 or 2;
$R_1$ is chosen from hydrogen, halogen, lower alkyl, hydroxyl, trifluoromethyl, $OR_2$, and $N(R_2)_2$;
each $R_2$ is independently chosen from hydrogen, hydroxyl, and lower alkyl;
$R_5$ is chosen from aryl, heteroaryl, heterocycloalkyl, cycloalkyl, carboxylic acid, and a carboxylic acid isostere, any of which may be optionally substituted;
$R_6$ is chosen from aryl, heteroaryl, heterocycloalkyl, cycloalkyl, lower alkoxy, lower cycloalkoxy, and lower heterocycloalkoxy, any of which may be optionally substituted.

In certain embodiments of Formula II, A is a five- to six-membered cycloalkyl or heterocycloalkyl.

In certain embodiments of Formula II, Y is N.

In certain embodiments of Formula II, X is N.

In certain embodiments of Formula II, X is $CR_1$.

In certain embodiments of Formula I, $R_1$ is hydrogen.

In certain embodiments of Formula II, Y is NH.

In certain embodiments of Formula II, Y is $CH_2$.

In other embodiments of Formula II, Y is O.

In certain embodiments of Formula II, Y is $NR_2$.

In certain embodiments of Formula II, $R_5$ is optionally substituted aryl.

In certain embodiments of Formula II, $R_5$ is substituted phenyl, which is either substituted in the ortho or meta position, or, if substituted in the para position, contains at least one additional substituent.

In further embodiments of Formula II, $R_5$ is substituted with between one and four substituents of the form $R_8$—$R_9$—$(R_{10})_p$, wherein:
$R_8$ is chosen from a bond, lower alkyl, lower alkoxy, amino, lower alkylamino, and sulfonamide;
$R_9$ is chosen from halogen, lower alkyl, lower haloalkyl, lower hydroxyalkyl, lower alkoxy, lower haloalkoxy, amino, carboxyl, carboxamido, a carboxylic acid isostere, cyano, and tetrazole;
$R_{10}$ is chosen from null, hydrogen and lower alkyl; and
p is an integer chosen from 0, 1 or 2.

In yet further embodiments of Formula II,
$R_8$ is chosen from a bond, methyl, ethyl, methoxy, and ethoxy; and
$R_9$ is chosen from methyl, ethyl, methoxy, ethoxy, fluorine, chlorine, bromine, perfluoromethyl, perfluoromethoxy, carboxyl, carboxamide, cyano, and tetrazole.

In further embodiments of Formula II, $R_9$ is a carboxylic acid isostere chosen from tetrazole, oxazole, isoxazole, isothiazole, $—SO_3H$, $—SO_2NHR$, $—PO_2(R)_2$, $—CN$, $—PO_3(R)_2$, $—OR$, $—SR$, $—N(R)_2$, $—NHC(O)R$, $—NN(R)_2$, $—C(O)N(R)_2$, $—RC(O)N(CN)H$, $—N(CN)C(O)(R)$, $—C(O)NHOR$, $—C(O)NHNHSO_2R$, $—C(O)NHSO_2R$, $—C(O)ONRCN$, boronic acid, benzoxaborole, acyl sulfonamide, cyclobutenedione, cyclopentenedione, wherein R is hydrogen or a carbon chain or ring or a carbon-linked group, such as an alkyl, alkenyl, alkynyl, cycloalkyl, or aryl group, or a heterocycloalkyl or heteroaryl group where the bond is to a carbon, any of which may be optionally substituted.

In further embodiments of Formula I, $R_9$ is a carboxylic acid isostere chosen from boronic acid, benzoxaborole, 3,3-dimethylbenzoxaborole, 3-hydroxy-cyclopent-2-enone and cyclopentenedione.

In certain embodiments of Formula II, $R_5$ is heteroaryl.

In certain embodiments of Formula II, $R_5$ is a carboxylic acid isostere.

In certain embodiments of Formula II, R$_5$ is chosen from benzoxaborole, 3,3-dimethylbenzoxaborole, 3-hydroxy-cyclopent-2-enone and cyclopentenedione.

In certain embodiments of Formula II, R$_5$ is benzoxaborole.

In yet further embodiments of Formula II,
R$_8$ is chosen from a bond, methyl, ethyl, methoxy, and ethoxy; and
R$_9$ is chosen from methyl, ethyl, methoxy, ethoxy, fluorine, chlorine, bromine, perfluoromethyl, perfluoromethoxy, carboxyl, carboxamide, cyano, and tetrazole.

In further embodiments of Formula II, R$_5$ has the structure

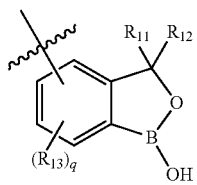

wherein
R$_{11}$ and R$_{12}$ are independently chosen from hydrogen and lower alkyl;
each R$_{13}$ is chosen from halogen, hydroxy, lower haloalkyl, lower alkoxy, lower haloalkoxy, lower acyl, amino, cyano, and sulfonyl; and
q is an integer from 0 to 3.

In certain embodiments of Formula II, R$_6$ is chosen from:
substituted phenyl or naphthyl;
substituted monocyclic or bicyclic heteroaryl, having between four and twelve ring atoms, of which up to six are heteroatoms chosen from O, S, and N;
optionally substituted monocyclic or bicyclic heterocycloalkyl, having between four and twelve ring atoms, of which up to six are heteroatoms chosen from O, S, and N; and
optionally substituted monocyclic or bicyclic C$_3$-C$_{10}$ cycloalkyl.

In further embodiments of Formula II, R$_6$ is substituted with between one and four substituents chosen from halogen, hydroxy, lower haloalkyl, lower alkoxy, lower haloalkoxy, lower acyl, amino, cyano, and sulfonyl.

In certain further embodiments of Formula II, R$_6$ is substituted phenyl or naphthyl.

In certain further embodiments of Formula II, R$_6$ is optionally substituted monocyclic heteroaryl, having between five and six ring atoms, of which up to four are heteroatoms chosen from O, S, and N.

In yet further embodiments of Formula II, R$_6$ is chosen from thiophene, pyrrole, pyrimidine, oxazole, isoxazole, pyrazole, imidazole, thiazole, isothiazole, pyridine, pyrazine and pyridazine, any of which may be optionally substituted with between a substituent chosen from halogen, hydroxy, trifluoromethyl, methoxy.

In still further embodiments of Formula II, R$_6$ is thiophene.

In certain further embodiments of Formula II, R$_6$ is optionally substituted bicyclic heteroaryl, having between eight and nine ring atoms, of which up to six are heteroatoms chosen from O, S, and N.

In yet further embodiments of Formula II, R$_6$ is chosen from indole, benzoxazole, benzisoxazole, benzothiazole, quinoline, isoquinoline, and coumarin.

In certain further embodiments of Formula II, R$_6$ is optionally substituted monocyclic heterocycloalkyl, having between five and seven ring atoms, of which up to six are heteroatoms chosen from O, S, and N.

In yet further embodiments of Formula II, R$_6$ is chosen from pyrrolidine, furan, morpholine, piperazine, and piperidine.

In further embodiments of Formula II, R$_6$ is optionally substituted monocyclic cycloalkyl having between five and seven ring atoms, and optionally substituted monocyclic cycloalkoxy having between five and seven ring atoms.

In further embodiments of Formula II, R$_6$ is optionally substituted cyclopentyl or optionally substituted cyclopentyloxy.

In further embodiments of Formula II, R$_6$ is optionally substituted cyclopentyloxy.

In further embodiments of Formula II, R$_6$ is chosen from 3-chlorophenyl and 5-chloro-2-thienyl.

Also provided are embodiments wherein any of embodiment above in paragraphs [079]-[0114] above may be combined with any one or more of these embodiments, provided the combination is not mutually exclusive.

In certain embodiments are provided compounds of structural Formula III:

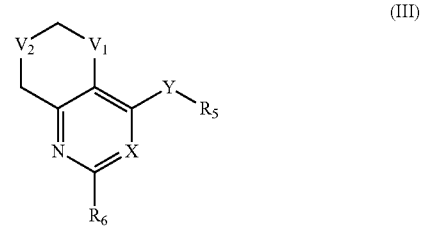

or a salt, ester, amide, or prodrug thereof, wherein:
V$_1$ is chosen from CH$_2$, N, O, SO$_2$, and S;
V$_2$ is chosen from a bond, N, O and CH$_2$;
Y is chosen from O, NH, NR$_2$, CH$_2$, C(R$_2$)$_2$, S(O)$_n$ and CO;
X is chosen from CH and N;
n is an integer chosen from 0, 1 or 2;
each R$_2$ is independently chosen from hydrogen, hydroxyl, and lower alkyl;
R$_5$ is chosen from aryl, heteroaryl, heterocycloalkyl, cycloalkyl, carboxylic acid, and a carboxylic acid isostere, any of which may be optionally substituted;
R$_6$ is chosen from aryl, heteroaryl, heterocycloalkyl, cycloalkyl, lower alkoxy, lower cycloalkoxy, and lower heterocycloalkoxy, any of which may be optionally substituted.

In certain embodiments of Formula III,
V$_1$ is chosen from CH$_2$, SO$_2$, and S; and
V$_2$ is chosen from a bond and CH$_2$;

In certain embodiments of Formula III, V$_1$ is SO$_2$ and V$_2$ is CH$_2$.

In certain embodiments of Formula III, V$_1$ is S and V$_2$ is CH$_2$.

In certain embodiments of Formula III, V$_1$ is CH$_2$ and V$_2$ is a bond.

In certain embodiments of Formula III, X is N.
In certain embodiments of Formula III, X is CH.
In certain embodiments of Formula III, Y is NH.
In certain embodiments of Formula III, Y is CH$_2$.
In other embodiments of Formula III, Y is O.

In certain embodiments of Formula III, Y is $NR_2$.

In certain embodiments of Formula III, $R_5$ is optionally substituted aryl.

In certain embodiments of Formula III, $R_5$ is substituted phenyl, which is either substituted in the ortho or meta position, or, if substituted in the para position, contains at least one additional substituent.

In further embodiments of Formula III, $R_5$ is substituted with between one and four substituents of the form $R_8$—$R_9$—$(R_{10})_p$, wherein:
  $R_8$ is chosen from a bond, lower alkyl, lower alkoxy, amino, lower alkylamino, and sulfonamide;
  $R_9$ is chosen from halogen, lower alkyl, lower haloalkyl, lower hydroxyalkyl, lower alkoxy, lower haloalkoxy, amino, carboxyl, carboxamido, a carboxylic acid isostere, cyano, and tetrazole;
  $R_{10}$ is chosen from null, hydrogen and lower alkyl; and
  p is an integer chosen from 0, 1 or 2.

In yet further embodiments of Formula III,
  $R_8$ is chosen from a bond, methyl, ethyl, methoxy, and ethoxy; and
  $R_9$ is chosen from methyl, ethyl, methoxy, ethoxy, fluorine, chlorine, bromine, perfluoromethyl, perfluoromethoxy, carboxyl, carboxamide, cyano, and tetrazole.

In further embodiments of Formula III, $R_9$ is a carboxylic acid isostere chosen from tetrazole, oxazole, isoxazole, isothiazole, —$SO_3H$, —$SO_2NHR$, —$PO_2(R)_2$, —CN, —$PO_3(R)_2$, —OR, —SR, —$N(R)_2$, —NHC(O)R, —NN$(R)_2$, —C(O)N$(R)_2$, —RC(O)N(CN)H, —N(CN)C(O)(R), —C(O)NHOR, —C(O)NHNHSO$_2$R, —C(O)NHSO$_2$R, —C(O)ONRCN, boronic acid, benzoxaborole, acyl sulfonamide, cyclobutenedione, cyclopentenedione, wherein R is hydrogen or a carbon chain or ring or a carbon-linked group, such as an alkyl, alkenyl, alkynyl, cycloalkyl, or aryl group, or a heterocycloalkyl or heteroaryl group where the bond is to a carbon, any of which may be optionally substituted.

In further embodiments of Formula I, $R_9$ is a carboxylic acid isostere chosen from boronic acid, benzoxaborole, 3,3-dimethylbenzoxaborole, 3-hydroxy-cyclopent-2-enone and cyclopentenedione.

In certain embodiments of Formula III, $R_5$ is heteroaryl.

In certain embodiments of Formula III, $R_5$ is a carboxylic acid isostere.

In certain embodiments of Formula III, $R_5$ is chosen from benzoxaborole, 3,3-dimethylbenzoxaborole, 3-hydroxy-cyclopent-2-enone and cyclopentenedione.

In certain embodiments of Formula III, $R_5$ is benzoxaborole.

In yet further embodiments of Formula III,
  $R_8$ is chosen from a bond, methyl, ethyl, methoxy, and ethoxy; and
  $R_9$ is chosen from methyl, ethyl, methoxy, ethoxy, fluorine, chlorine, bromine, perfluoromethyl, perfluoromethoxy, carboxyl, carboxamide, cyano, and tetrazole.

In further embodiments of Formula III, $R_5$ has the structure

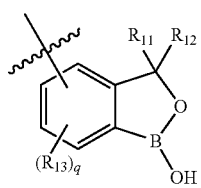

wherein
  $R_{11}$ and $R_{12}$ are independently chosen from hydrogen and lower alkyl;
  each $R_{13}$ is chosen from halogen, hydroxy, lower haloalkyl, lower alkoxy, lower haloalkoxy, lower acyl, amino, cyano, and sulfonyl; and In certain embodiments of Formula II, $R_6$ is chosen from:
  substituted phenyl or naphthyl;
  substituted monocyclic or bicyclic heteroaryl, having between four and twelve ring atoms, of which up to six are heteroatoms chosen from O, S, and N;
  optionally substituted monocyclic or bicyclic heterocycloalkyl, having between four and twelve ring atoms, of which up to six are heteroatoms chosen from O, S, and N; and
  optionally substituted monocyclic or bicyclic $C_3$-$C_{10}$ cycloalkyl.

In further embodiments of Formula III, $R_6$ is substituted with between one and four substituents chosen from halogen, hydroxy, lower haloalkyl, lower alkoxy, lower haloalkoxy, lower acyl, amino, cyano, and sulfonyl.

In certain further embodiments of Formula III, $R_6$ is substituted phenyl or naphthyl.

In certain further embodiments of Formula III, $R_6$ is optionally substituted monocyclic heteroaryl, having between five and six ring atoms, of which up to four are heteroatoms chosen from O, S, and N.

In yet further embodiments of Formula III, $R_6$ is chosen from thiophene, pyrrole, pyrimidine, oxazole, isoxazole, pyrazole, imidazole, thiazole, isothiazole, pyridine, pyrazine and pyridazine, any of which may be optionally substituted with between a substituent chosen from halogen, hydroxy, trifluoromethyl, methoxy.

In still further embodiments of Formula III, $R_6$ is thiophene.

In certain further embodiments of Formula III, $R_6$ is optionally substituted bicyclic heteroaryl, having between eight and nine ring atoms, of which up to six are heteroatoms chosen from O, S, and N.

In yet further embodiments of Formula III, $R_6$ is chosen from indole, benzoxazole, benzisoxazole, benzothiazole, quinoline, isoquinoline, and coumarin.

In certain further embodiments of Formula III, $R_6$ is optionally substituted monocyclic heterocycloalkyl, having between five and seven ring atoms, of which up to six are heteroatoms chosen from O, S, and N.

In yet further embodiments of Formula III, $R_6$ is chosen from pyrrolidine, furan, morpholine, piperazine, and piperidine.

In further embodiments of Formula III, $R_6$ is optionally substituted monocyclic cycloalkyl having between five and seven ring atoms, and optionally substituted monocyclic cycloalkoxy having between five and seven ring atoms.

In further embodiments of Formula III, $R_6$ is optionally substituted cyclopentyl or optionally substituted cyclopentyloxy.

In further embodiments of Formula III, $R_6$ is optionally substituted cyclopentyloxy.

In further embodiments of Formula III, $R_6$ is chosen from 3-chlorophenyl and 5-chloro-2-thienyl.

Also provided are embodiments wherein any of embodiment above in paragraphs [0116]-[0152] above may be combined with any one or more of these embodiments, provided the combination is not mutually exclusive.

In certain embodiments are provided compounds of structural Formula IV:

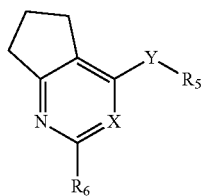

(IV)

or a salt, ester, amide, or prodrug thereof, wherein:
Y is chosen from O, NH, $NR_2$, $C(R_2)_2$, $S(O)_n$ and CO;
X is chosen from CH and N;
n is an integer chosen from 0, 1 or 2;
$R_1$ is chosen from hydrogen, halogen, lower alkyl, hydroxyl, trifluoromethyl, $OR_2$, and $N(R_2)_2$;
each $R_2$ is independently chosen from hydrogen, hydroxyl, and lower alkyl;
$R_5$ is chosen from aryl, heteroaryl, heterocycloalkyl, cycloalkyl, carboxylic acid, and a carboxylic acid isostere, any of which may be optionally substituted;
$R_6$ is chosen from aryl, heteroaryl, heterocycloalkyl, cycloalkyl, lower alkoxy, lower cycloalkoxy, and lower heterocycloalkoxy, any of which may be optionally substituted.

In certain embodiments of Formula IV, X is N.
In certain embodiments of Formula IV, X is $CR_1$.
In certain embodiments are provided compounds of structural Formula IVa or IVb:

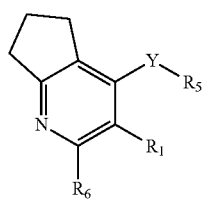

(IVa)

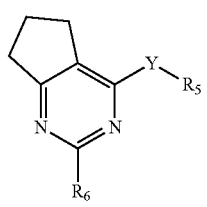

(IVb)

or a salt thereof, wherein:
Y is chosen from O, NH, $NR_2$, $C(R_2)_2$, $S(O)_n$ and CO;
n is an integer chosen from 0, 1 or 2;
$R_1$ (in Formula Iva only) is hydrogen;
each $R_2$ is independently chosen from hydrogen and lower alkyl; and
$R_5$ is chosen from aryl, heteroaryl, heterocycloalkyl, cycloalkyl, carboxylic acid, and a carboxylic acid isostere, any of which may be optionally substituted; and
$R_6$ is chosen from aryl, heteroaryl, heterocycloalkyl, cycloalkyl, lower alkoxy, lower cycloalkoxy, and lower heterocycloalkoxy, any of which may be optionally substituted.

In certain embodiments of Formula I IV, IVa, or IVb, $R_1$ is hydrogen.
In certain embodiments of Formula IV, IVa, or IVb, Y is NH.
In certain embodiments of Formula IV, IVa, or IVb, Y is $CH_2$.
In other embodiments of Formula IV, IVa, or IVb, Y is O.
In certain embodiments of Formula IV, IVa, or IVb, Y is $NR_2$.
In certain embodiments of Formula IV, IVa, or IVb, $R_5$ is optionally substituted aryl.
In certain embodiments of Formula IV, IVa, or IVb, $R_5$ is substituted phenyl, which is either substituted in the ortho or meta position, or, if substituted in the para position, contains at least one additional substituent.
In further embodiments of Formula IV, IVa, or IVb, $R_5$ is substituted with between one and four substituents of the form $R_8-R_9-(R_{10})_p$, wherein:
$R_8$ is chosen from a bond, lower alkyl, lower alkoxy, amino, lower alkylamino, and sulfonamide;
$R_9$ is chosen from halogen, lower alkyl, lower haloalkyl, lower hydroxyalkyl, lower alkoxy, lower haloalkoxy, amino, carboxyl, carboxamido, a carboxylic acid isostere, cyano, and tetrazole;
$R_{10}$ is chosen from null, hydrogen and lower alkyl; and
p is an integer chosen from 0, 1 or 2.

In yet further embodiments of Formula IV, IVa, or IVb,
$R_8$ is chosen from a bond, methyl, ethyl, methoxy, and ethoxy; and
$R_9$ is chosen from methyl, ethyl, methoxy, ethoxy, fluorine, chlorine, bromine, perfluoromethyl, perfluoromethoxy, carboxyl, carboxamide, cyano, and tetrazole.

In further embodiments of Formula IV, IVa, or IVb, $R_9$ is a carboxylic acid isostere chosen from tetrazole, oxazole, isoxazole, isothiazole, $-SO_3H$, $-SO_2NHR$, $-PO_2(R)_2$, $-CN$, $-PO_3(R)_2$, $-OR$, $-SR$, $-N(R)_2$, $-NHC(O)R$, $-NN(R)_2$, $-C(O)N(R)_2$, $-RC(O)N(CN)H$, $-N(CN)C(O)(R)$, $-C(O)NHOR$, $-C(O)NHNHSO_2R$, $-C(O)NHSO_2R$, $-C(O)ONRCN$, boronic acid, benzoxaborole, acyl sulfonamide, cyclobutenedione, cyclopentenedione, wherein R is hydrogen or a carbon chain or ring or a carbon-linked group, such as an alkyl, alkenyl, alkynyl, cycloalkyl, or aryl group, or a heterocycloalkyl or heteroaryl group where the bond is to a carbon, any of which may be optionally substituted.

In further embodiments of Formula I, $R_9$ is a carboxylic acid isostere chosen from boronic acid, benzoxaborole, 3,3-dimethylbenzoxaborole, 3-hydroxy-cyclopent-2-enone and cyclopentenedione.

In certain embodiments of Formula IV, IVa, or IVb, $R_5$ is heteroaryl.
In certain embodiments of Formula IV, IVa, or IVb, $R_5$ is a carboxylic acid isostere.
In certain embodiments of Formula IV, IVa, or IVb, $R_5$ is chosen from benzoxaborole, 3,3-dimethylbenzoxaborole, 3-hydroxy-cyclopent-2-enone and cyclopentenedione.
In certain embodiments of Formula IV, IVa, or IVb, $R_5$ is benzoxaborole.

In yet further embodiments of Formula IV, IVa, or IVb,
$R_8$ is chosen from a bond, methyl, ethyl, methoxy, and ethoxy; and
$R_9$ is chosen from methyl, ethyl, methoxy, ethoxy, fluorine, chlorine, bromine, perfluoromethyl, perfluoromethoxy, carboxyl, carboxamide, cyano, and tetrazole.

In further embodiments of Formula IV, IVa, or IVb, $R_5$ has the structure

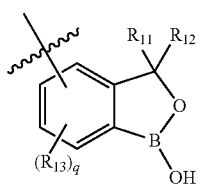

wherein
  $R_{11}$ and $R_{12}$ are independently chosen from hydrogen and lower alkyl;
  each $R_{13}$ is chosen from halogen, hydroxy, lower haloalkyl, lower alkoxy, lower haloalkoxy, lower acyl, amino, cyano, and sulfonyl; and
  q is an integer from 0 to 3.

In certain embodiments of Formula IV, IVa, or IVb, $R_6$ is chosen from:
  substituted phenyl or naphthyl;
    substituted monocyclic or bicyclic heteroaryl, having between four and twelve ring atoms, of which up to six are heteroatoms chosen from O, S, and N;
    optionally substituted monocyclic or bicyclic heterocycloalkyl, having between four and twelve ring atoms, of which up to six are heteroatoms chosen from O, S, and N; and
    optionally substituted monocyclic or bicyclic $C_3$-$C_{10}$ cycloalkyl.

In further embodiments of Formula IV, IVa, or IVb, $R_6$ is substituted with between one and four substituents chosen from halogen, hydroxy, lower haloalkyl, lower alkoxy, lower haloalkoxy, lower acyl, amino, cyano, and sulfonyl.

In certain further embodiments of Formula IV, IVa, or IVb, $R_6$ is substituted phenyl or naphthyl.

In certain further embodiments of Formula IV, IVa, or IVb, $R_6$ is optionally substituted monocyclic heteroaryl, having between five and six ring atoms, of which up to four are heteroatoms chosen from O, S, and N.

In yet further embodiments of Formula IV, IVa, or IVb, $R_6$ is chosen from thiophene, pyrrole, pyrimidine, oxazole, isoxazole, pyrazole, imidazole, thiazole, isothiazole, pyridine, pyrazine and pyridazine, any of which may be optionally substituted with between a substituent chosen from halogen, hydroxy, trifluoromethyl, methoxy.

In still further embodiments of Formula IV, IVa, or IVb, $R_6$ is thiophene.

In certain further embodiments of Formula IV, IVa, or IVb, $R_6$ is optionally substituted bicyclic heteroaryl, having between eight and nine ring atoms, of which up to six are heteroatoms chosen from O, S, and N.

In yet further embodiments of Formula IV, IVa, or IVb, $R_6$ is chosen from indole, benzoxazole, benzisoxazole, benzothiazole, quinoline, isoquinoline, and coumarin.

In certain further embodiments of Formula IV, IVa, or IVb, $R_6$ is optionally substituted monocyclic heterocycloalkyl, having between five and seven ring atoms, of which up to six are heteroatoms chosen from O, S, and N.

In yet further embodiments of Formula IV, IVa, or IVb, $R_6$ is chosen from pyrrolidine, furan, morpholine, piperazine, and piperidine.

In further embodiments of Formula IV, IVa, or IVb, $R_6$ is optionally substituted monocyclic cycloalkyl having between five and seven ring atoms, and optionally substituted monocyclic cycloalkoxy having between five and seven ring atoms.

In further embodiments of Formula IV, IVa, or IVb, $R_6$ is optionally substituted cyclopentyl or optionally substituted cyclopentyloxy.

In further embodiments of Formula IV, IVa, or IVb, $R_6$ is optionally substituted cyclopentyloxy.

In further embodiments of Formula IV, IVa, or IVb, $R_6$ is chosen from 3-chlorophenyl and 5-chloro-2-thienyl.

Also provided are embodiments wherein any of embodiment above in paragraphs [0154]-[0188] above may be combined with any one or more of these embodiments, provided the combination is not mutually exclusive.

In certain embodiments are provided compounds of structural Formula V:

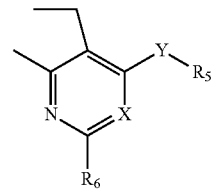

or a salt thereof, wherein:
  Y is chosen from O, NH, $NR_2$, $C(R_2)_2$, $S(O)_n$ and CO;
  X is chosen from CH and N;
  n is an integer chosen from 0, 1 or 2;
  $R_1$ (in Formula Va only) is hydrogen
  each $R_2$ is independently chosen from hydrogen and lower alkyl; and
  $R_5$ is chosen from aryl, heteroaryl, heterocycloalkyl, cycloalkyl, carboxylic acid, and a carboxylic acid isostere, any of which may be optionally substituted; and
  $R_6$ is chosen from aryl, heteroaryl, heterocycloalkyl, cycloalkyl, lower alkoxy, lower cycloalkoxy, and lower heterocycloalkoxy, any of which may be optionally substituted.

In certain embodiments of Formula V, X is N.
In certain embodiments of Formula V, X is $CR_1$.
In certain embodiments are provided compounds of structural Formula Va or Vb:

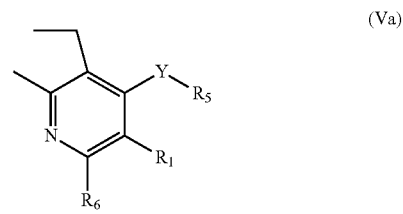

(Va)

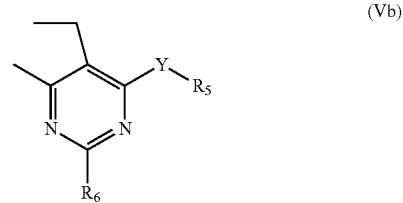

(Vb)

or a salt thereof, wherein:
  Y is chosen from O, NH, $NR_2$, $C(R_2)_2$, $S(O)_n$ and CO;
  n is an integer chosen from 0, 1 or 2;
  $R_1$ (in Formula Va only) is hydrogen
  each $R_2$ is independently chosen from hydrogen and lower alkyl; and R₅ is chosen from aryl, heteroaryl, heterocycloalkyl, cycloalkyl, carboxylic acid, and a carboxylic acid isostere, any of which may be optionally substituted; and R₆ is chosen from aryl, heteroaryl, heterocycloalkyl, cycloalkyl, lower alkoxy, lower cycloalkoxy, and lower heterocycloalkoxy, any of which may be optionally substituted.

In certain embodiments of Formula V, Va, or Vb, Y is $CH_2$.

In certain embodiments of Formula V, Va, or Vb, Y is NH.

In other embodiments of Formula V, Va, or Vb, Y is O.

In certain embodiments of Formula V, Va, or Vb, Y is $NR_2$.

In certain embodiments of Formula V, Va, or Vb, R₅ is optionally substituted aryl.

In certain embodiments of Formula V, Va, or Vb, R₅ is substituted phenyl, which is either substituted in the ortho or meta position, or, if substituted in the para position, contains at least one additional substituent.

In further embodiments of Formula V, Va, or Vb, R₅ is substituted with between one and four substituents of the form $R_8—R_9—(R_{10})_p$, wherein:
R₈ is chosen from a bond, lower alkyl, lower alkoxy, amino, lower alkylamino, and sulfonamide;
R₉ is chosen from halogen, lower alkyl, lower haloalkyl, lower hydroxyalkyl, lower alkoxy, lower haloalkoxy, amino, carboxyl, carboxamido, a carboxylic acid isostere, cyano, and tetrazole;
R₁₀ is chosen from null, hydrogen and lower alkyl; and
p is an integer chosen from 0, 1 or 2.

In yet further embodiments of Formula V, Va, or Vb,
R₈ is chosen from a bond, methyl, ethyl, methoxy, and ethoxy; and
R₉ is chosen from methyl, ethyl, methoxy, ethoxy, fluorine, chlorine, bromine, perfluoromethyl, perfluoromethoxy, carboxyl, carboxamide, cyano, and tetrazole.

In further embodiments of Formula V, Va, or Vb, R₉ is a carboxylic acid isostere chosen from tetrazole, oxazole, isoxazole, isothiazole, —SO₃H, —SO₂NHR, —PO₂(R)₂, —CN, —PO₃(R)₂, —OR, —SR, —N(R)₂, —NHC(O)R, —NN(R)₂, —C(O)N(R)₂, —RC(O)N(CN)H, —N(CN)C(O)(R), —C(O)NHOR, —C(O)NHNHSO₂R, —C(O)NHSO₂R, —C(O)ONRCN, boronic acid, benzoxaborole, acyl sulfonamide, cyclobutenedione, cyclopentenedione, wherein R is hydrogen or a carbon chain or ring or a carbon-linked group, such as an alkyl, alkenyl, alkynyl, cycloalkyl, or aryl group, or a heterocycloalkyl or heteroaryl group where the bond is to a carbon, any of which may be optionally substituted.

In further embodiments of Formula V, Va, or Vb, R₉ is a carboxylic acid isostere chosen from boronic acid, benzoxaborole, 3,3-dimethylbenzoxaborole, 3-hydroxy-cyclopent-2-enone and cyclopentenedione.

In certain embodiments of Formula V, Va, or Vb, R₅ is substituted phenyl, which is either substituted in the ortho or meta position, or, if substituted in the para position, contains at least one additional substituent.

In certain embodiments of Formula V, Va, or Vb, R₅ is heteroaryl.

In certain embodiments of Formula V, Va, or Vb, R₅ is a carboxylic acid isostere.

In certain embodiments of Formula V, Va, or Vb, R₅ is chosen from benzoxaborole, 3,3-dimethylbenzoxaborole, 3-hydroxy-cyclopent-2-enone and cyclopentenedione.

In certain embodiments of Formula V, Va, or Vb, R₅ is benzoxaborole.

In further embodiments of Formula V, Va, or Vb, R₅ has the structure

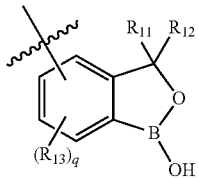

wherein
R₁₁ and R₁₂ are independently chosen from hydrogen and lower alkyl;
each R₁₃ is chosen from halogen, hydroxy, lower haloalkyl, lower alkoxy, lower haloalkoxy, lower acyl, amino, cyano, and sulfonyl; and
q is an integer from 0 to 3.

In yet further embodiments of Formula I,
R₈ is chosen from a bond, methyl, ethyl, methoxy, and ethoxy; and
R₉ is chosen from methyl, ethyl, methoxy, ethoxy, fluorine, chlorine, bromine, perfluoromethyl, perfluoromethoxy, carboxyl, carboxamide, cyano, and tetrazole.

In certain embodiments of Formula V, Va, or Vb, R₆ is chosen from:
substituted phenyl or naphthyl;
substituted monocyclic or bicyclic heteroaryl, having between four and twelve ring atoms, of which up to six are heteroatoms chosen from O, S, and N;
optionally substituted monocyclic or bicyclic heterocycloalkyl, having between four and twelve ring atoms, of which up to six are heteroatoms chosen from O, S, and N; and
optionally substituted monocyclic or bicyclic $C_3$-$C_{10}$ cycloalkyl.

In further embodiments of Formula V, Va, or Vb, R₆ is substituted with between one and four substituents chosen from halogen, hydroxy, lower haloalkyl, lower alkoxy, lower haloalkoxy, lower acyl, amino, cyano, and sulfonyl.

In certain further embodiments of Formula V, Va, or Vb, R₆ is substituted phenyl or naphthyl.

In certain further embodiments of Formula V, Va, or Vb, R₆ is optionally substituted monocyclic heteroaryl, having between five and six ring atoms, of which up to four are heteroatoms chosen from O, S, and N.

In yet further embodiments of Formula V, Va, or Vb, R₆ is chosen from thiophene, pyrrole, pyrimidine, oxazole, isoxazole, pyrazole, imidazole, thiazole, isothiazole, pyridine, pyrazine and pyridazine, any of which may be optionally substituted with between a substituent chosen from halogen, hydroxy, trifluoromethyl, methoxy.

In still further embodiments of Formula V, Va, or Vb, R₆ is thiophene.

In certain further embodiments of Formula V, Va, or Vb, R₆ is optionally substituted bicyclic heteroaryl, having between eight and nine ring atoms, of which up to six are heteroatoms chosen from O, S, and N.

In yet further embodiments of Formula V, Va, or Vb, R₆ is chosen from indole, benzoxazole, benzisoxazole, benzothiazole, quinoline, isoquinoline, and coumarin.

In certain further embodiments of Formula V, Va, or Vb, $R_6$ is optionally substituted monocyclic heterocycloalkyl, having between five and seven ring atoms, of which up to six are heteroatoms chosen from O, S, and N.

In yet further embodiments of Formula V, Va, or Vb, $R_6$ is chosen from pyrrolidine, furan, morpholine, piperazine, and piperidine.

In further embodiments of Formula V, Va, or Vb, $R_6$ is optionally substituted monocyclic cycloalkyl having between five and seven ring atoms, and optionally substituted monocyclic cycloalkoxy having between five and seven ring atoms.

In further embodiments of Formula V, Va, or Vb, $R_6$ is optionally substituted cyclopentyl or optionally substituted cyclopentyloxy.

In further embodiments of Formula V, Va, or Vb, $R_6$ is optionally substituted cyclopentyloxy.

In further embodiments of Formula V, Va, or Vb, $R_6$ is chosen from 3-chlorophenyl and 5-chloro-2-thienyl.

Also provided are embodiments wherein any of embodiment above in paragraphs [0190]-[0224] above may be combined with any one or more of these embodiments, provided the combination is not mutually exclusive.

In certain embodiments are provided compounds of structural Formula VI, VII, VIII, or IX:

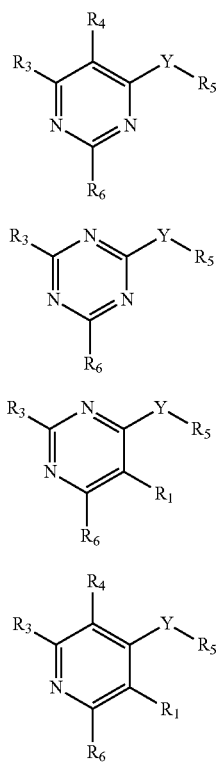

or a salt thereof, wherein:
Y is chosen from O, NH, $NR_2$, $C(R_2)_2$, $S(O)_n$, and CO;
n is an integer chosen from 0, 1 or 2;
$R_1$ (in Formulas VI and IX) is hydrogen;
each $R_2$ is independently chosen from hydrogen and lower alkyl;
$R_3$ is chosen from lower alkyl and lower cycloalkyl; and
$R_4$ (in Formulas VI and VII) is chosen from hydrogen and lower alkyl;
$R_5$ is chosen from aryl, heteroaryl, heterocycloalkyl, cycloalkyl, carboxylic acid, and a carboxylic acid isostere, any of which may be optionally substituted; and
$R_6$ is chosen from aryl, heteroaryl, heterocycloalkyl, cycloalkyl, lower alkoxy, lower cycloalkoxy, and lower heterocycloalkoxy, any of which may be optionally substituted.

In certain embodiments of Formula VI, VII, VIII, or IX, Y is $NR_2$.

In certain embodiments of Formula VI, VII, VIII, or IX, Y is NH.

In certain embodiments of Formula VI, VII, VIII, or IX, Y is $CH_2$.

In other embodiments of Formula VI, VII, VIII, or IX, Y is O.

In certain embodiments of Formula VI, VII, VIII, or IX, $R_5$ is optionally substituted aryl.

certain embodiments of Formula VI, VII, VIII, or IX, $R_5$ is substituted phenyl, which is either substituted in the ortho or meta position, or, if substituted in the para position, contains at least one additional substituent.

In further embodiments of Formula VI, VII, VIII, or IX, $R_5$ is substituted with between one and four substituents of the form $R_8$—$R_9$—$(R_{10})_p$, wherein:
$R_8$ is chosen from a bond, lower alkyl, lower alkoxy, amino, lower alkylamino, and sulfonamide;
$R_9$ is chosen from halogen, lower alkyl, lower haloalkyl, lower hydroxyalkyl, lower alkoxy, lower haloalkoxy, amino, carboxyl, carboxamido, a carboxylic acid isostere, cyano, and tetrazole;
$R_{10}$ is chosen from null, hydrogen and lower alkyl; and
p is an integer chosen from 0, 1 or 2.

In yet further embodiments of Formula VI, VII, VIII, or IX,
$R_8$ is chosen from a bond, methyl, ethyl, methoxy, and ethoxy; and
$R_9$ is chosen from methyl, ethyl, methoxy, ethoxy, fluorine, chlorine, bromine, perfluoromethyl, perfluoromethoxy, carboxyl, carboxamide, cyano, and tetrazole.

In further embodiments of Formula VI, VII, VIII, or IX, $R_9$ is a carboxylic acid isostere chosen from tetrazole, oxazole, isoxazole, isothiazole, —$SO_3H$, —$SO_2NHR$, —$PO_2(R)_2$, —CN, —$PO_3(R)_2$, —OR, —SR, —$N(R)_2$, —NHC(O)R, —$NN(R)_2$, —$C(O)N(R)_2$, —RC(O)N(CN)H, —N(CN)C(O)(R), —C(O)NHOR, —$C(O)NHNHSO_2R$, —$C(O)NHSO_2R$, —C(O)ONRCN, boronic acid, benzoxaborole, acyl sulfonamide, cyclobutenedione, cyclopentenedione, wherein R is hydrogen or a carbon chain or ring or a carbon-linked group, such as an alkyl, alkenyl, alkynyl, cycloalkyl, or aryl group, or a heterocycloalkyl or heteroaryl group where the bond is to a carbon, any of which may be optionally substituted.

In further embodiments of Formula VI, VII, VIII, or IX, $R_9$ is a carboxylic acid isostere chosen from boronic acid, benzoxaborole, 3,3-dimethylbenzoxaborole, 3-hydroxy-cyclopent-2-enone and cyclopentenedione.

In certain embodiments of Formula VI, VII, VIII, or IX, $R_5$ is heteroaryl.

In certain embodiments of Formula VI, VII, VIII, or IX, $R_5$ is a carboxylic acid isostere.

In certain embodiments of Formula VI, VII, VIII, or IX, $R_5$ is chosen from benzoxaborole, 3,3-dimethylbenzoxaborole, 3-hydroxy-cyclopent-2-enone and cyclopentenedione.

In certain embodiments of Formula VI, VII, VIII, or IX, $R_5$ is benzoxaborole.

In further embodiments of Formula VI, VII, VIII, or IX, $R_5$ has the structure

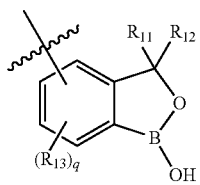

wherein
$R_{11}$ and $R_{12}$ are independently chosen from hydrogen and lower alkyl;
each $R_{13}$ is chosen from halogen, hydroxy, lower haloalkyl, lower alkoxy, lower haloalkoxy, lower acyl, amino, cyano, and sulfonyl; and
q is an integer from 0 to 3.

In yet further embodiments of Formula VI, VII, VIII, or IX,
$R_8$ is chosen from a bond, methyl, ethyl, methoxy, and ethoxy; and
$R_9$ is chosen from methyl, ethyl, methoxy, ethoxy, fluorine, chlorine, bromine, perfluoromethyl, perfluoromethoxy, carboxyl, carboxamide, cyano, and tetrazole.

In certain embodiments of Formula VI, VII, VIII, or IX, $R_6$ is chosen from:
substituted phenyl or naphthyl;
substituted monocyclic or bicyclic heteroaryl, having between four and twelve ring atoms, of which up to six are heteroatoms chosen from O, S, and N;
optionally substituted monocyclic or bicyclic heterocycloalkyl, having between four and twelve ring atoms, of which up to six are heteroatoms chosen from O, S, and N; and
optionally substituted monocyclic or bicyclic $C_3$-$C_{10}$ cycloalkyl.

In further embodiments of Formula VI, VII, VIII, or IX, $R_6$ is substituted with between one and four substituents chosen from halogen, hydroxy, lower haloalkyl, lower alkoxy, lower haloalkoxy, lower acyl, amino, cyano, and sulfonyl.

In certain further embodiments of Formula VI, VII, VIII, or IX, $R_6$ is substituted phenyl or naphthyl.

In certain further embodiments of Formula VI, VII, VIII, or IX, $R_6$ is optionally substituted monocyclic heteroaryl, having between five and six ring atoms, of which up to four are heteroatoms chosen from O, S, and N.

In yet further embodiments of Formula VI, VII, VIII, or IX, $R_6$ is chosen from thiophene, pyrrole, pyrimidine, oxazole, isoxazole, pyrazole, imidazole, thiazole, isothiazole, pyridine, pyrazine and pyridazine, any of which may be optionally substituted with between a substituent chosen from halogen, hydroxy, trifluoromethyl, methoxy.

In still further embodiments of Formula VI, VII, VIII, or IX, $R_6$ is thiophene.

In certain further embodiments of Formula VI, VII, VIII, or IX, $R_6$ is optionally substituted bicyclic heteroaryl, having between eight and nine ring atoms, of which up to six are heteroatoms chosen from O, S, and N.

In yet further embodiments of Formula VI, VII, VIII, or IX, $R_6$ is chosen from indole, benzoxazole, benzisoxazole, benzothiazole, quinoline, isoquinoline, and coumarin.

In certain further embodiments of Formula VI, VII, VIII, or IX, $R_6$ is optionally substituted monocyclic heterocycloalkyl, having between five and seven ring atoms, of which up to six are heteroatoms chosen from O, S, and N.

In yet further embodiments of Formula VI, VII, VIII, or IX, $R_6$ is chosen from pyrrolidine, furan, morpholine, piperazine, and piperidine.

In further embodiments of Formula VI, VII, VIII, or IX, $R_6$ is optionally substituted monocyclic cycloalkyl having between five and seven ring atoms, and optionally substituted monocyclic cycloalkoxy having between five and seven ring atoms.

In further embodiments of Formula VI, VII, VIII, or IX, $R_6$ is optionally substituted cyclopentyl or optionally substituted cyclopentyloxy.

In further embodiments of Formula VI, VII, VIII, or IX, $R_6$ is optionally substituted cyclopentyloxy.

In further embodiments of Formula VI, VII, VIII, or IX, $R_6$ is chosen from 3-chlorophenyl and 5-chloro-2-thienyl.

In certain embodiments of Formula VI, VII, VIII, or IX, $R_3$ is chosen from lower alkyl, lower cycloalkyl, and trifluoromethyl.

Also provided are embodiments wherein any of embodiment above in paragraphs [0226]-[0257] above may be combined with any one or more of these embodiments, provided the combination is not mutually exclusive.

In certain embodiments are provided compounds of structural Formula X:

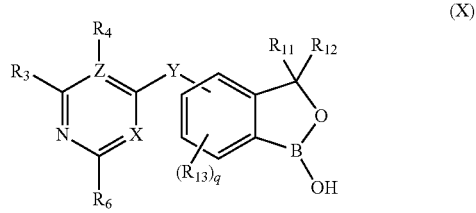

or a salt, ester, amide, or prodrug thereof, wherein:
X is chosen from $CR_1$ and N;
Y is chosen from O, NH, $NR_2$, $CH_2$, $C(R_2)_2$, $S(O)_n$ and CO;
Z is chosen from C and N;
n is an integer chosen from 0, 1 or 2;
$R_1$ is chosen from hydrogen, halogen, lower alkyl, hydroxyl, $OR_2$, and $N(R_2)_2$;
Each $R_2$ is independently chosen from hydrogen and lower alkyl;
$R_3$ is chosen from lower alkyl and lower cycloalkyl;
$R_4$ is chosen from:
null if Z is N; and
hydrogen, heteroalkyl, and lower alkyl if Z is C;
or $R_3$ and $R_4$, together with the atoms to which they are attached, join to form a 4 to 7 membered ring, which may be optionally substituted;
$R_{11}$ and $R_{12}$ are independently chosen from hydrogen and lower alkyl;
each $R_{13}$ is chosen from halogen, hydroxy, lower haloalkyl, lower alkoxy, lower haloalkoxy, lower acyl, amino, cyano, and sulfonyl; and
q is an integer from 0 to 3.

In certain embodiments of Formula X, Z is C.
In other embodiments of Formula X, Z is N.
In certain embodiments of Formula X, X is N.
In certain embodiments of Formula X, X is $CR_1$.
In certain embodiments of Formula X, $R_1$ is hydrogen.
In certain embodiments of Formula X, $R_3$ and $R_4$ join to form a 4- to 7-membered cycloalkyl or heterocycloalkyl.
In certain embodiments of Formula X, $R_3$ and $R_4$ join to form a 5-membered cycloalkyl or 5- or 6-membered heterocycloalkyl.
In certain embodiments of Formula X,
$R_3$ and is chosen from lower alkyl, lower cycloalkyl, and trifluoromethyl;
$R_4$ is chosen from hydrogen and lower alkyl.
In certain embodiments of Formula X, $R_3$ and $R_4$ are each lower alkyl.
In certain embodiments of Formula X:
$R_3$ and $R_4$ are each lower alkyl; and
Z is C.
In certain embodiments of Formula X, $R_3$ and $R_4$ are each chosen from methyl and ethyl.
In certain embodiments of Formula X, $R_3$ is methyl and $R_4$ is ethyl.
In certain embodiments of Formula X, $R_3$ is ethyl and $R_4$ is hydrogen.
In certain embodiments of Formula X, $R_3$ is trifluoromethyl and $R_4$ is hydrogen.
In certain embodiments of Formula X, $R_3$ is cyclopropyl and $R_4$ is hydrogen.
In certain embodiments of Formula X, the compound has a structure chosen from:

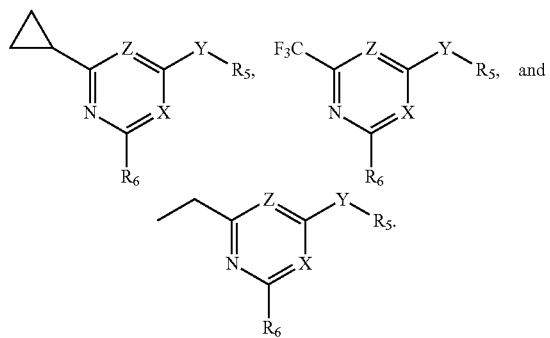

In certain embodiments of Formula X, the compound has a structure chosen from:

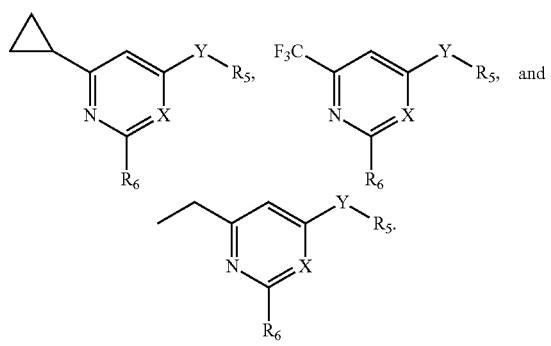

In certain embodiments of Formula X, $R_4$ is null.
In certain embodiments of Formula X, Y is $CH_2$.
In certain embodiments of Formula X, Y is NH.
In other embodiments of Formula X, Y is O.
In certain embodiments of Formula X, Y is $NR_2$.
In certain embodiments of Formula X wherein Z is C, X is N, and $R_5$ is substituted phenyl, the phenyl is either substituted in the ortho or meta position, or, if substituted in the para position, contains at least one additional substituent.
In certain further embodiments of Formula X, $R_1$ is chosen from hydrogen, halogen, hydroxyl, and $NH_2$.
In certain further embodiments of Formula X:
$R_1$ is chosen from lower alkyl, $OR_2$, and $N(R_2)_2$; and
at least one of $R_2$ is lower alkyl.
In further embodiments of Formula X, $R_2$ is chosen from methyl, ethyl, propyl, isopropyl, butyl, and t-butyl.
Also provided are embodiments wherein any of embodiment above in paragraphs [0259]-[0285] above may be combined with any one or more of these embodiments, provided the combination is not mutually exclusive.
In certain embodiments are provided compounds of structural Formula XI:

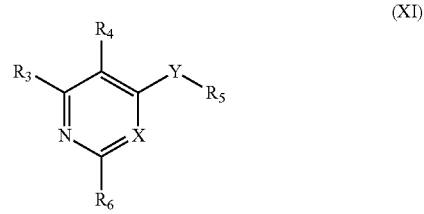

or a salt thereof, wherein:
Y is chosen from O, NH, $NR_2$, $CH_2$, $C(R_2)_2$, and $S(O)_n$;
X is chosen from CH and N;
n is an integer chosen from 0, 1 or 2;
each $R_2$ is independently chosen from hydrogen and lower alkyl;
$R_3$ is chosen from methyl, ethyl, and cyclopropyl;
$R_4$ is chosen from hydrogen and ethyl;
or $R_3$ and $R_4$, together with the atoms to which they are attached, join to form a 5 to 6 membered cycloalkyl or heterocycloalkyl of the form:

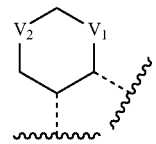

$V_1$ is chosen from $CH_2$, N, O, $SO_2$, and S;
$V_2$ is chosen from a bond, N, O and $CH_2$;
$R_5$ is either benzoxaborole, or is chosen from phenyl and pyridinyl, either of which is para-substituted with a substituent of the form $R_8$—$R_9$—$(R_{10})_a$ $(R_{10})_b$, and is optionally substituted with a substituent $R_{13}$;
$R_8$ is chosen from a bond and lower alkyl;
$R_9$ is chosen from halogen, lower alkyl, lower haloalkyl, lower hydroxyalkyl, lower alkoxy, lower haloalkoxy, cyano, —C(O)N—, $S(O)_2$—, $B(OH)_2$, 5-6 membered monocyclic heterocycloalkyl, and 5-6 membered monocyclic heteroaryl;
$(R_{10})_a$ and $(R_{10})_b$ are each independently chosen from null, hydrogen, halogen, trifluoromethyl, trifluoromethoxy, hydroxyl, lower hydroxyalkyl, cyano, oxo, lower alkyl, C(O)OH, and C(O)O lower alkyl;

$R_{13}$ is chosen from halogen, hydroxy, lower alkyl, trifluoromethyl, lower alkoxy, trifluoromethoxy, $NH_2$, and cyano;

$R_6$ is chosen from 3-chlorophenyl, 5-chloro-2-thienyl, cyclopentyl optionally substituted with one or two $R_{14}$, and cyclopentoxy optionally substituted with one or two $R_{14}$; and $R_{13}$ and $R_{14}$ is chosen from halogen, hydroxy, lower alkyl, trifluoromethyl, lower alkoxy, trifluoromethoxy, $NH_2$, and cyano In certain embodiments of Formula XI, $R_5$ is either benzoxaborole, or is phenyl which is para-substituted with a substituent of the form $R_8$—$R_9$—$(R_{10})_a(R_{10})_b$, and is optionally substituted with a substituent $R_{13}$.

In certain embodiments of Formula XI, Y is chosen from O, NH, and $CH_2$.

In certain embodiments of Formula XI, Y is NH.

In certain embodiments of Formula XI, Y is $CH_2$.

In certain embodiments of Formula XI, $R_9$ is chosen from 5-6 membered monocyclic heterocycloalkyl, and 5-6 membered monocyclic heteroaryl.

In certain embodiments of Formula XI,
$R_9$ is —C(O)N—;
$R_{10a}$ is lower hydroxyalkyl; and
$R_{10b}$ is null.

In certain embodiments of Formula XI,
$R_9$ is —C(O)N—;
$R_{10a}$ is cyano; and
$R_{10b}$ is null.

In certain embodiments of Formula XI, $R_9$ is lower hydroxyalkyl.

In certain embodiments of Formula XI, $R_9$ is chosen from methanol, ethanol, isopropanol, N-propanol, and t-butanol.

In certain embodiments of Formula XI, $R_9$ is chosen from ethanol and N-propanol.

In certain embodiments of Formula XI, —$R_9$—$(R_{10})_a(R_{10})_b$ is chosen from:

In certain embodiments of Formula XI, —$R_9$—$(R_{10})_a(R_{10})_b$ is chosen from:

In certain embodiments of Formula XI, $R_8$ is a bond.

In certain embodiments of Formula XI, $R_8$ is lower alkyl.

In certain embodiments of Formula XI, $R_8$ is methyl.

In certain embodiments of Formula XI, X is N.

In certain embodiments of Formula XI, X is CH.

In certain embodiments of Formula XI, $R_5$ is benzoxaborole.

In certain embodiments of Formula XI, $R_5$ is phenyl which is para-substituted with a substituent of the form $R_8$—$R_9$—$(R_{10})_a(R_{10})_b$.

In certain embodiments of Formula XI, $R_6$ is chosen from 3-chlorophenyl and 5-chloro-2-thienyl.

In certain embodiments of Formula XI, $R_6$ is 3-chlorophenyl.

In certain embodiments of Formula XI, $R_6$ is 5-chloro-2-thienyl.

In certain embodiments of Formula XI, $R_6$ is chosen from cyclopentyl optionally substituted with one or two $R_{14}$, and cyclopentoxy optionally substituted with one or two $R_{14}$.

Also provided are embodiments wherein any of embodiment above in paragraphs [0287]-[0310] above may be combined with any one or more of these embodiments, provided the combination is not mutually exclusive.

In certain embodiments are provided compounds of structural Formula XII:

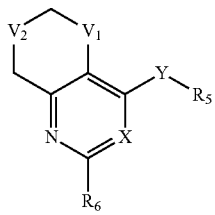

(XII)

or a salt thereof, wherein:
  Y is chosen from O, NH, and $CH_2$;
  X is chosen from CH and N;
  $V_1$ is chosen from $CH_2$, N, O, $SO_2$, and S;
  $V_2$ is chosen from a bond, N, O and $CH_2$;
  $R_5$ is either benzoxaborole, or is chosen from phenyl and pyridinyl, either of which is para-substituted with a substituent of the form $R_8$—$R_9$—$(R_{10})_a$ $(R_{10})_b$, and is optionally substituted with a substituent $R_{13}$;
  $R_8$ is chosen from a bond and lower alkyl;
  $R_9$ is chosen from halogen, lower alkyl, lower haloalkyl, lower hydroxyalkyl, lower alkoxy, lower haloalkoxy, cyano, —C(O)N—, $S(O)_2$—, $B(OH)_2$, 5-6 membered monocyclic heterocycloalkyl, and 5-6 membered monocyclic heteroaryl;
  $(R_{10})_a$ and $(R_{10})_b$ are each independently chosen from null, hydrogen, halogen, trifluoromethyl, trifluoromethoxy, hydroxyl, lower hydroxyalkyl, cyano, oxo, lower alkyl, C(O)OH, and C(O)O lower alkyl;
  $R_{13}$ is chosen from halogen, hydroxy, lower alkyl, trifluoromethyl, lower alkoxy, trifluoromethoxy, $NH_2$, and cyano;
  $R_6$ is chosen from 3-chlorophenyl, 5-chloro-2-thienyl, cyclopentyl optionally substituted with one or two $R_{14}$, and cyclopentoxy optionally substituted with one or two $R_{14}$; and
  $R_{13}$ is chosen from halogen, hydroxy, lower alkyl, trifluoromethyl, lower alkoxy, trifluoromethoxy, $NH_2$, and cyano.

In certain embodiments of Formula XII are provided compounds having a structural formula chosen from structural Formulas XIIa, XIIb, XIIc, XIId, XIIe, and XIIf:

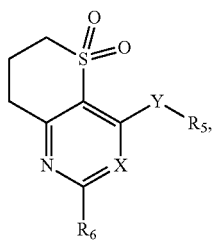

(XIIa)

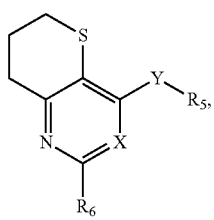

(XIIb)

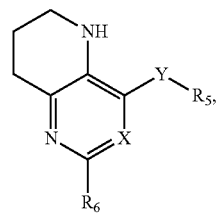

(XIIc)

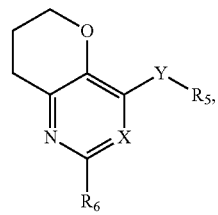

(XIId)

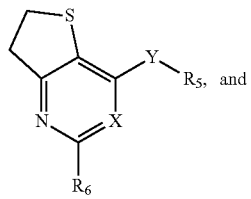

(XIIe)

(XIIf)

or a salt thereof, wherein:
  Y is chosen from O, NH, and $CH_2$;
  X is chosen from CH and N;
  $R_5$ is either benzoxaborole, or is chosen from phenyl and pyridinyl, either of which is para-substituted with a substituent of the form $R_8$—$R_9$—$(R_{10})_a$ $(R_{10})_b$, and is optionally substituted with a substituent $R_{13}$;
  $R_8$ is chosen from a bond and lower alkyl;
  $R_9$ is chosen from halogen, lower alkyl, lower haloalkyl, lower hydroxyalkyl, lower alkoxy, lower haloalkoxy, cyano, —C(O)N—, $S(O)_2$—, $B(OH)_2$, 5-6 membered monocyclic heterocycloalkyl, and 5-6 membered monocyclic heteroaryl;
  $(R_{10})_a$ and $(R_{10})_b$ are each independently chosen from null, hydrogen, halogen, trifluoromethyl, trifluoromethoxy, hydroxyl, lower hydroxyalkyl, cyano, oxo, lower alkyl, C(O)OH, and C(O)O lower alkyl;
  $R_{13}$ is chosen from halogen, hydroxy, lower alkyl, trifluoromethyl, lower alkoxy, trifluoromethoxy, $NH_2$, and cyano;
  $R_6$ is chosen from 3-chlorophenyl, 5-chloro-2-thienyl, cyclopentyl optionally substituted with one or two $R_{14}$, and cyclopentoxy optionally substituted with one or two $R_{14}$; and
  $R_{13}$ is chosen from halogen, hydroxy, lower alkyl, trifluoromethyl, lower alkoxy, trifluoromethoxy, $NH_2$, and cyano.

In certain embodiments are provided compounds of any of structural Formulas XIII, XIV, XV, and XVI:

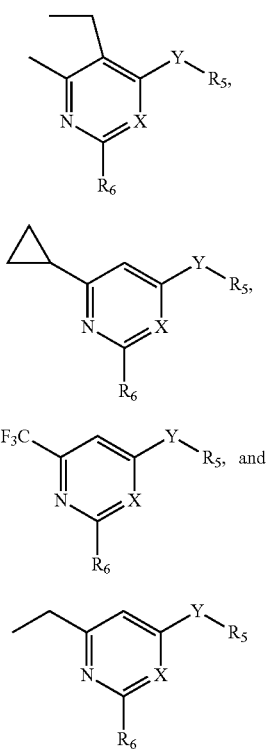

(XIII)

(XIV)

(XV)

(XVI)

or a salt thereof, wherein:
Y is chosen from O, NH, and $CH_2$;
X is chosen from CH and N;
$R_5$ is either benzoxaborole, or is chosen from phenyl and pyridinyl, either of which is para-substituted with a substituent of the form $R_8$—$R_9$—$(R_{10})_a$ $(R_{10})_b$, and is optionally substituted with a substituent $R_{13}$;
$R_8$ is chosen from a bond and lower alkyl;
$R_9$ is chosen from halogen, lower alkyl, lower haloalkyl, lower hydroxyalkyl, lower alkoxy, lower haloalkoxy, cyano, —C(O)N—, $S(O)_2$—, $B(OH)_2$, 5-6 membered monocyclic heterocycloalkyl, and 5-6 membered monocyclic heteroaryl;
$(R_{10})_a$ and $(R_{10})_b$ are each independently chosen from null, hydrogen, halogen, trifluoromethyl, trifluoromethoxy, hydroxyl, lower hydroxyalkyl, cyano, oxo, lower alkyl, C(O)OH, and C(O)O lower alkyl;
$R_{13}$ is chosen from halogen, hydroxy, lower alkyl, trifluoromethyl, lower alkoxy, trifluoromethoxy, $NH_2$, and cyano;
$R_6$ is chosen from 3-chlorophenyl, 5-chloro-2-thienyl, cyclopentyl optionally substituted with one or two $R_{14}$, and cyclopentoxy optionally substituted with one or two $R_{14}$; and
$R_{13}$ is chosen from halogen, hydroxy, lower alkyl, trifluoromethyl, lower alkoxy, trifluoromethoxy, $NH_2$, and cyano.

In certain embodiments of Formulas XII, XIIa-XIIf, XIII, XIV, XV, and XVI, $R_5$ is either benzoxaborole, or is phenyl which is para-substituted with a substituent of the form $R_8$—$R_9$—$(R_{10})_a(R_{10})_b$, and is optionally substituted with a substituent $R_{13}$.

In certain embodiments of Formulas XII, XIIa-XIIf, XIII, XIV, XV, and XVI, Y is chosen from O, NH, and $CH_2$.

In certain embodiments of Formulas XII, XIIa-XIIf, XIII, XIV, XV, and XVI, Y is NH.

In certain embodiments of Formulas XII, XIIa-XIIf, XIII, XIV, XV, and XVI, Y is $CH_2$.

In certain embodiments of Formulas XII, XIIa-XIIf, XIII, XIV, XV, and XVI,
$R_9$ is —C(O)N—;
$R_{10a}$ is lower hydroxyalkyl; and
$R_{10b}$ is null.

In certain embodiments of Formulas XII, XIIa-XIIf, XIII, XIV, XV, and XVI,
$R_9$ is —C(O)N—;
$R_{10a}$ is cyano; and
$R_{10b}$ is null.

In certain embodiments of Formula XII, XIIa-XIIf, XIII, XIV, XV, and XVI, $R_9$ is lower hydroxyalkyl.

In certain embodiments of Formula XII, XIIa-XIIf, XIII, XIV, XV, and XVI, $R_9$ is chosen from methanol, ethanol, isopropanol, N-propanol, and t-butanol.

In certain embodiments of Formula XII, XIIa-XIIf, XIII, XIV, XV, and XVI, $R_9$ is chosen from ethanol and N-propanol.

In certain embodiments of Formulas XII, XIIa-XIIf, XIII, XIV, XV, and XVI, $R_9$ is chosen from 5-6 membered monocyclic heterocycloalkyl, and 5-6 membered monocyclic heteroaryl.

In certain embodiments of Formulas XII, XIIa-XIIf, XIII, XIV, XV, and XVI, —$R_9$—$(R_{10})_a(R_{10})_b$ is chosen from:

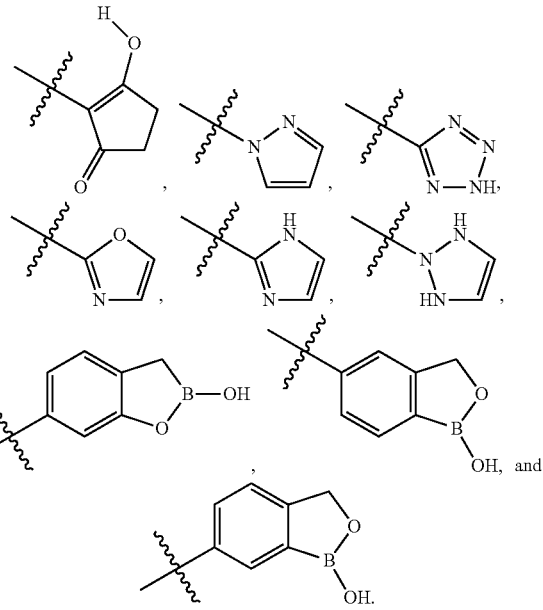

In certain embodiments of Formulas XII, XIIa-XIIf, XIII, XIV, XV, and XVI, —$R_9$—$(R_{10})_a(R_{10})_b$ is chosen from:

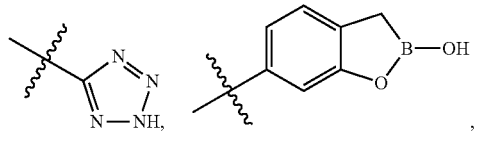

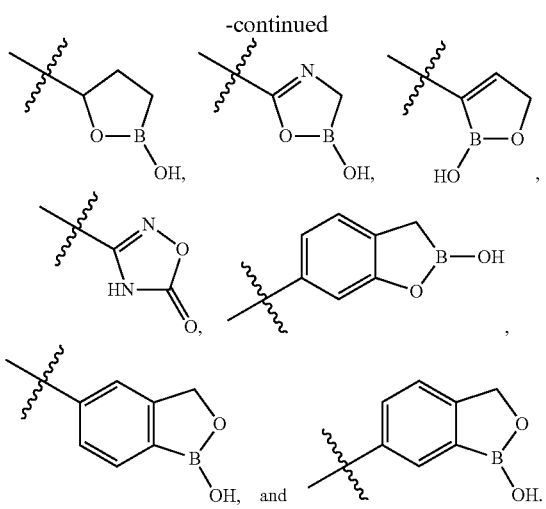

In certain embodiments of any of Formulas XII, XIIa-XIIf, XIII, XIV, XV, and XVI, $R_8$ is a bond.

In certain embodiments of any of Formulas XII, XIIa-XIIf, XIII, XIV, XV, and XVI, $R_8$ is lower alkyl.

In certain embodiments of Formula XII, XIIa-XIIf, XIII, XIV, XV, and XVI, $R_8$ is methyl.

In certain embodiments of any of Formulas XII, XIIa-XIIf, XIII, XIV, XV, and XVI, X is N.

In certain embodiments of any of Formulas XII, XIIa-XIIf, XIII, XIV, XV, and XVI, X is CH.

In certain embodiments of any of Formulas XII, XIIa-XIIf, XIII, XIV, XV, and XVI, $R_5$ is benzoxaborole.

In certain embodiments of any of Formulas XII, XIIa-XIIf, XIII, XIV, XV, and XVI, $R_5$ is phenyl which is para-substituted with a substituent of the form $R_8$—$R_9$—$(R_{10})_a(R_{10})_b$.

In certain embodiments of any of Formulas XII, XIIa-XIIf, XIII, XIV, XV, and XVI, $R_6$ is chosen from 3-chlorophenyl and 5-chloro-2-thienyl.

In certain embodiments of any of Formulas XII, XIIa-XIIf, XIII, XIV, XV, and XVI, $R_6$ is 3-chlorophenyl.

In certain embodiments of any of Formulas XII, XIIa-XIIf, XIII, XIV, XV, and XVI, $R_6$ is 5-chloro-2-thienyl.

In certain embodiments of any of Formulas XII, XIIa-XIIf, XIII, XIV, XV, and XVI, $R_6$ is chosen from cyclopentyl optionally substituted with one or two $R_{14}$, and cyclopentoxy optionally substituted with one or two $R_{14}$.

Also provided are embodiments wherein any of embodiment above in paragraphs [0312]-[0337] above may be combined with any one or more of these embodiments, provided the combination is not mutually exclusive.

Also provided are compounds of structural Formula Ia:

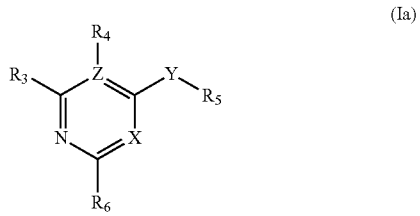

(Ia)

or a salt thereof, wherein:
X is chosen from $CR_1$ and N;
Y is chosen from O, NH, $NR_2$, $C(R_2)_2$, $S(O)_n$, and CO;
Z is chosen from C and N;
n is an integer chosen from 0, 1 or 2;
$R_1$ is chosen from hydrogen, halogen, lower alkyl, hydroxyl, $OR_2$, and $N(R_2)_2$;
each $R_2$ is independently chosen from hydrogen and lower alkyl;
$R_3$ is chosen from lower alkyl and lower cycloalkyl;
$R_4$ is chosen from:
  null if Z is N; and
  hydrogen or lower alkyl if Z is C;
or $R_3$ and $R_4$, together with the atoms to which they are attached, join to form a 4 to 7 membered ring, which may be optionally substituted; and
$R_5$ and $R_6$ are each independently chosen from aryl, heteroaryl, heterocycloalkyl, cycloalkyl, and a carboxylic acid isostere, any of which may be optionally substituted.

Each embodiment as disclosed in each of the priority applications cited in paragraph [0001] of this application is explicitly incorporated by reference as if written herein in its entirety.

Also provided is a compound chosen from the Examples disclosed herein.

The present invention also relates to a method of inhibiting at least one PDE4 function comprising the step of contacting the PDE4 with a compound of Formula I, as described herein. The cell phenotype, cell proliferation, activity of PDE4, change in biochemical output produced by active PDE4, expression of PDE4, or binding of PDE4 with a natural binding partner may be monitored. Such methods may be modes of treatment of disease, biological assays, cellular assays, biochemical assays, or the like.

Also provided herein is a method of treatment of a PDE4-mediated disease comprising the administration of a therapeutically effective amount of a compound as disclosed herein, or a salt thereof, to a patient in need thereof.

In certain embodiments, the disease is chosen from depression, depression secondary to illness, Alzheimer's disease, and traumatic brain injury.

Also provided herein is a compound as disclosed herein for use as a medicament.

Also provided herein is a compound as disclosed herein for use as a medicament for the treatment of a PDE4-mediated disease.

Also provided is the use of a compound as disclosed herein as a medicament.

Also provided is the use of a compound as disclosed herein as a medicament for the treatment of a PDE4-mediated disease.

Also provided is a compound as disclosed herein for use in the manufacture of a medicament for the treatment of a PDE4-mediated disease.

Also provided is the use of a compound as disclosed herein for the treatment of a PDE4-mediated disease.

Also provided herein is a method of inhibition of PDE4 comprising contacting PDE4 with a compound as disclosed herein, or a salt thereof.

Also provided herein is a method for achieving an effect in a patient comprising the administration of a therapeutically effective amount of a compound as disclosed herein, or a salt thereof, to a patient, wherein the effect is chosen from cognition enhancement.

Compounds of the present invention may be selective amongst the PDE4 isoforms PDE4A, PDE4B, PDE4C, and PDE4D in various ways. For example, compounds described herein may be selective for PDE4B and/or PDE4D over the other two isoforms, be a pan-inhibitor of all the isoforms, or be selective for only one isoform. In certain embodiments, compounds of the present invention may be selective for PDE4B over other isoforms.

In certain embodiments, the PDE4 is PDE4D.

In certain embodiments, the PDE4 is PDE4B.

In certain embodiments, the PDE4B-mediated disease is chosen from depression and depression secondary to illness.

Also provided is a method of modulation of a PDE4-mediated function in a subject comprising the administration of a therapeutically effective amount of a compound as disclosed herein.

In certain embodiments, the PDE4 is PDE4.

In certain embodiments, the modulation is enhancement.

In certain embodiments, the function is cognition.

Also provided is a pharmaceutical composition comprising a compound as disclosed herein, together with a pharmaceutically acceptable carrier.

In certain embodiments, the pharmaceutical composition is formulated for oral administration.

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.). When n is set at 0 in the context of "0 carbon atoms", it is intended to indicate a bond or null.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) group wherein the term alkyl is as defined above and wherein the sulfur may be singly or doubly oxidized. Examples of suitable alkyl thioether groups include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched-chain hydrocarbon group having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, hydroxyalkyl, acyl, heteroalkyl, aryl, cycloalkyl, heteroaryl, and heterocycloalkyl, any of which may themselves be optionally substituted.

Additionally, R and R' may combine to form heterocycloalkyl, either of which may be optionally substituted.

The term "amino acid", as used herein, alone or in combination, refers to a —NHCHRC(O)O— group, which may be attached to the parent molecular moiety to give either an N-terminus or C-terminus amino acid, wherein R is independently chosen from hydrogen, alkyl, aryl, heteroaryl, heterocycloalkyl, aminoalkyl, amido, amidoalkyl, carboxyl, carboxylalkyl, guanidinealkyl, hydroxyl, thiol, and thioalkyl, any of which themselves may be optionally substituted. The term C-terminus, as used herein, alone or in combination, refers to the parent molecular moiety being bound to the amino acid at the amino group, to give an amide as described herein, with the carboxyl group unbound, resulting in a terminal carboxyl group, or the corresponding carboxylate anion. The term N-terminus, as used herein, alone or in combination, refers to the parent molecular moiety being bound to the amino acid at the carboxyl group, to give an ester as described herein, with the amino group unbound resulting in a terminal secondary amine, or the corresponding ammonium cation. In other words, C-terminus refers to —NHCHRC(O)OH or to —NHCHRC(O)O$^-$ and N-terminus refers to H$_2$NCHRC(O)O— or to H$_3$N$^+$CHRC(O)O—.

The term "aryl", as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl group derived from an aryl-substituted alkanecarboxylic acid such as benzoyl, naphthoyl, phenylacetyl, 3-phenylpropionyl(hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent group C$_6$H$_4$=derived from benzene. Examples include benzothiophene and benzimidazole.

The term "benzoxaborole" may be used to refer to any of the following structures, and may encompass both substituted and unsubstituted examples:

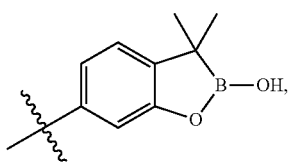

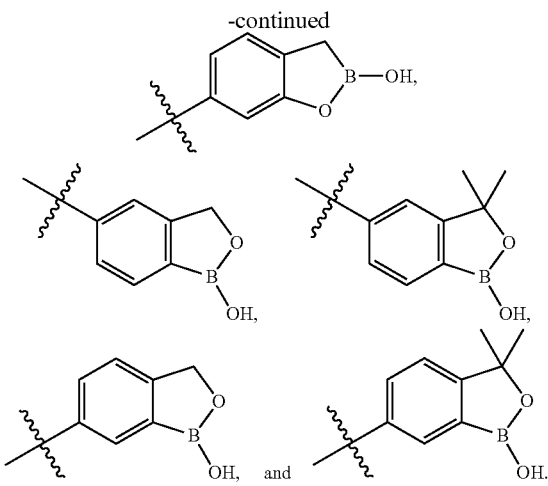

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR' group, with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH ("carboxylic acid") or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

"Isosteres" are different compounds that have different molecular formulae but exhibit the same or similar properties. For example, tetrazole is an isostere of carboxylic acid because it mimics the properties of carboxylic acid even though they both have different molecular formulae. Tetrazole is one of many possible isosteric replacements for carboxylic acid. Other carboxylic acid isosteres contemplated by the present invention include —RC(O)OH, —SO$_3$H, —SO$_2$NHR, —PO$_2$(R)$_2$, —CN, —PO$_3$(R)$_2$, —OR, —SR, —N(R)$_2$, —NHC(O)R, —NN(R)$_2$, —C(O)N(R)$_2$, —RC(O)N(CN)H, —N(CN)C(O)(R), —C(O)NHOR, —C(O)NHNHSO$_2$R, —C(O)NHSO$_2$R, —C(O)ONRCN, boronic acid and boronic acid analogues such as benzoxaborole, and acyl sulfonamide, wherein each R may be the same or different and is chosen from hydrogen, a carbon chain or ring or a carbon-linked group, such as an alkyl, alkenyl, alkynyl, cycloalkyl, or aryl group, and a heterocycloalkyl or heteroaryl group where the bond is to a carbon, any of which may be optionally substituted.

In addition, carboxylic acid isosteres can include 4-7 membered carbocycles or heterocycles (aromatic and non-aromatic) containing any combination of C, O, S, or N in any chemically stable oxidation state, where any of the atoms of said ring structure are optionally substituted in one or more positions. Examples of carbocyclic and heterocyclic isosteres contemplated include squaric acid and derivatives such as cyclobutenediones (e.g. 3-hydroxy-cyclobutene-1,2-dione and 3,4-diamino-3-cyclobutene-1,2-dione), cyclopentadiones, and heterocyclic groups such as:
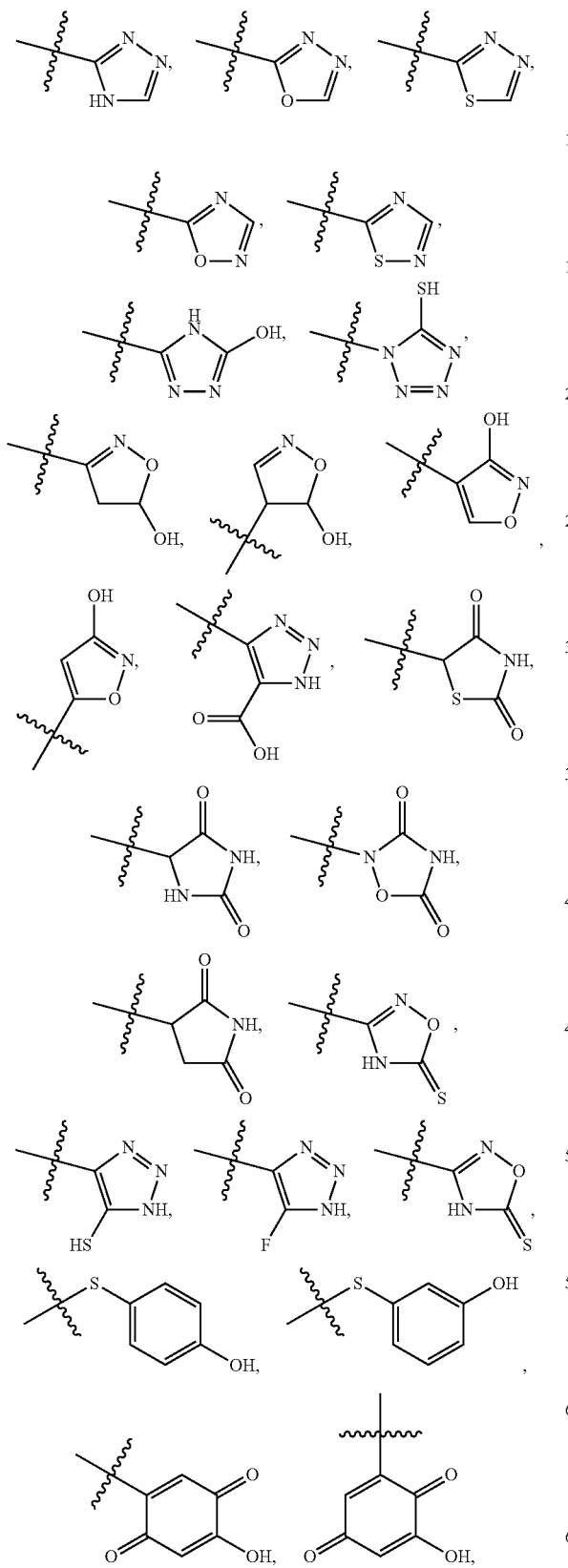
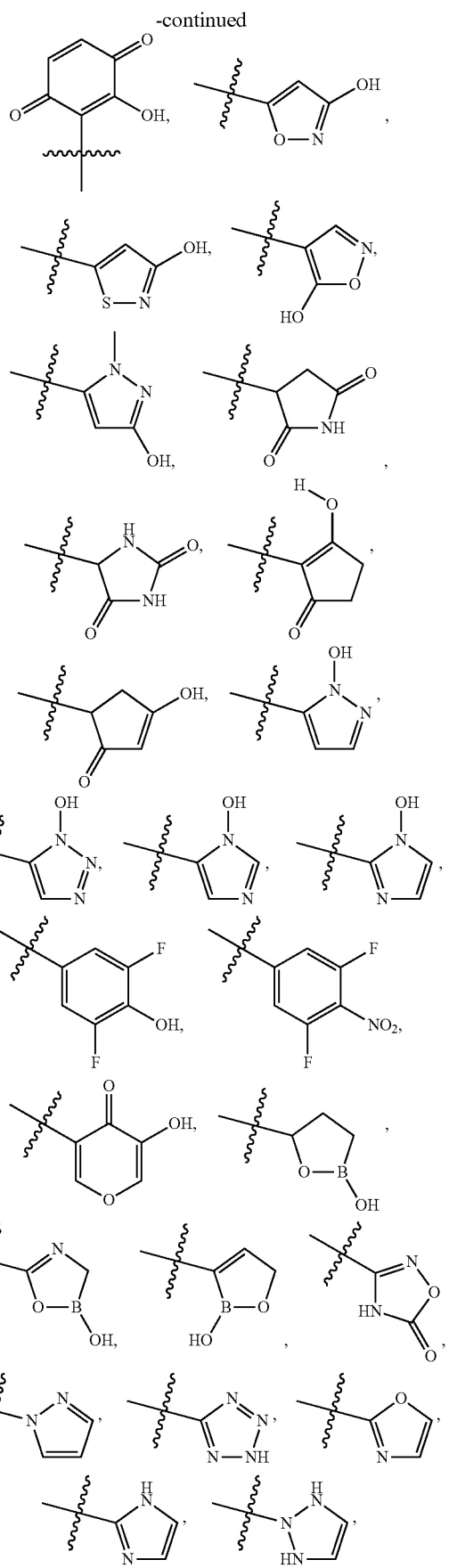

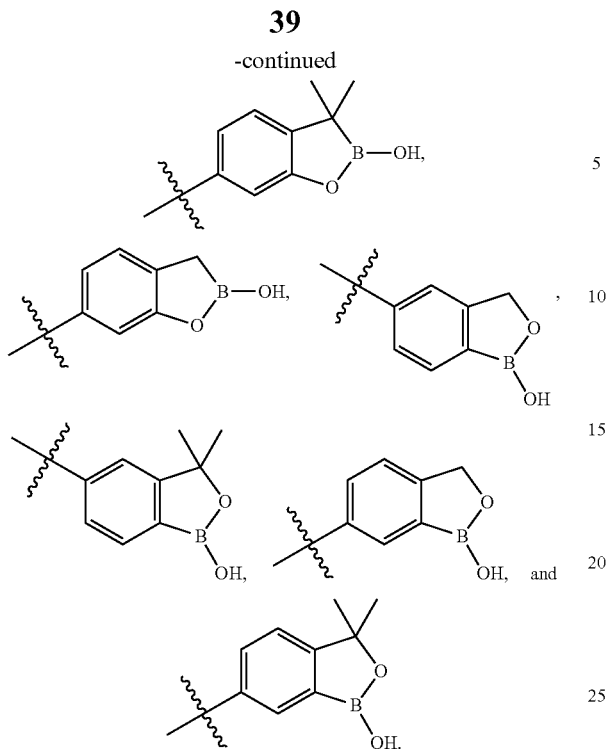

In addition, carboxylic acid isosteres can include carboxylic acids which are themselves substituted with isosteric functional groups. Examples of such groups include:

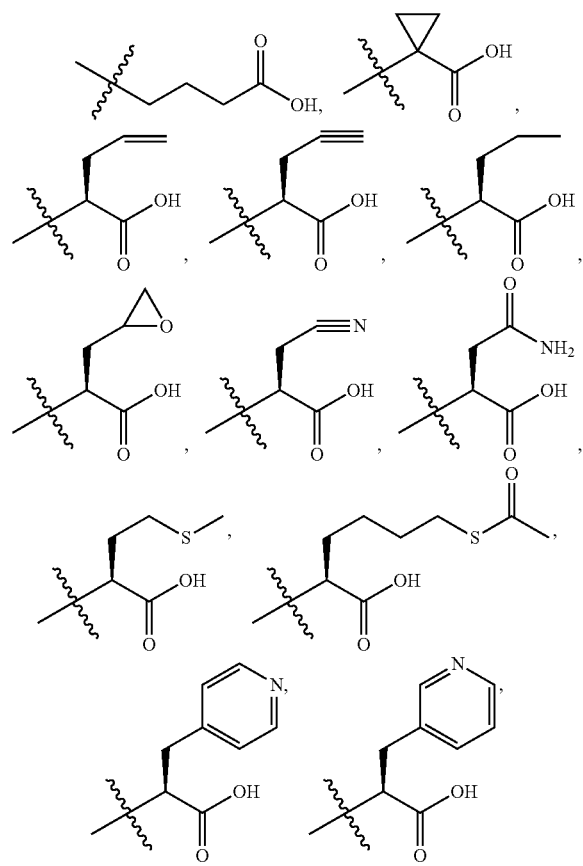

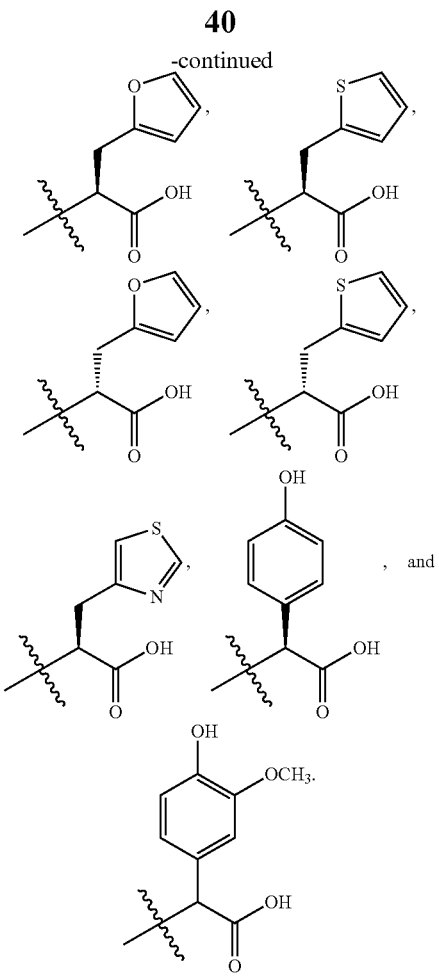

The present invention contemplates that when chemical substituents are added to a carboxylic isostere then the inventive compound retains the properties of a carboxylic isostere. The present invention contemplates that when a carboxylic isostere is optionally substituted with one or more moieties selected from R3, then the substitution cannot eliminate the carboxylic acid isosteric properties of the inventive compound. The present invention contemplates that the placement of one or more R3 substituents upon a carbocyclic or heterocyclic carboxylic acid isostere shall not be permitted at one or more atom(s) which maintain(s) or is/are integral to the carboxylic acid isosteric properties of the inventive compound, if such substituent(s) would destroy the carboxylic acid isosteric properties of the inventive compound.

Other carboxylic acid isosteres not specifically exemplified or described in this specification are also contemplated by the present invention.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein, provided that at least one of the rings is non-aromatic. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "guanidine", as used herein, alone or in combination, refers to —NHC(=NH)NH$_2$, or the corresponding guanidinium cation.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogen atoms are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon group, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom chosen from B, O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzoxaborole, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from nitrogen, oxygen, and sulfur In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, methylpiperazinyl, N-methylpiperazinyl, pyrrolidinyl, tetrahydropyridinyl, piperidinyl, thiomorpholinyl, diazepanyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "hydroxamic acid", as used herein, alone or in combination, refers to —C(=O)NHOH, wherein the parent molecular moiety is attached to the hydroxamic acid group by means of the carbon atom.

The term "imino," as used herein, alone or in combination, refers to =N—.

The term "iminohydroxy," as used herein, alone or in combination, refers to =N(OH) and =N—O—.

The phrase "the main chain" refers to the longest contiguous or adjacent chain of carbon atoms starting at the point of attachment of a group to the compounds of any one of the formulas disclosed herein.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms. Lower alkyl may not be cyclic.

The term "lower heteroalkyl," as used herein, alone or in combination, means an alkyl chain comprising between one and three heteroatoms chosen from O, S, and N, wherein the main chain comprises between two and six atoms. A heteroatom in a heteroalkyl chain may be substituted as follows: S may be substituted with zero, one, or two oxy substituents; N may be substituted with hydrogen, oxygen, lower alkyl, lower alkoxy, or lower cycloalkyl; and O may be substituted with lower alkyl or lower cycloalkyl.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "phosphonate," as used herein, alone or in combination, refers to a —P(=O)(OR)$_2$ group, wherein R is chosen from alkyl and aryl. The term "phosphonic acid", as used herein, alone or in combination, refers to a —P(=O)(OH)$_2$ group.

The terms "sulfonate," "sulfonic acid," and "sulfonic," as used herein, alone or in combination, refer to the —$SO_3H$ group and its anion as the sulfonic acid is used in salt formation.

The term "sulfanyl," as used herein, alone or in combination, refers to —S—.

The term "sulfinyl," as used herein, alone or in combination, refers to S(O)—.

The term "sulfonyl," as used herein, alone or in combination, refers to —S(O)$_2$—.

The term "N-sulfonamido" refers to a RS(O)$_2$NR'— group with R and R' as defined herein.

The term "S-sulfonamido" refers to a —S(O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "trihalomethoxy" refers to a $X_3$CO— group where X is a halogen.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent. When any one or more of $G^1$, $G^2$, and $G^3$ of —$(CH_2)_sG^1G^2G^3$ is designated to be "null", said group condenses to either a bond if it occupies an interior position (as with $G^1$ and $G^2$), or is absent if it occupies a terminal position (as with $G^3$). Thus, for example, if $G^1$ and $G^3$ are both null, then —$(CH_2)_sG^1G^2G^3$ condenses to —$(CH_2)_sG^2$. If $G^2$ and $G^3$ are both null, then —$(CH_2)_sG^1G^2G^3$ condenses to —$(CH_2)_sG^1$. Similarly, if $G^1$ and $G^2$ are both null, then —$(CH_2)_sG^1G^2G^3$ condenses to —$(CH_2)_sG^3$. When s is designated to be 0, then the $(CH_2)_s$ portion of —$(CH_2)_sG^1G^2G^3$ collapses to a bond connecting O to $G^1G^2G^3$. Each of G', $G^2$, and $G^3$ are not meant to be null simultaneously and only two of $G^1$, $G^2$, and $G^3$ may be null at once.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, C(O)$CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R″ where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A combination of a straight and a dashed line parallel between two atoms in a drawing of a molecule indicates that an additional bond may be present or absent at that position; a dashed bond alone, bisected by a wavy line, indicates that the structure depicted is connected to another structure, not shown.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"PDE4 inhibitor" is used herein to refer to a compound that exhibits an $IC_{50}$ with respect to PDE4 activity of no more than about 100 μM and more typically not more than about 50 μM, as measured in the PDE4 assay described generally hereinbelow. "$IC_{50}$" is that concentration of inhibitor which reduces the activity of an enzyme (e.g., PDE4) to half-maximal level. Certain representative compounds of the present invention have been discovered to exhibit inhibition against PDE4. In certain embodiments, compounds will exhibit an $IC_{50}$ with respect to PDE4 of no more than about 10 μM; in further embodiments, compounds will exhibit an $IC_{50}$ with respect to PDE4 of no more than about 5 μM; in yet further embodiments, compounds will exhibit an $IC_{50}$ with respect to PDE4 of not more than about 1 μM, as measured in the PDE4 assay described herein. In yet further embodiments, compounds will exhibit an $IC_{50}$ with respect to PDE4 of not more than about 200 nM.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reaction of a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reaction of the appropriate compound, in the form of the free base, with the appropriate acid.

While it may be possible for the compounds of the subject invention to be administered as the raw chemical, it is also possible to present them as a pharmaceutical formulation (equivalently, a "pharmaceutical composition"). Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Topical ophthalmic, otic, and nasal formulations of the present invention may comprise excipients in addition to the active ingredient. Excipients commonly used in such formulations include, but are not limited to, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants. Any of a variety of excipients may be used in formulations of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, guar gum, xanthan gum, carrageenan, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the active ingredient. In preferred embodiments, the excipients to be included in the formulations are typically selected on the basis of their inertness towards the active ingredient component of the formulations.

Relative to ophthalmic, otic, and nasal formulations, suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants (though nonionic surfactants are preferred), RLM 100, POE 20 cetylstearyl ethers such as PROCOL® CS20 and poloxamers such as PLURONIC® F68.

The formulations set forth herein may comprise one or more preservatives. Examples of such preservatives include p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquaternium-1, amino alcohols such as AMP-95, or sorbic acid. In certain embodiments, the formulation may be self-preserved so that no preservation agent is required.

For ophthalmic, otic, or nasal administration, the formulation may be a solution, a suspension, or a gel. In preferred aspects, the formulations are for topical application to the eye, nose, or ear in aqueous solution in the form of drops. The term "aqueous" typically denotes an aqueous formulation wherein the formulation is >50%, more preferably >75% and in particular >90% by weight water. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the formulation as it is delivered, such devices being known in the art.

For ophthalmic disorders, components of the invention may be delivered to the eye as a concentrated gel or a similar vehicle, or as dissolvable inserts that are placed beneath the eyelids.

The formulations of the present invention that are adapted for topical administration to the eye are preferably isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The formulations of the present invention generally have an osmolality in the range of 220-320 mOsm/kg, and preferably have an osmolality in the range of 235-300 mOsm/kg. The ophthalmic formulations will generally be formulated as sterile aqueous solutions.

In certain ophthalmic embodiments, the compositions of the present invention are formulated with one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; and carbomers, such as carbomer 934P, carbomer 941, carbomer 940 and carbomer 974P. Certain formulations of the present invention may be used with contact lenses or other ophthalmic products.

In certain embodiments, formulations are prepared using a buffering system that maintains the formulation at a pH of about 4.5 to a pH of about 8. A most preferred formulation pH is from 7 to 8.

In certain embodiments, a formulation of the present invention is administered once a day. However, the formulations may also be formulated for administration at any frequency of administration, including once a week, once every 5 days, once every 3 days, once every 2 days, twice a day, three times a day, four times a day, five times a day, six times a day, eight times a day, every hour, or any greater frequency. Such dosing frequency is also maintained for a varying duration of time depending on the therapeutic regimen. The duration of a particular therapeutic regimen may vary from one-time dosing to a regimen that extends for months or years. The formulations are administered at varying dosages, but typical dosages are one to two drops at each administration, or a comparable amount of a gel or other formulation. One of ordinary skill in the art would be familiar with determining a therapeutic regimen for a specific indication.

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used.

The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, galactomannan polymers (such as guar and derivatives thereof), and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of the compounds of the invention with anti-nausea medications (for example, odansetron), antidepressants, nootropics, anti-acetylcholinesterases, N-methyl D-aspartate (NMDA) receptor antagonists, amyloid beta therapeutics, and tau therapeutics, neurotrophic growth factors, cell based therapies and other regenerative medicine therapies for treatment of neurodegenerative diseases, amongst other therapies which will be apparent to one skilled in the art.

Antidepressants include, for example:
selective serotonin reuptake inhibitors (SSRIs), such as citalopram, dapoxetine, escitalopram, fluoxetine, fluvoxamine, paroxetine, and sertraline;
serotonin-norepinephrine reuptake inhibitors (SNRIs), such as venlafaxine, desvenlafaxine, minalcipran, levominalcipran, duloxetine, sibutramine, and bicifadine;
noradrenergic and specific serotonergic antidepressants (NaSSAs), such as mianserin, mirtazepine, esmirtazepine, and setiptiline;
norepinephrine reuptake inhibitors (NRIs), such asatomoxetine, mazindol, reboxetine, esreboxetine, viloxazine, and other specific and nonspecific agents which prevent or mitigate reuptake of norepinephrine (e.g., SNRIs, NDRIs);
norepinephrine-dopamine reuptake inhibitors (NDRIs), such as buproprion;
selective serotonin reuptake enhancers, such as tianeptine and amineptine;
norepinephrine-dopamine disinhibitors (NDDIs), such agomelatine;
tricyclic antidepressants, including tertiary and secondary amine varieties, such as amitriptyline, clomipramine, doxepin, imipramine, trimipramine, desipramine, nortriptyline, and protriptyline; and
monoamine oxidase inhibitors (MAOIs), such as isocarboxazid, moclobemide, phenelzine, selegiline, and tranylcyrpomine.

Nootropic drugs, also known as cognition enhancers, include stimulants, dopaminergics, cholinergics, serotonergics, and many of the antidepressants listed above, as well as certain natural products (e.g., caffeine, tryptophan, 5-HTP, nicotine).

racetams such as piracetam, pramiracetam, oxiracetam, and aniracetam
amphetamine analogues such as amphetamine (Adderall, Dexedrine), lisdexamfetamine, and methamphetamine;
wakefulness enhancers such as modafinil;
dopamine reuptake inhibitors such as methylphenidate, and possibly modafinil;
acetylcholinesterase inhibitors used to treat Alzheimer's disease such as tacrine, donepezil, galantamine, rivastigmine;
NMDA receptor antagonists such as memantine;

Selective 5-HT6 receptor antagonists such as Lu AE58054;

Nicotinic alpha-7 receptor agonists such as EVP-6124;

Amyloid beta (a-beta or αβ) therapies and tau therapies target the pathological accumulation of a-beta and tau proteins associated with neurodegenerative diseases such as Alzheimer's disease and progressive supernuclear palsy, respectively. A-beta therapies include β-secretase inhibitors, γ-secretase inhibitors, $Aβ_{42}$-lowering agents (e.g. tarenflurbil), anti-aggregation agents (e.g. apomorphine), antibodies and other immunotherapies. Tau therapies include Tau phosphorylation inhibitors, tau fibrillization inhibitors, and tau degradation enhancers.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, the present invention provides methods for treating PDE4-mediated disorders in a human or animal subject in need of such treatment comprising administering to said subject an amount of a compound of the present invention effective to reduce or prevent said disorder in the subject in combination with at least one additional agent for the treatment of said disorder that is known in the art. In a related aspect, the present invention provides therapeutic compositions comprising at least one compound of the present invention in combination with one or more additional agents for the treatment of PDE4-mediated disorders.

The compounds of the subject invention may also be useful for the treatment of certain diseases and disorders of the nervous system. Central nervous system disorders in which PDE4 inhibition may be useful include cortical dementias including Alzheimer's disease, AIDS-related dementia (HIV dementia), and mild cognitive impairment (MCI). Neurodegenerative disorders in which PDE4 inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia e.g. pre-senile dementia, and HIV-associated neurodegenerative disorder (HAND), cachexia, Sydenham's chorea, Huntington's disease, Parkinson's Disease, amyotrophic lateral sclerosis (ALS), Korsakoff's syndrome, and impairment relating to a cerebral vessel disorder. Further disorders in which PDE4 inhibition might prove useful include neuropathies of the central and peripheral nervous system, including, for example, IgA neuropathy, membranous neuropathy, idiopathic neuropathy, drug-induced peripheral neuropathy, diabetic neuropathy, HIV-associated neuropathy, and chronic inflammatory demyelinating polyneuropathy; as well as transverse myelitis, Guillain-Barré disease, encephalitis, and cancers of the nervous system. Compounds disclosed herein may also be used in the treatment of psychological disorders including anxiety, depression, major depressive disorder (MDD), bipolar disorder, and post-traumatic stress disorder. Compounds disclosed herein may also be used in the treatment of nervous system damage, for example that resulting from stroke, ischemias including cerebral ischemia (both focal ischemia, thrombotic stroke and global ischemia, for example, secondary to cardiac arrest and ischemic heart disease) and ischemia/reperfusion, ototoxicity and hearing loss, acute insults to the inner ear, including acoustic trauma, blast noise (for example, as experienced by military personnel), exposure to ototoxic chemotherapeutic agents for cancer therapy (such as cisplatin) and treatment with aminoglycoside antibiotics and other nervous system trauma.

Compounds disclosed herein may also be used in the treatment of traumatic brain injury (TBI), spinal cord injury (SCI), or a symptom thereof. In certain embodiments, a selective PDE4 B inhibitor as disclosed herein will be used to treat SCI, in an amount sufficient to cause a detectable improvement in one or more symptoms, or a reduction in the progression of one or more symptoms of SCI. Additionally, the selective PDE4 B inhibitor can be administered in combination with transplantation into the spinal cord of cells. Contemplated cells include stem cells and glial (e.g., Schwann) cells.

Furthermore, compounds of the subject invention may be used in the treatment or prevention of opiate tolerance in patients needing protracted opiate analgesics, and benzodiazepine tolerance in patients taking benzodiazepines, and other addictive behavior, for example, nicotine addiction, alcoholism, and eating disorders. Moreover, the compounds and methods of the present invention may be useful in the treatment or prevention of drug withdrawal symptoms, for example treatment or prevention of symptoms of withdrawal from opiate, alcohol, or tobacco addiction.

Compounds disclosed herein may also be used in the treatment of acute and chronic pain and inflammation. The compounds of the present invention may be useful to treat patients with neuropathy, neuropathic pain, or inflammatory pain such as reflex sympathetic dystrophy/causalgia (nerve injury), peripheral neuropathy (including diabetic neuropathy), intractable cancer pain, complex regional pain syndrome, and entrapment neuropathy (carpel tunnel syndrome). The compounds may also be useful in the treatment of pain associated with acute herpes zoster (shingles), postherpetic neuralgia (PHN), and associated pain syndromes such as ocular pain. The compounds may further be useful as analgesics in the treatment of pain such as surgical analgesia, or as an antipyretic for the treatment of fever. Pain indications include, but are not limited to, post-surgical pain for various surgical procedures including post-cardiac surgery, dental pain/dental extraction, pain resulting from cancer, muscular pain, mastalgia, pain resulting from dermal injuries, lower back pain, headaches of various etiologies, including migraine, and the like. The compounds may also be useful for the treatment of pain-related disorders such as tactile allodynia and hyperalgesia. The pain may be somatogenic (either nociceptive or neuropathic), acute and/or chronic. The PDE4 inhibitors of the subject invention may also be useful in conditions where NSAIDs, morphine or fentanyl opiates and/or other opioid analgesics would traditionally be administered.

In addition, compounds disclosed herein may be used in the treatment of insulin resistance and other metabolic disorders such as atherosclerosis that are typically associated with an exaggerated inflammatory signaling.

Compounds disclosed herein may also be used in the treatment of respiratory disease or conditions, including therapeutic methods of use in medicine for preventing and treating a respiratory disease or condition including: asthmatic conditions including allergen-induced asthma, exercise-induced asthma, pollution-induced asthma, cold-induced asthma, and viral-induced-asthma; asthma-related diseases such as airway hyperreactivity and small airway disease; chronic obstructive pulmonary diseases including chronic bronchitis with normal airflow, chronic bronchitis with airway obstruction (chronic obstructive bronchitis), emphysema, asthmatic bronchitis, and bullous disease; and other pulmonary diseases involving inflammation including bronchiolitis, bronchioectasis, cystic fibrosis, pigeon fancier's disease, farmer's lung, acute respiratory distress syndrome, pneumonia, pneumonitis, aspiration or inhalation injury, fat embolism in the lung, acidosis inflammation of the lung, acute pulmonary edema, acute mountain sickness, acute pulmonary hypertension, persistent pulmonary hypertension of the newborn, perinatal aspiration syndrome, hyaline membrane disease, acute pulmonary thromboembolism, heparin-protamine reactions, sepsis, status asthamticus, hypoxia, dyspnea, hypercapnea, hyperinflation, hypoxemia, and cough. Further, compounds disclosed herein would find use in the treatment of allergic disorders such as delayed type hypersensitivity reaction, allergic contact dermatitis, allergic rhinitis, and chronic sinusitis.

Compounds disclosed herein may also be used in the treatment of inflammation and related disorders. The compounds disclosed herein may be useful as anti-inflammatory agents with the additional benefit of having significantly less harmful side effects. The compounds may be useful to treat arthritis, including but not limited to rheumatoid arthritis, spondyloarthropathies, gouty arthritis, osteoarthritis, juvenile arthritis, acute rheumatic arthritis, enteropathic arthritis, neuropathic arthritis, psoriatic arthritis, reactive arthritis (Reiter's syndrome), and pyogenic arthritis, and autoimmune diseases, including systemic lupus erythematosus, hemolytic syndromes, autoimmune hepatitis, autoimmune neuropathy, vitiligo (autoimmune thyroiditis), Hashimoto's thyroiditis, anemias, myositis including polymyositis, alopecia greata, Goodpasture's syndrome, hypophytis, and pulmonary fibrosis.

Compounds disclosed herein may also be used in the treatment of osteoporosis and other related bone disorders.

Compounds disclosed herein may also be used in the treatment of gastrointestinal conditions such as reflux esophagitis, diarrhea, inflammatory bowel disease, Crohn's disease, gastritis, irritable bowel syndrome, Graves' disease (hyperthyroidism), necrotizing enterocolitis, and ulcerative colitis. The compounds may also be used in the treatment of pulmonary inflammation, such as that associated with viral infections and cystic fibrosis.

In addition, compounds of invention may also be useful in organ transplant patients either alone or in combination with conventional immunomodulators. Examples of conditions to be treated in said patients include graft vs. host reaction (i.e., graft vs. host disease), allograft rejections (e.g., acute allograft rejection, and chronic allograft rejection), transplant reperfusion injury, and early transplantation rejection (e.g., acute allograft rejection).

Yet further, the compounds of the invention may be useful in the treatment of pruritus and vitiligo.

Compounds disclosed herein may also be used in the treatment of tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephritis, nephrotic syndrome, Langerhans' cell histiocytosis, glomerulonephritis, reperfusion injury, pancreatitis, interstitial cystitis, Behcet's syndrome, polymyositis, gingivitis, periodontis, hypersensitivity, swelling occurring after injury, ischemias including myocardial ischemia, cardiovascular ischemia, and ischemia secondary to cardiac arrest, cirrhosis, septic shock, endotoxic shock, gram negative sepsis, toxic shock syndrome, stroke, ischemia reperfusion injury, multi-organ dysfunction, restenosis including restenosis following coronary bypass surgery, and the like.

Furthermore, the compounds disclose herein may also be useful in inhibiting PDE4 activity for the amelioration of systemic disorders including systemic hypotension associated with septic and/or toxic hemorrhagic shock induced by a wide variety of agents; as a therapy with cytokines such as TNF, IL-1 and IL-2; and as an adjuvant to short term immunosuppression in transplant therapy.

Compounds disclosed herein may also be used in the treatment of cancer, such as colorectal cancer, and cancer of the breast, lung, prostate, bladder, cervix and skin. Compounds of the invention may be used in the treatment and prevention of neoplasias including but not limited to brain cancer, bone cancer, leukemia, lymphoma, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. The neoplasia can be selected from gastrointestinal cancer, liver cancer, bladder cancer, pancreas cancer, ovary cancer, prostate cancer, cervical cancer, lung cancer, breast cancer and skin cancer, such as squamous cell and basal cell cancers. The present compounds and methods may also be used to treat the fibrosis which occurs with radiation therapy. The present compounds and methods may be used to treat subjects having adenomatous polyps, including those with familial adenomatous polyposis (FAP). Additionally, the present compounds and methods may be used to prevent polyps from forming in patients at risk of FAP.

Compounds disclosed herein may also be used in the treatment of otic diseases and otic allergic disorders, including eustachian tube itching.

Compounds disclosed herein may also be used in the treatment of ophthalmic diseases.

Moreover, compounds of the subject invention may be used in the treatment of menstrual cramps, dysmenorrhea, premature labor, endometriosis, tendonitis, bursitis, skin-related conditions such as psoriasis, eczema, burns, sunburn, dermatitis, pancreatitis, hepatitis, lichen planus, scleritis, scleroderma, dermatomyositis, and the like. Other conditions in which the compounds of the subject invention may be used include diabetes (type I or type II), atherosclerosis, congestive heart failure, myocarditis, atherosclerosis, cerebral ischemia, angiogenesis, pulmonary hypertension, and aortic aneurysm.

The compounds disclosed herein may also be used in co-therapies, partially or completely, in place of other conventional anti-inflammatory therapies, such as together with steroids, NSAIDs, COX-2 selective inhibitors, 5-lipoxygenase inhibitors, $LTB_4$ antagonists and $LTA_4$ hydrolase inhibitors. Additional co-therapies comprising the compounds disclosed herein with biologics include:

tumor necrosis factor alpha (TNFα) blockers such as etanercept (Enbrel), infliximab (Remicade), adalimumab (Humira), certolizumab pegol (Cimzia), and golimumab (Simponi);

Interleukin 1 (IL-1) blockers such as anakinra (Kineret);

monoclonal antibodies against B cells such as rituximab (Rituxan);

T cell costimulation blocker such as abatacept (Orencia); and

Interleukin 6 (IL-6) blockers such as tocilizumab (RoActemra or Actemra, an anti-IL-6 receptor antibody).

Compounds disclosed herein may also be used to prevent tissue damage when therapeutically combined with antibacterial or antiviral agents. In certain embodiments, the compounds disclosed herein may be combined with neuraminidase inhibitors for the treatment of a viral disease such as influenza.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

All references, patents or applications, U.S. or foreign, cited in the application are hereby incorporated by reference as if written herein in their entireties. Where any inconsistencies arise, material literally disclosed herein controls.

General Synthetic Methods for Preparing Compounds

The following schemes and general procedures can be used to practice the present invention.

Scheme 1: Synthesis of Triazine Analogs

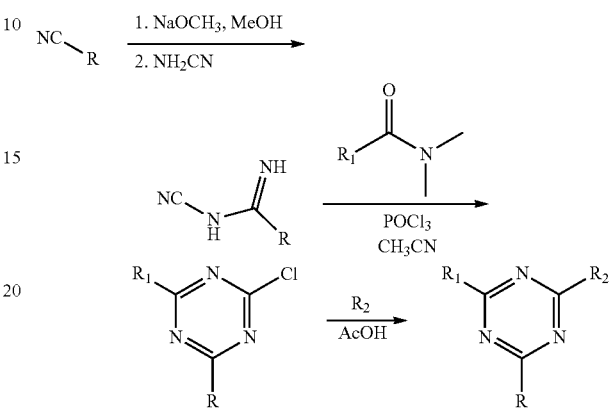

| Example | R | $R_1$ | $R_2$ |
|---|---|---|---|
| 22 | 5-chlorothien-2-yl | Me | 4-(carboxymethyl)phenylamino |
| 23 | 5-chlorothien-2-yl | Me | 4-fluorophenylamino |
| 24 | furan-2-yl | Me | 4-(carboxymethyl)phenylamino |
| 25 | 5-chlorothien-2-yl | iPr | 4-(carboxymethyl)phenylamino |
| 26 | 5-chlorothien-2-yl | iPr | 4-fluorophenylamino |
| 27 | 5-chlorothien-2-yl | Et | 4-(carboxymethyl)phenylamino |

-continued
| Example | R | R₁ | R₂ |
|---|---|---|---|
| 28 | 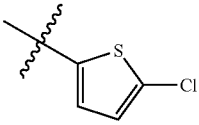 [SMILES: *c1ccc(Cl)s1] |  | 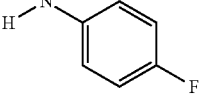 |
| 29 | 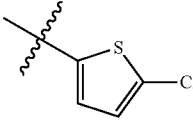 | 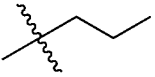 [SMILES: *CCC] | 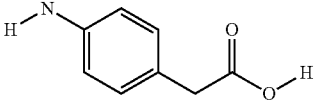 |
| 33 | 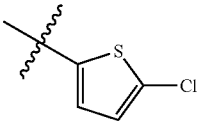 [SMILES: *c1ccc(Cl)s1] |  | 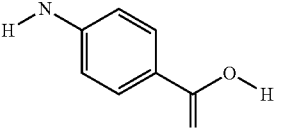 |
| 35 | 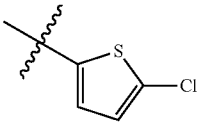 [SMILES: *c1ccc(Cl)s1] | Cl | 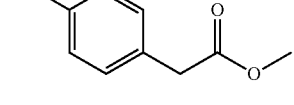 |
| 37 | 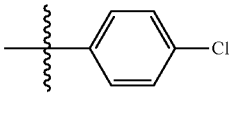 | 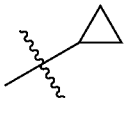 [SMILES: *C1CC1] | 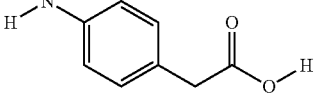 |
| 38 | 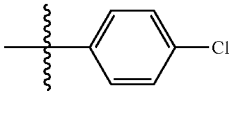 | 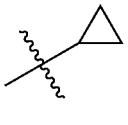 | 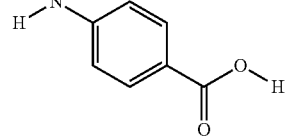 |
| 39 | 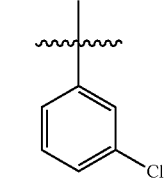 [SMILES: *c1cccc(Cl)c1] |  | 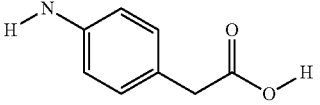 |
| 40 | 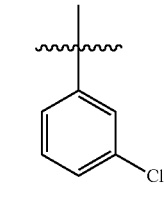 [SMILES: *c1cccc(Cl)c1] |  | 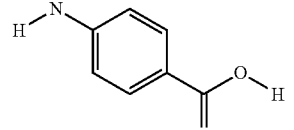 |
| 41 | 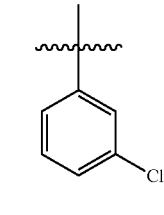 [SMILES: *c1cccc(Cl)c1] |  | 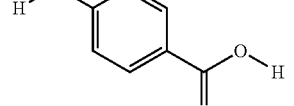 |

-continued
| Example | R | R₁ | R₂ |
|---|---|---|---|
| 43 | 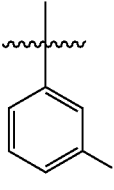 | 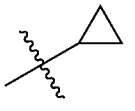 | 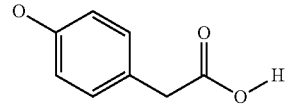 |
| 44 | 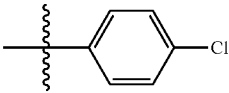 |  | 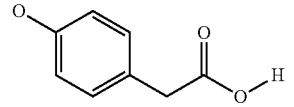 |
| 45 | 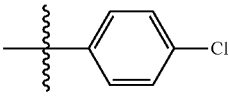 |  | 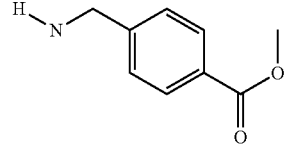 |
| 46 | 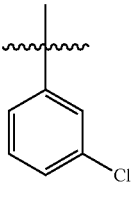 [SMILES: *c1cccc(Cl)c1] | 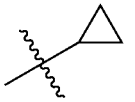 [SMILES: *C1CC1] | 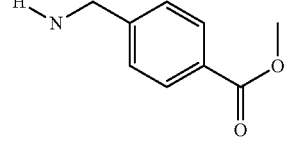 |
| 46 | 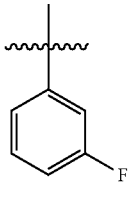 [SMILES: *c1cccc(F)c1] |  | 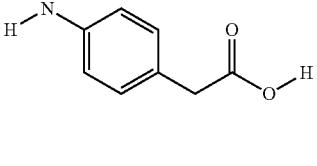 |
| 48 | 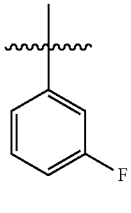 [SMILES: *c1cccc(F)c1] |  | 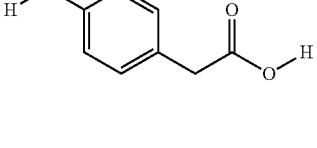 |
| 49 | 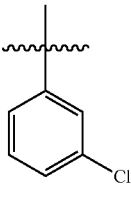 [SMILES: *c1cccc(Cl)c1] | 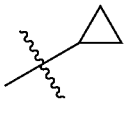 [SMILES: *C1CC1] | 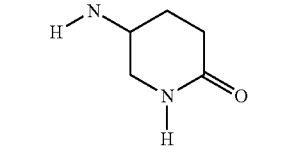 |
| 50 | 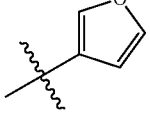 | 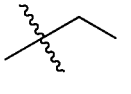 | 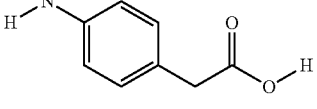 |

-continued

| Example | R | R₁ | R₂ |
|---|---|---|---|
| 53 | 3-chlorophenyl | cyclopropyl | 4-(2-oxoimidazolidin-1-yl)phenylamino |
| 54 | 3-chlorophenyl | sec-butyl | 4-cyanophenylamino |
| 55 | 3-chlorophenyl | sec-butyl | 4-cyanophenylamino |
| 56 | 3-chlorophenyl | sec-butyl | 4-(sulfamoylamino)phenylamino |
| 59 | 3-chlorophenyl | sec-butyl | 4-(1-carboxyethyl)phenylamino |
| 61 | 3-chlorophenyl | sec-butyl | 4-(2-amino-2-oxoethyl)phenoxy |
| 63 | 3-chlorophenyl | sec-butyl | 4-carboxyphenylamino |
| 64 | 3-chlorophenyl | sec-butyl | 1-(2-methoxy-2-oxoethyl)piperidin-4-ylamino |

Scheme 2:
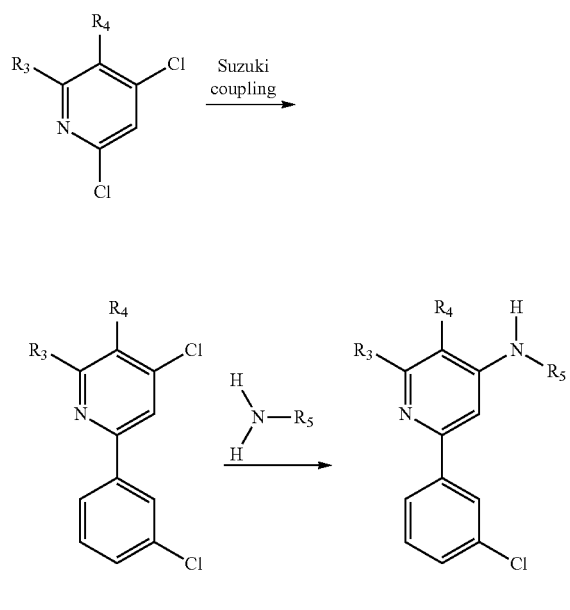
Variation on Scheme 2: Synthesis of cyclopenta[b]pyridine analogs
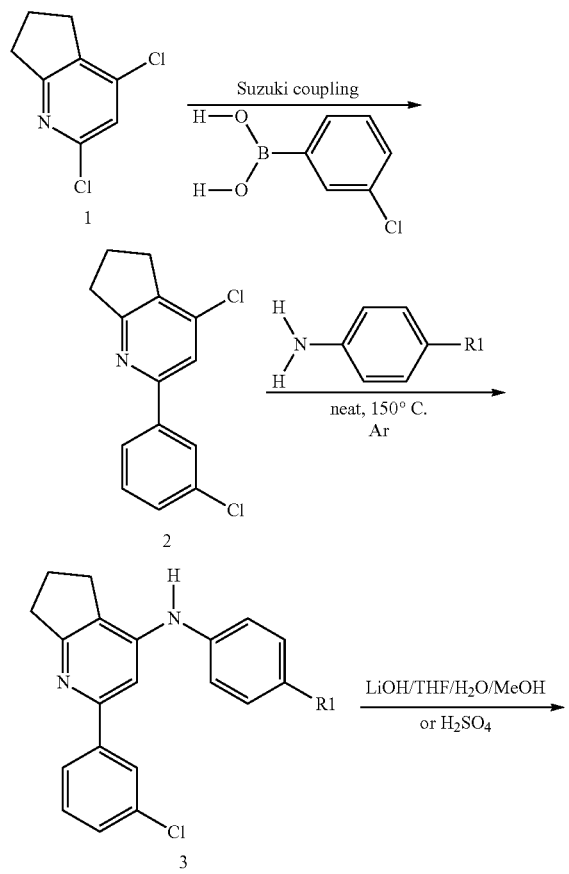
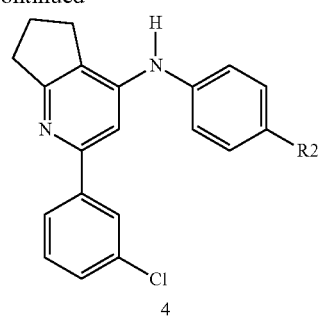
| EXAMPLE | R1 | R2 |
|---|---|---|
| 1 | $CH_2CN$ | |
| 2 | $CH_2(CO)OMe$ | $CH_2CO_2H$ |
| 3 | $CH_2CN$ | $CH_2(CO)NH_2$ |
| 4 | $OCH_2C(O)OMe$ | $OCH_2CO_2H$ |
| 5 | $C(O)OMe$ | $CO_2H$ |
| 6 | $CH_2C(O)OMe$ | $CH_2CH_2OH$ |
| 8 | $CH_2CH_2CH_2C(O)OMe$ | $CH_2CH_2CH_2CO_2H$ |
| 9 | $CH_2CH_2C(O)OMe$ | $CH_2CH_2CO_2H$ |
Scheme 3: Synthesis of Ethyl methyl pyridine analogs
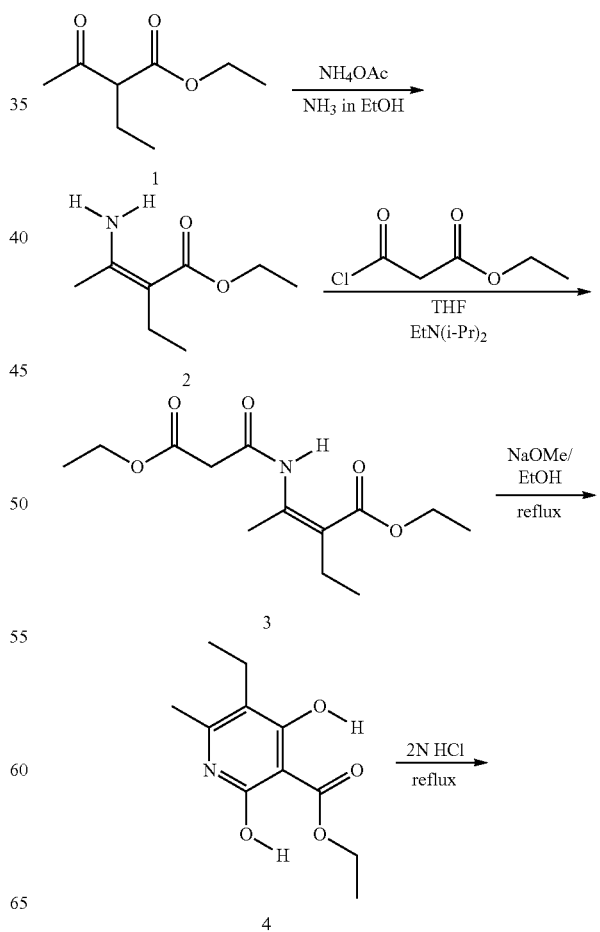

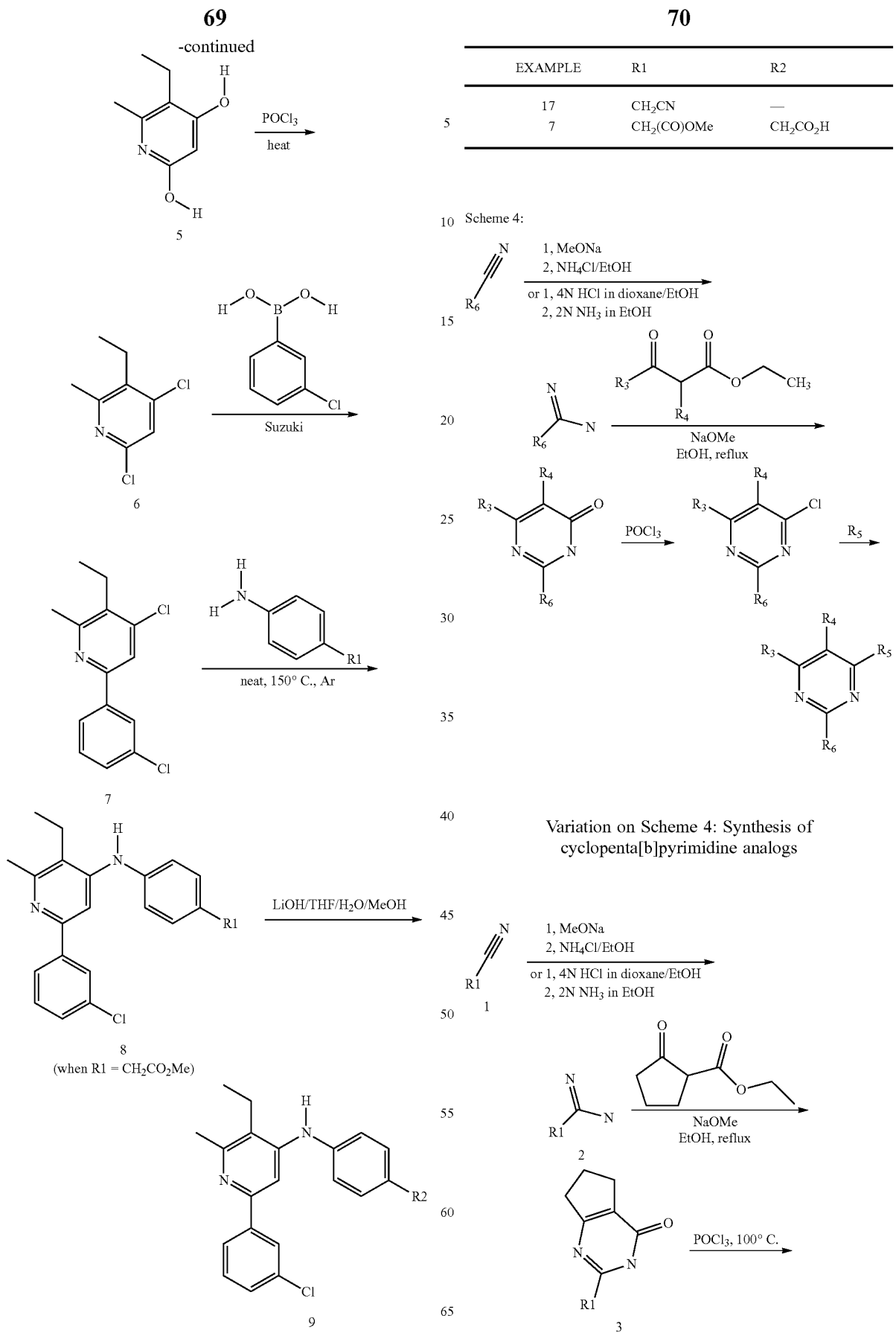
| EXAMPLE | R1 | R2 |
|---|---|---|
| 17 | CH$_2$CN | — |
| 7 | CH$_2$(CO)OMe | CH$_2$CO$_2$H |
Scheme 4:
Variation on Scheme 4: Synthesis of cyclopenta[b]pyrimidine analogs -continued
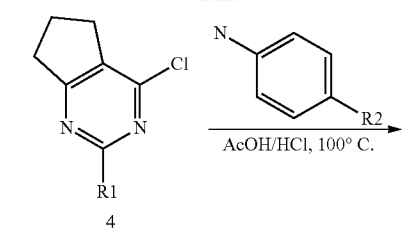
| EXAMPLE | R1 | R2 |
|---|---|---|
| 9 | 5-chlorothiophen-2-yl | CH2COOH |
| 10 | 3-chlorophenyl | CH2COOH |
| 11 | 5-chlorothiophen-2-yl | CH(NHAc)COOH |
| 12 | 5-chlorothiophen-2-yl | CH(NH2)COOH |
| 13 | 5-chlorothiophen-2-yl | (CH2)3COOH |
| 14 | 3-chlorophenyl | (CH2)3COOH |
| 15 | 5-chlorothiophen-2-yl | C(CH3)2CH2COOH |
| 16 | 3-chlorophenyl | C(CH3)2CH2COOH |
| 18 | 5-chlorothiophen-2-yl | C(CH3)2CH2CN |
| 19 | 3-chlorophenyl | C(CH3)2CH2CN |
| 20 | 5-chlorothiophen-2-yl | C(CH3)2CH2CONH2 |

| EXAMPLE | R1 | R2 |
|---|---|---|
| 21 | 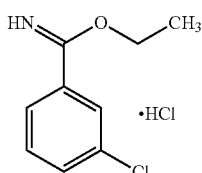 | 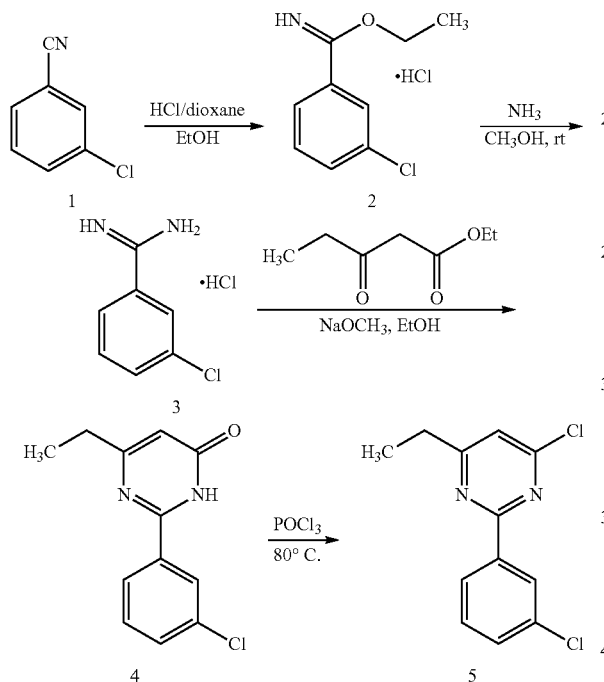 |

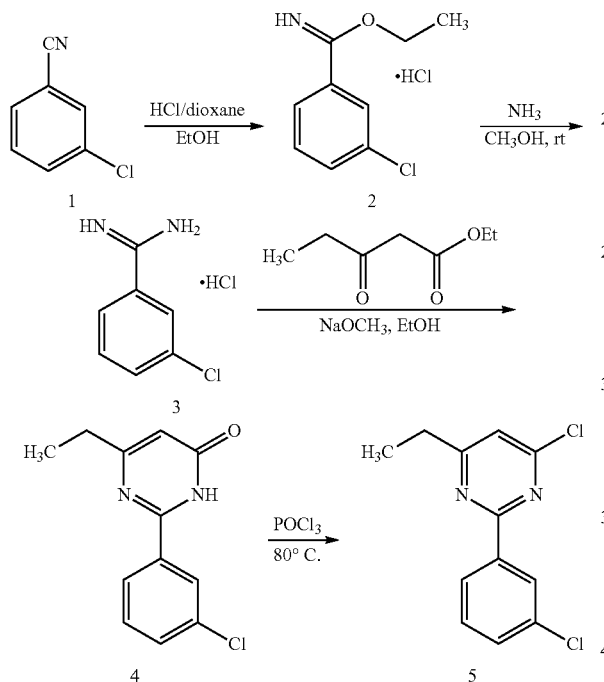

Scheme 5: Synthesis of ethylchloropyrimidine core

Step 1. Ethyl 3-chlorobenzimidate hydrochloride

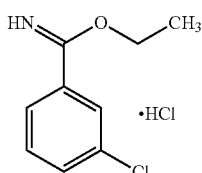

A 500-mL round bottomed flask was charged with 3-chlorobenzonitrile (23.3 g, 169 mmol, 1 eq.), ethanol (8.48 g, 184 mmol, 1.09 eq.), and HCl (4 N in dioxane, 169 mL, 676 mmol, 4 eq.). The resulting mixture was stirred at room temperature for 54 hr. The volatile material was removed under reduced pressure and the residue was treated with ether. The resulting solid was collected by filtration and washed with ether. The product was used in the next step without further purification (26.9 g, 84% yield). $^1$H NMR (DMSO-d$_6$, 500 MHz) δ 12.0 (br s, 2H), 8.25-8.20 (m, 1H), 8.12-8.08 (m, 1H), 7.90-7.85 (m, 1H), 7.67 (t, J=8.0 Hz, 1H), 4.63 (q, J=7.0 Hz, 2H), 1.48 (t, J=7.0 Hz, 3H).

Step 2. 3-Chlorobenzimidamide

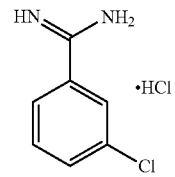

A 1-L round bottom flask was charged with ethyl 3-chlorobenzimidate hydrochloride (26.9 g, mmol, 122 mmol, 1 eq.) and NH$_3$ (7N in methanol, 360 mL, 2.52 mol, 20 eq.) in methanol (270 mL). The resulting mixture was stirred at room temperature for 3 days. The volatile material was removed under reduced pressure and the resultant off-white solid was used in the next step without further purification (23.9 g, 89% yield). $^1$H NMR (DMSO-d$_6$, 500 MHz) δ 9.48 (br s, 4H), 7.97-7.94 (m, 1H), 7.84-7.79 (m, 2H), 7.65 (t, J=8.0 Hz, 1H).

Step 3. 2-(3-Chlorophenyl)-6-ethylpyrimidin-4(3H)-one

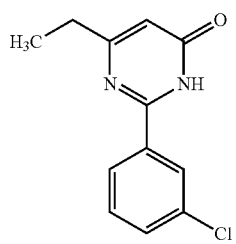 [SMILES: CCc1cc(=O)[nH]c(-c2cccc(Cl)c2)n1]

A 1-L round bottomed flask was charged with 3-chlorobenzimidamide (23.9 g, 154 mmol, 1 eq.), ethyl 3-oxopentanoate (27.8 g, 193 mmol, 1.25 eq.), and ethanol (500 mL). To the mixture was added sodium methoxide (10.0 g, 185 mmol, 1.20 eq.). The resulting mixture was stirred under reflux for 20 hr. After cooling to room temperature, the mixture was evaporated under reduced pressure to 50 mL. The residual slurry was cautiously treated with 2N HCl (219 mL). Solid was collected by filtration and washed with water followed by ether to afford 2-(3-chlorophenyl)-6-ethylpyrimidin-4(3H)-one (9.3 g, 39% yield), which was carried forward into the next step without further purification. $^1$H NMR (CD$_3$OD, 500 MHz) δ 8.07 (s, 1H), 7.96 (d, J=8.0 Hz, 1H), 7.62-7.58 (m, 1H), 7.52 (t, J=8.0, Hz, 1H), 6.27 (s, 1H), 2.66 (q, J=7.5 Hz, 2H), 1.29 (t, J=7.5 Hz, 3H).

Step 4. 4-Chloro-2-(3-chlorophenyl)-6-ethylpyrimidine

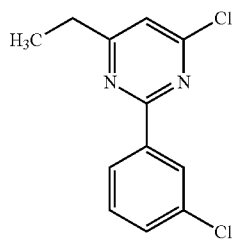 [SMILES: CCc1cc(Cl)nc(-c2cccc(Cl)c2)n1]

A 250-mL round bottom flask was charged with 2-(3-chlorophenyl)-6-ethylpyrimidin-4(3H)-one (9.3 g, 39.8 mmol, 1 eq.). POCl₃ (50 mL, 536 mm01, 13.4 eq.) was cautiously added at 0° C. The resulting mixture was stirred at 100° C. for 5 hr. After cooling to room temperature, the mixture was added slowly dropwise to cold aq. NaHCO₃. NaOH was added to keep the pH~7 during quenching. The mixture was extracted with ethyl acetate. The organic extract was dried over sodium sulfate, filtered and concentrated under reduced pressure. Purification by silica gel chromatography using dichloromethane/ethyl acetate as eluent afforded 4-chloro-2-(3-chlorophenyl)-6-ethylpyrimidine (9.3 g, 99% yield) as a white solid. ¹H NMR (CD₃OD, 500 MHz) δ 8.32 (s, 1H), 8.28 (d, J=7.5 Hz, 1H), 7.50-7.46 (m, 1H), 7.45-7.40 (m, 1H), 7.27 (s, 1H), 2.83 (q, J=7.5 Hz, 2H), 1.34 (t, J=7.5 Hz, 3H).

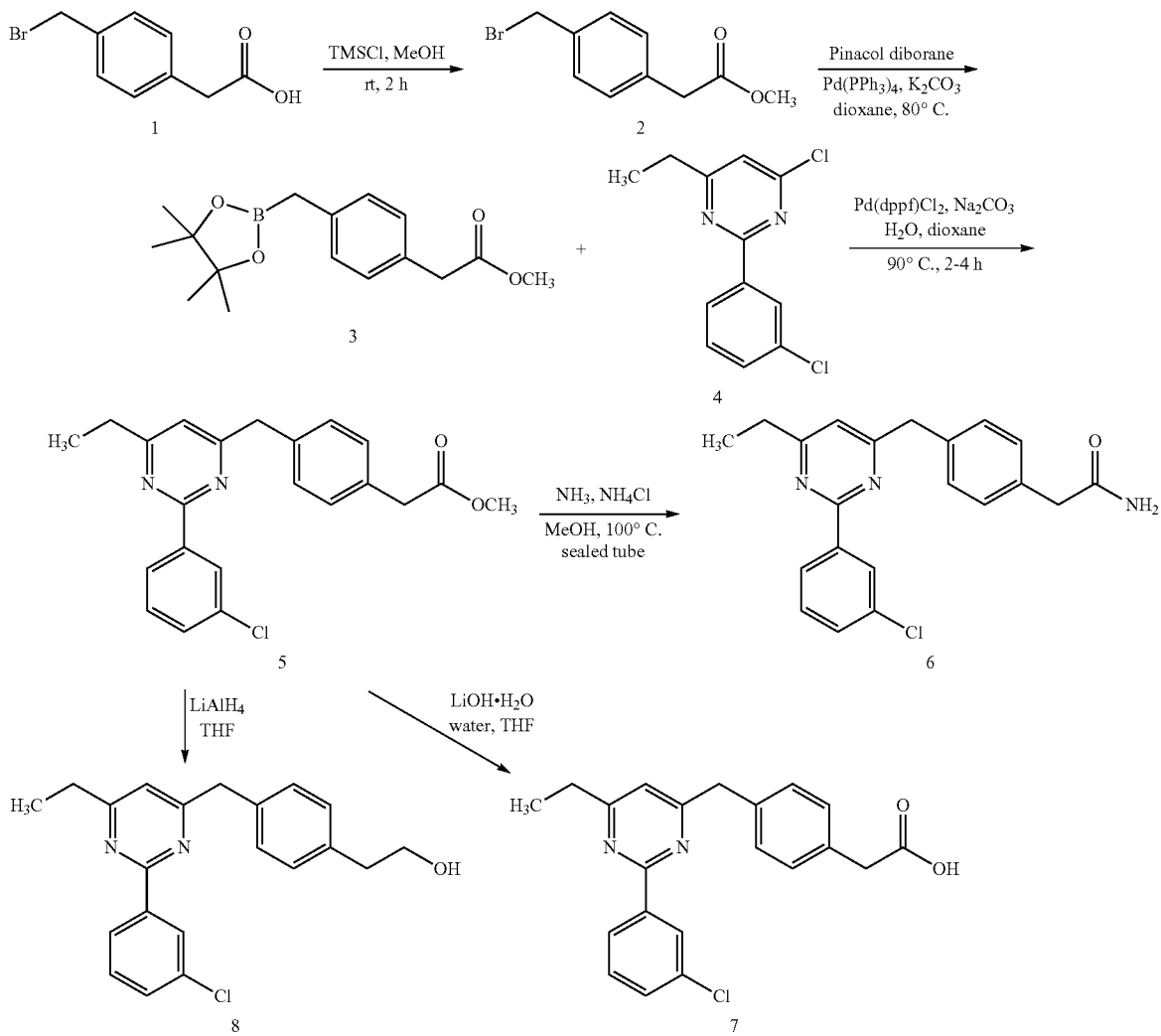

Scheme 6: Synthesis of Carbon Linked Ethylpyrimidine Analogues

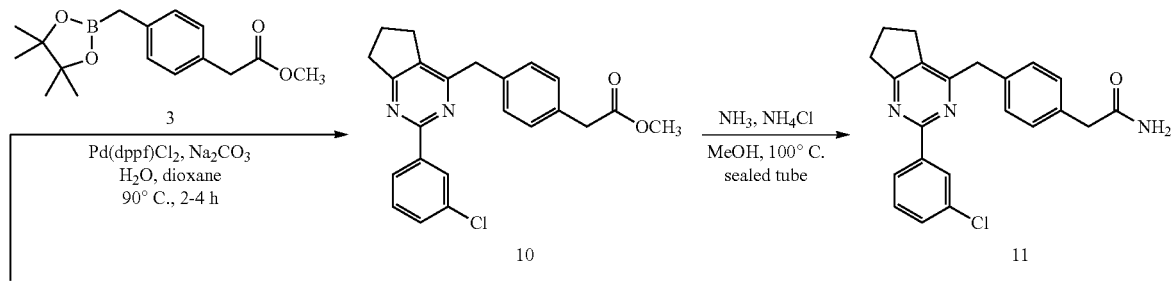

Scheme 7: Synthesis of carbon linked cyclopentylpyrimidine analogs

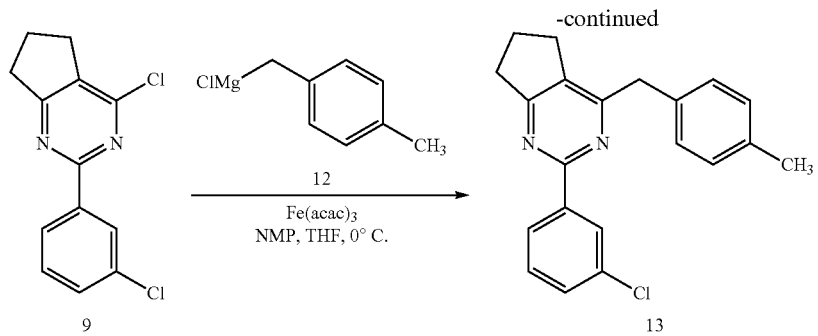
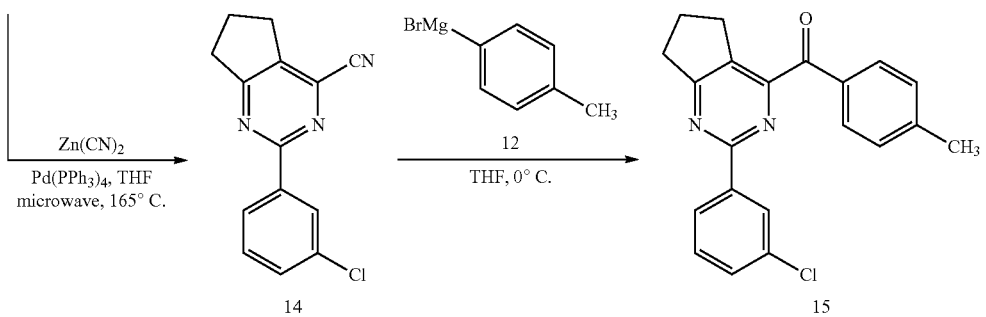
Scheme 8: Synthesis of boronic acid analogs
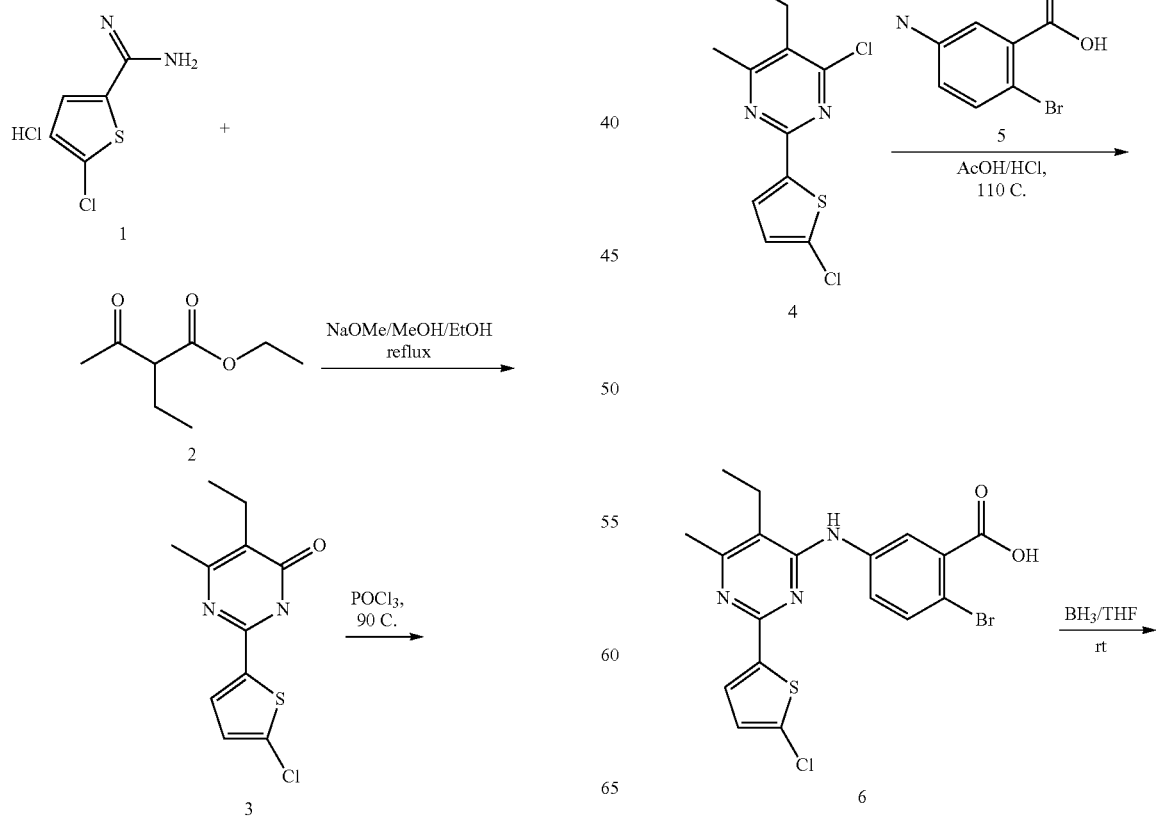

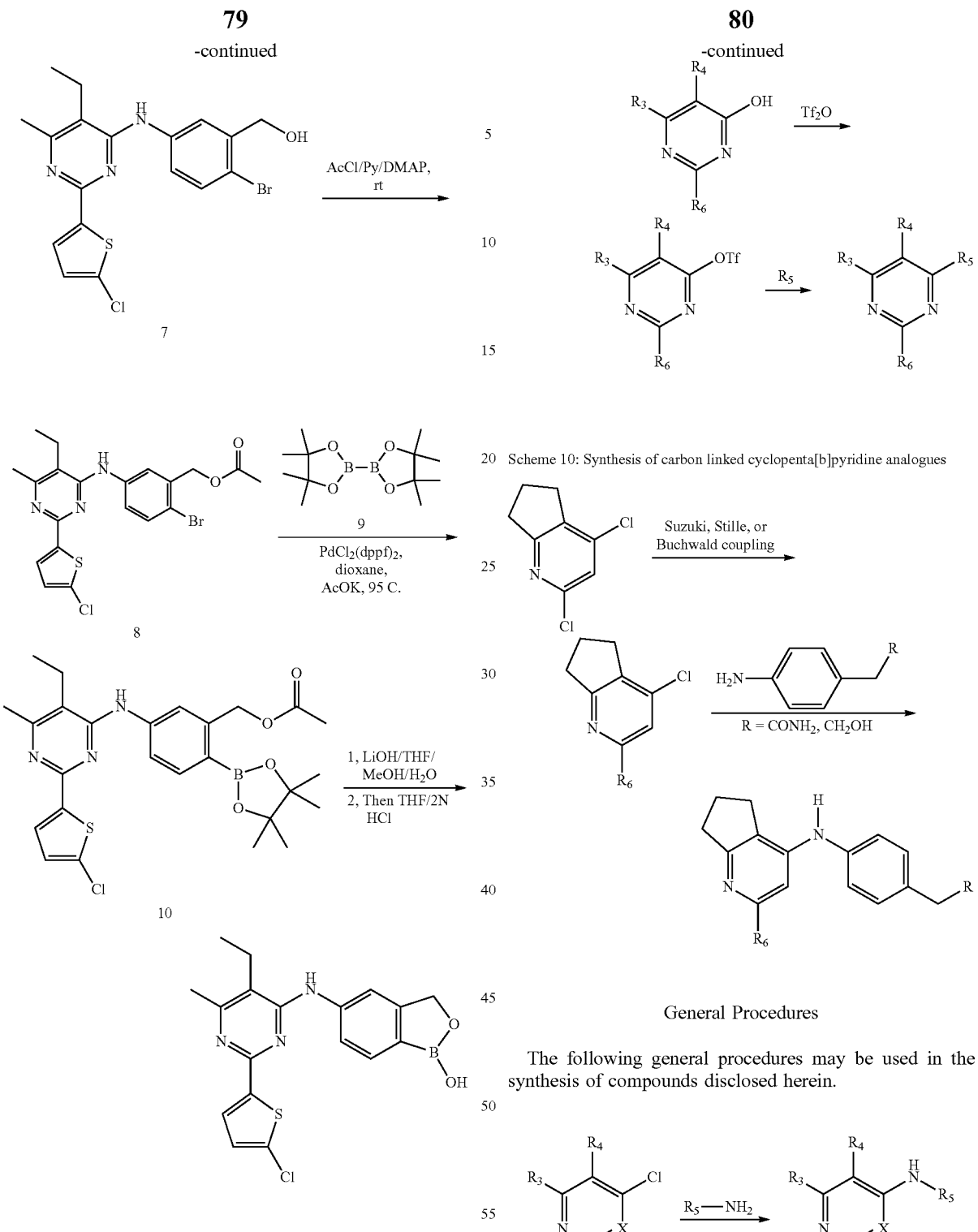

Scheme 9: Synthesis of pyrimidine analogues

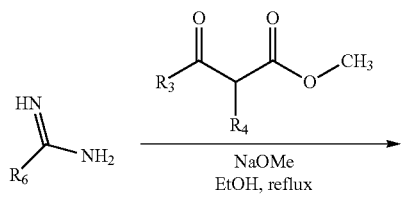

General Procedures

The following general procedures may be used in the synthesis of compounds disclosed herein.

General Procedure A1 (Nucleophilic Addition)

To a solution of chloropyridine.HCl or chloropyrimidine (1.0 equiv) in DMF or NMP was added the requisite aniline (1.0-1.5 equiv) and the reaction mixture was stirred with heat between 120-160° C. for 12-24 h or until the starting material was consumed (monitored by LCMS analysis). The reaction mixture was cooled, diluted with saturated aqueous sodium bicarbonate and/or water and extracted with ethyl acetate. The combined organic layer was dried over anhydrous sodium sulfate, filtered, and the filtrate was concentrated. The residue was purified by column chromatography (silica, hexanes/ethyl acetate or methanol/dichloromethane) or preparative HPLC (water/acetonitrile with 0.05% TFA) to afford the desired product. In some cases, HCl in methanol was used to form HCl salt of the desired product.

General Procedure A2 (Nucleophilic Addition)

To a solution of chloropyridine.HCl or chloropyrimidine (1.0 equiv) in DMF or NMP was added the requisite aniline (1.0-1.5 equiv) and the reaction mixture was heated with microwave irradiation between 120-160° C. for 1-4 h or until the starting material was consumed (monitored by LCMS analysis). The reaction mixture was cooled, diluted with satd. aq. sodium bicarbonate and/or water and extracted with ethyl acetate. The combined organic layer was dried over anhydrous sodium sulfate, filtered and the filtrate was concentrated. The residue was purified by column chromatography (silica, hexanes/ethyl acetate or methanol/dichloromethane) or preparative HPLC (water/acetonitrile with 0.05% TFA) to afford the desired product. In some cases, HCl in methanol was used to form HCl salt of the desired product.

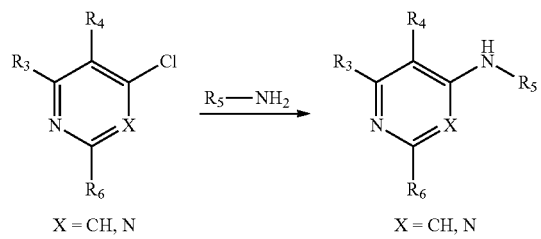

General Procedure B1 (Palladium Coupling)

To a solution of chloropyridine or chloropyrimidine (1.0 equiv) in dioxane was added palladium acetate (5 mol %), rac-BINAP (7.5 mol %), cesium carbonate (2.5 equiv), and the requisite aniline or amine (1-1.2 equiv). Nitrogen gas was passed through the suspension for 10 min. The reaction mixture was stirred with heat between 80-120° C. for 2-24 h or until the starting material was consumed (monitored by LCMS analysis). The reaction mixture was cooled, diluted with water and extracted with ethyl acetate. The combined organic layer was dried over anhydrous sodium sulfate, filtered, and the filtrate was concentrated. The residue was purified by column chromatography (silica, hexanes/ethyl acetate or methanol/dichloromethane) or preparative HPLC (water/acetonitrile with 0.05% TFA) to afford the desired product. In some cases, HCl in methanol was used to form HCl salt of the desired product.

General Procedure B2 (Palladium Coupling)

To a solution of chloropyridine or chloropyrimidine (1.0 equiv) in dioxane was added palladium acetate (5 mol %), rac-BINAP (7.5 mol %), cesium carbonate (2.5 equiv), and the requisite aniline or amine (1-1.2 equiv). The reaction mixture was heated with microwave irradiation between 100-120° C. for 1-4 h or until the starting material was consumed (monitored by LCMS analysis). The reaction mixture was cooled, diluted with water, and extracted with ethyl acetate. The combined organic layer was dried over anhydrous sodium sulfate, filtered, and the filtrate was concentrated. The residue was purified by column chromatography (silica, hexanes/ethyl acetate or methanol/dichloromethane) or preparative HPLC (water/acetonitrile with 0.05% TFA) to afford the desired product. In some cases, HCl in methanol was used to form HCl salt of the desired product.

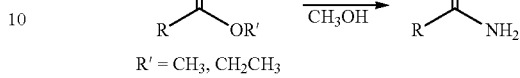

General Procedure C (Amide Formation)

To a microwave vessel was added the methyl or ethyl ester Ammonia in methanol (7 M, 3-10 mL) was added and the vessel was sealed with an aluminum cap. The resulting mixture was stirred at 100° C. for 24-48 h. The crude reaction solution was cooled, evaporated and purified by column chromatography (silica, hexanes/ethyl acetate or methanol/dichloromethane) or preparative HPLC (water/acetonitrile with 0.05% TFA) to afford the desired product. In some cases, HCl in methanol was used to form HCl salt of the desired product.

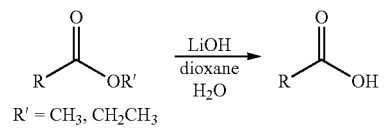

General Procedure D (Saponification)

To a solution of methyl or ethyl ester (1.0 equiv) in dioxane and water (2:1) was added lithium hydroxide (5 equiv). The suspension was stirred for 4-24 h or until the starting material was consumed (monitored by LCMS analysis). The reaction was diluted with water, acidified with HCl (2 M), and extracted with ethyl acetate. The combined organic layer was dried over anhydrous sodium sulfate, filtered, and the filtrate was concentrated. The residue was purified by column chromatography (silica, hexanes/ethyl acetate or methanol/dichloromethane) or preparative HPLC (water/acetonitrile with 0.05% TFA) to afford the desired product.

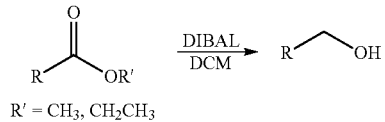

General Procedure E1 (Reduction—DIBAL)

To a solution of methyl or ethyl ester (1.0 equiv) in DCM at 0° C. was added DIBAL (3 equiv, 1.0 M in THF). The mixture was stirred for 2 h and warmed to rt for 30 min or until the starting material was consumed (monitored by LCMS analysis). The reaction was quenched with methanol, HCl (2 M), and water and then extracted with DCM. The combined organic layer was dried over anhydrous sodium sulfate, filtered, and the filtrate was concentrated. The residue was purified by column chromatography (silica, hexanes/ethyl acetate or methanol/dichloromethane) or preparative HPLC (water/acetonitrile with 0.05% TFA) to afford the desired product.

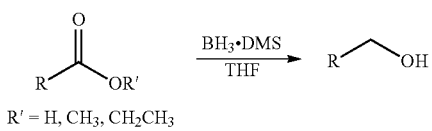

General Procedure E2 (Reduction—BH₃)

To a solution of methyl or ethyl ester or carboxylic acid (1.0 equiv) in THF at 0° C. was added BH₃.DMS (2 equiv). The mixture was warmed to rt and stirred for 4 h or until the starting material was consumed (monitored by LCMS analysis). The reaction was quenched with HCl (0.5 M), diluted with satd. aq. sodium bicarbonate, and extracted with ethyl acetate. The combined organic layer was dried over anhydrous sodium sulfate, filtered, and the filtrate was concentrated. The residue was purified by column chromatography (silica, hexanes/ethyl acetate or methanol/dichloromethane) or preparative HPLC (water/acetonitrile with 0.05% TFA) to afford the desired product. In some cases, HCl in methanol was used to form HCl salt of the desired product.

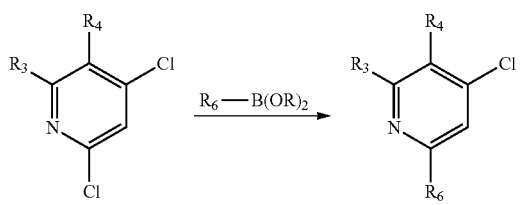

General Procedure F (Suzuki Coupling)

To a solution of dichloropyridine (1.0 equiv) in toluene/ethanol (2:1) was added boronic acid or ester (1.1 equiv), cesium carbonate (3 equiv) and tetrakis(triphenylphosphine)palladium (5 mol %). Nitrogen gas was passed through the suspension for 10 min. The reaction mixture was stirred with heat at 90° C. for 2-6 h or until the starting material was consumed (monitored by LCMS analysis). The reaction mixture was cooled, diluted with water, and extracted with ethyl acetate. The combined organic layer was dried over anhydrous sodium sulfate, filtered, and the filtrate was concentrated. The residue was purified by column chromatography (silica, hexanes/ethyl acetate) to afford the desired product.

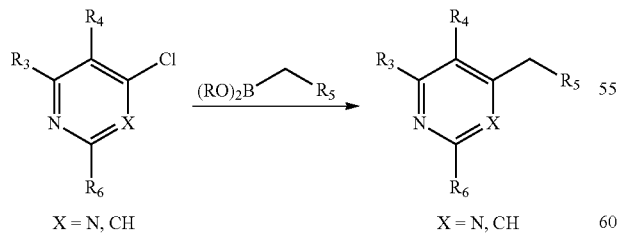

General Procedure G (Suzuki Coupling)

To a solution of chloropyridine or chloropyrimidine (1.0 equiv) in dioxane was added boronic ester (1.0-1.2 equiv), Pd(dppf)Cl₂ (10 mol %), and sodium carbonate (3 equiv). The mixture was degassed with a series of vacuum/argon exchanges. The reaction mixture was stirred with heat between 80-90° C. for 1-4 h or until the starting material was consumed (monitored by LCMS analysis). The reaction mixture was cooled, diluted with water, and extracted with ethyl acetate. The combined organic layer was dried over anhydrous sodium sulfate, filtered, and the filtrate was concentrated. The residue was purified by column chromatography (silica, hexanes/ethyl acetate or methanol/dichloromethane) or preparative HPLC (water/acetonitrile with 0.05% TFA) to afford the desired product. In some cases, HCl in methanol was used to form HCl salt of the desired product.

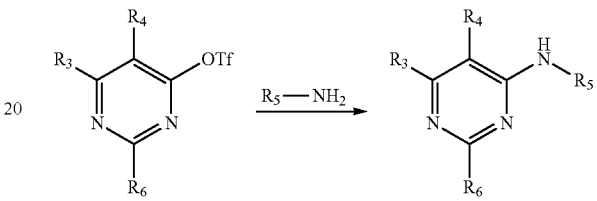

General Procedure H

To a solution of pyrimidinyl trifluoromethanesulfonate (1.0 equiv) in DMF was added the requisite aniline (1.0-1.5 equiv) and the reaction mixture was stirred with heat between 70-85° C. for 1-16 h or until the starting material was consumed (monitored by LCMS analysis). The reaction mixture was cooled, diluted with ethyl acetate and washed with water. The combined organic layer was dried over anhydrous sodium sulfate, filtered and the filtrate was concentrated. The residue was purified by column chromatography (silica, hexanes/ethyl acetate or methanol/dichloromethane) or preparative HPLC (water/acetonitrile with 0.05% TFA) to afford the desired product.

The invention is further illustrated by the following examples. In the Examples below, abbreviations are used which have meanings known in the art. For example: rt means room temperature; aq means aqueous; eq means equivalent; TLC means thin layer chromatography; Ar means argon; atm means atmosphere, a measurement; m.p. means melting point; and DCM means dichloromethane.

EXAMPLE 1

2-[4-[[2-(3-Chlorophenyl)-6,7-dihydro-5H-cyclopenta[b]pyridin-4-yl]amino]phenyl]acetonitrile

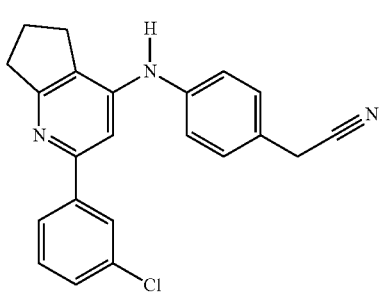 [SMILES: N#CCc1ccc(Nc2cc(-c3cccc(Cl)c3)nc3c2CCC3)cc1]

Step 1. 4-Chloro-2-(3-chlorophenyl)-6,7-dihydro-5H-cyclopenta[b]pyridine HCl salt

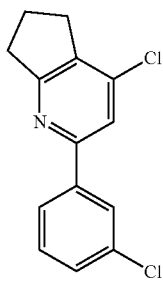

An 18-mL vial was charged with 2,4-dichloro-6,7-dihydro-5H-cyclopenta[b]pyridine HCl salt (225 mg, 1 mmol, 1 eq.), (3-chlorophenyl)boronic acid (165 mg, 1.06 mmol, 1.06 eq.), tetrakis(triphenylphosphine)palladium(0) (84 mg, 0.07 mmol, 0.07 eq.), and $K_2CO_3$ (500 mg, 3.6 mmol, 3.6 eq.). Toluene (6 ml), EtOH (2 ml) and water (2.5 ml) were added. The resulting mixture was stirred under Ar at 90° C. for 4 hr. until the starting chloride was consumed. After cooling to room temperature, the aqueous layer was separated and the organic layer was concentrated on a rotary evaporator. The residue was purified by chromatography on silica gel using hexane/dichloromethane (9:1 then 8:1) as eluent to afford 4-chloro-2-(3-chlorophenyl)-6,7-dihydro-5H-cyclopenta[b]pyridine, which was converted into its corresponding HCl salt by treating with 4N HCl in dioxane (228 mg, 76% yield).

Step 2. 2-[4-[[2-(3-Chlorophenyl)-6,7-dihydro-5H-cyclopenta[b]pyridin-4-yl]amino]phenyl]acetonitrile

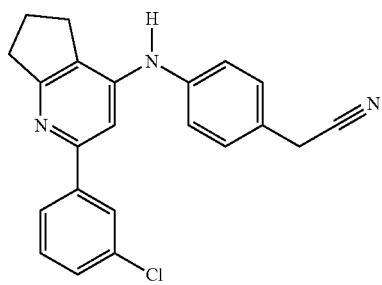 [SMILES: N#CCc1ccc(Nc2cc(-c3cccc(Cl)c3)nc3c2CCC3)cc1]

An 18-mL test tube was charged with 4-chloro-2-(3-chlorophenyl)-6,7-dihydro-5H-cyclopenta[b]pyridine HCl salt (30 mg, 0.1 mmol, 1 eq.) and 2-(4-aminophenyl)acetonitrile (30 mg, 0.23 mmol, 2.3 eq.). The resulting mixture was heated at 150° C. under Ar for 1 hr. After cooling to room temperature, the mixture was partitioned between $NaHCO_3$ aq. (10 ml) and dichloromethane (10 ml). The organic layer was collected and concentrated on a rotary evaporator. The residue was purified by chromatography on silica gel using dichloromethane followed by ethyl acetate as eluent to give 2-[4-[[2-(3-chlorophenyl)-6,7-dihydro-5H-cyclopenta[b]pyridin-4-yl]amino]phenyl]acetonitrile (16 mg, 44% yield). MW=359.85. $^1$H NMR (CDCl$_3$, 360 MHz) δ 7.84 (s, 1H), 7.68 (m, 1H), 7.32 (m, 4H), 7.21 (m, 2H), 7.15 (s, 1H), 5.82 (brs, 1H), 3.75 (s, 2H), 3.09 (t, J=7.50 Hz, 2H), 2.83 (t, J=7.20 Hz, 2H), 2.21 (m, 2H).

EXAMPLE 2

2-[4-[[2-(3-Chlorophenyl)-6,7-dihydro-5H-cyclopenta[b]pyridin-4-yl]amino]phenyl]acetic acid

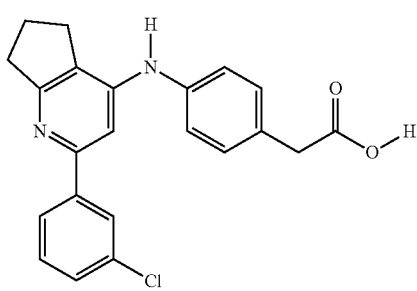 [SMILES: O=C(O)Cc1ccc(Nc2cc(-c3cccc(Cl)c3)nc3c2CCC3)cc1]

Step 1. Methyl 2-(4-aminophenyl)acetate

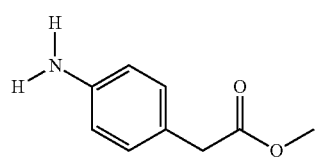

To a solution of 2-(4-aminophenyl)acetic acid (170 mg, 1.1 mmol) in a mixture of THF (4 ml), MeOH (1 ml) and dichloromethane (1 ml) in a 20-mL vial was added dropwise (trimethylsilyl)diazo-methane (1 ml, 2N in hexane) at OC. After the addition was complete, the resulting mixture was stirred at room temperature for 1 hr. The volatile material was removed under reduced pressure and the residue was purified by chromatography on silica gel using hexane/dichloromethane (2:1) followed by dichloromethane as eluent to give methyl 2-(4-aminophenyl)acetate as an yellowish oil (97 mg, 53% yield).

Step 2. Methyl 2-[4-[[2-(3-chlorophenyl)-6,7-dihydro-5H-cyclopenta[b]pyridin-4-yl]amino]phenyl]acetate

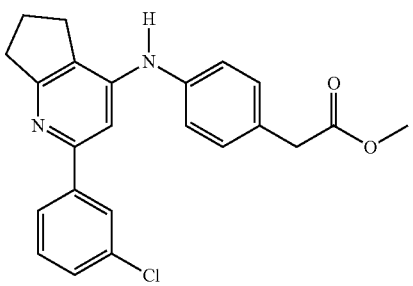 [SMILES: COC(=O)Cc1ccc(Nc2cc(-c3cccc(Cl)c3)nc3c2CCC3)cc1]

An 18-mL test tube was charged with 4-chloro-2-(3-chlorophenyl)-6,7-dihydro-5H-cyclopenta[b]pyridine HCl salt (30 mg, 0.1 mmol, 1 eq. Synthesis of this compound was described in step 1 of EXAMPLE 1) and methyl 2-(4-aminophenyl)acetate (33 mg, 0.2 mmol, 2 eq.). The resulting mixture was heated at 150° C. under Ar for 1 hr. After cooling to room temperature, the mixture was partitioned between NaHCO₃ aq. (10 ml) and dichloromethane (10 ml). The organic layer was collected and concentrated on a rotary evaporator. The residue was purified by chromatography on silica gel using dichloromethane followed by 1~3% of MeOH in dichloromethane as eluent to give methyl 2-[4-[[2-(3-chlorophenyl)-6,7-dihydro-5H-cyclopenta[b]pyridin-4-yl]amino]phenyl]acetate (31 mg, 77% yield).

Step 3. 2-[4-[[2-(3-Chlorophenyl)-6,7-dihydro-5H-cyclopenta[b]pyridin-4-yl]amino]phenyl]acetic acid

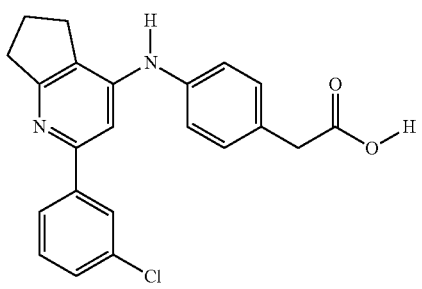

An 18-mL vial was charged with methyl 2-[4-[[2-(3-chlorophenyl)-6,7-dihydro-5H-cyclopenta[b]pyridin-4-yl]amino]phenyl]acetate (31 mg, 0.77 mmol, 1 eq.) and lithium hydroxide monohydrate (48 mg, 1.14 mmol, 1.48 eq.). To this was added THF (1 ml) and water (0.5 ml). The resulting mixture was stirred at room temperature overnight. Then 2N HCl aq. (0.6 ml) was added. The volatile materials were removed under reduced pressure to give a residue, which was purified by chromatography on silica gel using 2~5% of MeOH in dichloromethane as eluent to give 2-[4-[[2-(3-Chlorophenyl)-6,7-dihydro-5H-cyclopenta[b]pyridin-4-yl]amino]phenyl]acetic acid (26 mg, HCl salt, 81% yield). MW=378.85. ¹H NMR (DMSO-D₆, 360 MHz) δ 14.23 (brs, 1H), 12.39 (brs, 1H), 9.84 (brs, 1H), 7.91 (s, 1H), 7.70 (d, J=7.70 Hz, 1H), 7.63 (d, J=8.40, 1H), 7.57 (dd, J=7.70, 8.40 Hz, 1H), 7.36 (brs, 4H), 7.02 (s, 1H), 3.60 (s, 2H), 3.11 (t, J=7.90 Hz, 2H), 2.90 (t, J=7.40 Hz, 2H), 2.20 (m, 2H).

EXAMPLE 3

2-[4-[[2-(3-Chlorophenyl)-6,7-dihydro-5H-cyclopenta[b]pyridin-4-yl]amino]phenyl]acetamide

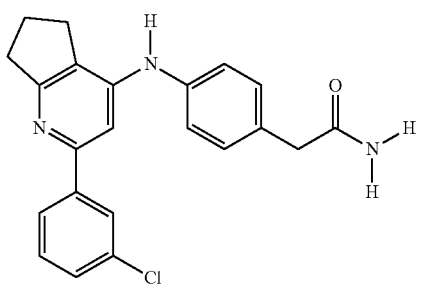 [SMILES: NC(=O)Cc1ccc(Nc2cc(-c3cccc(Cl)c3)nc3c2CCC3)cc1]

An 18 mL-vial was charged with 2-[4-[[2-(3-Chlorophenyl)-6,7-dihydro-5H-cyclopenta[b]pyridin-4-yl]amino]phenyl]acetonitrile (12 mg, 0.033 mmol, synthesis of this compound was described in EXAMPLE 1). Concentrated H₂SO₄ (0.5 ml) was added at 0° C. The mixture was standing at room temperature for 6 hr. And then the mixture was added very slowly to NaHCO₃ aq. at 0° C. The precipitate was collected and washed with water, dried. The product thus obtained was treated with 4N HCl in dioxane and the volatile material was removed under reduced pressure to give the desired product 2-[4-[[2-(3-chlorophenyl)-6,7-dihydro-5H-cyclopenta[b]pyridin-4-yl]amino]phenyl]acetamide as HCl salt (2.6 mg, 19% yield). MW=377.87. ¹H NMR (CDCl₃, 360 MHz) δ 7.83 (s, 1H), 7.69 (m, 1H), 7.18~7.30 (m, 7H), 5.77 (brs, 1H), 5.44 (brs, 2H), 3.58 (s, 2H), 3.08 (t, J=7.70 Hz, 2H), 2.83 (t, J=7.10 Hz, 2H), 2.21 (m, 2H).

EXAMPLE 4

2-[4-[[2-(3-Chlorophenyl)-6,7-dihydro-5H-cyclopenta[b]pyridin-4-yl]amino]phenoxy]acetic acid

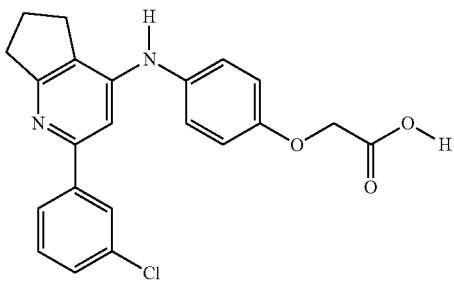 [SMILES: O=C(O)COc1ccc(Nc2cc(-c3cccc(Cl)c3)nc3c2CCC3)cc1]

Step 1. Methyl 2-[4-[[2-(3-chlorophenyl)-6,7-dihydro-5H-cyclopenta[b]pyridin-4-yl]amino]phenoxy]acetate

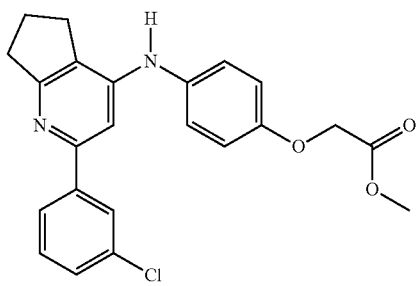 [SMILES: COC(=O)COc1ccc(Nc2cc(-c3cccc(Cl)c3)nc3c2CCC3)cc1]

An 18-mL vial was charged with methyl 2-(4-aminophenoxy)acetate (24 mg, 0.13 mmol, 2 eq.) and 4-Chloro-2-(3-chlorophenyl)-6,7-dihydro-5H-cyclopenta[b]pyridine HCl salt (20 mg, 0.066 mmol, 1 eq. See step 1 of EXAMPLE 1). The mixture was dissolved in a mixture of MeOH (1 ml) and dichloromethane (2 ml). After the volatile material was removed under reduced pressure, the residue was heated at 150° C. under argon for 1 hr. After cooling to room temperature, the reaction mixture was partitioned between NaHCO₃ aq. (10 ml) and ethyl acetate (10 ml). The organics was separated and dried over MgSO4. The solvent was removed under reduced pressure to give a residue, which was purified by chromatography on silica gel using dichloromethane followed by 0.1~0.3% methanol in dichloromethane as eluent to give the desired product methyl 2-[4-[[2-(3-chlorophenyl)-6,7-dihydro-5H-cyclopenta[b]pyridin-4-yl]amino]phenoxy]acetate as white solid (11.8 mg, 44% yield).

Step 2. 2-[4-[[2-(3-chlorophenyl)-6,7-dihydro-5H-cyclopenta[b]pyridin-4-yl]amino]phenoxy]acetic acid HCl salt

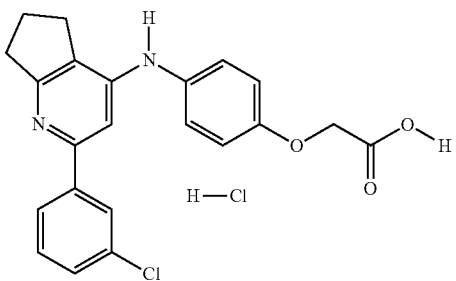

An 18-mL vial was charged with methyl 2-[4-[[2-(3-chlorophenyl)-6,7-dihydro-5H-cyclopenta[b]pyridin-4-yl]amino]phenoxy]acetate (11.8 mg, 0.029 mmol, 1 eq.) and LiOH/H$_2$O (42 mg, 1 mmol, 34 eq.). THF (1 ml) and H$_2$O (0.5 ml) was added to the vial. The resulting mixture was stirred at room temperature overnight. 2 N HCl aq. (0.5 ml) was added and the volatile material was removed under reduced pressure. The residue was purified by chromatography on silica gel using dichloromethane followed by 10% of methanol in dichloromethane as eluent to give 2-[4-[[2-(3-chlorophenyl)-6,7-dihydro-5H-cyclopenta[b]pyridin-4-yl]amino]phenoxy]acetic acid, which was treated with 4N HCl in dioxane (2 ml). After the volatile material was removed under reduced pressure, 2-[4-[[2-(3-chlorophenyl)-6,7-dihydro-5H-cyclopenta[b]pyridin-4-yl]amino]phenoxy]acetic acid HCl salt was obtained (8 mg, 65% yield). MW=431.31. $^1$H NMR (DMSO-D$_6$, 360 MHz) δ 7.88 (s, 1H), 7.70 (s, 1H), 7.47 (m, 2H), 7.23 (m, 2H), 6.94 (m, 3H), 4.67 (s, 2H), 2.95 (m, 2H), 2.82 (m, 2H), 2.09 (m, 2H).

EXAMPLE 5

4-[[2-(3-Chlorophenyl)-6,7-dihydro-5H-cyclopenta[b]pyridin-4-yl]amino]benzoic acid

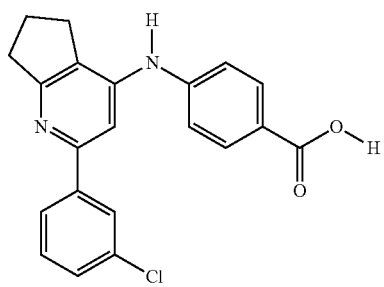 [SMILES: O=C(O)c1ccc(Nc2cc(-c3cccc(Cl)c3)nc3c2CCC3)cc1]

Step 1. Methyl 4-[[2-(3-chlorophenyl)-6,7-dihydro-5H-cyclopenta[b]pyridin-4-yl]amino]benzoate An 18-mL vial was charged with methyl 4-aminobenzoate (20 mg, 0.13 mmol, 2 eq.) and 4-Chloro-2-(3-chlorophenyl)-6,7-dihydro-5H-cyclopenta[b]pyridine HCl salt (20 mg, 0.066 mmol, 1 eq. See step 1 of EXAMPLE 1). The mixture was dissolved in a mixture of MeOH (1 ml) and dichloromethane (2 ml). After the volatile material was removed under reduced pressure, the residue was heated at 150° C. under argon for 1 hr. After cooling to room temperature, the reaction mixture was partitioned between NaHCO$_3$ aq. (10 ml) and ethyl acetate (10 ml). The organics was separated and dried over MgSO4. The solvent was removed under reduced pressure to give a residue, which was purified by chromatography on silica gel using dichloromethane followed by ethyl acetate as eluent to give the desired product methyl 4-[[2-(3-chlorophenyl)-6,7-dihydro-5H-cyclopenta[b]pyridin-4-yl]amino]benzoate (21.6 mg, 86% yield).

Step 2. 4-[[2-(3-chlorophenyl)-6,7-dihydro-5H-cyclopenta[b]pyridin-4-yl]amino]benzoic acid An 18-mL vial was charged with methyl 4-[[2-(3-chlorophenyl)-6,7-dihydro-5H-cyclopenta[b]pyridin-4-yl]amino]benzoate (20 mg, 0.053 mmol, 1 eq.) and LiOH/H$_2$O (47.4 mg, 1.13 mmol, 21 eq.). THF (1 ml), H$_2$O (0.3 ml) and MeOH (0.2 ml) was added to the vial. The resulting mixture was stirred at room temperature overnight. 2 N HCl aq. (0.5 ml) was added and the volatile material was removed under reduced pressure. The residue was purified by chromatography on silica gel using 5% of methanol in dichloromethane as eluent to give 4-[[2-(3-chlorophenyl)-6,7-dihydro-5H-cyclopenta[b]pyridin-4-yl]amino]benzoic acid (4.8 mg, 25% yield). MW=364.82. $^1$H NMR (DMSO-D$_6$, 360 MHz) δ 8.65 (s, 1H), 7.96 (s, 1H), 7.86 (m, 3H), 7.42 (m, 3H), 7.25 (d, J=8.31 Hz, 2H), 2.92 (t, J=7.86, 2H), 2.82 (t, J=6.93, 2H), 2.06 (m, 2H).

EXAMPLE 6

2-[4-[[2-(3-Chlorophenyl)-6,7-dihydro-5H-cyclopenta[b]pyridin-4-yl]amino]phenyl]ethanol

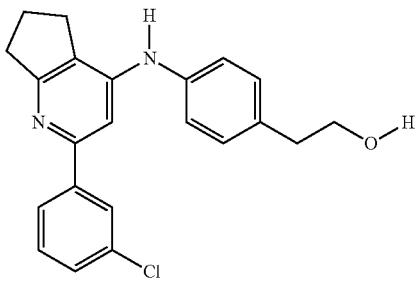 [SMILES: OCCc1ccc(Nc2cc(-c3cccc(Cl)c3)nc3c2CCC3)cc1]

Step 1. Methyl 2-[4-[[2-(3-chlorophenyl)-6,7-dihydro-5H-cyclopenta[b]pyridin-4-yl]amino]phenyl]acetate

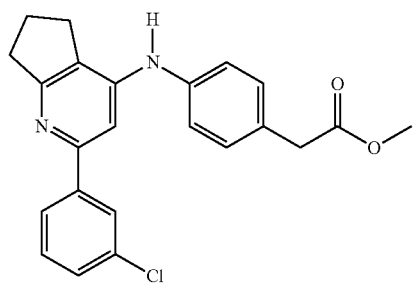 [SMILES: COC(=O)Cc1ccc(Nc2cc(-c3cccc(Cl)c3)nc3c2CCC3)cc1]

See step 2 in EXAMPLE 2.

Step 2. 2-[4-[[2-(3-Chlorophenyl)-6,7-dihydro-5H-cyclopenta[b]pyridin-4-yl]amino]phenyl]ethanol

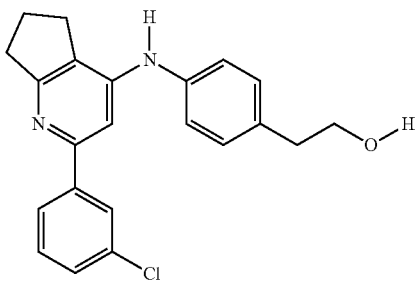 [SMILES: OCCc1ccc(Nc2cc(-c3cccc(Cl)c3)nc3c2CCC3)cc1]

An 18-mL vial was charged with methyl 2-[4-[[2-(3-chlorophenyl)-6,7-dihydro-5H-cyclopenta[b]pyridin-4-yl]amino]phenyl]acetate (20.7 mg, 0.053 mmol) and THF (2 ml). To the mixture was added LiAlH$_4$ (20 mg, 0.53 mmol, 10 eq.) portion-wise at 0 C. After the addition was complete, the resulting mixture was stirred under Ar at rt overnight. 2N HCl aq. (2 ml) was added followed by saturated NaHCO$_3$ aq. The mixture was extracted with ethyl acetate (3×5 ml). The organic layer was combined and concentrated on a rotary evaporator. The residue was purified by chromatography on silica gel using dichloromethane followed by ethyl acetate as eluent to afford the desired product (15 mg), of which $^1$H NMR indicates it contains impurities. The product thus obtained was re-purified by chromatography on silica gel using DCM followed by DCM/EA with a ratio of 9:1 to 2:1 in favor of DCM as eluent to give 2-[4-[[2-(3-chlorophenyl)-6,7-dihydro-5H-cyclopenta[b]pyridin-4-yl]amino]phenyl]ethanol (3.5 mg, 18% yield). MW=264.87. $^1$H NMR (CDCl$_3$, 360 MHz) δ 7.84 (m, 2H), 7.41 (m, 3H), 7.21 (m, 3H), 7.16 (s, 1H), 5.95 (brs, 1H), 3.90 (m, 2H), 3.18 (m, 2H), 2.87 (m, 4H), 2.24 (m, 2H).

EXAMPLE 7

2-[4-[[6-(3-Chlorophenyl)-3-ethyl-2-methyl-4-pyridyl]amino]phenyl]acetic acid

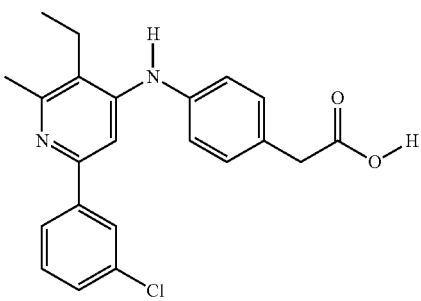 [SMILES: CCc1c(Nc2ccc(CC(=O)O)cc2)cc(-c2cccc(Cl)c2)nc1C]

Step 1. Ethyl(Z)-3-amino-2-ethyl-but-2-enoate

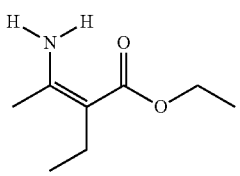

A 100-mL round bottom flask was charged with ethyl 2-ethyl-3-oxo-butanoate (5 g, 90% purity, 28 mmol), ammonium acetate (22 g, 280 mmol, 10 eq), ammonia (2N in EtOH, 14 ml, 1 eq.), anhydrous sodium sulfate (8 g, 56 mmol, 2 eq.) and MeOH (30 ml). The resulting mixture was stirred at room temperature overnight. The volatile material was removed under reduced pressure and the residue was treated with dichloromethane (40 ml). Insoluble material was removed by filtration and washed with dichloromethane (2×20 ml). The organics was washed with aqueous sodium bicarbonate, dried over Na$_2$SO$_4$. Removal of solvent gave ethyl(Z)-3-amino-2-ethyl-but-2-enoate (4.1 g, 82% yield) as a white solid.

Step 2. Ethyl(Z)-3-[(3-ethoxy-3-oxo-propanoyl)amino]-2-ethyl-but-2-enoate

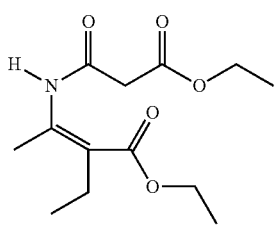 [SMILES: CCOC(=O)CC(=O)N/C(C)=C(/CC)C(=O)OCC]

A 100-mL round bottom flask was charged with ethyl(Z)-3-amino-2-ethyl-but-2-enoate (880 mg, 5.6 mmol, 1 eq.), diisopropylethylamine (750 mg, 5.8 mmol, 1.04 eq.) and THF (10 ml). To the mixture was added ethyl 3-chloro-3-oxo-propanoate (840 mg, 5.6 mmol, 1 eq.) drop-wise by a syringe at 0° C. After the addition was complete, the resulting mixture was stirred at room temperature overnight and then added to aqueous sodium bicarbonate solution. The mixture was extracted with ethyl acetate (3×15 ml). The combined organic layer was dried over anhydrous Na$_2$SO$_4$. Removal of solvent gave the crude product ethyl(Z)-3-[(3-ethoxy-3-oxo-propanoyl)amino]-2-ethyl-but-2-enoate as yellow oil (1.3 g, 86% yield).

Step 3. Ethyl 5-ethyl-4-hydroxy-6-methyl-2-oxo-1H-pyridine-3-carboxylate

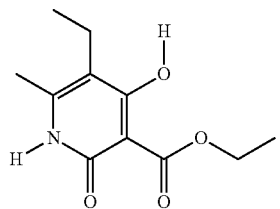 [SMILES: CCOC(=O)c1c(O)c(CC)c(C)[nH]c1=O]

A 50-mL round bottom flask was charged with ethyl(Z)-3-[(3-ethoxy-3-oxo-propanoyl)amino]-2-ethyl-but-2-enoate (540 mg, 2 mmol, 1 eq.), sodium methoxide (750 mg, 6.8 mmol, 3.4 eq. 25 wt. % in MeOH) and EtOH (10 ml). The mixture was stirred under reflux for 1 hr. After cooling to room temperature, the mixture was acidified by addition of 2N HCl aq. (5 ml) and extracted with ethyl acetate (3×10 ml). The combined organic layers were dried over anhydrous sodium sulfate and concentrated on a rotary evaporator to afford crude ethyl 5-ethyl-4-hydroxy-6-methyl-2-oxo-1H-pyridine-3-carboxylate (205 mg, 46% yield) as yellow solid.

Step 4. 5-Ethyl-4-hydroxy-6-methyl-1H-pyridin-2-one

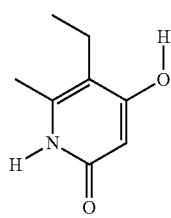

A 50-mL round bottom flask was charged with ethyl 5-ethyl-4-hydroxy-6-methyl-2-oxo-1H-pyridine-3-carboxylate (117 mg, 0.52 mmol) and 1N HCl (10 ml). The mixture was stirred under reflux overnight. After cooling to room temperature, the mixture was neutralized by addition of aqueous NaHCO$_3$ to pH=7. The precipitate was collected by filtration and washed with water. After dried, 5-ethyl-4-hydroxy-6-methyl-1H-pyridin-2-one was obtained (43 mg, 54% yield).

Step 5. 4,6-Dichloro-3-ethyl-2-methyl-pyridine

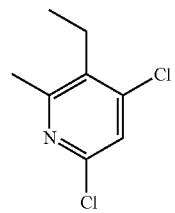

A 18-mL vial was charged with 5-ethyl-4-hydroxy-6-methyl-1H-pyridin-2-one (200 mg, 1.3 mmol). POCl$_3$ (1 ml) was added. The resulting mixture was stirred at 90 C overnight. After cooling to room temperature, the volatile material was removed under reduced pressure and the residue was partitioned between ethyl acetate and aqueous sodium bicarbonate solution. The organic layer was separated and passed through a plug of silica gel. Removal of solvent under reduced pressure gave 4,6-dichloro-3-ethyl-2-methyl-pyridine (100 mg, 40% yield).

Step 6. 4-Chloro-6-(3-chlorophenyl)-3-ethyl-2-methyl-pyridine

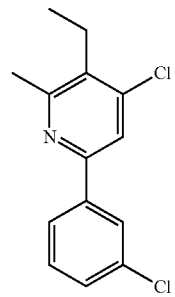 [SMILES: CCc1c(Cl)cc(-c2cccc(Cl)c2)nc1C]

A 50-mL round bottomed flask was charged with 2,4-dichloro-5-ethyl-6-methyl-1,2-dihydropyridine (94 mg, 0.49 mmol, 1 eq.), (3-chlorophenyl)boronic acid (77 mg, 0.49 mmol, 1 eq.), tetrakis(triphenylphosphine)palladium(0) (50 mg, 0.09 mmol, 0.09 eq.), and K$_2$CO$_3$ (200 mg, 1.45 mmol, 3 eq.). Toluene (4 ml), EtOH (1.6 ml) and water (1.6 ml) were added. The resulting mixture was stirred under Ar at 90° C. for 3 hr. until the starting chloride was consumed. After cooling to room temperature, the aqueous layer was separated and the organic layer was concentrated on a rotary evaporator. The residue was purified by chromatography on silica gel using hexane/dichloromethane (49:1, then 9:1 and 8:1) as eluent to afford 4-chloro-6-(3-chlorophenyl)-3-ethyl-2-methyl-pyridine, which was converted into its corresponding HCl salt by treating with 4N HCl in dioxane (120 mg, 81% yield).

Step 7. Methyl 2-[4-[[6-(3-chlorophenyl)-3-ethyl-2-methyl-4-pyridyl]amino]phenyl]acetate

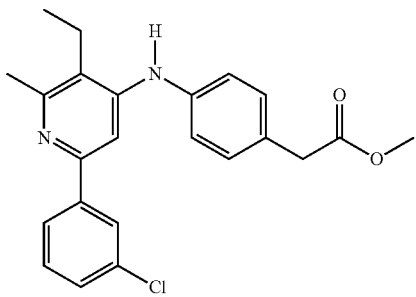

An 18-mL test tube was charged with 4-Chloro-6-(3-chlorophenyl)-3-ethyl-2-methyl-pyridine HCl salt (15 mg, 0.05 mmol, 1 eq.) and methyl 2-(4-aminophenyl)acetate (20 mg, 0.12 mmol, 2.4 eq.). The resulting mixture was heated at 150° C. under Ar for 1 hr. After cooling to room temperature, the mixture was partitioned between NaHCO$_3$ aq. (10 ml) and dichloromethane (10 ml). The organic layer was collected and concentrated on a rotary evaporator. The residue was purified by chromatography on silica gel using dichloromethane/ethyl acetate (9:1 then 3:1) as eluent to give methyl 2-[4-[[6-(3-chlorophenyl)-3-ethyl-2-methyl-4-pyridyl]amino]phenyl]acetate (8 mg, 41% yield).

Step 8. 2-[4-[[6-(3-Chlorophenyl)-3-ethyl-2-methyl-4-pyridyl]amino]phenyl]acetic acid

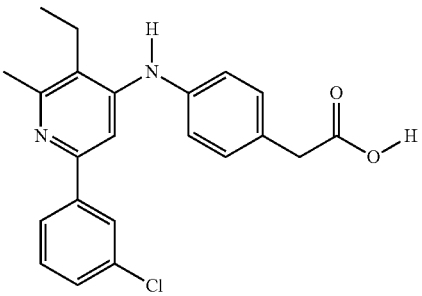 [SMILES: CCc1c(Nc2ccc(CC(=O)O)cc2)cc(-c2cccc(Cl)c2)nc1C]

An 18-mL vial was charged with methyl 2-[4-[[6-(3-chlorophenyl)-3-ethyl-2-methyl-4-pyridyl]amino]phenyl]acetate (8 mg, 0.02 mmol, 1 eq.) and lithium hydroxide monohydrate (13 mg, 0.31 mmol, 15 eq.). To this was added THF (1 ml) and water (0.4 ml). The resulting mixture was stirred at room temperature overnight. Then 2N HCl aq. (0.12 ml) was added. The volatile materials were removed under reduced pressure to give a residue, which was purified by chromatography on silica gel using 2~4% of MeOH in dichloromethane as eluent to give 2-[4-[[6-(3-Chlorophenyl)-3-ethyl-2-methyl-4-pyridyl]amino]phenyl]acetic acid (7 mg, 91% yield). MW=380.87. $^1$H NMR (Methanol-D$_4$, 360 MHz) δ 7.69 (s, 1H), 7.48~7.58 (m, 3H), 7.44 (d, J=8.2 Hz, 2H), 7.33 (d, J=8.2 Hz, 2H), 6.89 (s, 1H), 3.67 (s, 2H), 2.85 (q, J=7.5 Hz, 2H), 2.66 (s, 3H), 1.24 (t, J=7.5 Hz, 3H).

EXAMPLE 8

4-[4-[[2-(3-Chlorophenyl)-6,7-dihydro-5H-cyclopenta[b]pyridin-4-yl]amino]phenyl]butanoic acid

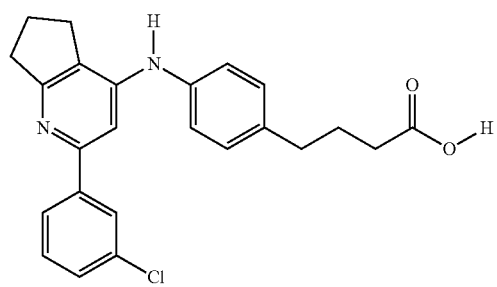 [SMILES: O=C(O)CCCc1ccc(Nc2cc(-c3cccc(Cl)c3)nc3c2CCC3)cc1]

Step 1. Methyl 4-(4-aminophenyl)butanoate

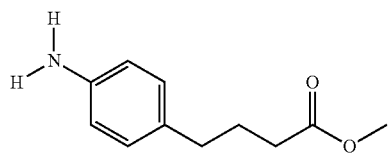

To a solution of 4-(4-aminophenyl)butanoic acid (180 mg, 1 mmol) in a mixture of THF (4 ml), MeOH (1 ml) and dichloromethane (1 ml) in a 20-mL vial was added dropwise (trimethylsilyl)diazo-methane (1 ml, 2N in hexane) at 0° C. After the addition was complete, the resulting mixture was stirred at room temperature for 1 hr. The volatile material was removed under reduced pressure and the residue was purified by chromatography on silica gel using hexane/dichloromethane (2:1) followed by dichloromethane as eluent to give methyl 4-(4-aminophenyl)butanoate as an yellowish oil (55 mg, 28% yield).

Step 2. Methyl 4-[4-[[2-(3-chlorophenyl)-6,7-dihydro-5H-cyclopenta[b]pyridin-4-yl]amino]phenyl]butanoate

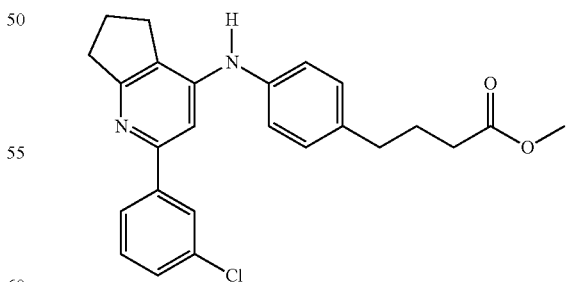

An 18-mL test tube was charged with 4-chloro-2-(3-chlorophenyl)-6,7-dihydro-5H-cyclopenta[b]pyridine HCl salt (10 mg, 0.033 mmol, 1 eq. Synthesis of this compound was described in step 1 of EXAMPLE 1) and methyl 4-(4-aminophenyl)butanoate (17 mg, 0.088 mmol, 2.7 eq.). The resulting mixture was heated at 150° C. under Ar for 1 hr. After cooling to room temperature, the mixture was partitioned between NaHCO₃ aq. (10 ml) and dichloromethane (10 ml). The organic layer was collected and concentrated on a rotary evaporator. The residue was purified by chromatography on silica gel using dichloromethane followed by 5% of ethyl acetate in dichloromethane as eluent to give methyl 4-[4-[[2-(3-chlorophenyl)-6,7-dihydro-5H-cyclopenta[b]pyridin-4-yl]amino]phenyl]butanoate (11 mg, 79% yield).

Step 3 4-[4-[[2-(3-Chlorophenyl)-6,7-dihydro-5H-cyclopenta[b]pyridin-4-yl]amino]phenyl]butanoic acid

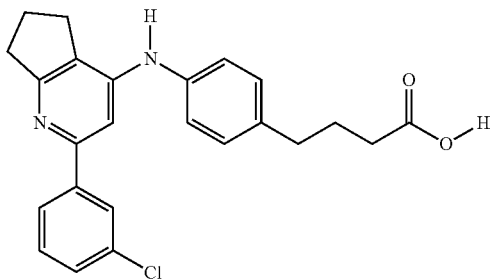 [SMILES: O=C(O)CCCc1ccc(Nc2cc(-c3cccc(Cl)c3)nc3c2CCC3)cc1]

An 18-mL vial was charged with methyl 4-[4-[[2-(3-chlorophenyl)-6,7-dihydro-5H-cyclopenta[b]pyridin-4-yl]amino]phenyl]butanoate (10 mg, 0.024 mmol, 1 eq.) and lithium hydroxide monohydrate (45 mg, 1.07 mmol, 44 eq.). To this was added THF (1 ml) and water (0.5 ml). The resulting mixture was stirred at room temperature overnight. Then 1N HCl aq. (1 ml) was added. The volatile materials were removed under reduced pressure to give a residue, which was purified by chromatography on silica gel using 2~4% of MeOH in dichloromethane as eluent to give the title compound (7.8 mg, 80% yield). MW=406.90. ¹H NMR (DMSO-D₆, 400 MHz) δ 8.11 (s, 1H), 7.91 (s, 1H), 7.74 (m, 1H), 7.42 (m, 2H), 7.20 (m, 5H), 2.93 (m, 2H), 2.82 (m, 2H), 2.58 (m, 2H), 2.26 (m, 2H), 2.10 (m, 2H), 1.79 (m, 2H).

EXAMPLE 9

2-[4-[[2-(5-Chloro-2-thienyl)-6,7-dihydro-5H-cyclopenta[d]pyrimidin-4-yl]amino]phenyl]acetic acid

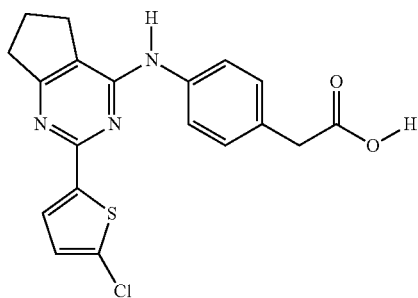 [SMILES: O=C(O)Cc1ccc(Nc2nc(-c3ccc(Cl)s3)nc3c2CCC3)cc1]

Step 1, 5-Chlorothiophene-2-carboxamidine HCl salt

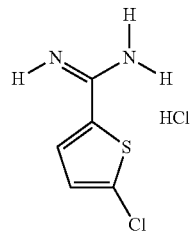

An 18-mL vial was charged with 5-chlorothiophene-2-carbonitrile (1 g, 7 mmol, 1 eq.), methanol (5 ml), Sodium methoxide (25 w % in methanol, 151 mg, 0.7 mmol, 0.1 eq.) was added. The mixture was stirred at rt for 3 hr. and then ammonium chloride (470 mg, 8.8 mmol, 1.25 eq.) was added. The resulting mixture was stirred at rt for 48 hr. The volatile material was removed under reduced pressure and the residue was treated with ether. The solid was collected by filtration and washed with ether, dried. The crude product (1.42 g) thus obtained contains inorganic salt and was forwarded to the next step without any further purification.

Step 2, 2-(5-Chloro-2-thienyl)-3,5,6,7-tetrahydrocyclopenta[d]pyrimidin-4-one

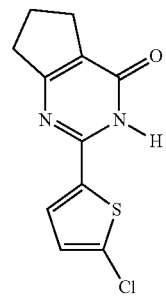 [SMILES: O=c1[nH]c(-c2ccc(Cl)s2)nc2c1CCC2]

A 50-mL round bottomed flask was charged with 5-chlorothiophene-2-carboxamidine HCl salt (400 mg, ~2 mmol, 1 eq.), ethyl 2-oxocyclopentanecarboxylate (320 mg, 2 mmol, 1 eq.), and ethanol (10 ml). To the mixture was added sodium methoxide (25 w % in methanol, 540 mg, 2.5 mmol, 1.25 eq.). The resulting mixture was stirred under reflux for 20 hr. After cooling to room temperature, the mixture was evaporated under reduced pressure to dryness and the residue was treated with 1N HCl (6 ml). Solid was collected by filtration and washed water followed by ether. The product thus obtained was forwarded to the next step without any further purification (360 mg, 71% yield).

Step 3, 4-Chloro-2-(5-chloro-2-thienyl)-6,7-dihydro-5H-cyclopenta[d]pyrimidine

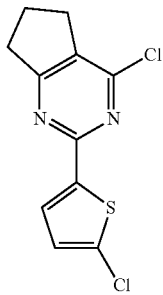 [SMILES: Clc1ccc(-c2nc(Cl)c3c(n2)CCC3)s1]

An 18-mL vial was charged with 2-(5-chloro-2-thienyl)-3,5,6,7-tetrahydrocyclopenta[d]pyrimidin-4-one (180 mg, 0.71 mmol). POCl₃ (1 ml) was added. The resulting mixture was stirred at 90 C for 4 hr. After cooling to room temperature, the mixture was added dropwise slowly to cold NaHCO₃ aq. Dichloromethane was added. The organic layer was separated and passed through a plug of silica gel, using dichloromethane as eluent to give 4-chloro-2-(5-chloro-2-thienyl)-6,7-dihydro-5H-cyclopenta[d]pyrimidine (178 mg, 92% yield).

Step 4, 2-[4-[[2-(5-Chloro-2-thienyl)-6,7-dihydro-5H-cyclopenta[d]pyrimidin-4-yl]amino]phenyl]acetic acid

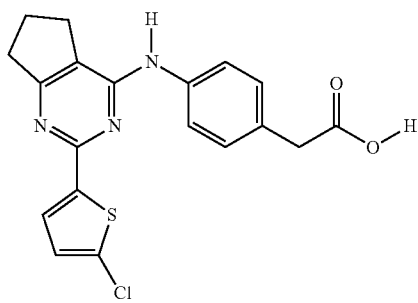 [SMILES: O=C(O)Cc1ccc(Nc2nc(-c3ccc(Cl)s3)nc3c2CCC3)cc1]

An 18-mL vial was charged with 4-chloro-2-(5-chloro-2-thienyl)-6,7-dihydro-5H-cyclopenta[d]pyrimidine (30 mg, 0.11 mmol, 1.1 eq.), 2-(4-aminophenyl)acetic acid (15 mg, 0.1 mmol, 1 eq.), and AcOH (1 ml). To the mixture was added HCl (4 N in dioxane, 5 drops) The resulting mixture was stirred at 100° C. for 2 hr. After cooling to rt, the reaction mixture was diluted with addition of water. The precipitate was collected by filtration and washed with water followed by dichloromethane, The product thus obtained (30 mg, 78% yield) was further treated with ethyl acetate to afford 2-[4-[[2-(5-chloro-2-thienyl)-6,7-dihydro-5H-cyclopenta[d]pyrimidin-4-yl]amino]phenyl]acetic acid (7.2 mg). MW=385.87. ¹H NMR (DMSO-D₆, 360 MHz) δ 9.22 (brs, 1H), 7.76 (d, J=3.9 Hz, 1H), 7.70 (d, J=8.2 Hz, 2H), 7.26 (d, J=8.2 Hz, 2H), 7.21 (d, J=3.9 Hz, 1H), 3.55 (s, 2H), 2.87 (m, 4H), 2.09 (m, 2H).

EXAMPLE 10

2-[4-[[2-(3-Chlorophenyl)-6,7-dihydro-5H-cyclopenta[d]pyrimidin-4-yl]amino]phenyl]acetic acid

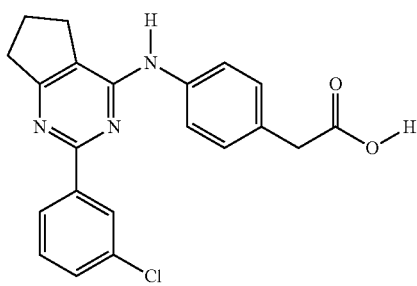

Step 1, Ethyl 3-chlorobenzenecarboximidate hydrochloride

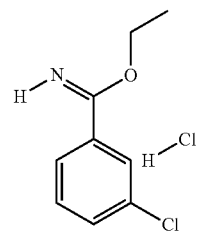

An 100-mL round bottomed flask was charged with 3-chlorobenzonitrile (2.75 g, 20 mmol, 1 eq.), ethanol (1 g, 22 mmol, 1.1 eq.), HCl (4 N in dioxane, 20 ml, 80 mmol, 4 eq.). The resulting mixture was stirred at rt for 48 hr. The volatile material was removed under reduced pressure and the residue was treated with ether. Solid was collected by filtration and washed with ether. The product thus obtained was forwarded to the next step without any further purification (2.87 g, 65% yield).

Step 2, 3-Chlorobenzamidine hydrochloride

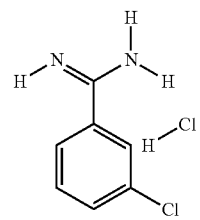

A 18-mL vial was charged with ethyl 3-chlorobenzenecarboximidate hydrochloride (450 mg, 2 mmol, 1 eq.) and NH₃ (2N in ethanol, 12 ml, 24 mmol, 12 eq.). The resulting mixture was stirred at rt overnight. The volatile material was removed under reduced pressure and the product thus obtained was forwarded to the next step without any further purification.

Step 3, 2-(3-Chlorophenyl)-3,5,6,7-tetrahydrocyclopenta[d]pyrimidin-4-one

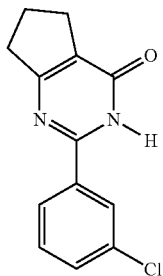 [SMILES: O=c1[nH]c(-c2cccc(Cl)c2)nc2c1CCC2]

2-(3-Chlorophenyl)-3,5,6,7-tetrahydrocyclopenta[d]pyrimidin-4-one was prepared in a similar manner to that described in Step 2 of EXAMPLE 9 in 45% yield on 2 mmol scale reaction (276 mg).

Step 4, 4-Chloro-2-(3-chlorophenyl)-6,7-dihydro-5H-cyclopenta[d]pyrimidine

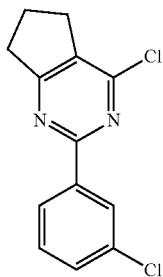

4-Chloro-2-(3-chlorophenyl)-6,7-dihydro-5H-cyclopenta[d]pyrimidine was prepared in a similar manner to that described in Step 3 of EXAMPLE 9 in 98% yield on 0.57 mmol scale reaction (147 mg).

Step 5, 2-[4-[[2-(3-Chlorophenyl)-6,7-dihydro-5H-cyclopenta[d]pyrimidin-4-yl]amino]phenyl]acetic acid

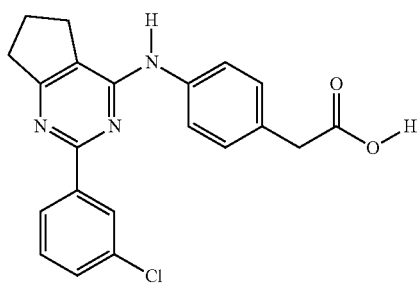 [SMILES: O=C(O)Cc1ccc(Nc2nc(-c3cccc(Cl)c3)nc3c2CCC3)cc1]

2-[4-[[2-(3-Chlorophenyl)-6,7-dihydro-5H-cyclopenta[d]pyrimidin-4-yl]amino]phenyl]acetic acid was prepared in a similar manner to that described in Step 4 of EXAMPLE 9 in 38% yield on 0.1 mmol scale reaction (15 mg). MW=379.84. $^1$H NMR (DMSO-D$_6$, 360 MHz) δ 9.27 (brs, 1H), 8.24 (s, 1H), 8.19 (d, J=7.3 Hz, 1H), 7.70 (d, J=8.3 Hz, 2H), 7.56 (m, 2H), 7.27 (d, J=8.3 Hz, 2H), 3.56 (s, 2H), 2.95 (t, J=8.2 Hz, 2H), 2.89 (t, J=7.0 Hz, 2H), 2.12 (m, 2H).

EXAMPLE 11

2-Acetamido-2-[4-[[2-(5-chloro-2-thienyl)-6,7-dihydro-5H-cyclopenta[d]pyrimidin-4-yl]amino]phenyl]acetic acid

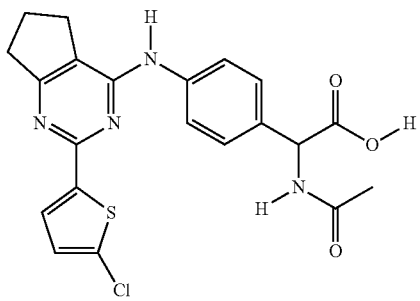 [SMILES: CC(=O)NC(C(=O)O)c1ccc(Nc2nc(-c3ccc(Cl)s3)nc3c2CCC3)cc1]

2-Acetamido-2-[4-[[2-(5-chloro-2-thienyl)-6,7-dihydro-5H-cyclopenta[d]pyrimidin-4-yl]amino]phenyl]acetic acid was prepared in a similar manner to that described in Step 4 of EXAMPLE 9 using 2-acetamido-2-(4-aminophenyl)acetic acid instead of 2-(4-aminophenyl)acetic acid as reactant in 99% yield on 0.058 mmol scale reaction (24.8 mg). MW=442.92. $^1$H NMR (Methanol-D$_4$, 360 MHz) δ 7.81 (d, J=8.6 Hz, 2H), 7.68 (d, J=4.0 Hz, 1H), 7.41 (d, J=8.6 Hz, 2H), 7.01 (d, J=4.0 Hz, 1H), 5.42 (s, 1H), 2.94 (t, J=7.7 Hz, 2H), 2.88 (t, J=7.4 Hz, 2H), 2.18 (m, 2H), 2.01 (s, 3H).

EXAMPLE 12

2-Amino-2-[4-[[2-(5-chloro-2-thienyl)-6,7-dihydro-5H-cyclopenta[d]pyrimidin-4-yl]amino]phenyl]acetic acid hydrochloride

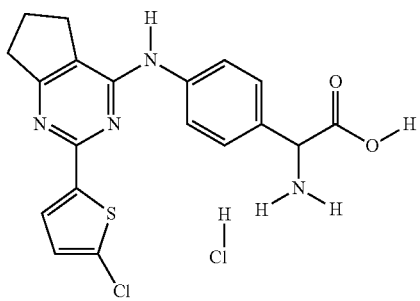

An 18-mL vial was charged with 2-acetamido-2-[4-[[2-(5-chloro-2-thienyl)-6,7-dihydro-5H-cyclopenta[d]pyrimidin-4-yl]amino]phenyl]acetic acid (11 mg, 0.025 mmol) and 1N HCl aq. (1 ml). The mixture was stirred at 100° C. for 24 hr. The volatile material was removed under reduced pressure to dryness, generating the title compound as HCl salt (5.2 mg, 48% yield). MW=437.34. $^{1}$H NMR (Methanol-$D_4$, 360 MHz) δ 7.97 (d, J=4.2 Hz, 1H), 7.84 (d, J=8.6 Hz, 2H), 7.62 (d, J=8.6 Hz, 2H), 7.2 (d, J=4.0 Hz, 1H), 5.17 (s, 1H), 3.17 (t, J=7.6 Hz, 2H), 3.01 (t, J=7.4 Hz, 2H), 2.35 (m, 2H).

EXAMPLE 13

4-[4-[[2-(5-Chloro-2-thienyl)-6,7-dihydro-5H-cyclopenta[d]pyrimidin-4-yl]amino]phenyl]butanoic acid

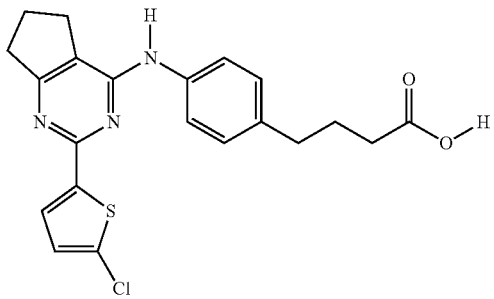 [SMILES: O=C(O)CCCc1ccc(Nc2nc(-c3ccc(Cl)s3)nc3c2CCC3)cc1]

The title compound was prepared in a similar manner to that described in Step 4 of EXAMPLE 9 using 4-(4-aminophenyl)butanoic acid instead of 2-(4-aminophenyl)acetic acid as reactant in 42% yield on 0.033 mmol scale reaction (10 mg). MW=413.92. $^{1}$H NMR (DMSO-$D_6$, 360 MHz) δ 8.87 (s, 1H), 7.68 (d, J=7.8 Hz, 2H), 7.63 (brs, 1H), 7.16 (m, 3H), 2.83 (m, 4H), 2.56 (m, 2H), 2.20 (t, J=7.4 Hz, 2H), 2.06 (m, 2H), 1.79 (m, 2H).

EXAMPLE 14

4-[4-[[2-(3-Chlorophenyl)-6,7-dihydro-5H-cyclopenta[d]pyrimidin-4-yl]amino]phenyl]butanoic acid

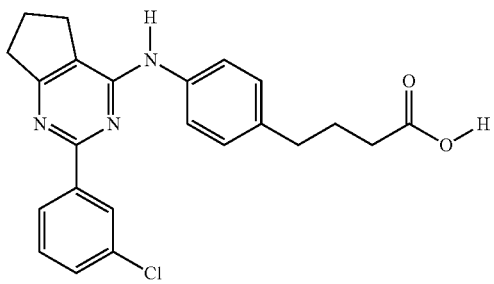 [SMILES: O=C(O)CCCc1ccc(Nc2nc(-c3cccc(Cl)c3)nc3c2CCC3)cc1]

The title compound was prepared in a similar manner to that described in Step 4 of EXAMPLE 9 using 4-(4-aminophenyl)butanoic acid instead of 2-(4-aminophenyl)acetic acid as reactant in 24% yield on 0.033 mmol scale reaction (5.6 mg). MW=407.89. $^{1}$H NMR (DMSO-$D_6$, 360 MHz) δ 8.80 (s, 1H), 8.25 (m, 2H), 7.68 (d, J=8.4 Hz, 2H), 7.51 (m, 2H), 7.17 (d, J=8.4 Hz, 2H), 2.86 (m 4H), 2.56 (m, 2H), 2.22 (m, 2H), 2.08 (m, 2H), 1.79 (m, 2H).

EXAMPLE 15

3-[4-[[2-(5-Chloro-2-thienyl)-6,7-dihydro-5H-cyclopenta[d]pyrimidin-4-yl]amino]phenyl]propanoic acid

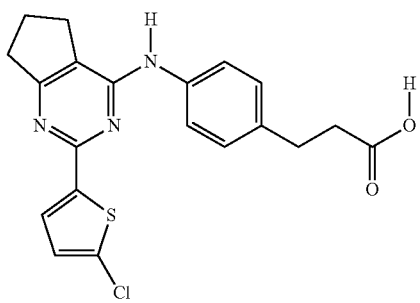 [SMILES: O=C(O)CCc1ccc(Nc2nc(-c3ccc(Cl)s3)nc3c2CCC3)cc1]

The title compound was prepared in a similar manner to that described in Step 4 of EXAMPLE 9 using 3-(4-aminophenyl)propanoic acid instead of 2-(4-aminophenyl)acetic acid as reactant in 41% yield on 0.036 mmol scale reaction (6 mg). MW=399.89. $^{1}$H NMR (DMSO-$D_6$, 400 MHz) δ 8.80 (s, 1H), 7.71 (d, J=8.4 Hz, 2H), 7.62 (d, J=4.0 Hz, 1H), 7.22 (d, J=8.4 Hz, 2H), 7.16 (d, J=4.0 Hz, 1H), 2.83 (m, 6H), 2.55 (t, J=8.0 Hz, 2H), 2.07 (m, 2H).

EXAMPLE 16

3-[4-[[2-(3-Chlorophenyl)-6,7-dihydro-5H-cyclopenta[d]pyrimidin-4-yl]amino]phenyl]propanoic acid

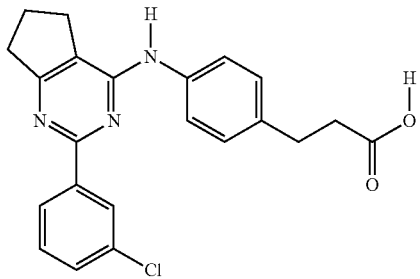 [SMILES: O=C(O)CCc1ccc(Nc2nc(-c3cccc(Cl)c3)nc3c2CCC3)cc1]

The title compound was prepared in a similar manner to that described in Step 4 of EXAMPLE 9 using 3-(4-aminophenyl)propanoic acid instead of 2-(4-aminophenyl)acetic acid as reactant in 70% yield on 0.036 mmol scale reaction (10 mg). MW=393.87. $^{1}$H NMR (DMSO-$D_6$, 400 MHz) δ

8.82 (s, 1H), 8.25 (m, 2H), 7.71 (d, J=8.4 Hz, 2H), 7.53 (m, 2H), 7.23 (d, J=8.4 Hz, 2H), 2.88 (m, 6H), 2.52 (m, 2H), 2.10 (m, 2H).

EXAMPLE 17

2-(4-(6-(3-chlorophenyl)-3-ethyl-2-methylpyridin-4-ylamino)phenyl)acetonitrile

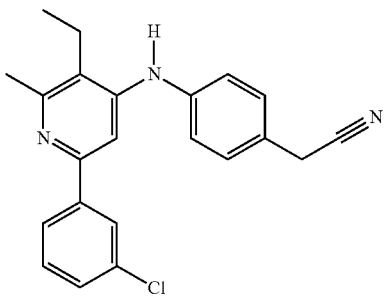 [SMILES: CCc1c(Nc2ccc(CC#N)cc2)cc(-c2cccc(Cl)c2)nc1C]

The title compound was prepared in a similar manner to those described in step 7 of EXAMPLE 7 using 2-(4-aminophenyl)acetonitrile instead of methyl 2-(4-aminophenyl)acetate as reactant in 14% yield on 0.05 mmol scale reaction (2.7 mg). MW=361.87. 1H NMR (Methanol-$D_4$, 360 MHz) δ 7.70 (s, 1H), 7.54 (m, 1H), 7.36 (m, 4H), 7.23 (d, J=8.4 Hz, 2H), 7.11 (s, 1H), 3.88 (s, 2H), 2.76 (q, J=7.5 Hz, 2H), 2.54 (s, 3H), 1.20 (t, J=7.5 Hz, 3H).

EXAMPLE 18

2-[4-[[2-(5-chloro-2-thienyl)-6,7-dihydro-5H-cyclopenta[d]pyrimidin-4-yl]amino]phenyl]acetonitrile

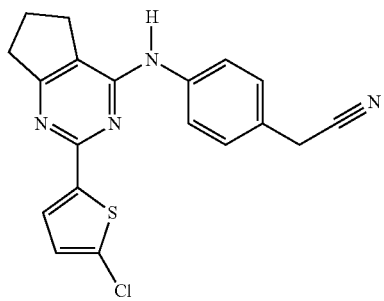 [SMILES: N#CCc1ccc(Nc2nc(-c3ccc(Cl)s3)nc3c2CCC3)cc1]

The title compound was prepared in a similar manner to that described in Step 4 of EXAMPLE 9 using 2-(4-aminophenyl)acetonitrile instead of 2-(4-aminophenyl)acetic acid as reactant in 57% yield on 0.1 mmol scale reaction (21 mg). MW=366.87. $^1$H NMR (CDCl$_3$, 360 MHz) δ 7.70 (d, J=8.5 Hz, 2H), 7.67 (d, J=3.9 Hz, 1H), 7.34 (d, J=8.5 Hz, 2H), 6.91 (d, J=3.9 Hz, 1H), 6.27 (brs, 1H), 3.75 (s, 2H), 2.98 (t, J=7.7 Hz, 2H), 2.79 (t, J=7.3 Hz, 2H), 2.18 (m, 2H).

EXAMPLE 19

2-[4-[[2-(3-chlorophenyl)-6,7-dihydro-5H-cyclopenta[d]pyrimidin-4-yl]amino]phenyl]acetonitrile

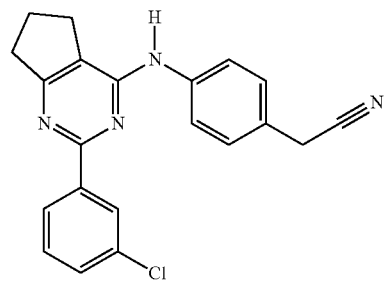 [SMILES: N#CCc1ccc(Nc2nc(-c3cccc(Cl)c3)nc3c2CCC3)cc1]

The title compound was prepared in a similar manner to that described in Step 4 of EXAMPLE 9 using 2-(4-aminophenyl)acetonitrile instead of 2-(4-aminophenyl)acetic acid as reactant in 51% yield on 0.1 mmol scale reaction (18 mg). MW=360.84. $^1$H NMR (CDCl$_3$, 360 MHz) δ 8.37 (s, 1H), 8.25 (m, 1H), 7.73 (d, J=8.5 Hz, 2H), 7.36 (m, 4H), 6.31 (s, 1H), 3.76 (s, 2H), 3.04 (t, J=7.6 Hz, 2H), 2.83 (t, J=7.1 Hz, 2H), 2.21 (m, 2H).

EXAMPLE 20

2-[4-[[2-(5-chloro-2-thienyl)-6,7-dihydro-5H-cyclopenta[d]pyrimidin-4-yl]amino]phenyl]acetamide

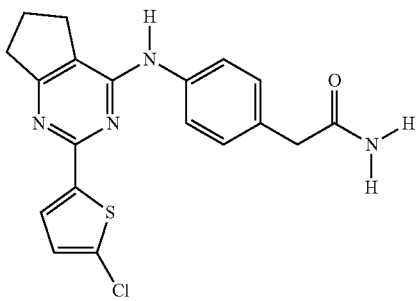 [SMILES: NC(=O)Cc1ccc(Nc2nc(-c3ccc(Cl)s3)nc3c2CCC3)cc1]

The title compound was prepared in a similar manner to that described in EXAMPLE 3 in 69% yield on 0.049 mmol scale reaction (13 mg). MW=384.88. $^1$H NMR (Methanol-$D_4$, 360 MHz) δ 7.72 (d, J=8.6 Hz, 2H), 7.65 (d, J=4.0 Hz, 1H), 7.29 (d, J=8.6 Hz, 2H), 6.98 (d, J=4.0 Hz, 1H), 3.50 (s, 2H), 2.89 (m, 4H), 2.16 (m, 2H).

EXAMPLE 21

2-[4-[[2-(3-chlorophenyl)-6,7-dihydro-5H-cyclopenta[d]pyrimidin-4-yl]amino]phenyl]acetamide

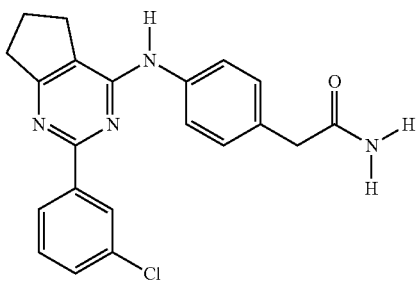 [SMILES: NC(=O)Cc1ccc(Nc2nc(-c3cccc(Cl)c3)nc3c2CCC3)cc1]

The title compound was prepared in a similar manner to that described in EXAMPLE 3 in 90% yield on 0.038 mmol scale reaction (13 mg). MW=378.85. $^1$H NMR (Methanol-D$_4$, 360 MHz) δ 8.26 (s, 1H), 8.18 (m, 1H), 7.73 (d, J=8.5 Hz, 2H), 7.41 (m, 2H), 7.30 (d, J=8.5 Hz, 2H), 3.50 (s, 2H), 2.95 (t, J=7.8 Hz, 2H), 2.88 (t, J=7.4 Hz, 2H), 2.17 (m, 2H).

EXAMPLE 22

2-chloro-4-(5-chlorothiophen-2-yl)-6-methyl-1,3,5-triazine

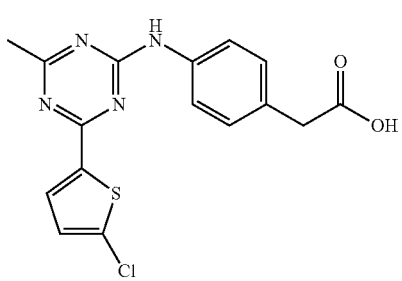 [SMILES: Cc1nc(Nc2ccc(CC(=O)O)cc2)nc(-c2ccc(Cl)s2)n1]

Step 1.
5-Chloro-N-cyanothiophene-2-carboximidamide

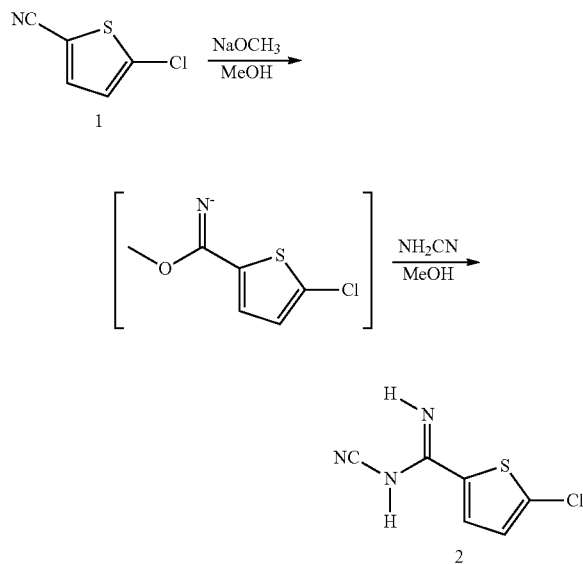

To a solution of 5-chlorothiophene-2-carbonitrile 1 in MeOH was added NaOCH$_3$. The reaction mixture was stirred at room temperature for 4 h and then NH$_2$CN was added. The reaction was allowed stir for overnight under N$_2$. The mixture was then poured into NH$_4$Cl (aq) and the precipitate collected and washed with water. The dried sample was confirmed as desired product 5-chloro-N-cyanothiophene-2-carboximidamide 2.

Step 2. 2-chloro-4-(5-chlorothiophen-2-yl)-6-methyl-1,3,5-triazine

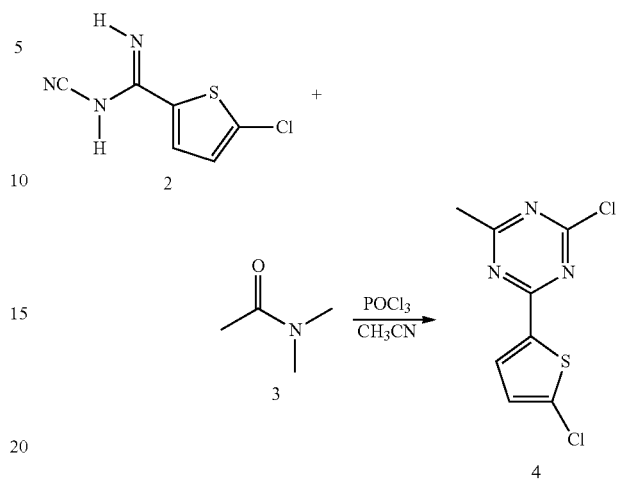

To a solution of reactant 3 in CH$_3$CN was added reactant 2 and POCl$_3$. The mixture was stirred at 70° C. overnight under N$_2$. TLC showed starting material was consumed. The mixture was then poured into NaHCO$_3$ (aq) carefully and the precipitate collected. The dried sample was confirmed as desired product 2-chloro-4-(5-chlorothiophen-2-yl)-6-methyl-1,3,5-triazine 4.

Step 3. 2-chloro-4-(5-chlorothiophen-2-yl)-6-methyl-1,3,5-triazine

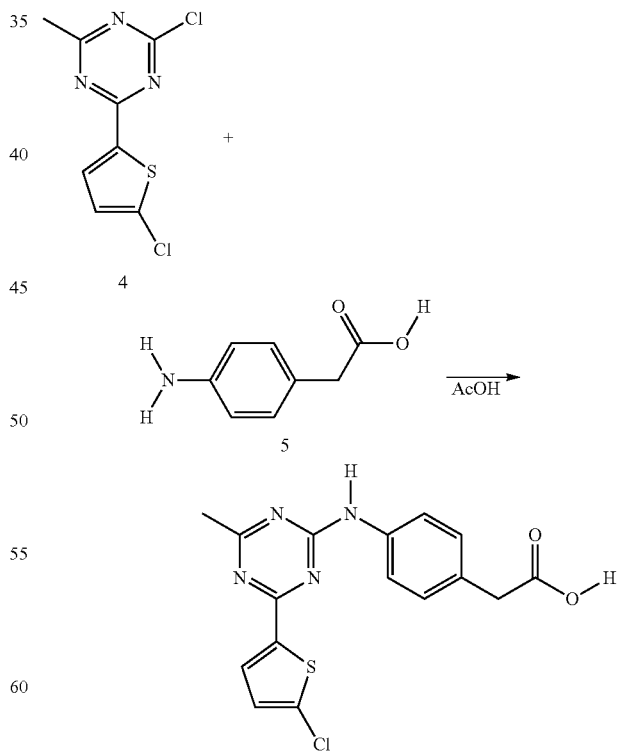

To a solution of reactant 4 in AcOH was added reactant 5. The mixture was stirred at 100° C. for 1 hour. TLC showed starting material was consumed. The mixture was then poured into water to collect the precipitate. After washing with water, the precipitate was further treated with EtOAc and filtered to yield dried product the title compound, 2-chloro-4-(5-chlorothiophen-2-yl)-6-methyl-1,3,5-triazine 6 (45 mg, 63% yield). MW=360.82. $^1$H NMR (300 MHz, DMSO-d$_6$) δ 10.25 (s, 1H), 7.88 (d, J=3.9 Hz, 1H), 7.68 (d, J=8.4 Hz, 2H), 7.23~7.29 (m, 3H), 3.52 (s, 2H), 2.43 (s, 3H).

EXAMPLE 23

4-(5-chlorothiophen-2-yl)-N-(4-fluorophenyl)-6-methyl-1,3,5-triazin-2-amine

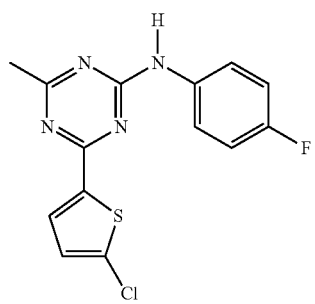 [SMILES: Cc1nc(Nc2ccc(F)cc2)nc(-c2ccc(Cl)s2)n1]

4-(5-chlorothiophen-2-yl)-N-(4-fluorophenyl)-6-methyl-1,3,5-triazin-2-amine was prepared using 2-chloro-4-(5-chlorothiophen-2-yl)-6-methyl-1,3,5-triazine and 4-fluoroaniline by the method described for Step 3 of EXAMPLE 1 (13 mg, 24% yield). MW=320.77. $^1$H NMR (300 MHz, CDCl$_3$) δ 7.93 (d, J=4.2 Hz, 1H), 7.64 (dd, J=9, 4.8 Hz, 2H), 7.11 (t, J=8.7 Hz, 2H), 7.01 (d, J=4.2 Hz, 1H), 2.55 (s, 3H).

EXAMPLE 24

2-(4-((4-(furan-2-yl)-6-methyl-1,3,5-triazin-2-yl)amino)phenyl)acetic acid

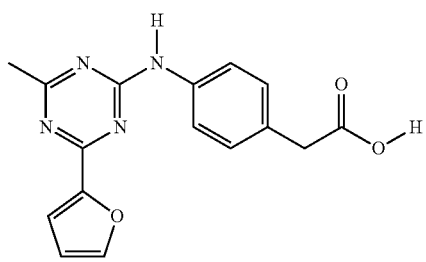 [SMILES: Cc1nc(Nc2ccc(CC(=O)O)cc2)nc(-c2ccco2)n1]

The title compound was prepared in a similar manner to those described herein, with modifications within the skill of one skilled in the art (20 mg, 32% yield). MW=310.31. $^1$H NMR (360 MHz, DMSO-D$_6$): δ 12.3 (brs, 1H), 10.2 (s, 1H), 7.98 (s, 1H), 7.71 (d, J=7.1 Hz, 2H), 7.42 (s, 1H), 7.21 (d, J=7.1 Hz, 2H), 6.71 (m, 1H), 3.51 (s, 2H), 2.42 (s, 3H).

EXAMPLE 25

2-(4-((4-(5-chlorothiophen-2-yl)-6-isopropyl-1,3,5-triazin-2-yl)amino)phenyl)acetic acid

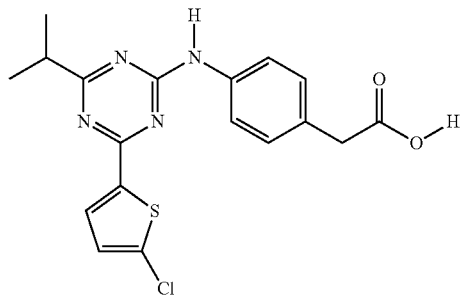 [SMILES: CC(C)c1nc(Nc2ccc(CC(=O)O)cc2)nc(-c2ccc(Cl)s2)n1]

The title compound was prepared in a similar manner to those described herein, with modifications within the skill of one skilled in the art (28 mg, 36% yield). MW=388.87. $^1$H NMR (360 MHz, DMSO-D$_6$) δ 12.3 (brs, 1H), 10.2 (s, 1H), 7.88 (d, J=4.0 Hz, 1H), 7.70 (d, J=8.1 Hz, 2H), 7.26 (d, J=4.0 Hz, 1H), 7.22 (d, J=8.1 Hz, 2H), 3.52 (s, 2H), 2.85 (m, 1H), 1.27 (d, J=6.9 Hz, 6H).

EXAMPLE 26

4-(5-chlorothiophen-2-yl)-N-(4-fluorophenyl)-6-isopropyl-1,3,5-triazin-2-amine

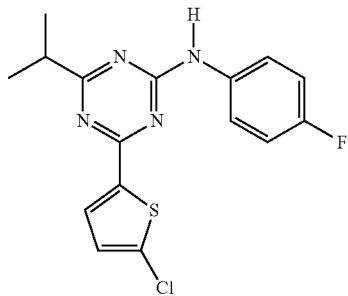 [SMILES: CC(C)c1nc(Nc2ccc(F)cc2)nc(-c2ccc(Cl)s2)n1]

The title compound was prepared in a similar manner to those described herein, with modifications within the skill of one skilled in the art (32 mg, 46% yield). MW=348.82. $^1$H NMR (360 MHz, CDCl$_3$) δ 7.87 (d, J=4.0 Hz, 1H), 7.61~7.63 (m, 2H), 7.08~7.16 (m, 2H), 6.97 (d, J=4.0 Hz, 1H), 2.95 (m, 1H), 1.33 (d, J=6.8 Hz, 6H).

EXAMPLE 27

2-(4-((4-(5-chlorothiophen-2-yl)-6-ethyl-1,3,5-triazin-2-yl)amino)phenyl)acetic acid

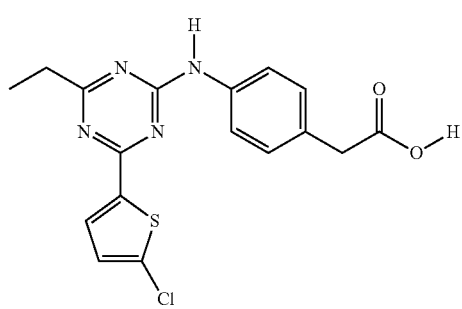 [SMILES: CCc1nc(Nc2ccc(CC(=O)O)cc2)nc(-c2ccc(Cl)s2)n1]

The title compound was prepared in a similar manner to those described herein, with modifications within the skill of one skilled in the art (57 mg, 76% yield). MW=374.84. $^1$H NMR (360 MHz, DMSO-D$_6$) δ 10.24 (brs, 1H), 7.88 (d, J=3.7 Hz, 1H), 7.69 (d, J=8.3 Hz, 2H), 7.27 (d, J=3.7 Hz, 1H), 7.22 (d, J=8.3 Hz, 2H), 3.52 (s, 2H), 2.70 (q, J=7.5 Hz, 2H), 1.26 (t, J=7.5 Hz, 3H).

EXAMPLE 28

4-(5-chlorothiophen-2-yl)-6-ethyl-N-(4-fluorophenyl)-1,3,5-triazin-2-amine

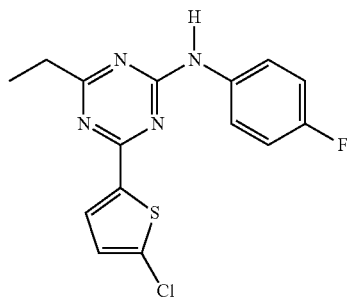 [SMILES: CCc1nc(Nc2ccc(F)cc2)nc(-c2ccc(Cl)s2)n1]

The title compound was prepared in a similar manner to those described herein, with modifications within the skill of one skilled in the art (37 mg, 55% yield). MW=334.80. $^1$H NMR (360 MHz, DMSO-D$_6$) δ 10.31 (brs, 1H), 7.89 (d, J=3.9 Hz, 1H), 7.78 (m, 2H), 7.27 (d, J=3.9 Hz, 1H), 7.22 (m, 2H), 2.70 (q, J=7.6 Hz, 2H), 1.25 (t, J=7.6 Hz, 3H).

EXAMPLE 29

4-(4-(5-chlorothiophen-2-yl)-6-isopropyl-1,3,5-triazin-2-ylamino)benzoic acid

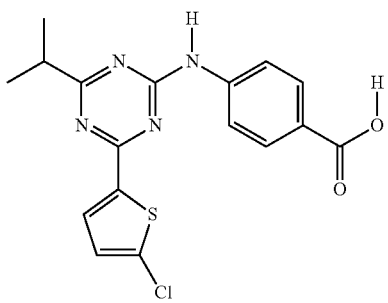 [SMILES: CC(C)c1nc(Nc2ccc(C(=O)O)cc2)nc(-c2ccc(Cl)s2)n1]

The title compound was prepared in a similar manner to those described herein, with modifications within the skill of one skilled in the art (40 mg, 53% yield). MW=374.84. $^1$H NMR (360 MHz, DMSO-D$_6$) δ 10.59 (s, 1H), 7.92 (m, 5H), 7.28 (d, J=4 Hz, 1H), 2.93 (m, 1H), 1.28 (d, J=6.9 Hz, 6H).

EXAMPLE 30

4-(4-(5-chlorothiophen-2-yl)-6-ethyl-1,3,5-triazin-2-ylamino)benzoic acid

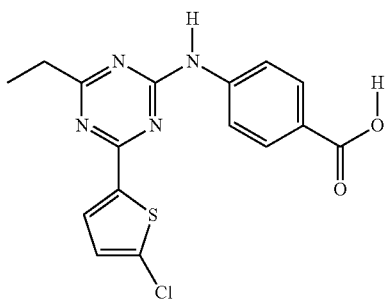 [SMILES: CCc1nc(Nc2ccc(C(=O)O)cc2)nc(-c2ccc(Cl)s2)n1]

The title compound was prepared in a similar manner to those described herein, with modifications within the skill of one skilled in the art (50 mg, 69% yield). MW=360.82. $^1$H NMR (360 MHz, DMSO-D$_6$) δ 10.60 (s, 1H), 7.93 (m, 5H), 7.28 (d, J=4.0 Hz, 1H), 2.74 (q, J=7.5 Hz, 2H), 1.27 (t, J=7.5 Hz, 3H).

EXAMPLE 31

4-(4-(5-chlorothiophen-2-yl)-6-methyl-1,3,5-triazin-2-ylamino)benzoic acid

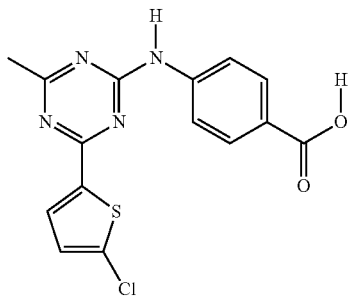 [SMILES: Cc1nc(Nc2ccc(C(=O)O)cc2)nc(-c2ccc(Cl)s2)n1]

The title compound was prepared in a similar manner to those described herein, with modifications within the skill of one skilled in the art (50 mg, 72% yield). MW=346.79. $^1$H NMR (360 MHz, DMSO-D$_6$) δ 10.60 (s, 1H), 7.89 (m, 5H), 7.28 (d, J=4.0 Hz, 1H), 2.46 (s, 3H).

EXAMPLE 32

2-(4-((4-(5-chlorothiophen-2-yl)-6-propyl-1,3,5-triazin-2-yl)amino)phenyl)acetic acid

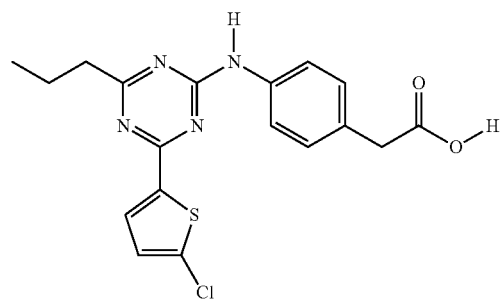 [SMILES: CCCc1nc(Nc2ccc(CC(=O)O)cc2)nc(-c2ccc(Cl)s2)n1]

The title compound was prepared in a similar manner to those described herein, with modifications within the skill of one skilled in the art (30 mg, 64% yield). MW=388.87. $^1$H NMR (360 MHz, DMSO-D$_6$) δ 12.30 (s, 1H), 10.24 (s, 1H), 7.87 (d, J=3.9 Hz, 1H), 7.68 (d, J=8.4 Hz, 2H), 7.26 (d, J=3.9 Hz, 1H), 7.22 (d, J=8.4 Hz, 2H), 3.53 (s, 2H), 2.64 (t, J=7.4 Hz, 2H), 1.77 (m, 2H), 0.95 (t, J=7.3 Hz, 3H).

EXAMPLE 33

4-((4-(5-chlorothiophen-2-yl)-6-propyl-1,3,5-triazin-2-yl)amino)benzoic acid

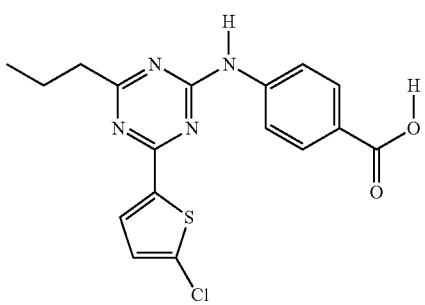 [SMILES: CCCc1nc(Nc2ccc(C(=O)O)cc2)nc(-c2ccc(Cl)s2)n1]

The title compound was prepared in a similar manner to those described herein, with modifications within the skill of one skilled in the art (MW=374.84. $^1$H NMR (360 MHz, DMSO-D$_6$) δ 10.60 (s, 1H), 7.92 (m, 5H), 7.28 (d, J=4.0 Hz, 1H), 2.68 (t, J=7.5 Hz, 2H), 1.79 (m, 2H), 0.96 (t, J=7.3 Hz, 3H).

EXAMPLE 34

2-(4-(4-(5-chlorothiophen-2-yl)-6-cyclopropyl-1,3,5-triazin-2-ylamino)phenyl)acetic acid

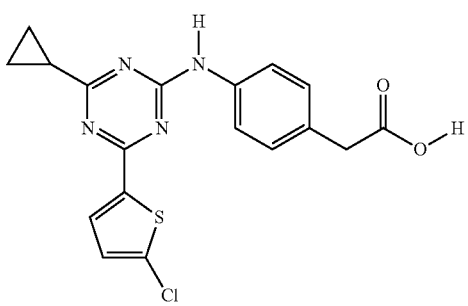 [SMILES: O=C(O)Cc1ccc(Nc2nc(-c3ccc(Cl)s3)nc(C3CC3)n2)cc1]

The title compound was prepared in a similar manner to those described herein, with modifications within the skill of one skilled in the art (9 mg, 27% yield). MW=386.86. $^1$H NMR (360 MHz, DMSO-D$_6$) δ 12.27 (s, 1H), 10.12 (s, 1H), 7.85 (d, J=4.0 Hz, 1H), 7.65 (d, J=8.2 vHz, 2H), 7.25 (d, J=4.0 Hz, 1H), 7.21 (d, J=8.2 Hz, 2H), 2.0 (m, 1H), 1.09 (m, 4H).

EXAMPLE 35 methyl 2-(4-((4-chloro-6-(5-chlorothiophen-2-yl)-1,3,5-triazin-2-yl)amino)phenyl)acetate

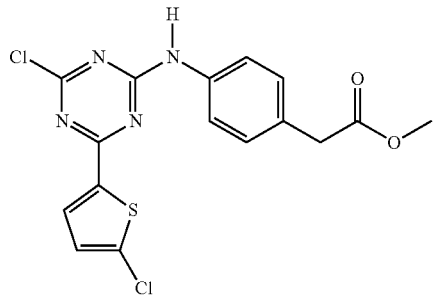 [SMILES: COC(=O)Cc1ccc(Nc2nc(Cl)nc(-c3ccc(Cl)s3)n2)cc1]

The title compound was prepared in a similar manner to those described herein, with modifications within the skill of one skilled in the art (25 mg, 63% yield). MW=395.26. $^1$H NMR (360 MHz, CDCl$_3$) δ 7.92 (d, J=4.1 Hz, 1H) m 7.55 (d, J=8.1 Hz, 2H), 7.32 (d, J=8.1 Hz, 2H), 3.70 (s, 3H), 3.63 (s, 2H).

EXAMPLE 36

2-(4-((4-(3-chlorophenyl)-6-cyclopropyl-1,3,5-triazin-2-yl)amino)phenyl)acetic acid

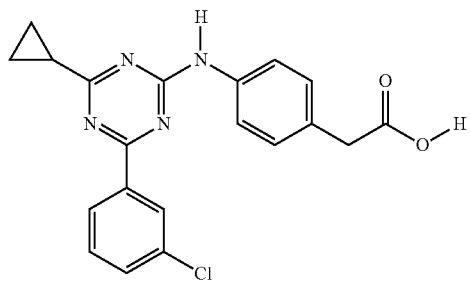 [SMILES: O=C(O)Cc1ccc(Nc2nc(-c3cccc(Cl)c3)nc(C3CC3)n2)cc1]

The title compound was prepared in a similar manner to those described herein, with modifications within the skill of one skilled in the art (18 mg, 65% yield). MW=380.83. $^1$H NMR (360 MHz, DMSO-D$_6$) δ 10.18 (s, 1H), 8.29 (m, 2H), 7.67 (m, 3H), 7.58 (dd, J=7.9 and 8.0 Hz, 1H), 7.23 (d, J=7.7 Hz, 2H), 3.53 (s, 2H), 2.07 (m, 1H), 1.18 (m, 2H), 1.11 (m, 2H).

EXAMPLE 37

2-(4-((4-(4-chlorophenyl)-6-cyclopropyl-1,3,5-triazin-2-yl)amino)phenyl)acetic acid

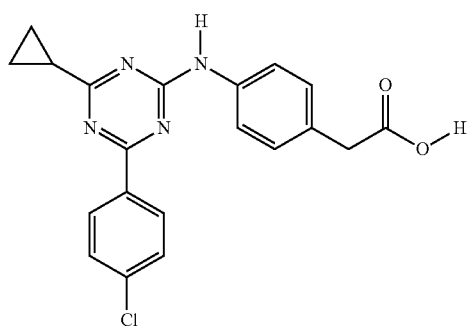 [SMILES: O=C(O)Cc1ccc(Nc2nc(-c3ccc(Cl)cc3)nc(C3CC3)n2)cc1]

The title compound was prepared in a similar manner to those described herein, with modifications within the skill of one skilled in the art (13 mg, 34% yield). MW=380.83. $^1$H NMR (360 MHz, DMSO-D$_6$) δ 12.28 (s, 1H), 10.14 (s, 1H), 8.34 (d, J=8.4 Hz, 2H), 7.69 (d, J=8.1 Hz, 2H), 7.61 (d, 8.4 Hz, 2H), 7.22 (d, J=8.1 Hz, 2H), 3.53 (s, 2H), 2.05 (m, 1H), 1.17 (m, 2H), 1.10 (m, 2H).

EXAMPLE 38

4-((4-(4-chlorophenyl)-6-cyclopropyl-1,3,5-triazin-2-yl)amino)benzoic acid

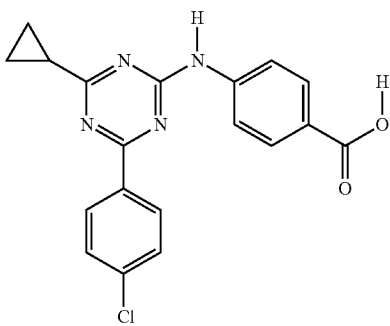 [SMILES: O=C(O)c1ccc(Nc2nc(-c3ccc(Cl)cc3)nc(C3CC3)n2)cc1]

The title compound was prepared in a similar manner to those described herein, with modifications within the skill of one skilled in the art (12 mg, 32% yield). MW=366.80. $^1$H NMR (360 MHz, DMSO-D$_6$) δ 10.51 (s, 1H), 8.37 (d, J=8.5 Hz, 2H), 7.93 (m, 4H), 7.62 (d, J=8.5 Hz, 2H), 2.10 (m, 1H), 1.20 (m, 2H), 1.14 (m, 2H).

EXAMPLE 39

2-(4-((4-(3-chlorophenyl)-6-ethyl-1,3,5-triazin-2-yl)amino)phenyl)acetic acid

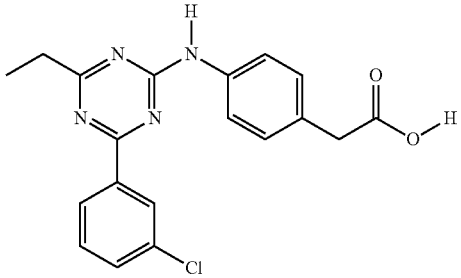 [SMILES: CCc1nc(Nc2ccc(CC(=O)O)cc2)nc(-c2cccc(Cl)c2)n1]

The title compound was prepared in a similar manner to those described herein, with modifications within the skill of one skilled in the art (38 mg, 100% yield). MW=368.82. $^1$H NMR (360 MHz, DMSO-d$_6$) δ 10.29 (s, 1H), 8.32 (m, 2H), 7.58~7.73 (m, 4H), 7.24 (d, J=7.4 Hz, 2H), 3.53 (s, 2H), 2.76~2.80 (q, J=7.5 Hz, 2H), 1.30 (t, J=7.5 Hz, 3H).

EXAMPLE 40

4-((4-(3-chlorophenyl)-6-ethyl-1,3,5-triazin-2-yl)amino)benzoic acid

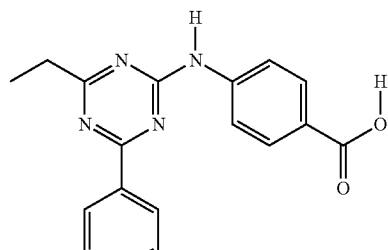

The title compound was prepared in a similar manner to those described herein, with modifications within the skill of one skilled in the art (38 mg, 100% yield). MW=354.79. $^1$H NMR (360 MHz, DMSO-d$_6$) δ 10.65 (s, 1H), 8.36 (m, 2H), 7.95 (br, 4H), 7.70 (d, J=7.4 Hz, 1H), 7.61 (dd, J=7.7 and 8.2 Hz, 1H), 2.81 (q, J=7.5 Hz, 2H), 1.33 (t, J=7.6 Hz, 3H).

EXAMPLE 41

4-((4-(3-chlorophenyl)-6-cyclopropyl-1,3,5-triazin-2-yl)amino)benzoic acid

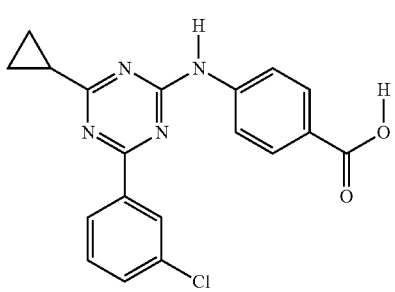 [SMILES: O=C(O)c1ccc(Nc2nc(-c3cccc(Cl)c3)nc(C3CC3)n2)cc1]

The title compound was prepared in a similar manner to those described herein, with modifications within the skill of one skilled in the art (19 mg, 70% yield). MW=366.80. $^1$H NMR (360 MHz, DMSO-d$_6$) δ 10.54 (s, 1H), 8.32 (m, 2H), 7.92 (br, 4H), 7.70 (d, J=7.7 Hz, 1H), 7.61 (dd, J=7.7 and 8.0 Hz, 1H), 2.12 (m, 1H), 1.21 (m, 2H), 1.15 (m 2H).

EXAMPLE 42

This Example is intentionally left blank.

EXAMPLE 43

2-(4-((4-(3-chlorophenyl)-6-cyclopropyl-1,3,5-tri-azin-2-yl)oxy)phenyl)acetic acid

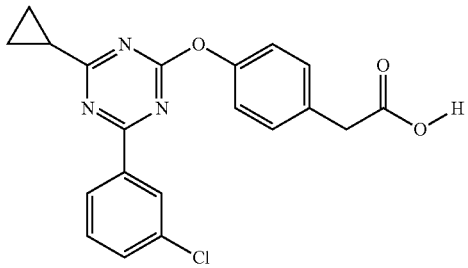 [SMILES: O=C(O)Cc1ccc(Oc2nc(-c3cccc(Cl)c3)nc(C3CC3)n2)cc1]

The title compound was prepared in a similar manner to those described herein, with modifications within the skill of one skilled in the art (10 mg, 29% yield). MW=381.81. $^1$H NMR (360 MHz, DMSO-$d_6$) δ 12.41 (brs, 1H), 8.2 (m, 2H), 7.69 (d, J=8.2 Hz, 1H), 7.57 (dd, J=8.1 and 8.2 Hz, 1H), 7.35 (d, J=8.5 Hz, 2H), 7.24 (d, J=8.5 Hz, 2H), 3.62 (s, 2H), 2.13 (m, 1H), 1.16 (m, 4H).

EXAMPLE 44

2-(4-((4-(4-chlorophenyl)-6-cyclopropyl-1,3,5-tri-azin-2-yl)oxy)phenyl)acetic acid

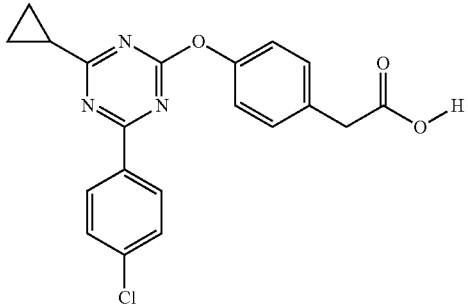 [SMILES: O=C(O)Cc1ccc(Oc2nc(-c3ccc(Cl)cc3)nc(C3CC3)n2)cc1]

The title compound was prepared in a similar manner to those described herein, with modifications within the skill of one skilled in the art (11 mg, 61% yield). MW=381.81. $^1$H NMR (360 MHz, DMSO-$d_6$) δ 12.41 (brs, 1H), 8.26 (d, J=8.5 Hz, 2H), 7.60 (d, J=8.5 Hz, 2H), 7.34 (d, J=8.4 Hz, 2H), 7.24 (d, J=8.4 Hz, 2H), 3.62 (s, 2H), 2.12 (m, 1H), 1.14 (m, 4H).

EXAMPLE 45

4-(((4-(4-chlorophenyl)-6-cyclopropyl-1,3,5-triazin-2-yl)amino)methyl)benzoic acid

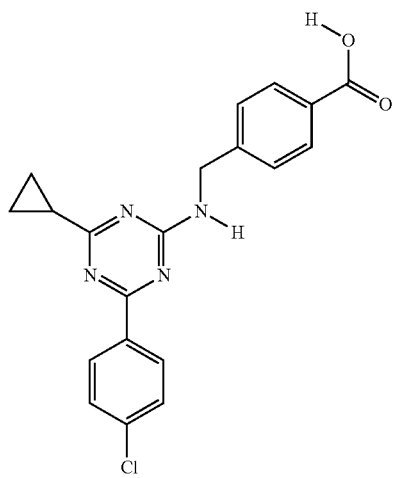 [SMILES: O=C(O)c1ccc(CNc2nc(-c3ccc(Cl)cc3)nc(C3CC3)n2)cc1]

The title compound was prepared in a similar manner to those described herein, with modifications within the skill of one skilled in the art (24 mg, 100% yield). MW=380.83. $^1$H NMR (360 MHz, DMSO-$d_6$) δ 12.86 (brs, 1H), 8.56 (br, 1H), 8.28 (m, 2H), 7.88 (d, J=7.5 Hz, 2H), 7.54 (m, 2H), 7.42 (m, 2H), 4.66 (d, J=5.5 Hz, 1H), 4.58 (d, J=4.9 Hz, 1H), 3.35 (s, 2H), 1.93 (m, 1H), 1.01 (m, 4H).

EXAMPLE 46

4-(((4-(3-chlorophenyl)-6-cyclopropyl-1,3,5-triazin-2-yl)amino)methyl)benzoic acid

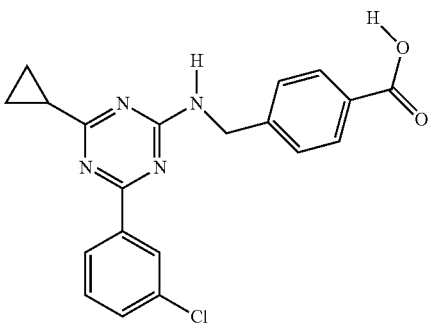 [SMILES: O=C(O)c1ccc(CNc2nc(-c3cccc(Cl)c3)nc(C3CC3)n2)cc1]

The title compound was prepared in a similar manner to those described herein, with modifications within the skill of one skilled in the art (12 mg, 30% yield). MW=380.83. $^1$H NMR (360 MHz, DMSO-$d_6$) δ 12.85 (brs, 1H), 8.61 (brs, 1H), 8.25 (m, 2H), 7.88 (d, J=7.2 Hz, 2H), 7.62 (m, 1H), 7.53 (m, 1H), 7.43 (m, 2H), 4.66 (d, J=5.8 Hz, 1H), 4.58 (d, J=5.8 Hz, 1H), 1.96 (m, 1H), 1.02 (m, 4H).

EXAMPLE 47

2-(4-((4-cyclopropyl-6-(3-fluorophenyl)-1,3,5-triazin-2-yl)amino)phenyl)acetic acid

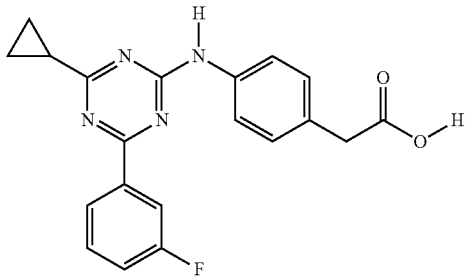 [SMILES: O=C(O)Cc1ccc(Nc2nc(-c3cccc(F)c3)nc(C3CC3)n2)cc1]

The title compound was prepared in a similar manner to those described herein, with modifications within the skill of one skilled in the art (13 mg, 38% yield). MW=364.37. $^1$H NMR (360 MHz, DMSO-$d_6$) δ 12.28 (s, 1H), 10.15 (s, 1H), 8.19 (d, J=7.8 Hz, 1H), 8.03 (m, 1H), 7.69 (d, J=8.2 Hz, 2H), 7.59 (m, 1H), 7.47 (m, 1H), 7.24 (d, J=8.2 Hz, 2H), 3.53 (s, 2H), 2.06 (m, 1H), 1.18 (m, 2H), 1.11 (m, 2H).

EXAMPLE 48

2-(4-((4-ethyl-6-(3-fluorophenyl)-1,3,5-triazin-2-yl)amino)phenyl)acetic acid

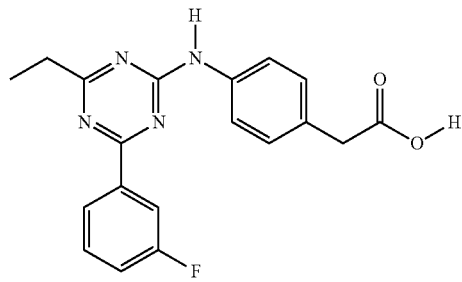 [SMILES: CCc1nc(Nc2ccc(CC(=O)O)cc2)nc(-c2cccc(F)c2)n1]

The title compound was prepared in a similar manner to those described herein, with modifications within the skill of one skilled in the art (18 mg, 37% yield). MW=352.36. $^1$H NMR (360 MHz, DMSO-$d_6$) δ 12.29 (s, 1H), 10.25 (s, 1H), 8.23 (d, J=7.8 Hz, 1H), 8.06 (m, 1H), 7.72 (d, J=8.4 Hz, 2H), 7.61 (m, 1H), 7.46 (m, 1H), 7.24 (d, J=8.4 Hz, 2H), 3.53 (s, 2H), 2.75 (q, J=7.5 Hz, 2H), 1.31 (t, J=7.5 Hz, 3H).

EXAMPLE 49

5-((6-(3-chlorophenyl)-4-cyclopropyl-4,5-dihydro-1,3,5-triazin-2-yl)amino)piperidin-2-one

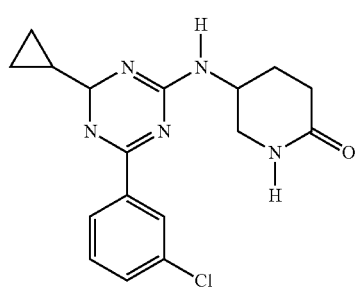 [SMILES: O=C1CCC(NC2=NC(C3CC3)NC(c3cccc(Cl)c3)=N2)CN1]

The title compound was prepared in a similar manner to those described herein, with modifications within the skill of one skilled in the art (17 mg, 81% yield). MW=345.83. $^1$H NMR (360 MHz, DMSO-$d_6$) δ 8.28 (m, 2H), 8.13 (d, J=6.9 Hz, 1H), 7.62 (m, 1H), 7.54 (m, 1H), 7.43 (brs, 1H), 4.30 (m, 0.5H), 4.18 (m, 0.5H), 3.38 (m, 1H), 3.08 (m, 1H), 2.33 (m, 2H), 1.96 (m, 2H), 1.80 (m, 1H), 1.11 (m, 2H), 1.06 (m, 2H).

EXAMPLE 50

2-(4-((4-ethyl-6-(furan-3-yl)-4,5-dihydro-1,3,5-triazin-2-yl)amino)phenyl)acetic acid

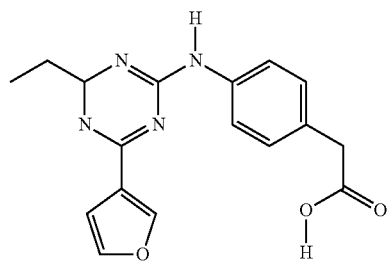 [SMILES: CCC1N=C(Nc2ccc(CC(=O)O)cc2)N=C(c2ccoc2)N1]

The title compound was prepared in a similar manner to those described herein, with modifications within the skill of one skilled in the art (19 mg, 58% yield). MW=326.35. $^1$H NMR (360 MHz, DMSO-$d_6$) δ 12.27 (s, 1H), 10.11 (s, 1H), 8.47 (brs, 1H), 7.83 (s, 1H), 7.72 (d, J=8.6 Hz, 2H), 7.18 (d, J=8.6 Hz, 2H), 6.99 (s, 1H), 3.51 (s, 2H), 2.71 (q, J=7.5 Hz, 2H), 1.27 (t, J=7.5 Hz, 3H).

EXAMPLE 51

4-(4-(3-chlorophenyl)-6-ethyl-1,3,5-triazin-2-ylamino)benzonitrile

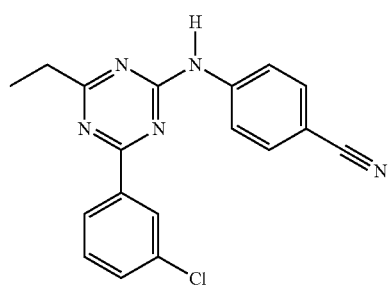 [SMILES: CCc1nc(Nc2ccc(C#N)cc2)nc(-c2cccc(Cl)c2)n1]

The title compound was prepared in a similar manner to those described herein, with modifications within the skill of one skilled in the art (29 mg, 85% yield). MW=335.79. $^1$H NMR (360 MHz, CDCl$_3$) δ 8.45 (s, 1H), 8.35 (d, J=7.8 Hz, 1H), 7.88 (d, J=8.8 Hz, 2H), 7.68 (d, J=8.8 Hz, 2H), 7.53 (d, J=8.0 Hz, 1H), 7.45 (dd, J=7.8 and 8.0 Hz, 1H), 2.88 (q, J=7.6 Hz, 2H), 1.41 (t, J=7.6 Hz, 3H).

EXAMPLE 52

2-(4-(4-(3-chlorophenyl)-6-ethyl-1,3,5-triazin-2-ylamino)phenyl)acetonitrile

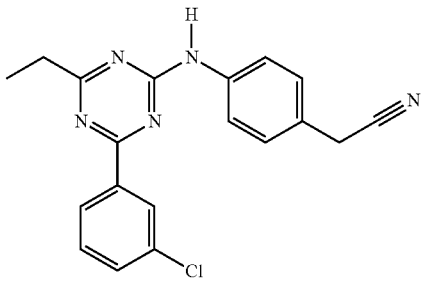 [SMILES: CCc1nc(Nc2ccc(CC#N)cc2)nc(-c2cccc(Cl)c2)n1]

The title compound was prepared in a similar manner to those described herein, with modifications within the skill of one skilled in the art (35 mg, 100% yield). MW=349.82. $^1$H NMR (360 MHz, CDCl$_3$) δ 8.44 (s, 1H), 8.33 (d, J=7.7 Hz, 1H), 7.75 (d, J=8.5 Hz, 2H), 7.51 (d, J=8.0 Hz, 1H), 7.43 (dd, J=7.7 and 8.0 Hz, 1H), 7.35 (d, J=8.5 Hz, 2H), 3.76 (s, 2H), 2.84 (q, J=7.6 Hz, 2H), 1.39 (t, J=7.6 Hz, 3H).

EXAMPLE 53

1-(4-((4-(3-chlorophenyl)-6-cyclopropyl-1,3,5-triazin-2-yl)amino)phenyl)imidazolidin-2-one

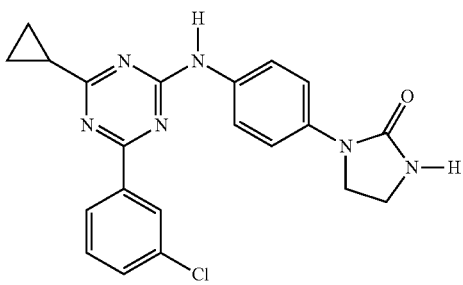 [SMILES: O=C1NCCN1c1ccc(Nc2nc(-c3cccc(Cl)c3)nc(C3CC3)n2)cc1]

The title compound was prepared in a similar manner to those described herein, with modifications within the skill of one skilled in the art (18 mg, 72% yield). MW=406.87. $^1$H NMR (360 MHz, CDCl$_3$) δ 8.39 (s, 1H), 8.30 (d, J=7.7 Hz, 1H), 7.65 (d, J=8.9 Hz, 2H), 7.47 (d, J=7.9 Hz, 1H), 7.40 (dd, J=7.7 and 7.9 Hz, 1H), 3.97 (dd, J=7.5 and 8.3 Hz, 2H), 3.59 (dd, J=7.5 and 8.3 Hz, 2H), 1.58 (m, 1H), 1.30 (m, 2H), 1.11 (m, 2H).

EXAMPLE 54

N-(4-(2H-tetrazol-5-yl)phenyl)-4-(3-chlorophenyl)-6-ethyl-1,3,5-triazin-2-amine

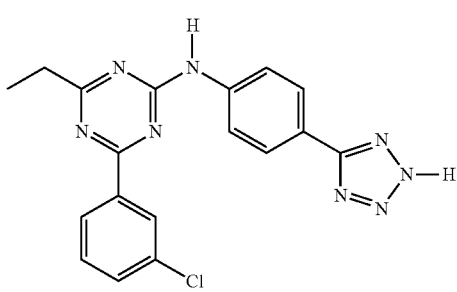 [SMILES: CCc1nc(Nc2ccc(-c3nn[nH]n3)cc2)nc(-c2cccc(Cl)c2)n1]

The title compound was prepared in a similar manner to those described herein, with modifications within the skill of one skilled in the art (15 mg, 79% yield). MW=378.82. $^1$H NMR (360 MHz, DMSO-d$_6$) δ 10.62 (brs, 1H), 8.35 (m, 2H), 8.04 (br, 4H), 7.69 (d, J=8.0 Hz, 1H), 7.60 (dd, J=7.8 and 8.0 Hz, 1H), 2.82 (q, J=7.5 Hz, 2H), 1.33 (t, J=7.5 Hz, 3H).

EXAMPLE 55

N-(4-((2H-tetrazol-5-yl)methyl)phenyl)-4-(3-chlorophenyl)-6-ethyl-1,3,5-triazin-2-amine

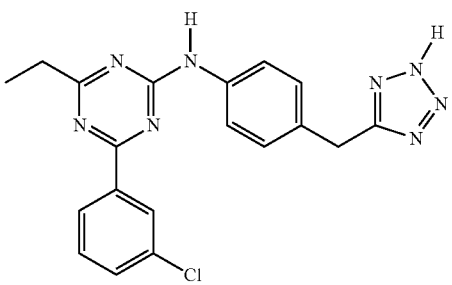 [SMILES: CCc1nc(Nc2ccc(Cc3nn[nH]n3)cc2)nc(-c2cccc(Cl)c2)n1]

The title compound was prepared in a similar manner to those described herein, with modifications within the skill of one skilled in the art (17 mg, 85% yield). MW=392.84. $^1$H NMR (360 MHz, DMSO-d$_6$) δ 10.30 (brs, 1H), 8.31 (m, 2H), 7.75 (d, J=8.4 Hz, 2H), 7.66 (d, J=8.1 Hz, 1H), 7.58 (dd, J=7.8 and 8.1 Hz, 1H), 7.26 (d, J=8.4 Hz, 2H), 4.26 (s, 2H), 2.75 (q, J=7.5 Hz, 2H), 1.29 (t, J=7.5 Hz, 3H).

EXAMPLE 56

N-(4-((4-(3-chlorophenyl)-6-ethyl-1,3,5-triazin-2-yl)amino)phenyl)methanesulfonylurea

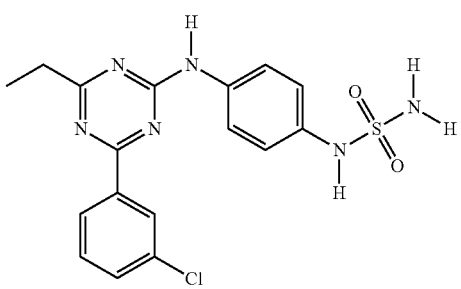 [SMILES: CCc1nc(Nc2ccc(NS(N)(=O)=O)cc2)nc(-c2cccc(Cl)c2)n1]

The title compound was prepared in a similar manner to those described herein, with modifications within the skill of one skilled in the art (20 mg, 51% yield). MW=404.87. $^1$H NMR (360 MHz, DMSO-d$_6$) δ 11.94 (brs, 1H), 10.64 (s, 1H), 8.36 (m, 2H), 7.98 (d, J=8.8 Hz, 2H), 7.81 (d, J=8.8 Hz, 2H), 7.70 (m, 1H), 7.61 (dd, J=8.0 and 8.1 Hz, 1H), 7.26 (br, 2H), 2.81 (q, J=7.5 Hz, 2H), 1.32 (t, J=7.5 Hz, 3H).

EXAMPLE 57

2-(4-(4-(3-chlorophenyl)-6-ethyl-1,3,5-triazin-2-ylamino)phenyl)acetamide

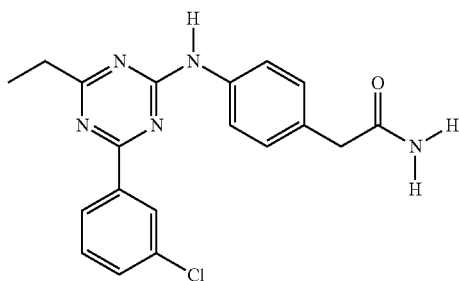 [SMILES: CCc1nc(Nc2ccc(CC(N)=O)cc2)nc(-c2cccc(Cl)c2)n1]

The title compound was prepared in a similar manner to those described herein, with modifications within the skill of one skilled in the art (7.6 mg, 48% yield). MW=367.83. $^1$H NMR (360 MHz, CDCl$_3$) δ 8.44 (s, 1H), 8.35 (d, J=7.7 Hz, 1H), 7.71 (d, J=8.4 Hz, 2H), 7.50 (m, 1H), 7.42 (dd, J=7.7 and 8.0 Hz, 1H), 7.32 (d, J=8.4 Hz, 2H), 5.40 (br, 2H), 3.59 (s, 2H), 2.84 (q, J=7.5 Hz, 2H), 1.39 (t, J=7.5 Hz, 3H).

EXAMPLE 58

2-(4-(4-(3-chlorophenyl)-6-ethyl-1,3,5-triazin-2-ylamino)phenyl)ethanol

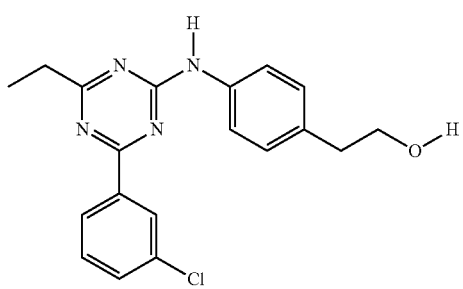 [SMILES: CCc1nc(Nc2ccc(CCO)cc2)nc(-c2cccc(Cl)c2)n1]

The title compound was prepared in a similar manner to those described herein, with modifications within the skill of one skilled in the art (8 mg, 21% yield). MW=354.83. $^1$H NMR (360 MHz, CDCl$_3$) δ 8.46 (s, 1H), 8.35 (d, J=7.6 Hz, 1H), 7.66 (d, J=8.4 Hz, 2H), 7.50 (m, 1H), 7.43 (dd, J=7.6 and 7.8 Hz, 1H), 7.28 (d, J=8.4 Hz, 2H), 3.89 (m, 2H), 2.89 (m, 4H), 1.40 (t, J=7.5 Hz, 3H).

EXAMPLE 59

2-(4-(4-(3-chlorophenyl)-6-ethyl-1,3,5-triazin-2-ylamino)phenyl)propanoic acid

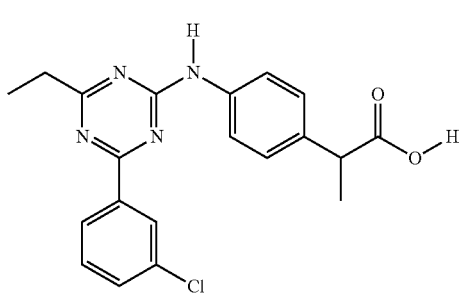 [SMILES: CCc1nc(Nc2ccc(C(C)C(=O)O)cc2)nc(-c2cccc(Cl)c2)n1]

The title compound was prepared in a similar manner to those described herein, with modifications within the skill of one skilled in the art (7 mg, 18% yield). MW=382.84. $^1$H NMR (360 MHz, DMSO-d$_6$) δ 12.26 (s, 1H), 10.28 (s, 1H), 8.32 (m, 2H), 7.73 (d, J=8.4 Hz, 2H), 7.68 (d, J=7.7 Hz, 1H), 7.60 (dd, J=7.7 and 7.9 Hz, 1H), 7.27 (d, J=8.4 Hz, 2H), 3.64 (q, J=7.1 Hz, 1H), 2.76 (q, J=7.5 Hz, 2H), 1.35 (d, J=7.1 Hz, 3H), 1.30 (t, J=7.5 Hz, 3H).

EXAMPLE 60

2-(4-(4-(3-chlorophenyl)-6-ethyl-1,3,5-triazin-2-ylamino)phenyl)-2-methylpropanoic

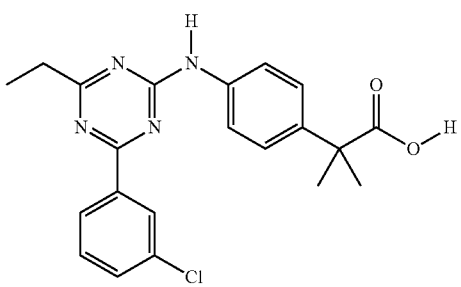 [SMILES: CCc1nc(Nc2ccc(C(C)(C)C(=O)O)cc2)nc(-c2cccc(Cl)c2)n1]

The title compound was prepared in a similar manner to those described herein, with modifications within the skill of one skilled in the art (20 mg, 50% yield). MW=396.87. $^1$H NMR (360 MHz, CDCl$_3$) δ 8.45 (brs, 1H), 8.35 (d, J=7.6 Hz, 1H), 7.72 (d, J=8.6 Hz, 2H), 7.51 (d, J=8.1 Hz, 1H), 7.46 (d, J=8.6 Hz, 2H), 7.43 (dd, J=7.6 and 8.1 Hz, 1H), 2.81 (q, J=7.5 Hz, 2H), 1.39 (t, J=7.5 Hz, 3H).

EXAMPLE 61

2-(4-((4-(3-chlorophenyl)-6-ethyl-1,3,5-triazin-2-yl)oxy)phenyl)acetamide

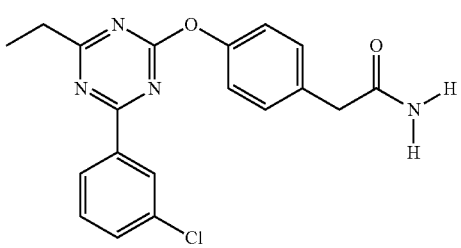 [SMILES: CCc1nc(Oc2ccc(CC(N)=O)cc2)nc(-c2cccc(Cl)c2)n1]

The title compound was prepared in a similar manner to those described herein, with modifications within the skill of one skilled in the art (18 mg, 49% yield). MW=368.82. $^1$H NMR (360 MHz, DMSO-d$_6$) δ 8.24 (m, 2H), 7.71 (d, J=7.7 Hz, 1H), 7.59 (dd, J=7.7 and 8.2 Hz, 1H), 7.51 (brs, 1H), 7.35 (d, J=8.4 Hz, 2H), 7.24 (d, J=8.4 Hz, 2H), 6.93 (brs, 1H), 3.42 (s, 2H), 2.83 (q, J=7.5 Hz, 2H), 1.26 (t, J=7.5 Hz, 3H).

EXAMPLE 62

4-(4-(3-chlorophenyl)-6-ethyl-1,3,5-triazin-2-ylamino)benzamide

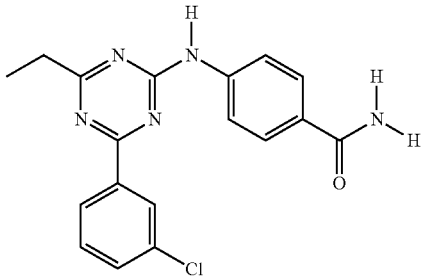 [SMILES: CCc1nc(Nc2ccc(C(N)=O)cc2)nc(-c2cccc(Cl)c2)n1]

The title compound was prepared in a similar manner to those described herein, with modifications within the skill of one skilled in the art (20 mg, 57% yield). MW=353.80. $^1$H NMR (360 MHz, DMSO-d$_6$) δ 10.53 (s, 1H), 8.35 (m, 2H), 7.89 (br, 4H), 7.70 (d, J=7.7 Hz, 2H), 7.61 (dd, J=7.8 and 8.0 Hz, 1H), 7.26 (brs, 2H), 2.82 (q, J=7.5 Hz, 2H), 1.32 (t, J=7.5 Hz, 3H).

EXAMPLE 63

4-((4-(3-chlorophenyl)-6-ethyl-1,3,5-triazin-2-yl)oxy)benzamide

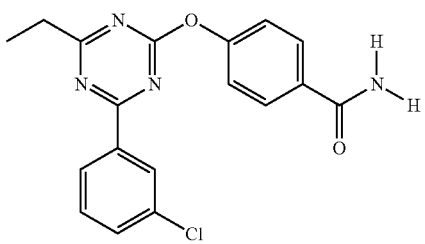 [SMILES: CCc1nc(Oc2ccc(C(N)=O)cc2)nc(-c2cccc(Cl)c2)n1]

The title compound was prepared in a similar manner to those described herein, with modifications within the skill of one skilled in the art (10 mg, 29% yield). MW=354.79. $^1$H NMR (360 MHz, DMSO-d$_6$) δ 8.23 (m, 2H), 8.03 (s, 1H), 7.96 (d, J=8.6 Hz, 2H), 7.70 (d, J=7.7 Hz, 1H), 7.58 (dd, J=7.7 and 7.9 Hz, 1H), 7.42 (s, 1H), 7.40 (d, J=8.6 Hz, 2H), 2.84 (q, J=7.5 Hz, 2H), 1.25 (t, J=7.5 Hz, 3H).

EXAMPLE 64

2-(4-((4-(3-chlorophenyl)-6-ethyl-1,3,5-triazin-2-yl)amino)piperidin-1-yl)acetic acid

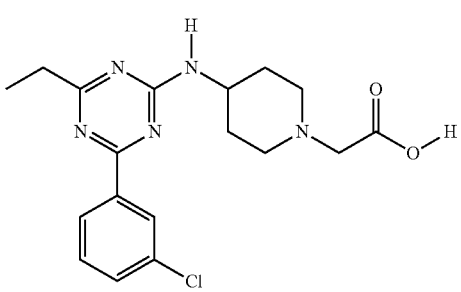 [SMILES: CCc1nc(NC2CCN(CC(=O)O)CC2)nc(-c2cccc(Cl)c2)n1]

The title compound was prepared in a similar manner to those described herein, with modifications within the skill of one skilled in the art (60 mg, 100% yield as HCl salt). MW=412.31. $^1$H NMR (360 MHz, DMSO-d$_6$) δ 10.40 (brs, 1H), 8.31 (m, 2H), 8.26 (d, J=7.9 Hz, 1H), 7.65 (m, 1H), 7.55 (dd, J=7.6 and 7.9 Hz, 1H), 4.10 (s, 2H), 3.67 (m, 1H), 2.65 (m, 2H), 2.11 (m, 2H), 1.94 (m, 2H), 1.25 (m, 3H).

EXAMPLE 65

2-(4-((2-(3-Chlorophenyl)-6-ethylpyrimidin-4-yl)methyl)phenyl)acetamide

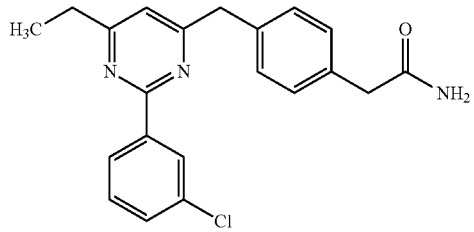 [SMILES: CCc1cc(Cc2ccc(CC(N)=O)cc2)nc(-c2cccc(Cl)c2)n1]

Step 1. Methyl 2-(4-(bromomethyl)phenyl)acetate

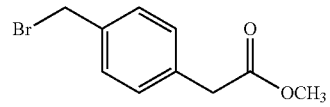

To a stirred suspension of 2-(4-(bromomethyl)phenyl) acetic acid (5.00 g, 21.8 mmol, 1.0 eq.) in methanol (75 mL) was added chlorotrimethylsilane (0.64 mL, 5.02 mmol, 0.23 eq.) at room temperature. The resulting mixture was stirred at room temperature for 2 hr, at which time the reaction was a clear colorless solution. The volatile material was removed under reduced pressure, the residue dissolved in methanol (25 mL), and the volatile material was removed under reduced pressure. This process was repeated two additional times to afford methyl 2-(4-(bromomethyl)phenyl)acetate as an orange solid (5.30 g, quantitative yield). $^1$H NMR (CDCl$_3$, 500 MHz) δ 7.37-7.33 (m, 2H), 7.26-7.24 (m, 2H), 4.48 (s, 2H), 3.69 (s, 3H), 3.62 (s, 2H). [Lit. J. Med. Chem. 2009, 52, 1180-9.]

Step 2. Methyl 2-(4-((4,4,5,5-tetramethyl-1,3,2-dioxaborolan-2-yl)methyl)phenyl)acetate

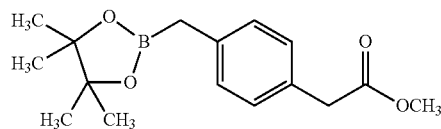 [SMILES: COC(=O)Cc1ccc(CB2OC(C)(C)C(C)(C)O2)cc1]

A 250-mL round bottom flask, with stirrer bar, was charged with 2-(4-(bromomethyl)phenyl)acetate (3.45 g, 14.2 mmol, 1.0 eq.), pinacol diborane (4.32 g, 17.0 mmol, 1.2 eq.), tetrakis(triphenylphosphine)palladium(0) (1.64 g, 1.42 mmol, 0.10 eq.), and K$_2$CO$_3$ (5.88 g, 42.6 mmol, 3.0 eq.). Dioxane (80 mL) was added. The resulting mixture was stirred under Ar at 80° C. for 23 hrs. After cooling to room temperature, the reaction was diluted with ethyl acetate (200 mL) and then filtered through celite. The filtrate was washed with sat. sodium chloride (3×25 mL), dried over sodium sulfate, filtered, and concentrated under reduced pressure. The residue (9.5 g) was purified by chromatography on silica gel using hexane/ethyl acetate (10:0 to 0:10) as eluent to afford methyl 2-(4-((4,4,5,5-tetramethyl-1,3,2-dioxaborolan-2-yl)methyl)phenyl)acetate (2.88 g, 70% yield) as a colorless semisolid. $^1$H NMR (CDCl$_3$, 500 MHz) δ 7.14 (s, 4H), 3.67 (s, 3H), 3.57 (s, 2H), 2.27 (s, 2H), 1.23 (s, 12H).

Step 3. Methyl 2-(4-((2-(3-chlorophenyl)-6-ethylpyrimidin-4-yl)methyl)phenyl)acetate

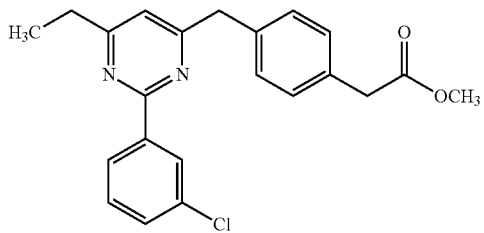 [SMILES: CCc1cc(Cc2ccc(CC(=O)OC)cc2)nc(-c2cccc(Cl)c2)n1]

A 50-mL flask, with stirrer bar, was charged with 4-chloro-2-(3-chlorophenyl)-6-ethylpyrimidine (870 mg, 3.44 mol, 1 eq.), methyl 2-(4-((4,4,5,5-tetramethyl-1,3,2-dioxaborolan-2-yl)methyl)phenyl)acetate (1.00 g, 3.44 mmol, 1 eq.), Pd(dppf)Cl$_2$ (280 mg, 0.34 mmol, 0.10 eq.), and powdered Na$_2$CO$_3$ (1.09 g, 10.3 mmol, 3.0 eq.). Dioxane (16 mL) and water (8 mL) were added. The resulting mixture was stirred under Ar at 90° C. for 2 hr. until the starting chloride was consumed. After cooling to room temperature, the reaction mixture was filtered through celite washing with ethyl acetate until the filtrate was colorless. The filtrate was washed with sat. sodium chloride (3×25 mL), dried over sodium sulfate, filtered and concentrated under reduced pressure. The residue (1.8 g) was purified by chromatography on silica gel using hexane/dichloromethane (10:0 to 0:10) as eluent, followed by chromatography on silica gel using hexane/ethyl acetate (10:0 to 3:1) as eluent, to afford methyl 2-(4-((2-(3-chlorophenyl)-6-ethylpyrimidin-4-yl)methyl)phenyl)acetate (0.65 g, 50% yield) as a colorless oil. MW=380.87. $^1$H NMR (CDCl$_3$, 500 MHz) δ 8.49-8.47 (m, 1H), 8.37 (dt, J=7.5, 1.5 Hz, 1H), 7.44-7.38 (m, 2H), 7.31-7.27 (m, 2H), 7.27-7.23 (m, 2H, overlaps with CDCl$_3$), 6.85 (s, 1H), 4.10 (s, 2H), 3.69 (s, 3H), 3.61 (s, 2H), 2.76 (q, J=7.5 Hz, 2H), 1.31 (t, J=7.5 Hz, 3H).

Step 4. 2-(4-((2-(3-Chlorophenyl)-6-ethylpyrimidin-4-yl)methyl)phenyl)acetamide

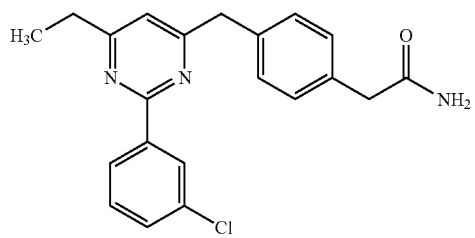 [SMILES: CCc1cc(Cc2ccc(CC(N)=O)cc2)nc(-c2cccc(Cl)c2)n1]

A 20-mL vial was charged with methyl 2-(4-((2-(3-chlorophenyl)-6-ethylpyrimidin-4-yl)methyl)phenyl)acetate (113 mg, 0.30 mmol, 1.0 eq.) and ammonium chloride (48 mg, 0.89 mmol, 3.0 eq.). To this was added methanol (3 mL) followed by NH$_3$ (7.5 mL, 7N in methanol, 53 mmol, 177 eq.). The vial was sealed and the resulting mixture was stirred at 100° C. for 43 hr. The crude reaction solution was adsorbed onto silica then purified by chromatography on silica gel using dichloromethane/methanol (0 to 5%) as eluent, followed by chromatography on silica gel using hexane/ethyl acetate (100:0 to 0:100) as eluent, to give 2-(4-((2-(3-chlorophenyl)-6-ethylpyrimidin-4-yl)methyl)phenyl)acetamide (37 mg, 35% yield) as a white solid. MW=365.86. $^1$H NMR (DMSO-d$_6$, 500 MHz) δ 8.38-8.33 (m, 2H), 7.61-7.53 (m, 2H), 7.41 (br s, 1H), 7.29 (d, J=8.0 Hz, 2H), 7.25 (s, 1H), 7.20 (d, J=8.0 Hz, 2H), 6.82 (br s, 1H), 4.09 (s, 2H), 3.32 (s, 2H), 2.77 (q, J=7.5 Hz, 2H), 1.26 (t, J=7.5 Hz, 3H).

EXAMPLE 66

2-(4-((2-(3-chlorophenyl)-6-ethylpyrimidin-4-yl)methyl)phenyl)acetic acid

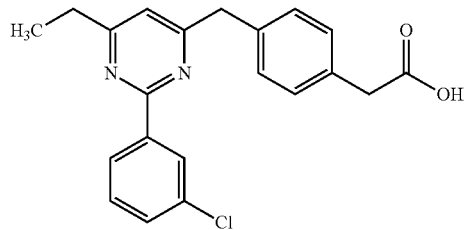 [SMILES: CCc1cc(Cc2ccc(CC(=O)O)cc2)nc(-c2cccc(Cl)c2)n1]

A 25-mL flask, with stirrer bar, was charged with methyl 2-(4-((2-(3-chlorophenyl)-6-ethylpyrimidin-4-yl)methyl)phenyl)acetate (64 mg, 0.17 mmol, 1.0 eq.) and THF (3 mL). Water (3 mL) and LiOH.H$_2$O (21 mg, 0.50 mmol, 3.0 eq.) were added. The resulting mixture was stirred at room temperature for 17 hrs until the starting ester was consumed. The reaction mixture was diluted with water (10 mL) and acidified with 2N HCl. The mixture was extracted with ethyl acetate. The organic extract was washed with sat. sodium chloride (5 mL), dried over sodium sulfate, filtered, and concentrated under reduced pressure. The residue (88 mg) was purified by chromatography on silica gel using dichloromethane/methanol (10:0 to 9:1) as eluent to afford 2-(4-((2-(3-chlorophenyl)-6-ethylpyrimidin-4-yl)methyl)phenyl)acetic acid (40 mg, 66% yield) as a white solid. MW=366.84. $^1$H NMR (DMSO-d$_6$, 500 MHz) δ 12.31 (br s, 1H), 8.40-8.33 (m, 2H), 7.62-7.53 (m, 2H), 7.31 (d, J=8.0 Hz, 2H), 7.26 (s, 1H), 7.21 (d, J=8.0 Hz, 2H), 4.10 (s, 2H), 3.51 (s, 2H), 2.78 (q, J=7.5 Hz, 2H), 1.26 (t, J=7.5 Hz, 3H).

EXAMPLE 67

2-(4-((2-(3-Chlorophenyl)-6-ethylpyrimidin-4-yl)methyl)phenyl)ethanol

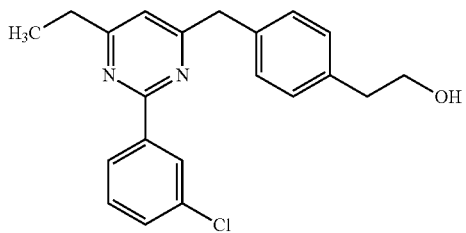 [SMILES: CCc1cc(Cc2ccc(CCO)cc2)nc(-c2cccc(Cl)c2)n1]

A 25-mL flask, with stirrer bar, was charged with methyl 2-(4-((2-(3-chlorophenyl)-6-ethylpyrimidin-4-yl)methyl)phenyl)acetate (52 mg, 0.13 mmol, 1.0 eq.) and THF (3 mL). The flask was cooled to 0° C. under nitrogen. A solution of 1M LiAlH$_4$ in THF (0.31 mL, 0.31 mmol, 2.3 eq.) was added and the reaction was allowed to slowly warm to room temperature. After 4.5 hrs, the reaction mixture was quenched with methanol, diluted with water (10 mL), and acidified with 2N HCl to pH~3. The mixture was extracted with ethyl acetate (3×12 mL). The organic extract was washed with sat. sodium chloride (5 mL), dried over sodium sulfate, filtered, and concentrated under reduced pressure. The residue (49 mg) was purified by chromatography on silica gel using hexanes/ethyl acetate (1:0 to 1:1) as eluent to afford 2-(4-((2-(3-chlorophenyl)-6-ethylpyrimidin-4-yl)methyl)phenyl)ethanol (17 mg, 36% yield) as a colorless oil. MW=352.86. $^1$H NMR (DMSO-d$_6$, 500 MHz) δ 8.38-8.33 (m, 2H), 7.61-7.53 (m, 2H), 7.28-7.25 (m, 3H), 7.16 (d, J=8.0 Hz, 2H), 4.58 (t, J=5.5 Hz, 1H), 4.08 (s, 2H), 3.60-3.53 (m, 2H), 2.77 (q, J=7.5 Hz, 2H), 2.67 (t, J=7.0 Hz, 2H), 1.26 (t, J=7.5 Hz, 3H).

EXAMPLE 68

2-(4-((2-(3-chlorophenyl)-6,7-dihydro-5H-cyclopenta[d]pyrimidin-4-yl)methyl)phenyl)acetamide

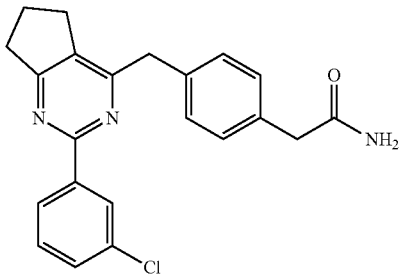

Step 1. Methyl 2-(4-((2-(3-chlorophenyl)-6,7-dihydro-5H-cyclopenta[d]pyrimidin-4-yl)methyl)phenyl)acetate

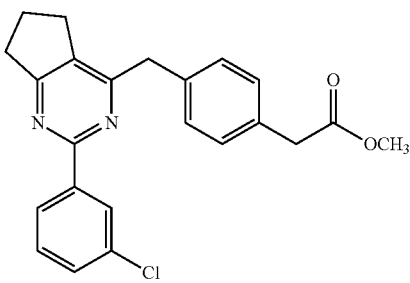

A 20-mL vial, with stirrer bar, was charged with 4-chloro-2-(3-chlorophenyl)-6,7-dihydro-5H-cyclopenta[d]pyrimidine (318 mg, 1.20 mol, 1.0 eq.), methyl 2-(4-((4,4,5,5-tetramethyl-1,3,2-dioxaborolan-2-yl)methyl)phenyl)acetate (350 mg, 1.20 mmol, 1.0 eq.), Pd(dppf)Cl$_2$ (98 mg, 0.12 mmol, 0.10 eq.), and powdered Na$_2$CO$_3$ (383 mg, 3.61 mmol, 3.0 eq.). Dioxane (8 mL) and water (4 mL) were added. The resulting mixture was stirred under Ar at 90° C. for 3.5 hrs until the starting chloride was consumed. After cooling to room temperature, the reaction mixture was filtered through celite washing with ethyl acetate until the filtrate was colorless. The filtrate was washed with sat. sodium chloride (3×10 mL), dried over sodium sulfate, filtered, and concentrated under reduced pressure. The residue (592 mg) was purified by chromatography on silica gel using hexane/ethyl acetate (1:0 to 3:1) as eluent, to afford methyl 2-(4-((2-(3-chlorophenyl)-6,7-dihydro-5H-cyclopenta[d]pyrimidin-4-yl)methyl)phenyl)acetate (98 mg, 21% yield) as a colorless oil. MW=392.88. $^1$H NMR (CDCl$_3$, 500 MHz) δ 8.46-8.44 (m, 1H), 8.35 (m, 1H), 7.43-7.36 (m, 2H), 7.27 (d, J=8.0 Hz, 2H), 7.21 (d, J=8.0 Hz, 2H), 4.09 (s, 2H), 3.68 (s, 3H), 3.59 (s, 2H), 3.02 (t, J=8.0 Hz, 2H), 2.86 (t, J=7.5 Hz, 2H), 2.11 (quintet, J=7.5 Hz, 2H).

Step 2. 2-(4-((2-(3-Chlorophenyl)-6,7-dihydro-5H-cyclopenta[d]pyrimidin-4-yl)methyl)phenyl)acetamide

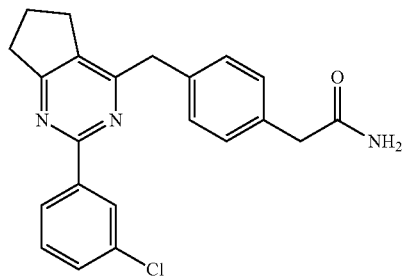 [SMILES: NC(=O)Cc1ccc(Cc2nc(-c3cccc(Cl)c3)nc3c2CCC3)cc1]

A 20-mL vial was charged with methyl 2-(4-((2-(3-chlorophenyl)-6,7-dihydro-5H-cyclopenta[d]pyrimidin-4-yl)methyl)phenyl)acetate (98 mg, 0.25 mmol, 1.0 eq.) and ammonium chloride (40 mg, 0.75 mmol, 3.0 eq.). Methanol (3 mL) was added to the mixture followed by NH$_3$ (7.1 mL, 7N in methanol, 50 mmol, 200 eq.). The vial was sealed and the resulting mixture was stirred at 100° C. for 40 hr. The crude reaction solution was adsorbed onto silica, then purified by chromatography on silica gel using dichloromethane/methanol (0 to 10%) as eluent, to give 2-(4-((2-(3-chlorophenyl)-6,7-dihydro-5H-cyclopenta[d]pyrimidin-4-yl)methyl)phenyl)acetamide (67 mg, 71% yield) as a white solid. MW=377.87. $^1$H NMR (DMSO-d$_6$, 500 MHz) δ 8.36-8.31 (m, 2H), 7.57-7.51 (m, 2H), 7.40 (br s, 1H), 7.25 (d, J=8.0 Hz, 2H), 7.18 (d, J=8.0 Hz, 2H), 6.82 (br s, 1H), 4.08 (s, 2H), 3.31 (s, 2H), 2.97 (t, J=8.0 Hz, 2H), 2.90 (t, J=7.5 Hz, 3H), 2.07 (quintet, J=7.5 Hz, 2H).

EXAMPLE 69

2-(4-((2-(3-Chlorophenyl)-6,7-dihydro-5H-cyclopenta[d]pyrimidin-4-yl)methyl)phenyl)acetamide

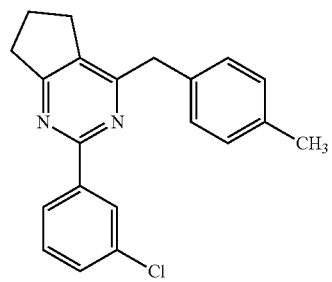 [SMILES: Cc1ccc(Cc2nc(-c3cccc(Cl)c3)nc3c2CCC3)cc1]

A 25-mL round bottom flask, with stirrer bar, was charged with 4-chloro-2-(3-chlorophenyl)-6,7-dihydro-5H-cyclopenta[d]pyrimidine (318 mg, 1.20 mol, 1.0 eq.) and Fe(acac)₃ (6.6 mg, 19 μmol, 0.05 eq.), NMP (0.4 mL) and THF (4.0 mL). The mixture was cooled to 0° C. under nitrogen. A solution of 4-methylbenzylmagnesium chloride (0.83 mL, 0.5M in THF, 0.41 mmol, 1.1 eq.) was added dropwise over 2 minutes. The resulting mixture was stirred 0° C. for 1.5 hr until the starting chloride was consumed. The reaction was quenched with a 9:1 sat. NH₄Cl/conc. NH₄OH solution (10 mL) then diluted with ethyl acetate (75 mL). The organic layer was washed with sat. sodium chloride (3×5 mL), dried over sodium sulfate, filtered, and concentrated under reduced pressure. The residue (175 mg) was purified by chromatography on silica gel using dichloromethane as the eluent, to afford 2-(3-chlorophenyl)-4-(4-methylbenzyl)-6,7-dihydro-5H-cyclopenta[d]pyrimidine (65 mg, 52% yield) as a white solid. MW=334.84. ¹H NMR (DMSO-d₆, 500 MHz) δ 8.35-8.30 (m, 2H), 7.58-7.51 (m, 2H), 7.20 (d, J=8.0 Hz, 2H), 7.11 (d, J=8.0 Hz, 2H), 4.07 (s, 2H), 2.97 (t, J=7.5 Hz, 2H), 2.88 (t, J=7.5 Hz, 2H), 2.25 (s, 3H), 2.06 (quintet, J=7.5 Hz, 2H).

EXAMPLE 70

(2-(3-Chlorophenyl)-6,7-dihydro-5H-cyclopenta[d]pyrimidin-4-yl)(p-tolyl)methanone

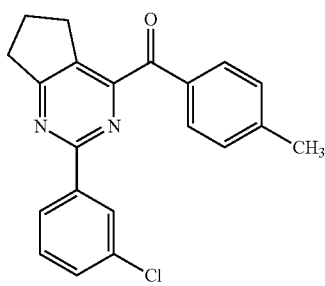 [SMILES: Cc1ccc(C(=O)c2nc(-c3cccc(Cl)c3)nc3c2CCC3)cc1]

Step 1. 2-(3-chlorophenyl)-6,7-dihydro-5H-cyclopenta[d]pyrimidine-4-carbonitrile

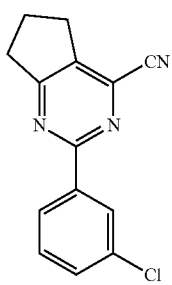 [SMILES: N#Cc1nc(-c2cccc(Cl)c2)nc2c1CCC2]

A 10-mL microwave vial, with stirrer bar, was charged with 4-chloro-2-(3-chlorophenyl)-6,7-dihydro-5H-cyclopenta[d]pyrimidine (250 mg, 0.94 mmol, 1.0 eq.), zinc cyanide (221 mg, 1.88 mmol, 2.0 eq.), tetrakis(triphenylphosphine)palladium(0) (109 mg, 0.094 mmol, 0.10 eq.) and THF (5 mL). The resulting mixture was subjected to microwave irradiation at 165° C. under Ar for 30 min. The cooled reaction mixture was preabsorbed onto silica gel and purified by chromatography on silica gel using hexane/ethyl acetate (10:0 to 7:3) as eluent to afford 2-(3-chlorophenyl)-6,7-dihydro-5H-cyclopenta[d]pyrimidine-4-carbonitrile (205 mg, 85% yield) as a white solid. MW=255.70. ¹H NMR (CDCl₃, 500 MHz) δ 8.46-8.42 (m, 1H), 8.35-8.30 (m, 1H), 7.49-7.46 (m, 1H), 7.45-7.40 (m, 1H), 3.21-3.14 (m, 4H), 2.29 (quintet, J=8.0 Hz, 2H).

Step 2: (2-(3-Chlorophenyl)-6,7-dihydro-5H-cyclopenta[d]pyrimidin-4-yl)(p-tolyl)methanone

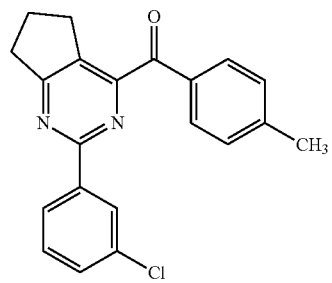 [SMILES: Cc1ccc(C(=O)c2nc(-c3cccc(Cl)c3)nc3c2CCC3)cc1]

A 25-mL round bottom flask, with stirrer bar, was charged with 4-chloro-2-(3-chlorophenyl)-6,7-dihydro-5H-cyclopenta[d]pyrimidine (97 mg, 0.38 mol, 1.0 eq.) and THF (5.0 mL). A solution of 4-tolylmagnesium bromide (1.14 mL, 1.0M in THF, 1.14 mmol, 3.0 eq.) was added dropwise over 1 minute at room temperature. After stirring for 2 hrs at room temperature the reaction was heated to reflux for 2.5 hrs. The reaction was cooled to room temperature and was quenched with 2N HCl and diluted with ethyl acetate (50 mL). The organic layer was washed with sat. sodium chloride (3×5 mL), dried over sodium sulfate, filtered, and concentrated under reduced pressure. The residue (227 mg) was purified by chromatography on silica gel using hexanes/ethyl acetate (10:0 to 8:2) as the eluent, to afford (2-(3-chlorophenyl)-6,7-dihydro-5H-cyclopenta[d]pyrimidin-4-yl)(p-tolyl)methanone (49 mg, 37% yield) as a yellow solid. MW=348.83. ¹H NMR (DMSO-d₆, 500 MHz) δ 8.31-8.26 (m, 2H), 7.29 (d, J=8.5 Hz, 2H), 7.62-7.53 (m, 2H), 7.41 (d, J=8.0 Hz, 2H), 3.12 (t, J=7.5 Hz, 2H), 3.06 (t, J=7.0 Hz, 2H), 2.43 (s, 3H), 2.06 (quintet, J=7.5 Hz, 2H).

EXAMPLE 71

2-(5-chloro-2-thienyl)-5-ethyl-N-(1-hydroxy-3H-2,1-benzoxaborol-5-yl)-6-methyl-pyrimidin-4-amine

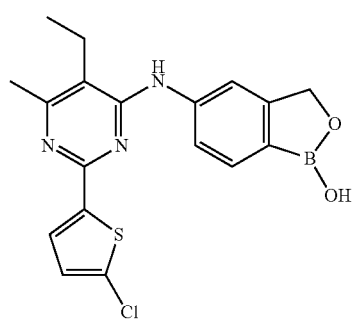 [SMILES: CCc1c(C)nc(-c2ccc(Cl)s2)nc1Nc1ccc2c(c1)COB2O]

Step 1, 2-(5-chloro-2-thienyl)-5-ethyl-4-methyl-1H-pyrimidin-6-one

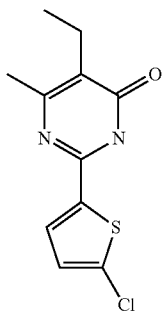 [SMILES: CCc1c(C)nc(-c2ccc(Cl)s2)[nH]c1=O]

A 100-mL round bottomed flask was charged with 5-chlorothiophene-2-carboxamidine HCl salt (394 mg, 2 mmol, 1 eq.), ethyl 2-ethyl-3-oxo-butanoate (950 mg, 6 mmol, 3 eq.), and ethanol (10 ml). To the mixture was added sodium methoxide (25 w % in methanol, 1.73 g, 8 mmol, 3 eq.). The resulting mixture was stirred under reflux for 7 hr. After cooling to room temperature, the mixture was evaporated under reduced pressure to dryness and the residue was treated with 2N HCl (4.5 ml). Solid was collected by filtration and washed with water followed by hexane. The product thus obtained was forwarded to the next step without any further purification (240 mg, 47% yield).

Step 2, 4-chloro-2-(5-chloro-2-thienyl)-5-ethyl-6-methyl-pyrimidine

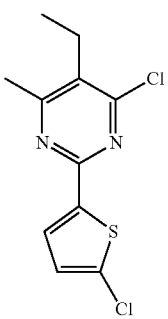 [SMILES: CCc1c(C)nc(-c2ccc(Cl)s2)nc1Cl]

A 18-mL vial was charged with 2-(5-chloro-2-thienyl)-5-ethyl-4-methyl-1H-pyrimidin-6-one (510 mg, 2 mmol). POCl$_3$ (2.5 ml) was added. The resulting mixture was stirred at 90 C for 4 hr. After cooling to room temperature, the mixture was added dropwise slowly to cold NaHCO$_3$ aq. Dichloromethane was added. The organic layer was separated and passed through a plug of silica gel, using dichloromethane as eluent to give 4-chloro-2-(5-chloro-2-thienyl)-5-ethyl-6-methyl-pyrimidine (283 mg, 52% yield).

Step 3, 2-bromo-5-[[2-(5-chloro-2-thienyl)-5-ethyl-6-methyl-pyrimidin-4-yl]amino]benzoic acid

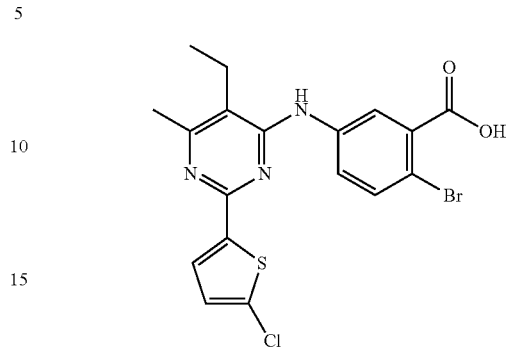

A 18-mL vial was charged with 4-chloro-2-(5-chloro-2-thienyl)-5-ethyl-6-methyl-pyrimidine (87 mg, 0.318 mmol, 1.05 eq.), 5-amino-2-bromo-benzoic acid (65 mg, 0.3 mmol, 1 eq.). AcOH (1 ml) and 4 N HCl in dioxane (5 drops). The resulting mixture was stirred under Ar at 110° C. for 2 hr. After cooling to rt, The volatile material was removed under reduced pressure and the residue was treated with dichloromethane to give the title compound (105 mg, 77% yield).

Step 4, [2-bromo-5-[[2-(5-chloro-2-thienyl)-5-ethyl-6-methyl-pyrimidin-4-yl]amino]phenyl]methanol

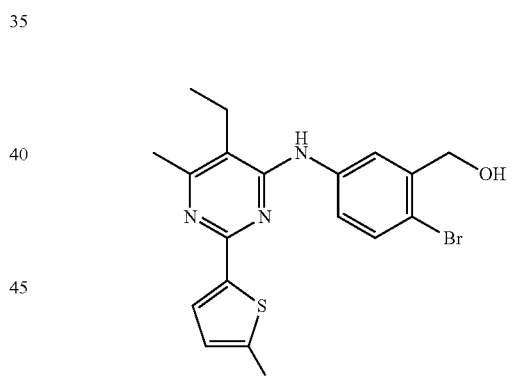

A 100-mL round bottomed flask was charged with 2-bromo-5-[[2-(5-chloro-2-thienyl)-5-ethyl-6-methyl-pyrimidin-4-yl]amino]benzoic acid (impure, obtained from several reactions on 1.3 mmol scale.), THF (20 ml). To the mixture was added BH$_3$ (1N in THF, 7.5 ml). The resulting mixture was stirred at rt overnight. Then treated with 2N HCl aq. (10 ml) followed by sodium bicarbonate to pH=7. The mixture was extracted with ethyl acetate (3×10 ml). The organic layers were combined and dried over Na2SO4. Removal of solvent gave a residue, which was purified by chromatography on silica gel using 0.5% of methanol in dichloromethane to give the title compound (198 mg, 35% yield).

Step 5, [2-bromo-5-[[2-(5-chloro-2-thienyl)-5-ethyl-6-methyl-pyrimidin-4-yl]amino]phenyl]methyl acetate

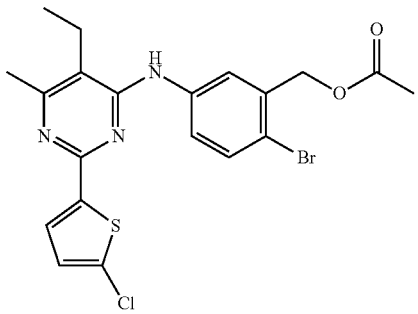 [SMILES: CCc1c(C)nc(-c2ccc(Cl)s2)nc1Nc1ccc(Br)c(COC(C)=O)c1]

A 18-mL vial was charged with [2-bromo-5-[[2-(5-chloro-2-thienyl)-5-ethyl-6-methyl-pyrimidin-4-yl]amino]phenyl]methanol (93 mg, 0.21 mmol), acetyl chloride (100 mg, 1.27 mmol, 6 eq.). Pyridine (1 ml) was added followed by 4-(dimethylamino)pyridine (5 mg, 0.2 eq.). The resulting mixture was stirred at rt for 2 hr. Then water was (5 ml) added. The precipitate was collected and washed with water. The crude product was purified by chromatography on silica gel using dichloromethane as eluent to give the tile compound (73 mg, 72% yield).

Step 6, [5-[[2-(5-chloro-2-thienyl)-5-ethyl-6-methyl-pyrimidin-4-yl]amino]-2-(4,4,5,5-tetramethyl-1,3,2-dioxaborolan-2-yl)phenyl]methyl acetate

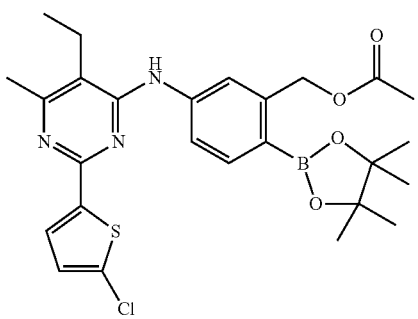 [SMILES: CCc1c(C)nc(-c2ccc(Cl)s2)nc1Nc1ccc(B2OC(C)(C)C(C)(C)O2)c(COC(C)=O)c1]

A 18-mL vial was charged with [2-bromo-5-[[2-(5-chloro-2-thienyl)-5-ethyl-6-methyl-pyrimidin-4-yl]amino]phenyl]methyl acetate (34 mg, 0.064 mmol, 1 eq.), 4,4,5,5-tetramethyl-2-(4,4,5,5-tetramethyl-1,3,2-dioxaborolan-2-yl)-1,3,2-dioxaborolane (20 mg, 0.077 mmol, 1.2 eq.), Pd(dppf)$_2$Cl$_2$ (6 mg, 0.11 eq.), KOAc (0.21 mmol, 3 eq.) and dioxane (2 ml). The resulting mixture was stirred under Ar at 95° C. for 4.5 hr. After cooling to rt, the volatile material was removed under reduced pressure and the residue was purified by chromatography on silica gel using dichloromethane as eluent to give the title compound (16.3 mg, 49% yield).

Step 7, 2-(5-chloro-2-thienyl)-5-ethyl-N-(1-hydroxy-3H-2,1-benzoxaborol-5-yl)-6-methyl-pyrimidin-4-amine

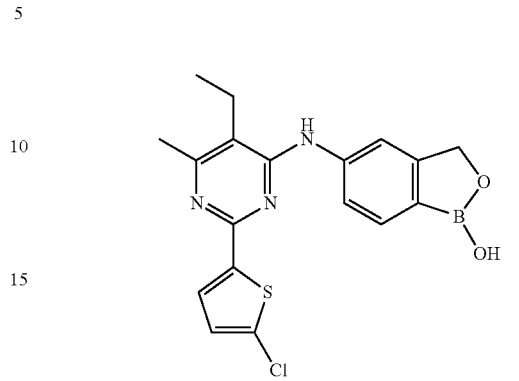

A 18-mL vial was charged with [5-[[2-(5-chloro-2-thienyl)-5-ethyl-6-methyl-pyrimidin-4-yl]amino]-2-(4,4,5,5-tetramethyl-1,3,2-dioxaborolan-2-yl)phenyl]methyl acetate (8.6 mg, 0.016 mmol) and lithium hydroxide (10 mg, 0.23 mmol). THF (1 ml), MeOH (0.2 ml) and water (0.2 ml) was added to the vial. The resulting mixture was stirred at rt overnight. Then the volatile material was removed. The residue was treated with THF (0.5 ml) and 2N HCl aq. (0.5 ml) for 1 hr. The mixture was neutralized by addition of NaHCO$_3$ aq. to pH=7. Then the mixture was extracted with ethyl acetate (3×2 ml). The ethyl acetate layers were combined and solvent was removed to dryness and the residue was purified by chromatography on silica gel using DCM followed by 0.4% MeOH in DCM as eluent to afford 2-[4-[[2-(5-chloro-2-thienyl)-6,7-dihydro-5H-cyclopenta[d]pyrimidin-4-yl]amino]phenyl]acetic acid (4.2 mg, 68% yield). MW=385.68. $^1$H NMR (CDCl$_3$, 400 MHz) δ 7.98 (s, 1H), 7.75 (d, J=8.0 Hz, 1H), 7.67 (d, J=4.0 Hz, 1H), 7.48 (d, J=8.0 Hz, 1H), 6.95 (d, J=4.0 Hz, 1H), 6.68 (brs, 1H), 5.18 (S, 2H), 2.68 (q, J=8.0 Hz, 2H), 2.51 (s, 3H), 1.27 (t, J=8.0 Hz, 3H).

EXAMPLE 72

2-(5-Chloro-2-thienyl)-5-ethyl-N-(1-hydroxy-3H-2,1-benzoxaborol-6-yl)-6-methyl-pyrimidin-4-amine

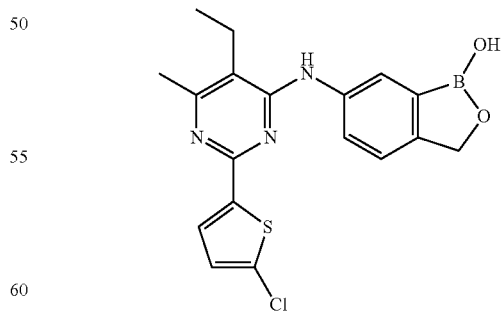

A 8-mL vial was charged with [2-(5-chloro-2-thienyl)-5-ethyl-6-methyl-pyrimidin-4-yl]trifluoromethanesulfonate (20 mg, 0.052 mmol, 1.05 eq.), 1-hydroxy-3H-2,1-benzoxaborol-6-amine (7.5 mg, 0.05 mmol, 1 eq.) and DMSO (0.5 ml). The mixture was stirred at 90° C. under Ar for 2 hr.

After cooling to room temperature, the mixture was added to water (5 ml). The precipitate was collected by filtration and washed with water. After dried, the mixture was purified by prep. TLC using 10% of ethyl acetate in dichloromethane as a mobile phase to give the title compound as a solid (10 mg, 52% yield). MW=385.68. ¹H NMR (400 MHz, CDCl₃) δ 7.96 (d, J=7.2 Hz, 1H), 7.85 (s, 1H), 7.65 (d, J=4.0 Hz, 1H), 7.41 (d, J=7.2 Hz, 1H), 6.92 (d, J=4.0 Hz, 1H), 6.58 (brs, 1H), 5.15 (s, 1H), 2.65 (q, J=7.6 Hz, 2H), 2.50 (s, 3H), 1.25 (t, J=7.6 Hz, 3H).

EXAMPLE 73

2-(5-Chloro-2-thienyl)-5-ethyl-6-methyl-N-[4-(1H-tetrazol-5-ylmethyl)phenyl]pyrimidin-4-amine

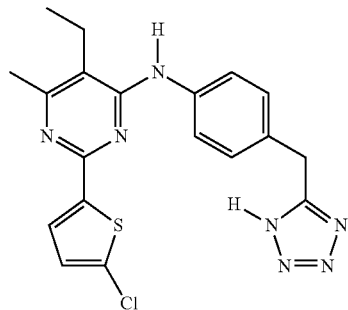 [SMILES: CCc1c(C)nc(-c2ccc(Cl)s2)nc1Nc1ccc(Cc2nnn[nH]2)cc1]

Step 1, 5-Chlorothiophene-2-carboxamidine HCl salt

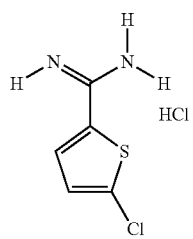

Synthesis of the title compound was described in step 1 of EXAMPLE 18.

Step 2, 2-(5-Chloro-2-thienyl)-5-ethyl-4-methyl-1H-pyrimidin-6-one

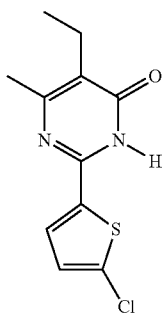 [SMILES: CCc1c(C)nc(-c2ccc(Cl)s2)[nH]c1=O]

A 250-mL round bottomed flask was charged with 5-chlorothiophene-2-carboxamidine HCl salt (6.81 g, 34.6 mmol, 1 eq.), ethyl 2-ethyl-3-oxo-butanoate (12 g, 72 mmol, 2 eq.), and ethanol (100 ml). To the mixture was added sodium methoxide (25 w % in methanol, 23 g, 107 mmol, 3 eq.). The resulting mixture was stirred under reflux for 7 hr. After cooling to room temperature, the mixture was evaporated under reduced pressure to dryness and the residue was treated with 2N HCl (60 ml). Solid was collected by filtration and washed with water followed by ether. The product thus obtained was forwarded to the next step without any further purification (4.53 g, 51% yield).

Step 3, 4-Chloro-2-(5-chloro-2-thienyl)-5-ethyl-6-methyl-pyrimidine

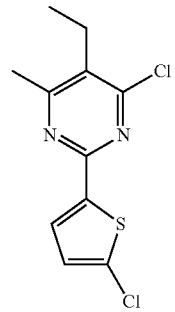 [SMILES: CCc1c(C)nc(-c2ccc(Cl)s2)nc1Cl]

An 100-mL round bottomed flask was charged 2-(5-Chloro-2-thienyl)-5-ethyl-4-methyl-1H-pyrimidin-6-one (4 g, 15.7 mmol). POCl₃ (16 ml) was added. The resulting mixture was stirred at 90 C for 6 hr. After cooling to room temperature, the volatile material was removed under reduced pressure and the residue was with NaHCO₃ aq (100 ml). Dichloromethane was added. The organic layer was separated and passed through a plug of silica gel, using dichloromethane as eluent to give the title compound as a solid (2.82 g, 66% yield).

Step 4, 2-[4-[[2-(5-Chloro-2-thienyl)-5-ethyl-6-methyl-pyrimidin-4-yl]amino]phenyl]acetonitrile

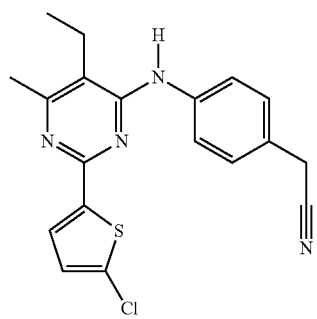 [SMILES: CCc1c(C)nc(-c2ccc(Cl)s2)nc1Nc1ccc(CC#N)cc1]

An 18-mL vial was charged 4-Chloro-2-(5-chloro-2-thienyl)-5-ethyl-6-methyl-pyrimidine (60 mg, 0.22 mmol, 1.07 eq.), 4-aminophenyl)acetonitrile (27 mg, 0.205 mmol, 1 eq.), and AcOH (1 ml). To the mixture was added HCl (4 N in dioxane, 5 drops). The resulting mixture was stirred at 110° C. for 2 hr. After cooling to rt, the reaction mixture was added to NaHCO₃ aq (20 ml). The mixture was extracted with dichloromethane. The organic layer was separated and passed through a plug of silica gel, using dichloromethane as eluent to give the title compound as a white solid (36 mg, 48% yield).

Step 5, 2-(5-Chloro-2-thienyl)-5-ethyl-6-methyl-N-[4-(1H-tetrazol-5-ylmethyl)phenyl]pyrimidin-4-amine (T-098)

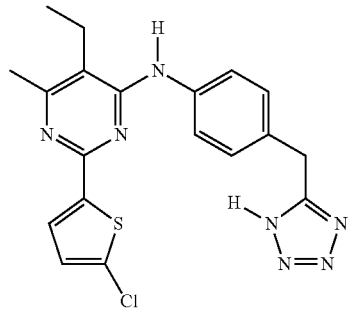 [SMILES: CCc1c(C)nc(-c2ccc(Cl)s2)nc1Nc1ccc(Cc2nnn[nH]2)cc1]

In an 4-mL was charged with 2-[4-[[2-(5-Chloro-2-thienyl)-5-ethyl-6-methyl-pyrimidin-4-yl]amino]phenyl]acetonitrile (16 mg, 0.043 mmol), azidotrimethylsilane (80 mg, 1.44 mmol) and tetrabutylammonium fluoride trihydrate (20 mg, 0.057 mmol). The mixture was stirred at 110° C. overnight. After cooling to room temperature, the mixture was dissolved in dichloromethane (2 ml) and 2N HCl (aq.) (1 ml) was added. The precipitate was collected by filtration and washed with water (5 ml) followed dichloromethane (5 ml). After dried, the title compound was obtained as a solid (13 mg, 71% yield, HCl salt, it is regioisomers). MW/HCl=448.41. $^1$H NMR (DMSO-D$_6$, 360 MHz) δ 8.0 (s, brs, 1H), 7.63 (d, J=7.6 Hz, 2H), 7.32 (d, J=7.6 Hz, 1H), 7.27 (d, J=3.6 Hz, 1H), 4.32 (s, 2H), 2.74 (q, J=6.8 Hz, 2H), 2.50 (s, 3H), 1.11 (t, J=6.8 Hz, 2H). MS: ESI$^+$, m/z 412 [M+H]$^+$. LCMS: 98.6%.

EXAMPLE 74

2-(5-Chloro-2-thienyl)-N-[4-(1H-tetrazol-5-ylmethyl)phenyl]-6,7-dihydro-5H-cyclopenta[d]pyrimidin-4-amine

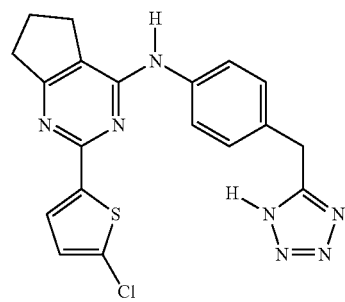 [SMILES: Clc1ccc(-c2nc3c(c(Nc4ccc(Cc5nnn[nH]5)cc4)n2)CCC3)s1]

Step 1, 2-[4-[[2-(5-Chloro-2-thienyl)-6,7-dihydro-5H-cyclopenta[d]pyrimidin-4-yl]amino]phenyl]acetonitrile

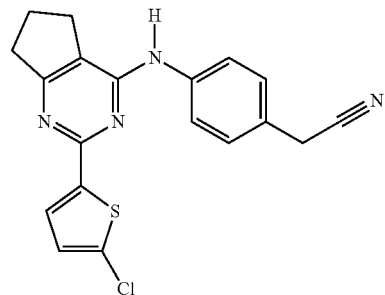 [SMILES: N#CCc1ccc(Nc2nc(-c3ccc(Cl)s3)nc3c2CCC3)cc1]

Synthesis of the title compound was described in EXAMPLE 18.

Step 2, 2-(5-Chloro-2-thienyl)-N-[4-(1H-tetrazol-5-ylmethyl)phenyl]-6,7-dihydro-5H-cyclopenta[d]pyrimidin-4-amine (T-101)

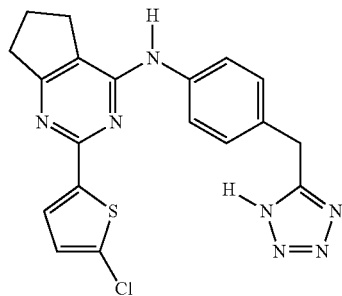 [SMILES: Clc1ccc(-c2nc3c(c(Nc4ccc(Cc5nnn[nH]5)cc4)n2)CCC3)s1]

In an 4-mL was charged with 2-[4-[[2-(5-Chloro-2-thienyl)-6,7-dihydro-5H-cyclopenta[d]pyrimidin-4-yl]amino]phenyl]acetonitrile (20 mg, 0.055 mmol), azidotrimethylsilane (80 mg, 1.44 mmol) and tetrabutylammonium fluoride trihydrate (25 mg, 0.07 mmol). The mixture was stirred at 110° C. overnight. After cooling to room temperature, the mixture was dissolved in dichloromethane (2 ml) and 2N HCl (aq.) (1 ml) was added. The precipitate was collected by filtration and washed with water (5 ml) followed dichloromethane (5 ml). The solid thus obtained was further triturated with dichloromethane (4 ml) to give the title compound (11 mg, 45% yield, HCl salt, it is regioisomers). MW/HCl=446.36. $^1$H NMR (DMSO-D$_6$, 360 MHz) δ 7.76 (m, 3H), 7.30 (d, J=7.9 Hz, 2H), 7.23 (d, J=3.6 Hz, 1H), 4.29 (s, 2H), 2.92 (t, J=6.8 Hz, 2H), 2.86 (t, J=6.8 Hz, 2H), 2.11 (t, J=6.8 Hz, 2H). MS: ESI$^+$, m/z 410 [M+H]$^+$. LCMS: 97%.

EXAMPLE 75

2-(3-Chlorophenyl)-N-[4-(1H-tetrazol-5-yl)phenyl]-6,7-dihydro-5H-cyclopenta[d]pyrimidin-4-amine

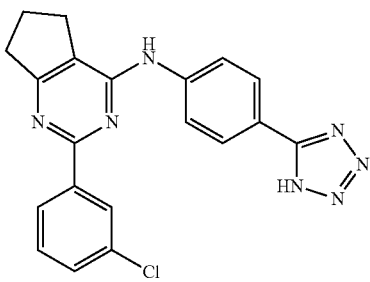 [SMILES: Clc1cccc(-c2nc3c(c(Nc4ccc(-c5nnn[nH]5)cc4)n2)CCC3)c1]

The title compound was prepared in a similar manner to those described herein, with modifications within the skill of one skilled in the art (17 mg, 77% yield, HCl salt). MW/HCl=426.34. $^1$H NMR (400 MHz, DMSO-D$_6$) δ 9.65 (brs, 1H), 8.31 (s, 1H), 8.26 (m, 1H), 8.12-8.05 (m, 4H), 7.67~7.64 (m, 2H), 3.04-2.95 (m, 4H), 2.19-2.15 (m, 2H).

EXAMPLE 76

2-(5-Chloro-2-thienyl)-5-ethyl-6-methyl-N-[4-(1H-tetrazol-5-yl)phenyl]pyrimidin-4-amine

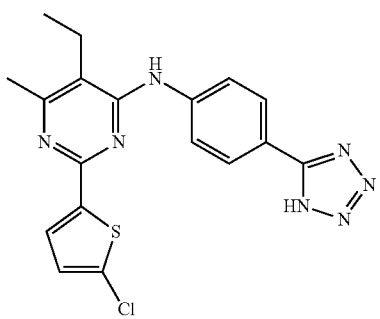 [SMILES: CCc1c(C)nc(-c2ccc(Cl)s2)nc1Nc1ccc(-c2nnn[nH]2)cc1]

The title compound was prepared in a similar manner to those described herein, with modifications within the skill of one skilled in the art (4.5 mg, 23% yield, HCl salt). MW/HCl=434.34. $^1$H NMR (400 MHz, Methanol-D$_4$) δ 8.03 (d, J=8.8 Hz, 2H), 7.98 (d, J=8.8 Hz, 2H), 7.7 (d, J=4.0 Hz, 1H), 7.02 (d, J=4.0 Hz, 1H), 2.79 (q, J=7.2 Hz, 2H), 2.51 (s, 3H), 1.23 (t, J=7.2 Hz, 3H).

EXAMPLE 77

2-(5-Chloro-2-thienyl)-N-[4-(1H-tetrazol-5-yl)phenyl]-6,7-dihydro-5H-cyclopenta[d]pyrimidin-4-amine

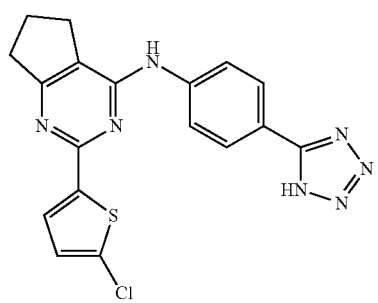 [SMILES: Clc1ccc(-c2nc3c(c(Nc4ccc(-c5nnn[nH]5)cc4)n2)CCC3)s1]

The title compound was prepared in a similar manner to those described herein, with modifications within the skill of one skilled in the art (18 mg, 73% yield, HCl salt). MW/HCl=432.33. $^1$H NMR (400 MHz, DMSO-D$_6$) δ 9.21 (brs, 1H), 8.07-8.04 (m, 4H), 7.70 (d, J=4.0 Hz, 1H), 7.20 (d, J=4.0 Hz, 1H), 2.91-2.88 (m, 4H), 2.12-2.08 (m, 2H).

EXAMPLE 78

2-(3-Chlorophenyl)-N-[4-(1H-tetrazol-5-ylmethyl)phenyl]-6,7-dihydro-5H-cyclopenta[d]pyrimidin-4-amine

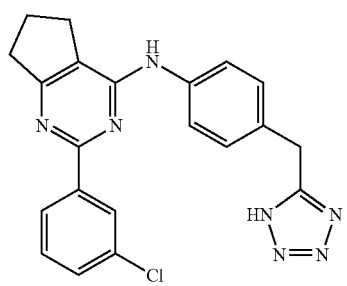 [SMILES: Clc1cccc(-c2nc3c(c(Nc4ccc(Cc5nnn[nH]5)cc4)n2)CCC3)c1]

The title compound was prepared in a similar manner to those described herein, with modifications within the skill of one skilled in the art (17 mg, 70% yield, HCl salt). MW/HCl=440.33. $^1$H NMR (400 MHz, DMSO-D$_6$) δ 9.50 (brs, 1H), 8.25 (s, 1H), 8.20 (d, J=7.6 Hz, 1H), 7.74 (d, J=8.8 Hz, 2H), 7.62-7.58 (m, 2H), 7.32 (d, J=8.8 Hz, 2H), 3.0 (t, J=6.8 Hz, 2H), 2.91 (t, J=6.8 Hz, 2H), 2.15 (m, 2H).

EXAMPLE 79

2-(5-Chloro-2-thienyl)-N-[4-(2H-tetrazol-5-ylmethyl)phenyl]-6-(trifluoromethyl)pyrimidin-4-amine

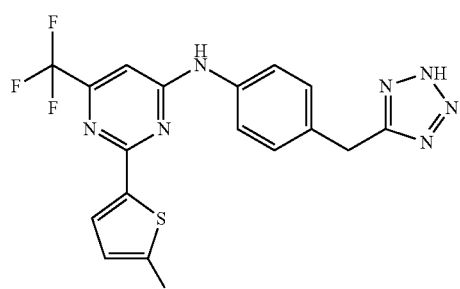

The title compound was prepared in a similar manner to those described herein, with modifications within the skill of one skilled in the art (6 mg, 67% yield, HCl salt). MW/HCl=474.29. $^1$H NMR (400 MHz, Methanol-D$_4$) δ 7.79 (d, J=4.0 Hz, 1H), 7.75 (d, brs, 2H), 7.34 (d, J=8.4 Hz, 2H), 7.06 (d, J=4.0 Hz, 1H), 6.89 (s, 1H), 4.35 (s, 2H).

EXAMPLE 80

(4-((4-(3-Chlorophenyl)-6-ethyl-1,3,5-triazin-2-yl)amino)phenyl)methanol

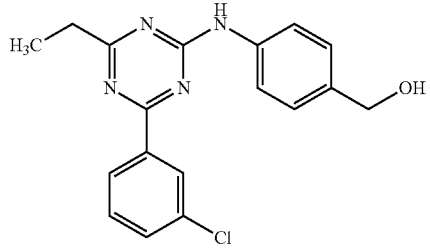 [SMILES: CCc1nc(Nc2ccc(CO)cc2)nc(-c2cccc(Cl)c2)n1]

Step 1. Preparation of methyl 3-chlorobenzimidate

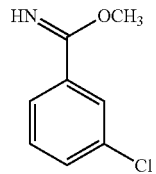

To a solution of 3-chlorobenzonitrile (4.0 g, 29.1 mmol) in methanol (30 mL) was added sodium methoxide (0.16 g, 2.9 mmol). The mixture stirred at rt for 2 d, diluted with water, and extracted with methylene chloride. The combined organic layer was dried over anhydrous sodium sulfate, filtered, and the filtrate was concentrated. The residue was purified by column chromatography (silica, hexanes/ethyl acetate) to afford the title compound (2.32 g, 47%) as a clear oil. MW=169.61. $^1$H NMR (CDCl$_3$, 500 MHz) δ 7.85 (s, 1H), 7.70 (s, 1H), 7.57 (s, 1H), 7.46-7.42 (m, 1H), 7.35 (t, J=7.9 Hz, 1H), 3.94 (s, 3H); APCI MS m/z 170 [M+H]$^+$.

Step 2. Preparation of 3-chloro-N-cyanobenzimidamide

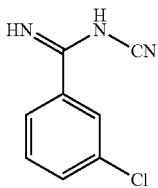 [SMILES: N#CNC(=N)c1cccc(Cl)c1]

To a solution of methyl 3-chlorobenzimidate (2.3 g, 13.6 mmol) in methanol (25 mL) was added cyanamide (0.572 g, 13.6 mmol). The mixture was stirred at rt for 16 h resulting in a thick white suspension. The mixture was filtered and dried under vacuum and heat to give 1.83 g of a white solid. The filtrate was purified by column chromatograhpy (silica, hexanes/ethyl acetate) to give 0.350 g of white solid. Both batches were combined to afford the title compound (2.18 g, 89%) as a white solid. MW=179.61. $^1$H NMR (DMSO-d$_6$, 500 MHz) δ 9.20 (s, 1H), 8.78 (br s, 1H), 8.04-7.82 (m, 2H), 7.71-7.66 (m, 1H), 7.54 (t, J=8.0 Hz, 1H); APCI MS m/z 180 [M+H]$^+$.

Step 3. Preparation of 2-chloro-4-(3-chlorophenyl)-6-ethyl-1,3,5-triazine

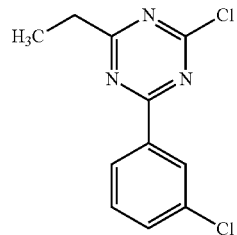 [SMILES: CCc1nc(Cl)nc(-c2cccc(Cl)c2)n1]

To a suspension of 3-chloro-N-cyanobenzimidamide (1.4 g, 7.8 mmol) was added N,N-dimethylpropionamide (0.790 g, 7.8 mmol) and POCl$_3$ (1.8 mL, 19.5 mmol). The mixture was heated to 70° C. for 16 h. The reaction was cooled, diluted with saturated aqueous sodium bicarbonate, and extracted with hexanes. The combined organic layer was dried over anhydrous sodium sulfate, filtered, and the filtrate was concentrated. The residue was purified by column chromatography (silica, hexanes/dichloromethane) to afford the title compound (1.41 g, 71%) as an off-white solid. MW=254.12. $^1$H NMR (CDCl$_3$, 500 MHz) δ 8.53-8.50 (m, 1H), 8.44-8.40 (m, 1H), 7.59-7.56 (m, 1H), 7.46 (t, J=8.0 Hz, 1H) 2.99 (q, J=7.5 Hz, 2H), 1.43 (t, J=7.5 Hz, 3H); APCI MS m/z 254 [M+H]$^+$.

EXAMPLE 80

(4-((4-(3-Chlorophenyl)-6-ethyl-1,3,5-triazin-yl)amino)phenyl)methanol

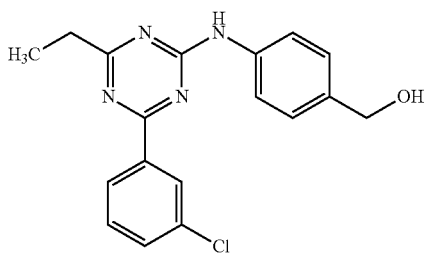 [SMILES: CCc1nc(Nc2ccc(CO)cc2)nc(-c2cccc(Cl)c2)n1]

2-Chloro-4-(3-chlorophenyl)-6-ethyl-1,3,5-triazine (0.140 g, 0.55 mmol) and 4-aminobenzyl alcohol (0.135 g, 1.1 mmol) were suspended in acetic acid (5 mL). The mixture was heated to 75° C. for 1 h. The reaction was cooled, diluted with saturated aqueous sodium bicarbonate, and extracted with ethyl acetate. The combined organic layer was dried over anhydrous sodium sulfate, filtered, and the filtrate was concentrated. The residue was purified by column chromatography (silica, dichloromethane/ethyl acetate) and then triturated with hexanes to afford the title compound (0.030 g, 16%) as a yellow solid. MW=340.81. $^1$H NMR (DMSO-d$_6$, 500 MHz) δ 10.24 (s, 1H), 8.42-8.31 (m, 2H), 7.75-7.68 (m, 3H), 7.61 (t, J=7.5 Hz, 1H), 7.36-7.28 (m, 2H), 5.11 (t, J=5.5 Hz, 1H), 4.48 (d, J=5.5 Hz, 2H), 2.78 (q, J=7.5 Hz, 2H), 1.32 (t, J=7.5 Hz, 3H); APCI MS m/z 341 [M+H]$^+$.

EXAMPLE 81

3-(4-((4-(3-Chlorophenyl)-6-ethyl-1,3,5-triazin-2-yl)amino)phenyl)propan-1-ol

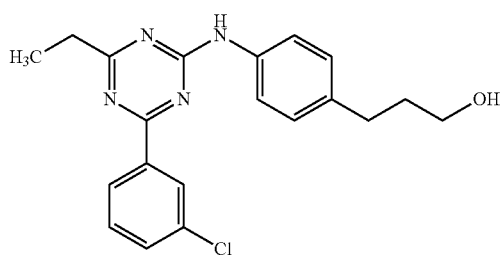 [SMILES: CCc1nc(Nc2ccc(CCCO)cc2)nc(-c2cccc(Cl)c2)n1]

2-Chloro-4-(3-chlorophenyl)-6-ethyl-1,3,5-triazine (0.150 g, 0.59 mmol) and 3-(4-aminophenyl)propan-1-ol (0.130 g, 0.89 mmol) were suspended in acetic acid (5 mL). The mixture was heated to 75° C. for 2 h. After this time, the reaction was cooled, diluted with saturated aqueous sodium bicarbonate, and extracted with ethyl acetate. The combined organic layer was dried over anhydrous sodium sulfate, filtered, and the filtrate was concentrated. The residue was purified by column chromatography (silica, hexanes/ethyl acetate) to afford the title compound (0.077 g, 35%) as a yellow solid. MW=368.86. $^1$H NMR (DMSO-$d_6$, 500 MHz) δ 10.19 (s, 1H), 8.41-8.31 (m, 2H), 7.71-7.67 (m, 3H), 7.60 (t, J=8.0 Hz, 1H), 7.24-7.16 (m, 2H), 4.45 (t, J=5.5 Hz, 1H), 3.43 (q, J=5.5 Hz, 2H), 2.77 (q, J=7.5 Hz, 2H), 2.60 (t, J=7.5 Hz, 2H), 2.51-2.49 (m, 2H), 1.75-1.69 (m, 2H), 1.32 (t, J=7.5 Hz, 3H); APCI MS m/z 369 [M+H]$^+$.

EXAMPLE 82

4-(3-Chlorophenyl)-6-ethyl-N-(4-(2-methoxyethyl)phenyl)-1,3,5-triazin-2-amine

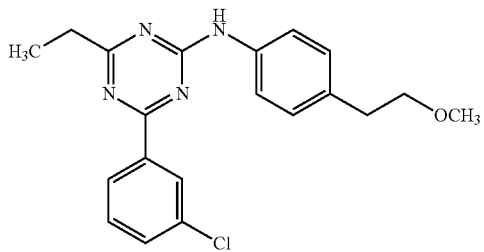 [SMILES: CCc1nc(Nc2ccc(CCOC)cc2)nc(-c2cccc(Cl)c2)n1]

A mixture of 2-chloro-4-(3-chlorophenyl)-6-ethyl-1,3,5-triazine (0.105 g, 0.41 mmol) and 4-(2-methoxyethyl)aniline (0.075 g, 0.49 mmol) were suspended in acetic acid (1 mL) and the mixture was heated at 75° C. for 3 h. After this time, the reaction was cooled, diluted with saturated aqueous sodium bicarbonate, and extracted with ethyl acetate. The combined organic layer was dried over anhydrous sodium sulfate, filtered, and the filtrate was concentrated. The residue was purified by column chromatography (silica, hexanes/ethyl acetate) to afford the title compound (0.094 g, 62%) as a white solid. MW=368.86. $^1$H NMR (DMSO-$d_6$, 500 MHz) δ 10.21 (s, 1H), 8.41-8.30 (m, 2H), 7.72-7.68 (m, 3H), 7.61 (t, J=7.5 Hz, 1H), 7.27-7.19 (m, 2H), 3.54 (t, J=7.0 Hz, 2H), 3.25 (s, 3H), 2.80-2.75 (m, 4H), 1.32 (t, J=7.5 Hz, 3H); APCI MS m/z 369 [M+H]$^+$.

EXAMPLE 83

2-(4-((2-(3-Chlorophenyl)pyridin-4-yl)amino)phenyl)acetamide hydrochloride

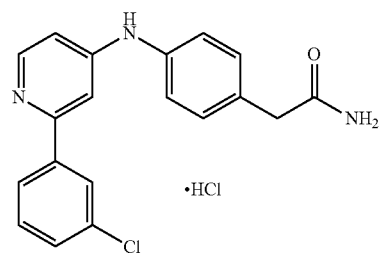 [SMILES: NC(=O)Cc1ccc(Nc2ccnc(-c3cccc(Cl)c3)c2)cc1 ; Cl]

Step 1. Preparation of 4-chloro-2-(3-chlorophenyl)pyridine hydrochloride

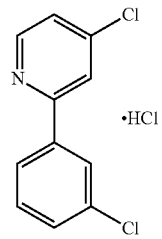

Following general procedure F, 2,4-dichloropyridine (4.0 g, 27 mmol) was reacted with (3-chlorophenyl)boronic acid (4.6 g, 30 mmol), followed by formation of the hydrochloride salt to afford the title compound (5.0 g, 71%) as a white solid. MW=260.55. $^1$H NMR (CDCl$_3$, 500 MHz) δ 8.92-8.79 (m, 1H), 8.16-8.09 (m, 1H), 8.03 (s, 1H), 7.95 (s, 1H), 7.74-7.64 (m, 1H), 7.58-7.52 (m, 2H); APCI MS m/z 224 [M+H]$^+$.

EXAMPLE 83

2-(4-((2-(3-Chlorophenyl)pyridin-4-yl)amino)phenyl)acetamide hydrochloride

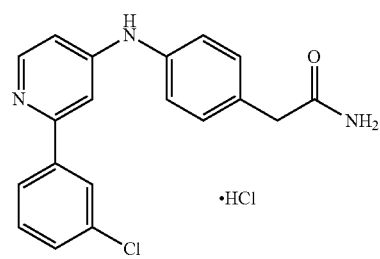 [SMILES: NC(=O)Cc1ccc(Nc2ccnc(-c3cccc(Cl)c3)c2)cc1 ; Cl]

Following general procedure A2, 4-chloro-2-(3-chlorophenyl)pyridine hydrochloride (0.115 g, 0.44 mmol) was reacted with 2-(4-aminophenyl)acetamide (0.080 g, 0.53 mmol), followed by formation of the hydrochloride salt to afford the title compound (0.066 g, 40%) as a light yellow solid. MW=374.26. ¹H NMR (DMSO-d$_6$, 500 MHz) δ 14.01 (s, 1H), 10.64 (s, 1H), 8.29 (d, J=7.0 Hz, 1H), 7.97-7.95 (m, 1H), 7.81-7.77 (m, 1H), 7.73-7.69 (m, 1H), 7.65 (t, J=8.0 Hz, 1H), 7.51 (s, 1H), 7.41-7.29 (m, 5H), 7.13-7.09 (m, 1H), 6.91 (s, 1H), 3.42 (s, 2H); APCI MS m/z 338 [M+H]⁺.

EXAMPLE 84

2-(4-((2-(3-Chlorophenyl)pyridin-4-yl)amino)phenyl)ethanol hydrochloride

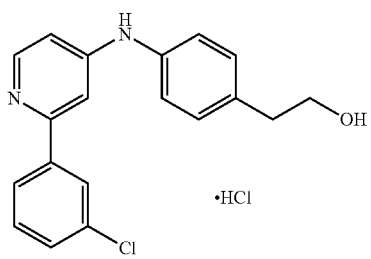 [SMILES: OCCc1ccc(Nc2ccnc(-c3cccc(Cl)c3)c2)cc1 ; Cl]

Following general procedure A2, 4-chloro-2-(3-chlorophenyl)pyridine hydrochloride (0.114 g, 0.44 mmol) was reacted with 2-(4-aminophenyl)ethanol (0.072 g, 0.53 mmol), followed by formation of the hydrochloride salt to afford the title compound (0.103 g, 65%) as a light yellow solid. MW=361.27. ¹H NMR (DMSO-d$_6$, 500 MHz) δ 14.08 (s, 1H), 10.70 (s, 1H), 8.28 (d, J=7.0 Hz, 1H), 7.96 (t, J=2.0 Hz, 1H), 7.79 (d, J=7.5 Hz, 1H), 7.73-7.69 (m, 1H), 7.65 (t, J=8.0 Hz, 1H), 7.37-7.28 (m, 5H), 7.13-7.08 (m, 1H), 3.64 (t, J=7.0 Hz, 2H), 2.76 (t, J=7.0 Hz, 2H); APCI MS m/z 325 [M+H]⁺.

EXAMPLE 85

3-(4-((2-(3-Chlorophenyl)-6,7-dihydro-5H-cyclopenta[b]pyridin-4-yl)amino)phenyl)propan-1-ol hydrochloride

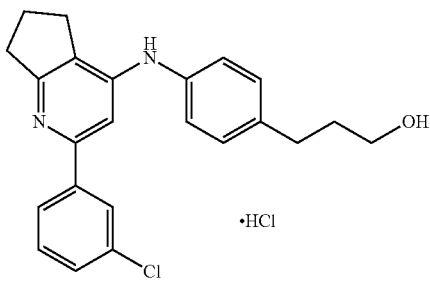 [SMILES: OCCCc1ccc(Nc2cc(-c3cccc(Cl)c3)nc3c2CCC3)cc1 ; Cl]

Following general procedure A2, employing iso-propanol as the solvent, 4-chloro-2-(3-chlorophenyl)-6,7-dihydro-5H-cyclopenta[b]pyridine hydrochloride (0.100 g, 0.33 mmol) was reacted with 3-(4-aminophenyl)propan-1-ol (0.075 g, 0.50 mmol), followed by formation of the hydrochloride salt to afford the title compound (0.022 g, 16%) as an off-white solid. MW=415.36. ¹H NMR (DMSO-d$_6$, 500 MHz) δ 14.00 (s, 1H), 9.74 (s, 1H), 7.89 (t, J=2.0 Hz, 1H), 7.71-7.64 (m, 2H), 7.62-7.57 (m, 1H), 7.32 (s, 4H), 6.98 (s, 1H), 3.43 (t, J=6.4 Hz, 2H), 3.15 (t, J=7.7 Hz, 2H), 2.91 (q, J=7.2 Hz, 2H), 2.67-2.63 (m, 2H), 2.24 (quin, J=7.5 Hz, 2H), 1.77-1.71 (m, 2H); APCI MS m/z 379 [M+H]⁺.

EXAMPLE 86

2-(3-Chlorophenyl)-N-(4-(2-methoxyethyl)phenyl)-6,7-dihydro-5H-cyclopenta[b]pyridin-4-amine hydrochloride

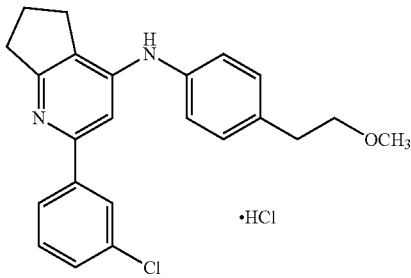 [SMILES: COCCc1ccc(Nc2cc(-c3cccc(Cl)c3)nc3c2CCC3)cc1 ; Cl]

Following general procedure A2 except using iso-propanol as a solvent, 4-chloro-2-(3-chlorophenyl)-6,7-dihydro-5H-cyclopenta[b]pyridine hydrochloride (0.107 g, 0.35 mmol) was reacted with 4-(2-methoxyethyl)aniline (0.108 g, 0.71 mmol), followed by formation of the hydrochloride salt to afford the title compound (0.094 g, 64%) as a white solid. MW=415.36. ¹H NMR (DMSO-d$_6$, 500 MHz) δ 14.03 (s, 1H), 9.75 (s, 1H), 7.89 (t, J=1.9 Hz, 1H), 7.71-7.67 (m, 2H), 7.59 (t, J=7.9 Hz, 1H), 7.36-7.32 (m, 4H), 6.99 (s, 1H), 3.57 (t, J=6.8 Hz, 2H), 3.25 (s, 3H), 3.15 (t, J=7.5 Hz, 2H), 2.91 (t, J=7.2 Hz, 2H), 2.85 (t, J=6.8 Hz, 2H), 2.24 (quin, J=7.5 Hz, 2H); APCI MS m/z 379 [M+H]⁺.

EXAMPLE 87

Methyl 4-((2-(3-chlorophenyl)-6,7-dihydro-5H-cyclopenta[b]pyridin-4-yl)amino)benzoate hydrochloride

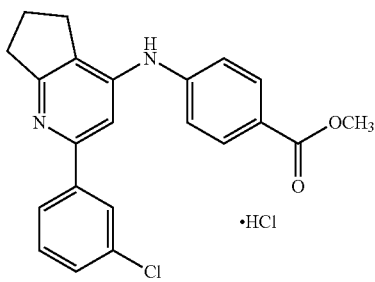 [SMILES: COC(=O)c1ccc(Nc2cc(-c3cccc(Cl)c3)nc3c2CCC3)cc1 ; Cl]

Following general procedure B1, 4-chloro-2-(3-chlorophenyl)-6,7-dihydro-5H-cyclopenta[b]pyridine hydrochloride (0.100 g, 0.33 mmol) was reacted with methyl 4-aminobenzoate (0.055 g, 0.36 mmol), followed by formation of the hydrochloride salt to afford the title compound (0.100 g, 80%) as a white solid. MW=415.31. ¹H NMR (DMSO-d$_6$, 500 MHz) δ 9.94 (s, 1H), 8.05 (d, J=8.5 Hz, 2H), 7.98-7.96 (m, 1H), 7.81-7.77 (m, 1H), 7.68-7.64 (m, 1H), 7.60 (t, J=7.5 Hz, 1H), 7.55 (d, J=8.5 Hz, 2H), 7.33 (s, 1H), 3.86 (s, 3H), 3.18 (t, J=7.5 Hz, 2H), 2.97 (t, J=7.5 Hz, 2H), 2.24 (quin, J=7.5 Hz, 2H); APCI MS m/z 379 [M+H]+.

EXAMPLE 88

(4-((2-(3-Chlorophenyl)-6,7-dihydro-5H-cyclopenta[b]pyridin-4-yl)amino)phenyl)methanol

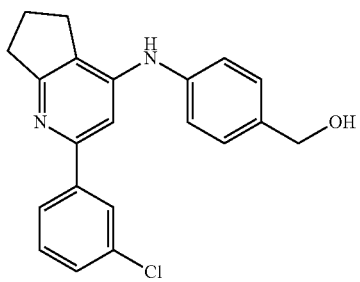 [SMILES: OCc1ccc(Nc2cc(-c3cccc(Cl)c3)nc3c2CCC3)cc1]

To a solution of methyl 4-((2-(3-chlorophenyl)-6,7-dihydro-5H-cyclopenta[b]pyridin-4-yl)amino)benzoate (0.075 g, 0.19 mmol) in THF (5 mL) at 0° C. was added lithium aluminum hydride (1.0 M, 0.6 mL, 0.6 mmol). The mixture warmed to rt and stirred for 2 d. After this time, the reaction was quenched with water and NaOH (2 M), dried over anhydrous sodium sulfate, filtered, and the filtrate was concentrated. The residue was purified by column chromatography (silica, hexanes/ethyl acetate) to afford the title compound (0.049 g, 71%) as an off-white solid. MW=350.84. $^1$H NMR (DMSO-$d_6$, 500 MHz) δ 8.15 (s, 1H), 7.91-7.89 (m, 1H), 7.76-7.73 (m, 1H), 7.45-7.40 (m, 2H), 7.32 (d, J=8.5 Hz, 2H), 7.23-7.19 (m, 3H), 5.11 (t, J=6.0 Hz, 1H), 4.48 (d, J=6.0 Hz, 2H), 2.91 (t, J=7.5 Hz, 2H), 2.83 (t, J=7.5 Hz, 2H), 2.08 (quin, J=7.5 Hz, 2H); APCI MS m/z 351 [M+H]+.

EXAMPLE 89

Methyl 2-(5-((2-(3-chlorophenyl)-6,7-dihydro-5H-cyclopenta[b]pyridin-4-yl)amino)pyridin-2-yl)acetate hydrochloride

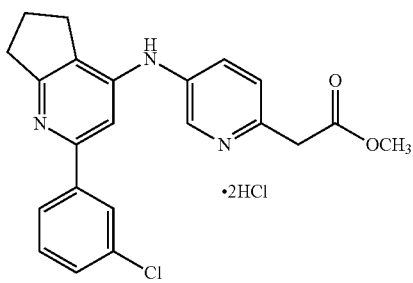 [SMILES: COC(=O)Cc1ccc(Nc2cc(-c3cccc(Cl)c3)nc3c2CCC3)cn1]

Following general procedure B1, 4-chloro-2-(3-chlorophenyl)-6,7-dihydro-5H-cyclopenta[b]pyridine hydrochloride (0.110 g, 0.36 mmol) was reacted with methyl 2-(5-aminopyridin-2-yl)acetate (0.067 g, 0.40 mmol), followed by formation of the hydrochloride salt to afford the title compound (0.110 g, 74%) as a white solid. MW=466.79. $^1$H NMR (DMSO-$d_6$, 500 MHz) δ 14.31 (s, 1H), 10.00 (s, 1H), 8.63 (d, J=2.5 Hz, 1H), 7.97-7.93 (m, 2H), 7.78-7.75 (m, 1H), 7.69-7.66 (m, 1H), 7.61 (t, J=7.5 Hz, 1H), 7.54 (d, J=8.5 Hz, 1H), 7.12 (s, 1H), 3.95 (s, 2H), 3.65 (s, 3H), 3.19 (t, J=7.5 Hz, 2H), 2.96 (t, J=7.5 Hz, 2H), 2.26 (quin, J=7.5 Hz, 2H); APCI MS m/z 394 [M+H]+.

EXAMPLE 90

2-(5-((2-(3-Chlorophenyl)-6,7-dihydro-5H-cyclopenta[b]pyridin-4-yl)amino)pyridin-2-yl)ethanol hydrochloride

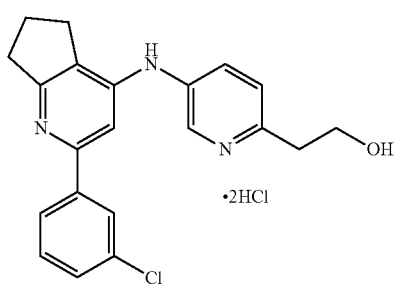 [SMILES: OCCc1ccc(Nc2cc(-c3cccc(Cl)c3)nc3c2CCC3)cn1]

Step 1. Preparation of 2-(5-aminopyridin-2-yl)ethanol

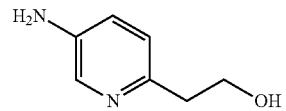

To a solution of methyl 2-(5-aminopyridin-2-yl)acetate (0.250 g, 1.5 mmol) in THF (20 mL) at 0° C. was added lithium aluminum hydride (1.0 M, 3.75 mL, 3.75 mmol). The mixture was warmed to rt and stirred for 2 h. After this time, the reaction was quenched with water and NaOH (2 M), dried over anhydrous sodium sulfate, filtered, and the filtrate was concentrated. The residue was purified by column chromatography (silica, dichloromethane/methanol) to afford the title compound (0.046 g, 22%) as an orange oil. MW=138.17. $^1$H NMR (CDCl$_3$, 500 MHz) δ 8.01-7.97 (m, 1H), 6.97-6.92 (m, 2H), 3.96 (t, J=5.5 Hz, 2H), 3.60 (s, 2H), 2.89 (t, J=5.5 Hz, 2H); APCI MS m/z 139 [M+H]+.

EXAMPLE 91

2-(5-((2-(3-Chlorophenyl)-6,7-dihydro-5H-cyclopenta[b]pyridin-4-yl)amino)pyridin-2-yl)ethanol hydrochloride

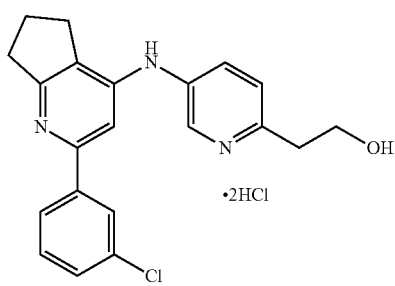 [SMILES: OCCc1ccc(Nc2cc(-c3cccc(Cl)c3)nc3c2CCC3)cn1]

Following general procedure B2, 4-chloro-2-(3-chlorophenyl)-6,7-dihydro-5H-cyclopenta[b]pyridine hydrochloride (0.075 g, 0.25 mmol) was reacted with 2-(5-aminopyridin-2-yl)ethanol (0.045 g, 0.33 mmol), followed by formation of the hydrochloride salt to afford the desired product (0.023 g, 21%) as a white solid. MW=438.78. $^1$H NMR (DMSO-d$_6$, 500 MHz) δ 14.38 (s, 1H), 10.12 (s, 1H), 8.72 (s, 1H), 8.10 (s, 1H), 7.98-7.95 (m, 1H), 7.78 (d, J=7.5 Hz, 1H), 7.71-7.58 (m, 3H), 7.21 (s, 1H), 3.80 (t, J=8.0 Hz, 2H), 3.20 (t, J=8.0 Hz, 2H), 3.03 (t, J=7.5 Hz, 2H), 2.98 (t, J=7.5 Hz, 2H), 2.26 (quin, J=7.5 Hz, 2H); APCI MS m/z 366 [M+H]$^+$.

EXAMPLE 92

2-(6-((2-(3-Chlorophenyl)-6,7-dihydro-5H-cyclopenta[b]pyridin-4-yl)amino)pyridin-3-yl)ethanol hydrochloride

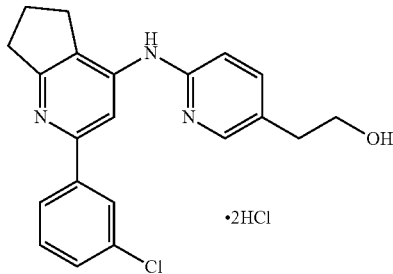 [SMILES: OCCc1ccc(Nc2cc(-c3cccc(Cl)c3)nc3c2CCC3)nc1]

Following general procedure B2, 4-chloro-2-(3-chlorophenyl)-6,7-dihydro-5H-cyclopenta[b]pyridine hydrochloride (0.110 g, 0.37 mmol) was reacted with 2-(6-aminopyridin-3-yl)ethanol (0.100 g, 0.74 mmol), followed by formation of the hydrochloride salt to afford the title compound (0.096 g, 65%) as a light yellow solid. MW=402.32. $^1$H NMR (DMSO-d$_6$, 500 MHz) δ 14.47 (s, 1H), 9.92 (s, 1H), 8.81-8.75 (m, 1H), 8.28 (s, 1H), 7.97 (m, 1H), 7.82-7.63 (m, 4H), 7.40 (d, J=8.5 Hz, 1H), 3.63 (t, J=6.5 Hz, 2H), 3.20 (t, J=7.5 Hz, 2H), 3.05 (t, J=7.5 Hz, 2H), 2.73 (t, J=6.5 Hz, 2H), 2.30-2.21 (m, 2H); APCI MS m/z 366 [M+H]$^+$.

EXAMPLE 93

Trans-4-((2-(3-Chlorophenyl)-6,7-dihydro-5H-cyclopenta[b]pyridin-4-yl)amino)cyclohexyl-methanol hydrochloride

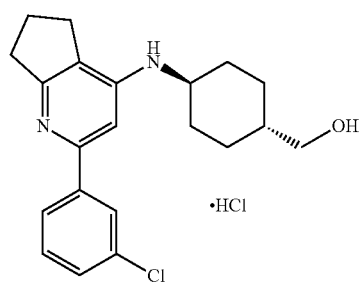

Following general procedure B2, 4-chloro-2-(3-chlorophenyl)-6,7-dihydro-5H-cyclopenta[b]pyridine hydrochloride (0.093 g, 0.31 mmol) was reacted with trans-(4-aminocyclohexyl)methanol hydrochloride (0.077 g, 0.47 mmol), followed by formation of the hydrochloride salt to afford the title compound (0.011 g, 9%) as a light yellow solid. MW=393.35. $^1$H NMR (DMSO-d$_6$, 500 MHz) δ 13.44 (s, 1H), 7.99-7.96 (m, 1H), 7.83 (d, J=7.5 Hz, 1H), 7.68 (d, J=8.0 Hz, 1H), 7.63 (t, J=8.0 Hz, 1H), 7.55 (br s, 1H), 7.10 (s, 1H), 4.45-4.43 (m, 1H), 3.84-3.80 (m, 1H), 3.28-3.23 (m, 2H), 3.05 (t, J=7.5 Hz, 2H), 2.78 (t, J=7.0 Hz, 2H), 2.17 (quin, J=7.5 Hz, 2H); 1.92-1.90 (m, 2H), 1.79-1.77 (m, 2H), 1.45-1.34 (m, 3H), 1.16-1.10 (m, 2H); APCI MS m/z 357 [M+H]$^+$.

EXAMPLE 94

2-(6-((2-(3-Chlorophenyl)-6,7-dihydro-5H-cyclopenta[b]pyridin-4-yl)amino)pyridin-3-yl)acetamide hydrochloride

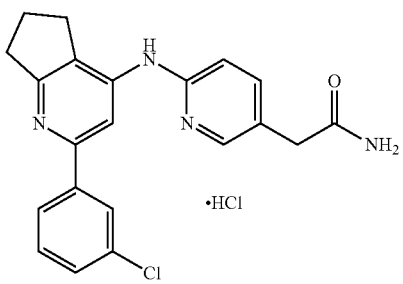 [SMILES: NC(=O)Cc1ccc(Nc2cc(-c3cccc(Cl)c3)nc3c2CCC3)nc1 ; Cl]

Step 1. Preparation of ethyl 2-(6-((2-(3-chlorophenyl)-6,7-dihydro-5H-cyclopenta[b]pyridin-4-yl)amino)pyridin-3-yl)acetate hydrochloride

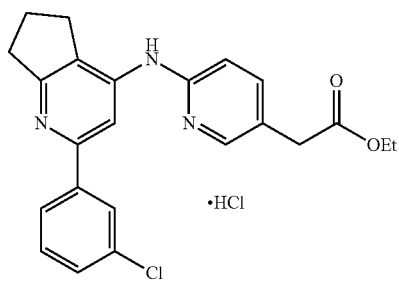 [SMILES: CCOC(=O)Cc1ccc(Nc2cc(-c3cccc(Cl)c3)nc3c2CCC3)nc1 ; Cl]

Following general procedure B1, 4-chloro-2-(3-chlorophenyl)-6,7-dihydro-5H-cyclopenta[b]pyridine hydrochloride (0.112 g, 0.37 mmol) was reacted with ethyl 2-(6-aminopyridin-3-yl)acetate (0.134 g, 0.75 mmol), followed by formation of the hydrochloride salt to afford the title compound (0.136 g, 85%) as a light yellow solid. MW=444.35. $^1$H NMR (DMSO-d$_6$, 300 MHz) δ 14.47 (s, 1H), 9.92 (s, 1H), 8.83-8.76 (m, 1H), 8.35-8.29 (m, 1H), 7.99-7.95 (m, 1H), 7.84-7.75 (m, 2H), 7.74-7.61 (m, 2H), 7.42 (d, J=8.5 Hz, 1H), 4.10 (q, J=7.0 Hz, 2H), 3.73 (s, 2H), 3.20 (t, J=7.5 Hz, 2H), 3.06 (t, J=7.5 Hz, 2H), 2.26 (quin, J=7.5 Hz, 2H), 1.20 (t, J=7.0 Hz, 3H); APCI MS m/z 408 [M+H]$^+$.

EXAMPLE 94

2-(6-((2-(3-Chlorophenyl)-6,7-dihydro-5H-cyclopenta[b]pyridin-4-yl)amino)pyridin-3-yl)acetamide hydrochloride

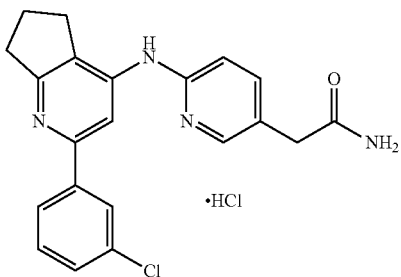 [SMILES: NC(=O)Cc1ccc(Nc2cc(-c3cccc(Cl)c3)nc3c2CCC3)nc1 ; Cl]

Following general procedure C, ethyl 2-(6-((2-(3-chlorophenyl)-6,7-dihydro-5H-cyclopenta[b]pyridin-4-yl)amino)pyridin-3-yl)acetate (0.100 g, 0.24 mmol) was reacted with ammonia in methanol (7.0 M, 3 mL), followed by formation of the hydrochloride salt to afford the title compound (0.100 g, 75%) as a white solid. MW=415.32. $^1$H NMR (DMSO-$d_6$, 500 MHz) δ 14.36 (s, 1H), 9.86 (s, 1H), 8.80-8.76 (m, 1H), 8.31-8.27 (m, 1H), 7.98-7.95 (m, 1H), 7.82-7.78 (m, 1H), 7.77-7.74 (m, 1H), 7.72-7.63 (m, 2H), 7.58-7.53 (m, 1H), 7.38 (d, J=8.5 Hz, 1H), 6.97 (s, 1H), 3.42 (s, 2H), 3.19 (t, J=7.5 Hz, 2H), 3.05 (t, J=7.5 Hz, 2H), 2.26 (t, J=7.5 Hz, 2H); APCI MS m/z 379 [M+H]$^+$.

EXAMPLE 95

Trans-2-(4-((2-(3-Chlorophenyl)-6,7-dihydro-5H-cyclopenta[b]pyridin-4-yl)amino)cyclohexyl)acetonitrile hydrochloride

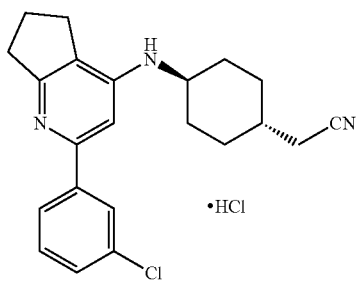

Following general procedure B1, 4-chloro-2-(3-chlorophenyl)-6,7-dihydro-5H-cyclopenta[b]pyridine hydrochloride (0.108 g, 0.36 mmol) was reacted with 2-(4-aminocyclohexyl)acetonitrile (0.120 g, 0.72 mmol), followed by formation of the hydrochloride salt to afford the title compound (0.068 g, 47%) as a white solid. MW=402.36. $^1$H NMR (DMSO-$d_6$, 500 MHz) δ 13.51 (s, 1H), 7.99-7.96 (m, 1H), 7.84 (d, J=7.5 Hz, 1H), 7.71-7.68 (m, 1H), 7.64 (t, J=7.5 Hz, 1H), 7.62-7.57 (m, 2H), 7.14 (s, 1H), 3.95-3.79 (m, 1H), 3.06 (t, J=7.5 Hz, 2H), 2.78 (t, J=7.5 Hz, 2H), 2.17 (quin, J=7.5 Hz, 2H), 1.95-1.88 (m, 2H), 1.85-1.77 (m, 2H), 1.68-1.58 (m, 1H), 1.37-1.22 (m, 2H); APCI MS m/z 366 [M+H]$^+$.

EXAMPLE 96

Trans-2-(4-((2-(3-Chlorophenyl)-6,7-dihydro-5H-cyclopenta[b]pyridin-4-yl)amino)cyclohexyl)acetamide hydrochloride

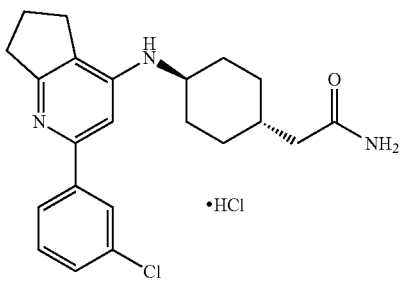 [SMILES: NC(=O)C[C@H]1CC[C@H](Nc2cc(-c3cccc(Cl)c3)nc3c2CCC3)CC1 ; Cl]

Trans-2-(4-((2-(3-chlorophenyl)-6,7-dihydro-5H-cyclopenta[b]pyridin-4-yl)amino)cyclohexyl)acetonitrile hydrochloride (0.056 g, 0.14 mmol) was suspended in sulfuric acid (2 mL) at 0° C. The reaction was warmed to rt and stirred for 16 h. After this time, the mixture was added dropwise to a saturated NaHCO$_3$ solution, extracted with ethyl acetate, dried over anhydrous sodium sulfate, filtered, and the filtrate was concentrated. The residue was purified by column chromatography (silica, dichloromethane/methanol), followed by formation of the hydrochloride salt to afford the title compound (0.048 g, 82%) as a white solid. MW=420.38. $^1$H NMR (DMSO-$d_6$, 500 MHz) δ 13.50 (s, 1H), 7.99-7.96 (m, 1H), 7.86-7.82 (m, 1H), 7.71-7.67 (m, 1H), 7.62-7.58 (m, 2H), 7.27 (s, 1H), 7.10 (s, 1H), 6.73 (s, 1H), 3.89-3.79 (m, 1H), 3.06 (t, J=7.5 Hz, 2H), 2.78 (t, J=7.5 Hz, 2H), 2.17 (quin, J=7.5 Hz, 2H), 1.96 (d, J=7.0 Hz, 2H), 1.92-1.85 (m, 2H), 1.78-1.71 (m, 2H), 1.70-1.60 (m, 1H), 1.50-1.38 (m, 2H), 1.21-1.09 (m, 1H); APCI MS m/z 384 [M+H]$^+$.

EXAMPLE 97

Trans-2-(4-((2-(3-chlorophenyl)-6,7-dihydro-5H-cyclopenta[b]pyridin-4-yl)amino)cyclohexyl)ethanol hydrochloride

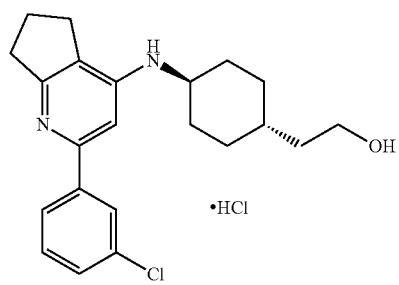 [SMILES: OCC[C@H]1CC[C@H](Nc2cc(-c3cccc(Cl)c3)nc3c2CCC3)CC1 ; Cl]

Following general procedure B2, 4-chloro-2-(3-chlorophenyl)-6,7-dihydro-5H-cyclopenta[b]pyridine hydrochloride (0.102 g, 0.34 mmol) was reacted with 2-(4-aminocyclohexyl)ethanol (0.140 g, 1.0 mmol), followed by formation of the hydrochloride salt to afford the title compound (0.006 g, 4%) as a white solid. MW=407.38. $^1$H NMR (DMSO-$d_6$, 500 MHz) δ 13.48 (s, 1H), 7.97 (s, 1H), 7.84 (d, J=8.0 Hz, 1H), 7.71-7.51 (m, 3H), 7.09 (s, 1H), 4.34 (br s, 1H), 3.85-3.82 (m, 1H), 3.45 (t, J=6.0 Hz, 2H), 3.06 (t, J=7.5 Hz, 2H), 2.78 (t, J=7.5 Hz, 2H), 2.17 (quin, J=7.5 Hz, 2H), 1.91-1.85 (m, 2H), 1.78-1.73 (m, 2H), 1.46-1.32 (m, 5H), 1.16-1.05 (m, 2H); APCI MS m/z 371 [M+H]⁺.

EXAMPLE 98

1-(4-((2-(3-Chlorophenyl)-6,7-dihydro-5H-cyclopenta[b]pyridin-4-yl)amino)phenyl)-2-methylpropan-2-ol

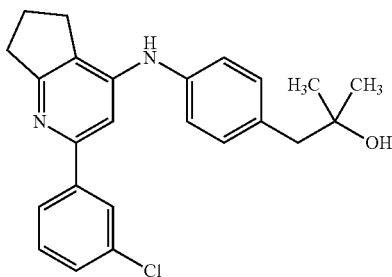 [SMILES: CC(C)(O)Cc1ccc(Nc2cc(-c3cccc(Cl)c3)nc3c2CCC3)cc1]

Following general procedure B1, 4-chloro-2-(3-chlorophenyl)-6,7-dihydro-5H-cyclopenta[b]pyridine hydrochloride (0.105 g, 0.35 mmol) was reacted with 1-(4-aminophenyl)-2-methylpropan-2-ol (0.086 g, 0.53 mmol) to afford the title compound (0.100 g, 73%) as a white solid. MW=392.92. ¹H NMR (DMSO-d₆, 500 MHz) δ 8.06 (s, 1H), 7.90-7.88 (m, 1H), 7.75-7.72 (m, 1H), 7.46-7.39 (m, 2H), 7.23-7.14 (m, 5H), 4.28 (s, 1H), 2.90 (t, J=7.5 Hz, 2H), 2.82 (t, J=7.5 Hz, 2H), 2.64 (s, 2H), 2.08 (quin, J=7.5 Hz, 2H), 1.08 (s, 6H); APCI MS m/z 393 [M+H]⁺.

EXAMPLE 99

1-(4-((2-(3-Chlorophenyl)-6,7-dihydro-5H-cyclopenta[b]pyridin-4-yl)amino)phenyl)-2-methylpropan-2-ol hydrochloride

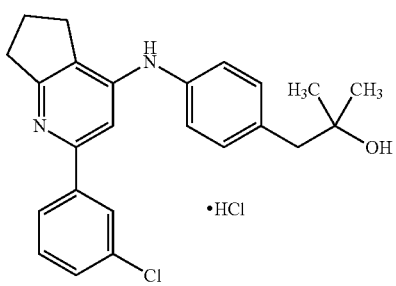 [SMILES: CC(C)(O)Cc1ccc(Nc2cc(-c3cccc(Cl)c3)nc3c2CCC3)cc1 ; Cl]

To a suspension of 1-(4-((2-(3-chlorophenyl)-6,7-dihydro-5H-cyclopenta[b]pyridin-4-yl)amino)phenyl)-2-methylpropan-2-ol (0.056 g, 0.14 mmol) in water (3 mL) and acetonitrile (1 mL) was added 6M HCl (2 drops). The solution was lyophillized to afford the title compound (0.060 g, 98%) as a yellow solid. MW=429.38. ¹H NMR (DMSO-d₆, 500 MHz) δ 14.11 (s, 1H), 9.84 (s, 1H), 7.89 (t, J=1.8 Hz, 1H), 7.72-7.64 (m, 2H), 7.60 (t, J=7.8 Hz, 1H), 7.34-7.29 (m, 4H), 6.97 (s, 1H), 3.16 (t, J=7.5 Hz, 2H), 2.93-2.89 (m, 2H), 2.69 (s, 2H), 2.24 (quin, J=7.5 Hz, 2H), 1.08 (s, 6H); APCI MS m/z 393 [M+H]⁺.

EXAMPLE 100

Methyl 2-(3-((2-(3-chlorophenyl)-6,7-dihydro-5H-cyclopenta[b]pyridin-4-yl)amino)phenyl)acetate hydrochloride

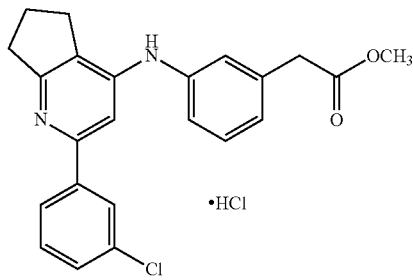 [SMILES: COC(=O)Cc1cccc(Nc2cc(-c3cccc(Cl)c3)nc3c2CCC3)c1 ; Cl]

Following general procedure B1, 4-chloro-2-(3-chlorophenyl)-6,7-dihydro-5H-cyclopenta[b]pyridine hydrochloride (0.160 g, 0.53 mmol) was reacted with methyl 2-(3-aminophenyl)acetate (0.130 g, 0.79 mmol), followed by formation of the hydrochloride salt to afford the title compound (0.190 g, 91%) as a white solid. MW=429.34. ¹H NMR (DMSO-d₆, 500 MHz) δ 14.04 (s, 1H), 9.81 (s, 1H), 7.92 (t, J=1.8 Hz, 1H), 7.76-7.71 (m, 1H), 7.69-7.64 (m, 1H), 7.60 (t, J=7.9 Hz, 1H), 7.44 (t, J=7.9 Hz, 1H), 7.38-7.34 (m, 1H), 7.33-7.28 (m, 1H), 7.23-7.17 (m, 1H), 7.09 (s, 1H), 3.77 (s, 2H), 3.62 (s, 3H), 3.16 (t, J=7.5 Hz, 2H), 2.93 (t, J=7.5 Hz, 2H), 2.24 (quin, J=7.5 Hz, 2H); APCI MS m/z 393 [M+H]⁺.

EXAMPLE 101

2-(3-((2-(3-Chlorophenyl)-6,7-dihydro-5H-cyclopenta[b]pyridin-4-yl)amino)phenyl)acetamide hydrochloride

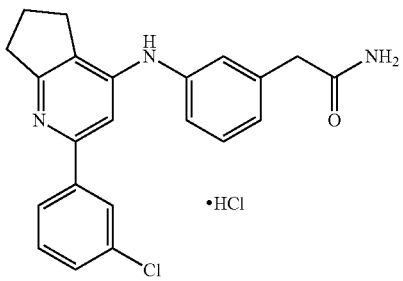 [SMILES: NC(=O)Cc1cccc(Nc2cc(-c3cccc(Cl)c3)nc3c2CCC3)c1 ; Cl]

Following general procedure C, methyl 2-(3-((2-(3-chlorophenyl)-6,7-dihydro-5H-cyclopenta[b]pyridin-4-yl)amino)phenyl)acetate (0.090 g, 0.23 mmol) was reacted with ammonia in methanol (7.0 M, 3 mL), followed by formation of the hydrochloride salt to afford the title compound (0.082 g, 86%) as a light yellow solid. MW=414.33. ¹H NMR (DMSO-d₆, 500 MHz) δ 14.13 (s, 1H), 9.87 (s, 1H), 7.94 (t, J=1.8 Hz, 1H), 7.79-7.74 (m, 1H), 7.68-7.64 (m, 1H), 7.63-7.54 (m, 2H), 7.42 (t, J=7.8 Hz, 1H), 7.36-

7.35 (m, 1H), 7.30-7.25 (m, 1H), 7.24-7.18 (m, 1H), 7.09 (s, 1H), 6.92 (s, 1H), 3.45 (s, 2H), 3.17 (t, J=7.5 Hz, 2H), 2.93 (t, J=7.5 Hz, 2H), 2.24 (quin, J=7.5 Hz, 2H); APCI MS m/z 378 [M+H]$^+$.

EXAMPLE 102

2-(3-((2-(3-Chlorophenyl)-6,7-dihydro-5H-cyclopenta[b]pyridin-4-yl)amino)phenyl)ethanol hydrochloride

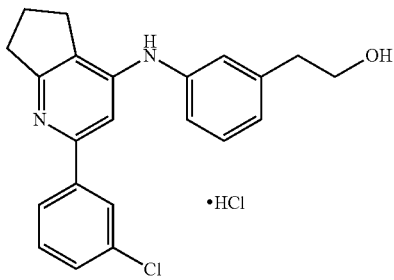 [SMILES: OCCc1cccc(Nc2cc(-c3cccc(Cl)c3)nc3c2CCC3)c1 ; Cl]

Following general procedure E2, methyl 2-(3-((2-(3-chlorophenyl)-6,7-dihydro-5H-cyclopenta[b]pyridin-4-yl)amino)phenyl)acetate (0.080 g, 0.20 mmol) was reacted with BH$_3$.DMS (2.0 M, 0.30 mL, 0.60 mmol), followed by formation of the hydrochloride salt to afford the title compound (0.064 g, 80%) as a light yellow solid. MW=401.33. $^1$H NMR (DMSO-d$_6$, 500 MHz) δ 14.08 (s, 1H), 9.81 (s, 1H), 7.90 (t, J=1.8 Hz, 1H), 7.76-7.68 (m, 1H), 7.67-7.63 (m, 1H), 7.59 (t, J=7.8 Hz, 1H), 7.40 (t, J=7.8 Hz, 1H), 7.30-7.27 (m, 1H), 7.26-7.23 (m, 1H), 7.20-7.16 (m, 1H), 7.09 (s, 1H), 3.65 (t, J=6.5 Hz, 2H), 3.16 (t, J=7.5 Hz, 2H), 2.92 (t, J=7.5 Hz, 2H), 2.77 (t, J=6.5 Hz, 2H), 2.24 (quin, J=7.5 Hz, 2H); APCI MS m/z 365 [M+H]$^+$.

EXAMPLE 103

4-((4-(2-Amino-2-oxoethyl)phenyl)amino)-2-(3-chlorophenyl)-6,7-dihydro-5H-cyclopenta[b]pyridine 1-oxide

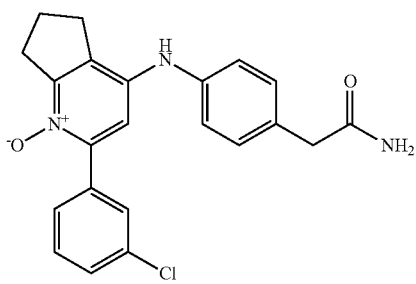

To a solution of 2-(4-((2-(3-chlorophenyl)-5H-cyclopenta[b]pyridin-4-yl)amino)phenyl)acetamide (0.070 g, 0.18 mmol) in chloroform (20 mL) at rt was added MCPBA (77%, 0.062 g, 0.28 mmol). The mixture stirred at rt for 16 h and then purified by preparative HPLC (water/acetonitrile with 0.05% TFA) to afford the title compound (0.017 g, 23%) as a white solid. MW=393.87. $^1$H NMR (DMSO-d$_6$, 500 MHz) δ 9.52 (s, 1H), 7.76-7.73 (m, 1H), 7.64-7.60 (m, 1H), 7.59-7.52 (m, 2H), 7.47 (s, 1H), 7.36-7.26 (m, 4H), 6.88 (s, 1H), 6.83 (s, 1H), 3.38 (s, 2H), 3.19 (t, J=7.5 Hz, 2H), 3.00 (t, J=7.5 Hz, 2H), 2.25 (quin, J=7.5 Hz, 2H); APCI MS m/z 394 [M+H]$^+$.

EXAMPLE 104

1-(4-((2-(3-Chlorophenyl)-6,7-dihydro-5H-cyclopenta[b]pyridin-4-yl)amino)phenyl)propan-2-ol

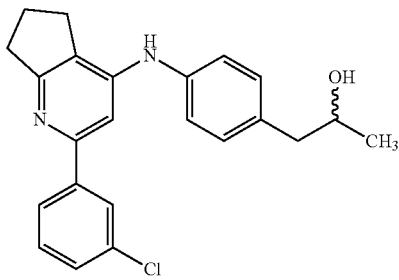 [SMILES: CC(O)Cc1ccc(Nc2cc(-c3cccc(Cl)c3)nc3c2CCC3)cc1]

To a solution of 1-(4-((2-(3-chlorophenyl)-6,7-dihydro-5H-cyclopenta[b]pyridin-4-yl)amino)phenyl)propan-2-one (0.076 g, 0.20 mmol) in methanol (5 mL) was added sodium borohydride (0.015 g, 0.40 mmol). The mixture stirred at rt for 30 min. After this time, the mixture was diluted with a saturated solution of NaHCO$_3$ and extracted with ethyl acetate. The organic layer was dried over anhydrous sodium sulfate, filtered, and the filtrate was concentrated. The residue was purified by preparative HPLC (water/acetonitrile with 0.05% TFA) to afford the title compound (0.015 g, 20%) as a white solid. MW=378.89. $^1$H NMR (DMSO-d$_6$, 500 MHz) δ 8.07 (s, 1H), 7.91-7.88 (m, 1H), 7.76-7.72 (m, 1H), 7.46-7.39 (m, 2H), 7.22-7.15 (m, 5H), 4.53 (d, J=4.5 Hz, 1H), 3.87-3.79 (m, 1H), 2.90 (t, J=7.5 Hz, 2H), 2.82 (t, J=7.5 Hz, 2H), 2.71-2.65 (m, 1H), 2.58-2.53 (m, 1H), 2.08 (quin, J=7.5 Hz, 2H), 1.05 (d, J=6.0 Hz, 3H); APCI MS m/z 379 [M+H]$^+$.

EXAMPLE 105

2-(3-Chlorophenyl)-N-(4-(2-(dimethylamino)ethyl)phenyl)-6,7-dihydro-5H-cyclopenta[b]pyridin-4-amine hydrochloride

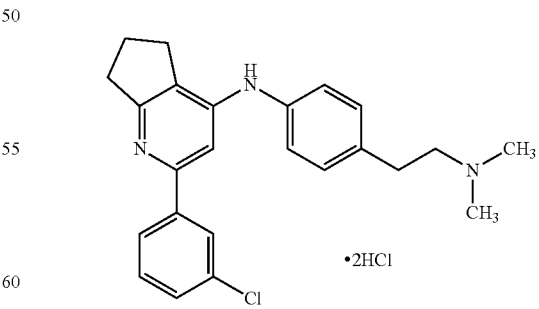

Following general procedure B1, 4-chloro-2-(3-chlorophenyl)-6,7-dihydro-5H-cyclopenta[b]pyridine (0.083 g, 0.31 mmol) was reacted with 4-(2-(dimethylamino)ethyl) aniline (0.062 g, 0.37 mmol), followed by formation of the hydrochloride salt to afford the title compound (0.098 g, 67%) as a light yellow solid. MW=464.86. $^1$H NMR (DMSO-d$_6$, 500 MHz) δ 10.16 (s, 1H), 8.33 (s, 1H), 7.91-7.89 (m, 1H), 7.79-7.74 (m, 1H), 7.48-7.42 (m, 2H), 7.31-7.28 (m, 4H), 7.21 (s, 1H), 3.29-3.26 (m, 2H), 3.02-2.90 (m, 4H), 2.87-2.78 (m, 8H), 2.10 (quin, J=7.5 Hz, 2H); APCI MS m/z 392 [M+H]$^+$.

EXAMPLE 106

(R)-1-(4-((2-(3-Chlorophenyl)-6,7-dihydro-5H-cyclopenta[b]pyridin-4-yl)amino)phenyl)propan-2-ol

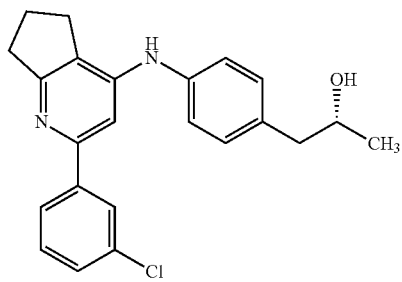

Following general procedure B1, 4-chloro-2-(3-chlorophenyl)-6,7-dihydro-5H-cyclopenta[b]pyridine (0.086 g, 0.32 mmol) was reacted with (R)-1-(4-aminophenyl)propan-2-ol (0.058 g, 0.38 mmol) to afford the title compound (0.027 g, 22%) as a light yellow solid. MW=378.89. $^1$H NMR (DMSO-d$_6$, 500 MHz) δ 8.06 (s, 1H), 7.91-7.88 (m, 1H), 7.76-7.72 (m, 1H), 7.46-7.38 (m, 2H), 7.23-7.14 (m, 5H), 4.53 (d, J=4.5 Hz, 1H), 3.86-3.78 (m, 1H), 2.90 (t, J=7.5 Hz, 2H), 2.82 (t, J=7.5 Hz, 2H), 2.71-2.65 (m, 1H), 2.58-2.52 (m, 1H), 2.08 (quin, J=7.5 Hz, 2H), 1.05 (d, J=6.5 Hz, 3H); APCI MS m/z 379 [M+H]$^+$.

EXAMPLE 107

(S)-1-(4-((2-(3-Chlorophenyl)-6,7-dihydro-5H-cyclopenta[b]pyridin-4-yl)amino)phenyl)propan-2-ol

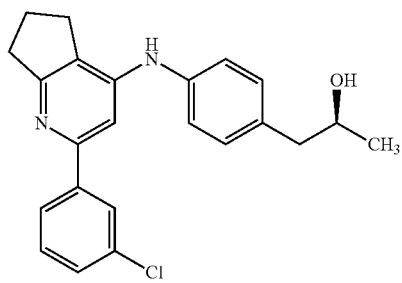

Following general procedure B1, 4-chloro-2-(3-chlorophenyl)-6,7-dihydro-5H-cyclopenta[b]pyridine (0.089 g, 0.34 mmol) was reacted with (S)-1-(4-aminophenyl)propan-2-ol (0.061 g, 0.41 mmol) to afford the title compound (0.034 g, 26%) as a light yellow solid. MW=378.89. $^1$H NMR (DMSO-d$_6$, 500 MHz) δ 8.06 (s, 1H), 7.91-7.88 (m, 1H), 7.76-7.72 (m, 1H), 7.46-7.38 (m, 2H), 7.23-7.14 (m, 5H), 4.53 (d, J=4.5 Hz, 1H), 3.86-3.78 (m, 1H), 2.90 (t, J=7.5 Hz, 2H), 2.82 (t, J=7.5 Hz, 2H), 2.71-2.65 (m, 1H), 2.58-2.52 (m, 1H), 2.08 (quin, J=7.5 Hz, 2H), 1.05 (d, J=6.5 Hz, 3H); APCI MS m/z 379 [M+H]$^+$.

EXAMPLE 108

2-(4-((2-(3-Chlorophenyl)-6,7-dihydro-5H-cyclopenta[b]pyridin-4-yl)amino)benzyl)-3-hydroxypropanamide hydrochloride

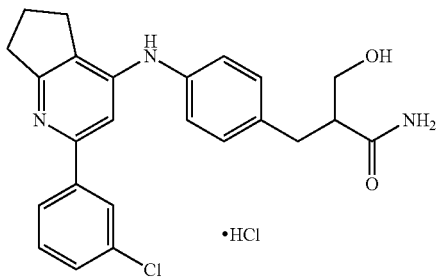 [SMILES: NC(=O)C(CO)Cc1ccc(Nc2cc(-c3cccc(Cl)c3)nc3c2CCC3)cc1 ; Cl]

Step 1. Preparation of isopropyl 3-amino-2-(4-((2-(3-chlorophenyl)-6,7-dihydro-5H-cyclopenta[b]pyridin-4-yl)amino)benzyl)-3-oxopropanoate

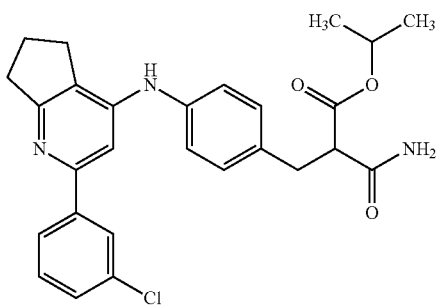 [SMILES: CC(C)OC(=O)C(Cc1ccc(Nc2cc(-c3cccc(Cl)c3)nc3c2CCC3)cc1)C(N)=O]

Following general procedure B2, 4-chloro-2-(3-chlorophenyl)-6,7-dihydro-5H-cyclopenta[b]pyridine (0.060 g, 0.23 mmol) was reacted with isopropyl 3-amino-2-(4-aminobenzyl)-3-oxopropanoate (0.057 g, 0.23 mmol) to afford the title compound (0.052 g, 47%) as a light yellow solid. MW=477.98. APCI MS m/z 478 [M+H]$^+$.

Example 108 HCl Salt 2-(4-((2-(3-Chlorophenyl)-6,7-dihydro-5H-cyclopenta[b]pyridin-4-yl)amino)benzyl)-3-hydroxypropanamide hydrochloride

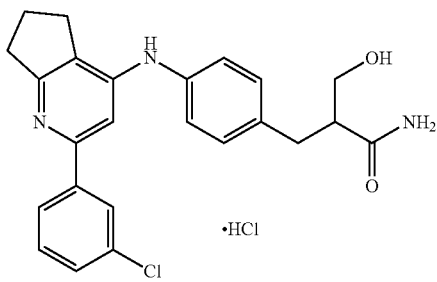 [SMILES: NC(=O)C(CO)Cc1ccc(Nc2cc(-c3cccc(Cl)c3)nc3c2CCC3)cc1 ; Cl]

To a solution of isopropyl 3-amino-2-(4-((2-(3-chlorophenyl)-6,7-dihydro-5H-cyclopenta[b]pyridin-4-yl)amino)benzyl)-3-oxopropanoate (0.052 g, 0.11 mmol) in THF (5 mL) was added lithium aluminum hydride (1.0 M, 0.22 mL, 0.22 mmol). The mixture stirred at 0° C. for 3 h. After this time, the mixture was quenched with water and sodium hydroxide (2M) and then extracted with ethyl acetate. The organic layer were dried over anhydrous sodium sulfate, filtered, and the filtrate was concentrated. The residue was purified by column chromatography (silica, dichloromethane/methanol) to afford the title compound (0.014 g, 28%) as a yellow solid. MW=458.38. $^1$H NMR (DMSO-$d_6$, 500 MHz) δ 13.93 (s, 1H), 9.74 (s, 1H), 7.89-7.86 (m, 1H), 7.70-7.65 (m, 2H), 7.63-7.58 (m, 1H), 7.33-7.27 (m, 4H), 7.23 (s, 1H), 6.96 (s, 1H), 6.74 (s, 1H), 3.59-3.53 (m, 1H), 3.15 (t, J=7.5 Hz, 2H), 2.94-2.87 (m, 2H), 2.82-2.69 (m, 2H), 2.65-2.56 (m, 1H), 2.24 (quin, J=7.5 Hz, 2H); APCI MS m/z 422 [M+H]$^+$.

EXAMPLE 109

2-(4-((2-(3-Chlorophenyl)-6,7-dihydro-5H-cyclopenta[b]pyridin-4-yl)amino)-2-methylphenyl)acetonitrile hydrochloride

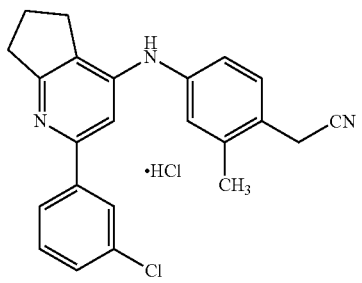 [SMILES: Cc1cc(Nc2cc(-c3cccc(Cl)c3)nc3c2CCC3)ccc1CC#N ; Cl]

Following General Procedure A2, 4-chloro-2-(3-chlorophenyl)-6,7-dihydro-5H-cyclopenta[b]pyridine hydrochloride (0.100 g, 0.33 mmol) was reacted with 2-(4-amino-2-methylphenyl)acetonitrile (0.073 g, 0.50 mmol), followed by the formation of the hydrochloride salt to afford the title compound (0.063 g, 63%) as a white solid. MW=410.34. $^1$H NMR (DMSO-$d_6$, 500 MHz) δ 13.96 (s, 1H), 9.71 (s, 1H), 7.89 (t, J=1.8 Hz, 1H), 7.78-7.69 (m, 1H), 7.65 (d, J=7.9 Hz, 1H), 7.59 (t, J=7.9 Hz, 1H), 7.45 (d, J=7.9 Hz, 1H), 7.30 (d, J=7.9 Hz, 1H), 7.26 (s, 1H), 7.07 (s, 1H), 4.03 (s, 2H), 3.14 (t, J=7.6 Hz, 2H), 2.91 (t, J=7.6 Hz, 2H), 2.34 (s, 3H), 2.28-2.19 (m, 2H); APCI MS m/z 374 [M+H]$^+$.

EXAMPLE 110

2-(3-Chlorophenyl)-N-(4-(2,2,2-trifluoroethyl)phenyl)-6,7-dihydro-5H-cyclopenta[b]pyridin-4-amine hydrochloride

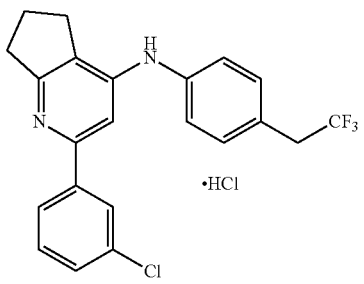 [SMILES: FC(F)(F)Cc1ccc(Nc2cc(-c3cccc(Cl)c3)nc3c2CCC3)cc1 ; Cl]

Following General Procedure A2, 4-chloro-2-(3-chlorophenyl)-6,7-dihydro-5H-cyclopenta[b]pyridine hydrochloride (0.075 g, 0.25 mmol) was reacted with 4-(2,2,2-trifluoroethyl)aniline (0.066 g, 0.37 mmol), followed by the formation of the hydrochloride salt to afford the title compound (0.047 g, 62%) as an off-white solid. MW=439.30. $^1$H NMR (DMSO-$d_6$, 500 MHz) δ 14.07 (s, 1H), 9.77 (s, 1H), 7.91 (t, J=1.8 Hz, 1H), 7.75-7.70 (m, 1H), 7.66 (d, J=7.9 Hz, 1H), 7.60 (t, J=7.9 Hz, 1H), 7.46 (q, J=7.9 Hz, 4H), 7.08 (s, 1H), 3.70 (q, J=11.6 Hz, 2H), 3.16 (t, J=7.6 Hz, 2H), 2.93 (t, J=7.6 Hz, 2H), 2.29-2.19 (m, 2H); APCI MS m/z 403 [M+H]$^+$.

EXAMPLE 111

2-(4-((2-(3-Chlorophenyl)-6,7-dihydro-5H-cyclopenta[b]pyridin-4-yl)amino)-2-methylphenyl)acetamide hydrochloride

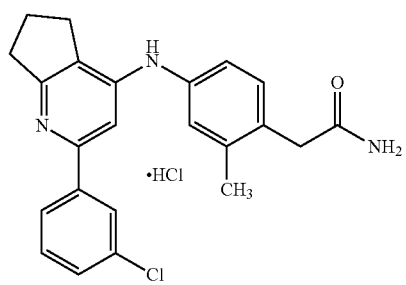 [SMILES: Cc1cc(Nc2cc(-c3cccc(Cl)c3)nc3c2CCC3)ccc1CC(N)=O ; Cl]

Step 1. Preparation of 2-(4-amino-2-methylphenyl)acetamide

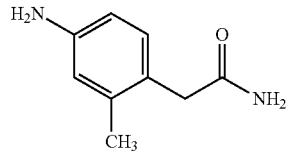

Sulfuric acid (26 mL) was added to 2-(4-amino-2-methylphenyl)acetonitrile (0.500 g, 3.42 mmol) at 0° C. The mixture was warmed to rt for 4 h, diluted with saturated aqueous sodium bicarbonate, and extracted with ethyl acetate. The combined organic layer was dried over anhydrous sodium sulfate and concentrated to afford the title compound (0.252 g, 50%) as a tan solid. MW=164.20. $^1$H NMR (DMSO-$d_6$, 500 MHz) δ 7.09 (s, 1H), 6.81 (d, J=7.9 Hz, 1H), 6.74 (s, 1H), 6.39-6.35 (m, 1H), 6.33-6.29 (m, 1H), 4.78 (s, 2H), 3.19 (s, 2H), 2.10 (s, 3H); APCI MS m/z 165 [M+H]$^+$.

EXAMPLE 111

2-(4-((2-(3-Chlorophenyl)-6,7-dihydro-5H-cyclopenta[b]pyridin-4-yl)amino)-2-methylphenyl)acetamide hydrochloride

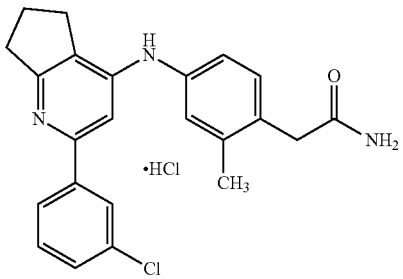

Following General Procedure A2, 4-chloro-2-(3-chlorophenyl)-6,7-dihydro-5H-cyclopenta[b]pyridine hydrochloride (0.075 g, 0.25 mmol) was reacted with 4-(2,2,2-trifluoroethyl)aniline (0.062 g, 0.38 mmol), followed by the formation of the hydrochloride salt to afford the title compound (0.018 g, 24%) as a tan solid. MW=428.35. $^1$H NMR (DMSO-$d_6$, 500 MHz) δ 13.95 (s, 1H), 9.69 (s, 1H), 7.88 (t, J=1.8 Hz, 1H), 7.71-7.65 (m, 2H), 7.60 (t, J=7.9 Hz, 1H), 7.44 (s, 1H), 7.29 (d, J=7.9 Hz, 1H), 7.22-7.16 (m, 2H), 7.01 (s, 1H), 6.93 (s, 1H), 3.45 (s, 2H), 3.14 (t, J=7.6 Hz, 2H), 2.91 (t, J=7.6 Hz, 2H), 2.29 (s, 3H), 2.27-2.20 (m, 2H); APCI MS m/z 392 [M+H]$^+$.

EXAMPLE 112

2-(4-((2-(3-Chlorophenyl)-6,7-dihydro-5H-cyclopenta[b]pyridin-4-yl)amino)-2-fluorophenyl)acetamide hydrochloride

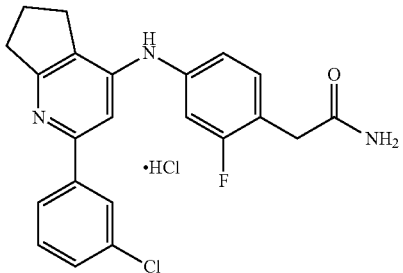 [SMILES: NC(=O)Cc1ccc(Nc2cc(-c3cccc(Cl)c3)nc3c2CCC3)cc1F ; Cl]

Step 1. Preparation of ethyl 2-(4-((2-(3-chlorophenyl)-6,7-dihydro-5H-cyclopenta[b]pyridin-4-yl)amino)-2-fluorophenyl)acetate

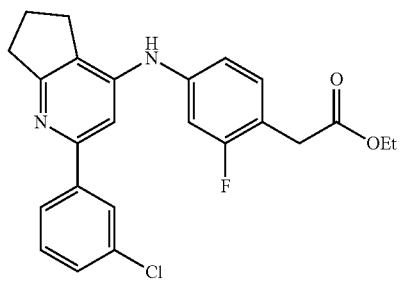 [SMILES: CCOC(=O)Cc1ccc(Nc2cc(-c3cccc(Cl)c3)nc3c2CCC3)cc1F]

Following General Procedure B2, 4-chloro-2-(3-chlorophenyl)-6,7-dihydro-5H-cyclopenta[b]pyridine (0.100 g, 0.33 mmol) was reacted with ethyl 2-(4-amino-2-fluorophenyl)acetate (0.098 g, 0.50 mmol) to afford the title compound (0.094 g, 94%). MW=424.90. $^1$H NMR (CD$_3$OD, 300 MHz) δ 7.79-7.75 (m, 1H), 7.66-7.60 (m, 1H), 7.45-7.36 (m, 2H), 7.30 (t, J=8.4 Hz, 1H), 7.20 (s, 1H), 7.11-7.05 (m, 1H), 7.04-6.97 (m, 1H), 4.17 (q, J=7.1 Hz, 2H), 3.68 (s, 2H), 3.02 (t, J=7.6 Hz, 2H), 2.89 (t, J=7.6 Hz, 2H), 2.30-2.13 (m, 2H), 1.26 (t, J=7.6 Hz, 3H); APCI MS m/z 425 [M+H]$^+$.

EXAMPLE 112

2-(4-((2-(3-Chlorophenyl)-6,7-dihydro-5H-cyclopenta[b]pyridin-4-yl)amino)-2-fluorophenyl)acetamide hydrochloride

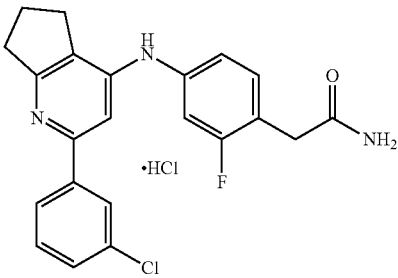 [SMILES: NC(=O)Cc1ccc(Nc2cc(-c3cccc(Cl)c3)nc3c2CCC3)cc1F ; Cl]

To a microwave vessel was added ethyl 2-(4-((2-(3-chlorophenyl)-6,7-dihydro-5H-cyclopenta[b]pyridin-4-yl)amino)-2-fluorophenyl)acetate (0.075 g, 0.18 mmol) and ammonia in methanol (7.0 M, 3 mL) and the vessel was sealed with an aluminum cap. The resulting mixture was stirred at 100° C. for 24 h. After this time, the crude reaction solution was cooled, concentrated, and purified by column chromatography (silica, hexanes/ethyl acetate), followed by the formation of the hydrochloride salt to afford the title compound (0.374 g, 49% yield) as an off-white solid. MW=431.32. $^1$H NMR (DMSO-$d_6$, 300 MHz) δ 14.10 (s, 1H), 9.80 (s, 1H), 7.93 (t, J=1.7 Hz, 1H), 7.77-7.71 (m, 1H), 7.71-7.60 (m, 2H), 7.59-7.52 (m, 1H), 7.42 (t, J=8.6 Hz, 1H), 7.31-7.20 (m, 2H), 7.14 (s, 1H), 7.02 (s, 1H), 3.48 (s, 2H), 3.16 (t, J=7.6 Hz, 2H), 2.94 (t, J=7.6 Hz, 2H), 2.03 (quin, J=7.6 Hz, 2H); APCI MS m/z 396 [M+H]$^+$.

EXAMPLE 113

2-(4-((2-(3-Chlorophenyl)-6,7-dihydro-5H-cyclopenta[b]pyridin-4-yl)amino)-2-fluorophenyl)ethanol hydrochloride

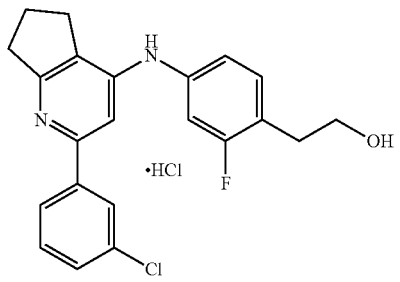 [SMILES: OCCc1ccc(Nc2cc(-c3cccc(Cl)c3)nc3c2CCC3)cc1F ; Cl]

To a solution of ethyl 2-(4-((2-(3-chlorophenyl)-6,7-dihydro-5H-cyclopenta[b]pyridin-4-yl)amino)-2-fluorophenyl)acetate (0.075 g, 0.18 mmol) in THF (2 mL) was added borane dimethyl sulfide complex solution (2.0 M in THF, 0.027 g, 0.35 mmol) at 0° C. The reaction mixture was slowly warmed to rt and stirred overnight. After this time, the mixture was quenched with 0.5 N HCl, and then basified with saturated aqueous sodium bicarbonate. The mixture was extracted with ethyl acetate and the residue purified by column chromatography (silica, dichloromethane/methanol), followed by the formation of the hydrochloride salt to afford the title compound (0.442 g, 44%) as a tan solid. MW=382.86. $^1$H NMR (DMSO-d$_6$, 500 MHz) δ 14.11 (s, 1H), 9.78 (s, 1H), 7.92 (t, J=1.8 Hz, 1H), 7.75-7.71 (m, 1H), 7.69-7.65 (m, 1H), 7.61 (t, J=7.9 Hz, 1H), 7.42 (t, J=7.9 Hz, 1H), 7.27-7.19 (m, 2H), 7.12 (s, 1H), 3.63 (t, J=6.9 Hz, 2H), 3.16 (t, J=7.6 Hz, 2H), 2.93 (t, J=7.6 Hz, 2H), 2.78 (t, J=6.9 Hz, 2H), 2.24 (quin, J=7.6 Hz, 2H); APCI MS m/z 383 [M+H]$^+$.

EXAMPLE 114

2-(3-Chlorophenyl)-N-(4-(oxazol-2-ylmethyl)phenyl)-6,7-dihydro-5H-cyclopenta[b]pyridin-4-amine hydrochloride

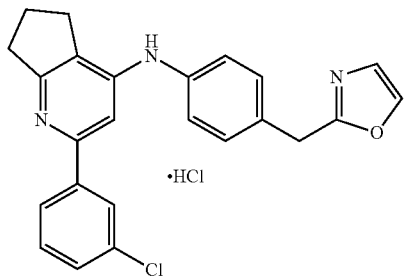 [SMILES: Clc1cccc(-c2cc(Nc3ccc(Cc4ncco4)cc3)c3c(n2)CCC3)c1 ; Cl]

Following General Procedure B2, 4-chloro-2-(3-chlorophenyl)-6,7-dihydro-5H-cyclopenta[b]pyridine (0.075 g, 0.25 mmol) was reacted with 4-(oxazol-2-ylmethyl)aniline (0.065 g, 0.37 mmol) followed by the formation of the hydrochloride salt to afford the title compound (0.022 g, 30%) as an off-white solid. MW=438.35. $^1$H NMR (DMSO-d$_6$, 300 MHz) δ 14.14 (s, 1H), 9.86 (s, 1H), 8.05-8.03 (m, 1H), 7.92 (t, J=1.8 Hz, 1H), 7.75-7.57 (m, 3H), 7.40 (s, 4H), 7.16 (s, 1H), 7.04 (s, 1H), 4.20 (s, 2H), 3.16 (t, J=7.6 Hz, 2H), 2.32-2.61 (m, 2H), 2.74 (t, J=7.6 Hz, 2H); APCI MS m/z 402 [M+H]$^+$.

EXAMPLE 115

1-(4-((2-(3-Chlorophenyl)-6,7-dihydro-5H-cyclopenta[b]pyridin-4-yl)amino)phenyl)ethane-1,2-diol hydrochloride

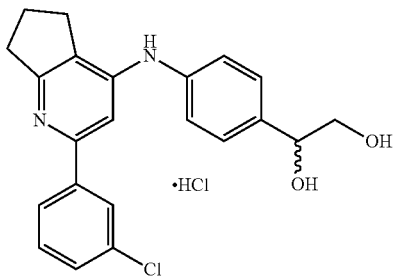 [SMILES: OCC(O)c1ccc(Nc2cc(-c3cccc(Cl)c3)nc3c2CCC3)cc1 ; Cl]

Step 1. Preparation of 2-(3-chlorophenyl)-N-(4-vinylphenyl)-6,7-dihydro-5H-cyclopenta[b]pyridin-4-amine

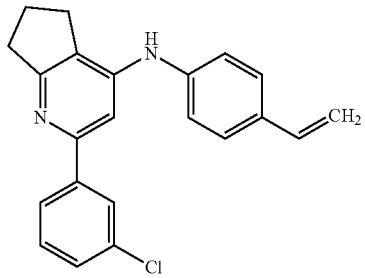 [SMILES: C=Cc1ccc(Nc2cc(-c3cccc(Cl)c3)nc3c2CCC3)cc1]

Following General Procedure B1, 4-chloro-2-(3-chlorophenyl)-6,7-dihydro-5H-cyclopenta[b]pyridine (0.200 g, 0.75 mmol) was reacted with 4-vinylaniline (0.099 g, 0.83 mmol) to afford the title compound (0.230 g, 100%) as a tan solid. MW=346.85. $^1$H NMR (CDCl$_3$, 500 MHz) δ 7.88-7.85 (m, 1H), 7.73-7.68 (m, 1H), 7.47-7.42 (m, 2H), 7.35-7.29 (m, 2H), 7.21 (s, 1H), 7.20-7.16 (m, 2H), 6.72 (q, J=10.5 Hz, 1H), 5.78 (s, 1H), 5.74-5.70 (m, 1H), 5.24-5.22 (m, 1H), 3.09 (t, J=7.6 Hz, 2H), 2.84 (t, J=7.6 Hz, 2H), 2.22 (quin, J=7.6 Hz, 2H); APCI MS m/z 347 [M+H]$^+$.

EXAMPLE 115

1-(4-((2-(3-Chlorophenyl)-6,7-dihydro-5H-cyclopenta[b]pyridin-4-yl)amino)phenyl)ethane-1,2-diol hydrochloride

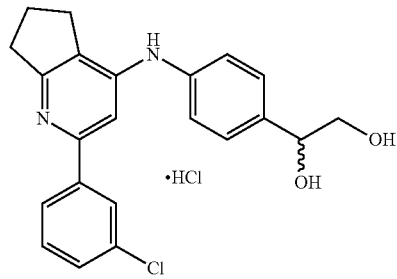 [SMILES: OCC(O)c1ccc(Nc2cc(-c3cccc(Cl)c3)nc3c2CCC3)cc1 ; Cl]

To a solution of 2-(3-chlorophenyl)-N-(4-vinylphenyl)-6,7-dihydro-5H-cyclopenta[b]pyridin-4-amine (0.100 g, 0.29 mmol) in acetone (10 mL) and water (5 mL) was added 4-methylmorpholine N-oxide (0.189 g, 1.44 mmol), followed by potassium osmate dehydrate (0.002 g, 0.06 mmol) and the reaction mixture was stirred at rt overnight. After this time, the mixture was diluted with saturated aqueous sodium bicarbonate and extracted with ethyl acetate. The combined organic layer was dried over anhydrous sodium sulfate, filtered, and the filtrate was concentrated. The residue was purified by column chromatography (silica, hexanes/ethyl acetate), followed by the formation of the hydrochloride salt to afford the title compound (0.033 g, 32%) as a light yellow solid. MW=417.33. $^1$H NMR (DMSO-d$_6$, 500 MHz) δ 14.03 (s, 1H), 9.79 (s, 1H), 7.89 (t, J=2.0 Hz, 1H), 7.72-7.64 (m, 2H), 7.63-7.57 (m, 1H), 7.45 (d, J=8.0 Hz, 2H), 7.36 (d, J=8.0 Hz, 2H), 7.00 (s, 1H), 4.57 (t, J=6.0 Hz, 1H), 3.51-3.45 (m, 2H), 3.15 (t, J=7.6 Hz, 2H), 2.92 (t, J=7.6 Hz, 2H), 2.29-2.20 (m, 2H); APCI MS m/z 381 [M+H]$^+$.

EXAMPLE 116

2-(4-((2-(3-Chlorophenyl)-6,7-dihydro-5H-cyclopenta[b]pyridin-4-yl)amino)phenoxy)propanamide hydrochloride

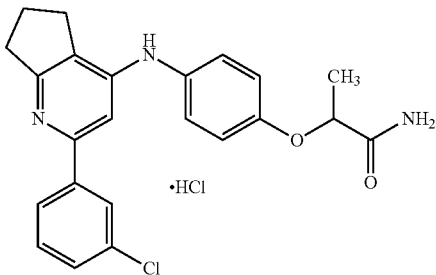 [SMILES: CC(Oc1ccc(Nc2cc(-c3cccc(Cl)c3)nc3c2CCC3)cc1)C(N)=O ; Cl]

Step 1. Preparation of methyl 2-(4-((2-(3-chlorophenyl)-6,7-dihydro-5H-cyclopenta[b]pyridin-4-yl)amino)phenoxy)propanoate

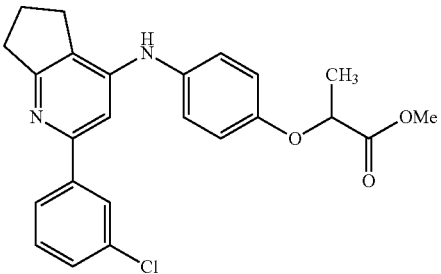 [SMILES: COC(=O)C(C)Oc1ccc(Nc2cc(-c3cccc(Cl)c3)nc3c2CCC3)cc1]

Following General Procedure B2, 4-chloro-2-(3-chlorophenyl)-6,7-dihydro-5H-cyclopenta[b]pyridine (0.150 g, 0.57 mmol) was reacted with methyl 2-(4-aminophenoxy)propanoate (0.133 g, 0.68 mmol) to afford the title compound (0.146 g, 97%) as an off-white solid. MW=422.90. $^1$H NMR (DMSO-d$_6$, 500 MHz) δ 7.98 (s, 1H), 7.88-7.86 (m, 1H), 7.74-7.69 (m, 1H), 7.46-7.38 (m, 2H), 7.22-7.17 (m, 2H), 7.02 (s, 1H), 6.96-6.89 (m, 2H), 4.96 (q, J=6.8 Hz, 1H), 3.69 (s, 3H), 2.89 (t, J=7.6 Hz, 2H), 2.80 (t, J=7.6 Hz, 2H), 2.13-2.03 (m, 2H), 1.51 (d, J=6.7 Hz, 3H); APCI MS m/z 423 [M+H]$^+$.

EXAMPLE 116

2-(4-((2-(3-Chlorophenyl)-6,7-dihydro-5H-cyclopenta[b]pyridin-4-yl)amino)phenoxy)propanamide hydrochloride

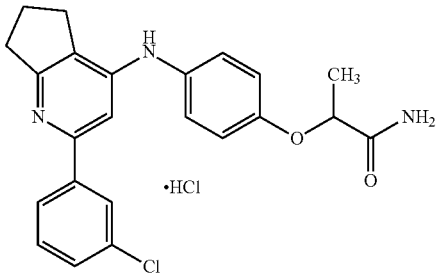 [SMILES: CC(Oc1ccc(Nc2cc(-c3cccc(Cl)c3)nc3c2CCC3)cc1)C(N)=O ; Cl]

Following General Procedure C, methyl 2-(4-((2-(3-chlorophenyl)-6,7-dihydro-5H-cyclopenta[b]pyridin-4-yl)amino)phenoxy)propanoate (0.140 g, 0.33 mmol) was reacted with ammonia in methanol (7.0 M, 4 mL), followed by the formation of the hydrochloride salt to form the title compound (0.093 g, 67% yield) as a yellow solid. MW=444.35. $^1$H NMR (DMSO-d$_6$, 300 MHz) δ 14.00 (s, 1H), 9.72 (s, 1H), 7.88 (t, J=1.8 Hz, 1H), 7.71-7.64 (m, 2H), 7.63-7.55 (m, 2H), 7.38-7.26 (m, 3H), 7.05-6.97 (m, 2H), 6.87 (s, 1H), 6.65 (q, J=6.7 Hz, 1H), 3.14 (t, J=7.6 Hz, 2H), 2.99-2.81 (m, 2H), 2.31-2.14 (m, 2H) 1.46 (d, J=6.6 Hz, 3H); APCI MS m/z 408 [M+H]$^+$.

EXAMPLE 117

2-(4-((2-(3-Chlorophenyl)-6,7-dihydro-5H-cyclopenta[b]pyridin-4-yl)amino)phenoxy)propan-1-ol hydrochloride

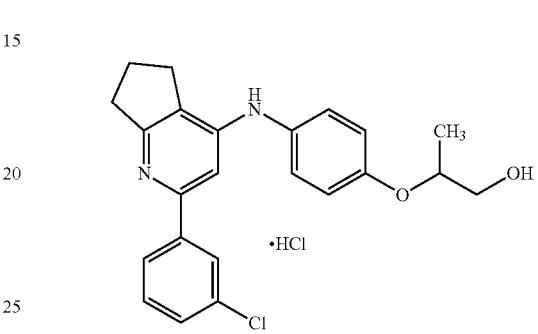

To a solution of methyl 2-(4-((2-(3-chlorophenyl)-6,7-dihydro-5H-cyclopenta[b]pyridin-4-yl)amino)phenoxy)propanoate (0.050 g, 0.12 mmol) in dichloromethane at 0° C. was added DIBAL (0.034 g, 0.24 mmol, 1.0 M in THF) over 15 min. Then, the mixture was stirred for 1 h at 0° C. and then warmed to rt for 15 min After this time, the reaction was quenched with methanol, HCl (2 M) and water, and then extracted with ethyl acetate. The combined organic layer was dried over anhydrous sodium sulfate, filtered, and the filtrate was concentrated. The residue was purified by column chromatography (silica, hexanes/ethyl acetate), followed by the formation of the hydrochloride salt to form the title compound (0.033 g, 66%) as a bright yellow gum. MW=431.35. $^1$H NMR (DMSO-d$_6$, 500 MHz) δ 13.97 (s, 1H), 9.73 (s, 1H), 7.86 (t, J=1.8 Hz, 1H), 7.68-7.62 (m, 2H), 7.57 (t, J=7.9 Hz, 1H), 7.31-7.26 (m, 2H), 7.06-7.01 (m, 2H), 6.86 (s, 1H), 4.49-4.39 (m, 2H), 3.61-3.41 (m, 2H), 3.17-3.09 (m, 2H), 2.88 (s, 2H), 2.26-2.17 (m, 2H), 1.21 (d, J=6.2 Hz, 3H); APCI MS m/z 395 [M+H]$^+$.

EXAMPLE 118

2-(4-((2-(3-Chlorophenyl)-6,7-dihydro-5H-cyclopenta[b]pyridin-4-yl)(methyl)amino)phenyl)acetamide

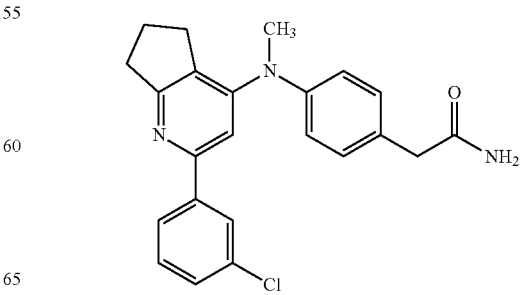

A mixture of 4-chloro-2-(3-chlorophenyl)-6,7-dihydro-5H-cyclopenta[b]pyridine hydrochloride (0.060 g, 0.20 mmol) and 2-(4-(methylamino)phenyl)acetamide (0.066 g, 0.40 mmol) in NMP (3 mL) was microwaved for 3 h at 140° C. After this time, the mixture was purified by silica gel chromatography followed by preparative HPLC to afford the title compound (0.012 g, 15%) as a white solid. MW=391.89. $^1$H NMR (DMSO-$d_6$, 500 MHz) δ 14.18 (br s, 1H), 8.10 (s, 1H), 7.94 (d, J=7.5 Hz, 1H), 7.70-7.66 (m, 2H), 7.55 (br s, 1H), 7.37-7.27 (m, 5H), 6.92 (br s, 1H), 3.57 (s, 3H), 3.01 (t, J=7.1 Hz, 2H), 1.96-1.85 (m, 4H); ESI MS m/z 392 [M+H]$^+$.

EXAMPLE 119

3-(4-((2-(3-chlorophenyl)-6,7-dihydro-5H-cyclopenta[b]pyridin-4-yl)amino)phenyl)propanamide hydrochloride

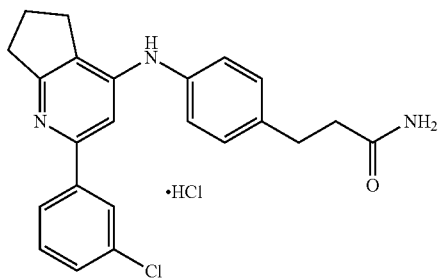 [SMILES: NC(=O)CCc1ccc(Nc2cc(-c3cccc(Cl)c3)nc3c2CCC3)cc1 ; Cl]

A mixture of 4-chloro-2-(3-chlorophenyl)-6,7-dihydro-5H-cyclopenta[b]pyridine hydrochloride (0.060 g, 0.20 mmol) and 3-(4-aminophenyl)propanamide (0.066 g, 0.40 mmol) in NMP (3 mL) was microwaved for 3 h at 120° C., then at 140° C. for 2.5 h. After this time, the mixture was purified by silica gel chromatography eluting first with ethyl acetate and hexanes followed by methylene chloride and methanol. The solids were further purified by preparative HPLC to afford the title compound (0.042 g, 54%) as a white solid. MW=391.89. $^1$H NMR (DMSO-$d_6$, 500 MHz) δ 14.09 (br s, 1H), 9.82 (s, 1H), 7.90-7.89 (m, 1H), 7.71-7.58 (m, 3H), 7.33-7.27 (m, 5H), 6.98 (s, 1H), 6.77 (br s, 1H), 3.18-3.15 (m, 2H), 2.93-2.80 (m, 4H), 2.40-2.34 (m, 2H), 2.27-2.21 (m, 2H); ESI MS m/z 392 [M+H]$^+$.

EXAMPLE 120

2-(4-((2-(3-chlorophenyl)-6,7-dihydro-5H-cyclopenta[b]pyridin-4-yl)amino)phenyl)-N-methylacetamide hydrochloride

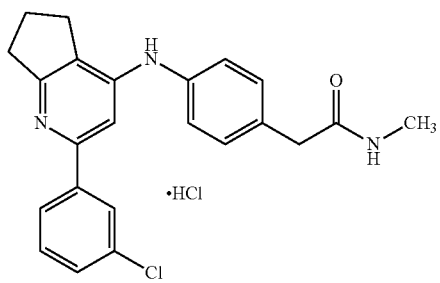 [SMILES: CNC(=O)Cc1ccc(Nc2cc(-c3cccc(Cl)c3)nc3c2CCC3)cc1 ; Cl]

A mixture of 4-chloro-2-(3-chlorophenyl)-6,7-dihydro-5H-cyclopenta[b]pyridine hydrochloride (0.100 g, 0.33 mmol) and 2-(4-aminophenyl)-N-methylacetamide (0.164 g, 1.0 mmol) was heated for 3 h at 150° C., then toluene added and the mixture continued heating for an additional 3 h. After this time, the mixture was purified by silica gel chromatography eluting with methylene chloride and methanol. The resulting solid was further purified by reverse phase preparative HPLC and then converted to the HCl salt to afford the title compound (0.065 g, 50%) as a white solid. MW=391.89. $^1$H NMR (DMSO-$d_6$, 500 MHz) δ 14.07 (br s, 1H), 9.82 (s, 1H), 8.04-8.03 (m, 1H), 7.90-7.89 (m, 1H), 7.71-7.58 (m, 3H), 7.38-7.34 (m, 4H), 7.01 (s, 1H), 3.44 (s, 2H), 3.18-3.14 (m, 2H), 2.93 (t, J=7.3 Hz, 2H), 2.59 (d, J=4.6 Hz, 3H), 2.27-2.21 (m, 2H); ESI MS m/z 392 [M+H]$^+$.

EXAMPLE 121

2-(4-((2-(3-chlorophenyl)-6,7-dihydro-5H-cyclopenta[b]pyridin-4-yl)amino)phenyl)-N,N-dimethylacetamide hydrochloride

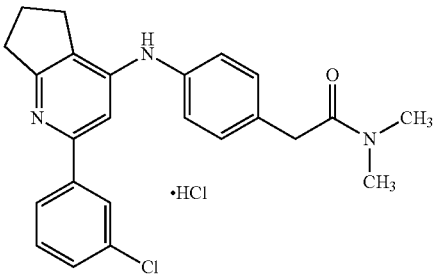 [SMILES: CN(C)C(=O)Cc1ccc(Nc2cc(-c3cccc(Cl)c3)nc3c2CCC3)cc1 ; Cl]

A mixture of 4-chloro-2-(3-chlorophenyl)-6,7-dihydro-5H-cyclopenta[b]pyridine hydrochloride (0.100 g, 0.33 mmol) and 2-(4-aminophenyl)-N,N-dimethylacetamide (0.178 g, 1.0 mmol) was heated for 3 h at 150° C., then toluene added and the mixture continued heating for an additional 7 h. After this time, the mixture was purified by silica gel chromatography eluting with methylene chloride and methanol. The resulting solid was converted to the HCl salt to afford the title compound (0.048 g, 33%) as a white solid. MW=405.92. $^1$H NMR (DMSO-$d_6$, 500 MHz) δ 14.2 (br s, 1H), 9.88 (s, 1H), 7.91-7.90 (m, 1H), 7.72-7.66 (m, 2H), 7.61-7.58 (m, 1H), 7.37-7.32 (m, 1H), 7.01 (s, 1H), 3.73 (s, 2H), 3.17 (t, J=7.7 Hz, 2H), 3.04 (s, 3H), 2.93 (t, J=7.2 Hz, 2H), 2.84 (s, 3H), 2.27-2.21 (m, 2H); ESI MS m/z 406 [M+H]$^+$.

EXAMPLE 122

2-(4-((2-(3-Chlorophenyl)-6,7-dihydro-5H-cyclopenta[b]pyridin-4-yl)amino)benzyl)malonamide hydrochloride

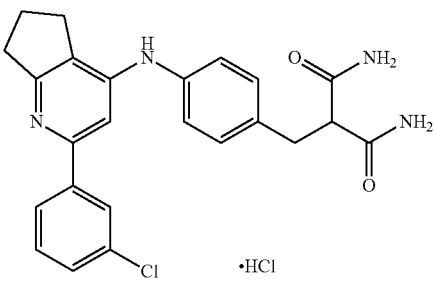 [SMILES: NC(=O)C(Cc1ccc(Nc2cc(-c3cccc(Cl)c3)nc3c2CCC3)cc1)C(N)=O ; Cl]

Step 1. Preparation of diisopropyl 2-(4-nitrobenzyl)malonate

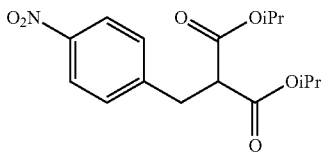 [SMILES: CC(C)OC(=O)C(Cc1ccc([N+](=O)[O-])cc1)C(=O)OC(C)C]

A 250-mL round bottom flask was charged with diisopropyl malonate (2.09 g, 11.1 mmol) in DMF (24 mL). Sodium hydride (60% suspension, 0.44 g, 11.1 mmol) was slowly added to this solution at 0° C. After 15 minutes, a solution of 4-nitrobenzyl bromide (2.00 g, 9.26 mmol, 1.0 eq.) in DMF (24 mL) was added in one portion and then the reaction was stirred for 19 h. After this time, the reaction was warmed to rt. The reaction was quenched with 2N HCl then diluted in water (300 mL) and extracted with methyl tert-butylether (3×50 mL). The combined extract was washed with saturated sodium chloride (2×25 mL), dried over sodium sulfate, filtered, and concentrated under reduced pressure. The residue was purified by column chromatography on silica eluting with 9:1 hexanes/ethyl acetate to afford the title compound (2.02 g, 67%) as a colorless oil. MW=323.34. $^1$H NMR (DMSO-$d_6$, 500 MHz) δ 8.15 (d, J=10.0 Hz, 2H), 7.53 (d, J=9.0 Hz, 2H), 4.88 (septet, J=6.5 Hz, 2H), 3.89 (t, J=8.5 Hz, 1H), 3.19 (d, J=8.5 Hz, 2H), 1.14 (d, J=6.5 Hz, 6H), 1.11 (d, J=6.5 Hz, 6H).

Step 2. Preparation of 2-(4-nitrobenzyl)malonamide

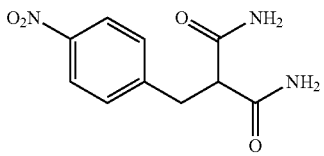 [SMILES: NC(=O)C(Cc1ccc([N+](=O)[O-])cc1)C(N)=O]

A 100-mL round bottom flask was charged with diisopropyl 2-(4-nitrobenzyl)malonate (2.00 g, 6.18 mmol) in methanol (10 mL). To this solution at rt was added 7N ammonia in methanol (8.8 mL, 61.8 mmol). The reaction was stirred for 44 h then concentrated under reduced pressure. The residue was suspended in dichloromethane and the solid isolated by filtration to afford the title compound (0.40 g, 27%) as a white solid. MW=237.21. $^1$H NMR (DMSO-$d_6$, 500 MHz) δ 8.14 (d, J=8.5 Hz, 2H), 7.48 (d, J=8.5 Hz, 2H), 7.27 (s, 2H), 7.07 (s, 2H), 3.39 (t, J=7.5 Hz, 1H), 3.10 (d, J=7.5 Hz, 2H).

Step 3. Preparation of 2-(4-aminobenzyl)malonamide

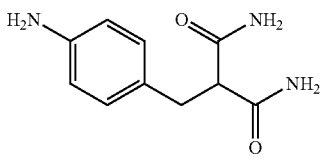

A 100-mL round bottom flask was charged with 2-(4-nitrobenzyl)malonamide (0.40 g, 1.68 mmol) and 10% palladium on carbon (0.10 g) in 1:2 ethyl acetate/ethanol (15 mL). This mixture was vigorously stirred under $H_2$ (1 atm) for 56 h. After this time, the mixture was filtered through celite to afford the title compound (0.17 g, 49%) as a white solid. MW=207.23. $^1$H NMR (DMSO-$d_6$, 500 MHz) δ 7.16 (s, 2H), 6.95 (s, 2H), 6.82 (d, J=8.5 Hz, 2H), 6.43 (d, J=8.5 Hz, 2H), 4.81 (s, 2H), 3.17 (t, J=8.0 Hz, 1H), 2.78 (d, J=7.5 Hz, 2H).

EXAMPLE 122

2-(4-((2-(3-Chlorophenyl)-6,7-dihydro-5H-cyclopenta[b]pyridin-4-yl)amino)benzyl)malonamide hydrochloride

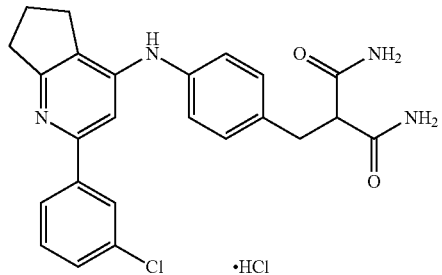 [SMILES: NC(=O)C(Cc1ccc(Nc2cc(-c3cccc(Cl)c3)nc3c2CCC3)cc1)C(N)=O ; Cl]

A 10-mL microwave vial was charged with 4-chloro-2-(3-chlorophenyl)-6,7-dihydro-5H-cyclopenta[b]pyridine hydrochloride (0.100 g, 0.33 mmol), 2-(4-aminobenzyl)malonamide (0.110 g, 0.53 mmol) and conc. HCl (1 drop) in NMP (3 mL). The resulting mixture was heated at 140° C. under microwave irradiation for 3 h. After this time, the reaction mixture was cooled, diluted with water (15 mL) and then treated with saturated sodium bicarbonate until pH~8. The resulting solid was isolated by filtration and purified by preparative HPLC (water/acetonitrile with 0.05% TFA) to afford the free base of the title compound (0.070 g, 56%) as an off-white solid. MW=434.92. $^1$H NMR (DMSO-$d_6$, 500 MHz) δ 8.07 (s, 1H), 7.90 (s, 1H), 7.75-7.70 (m, 1H), 7.46-7.38 (m, 2H), 7.24 (s, 2H), 7.21-7.13 (m, 5H), 7.02 (s, 2H), 4.08-4.00 (m, 1H), 2.96 (d, J=7.0 Hz, 2H), 2.93-2.87 (m, 2H), 2.85-2.78 (m, 2H), 2.22-2.13 (m, 2H). MS: ESI+, m/z 435 [M+H]+. Treatment with 1.25M HCl in methanol (0.19 mL, 0.24 mmol, 1.5 eq.) afforded the title compound (0.048 g, 64%) as an off-white solid. MW=471.38. m.p. 219-222° C. $^1$H NMR (DMSO-$d_6$, 500 MHz) δ 13.95 (br s, 1H), 9.71 (s, 1H), 7.90-7.87 (m, 1H), 7.70-7.74 (m, 2H), 7.60 (t, J=8.0 Hz, 1H), 7.31 (s, 5H), 7.03 (s, 2H), 6.97 (s, 1H), 3.36-3.33 (m, 1H), 3.13 (t, J=7.5 Hz, 2H), 3.01 (d, J=7.5 Hz, 2H), 3.13 (t, J=7.0 Hz, 2H), 2.28-2.19 (m, 2H); ESI MS m/z 435 [M+H]$^+$.

EXAMPLE 123

Diisopropyl 2-(4-((2-(3-chlorophenyl)-6,7-dihydro-5H-cyclopenta[b]pyridin-4-yl)amino)benzyl)malonate hydrochloride

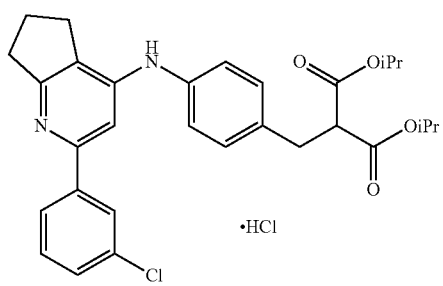 [SMILES: CC(C)OC(=O)C(Cc1ccc(Nc2cc(-c3cccc(Cl)c3)nc3c2CCC3)cc1)C(=O)OC(C)C ; Cl]

Step 1. Preparation of diisopropyl 2-(4-aminobenzyl)malonate

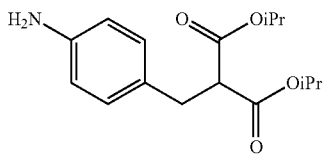

A 100-mL round bottom flask was charged with diisopropyl 2-(4-nitrobenzyl)malonate (1.19 g, 3.68 mmol) and 10% palladium on carbon (0.30 g) in 1:1 ethyl acetate/methanol (20 mL). This mixture was vigorously stirred under $H_2$ (1 atm) for 2.5 h. After this time, the mixture was filtered through celite and purified by chromatography on silica eluting with hexanes/ethyl acetate (10:1 to 0:10) to afford the title compound (0.34 g, 32%) as a white solid. MW=293.36. $^1$H NMR (DMSO-$d_6$, 500 MHz) δ 6.83 (d, J=7.5 Hz, 2H), 6.44 (d, J=7.0 Hz, 2H), 4.91-4.82 (m, 4H), 3.55 (t, J=8.0 Hz, 1H), 2.86 (d, J=8.0 Hz, 2H), 1.14 (d, J=6.0 Hz, 6H), 1.11 (d, J=8.0 Hz, 6H).

EXAMPLE 123

Diisopropyl 2-(4-((2-(3-chlorophenyl)-6,7-dihydro-5H-cyclopenta[b]pyridin-4-yl)amino)benzyl)malonate hydrochloride

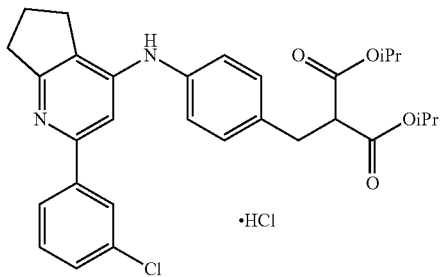 [SMILES: CC(C)OC(=O)C(Cc1ccc(Nc2cc(-c3cccc(Cl)c3)nc3c2CCC3)cc1)C(=O)OC(C)C ; Cl]

A 10-mL microwave vial was charged with 4-chloro-2-(3-chlorophenyl)-6,7-dihydro-5H-cyclopenta[b]pyridine hydrochloride (0.070 g, 0.23 mmol), diisopropyl 2-(4-aminobenzyl)malonate (0.136 g, 0.47 mmol) and conc. HCl (1 drop) in NMP (3 mL). The resulting mixture was heated at 140° C. under microwave irradiation for 2 h. After this time, the reaction mixture was cooled, diluted with water (15 mL), and then treated with saturated sodium bicarbonate until pH~8. The resulting solid was isolated by filtration and purified by preparative HPLC (water/acetonitrile with 0.05% TFA) followed by chromatography on silica using hexanes/ethyl acetate (10:0 to 0:10) as eluent to afford diisopropyl 2-(4-((2-(3-chlorophenyl)-6,7-dihydro-5H-cyclopenta[b]pyridin-4-yl)amino)benzyl)malonate (0.046 g, 38%) as an off-white solid. MW=521.05. $^1$H NMR (DMSO-$d_6$, 500 MHz) δ 8.14 (s, 1H), 7.86 (s, 1H), 7.89-7.84 (m, 1H), 7.46-7.38 (m, 2H), 7.25-7.12 (m, 5H), 4.94-4.84 (m, 2H), 3.78-3.72 (m, 1H), 3.04 (d, J=7.5 Hz, 2H), 2.93-2.87 (m, 2H), 2.85-2.77 (m, 2H), 2.12-2.03 (m, 2H), 1.15 (d, J=5.5 Hz, 6H), 1.11 (d, J=5.5 Hz, 6H). MS: ESI, m/z 521 [M+H]$^+$. Treatment with 1.25M HCl in methanol (0.11 mL, 0.13 mmol, 1.5 eq.) afforded the title compound (0.043 g, 88%) as an off-white solid. MW=557.51. M.p. 68-70° C. $^1$H NMR (DMSO-$d_6$, 500 MHz) δ 13.93 (br s, 1H), 7.86-7.84 (m, 1H), 7.67 (d, J=8.0 Hz, 1H), 7.62-7.50 (m, 2H), 7.34-7.24 (m, 4H), 6.97 (s, 1H), 4.88 (sept, J=6.0 Hz, 2H), 3.79 (t, J=7.5 Hz, 1H), 3.12-3.03 (m, 4H), 2.87 (t, J=7.5 Hz, 2H), 2.23-2.15 (m, 2H), 1.14 (d, J=5.0 Hz, 6H), 1.09 (d, J=5.5 Hz, 6H); ESI MS m/z 451 [M+H]$^+$.

EXAMPLE 124

2-(4-((2-(3-Chlorophenyl)-6,7-dihydro-5H-cyclopenta[b]pyridin-4-yl)amino)benzyl)-2-methylmalonamide hydrochloride

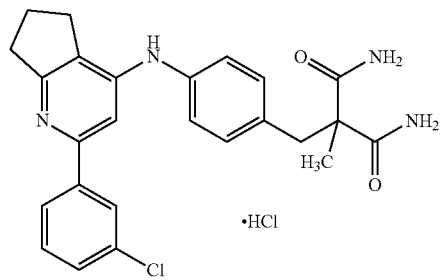 [SMILES: CC(Cc1ccc(Nc2cc(-c3cccc(Cl)c3)nc3c2CCC3)cc1)(C(N)=O)C(N)=O ; Cl]

Step 1. Preparation of diisopropyl 2-methyl-2-(4-nitrobenzyl)malonate

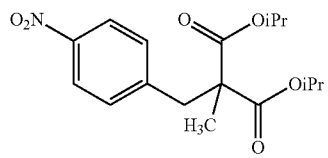 [SMILES: CC(C)OC(=O)C(C)(Cc1ccc([N+](=O)[O-])cc1)C(=O)OC(C)C]

A 250-mL round bottom flask was charged with diisopropyl 2-(4-nitrobenzyl)malonate (1.61 g, 4.98 mmol) in DMF (24 mL). To this solution at 0° C. was slowly added NaH (60% suspension, 0.24 g, 5.97 mmol). After 30 minutes, iodomethane (0.37 mL, 5.97 mmol) was added in one portion. The reaction was stirred for 21 h, at which time, the reaction was warmed to rt. The reaction was diluted in water (250 mL) and extracted with methyl tert-butylether (3×75 mL). The combined extract was washed with saturated sodium chloride (2×20 mL), dried over sodium sulfate, filtered, and concentrated under reduced pressure. The residue was purified by chromatography on silica using hexanes/ethyl acetate (10:0 to 8:2) as eluent to afford the title compound (1.44 g, 86%) as a white solid. MW=337.37. $^1$H NMR (CDCl$_3$, 300 MHz) δ 8.16-8.09 (m, 2H), 7.37-7.30 (m, 2H), 5.05 (sept, J=6.3 Hz, 2H), 3.30 (s, 2H), 1.33 (s, 3H), 1.27-1.20 (m, 12H).

Step 2. Preparation of 2-methyl-2-(4-nitrobenzyl)malonic acid

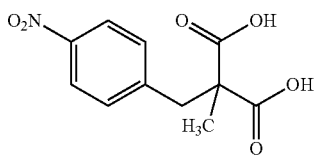 [SMILES: CC(Cc1ccc([N+](=O)[O-])cc1)(C(=O)O)C(=O)O]

An 250-mL round bottom flask was charged with diisopropyl 2-methyl-2-(4-nitrobenzyl)malonate (1.15 g, 3.55 mmol), dioxane (20 ml) and water (10 ml). To this solution was then added lithium hydroxide monohydrate (0.74 g, 17.8 mmol). The resulting mixture was stirred at 50° C. for 22 h. After this time, the reaction mixture was cooled and acidified with 2N aqueous HCl (10 mL). The mixture was diluted with ethyl acetate (100 mL) and the organic layer washed with saturated sodium chloride (2×10 mL), dried over sodium sulfate, filtered, and concentrated under reduced pressure to afford the title compound (0.96 g, 100%) as a white solid. MW=253.21. $^1$H NMR (DMSO-$d_6$, 300 MHz) δ 13.04 (br s, 2H), 8.20-8.12 (m, 2H), 7.49-7.42 (m, 2H), 3.21 (s, 2H), 1.17 (s, 3H).

Step 3. Preparation of 2-methyl-2-(4-nitrobenzyl)malonamide

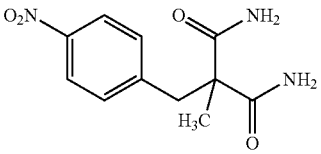 [SMILES: CC(Cc1ccc([N+](=O)[O-])cc1)(C(N)=O)C(N)=O]

An 250-mL round bottom flask was charged with 2-methyl-2-(4-nitrobenzyl)malonic acid (0.96 g, 3.55 mmol), dioxane (20 ml) and dichloromethane (20 ml). To this solution at 0° C. was added oxalyl chloride (3.0 mL, 35.5 mmol) followed by DMF (2 drops). After stirring for 4 h, the volatile material was removed under reduced pressure. The residue was dissolved in dichloromethane (24 mL), cooled to 0° C., then 7N ammonia in methanol (50 mL, 350 mmol) was added. After stirring for 15 h, the reaction mixture was concentrated under reduced pressure. The residue was suspended in water (100 mL) affording a solid. The solid was isolated by filtration to afford the title compound (0.69 g, 78%) as an off-white solid. MW=251.24. $^1$H NMR (DMSO-$d_6$, 300 MHz) δ 8.13 (d, J=8.7 Hz, 2H), 7.45 (d, J=8.7 Hz, 2H), 7.24 (d, J=11.4 Hz, 4H), 3.22 (s, 2H), 1.14 (s, 3H).

Step 4. Preparation of 2-(4-aminobenzyl)-2-methylmalonamide

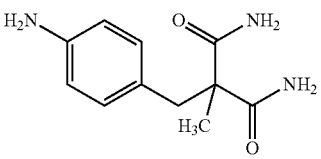

A 250-mL round bottom flask was charged with 2-methyl-2-(4-nitrobenzyl)malonamide (0.69 g, 2.74 mmol) and 10% palladium on carbon (0.17 g) in 1:2 ethyl acetate/ethanol (30 mL). This mixture was vigorously stirred under $H_2$ (1 atm) for 6 h. The mixture was then filtered through celite to afford the title compound (0.28 g, 46%) as an off-white solid. MW=221.26. $^1$H NMR (DMSO-$d_6$, 300 MHz) δ 7.15 (s, 2H), 7.08 (s, 2H), 6.80 (d, J=8.1 Hz, 2H), 6.41 (d, J=8.1 Hz, 2H), 4.87 (s, 2H), 2.86 (s, 2H), 1.07 (s, 3H).

EXAMPLE 124

2-(4-((2-(3-Chlorophenyl)-6,7-dihydro-5H-cyclopenta[b]pyridin-4-yl)amino)benzyl)-2-methylmalonamide hydrochloride

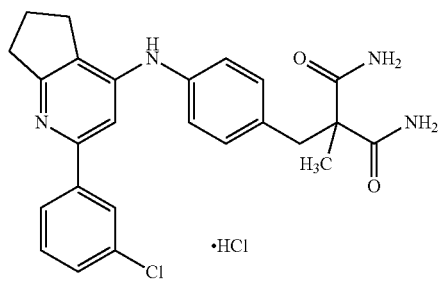 [SMILES: CC(Cc1ccc(Nc2cc(-c3cccc(Cl)c3)nc3c2CCC3)cc1)(C(N)=O)C(N)=O ; Cl]

A 10-mL microwave vial was charged with 4-chloro-2-(3-chlorophenyl)-6,7-dihydro-5H-cyclopenta[b]pyridine (0.100 g, 0.38 mmol), 2-(4-aminobenzyl)-2-methylmalonamide (0.167 g, 0.75 mmol) and 4M HCl in dioxane (0.095 mL, 0.38 mmol) in NMP (4 mL). The resulting mixture was heated at 150° C. under microwave irradiation for 8 h. After this time, the reaction mixture was cooled, diluted with water (20 mL) and saturated aqueous sodium bicarbonate (20 mL) affording a solid. The solid was isolated by filtration and chromatography on silica using dichloromethane/methanol (10:0 to 9:1) as eluent to afford 2-(4-((2-(3-chlorophenyl)-6,7-dihydro-5H-cyclopenta[b]pyridin-4-yl)amino)benzyl)-2-methylmalonamide (0.12 g, 72%) as an off-white solid. MW=448.94. $^1$H NMR (DMSO-$d_6$, 300 MHz) δ 8.10 (s, 1H), 7.92-7.89 (m, 1H), 7.74 (dt, J=6.6, 2.1 Hz, 1H), 7.48-7.39 (m, 2H), 7.23 (s, 2H), 7.20-7.10 (m, 7H), 3.05 (s, 2H), 2.91 (t, J=7.8 Hz, 2H), 2.81 (t, J=7.2 Hz, 2H), 2.08 (quin, J=7.2 Hz, 2H), 1.14 (s, 3H). Treatment with 1.25M HCl in methanol (0.44 mL, 0.55 mmol) afforded the title compound (0.11 g, 84%) as an off-white solid. MW=485.41. M.p. 162-165° C. $^1$H NMR (DMSO-$d_6$, 500 MHz) δ 14.01 (br s, 1H), 9.17 (s, 1H), 7.89 (t, J=2.0 Hz, 1H), 7.00 (dt, J=4.5, 1.5 Hz, 1H), 7.60-7.52 (m, 2H), 7.28-7.20 (m, 6H), 7.15 (s, 2H), 7.05 (s, 1H), 3.10 (s, 2H), 3.06 (t, J=7.5 Hz, 2H), 2.87 (d, J=7.5 Hz, 2H), 2.18 (quin, J=7.5 Hz, 2H), 1.15 (s, 3H); APCI MS m/z 449 [M+H]$^+$.

EXAMPLE 125

2-(4-((2-(3-Chlorophenyl)-6,7-dihydro-5H-cyclopenta[b]pyridin-4-yl)methyl)phenyl)acetamide hydrochloride

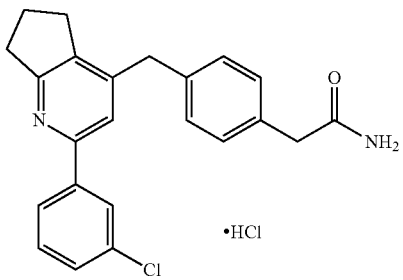 [SMILES: NC(=O)Cc1ccc(Cc2cc(-c3cccc(Cl)c3)nc3c2CCC3)cc1 ; Cl]

Step 1. Preparation of 2-(4-((2-(3-chlorophenyl)-6,7-dihydro-5H-cyclopenta[b]pyridin-4-yl)methyl)phenyl)acetic acid

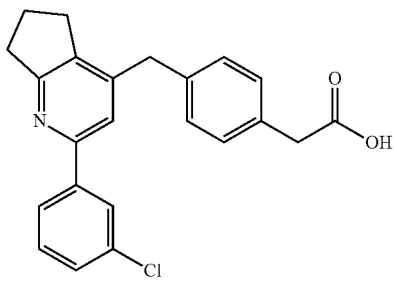 [SMILES: O=C(O)Cc1ccc(Cc2cc(-c3cccc(Cl)c3)nc3c2CCC3)cc1]

A 10-mL sealed tube, with stirrer bar, was charged with 4-chloro-2-(3-chlorophenyl)-6,7-dihydro-5H-cyclopenta[b]pyridine hydrochloride (0.100 g, 0.33 mol), methyl 2-(4-((4,4,5,5-tetramethyl-1,3,2-dioxaborolan-2-yl)methyl)phenyl)acetate (0.096 g, 0.33 mmol), Pd(dppf)Cl$_2$ (0.027 g, 0.033 mmol), and powdered Na$_2$CO$_3$ (0.141 g, 1.33 mmol). Dioxane (3 mL) and water (1.5 mL) were added. The resulting mixture was stirred under Ar at 90° C. for 3 d. until the starting chloride was consumed. After cooling to room temperature, the reaction mixture was adsorbed onto silica (4 g). Purification by chromatography on silica using dichloromethane/methanol (10:0 to 8:2) as eluent afforded the title compound (0.067 g, 53%) as a light brown solid. MW=377.86. $^1$H NMR (DMSO-d$_6$, 500 MHz) δ 12.24 (br s, 1H), 8.09-8.07 (m, 1H), 8.00-7.97 (m, 1H), 7.70 (s, 1H), 7.51-7.42 (m, 2H), 7.25-7.16 (m, 2H), 7.15-7.09 (m, 2H), 3.97 (s, 2H), 3.51 (s, 2H), 2.94 (t, J=7.5 Hz, 2H), 2.84 (t, J=7.5 Hz, 2H), 2.09-2.01 (m, 2H); ESI MS m/z 378 [M+H]$^+$.

Step 2. Preparation of methyl 2-(4-((2-(3-chlorophenyl)-6,7-dihydro-5H-cyclopenta[b]pyridin-4-yl)methyl)phenyl)acetate

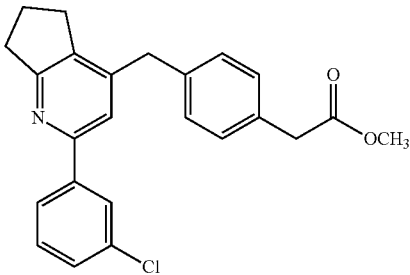

A 25-mL flask, with stirrer bar, was charged with 2-(4-((2-(3-chlorophenyl)-6,7-dihydro-5H-cyclopenta[b]pyridin-4-yl)methyl)phenyl)acetic acid (0.066 g, 0.17 mol), 4M HCl/methanol (0.22 mL, 0.87 mmol) and methanol (4 mL). After 23 h, the reaction was concentrated under reduced pressure. The residue was dissolved in ethyl acetate and saturated sodium bicarbonate (20 mL). The organic layer was washed with saturated sodium chloride (10 mL) then dried over sodium sulfate, filtered, and concentrated under reduced pressure. The residue was purified by chromatography on silica using hexanes/ethyl acetate (10:0 to 0:10) as eluent to afford the title compound (0.036 g, 48%) as an off-white solid. MW=391.89. $^1$H NMR (CDCl$_3$, 500 MHz) δ 7.94-7.91 (m, 1H), 7.77 (dt, J=7.0, 2.0 Hz, 1H), 7.36-7.30 (m, 2H), 7.24 (s, 1H), 7.21 (d, J=8.0 Hz, 2H), 7.13 (d, J=8.0 Hz, 2H), 3.95 (s, 2H), 3.69 (s, 3H), 3.60 (s, 2H), 3.08 (t, J=8.0 Hz, 2H), 2.86 (t, J=7.5 Hz, 2H), 2.18-2.09 (m, 2H); APCI MS m/z 392 [M+H]$^+$.

EXAMPLE 125

2-(4-((2-(3-Chlorophenyl)-6,7-dihydro-5H-cyclopenta[b]pyridin-4-yl)methyl)phenyl)acetamide hydrochloride

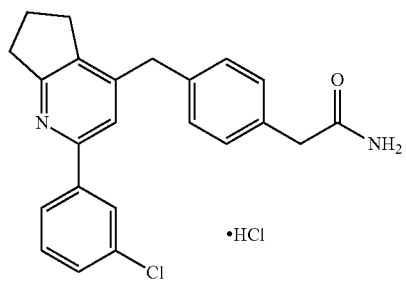 [SMILES: NC(=O)Cc1ccc(Cc2cc(-c3cccc(Cl)c3)nc3c2CCC3)cc1 ; Cl]

A 10-mL vial was charged with methyl 2-(4-((2-(3-chlorophenyl)-6,7-dihydro-5H-cyclopenta[b]pyridin-4-yl)methyl)phenyl)acetate (0.036 g, 0.09 mmol) and ammonium chloride (0.015 g, 0.27 mmol). To this was added methanol (2 mL) followed by NH$_3$ (4 mL, 7N in methanol, 27.6 mmol). The vial was sealed and the resulting mixture was stirred at 100° C. for 48 hr. After this time, the crude reaction solution concentrated under reduced pressure. The residue was adsorbed onto silica then purified by chromatography on silica using hexanes/ethyl acetate (10:0 to 0:10) as eluent to afford 2-(4-((2-(3-chlorophenyl)-6,7-dihydro-5H-cyclopenta[b]pyridin-4-yl)methyl)phenyl)acetamide (0.026 g, 79%) as a white solid. MW=376.88. $^1$H NMR (CDCl$_3$, 500 MHz) δ 7.93-7.89 (m, 1H), 7.81-7.74 (m, 1H), 7.39-7.30 (m, 2H), 7.26-7.14 (m, 5H), 5.55-5.25 (m, 2H), 3.97 (s, 2H), 3.56 (s, 2H), 3.08 (t, J=8.0 Hz, 2H), 2.87 (t, J=7.5 Hz, 2H), 2.14 (quin, J=7.5 Hz, 2H). MS: APCI+, m/z 377 [M+H]$^+$. Treatment of 2-(4-((2-(3-chlorophenyl)-6,7-dihydro-5H-cyclopenta[b]pyridin-4-yl)methyl)phenyl)acetamide with 1.25M HCl in methanol afforded the title compound (0.037 g, 99%) as a white solid. MW=413.34. M.p. 178-180° C. $^1$H NMR (DMSO-d$_6$, 500 MHz) δ 8.11-8.07 (m, 1H), 8.00-7.93 (m, 1H), 7.81 (s, 1H), 7.57-7.47 (m, 2H), 7.43 (br s, 1H), 7.25-7.34 (m, 4H), 6.84 (br s, 1H), 4.60 (br s, 1H), 4.00 (s, 2H), 3.31 (s, 2H), 3.00 (t, J=7.5 Hz, 2H), 2.87 (t, J=7.5 Hz, 2H), 2.07 (quin, J=7.5 Hz, 2H); APCI MS m/z 377 [M+H]$^+$.

EXAMPLE 126

2-(4-((2-(3-Chlorophenyl)-6,7-dihydro-5H-cyclopenta[b]pyridin-4-yl)methyl)phenyl)-2-methylpropanoic acid hydrochloride

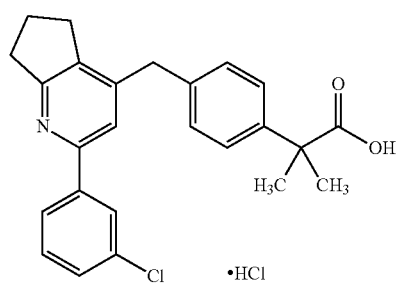 [SMILES: CC(C)(C(=O)O)c1ccc(Cc2cc(-c3cccc(Cl)c3)nc3c2CCC3)cc1 ; Cl]

Step 1. Preparation of methyl 2-(4-((2-(3-chloro-phenyl)-6,7-dihydro-5H-cyclopenta[b]pyridin-4-yl)methyl)phenyl)-2-methylpropanoate

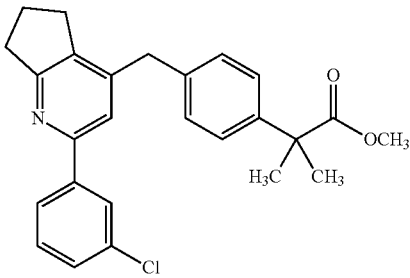 [SMILES: COC(=O)C(C)(C)c1ccc(Cc2cc(-c3cccc(Cl)c3)nc3c2CCC3)cc1]

A 20-mL sealed tube, with stirrer bar, was charged with 4-chloro-2-(3-chlorophenyl)-6,7-dihydro-5H-cyclopenta[b]pyridine (0.300 g, 1.13 mmol), methyl 2-methyl-2-(4-((4,4,5,5-tetramethyl-1,3,2-dioxaborolan-2-yl)methyl)phenyl)propanoate (0.361 g, 1.13 mmol), Pd(dppf)Cl$_2$ (0.093 g, 0.11 mmol), and powdered Na$_2$CO$_3$ (0.361 g, 3.41 mmol). Dioxane (8 mL) and water (4 mL) were added. The resulting mixture was stirred under Ar at 90° C. for 2 d. After cooling to room temperature, the reaction mixture was filtered through celite washing the solids with ethyl acetate. The filtrate layers were separated and the organic layer was washed with saturated sodium chloride (3×10 mL), dried over sodium sulfate, filtered, and concentrated under reduced pressure. The residue was purified by chromatography on silica using hexanes/ethyl acetate (10:0 to 3:1) as eluent to afford the title compound (0.201 g, 42%) as a colorless oil. MW=419.94. $^1$H NMR (CDCl$_3$, 500 MHz) δ 7.93-7.90 (m, 1H), 7.79-7.76 (m, 1H), 7.37-7.31 (m, 2H), 7.28-7.23 (m, 3H), 7.10-7.14 (m, 2H), 3.94 (s, 2H), 3.64 (s, 3H), 3.08 (t, J=7.5 Hz, 2H), 2.88 (t, J=7.5 Hz, 2H), 2.14 (quin, J=7.5 Hz, 2H), 1.56 (s, 6H); ESI MS m/z 420 [M+H]$^+$.

EXAMPLE 126

2-(4-((2-(3-Chlorophenyl)-6,7-dihydro-5H-cyclopenta[b]pyridin-4-yl)methyl)phenyl)-2-methylpropanoic acid hydrochloride

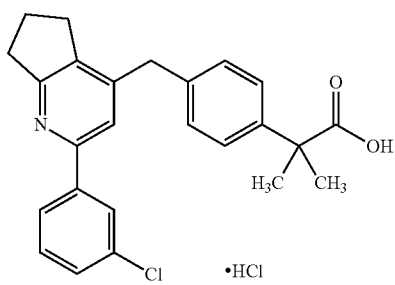 [SMILES: CC(C)(C(=O)O)c1ccc(Cc2cc(-c3cccc(Cl)c3)nc3c2CCC3)cc1 ; Cl]

An 250-mL round bottom flask was charged with methyl 2-(4-((2-(3-chlorophenyl)-6,7-dihydro-5H-cyclopenta[b]pyridin-4-yl)methyl)phenyl)-2-methylpropanoate (0.200 g, 0.47 mmol), dioxane (15 ml) and water (10 ml). To this solution was then added lithium hydroxide monohydrate (0.060 g, 1.43 mmol). The resulting mixture was stirred at 50° C. for 6.5 h. The cooled reaction mixture was treated with 2N aqueous HCl until pH~5. The volatile materials were removed under reduced pressure to afford impure 2-(4-((2-(3-chlorophenyl)-6,7-dihydro-5H-cyclopenta[b]pyridin-4-yl)methyl)phenyl)-2-methylpropanoic acid hydrochloride (0.44 g, >100%). A sample (0.112 g) was purified by preparative HPLC (water/acetonitrile with 0.05% TFA) and converted into HCl salt to afford the title compound (0.035 g, 16%) as a white solid. MW=432.38. M.p. 182-184° C. $^1$H NMR (DMSO-d$_6$, 500 MHz) δ 12.23 (br s, 1H), 8.10-8.07 (m, 1H), 7.99-7.94 (m, 1H), 7.88 (br s, 1H), 7.58-7.53 (m, 2H), 7.29-7.24 (m, 4H), 4.04 (s, 2H), 3.06 (t, J=7.5 Hz, 2H), 2.91 (t, J=7.5 Hz, 2H), 2.11 (quin, J=7.5 Hz, 2H), 1.43 (s, 6H); APCI MS m/z 406 [M+H]$^+$.

EXAMPLE 127

2-(4-((2-(3-Chlorophenyl)-6,7-dihydro-5H-cyclopenta[b]pyridin-4-yl)methyl)phenyl)-2-methylpropanamide hydrochloride

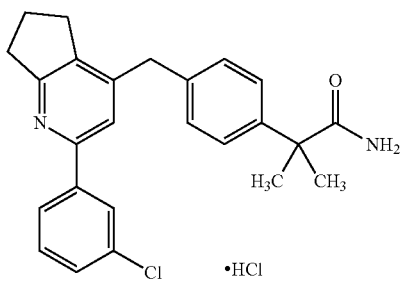 [SMILES: CC(C)(C(N)=O)c1ccc(Cc2cc(-c3cccc(Cl)c3)nc3c2CCC3)cc1 ; Cl]

An 250-mL round bottom flask was charged with 2-(4-((2-(3-chlorophenyl)-6,7-dihydro-5H-cyclopenta[b]pyridin-4-yl)methyl)phenyl)-2-methylpropanoic acid (0.33 g, ~0.40 mmol) in dichloromethane (10 ml). To this mixture at 0° C. was added oxalyl chloride (0.17 mL, 2.00 mmol) followed by DMF (1 drop). After stirring for 3 h, the volatile material was removed under reduced pressure to afford crude acid chloride. The residue was dissolved in dichloromethane (20 mL), cooled to 0° C. and 7N ammonia in methanol (14.0 mL, 98 mmol) was added. After stirring for 1.25 h the volatile material was removed under reduced pressure. The residue was absorbed onto silica (5 g). Purification by chromatography on silica using hexanes/ethyl acetate as eluent afforded 2-(4-((2-(3-chlorophenyl)-6,7-dihydro-5H-cyclopenta[b]pyridin-4-yl)methyl)phenyl)-2-methylpropanamide (0.128 g, 79%) as a white solid. MW=404.93. $^1$H NMR (CDCl$_3$, 500 MHz) δ 7.92-7.90 (m, 1H), 7.80-7.77 (m, 1H), 7.37-7.31 (m, 4H), 7.24 (s, 1H), 7.16 (d, J=8.5 Hz, 2H), 5.32 (br s, 1H), 5.16 (br s, 1H), 3.96 (s, 2H), 3.09 (t, J=7.5 Hz, 2H), 2.88 (t, J=7.5 Hz, 2H), 2.15 (quin, J=7.5 Hz, 2H), 1.57 (s, 6H). Treatment with 1.25M HCl in methanol (0.72 mL, 0.90 mmol) afforded the title compound (0.124 g, 94%) as a white solid. MW=441.39. M.p. 180-182° C. $^{1}$H NMR (DMSO-d$_{6}$, 500 MHz) δ 8.10-8.07 (m, 1H), 7.99-7.94 (m, 1H), 7.88 (br s, 1H), 7.58-7.52 (m, 2H), 7.29-7.22 (m, 4H), 6.83 (s, 2H), 5.50 (br s, 1H), 4.03 (s, 2H), 3.06 (t, J=7.5 Hz, 2H), 2.92 (t, J=7.5 Hz, 2H), 2.11 (quin, J=7.5 Hz, 2H), 1.39 (s, 6H); APCI MS m/z 405 [M+H]$^{+}$.

EXAMPLE 128

2-(4-((2-(3-Chlorophenyl)-6,7-dihydro-5H-cyclopenta[b]pyridin-4-yl)methyl)phenyl)-2-methylpropan-1-ol hydrochloride

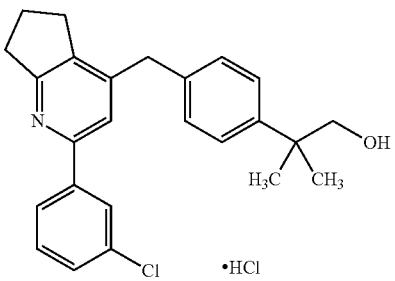 [SMILES: CC(C)(CO)c1ccc(Cc2cc(-c3cccc(Cl)c3)nc3c2CCC3)cc1 ; Cl]

A 25-mL round bottom flask was charged with methyl 2-(4-((2-(3-chlorophenyl)-6,7-dihydro-5H-cyclopenta[b]pyridin-4-yl)methyl)phenyl)-2-methylpropanoate (0.144 g, 0.31 mmol) and THF (5 mL) at rt. Borane-dimethylsulfide complex (0.090 mL, 0.95 mmol) was added and the resulting solution was stirred at 55° C. for 2 h. LCMS analysis indicated only partial reduction. Borane-dimethylsulfide complex (0.100 mL, 1.05 mmol) was added and the resulting solution was stirred at 55° C. for a further 20 h until the starting material was consumed (monitored by LCMS analysis). The reaction was quenched with methanol then treated with 2N aqueous HCl (0.1 mL) and concentrated under reduced pressure. The residue was diluted with methanol and then concentrated under reduced pressure. The residue absorbed onto silica (2 g) then purified by column chromatography on silica using hexanes/ethyl acetate (10:0 to 0:10) as the eluent to afford 2-(4-((2-(3-chlorophenyl)-6,7dihydro-5H-cyclopenta[b]pyridin-4-yl)methyl)phenyl)-2-methylpropan-1-ol (0.126 g, 100%) as a colorless oil. MW=391.93. $^{1}$H NMR (CDCl$_{3}$, 500 MHz) δ 7.93-7.91 (m, 1H), 7.79-7.76 (m, 1H), 7.37-7.30 (m, 4H), 7.26 (s, 1H), 7.15 (d, J=8.0 Hz, 2H), 3.95 (s, 2H), 3.60 (d, J=8.0 Hz, 2H), 3.08 (t, J=8.0 Hz, 2H), 2.88 (t, J=7.5 Hz, 2H), 2.14 (quin, J=7.5 Hz, 3H), 1.32 (s, 6H), 1.18 (t, J=8.0 Hz, 1H). MS: ESI+, m/z 392 [M+H]$^{+}$. Treatment with 1.25M HCl in methanol (0.52 mL, 2.0 eq.) afforded the title compound (0.121 g, 89%) as a white solid. MW=428.39. M.p. 95-97° C. $^{1}$H NMR (DMSO-d$_{6}$, 500 MHz) δ 8.10-8.07 (m, 1H), 7.99-7.94 (m, 1H), 7.86 (br s, 1H), 7.58-7.52 (m, 2H), 7.31-7.27 (m, 2H), 7.23-7.19 (m, 2H), 4.01 (s, 2H), 3.37 (s, 2H), 3.05 (t, J=7.5 Hz, 2H), 2.92 (t, J=7.5 Hz, 2H), 2.11 (quin, J=7.5 Hz, 2H), 1.17 (s, 6H); APCI MS m/z 392 [M+H]$^{+}$.

EXAMPLE 129

1-(4-((2-(3-Chlorophenyl)-6,7-dihydro-5H-cyclopenta[b]pyridin-4-yl)amino)phenyl)-1-methylurea hydrochloride

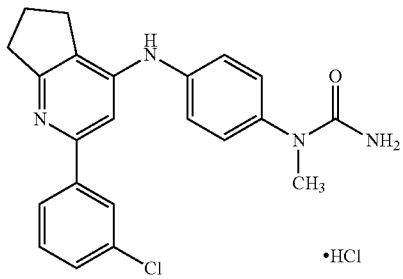 [SMILES: CN(C(N)=O)c1ccc(Nc2cc(-c3cccc(Cl)c3)nc3c2CCC3)cc1 ; Cl]

Step 1. Preparation of 1-methyl-1-(4-nitrophenyl)urea

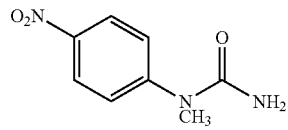

A 250-mL round bottom flask was charged with N-methyl-4-nitroaniline (1.94 g, 12.7 mmol) in tetrahydrofuran (50 mL). To this stirred solution at rt was added acetic acid (14.6 mL, 255 mmol) and sodium cyanate (8.29 g, 127.5 mmol). After 24 h, the reaction mixture was concentrated under reduced pressure. The residue was suspended in water (100 mL) and the resultant solid was isolated by filtration, washing sequentially with dichloromethane and ethyl acetate to afford the title compound (0.63 g, 25%) as a yellow solid. MW=195.18. $^{1}$H NMR (DMSO-d$_{6}$, 500 MHz) δ 8.19-8.14 (m, 2H), 7.58-7.54 (m, 2H), 6.54 (br s, 2H), 3.27 (s, 3H).

Step 2. Preparation of 1-(4-aminophenyl)-1-methylurea

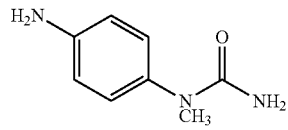

A 100-mL round bottom flask was charged with 1-methyl-1-(4-nitrophenyl)urea (0.63 g, 3.26 mmol) and 10% palladium on carbon (0.15 g) in 1:1 ethyl acetate/methanol (20 mL). This mixture was vigorously stirred under H$_{2}$ (1 atm) for 5 h. After this time, the mixture was filtered through celite to afford the title compound (0.54 g, 100%) as a white solid. MW=165.19. $^{1}$H NMR (DMSO-d$_{6}$, 500 MHz) δ 6.90-6.86 (m, 2H), 6.57-6.53 (m, 2H), 5.29 (br s, 2H), 5.11 (s, 2H), 3.00 (s, 3H).

Step 3. Preparation of N¹-(2-(3-chlorophenyl)-6,7-dihydro-5H-cyclopenta[b]pyridin-4-yl)-N⁴-methyl-benzene-1,4-diamine

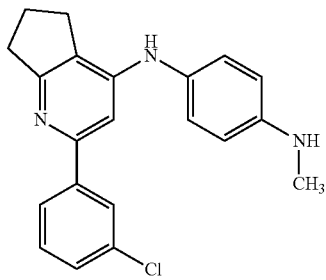 [SMILES: CNc1ccc(Nc2cc(-c3cccc(Cl)c3)nc3c2CCC3)cc1]

A 10-mL microwave vial was charged with 4-chloro-2-(3-chlorophenyl)-6,7-dihydro-5H-cyclopenta[b]pyridine hydrochloride (0.200 g, 0.67 mmol), 1-(4-aminophenyl)-1-methylurea (0.220 g, 1.33 mmol) and conc. HCl (2 drops) in NMP (5 mL). The resulting mixture was heated at 140° C. under microwave irradiation for 3 h. After this time, the reaction mixture was cooled, diluted with water (40 mL) and then saturated sodium bicarbonate was added until pH~8. The resulting solid was isolated by filtration then purified by chromatography on silica using hexanes/ethyl acetate (10:0 to 0:10) as eluent to afford the title compound (0.071 g, 30%) as a colorless oil. MW=349.86. ¹H NMR (CDCl₃, 500 MHz) δ 7.83-7.80 (m, 1H), 7.68-7.63 (m, 1H), 7.28-7.26 (m, 2H), 7.10-7.06 (m, 2H), 6.85 (s, 1H), 6.67-6.62 (m, 2H), 5.55 (s, 1H), 3.76 (br s, 1H), 3.06 (t, J=7.5 Hz, 2H), 2.87 (s, 3H), 2.81 (t, J=7.5 Hz, 2H), 2.20 (quin, J=7.5 Hz, 2H); ESI MS m/z 350 [M+H]⁺.

EXAMPLE 129

1-(4-((2-(3-Chlorophenyl)-6,7-dihydro-5H-cyclopenta[b]pyridin-4-yl)amino)phenyl)-1-methylurea hydrochloride

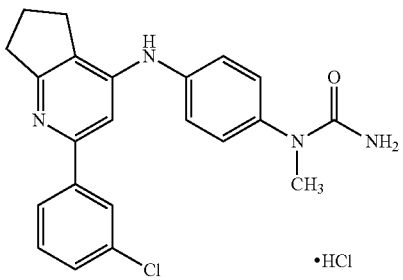 [SMILES: CN(C(N)=O)c1ccc(Nc2cc(-c3cccc(Cl)c3)nc3c2CCC3)cc1 ; Cl]

A 25-mL round bottom flask was charged with N¹-(2-(3-chlorophenyl)-6,7-dihydro-5H-cyclopenta[b]pyridin-4-yl)-N⁴-methylbenzene-1,4-diamine (0.100 g, 0.28 mmol) in tetrahydrofuran (1 mL). To this stirred solution at rt was added acetic acid (0.33 mL, 5.72 mmol) and sodium cyanate (0.186 g, 2.86 mmol). After 16 h, the reaction mixture was diluted with water (20 mL) and saturated sodium bicarbonate was added until pH~8, at which time, a solid formed. The resultant solid was isolated by filtration, and was purified by chromatography on silica using dichloromethane/methanol (10:0 to 19:1) as eluent to afford 1-(4-((2-(3-chlorophenyl)-6,7-dihydro-5H-cyclopenta[b]pyridin-4-yl)amino)phenyl)-1-methylurea (0.090 g, 80%) as a white solid. MW=392.88. ¹H NMR (DMSO-d₆, 500 MHz) δ 8.18 (s, 1H), 7.95 (t, J=2.0 Hz, 1H), 7.80 (dt, J=7.5, 1.5 Hz, 1H), 7.46-7.39 (m, 2H), 7.31 (s, 1H), 7.25 (s, 4H), 5.73 (s, 2H), 2.92 (t, J=7.5 Hz, 2H), 3.13 (s, 3H), 2.85 (t, J=7.5 Hz, 2H), 2.09 (quin, J=7.5 Hz, 2H). MS: ESI+, m/z 393 [M+H]⁺. Treatment with 1.25M HCl in methanol (0.15 mL, 0.19 mmol) afforded the title compound (0.048 g, 90%) as a light yellow solid. MW=429.34. M.p. 154-157° C. decomp. ¹H NMR (DMSO-d₆, 500 MHz) δ 13.93 (br s, 1H), 9.19 (br s, 1H), 7.92-7.89 (m, 1H), 7.76-7.71 (m, 1H), 7.60-7.52 (m, 2H), 7.33 (s, 4H), 7.18 (s, 1H), 5.87 (s, 2H), 3.16 (s, 3H), 3.07 (t, J=7.0 Hz, 2H), 2.90 (t, J=7.5 Hz, 2H), 2.19 (quin, J=7.5 Hz, 2H); ESI MS m/z 393 [M+H]⁺.

EXAMPLE 130

4-(4-((2-(3-Chlorophenyl)-6,7-dihydro-5H-cyclopenta[b]pyridin-4-yl)amino)phenyl)butanamide hydrochloride

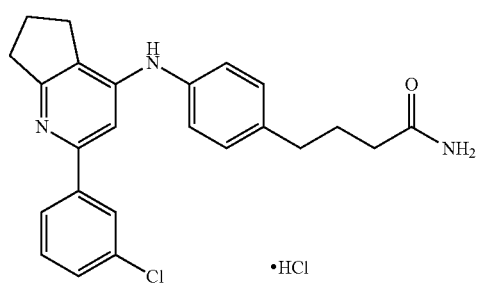 [SMILES: NC(=O)CCCc1ccc(Nc2cc(-c3cccc(Cl)c3)nc3c2CCC3)cc1 ; Cl]

Step 1. Preparation of methyl 4-(4-aminophenyl)butanoate

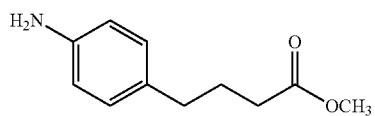 [SMILES: COC(=O)CCCc1ccc(N)cc1]

A 250-mL round bottom flask was charged with 4-(4-aminophenyl)butyric acid (2.00 g, 11.2 mmol) in methanol (50 mL) and treated with conc. sulfuric acid (1 mL). The resultant mixture was heated to reflux for 1.5 h. After this time, methanol (~25 mL) was distilled off. The reaction was cooled to 60° C. and methyl tert-butyl ether was added. The mixture was allowed to slowly cool to room temperature, then diluted with hexanes (50 mL) to afford a white solid. The solid was dissolved in THF (6 mL)/water (4 mL) and treated with conc. NH₄OH (6 mL). The mixture was diluted with dichloromethane (50 mL) and the layers separated. The organic layer was washed with saturated sodium chloride (5 mL), dried over sodium sulfate, filtered and concentrated under reduced pressure to afford the title compound (2.07 g, 96%) as a brown solid. MW=193.24. ¹H NMR (DMSO-d₆, 500 MHz) δ 6.83-6.79 (m, 2H), 6.50-6.46 (m, 2H), 4.81 (s, 2H), 3.57 (s, 3H), 2.39 (t, J=7.5 Hz, 2H), 2.25 (t, J=7.5 Hz, 2H), 1.73 (quin, J=7.5 Hz, 2H).

Step 2. Preparation of 4-(4-aminophenyl)butanamide

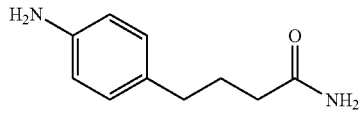 [SMILES: NC(=O)CCCc1ccc(N)cc1]

A 100-mL vial was charged with methyl 4-(4-aminophenyl)butanoate (2.07 g, 10.7 mmol), ammonium chloride (0.76 g, 14.2 mmol) in methanol (10 mL). To this mixture was added NH$_3$ (10 mL, 7N in methanol, 70.0 mmol, 6.5 eq.). The vial was sealed and the resulting mixture was stirred at 100° C. for 20 h. After this time, the crude reaction solution was concentrated under reduced pressure. The residue was absorbed on silica (10 g) then purified by chromatography on silica using dichloromethane/methanol (10:0 to 9:1) as eluent to afford the title compound (0.67 g, 35%) as a white solid. MW=178.23. $^1$H NMR (DMSO-d$_6$, 500 MHz) δ 7.20 (br s, 1H), 6.83-6.80 (m, 2H), 6.66 (br s, 1H), 6.49-6.46 (m, 2H), 2.37 (t, J=7.5 Hz, 2H), 2.01 (t, J=7.5 Hz, 2H), 1.68 (quin, J=7.5 Hz, 2H).

EXAMPLE 130

4-(4-((2-(3-Chlorophenyl)-6,7-dihydro-5H-cyclopenta[b]pyridin-4-yl)amino)phenyl)butanamide hydrochloride

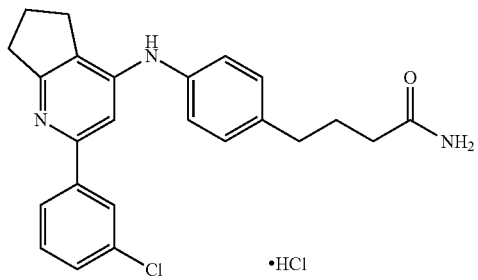 [SMILES: NC(=O)CCCc1ccc(Nc2cc(-c3cccc(Cl)c3)nc3c2CCC3)cc1 ; Cl]

A 10-mL microwave vial was charged with 4-chloro-2-(3-chlorophenyl)-6,7-dihydro-5H-cyclopenta[b]pyridine hydrochloride (0.100 g, 0.33 mmol), 4-(4-aminophenyl)butanamide (0.071 g, 0.40 mmol) and conc. HCl (2 drops) in NMP (3 mL). The resulting mixture was heated at 120° C. under microwave irradiation for 2 h. The reaction mixture was cooled, diluted with water (5 mL) then treated with 2M aqueous sodium hydroxide until pH~8 affording a solid. The solid was isolated by filtration and purified by chromatography on silica using dichloromethane/methanol (10:0 to 19:1) as eluent followed by chromatography on silica using hexanes/ethyl acetate (10:0 to 0:10) as eluent to afford 4-(4-((2-(3-chlorophenyl)-6,7-dihydro-5H-cyclopenta[b]pyridin-4-yl)amino)phenyl)butanamide (0.050 g, 37%) as a white solid. MW=405.92. $^1$H NMR (DMSO-d$_6$, 500 MHz) δ 8.07 (s, 1H), 7.91 (t, J=2.0 Hz, 1H), 7.74 (dt, J=7.5, 1.5 Hz, 1H), 7.46-7.38 (m, 2H), 7.25 (br s, 1H), 7.22-7.15 (m, 5H), 6.71 (br s, 1H), 2.91 (t, J=7.5 Hz, 2H), 2.82 (t, J=7.5 Hz, 2H), 2.55 (t, J=7.5 Hz, 2H), 2.08 (quin, J=7.5 Hz, 4H), 1.79 (quin, J=7.5 Hz, 2H); ESI MS m/z 406 [M+H]$^+$. Treatment with 1.25M HCl in methanol afforded the title compound (0.053 g, 99%) as an off-white solid. MW=442.38. M.p. 108-111° C. $^1$H NMR (DMSO-d$_6$, 500 MHz) δ 11.91 (br s, 1H), 8.84 (br s, 1H), 7.91-7.88 (m, 1H), 7.74-7.69 (m, 1H), 7.54-7.47 (m, 2H), 7.27-7.22 (m, 5H), 7.11 (br s, 1H), 6.72 (br s, 1H), 3.01 (t, J=7.5 Hz, 2H), 2.86 (t, J=7.5 Hz, 2H), 2.57 (t, J=7.5 Hz, 2H), 2.15 (quin, J=7.5 Hz, 2H), 2.09 (t, J=7.5 Hz, 2H), 1.80 (quin, J=7.5 Hz, 2H); ESI MS m/z 406 [M+H]$^+$.

EXAMPLE 131

2-(4-((2-(Cyclopentyloxy)-6,7-diydro-5H-cyclopenta[b]pyridin-4-yl)methyl)phenyl)acetamide hydrochloride

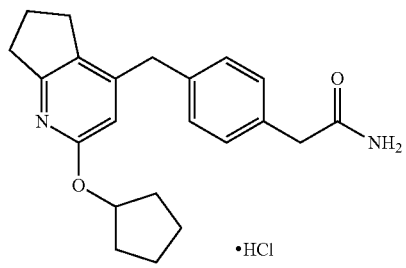 [SMILES: NC(=O)Cc1ccc(Cc2cc(OC3CCCC3)nc3c2CCC3)cc1 ; Cl]

Step 1. Preparation of methyl 2-(4-((2-(cyclopentyloxy)-6,7-dihydro-5H-cyclopenta[b]pyridin-4-yl)methyl)phenyl)acetate

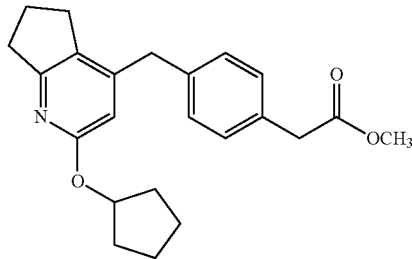 [SMILES: COC(=O)Cc1ccc(Cc2cc(OC3CCCC3)nc3c2CCC3)cc1]

A 20-mL sealed tube, with stirrer bar, was charged with 4-chloro-2-(cyclopentyloxy)-6,7-dihydro-5H-cyclopenta[b]pyridine (0.103 g, 0.43 mol), methyl 2-(4-((4,4,5,5-tetramethyl-1,3,2-dioxaborolan-2-yl)methyl)phenyl)acetate (0.126 g, 0.43 mmol), Pd(dppf)Cl$_2$ (0.035 g, 0.043 mmol), and powdered Na$_2$CO$_3$ (0.184 g, 1.74 mmol). Dioxane (4 mL) and water (2 mL) were added. The resulting mixture was stirred under Ar at 90° C. for 24 h. until the starting chloride was consumed. After this time, the mixture was cooled to room temperature and the reaction mixture absorbed onto silica (4 g). Purification by chromatography on silica using dichloromethane/methanol (10:0 to 8:2) as eluent to afford 2-(4-((2-(cyclopentyloxy)-6,7-dihydro-5H-cyclopenta[b]pyridin-4-yl)methyl)phenyl)acetic acid. MW=351.44. MS: ESI+, m/z 352 [M+H]+. This product was dissolved in methanol and treated with 4M HO/methanol and stirred for 3 days. The reaction was concentrated under reduced pressure. The residue (0.154 g) was treated with minimum saturated sodium bicarbonate then purified by chromatography on silica using hexanes/ethyl acetate (10:0 to 1:1) as eluent to afford the title compound (0.038 g, 24%) as a colorless oil. MW=365.47. ¹H NMR (CDCl₃, 300 MHz) δ 7.23-7.17 (m, 2H), 7.14-7.08 (m, 2H), 6.22 (s, 1H), 5.35-5.26 (m, 1H), 3.81 (s, 2H), 3.69 (s, 3H), 3.60 (s, 2H), 2.89 (t, J=8.0 Hz, 2H), 2.72 (t, J=7.5 Hz, 2H), 2.06 (quin, J=7.5 Hz, 2H), 1.98-1.88 (m, 2H), 1.85-1.68 (m, 4H), 1.66-1.53 (m, 2H); APCI MS 366 [M+H]⁺.

EXAMPLE 131

2-(4-((2-(Cyclopentyloxy)-6,7-dihydro-5H-cyclopenta[b]pyridin-4-yl)methyl)phenyl)acetamide hydrochloride

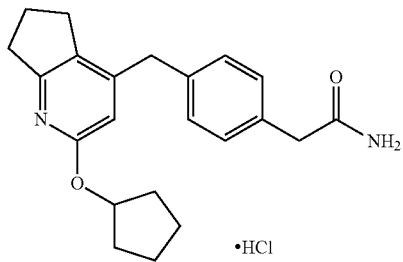 [SMILES: NC(=O)Cc1ccc(Cc2cc(OC3CCCC3)nc3c2CCC3)cc1 ; Cl]

A 20-mL vial was charged with methyl 2-(4-((2-(cyclopentyloxy)-6,7-dihydro-5H-cyclopenta[b]pyridin-4-yl)methyl)phenyl)acetate (0.038 g, 0.10 mmol) and ammonium chloride (0.017 g, 0.31 mmol). To this was added methanol (3 mL) followed by NH₃ (4.0 mL, 7N in methanol, 28 mmol). The vial was sealed and the resulting mixture was stirred at 100° C. for 42 hr. The crude reaction solution concentrated under reduced pressure. The residue was adsorbed onto silica then purified by chromatography on silica using dichloromethane/methanol (10:0 to 1:1) as eluent, followed by preparative HPLC (water/acetonitrile with 0.05% TFA), to afford the title compound (0.019 g, 54%) as a yellow solid. MW=386.91. M.p. 78-80° C. ¹H NMR (DMSO-d₆, 500 MHz) δ 7.43 (br s, 1H), 7.18 (d, J=8.0 Hz, 2H), 7.14 (d, J=8.0 Hz, 2H), 6.83 (br s, 1H), 6.51 (br s, 1H), 5.31-5.25 (m, 1H), 3.86 (s, 2H), 3.32 (s, 2H), 2.84 (t, J=7.5 Hz, 2H), 2.73 (t, J=7.5 Hz, 2H), 2.02 (quin, J=7.5 Hz, 2H), 1.96-1.86 (m, 2H), 1.73-1.63 (m, 4H), 1.62-1.53 (m, 2H); APCI MS m/z 351 [M+H]⁺.

EXAMPLE 132

2-(4-((2-(1H-Pyrrol-2-yl)-6,7-dihydro-5H-cyclopenta[b]pyridin-4-yl)amino)phenyl)ethanol hydrochloride

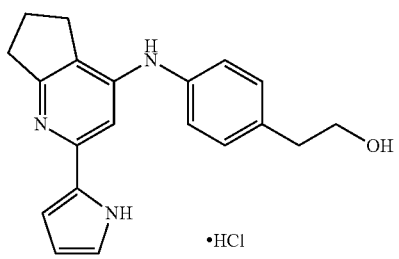 [SMILES: OCCc1ccc(Nc2cc(-c3ccc[nH]3)nc3c2CCC3)cc1 ; Cl]

Step 1. Preparation of tert-butyl 2-(4-chloro-6,7-dihydro-5H-cyclopenta[b]pyridin-2-yl)-1H-pyrrole-1-carboxylate and 4-chloro-2-(1H-pyrrol-2-yl)-6,7-dihydro-5H-cyclopenta[b]pyridine

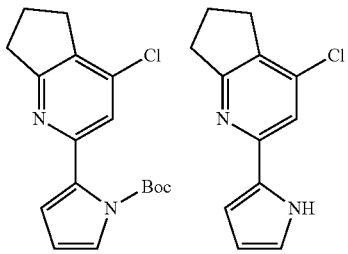

A 20-mL sealed tube was charged with 2,4-dichloro-6,7-dihydro-5H-cyclopenta[b]pyridine (0.250 g, 1.33 mmol), 1-Boc-pyrrole-2-boronic acid (0.308 g, 1.46 mmol), tetrakis(triphenylphosphine)palladium(0) (0.076 g, 0.066 mmol), and Cs₂CO₃ (1.30 g, 3.99 mmol). Toluene (8 ml), EtOH (2 ml) and water (4 ml) were added. The resulting mixture was stirred under Ar at 90° C. for 23 h. After cooling to room temperature, the reaction solution was diluted with water (5 mL) and ethyl acetate (60 mL). The aqueous layer was separated and the organic layer was washed with saturated sodium chloride (5 mL) then dried over sodium sulfate, filtered, and concentrated under reduced pressure. The residue was purified by chromatography on silica using hexane/ethyl acetate (100:0 to 75:250) as eluent to afford tert-butyl 2-(4-chloro-6,7-dihydro-5H-cyclopenta[b]pyridin-2-yl)-1H-pyrrole-1-carboxylate (0.138 g, 32%) as a yellow oil. MW=318.80. ¹H NMR (CDCl₃, 500 MHz) δ 7.33 (dd, J=3.5, 2.0 Hz, 1H), 7.17 (s, 1H), 6.37 (dd, J=3.0, 2.0 Hz, 1H), 6.21 (t, J=3.5 Hz, 1H), 3.09 (t, J=7.5 Hz, 2H), 3.04 (t, J=7.5 Hz, 2H), 2.17 (quin, J=7.5 Hz, 2H), 1.38 (s, 9H). MS: ESI+, m/z 319 [M+H]⁺ and 4-chloro-2-(1H-pyrrol-2-yl)-6,7-dihydro-5H-cyclopenta[b]pyridine (0.077 g, 26%) as an off-white solid. MW=218.68. ¹H NMR (CDCl₃, 500 MHz) δ 9.63 (br s, 1H), 7.30 (s, 1H), 6.87-6.85 (m, 1H), 6.65-6.62 (m, 1H), 6.29-6.25 (m, 1H), 3.01 (t, J=7.5 Hz, 2H), 2.96 (t, J=7.5 Hz, 2H), 2.13 (quin, J=7.5 Hz, 2H); ESI MS m/z 218 [M]⁺.

EXAMPLE 132

2-(4-((2-(1H-Pyrrol-2-yl)-6,7-dihydro-5H-cyclopenta[b]pyridin-4-yl)amino)phenyl)ethanol hydrochloride

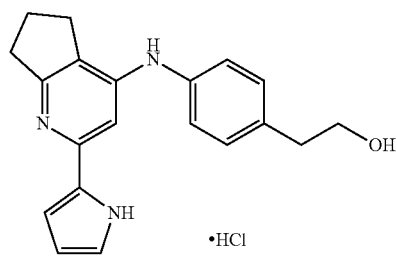 [SMILES: OCCc1ccc(Nc2cc(-c3ccc[nH]3)nc3c2CCC3)cc1 ; Cl]

A 10-mL microwave vial was charged with 4-chloro-2-(1H-pyrrol-2-yl)-6,7-dihydro-5H-cyclopenta[b]pyridine (0.077 g, 0.35 mmol), 4-aminophenethyl alcohol (0.072 g, 0.53 mmol) and conc. HCl (1 drop) in NMP (2.5 mL). The resulting mixture was heated at 140° C. under microwave irradiation for 1.5 h. After this time, the reaction mixture was cooled, diluted with saturated aqueous sodium bicarbonate (15 mL) affording a brown solid. The solid was isolated by filtration and chromatography on silica using dichloromethane/(90:10:0.25 dichloromethane/methanol. conc. NH$_4$OH) (10:0 to 0:10) as eluent followed by preparative HPLC (water/acetonitrile with 0.05% TFA) to afford 2-(4-((2-(1H-pyrrol-2-yl)-6,7-dihydro-5H-cyclopenta[b]pyridin-4-yl)amino)phenyl)ethanol (0.039 g, 35%) as a light brown. MW=319.40. $^1$H NMR (DMSO-d$_6$, 500 MHz) δ 11.16 (br s, 1H), 7.90 (br s, 1H), 7.22-7.18 (m, 2H), 7.15-7.11 (m, 2H), 7.01 (s, 1H), 6.73 (s, 1H), 6.38 (s, 1H), 6.06-6.01 (m, 1H), 4.62 (t, J=5.0 Hz, 1H), 3.65-3.58 (m, 2H), 2.86 (t, J=7.5 Hz, 2H), 2.78 (t, J=7.5 Hz, 2H), 2.71 (t, J=7.0 Hz, 2H), 2.05 (quin, J=7.5 Hz, 2H); ESI MS in/z 320 [M+H]$^+$. Treatment with 1.25 M HCl in methanol (0.25 mL, 0.32 mmol) afforded the title compound (0.034 g, 92%) as a light brown solid. MW=355.86. M.p. 138-140° C. $^1$H NMR (DMSO-d$_6$, 500 MHz) δ 13.50 (br s, 1H), 12.08 (br s, 1H), 9.44 (br s, 1H), 7.36-7.32 (m, 2H), 7.30-7.26 (m, 2H), 7.12-7.09 (m, 1H), 7.06 (s, 2H), 6.28-6.25 (m, 1H), 4.68 (br s, 1H), 3.66 (t, J=7.0 Hz, 2H), 3.11 (t, J=7.5 Hz, 2H), 2.87 (t, J=7.5 Hz, 2H), 2.78 (t, J=7.0 Hz, 2H), 2.20 (quin, J=7.5 Hz, 2H); ESI MS: ES in/z 320 [M+H]$^+$.

EXAMPLE 133

2-(4-((2-(1H-Pyrrol-2-yl)-6,7-dihydro-5H-cyclopenta[b]pyridin-4-yl)amino)phenyl)acetamide hydrochloride

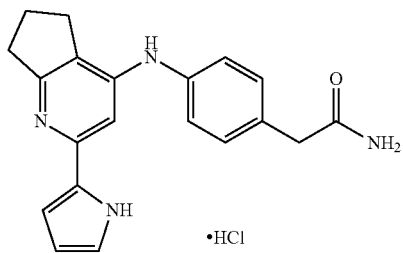 [SMILES: NC(=O)Cc1ccc(Nc2cc(-c3ccc[nH]3)nc3c2CCC3)cc1 ; Cl]

Step 1. Preparation of tert-butyl 2-(4-((4-(2-ethoxy-2-oxoethyl)phenyl)amino)-6,7-dihydro-5H-cyclopenta[b]pyridin-2-yl)-1H-pyrrole-1-carboxylate and ethyl 2-(4-((2-(1H-pyrrol-2-yl)-6,7-dihydro-5H-cyclopenta[b]pyridin-4-yl)amino)phenyl)acetate

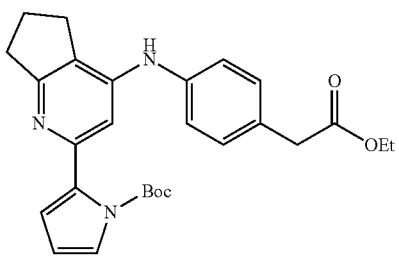

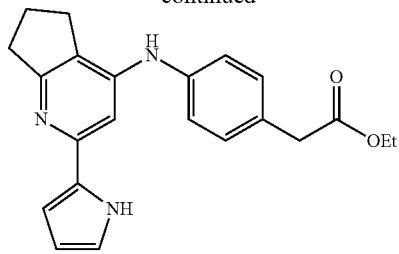

A 10-mL microwave vial was charged with tert-butyl 2-(4-chloro-6,7-dihydro-5H-cyclopenta[b]pyridin-2-yl)-1H-pyrrole-1-carboxylate (0.138 g, 0.43 mmol), 4-aminophenyl acetic acid ethyl ester (0.093 g, 0.52 mmol), palladium acetate (0.005 g, 0.021 mmol), rac-BINAP (0.020 g, 0.032 mmol) and cesium carbonate (0.353 g, 1.08 mmol) in dioxane (4 mL) under argon. The reaction mixture was heated to 120° C. under microwave irradiation for 2 h. After this time, the reaction mixture was cooled, diluted with ethyl acetate (50 mL) then filtered through celite. The filtrate was washed with saturated sodium chloride (10 mL), dried over anhydrous sodium sulfate, filtered and the filtrate was concentrated under reduced pressure. The residue was purified by chromatography on silica using dichloromethane/methanol (10:0 to 9:1) to afford an ~4:1 mixture of tert-butyl 2-(4-((4-(2-ethoxy-2-oxoethyl)phenyl)amino)-6,7-dihydro-5H-cyclopenta[b]pyridin-2-yl)-1H-pyrrole-1-carboxylate as a brown oil (0.110 g, 55%). MW=461.55 $^1$H NMR (CDCl$_3$, 500 MHz) δ 7.30-7.22 (m, 3H), 7.16-7.13 (m, 2H), 6.93 (s, 1H), 6.30 (dd, J=3.0, 1.5 Hz, 1H), 6.16 (t, J=3.5 Hz, 1H), 5.67 (s, 1H), 4.15 (q, J=7.5 Hz, 2H), 3.58 (s, 2H), 3.03 (t, J=7.5 Hz, 2H), 2.82 (t, J=7.5 Hz, 2H), 2.18 (quin, J=7.5 Hz, 2H), 1.39 (s, 9H), 1.26 (t, J=7.5 Hz, 3H); ESI MS m/z 462 [M+H]$^+$, and ethyl 2-(4-((2-(1H-pyrrol-2-yl)-6,7-dihydro-5H-cyclopenta[b]pyridin-4-yl)amino)phenyl)acetate. MW=361.44. $^1$H NMR (CDCl$_3$, 500 MHz) δ 9.60 (br s, 1H), 7.30-7.27 (m, 2H), 7.18-7.14 (m, 2H), 7.10 (s, 1H), 6.84-6.81 (m, 1H), 6.51-6.48 (m, 1H), 6.23-6.20 (m, 1H), 5.67 (s, 1H), 4.18 (q, J=7.0 Hz, 2H), 3.61 (s, 2H), 2.98 (t, J=7.5 Hz, 2H), 2.78 (t, J=7.0 Hz, 2H), 2.17 (quin, J=7.5 Hz, 2H), 1.28 (t, J=7.0 Hz, 3H); ESI MS m/z 362 [M+H]$^+$.

EXAMPLE 133

2-(4-((2-(1H-Pyrrol-2-yl)-6,7-dihydro-5H-cyclopenta[b]pyridin-4-yl)amino)phenyl)acetamide hydrochloride

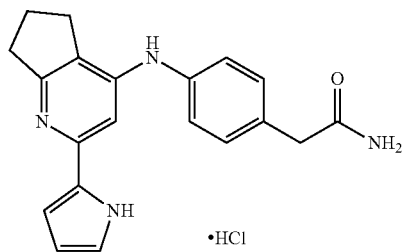 [SMILES: NC(=O)Cc1ccc(Nc2cc(-c3ccc[nH]3)nc3c2CCC3)cc1 ; Cl]

A 20-mL vial was charged with tert-butyl 2-(4-((4-(2-ethoxy-2-oxoethyl)phenyl)amino)-6,7-dihydro-5H-cyclopenta[b]pyridin-2-yl)-1H-pyrrole-1-carboxylate (0.110 g, 0.24 mmol, 1.0) and methanol (3 mL). To this solution was added NH$_3$ (6.8 mL, 7N in methanol, 476 mmol). The vial was sealed and the resulting mixture was stirred at 100° C. for 65 h. After this time, the crude reaction solution was concentrated under reduced pressure. The residue was adsorbed onto silica then purified by chromatography on silica using dichloromethane/(90:10:0.25 dichloromethane/methanol/aq. NH₄OH) (10:0 to 0:10) as eluent followed by preparative HPLC (water/acetonitrile with 0.05% TFA) to afford 2-(4-((2-(1H-pyrrol-2-yl)-6,7-dihydro-5H-cyclopenta[b]pyridin-4-yl)amino)phenyl)acetamide (0.030 g, 38%) as a brown solid. MW=332.40. $^1$H NMR (DMSO-$d_6$, 500 MHz) δ 11.16 (br s, 1H), 7.93 (br s, 1H), 7.42 (br s, 1H), 7.26-7.22 (m, 2H), 7.17-7.13 (m, 2H), 7.03 (s, 1H), 6.85 (s, 1H), 6.74-6.71 (m, 1H), 6.39 (s, 1H), 6.05-6.20 (m, 1H), 3.34 (s, 2H), 2.86 (t, J=7.5 Hz, 2H), 2.78 (t, J=7.5 Hz, 2H), 2.05 (quin, J=7.5 Hz, 2H). MS: ESI, m/z 333 [M+H]⁺. Treatment with 1.25M HCl in methanol afforded the title compound (0.035 g, 100%) as an off-white solid. MW=368.86. M.p. 163-165° C. $^1$H NMR (DMSO-$d_6$, 500 MHz) δ 13.43 (br s, 1H), 12.06 (br s, 1H), 9.46 (br s, 1H), 7.52 (br s, 1H), 7.40-7.36 (m, 2H), 7.32-7.28 (m, 2H), 7.12-7.09 (m, 1H), 7.08 (s, 1H), 7.06-7.03 (m, 1H), 6.92 (br s, 1H), 6.29-6.25 (m, 1H), 3.43 (s, 2H), 3.11 (t, J=7.5 Hz, 2H), 2.87 (t, J=7.5 Hz, 2H), 2.20 (quin, J=7.5 Hz, 2H); APCI MS m/z 333 [M+H]⁺.

EXAMPLE 134

2-(4-((2-(5-Chloropyridin-3-yl)-6,7-dihydro-5H-cyclopenta[b]pyridin-4-yl)amino)phenyl)acetamide hydrochloride

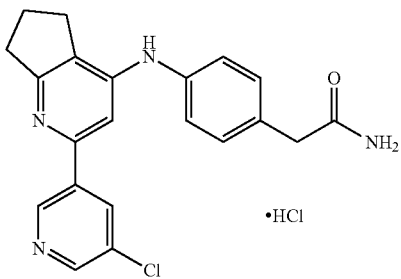

Step 1: Preparation of 4-chloro-2-(5-chloropyridin-3-yl)-6,7-dihydro-5H-cyclopenta[b]pyridine

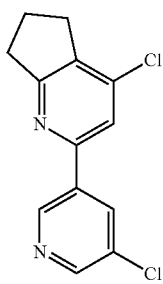 [SMILES: Clc1cncc(-c2cc(Cl)c3c(n2)CCC3)c1]

A 25-mL round bottom flask was charged with 2,4-dichloro-6,7-dihydro-5H-cyclopenta[b]pyridine (0.300 g, 1.59 mmol), 5-chloro3-pyridinyl boronic acid (0.301 g, 1.91 mmol), tetrakis(triphenylphosphine)palladium(0) (0.092 g, 0.08 mmol), and Cs₂CO₃ (1.56 g, 4.78 mmol). Toluene (8 ml), EtOH (2 ml) and water (4 ml) were added. The resulting mixture was stirred under Ar at 90° C. for 2.5 h. After this time, the mixture was cooled to rt, filtered through celite, and the filtrate concentrated under reduced pressure. The residue was purified by chromatography on silica using hexane/ethyl acetate (10:0 to 0:10) as eluent to afford the title compound (0.127 g, 30%) as a white solid. MW=265.14. $^1$H NMR (CDCl₃, 500 MHz) δ 8.99 (d, J=2.0 Hz, 1H), 8.59 (d, J=2.5 Hz, 1H), 8.30 (t, J=2.5 Hz, 1H), 7.50 (s, 1H), 3.15 (t, J=7.5 Hz, 2H), 3.05 (t, J=7.5 Hz, 2H), 2.21 (quin, J=7.5 Hz, 2H).

Step 2. Preparation of ethyl 2-(4-((2-(5-chloropyridin-3-yl)-6,7-dihydro-5H-cyclopenta[b]pyridin-4-yl)amino)phenyl)acetate hydrochloride

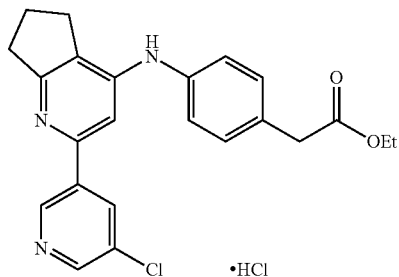 [SMILES: CCOC(=O)Cc1ccc(Nc2cc(-c3cncc(Cl)c3)nc3c2CCC3)cc1 ; Cl]

A 10-mL microwave vial was charged with 4-chloro-2-(5-chloropyridin-3-yl)-6,7-dihydro-5H-cyclopenta[b]pyridine (0.127 g, 0.48 mmol), 4-aminophenyl acetic acid ethyl ester (0.128 g, 0.72 mmol), palladium acetate (0.005 g, 0.024 mmol), rac-BINAP (0.022 g, 0.036 mmol) and cesium carbonate (0.390 g, 1.20 mmol) in dioxane (5 mL) under argon. The reaction mixture was absorbed onto silica (4 g) and purified by chromatography on silica using dichloromethane/methanol (10:0 to 9:1) as eluent to afford the free base of title compound (0.081 g). MW=407.89. $^1$H NMR (CDCl₃, 500 MHz) δ 8.86 (d, J=1.5 Hz, 1H), 8.52 (d, J=2.0 Hz, 1H), 8.22 (t, J=2.0 Hz, 1H), 7.34-7.30 (m, 2H), 7.20-7.16 (m, 3H), 4.18 (t, J=7.0 Hz, 2H), 3.62 (s, 2H), 3.09 (t, J=7.5 Hz, 2H), 2.85 (t, J=7.5 Hz, 2H), 2.23 (quin, J=7.5 Hz, 2H), 1.28 (t, J=7.5 Hz, 3H); ESI MS m/z 408 [M+H]⁺. Further purification by preparative HPLC (water/acetonitrile with 0.05% TFA) and treatment with 2M aqueous HCl afforded the title compound (0.074 g, 38%) as a yellow solid. MW=444.35. M.p. 235-237° C. $^1$H NMR (DMSO-$d_6$, 500 MHz) δ 14.21 (br s, 1H), 9.78 (br s, 1H), 8.90 (d, J=1.5 Hz, 1H), 8.83 (d, J=1.5 Hz, 1H), 8.41 (t, J=2.0 Hz, 1H), 7.39 (s, 4H), 7.15 (s, 1H), 4.09 (t, J=7.0 Hz, 2H), 3.72 (s, 2H), 3.16 (t, J=7.5 Hz, 2H), 2.94 (t, J=7.5 Hz, 2H), 2.25 (quin, J=7.5 Hz, 2H), 1.19 (t, J=7.0 Hz, 3H); APCI MS m/z 408 [M+H]⁺.

EXAMPLE 134

2-(4-((2-(5-Chloropyridin-3-yl)-6,7-dihydro-5H-cyclopenta[b]pyridin-4-yl)amino)phenyl)acetamide hydrochloride

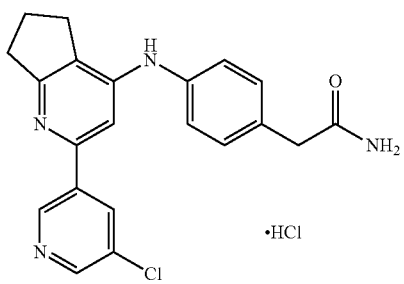 [SMILES: NC(=O)Cc1ccc(Nc2cc(-c3cncc(Cl)c3)nc3c2CCC3)cc1 ; Cl]

A 10-mL vial was charged with ethyl 2-(4-((2-(5-chloropyridin-3-yl)-6,7-dihydro-5H-cyclopenta[b]pyridin-4-yl)amino)phenyl)acetate (0.060 g, 0.13 mmol) and ammonium chloride (0.022 g, 0.40 mmol) in methanol (3 mL). To this mixture was added NH$_3$ (3.9 mL, 7N in methanol, 27.0 mmol). The vial was sealed and the resulting mixture was stirred at 100° C. for 72 h. After this time, the mixture was concentrated under reduced pressure and the residue purified by preparative HPLC (water/acetonitrile with 0.05% TFA) followed by chromatography on silica using dichloromethane/(90:10:0.25 dichloromethane/methanol/aqueous NH$_4$OH) (10:0 to 0:10) as eluent to afford 2-(4-((2-(5-chloropyridin-3-yl)-6,7-dihydro-5H-cyclopenta[b]pyridin-4-yl)amino)phenyl)acetamide (0.024 g, 48%) as a white solid. MW=378.85. $^1$H NMR (CD$_3$OD, 300 MHz) δ 8.77 (d, J=1.8 Hz, 1H), 8.52 (d, J=2.1 Hz, 1H), 8.20 (t, J=2.1 Hz, 1H), 7.36-7.30 (m, 2H), 7.27-7.21 (m, 2H), 7.15 (s, 1H), 3.52 (s, 2H), 3.00 (t, J=7.5 Hz, 2H), 2.88 (t, J=7.5 Hz, 2H), 2.19 (quin, J=7.5 Hz, 2H). MS: ESI, m/z 379 [M+H]$^+$. Treatment with 1.25 M HCl in methanol (0.25 mL, 0.31 mmol) afforded the title compound (0.026 g, 99%) as a yellow solid. MW=415.32. M.p. 193-195° C. $^1$H NMR (DMSO-d$_6$, 500 MHz) δ 14.32 (br s, 1H), 9.85 (br s, 1H), 8.91 (d, J=2.0 Hz, 1H), 8.83 (d, J=2.5 Hz, 1H), 8.43 (t, J=2.0 Hz, 1H), 7.51 (s, 1H), 7.40-7.32 (m, 4H), 7.14 (s, 1H), 6.91 (s, 1H), 3.42 (s, 2H), 3.17 (t, J=7.0 Hz, 2H), 2.95 (t, J=7.0 Hz, 2H), 2.25 (quin, J=7.5 Hz, 2H); ESI MS m/z 379 [M+H]$^+$.

EXAMPLE 135

2-(4-((2-(3-Hydroxycyclopentyl)-6,7-dihydro-5H-cyclopenta[b]pyridin-4-yl)amino)phenyl)acetamide: Diastereomer A

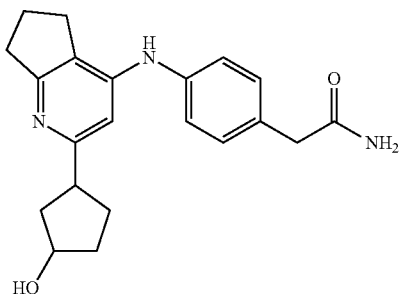 [SMILES: NC(=O)Cc1ccc(Nc2cc(C3CCC(O)C3)nc3c2CCC3)cc1]

Step 1. Preparation of 3-(4,4,5,5-tetramethyl-1,3,2-dioxaborolan-2-yl)cyclopent-2-enone

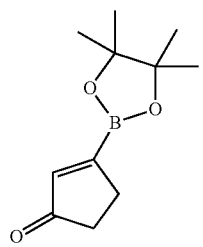

A 100-mL sealed tube was charged with 3-bromocyclopent-2-enone (2.00 g, 12.4 mmol), pinacol diborane (3.47 g, 13.7 mmol), Pd(dppf)Cl$_2$ (0.72 g, 0.88 mmol) and potassium acetate (2.43 g, 24.8 mmol) in dioxane (30 mL). The resulting mixture was heated at 100° C. under argon for 23 h. After this time, the reaction mixture was cooled, filtered through celite washing solids with ethyl acetate, then concentrated under reduced pressure. The residue was purified by chromatography on silica using hexanes/ethyl acetate (10:0 to 1:2) as eluent to afford the title compound (1.59 g, 61%) as a light yellow solid. MW=208.06. $^1$H NMR (CDCl$_3$, 500 MHz) δ 6.62 (t, J=2.0 Hz, 1H), 2.78-2.74 (m, 2H), 2.37-2.34 (m, 2H), 1.32 (s, 12H).

Step 2. Preparation of 3-(4-chloro-6,7-dihydro-5H-cyclopenta[b]pyridin-2-yl)cyclopent-2-enone

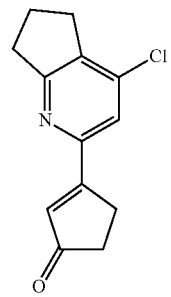 [SMILES: O=C1C=C(c2cc(Cl)c3c(n2)CCC3)CC1]

A 250-mL round bottomed flask was charged with 2,4-dichloro-6,7-dihydro-5H-cyclopenta[b]pyridine (1.05 g, 5.58 mmol), 3-(4,4,5,5-tetramethyl-1,3,2-dioxaborolan-2-yl)cyclopent-2-enone (1.27 g, 6.14 mmol), tetrakis(triphenylphosphine)palladium(0) (0.322 g, 0.28 mmol), and Cs$_2$CO$_3$ (5.45 g, 16.7 mmol). Toluene (30 ml), EtOH (7.5 ml) and water (15 ml) were added. The resulting mixture was stirred under argon at 90° C. for 18 h. After cooling to room temperature, the reaction mixture was diluted with ethyl acetate (150 mL), hexanes (50 mL) and water (25 mL). The aqueous layer was separated and extracted with ethyl acetate (2×100 mL). The combined organic extract was washed with saturated sodium chloride (2×20 mL), dried over sodium sulfate, filtered, and concentrated under reduced pressure. The residue was purified by chromatography on silica using hexane/ethyl acetate (10:0 to 0:10) as eluent to afford the title compound (0.305 g, 23%) as a yellow solid. MW=233.69. $^1$H NMR (CDCl$_3$, 500 MHz) δ 7.41 (s, 1H), 6.79 (t, J=2.0 Hz, 1H), 3.13 (t, J=7.5 Hz, 2H), 3.10-3.06 (m, 2H), 3.04 (t, J=7.5 Hz, 2H), 2.62-2.58 (m, 2H), 2.20 (quin, J=7.5 Hz, 2H).

Step 3. Preparation of 3-(4-chloro-6,7-dihydro-5H-cyclopenta[b]pyridin-2-yl)cyclopent-2-enol

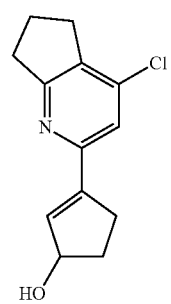 [SMILES: OC1C=C(c2cc(Cl)c3c(n2)CCC3)CC1]

A 25-mL round bottom flask was charged with 3-(4-chloro-6,7-dihydro-5H-cyclopenta[b]pyridin-2-yl)cyclopent-2-enone (0.434 g, 1.85 mmol) and THF (8 mL) at rt. Borane-dimethylsulfide complex (0.22 mL, 2.32 mmol) was added and the resulting solution was stirred at 55° C. for 4 h. After this time, the reaction was quenched with methanol, treated with 2N aqueous HCl (5 drops), and concentrated under reduced pressure. The residue was diluted with methanol and then concentrated under reduced pressure. The residue was then purified by chromatography on silica using hexanes/ethyl acetate (10:0 to 0:10) as the eluent to afford the title compound (0.123 g, 28%) as an off-white solid. MW=235.71. $^1$H NMR (CDCl$_3$, 500 MHz) δ 7.15 (s, 1H), 6.58 (q, J=2.0 Hz, 1H), 5.06-4.99 (m, 1H), 3.08 (t, J=7.5 Hz, 2H), 2.99 (t, J=7.5 Hz, 2H), 2.97-2.90 (m, 1H), 2.72-2.64 (m, 1H), 2.52-2.44 (m, 1H), 2.15 (quin, J=7.5 Hz, 2H), 1.93-1.85 (m, 1H).

Step 4. Ethyl 2-(4-((2-(3-hydroxycyclopent-1-en-1-yl)-6,7-dihydro-5H-cyclopenta[b]pyridin-4-yl)amino)phenyl)acetate

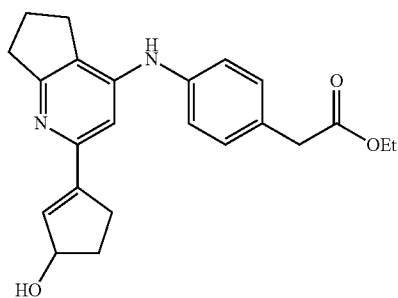 [SMILES: CCOC(=O)Cc1ccc(Nc2cc(C3=CC(O)CC3)nc3c2CCC3)cc1]

A 10-mL vial was charged with 3-(4-chloro-6,7-dihydro-5H-cyclopenta[b]pyridin-2-yl)cyclopent-2-enol (0.120 g, 0.51 mmol), 4-aminophenylacetic acid ethyl ester (0.096 g, 0.53 mmol), palladium acetate (0.006 g, 0.025 mmol), rac-BINAP (0.024 g, 0.038 mmol) and cesium carbonate (0.414 g, 1.27 mmol) in dioxane (6 mL) under argon. The reaction mixture was heated to 120° C. under microwave irradiation for 2 h. The reaction mixture was cooled, and diluted with ethyl acetate (75 mL) and water (5 mL). The organic layer was washed with saturated sodium chloride (2×5 mL), dried over sodium sulfate, filtered, and the filtrate concentrated under reduced pressure. The residue was purified by chromatography on silica using 80:20:1 dichloromethane/methanol/conc. NH$_4$OH as the eluent to afford the title compound (0.109 g, 56%) as an oil. MW=378.46. $^1$H NMR (CDCl$_3$, 500 MHz) δ 7.28 (d, J=8.0 Hz, 2H), 7.14 (d, J=8.0 Hz, 2H), 6.93 (s, 1H), 6.50 (d, J=1.5 Hz, 1H), 5.83 (s, 1H), 5.00-4.94 (m, 1H), 4.18 (q, J=7.0 Hz, 2H), 3.61 (s, 2H), 3.03 (t, J=7.5 Hz, 2H), 2.90-2.82 (m, 1H), 2.79 (t, J=7.5 Hz, 2H), 2.66-2.58 (m, 1H), 2.46-2.37 (m, 1H), 2.20-2.11 (m, 3H), 1.87-1.80 (m, 1H), 1.28 (t, J=7.0 Hz, 3H). ESI m/z 379 [M+H]$^+$.

Step 5. Preparation of ethyl 2-(4-((2-(3-hydroxycyclopentyl)-6,7-dihydro-5H-cyclopenta[b]pyridin-4-yl)amino)phenyl)acetate

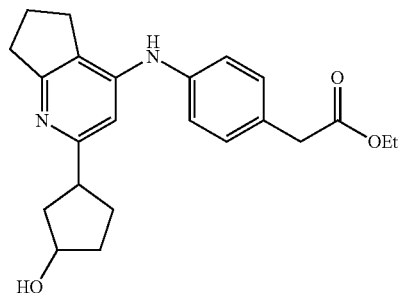 [SMILES: CCOC(=O)Cc1ccc(Nc2cc(C3CCC(O)C3)nc3c2CCC3)cc1]

A 250-mL round bottom flask was charged with ethyl 2-(4-((2-(3-hydroxycyclopent-1-en-1-yl)-6,7-dihydro-5H-cyclopenta[b]pyridin-4-yl)amino)phenyl)acetate (0.109 g, 0.29 mmol) and 10% palladium on carbon (0.028 g) in 1:1 ethyl acetate/ethanol (12 mL). This mixture was vigorously stirred under H$_2$ (1 atm) for 4 h. After this time, the mixture was filtered through celite and the filtrate concentrated under reduced pressure. The residue was purified by preparative HPLC (water/acetonitrile with 0.05% TFA) to afford two diastereomers of the title compound:

Diastereomer A: (0.022 g, 20%). MW=380.48. $^1$H NMR (CDCl$_3$, 500 MHz) δ 7.31-7.27 (m, 2H), 7.17-7.13 (m, 2H), 6.66 (s, 1H), 5.88 (s, 1H), 4.31 (t, J=4.0 Hz, 1H), 4.18 (q, J=7.0 Hz, 2H), 3.61 (s, 2H), 3.25-3.18 (m, 1H), 2.96 (t, J=7.5 Hz, 2H), 2.74 (t, J=7.5 Hz, 2H), 2.19-2.10 (m, 3H), 2.09-2.01 (m, 1H), 1.95-1.78 (m, 3H), 1.73-1.64 (m, 1H), 1.28 (t, J=7.5 Hz, 3H). MS: ESI+, m/z 381 [M+H]$^+$.

Diastereomer B: (0.056 g, 40%). MW=380.48. $^1$H NMR (CDCl$_3$, 500 MHz) δ 7.29-7.26 (m, 2H), 7.15-7.11 (m, 2H), 6.71 (s, 1H), 5.79 (s, 1H), 4.52-4.47 (m, 1H), 4.18 (q, J=7.0 Hz, 2H), 3.61 (s, 2H), 3.44-3.35 (m, 1H), 3.01 (t, J=7.5 Hz, 2H), 2.75 (t, J=7.5 Hz, 2H), 2.22-2.10 (m, 4H), 2.05-1.98 (m, 2H), 1.94-1.74 (m, 2H), 1.73-1.61 (m, 1H), 1.28 (t, J=7.5 Hz, 3H); ESI MS m/z 381 [M+H]$^+$.

EXAMPLE 136

2-(4-((2-(3-Hydroxycyclopentyl)-6,7-dihydro-5H-cyclopenta[b]pyridin-4-yl)amino)phenyl)acetamide (Diastereomer A)

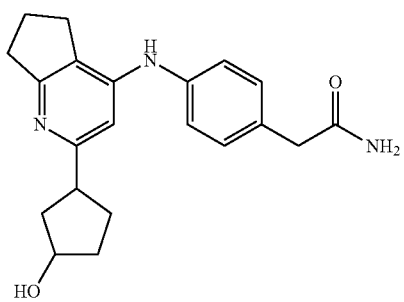 [SMILES: NC(=O)Cc1ccc(Nc2cc(C3CCC(O)C3)nc3c2CCC3)cc1]

A 10-mL vial was charged with ethyl 2-(4-((2-(3-hydroxycyclopentyl)-6,7-dihydro-5H-cyclopenta[b]pyridin-4-yl)amino)phenyl)acetate (diastereomer A, 0.022 g, 0.058 mmol), methanol (2 mL) and ammonia (1.7 mL, 7N in methanol, 11.5 mmol). The vial was sealed and the resulting mixture was stirred at 100° C. for 23 h. After this time, LCMS analysis of the cooled reaction showed ~88% conversion. Additional ammonia (1.0 mL, 7N in methanol, 7.0 mmol) was added and the mixture was heated at 100° C. for 2 h. Then, the cooled reaction mixture was concentrated under reduced pressure. The residue was absorbed on silica (2 g) and purified by chromatography on silica using dichloromethane/(80:20:1 dichloromethane/methanol/conc. NH$_4$OH) (10:0 to 0:10) as eluent to afford the title compound (0.005 g, 25%) as a light brown solid. MW=351.44 $^1$H NMR (DMSO-d$_6$, 500 MHz) δ 7.86 (s, 1H), 7.41 (s, 1H), 7.23-7.19 (m, 2H), 7.12-7.08 (m, 2H), 6.84 (br s, 1H), 6.60 (s, 1H), 4.39 (d, J=4.0 Hz, 1H), 4.25-4.20 (m, 1H), 3.33 (s, 2H), 3.18 (quin, J=6.5 Hz, 1H), 2.78 (t, J=7.5 Hz, 2H), 2.73 (t, J=7.5 Hz, 2H), 2.05-1.88 (m, 4H), 1.83-1.72 (m, 2H), 1.67-1.56 (m, 1H), 1.53-1.45 (m, 1H); APCI m/z 352 [M+H]$^+$.

EXAMPLE 137

2-(4-((2-(3-Hydroxycyclopentyl)-6,7-dihydro-5H-cyclopenta[b]pyridin-4-yl)amino)phenyl)acetamide (Diastereomer B)

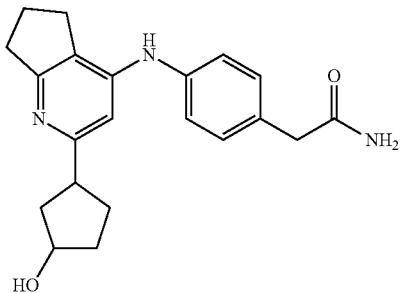 [SMILES: NC(=O)Cc1ccc(Nc2cc(C3CCC(O)C3)nc3c2CCC3)cc1]

A 10-mL vial was charged with ethyl 2-(4-((2-(3-hydroxycyclopentyl)-6,7-dihydro-5H-cyclopenta[b]pyridin-4-yl)amino)phenyl)acetate (Diastereomer B, 0.056 g, 0.147 mmol), methanol (3 mL) and ammonia (4.2 mL, 7N in methanol, 29.4 mmol). The vial was sealed and the resulting mixture was stirred at 100° C. for 23 h. LCMS analysis of the cooled reaction showed ~66% conversion. Additional ammonia (1.0 mL, 7N in methanol, 7.0 mmol) was added and the mixture was heated at 100° C. for 2 h. The cooled reaction mixture solution was concentrated under reduced pressure. The residue was absorbed on silica (4 g) then purified by chromatography on silica using dichloromethane/(80:20:1 dichloromethane/methanol/conc. NH$_4$OH) (10:0 to 0:10) as the eluent to afford the title compound (0.034 g, 67%) as an off-white solid. MW=351.44. M.p. 93-95° C. $^1$H NMR (DMSO-d$_6$, 500 MHz) δ 7.95 (s, 1H), 7.42 (s, 1H), 7.24-7.20 (m, 2H), 7.13-7.09 (m, 2H), 6.85 (br s, 1H), 6.64 (s, 1H), 5.60 (br s, 1H), 4.13-4.07 (m, 1H), 3.33 (s, 2H), 3.03 (quin, J=7.7 Hz, 1H), 2.78 (t, J=7.5 Hz, 2H), 2.74 (t, J=7.0 Hz, 2H), 2.09-1.98 (m, 3H), 1.95-1.86 (m, 1H), 1.77-1.56 (m, 4H). MS: APCI, m/z 352 [M+H]$^+$.

EXAMPLE 138

2-(4-((2-(3-Cyanocyclopentyl)-6,7-dihydro-5H-cyclopenta[b]pyridin-4-yl)amino)phenyl)acetamide hydrochloride

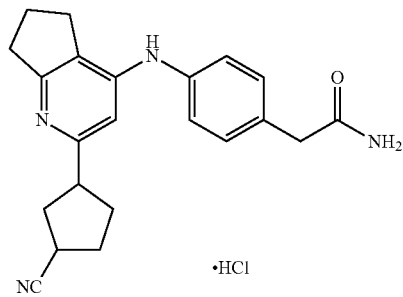 [SMILES: N#CC1CCC(c2cc(Nc3ccc(CC(N)=O)cc3)c3c(n2)CCC3)C1 ; Cl]

A 25-mL round bottom flask was charged with 2-(4-((2-(3-hydroxycyclopentyl)-6,7-dihydro-5H-cyclopenta[b]pyridin-4-yl)amino)phenyl)acetamide (Diastereomer B, 0.030 g, 0.085 mmol) and triphenylphosphine (0.112 g, 0.43 mmol) and acetone cyanohydrin (0.039 mL, 0.43 mmol) in THF. To this stirred solution at 0° C. was added di-tert-butyl azodicarboxylate (0.098 g, 0.43 mmol). After stirring for 24 h, the reaction mixture was absorbed onto silica (2 g) and was purified by chromatography on silica using dichloromethane/methanol (10:0 to 9:1) as the eluent to afford 2-(4-((2-(3-cyanocyclopentyl)-6,7-dihydro-5H-cyclopenta[b]pyridin-4-yl)amino)phenyl)acetamide (Diastereomer A: 0.021 g, 68%) as a colorless oil. MW=360.45. $^1$H NMR (CD$_3$OD, 300 MHz) δ 7.34-7.28 (m, 2H), 7.20-7.14 (m, 2H), 6.69 (s, 1H), 3.50 (s, 2H), 3.28-3.10 (m, 2H), 2.93 (t, J=7.5 Hz, 2H), 2.81 (t, J=7.5 Hz, 2H), 2.23-2.08 (m, 6H), 2.00-1.86 (m, 1H), 1.83-1.67 (m, 1H); ESI MS m/z 361 [M+H]$^+$. Treatment with 1.25M HCl in methanol (0.093 mL, 0.115 mmol) afforded the title compound (Diastereomer A: 0.020 g, 89%) as a white solid. MW=396.91. M.p. 215-217° C. decomp. $^1$H NMR (DMSO-d$_6$, 500 MHz) δ 13.74 (br s, 1H), 9.47 (br s, 1H), 7.50 (s, 1H), 7.37-7.31 (m, 2H), 7.27-7.20 (m, 2H), 6.90 (s, 1H), 6.72 (s, 1H), 3.40 (s, 2H), 3.03 (br s, 2H), 2.82 (t, J=7.5 Hz, 2H), 2.32-2.05 (m, 7H), 1.89-1.80 (m, 1H), 1.77-1.65 (m, 1H); APCI MS m/z 361 [M+H]$^+$.

EXAMPLE 139

2-(4-((2-(3-Chlorophenyl)-6-cyclopropylpyridin-4-yl)amino)phenyl)acetamide hydrochloride

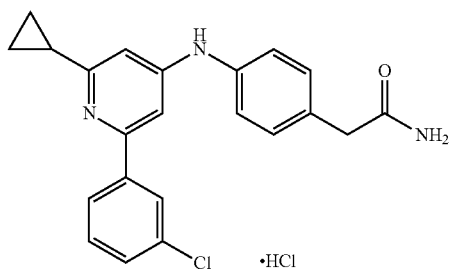 [SMILES: NC(=O)Cc1ccc(Nc2cc(-c3cccc(Cl)c3)nc(C3CC3)c2)cc1 ; Cl]

Step 1. Preparation of 2,4-dichloro-6-cyclopropylpyridine

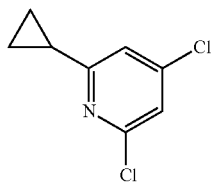 [SMILES: Clc1cc(Cl)nc(C2CC2)c1]

A 250-mL round bottomed flask was charged with 2,4,6-trichloropyridine (2.50 g, 13.7 mmol), cyclopropylboronic acid (1.29 g, 15.1 mmol), palladium acetate (0.307 g, 1.37 mmol), tricyclhexylphosphine (0.768 g, 2.74 mmol) and K₃PO₄ (10.2 g, 47.9 mmol). Toluene (75 ml) and water (4 ml) were added. The resulting mixture was stirred under Ar at 90° C. for 24 h. After cooling to room temperature, the reaction mixture was diluted with water (50 mL) and dichloromethane (50 mL). The mixture was filtered through celite washing solids with dichloromethane. The aqueous layer was separated and extracted with dichloromethane (3×50 mL). The combined organic extract was washed with saturated sodium chloride (25 mL) then dried over sodium sulfate, filtered, and concentrated under reduced pressure. The residue was purified by chromatography on silica using hexane/dichloromethane (100:0 to 0:100) as eluent to afford an approximate 1:2 mixture of trichloropyridine and 2,4-dichloro-6-cyclopropylpyridine (1.09 g, 42%) as a colorless oil. MW=188.05. ¹H NMR (CDCl₃, 500 MHz) δ 7.08 (d, J=2.0 Hz, 1H), 7.05 (d, J=2.0 Hz, 1H), 2.00-1.93 (m, 1H), 1.09-1.00 (m, 4H). This was used without further manipulation.

Step 2. Preparation of 4-chloro-2-(3-chlorophenyl)-6-cyclopropylpyridine

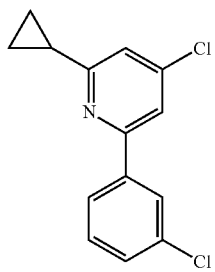 [SMILES: Clc1cccc(-c2cc(Cl)cc(C3CC3)n2)c1]

A 250-mL round bottomed flask was charged with 2,4-dichloro-6-cyclopropylpyridine (1.08 g, 5.74 mmol), (3-chlorophenyl)boronic acid (0.99 g, 6.32 mmol), tetrakis(triphenylphosphine)palladium(0) (0.332 g, 0.28 mmol), and Cs₂CO₃ (5.61 g, 17.2 mmol). Toluene (40 ml), EtOH (10 ml) and water (20 ml) were added. The resulting mixture was stirred under Ar at 90° C. for 23 h. After cooling to room temperature, the reaction mixture was diluted with water (50 mL) and dichloromethane (50 mL). The mixture was filtered through celite washing solids with dichloromethane. The aqueous layer was separated and extracted with dichloromethane (2×50 mL). The combined organic extract was washed with saturated sodium chloride (25 mL) then dried over sodium sulfate, filtered, and concentrated under reduced pressure. The residue was purified by chromatography on silica using hexane/dichloromethane (100:0 to 0:100) as eluent to afford the title compound (0.30 g, 20%) as a colorless oil. MW=264.15. ¹H NMR (CDCl₃, 500 MHz) δ 7.98-7.96 (m, 1H), 7.85-7.80 (m, 1H), 7.45 (d, J=1.5 Hz, 1H), 7.39-7.35 (m, 2H), 7.12 (d, J=1.5 Hz, 1H), 2.18-2.01 (m, 1H), 1.18-1.12 (m, 2H), 1.06-1.00 (m, 2H).

Step 3. Preparation of ethyl 2-(4-((2-(3-chlorophenyl)-6-cyclopropylpyridin-4-yl)amino)phenyl)acetate

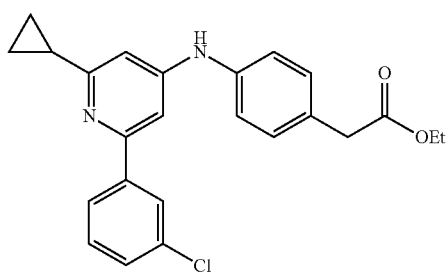 [SMILES: CCOC(=O)Cc1ccc(Nc2cc(-c3cccc(Cl)c3)nc(C3CC3)c2)cc1]

A 10-mL microwave vial was charged with 4-chloro-2-(3-chlorophenyl)-6-cyclopropylpyridine (0.300 g, 1.14 mmol), 4-aminophenyl acetic acid ethyl ester (0.203 g, 1.14 mmol), palladium acetate (0.013 g, 0.057 mmol), rac-BINAP (0.053 g, 0.085 mmol) and cesium carbonate (0.925 g, 2.84 mmol) in dioxane (6 mL) under argon. The reaction mixture was heated to 120° C. under microwave irradiation for 2 h. After this time, the reaction mixture was cooled, diluted with ethyl acetate (25 mL) and water (25 mL). The aqueous layer was extracted with ethyl acetate (25 mL). The combined extract was washed with saturated sodium chloride (2×5 mL), dried over anhydrous sodium sulfate, filtered, and the filtrate was concentrated under reduced pressure. The residue was purified by chromatography on silica using hexanes/ethyl acetate (10:0 to 0:10) to afford the title compound (0.152 g, 33%) as a colorless oil. MW=406.90. ¹H NMR (CDCl₃, 500 MHz) δ 7.94-7.92 (m, 1H), 7.80-7.76 (m, 1H), 7.34-7.31 (m, 2H), 7.31-7.27 (m, 2H), 7.18-7.15 (m, 2H), 6.66 (d, J=2.5 Hz, 1H), 5.96 (s, 1H), 4.18 (q, J=7.5 Hz, 2H), 3.61 (s, 2H), 1.99-1.92 (m, 1H), 1.28 (t, J=7.0 Hz, 3H), 1.13-1.08 (m, 2H), 0.96-0.91 (m, 2H); ESI MS m/z 407 [M+H]⁺.

EXAMPLE 139

2-(4-((2-(3-Chlorophenyl)-6-cyclopropylpyridin-4-yl)amino)phenyl)acetamide hydrochloride

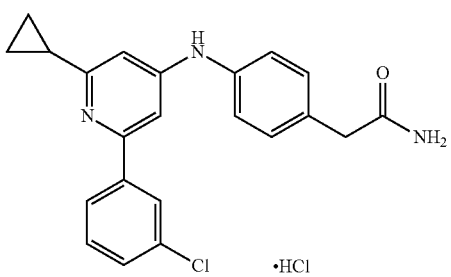 [SMILES: NC(=O)Cc1ccc(Nc2cc(-c3cccc(Cl)c3)nc(C3CC3)c2)cc1 ; Cl]

A 20-mL vial was charged with ethyl 2-(4-((2-(3-chlorophenyl)-6-cyclopropylpyridin-4-yl)amino)phenyl)acetate (0.090 g, 0.23 mmol), dioxane (1 mL) and methanol (3 mL). To this solution was added NH$_3$ (6.0 mL, 7N in methanol, 42.0 mmol). The vial was sealed and the resulting mixture was stirred at 100° C. for 47 h. The crude reaction mixture was concentrated under reduced pressure. The residue was adsorbed onto silica then purified by chromatography on silica using hexanes/ethyl acetate (10:0 to 0:10) as eluent followed by chromatography on silica using dichloromethane/methanol (10:0 to 9:1) as eluent to afford 2-(4-((2-(3-chlorophenyl)-6-cyclopropylpyridin-4-yl)amino)phenyl)acetamide (0.024 g, 27%) as a colorless oil. MW=377.87. $^1$H NMR (CDCl$_3$, 500 MHz) δ 7.94-7.91 (m, 1H), 7.81-7.76 (m, 1H), 7.36-7.31 (m, 2H), 7.30-7.26 (m, 2H), 7.21-7.17 (m, 2H), 7.01 (d, J=2.0 Hz, 1H), 6.68 (d, J=2.5 Hz, 1H), 6.02 (s, 1H), 5.45 (br s, 2H), 3.58 (s, 2H), 1.99-1.93 (m, 1H), 1.13-1.08 (m, 2H), 0.97-0.92 (m, 2H); ESI MS m/z 378 [M+H]$^+$. Treatment with 1.25M HCl (0.103 mL, 0.130 mol) in methanol afforded the title compound (0.022 g, 84%) as an off-white solid. MW=414.33. M.p. 104-106° C. $^1$H NMR (DMSO-d$_6$, 500 MHz) δ 13.48 (br s, 1H), 8.78 (br s, 1H), 7.92 (d, J=1.0 Hz, 1H), 7.84-7.76 (m, 1H), 7.52 (br s, 2H), 7.45 (s, 1H), 7.30-7.25 (m, 2H), 7.25-7.16 (m, 2H), 7.11 (s, 1H), 6.87 (s, 1H), 6.74 (s, 1H), 3.36 (s, 2H), 2.15-2.02 (m, 1H), 1.10-0.90 (m, 4H); ESI MS m/z 378 [M+H]$^+$.

EXAMPLE 140

2-(4-((2-(3-Chlorophenyl)-6-cyclopropylpyridin-4-yl)amino)phenyl)ethanol hydrochloride

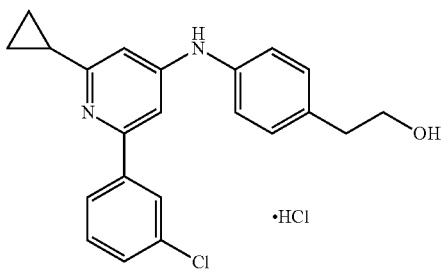 [SMILES: OCCc1ccc(Nc2cc(-c3cccc(Cl)c3)nc(C3CC3)c2)cc1 ; Cl]

A 25-mL round bottom flask was charged with ethyl 2-(4-((2-(3-chlorophenyl)-6-cyclopropylpyridin-4-yl)amino)phenyl)acetate (0.152 g, 0.37 mmol) and THF (6 mL) at rt. Borane-dimethylsulfide complex (0.106 mL, 1.12 mmol) was added and the resulting solution was stirred at 50° C. for 2.5 h until the starting material was consumed (monitored by LCMS analysis). The reaction was quenched with methanol then treated with 2N aqueous HCl (5 drops) and concentrated under reduced pressure. The residue was diluted with methanol and then concentrated under reduced pressure. The residue was treated with saturated sodium bicarbonate (0.1 mL) and then purified by column chromatography on silica using hexanes/ethyl acetate (10:0 to 0:10) as the eluent to afford 2-(4-((2-(3-chlorophenyl)-6-cyclopropylpyridin-4-yl)amino)phenyl)ethanol (0.107 g, 78%) as a colorless oil. MW=364.87. $^1$H NMR (CDCl$_3$, 500 MHz) δ 7.94-7.92 (m, 1H), 7.81-7.76 (m, 1H), 7.35-7.30 (m, 2H), 7.27-7.23 (m, 2H), 7.18-7.14 (m, 2H), 6.99 (d, J=2.0 Hz, 1H), 6.65 (d, J=2.0 Hz, 1H), 5.94 (s, 1H), 3.90 (q, J=6.0 Hz, 2H), 2.88 (t, J=1.5 Hz, 2H), 1.99-1.92 (m, 1H), 1.40 (t, J=2.0 Hz, 1H), 1.12-1.07 (m, 2H), 0.96-0.90 (m, 2H); ESI MS m/z 365 [M+H]$^+$. Treatment with 1.25M HCl in methanol (0.70 mL, 0.88 mmol) afforded the title compound (0.105 g, 90%) as a light yellow solid. MW=401.33. M.p. 125-128° C. $^1$H NMR (DMSO-d$_6$, 500 MHz) δ 13.57 (br s, 1H), 10.50 (br s, 1H), 7.95-7.93 (m, 1H), 7.77-7.73 (m, 1H), 7.72-7.66 (m, 1H), 7.65-7.59 (m, 1H), 7.34-7.29 (m, 2H), 7.28-7.24 (m, 2H), 7.07 (s, 1H), 6.58 (br s, 1H), 3.63 (t, J=7.0 Hz, 2H), 2.74 (t, J=7.0 Hz, 2H), 2.40-2.29 (m, 1H), 1.22 (s, 2H), 1.05-0.96 (m, 2H); APCI MS m/z 365 [M+H]$^+$.

EXAMPLE 141 and EXAMPLE 142

Methyl 2-(4-((2-(3-chlorophenyl)-6-(trifluoromethyl)pyridin-4-yl)methyl)phenyl)acetate and 2-(4-((2-(3-chlorophenyl)-6-(trifluoromethyl)pyridin-4-yl)methyl)phenyl)acetic acid

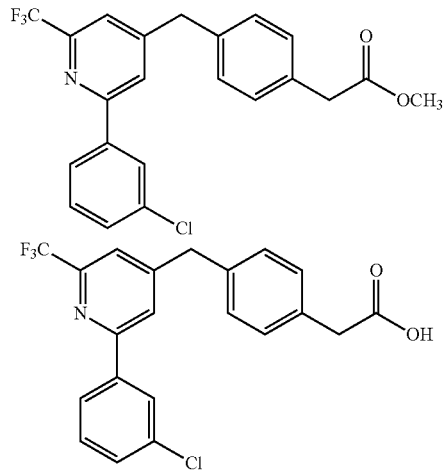

Step 1. Preparation of 4-chloro-2-(3-chlorophenyl)-6-(trifluoromethyl)pyridine

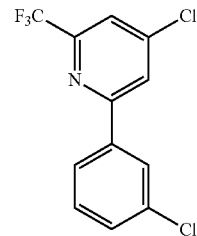 [SMILES: FC(F)(F)c1cc(Cl)cc(-c2cccc(Cl)c2)n1]

A 500-mL round bottomed flask was charged with 2,4-dichloro-6-trifluoromethylpyridine (2.00 g, 9.26 mmol), (3-chlorophenyl)boronic acid (1.59 g, 10.2 mmol), tetrakis(triphenylphosphine)palladium(0) (0.535 g, 0.46 mmol), and Cs$_2$CO$_3$ (9.05 g, 27.8 mmol). Toluene (40 ml), EtOH (10 ml) and water (20 ml) were added. The resulting mixture was stirred under Ar at 90° C. for 4 h. After cooling to room temperature, the reaction mixture was diluted with ethyl acetate (100 mL) and hexanes (100 mL). The aqueous layer was separated and the organic layer was washed with saturated sodium chloride (2×25 mL), dried over sodium sulfate, filtered, and concentrated under reduced pressure. The residue was purified by chromatography on silica using hexane/ethyl acetate (100:1 to 95:5) as eluent followed by chromatography on silica using hexane/dichloromethane (100:0 to 80:20) as eluent to afford the title compound (1.48 g, 55%) as a white solid. MW=292.08. $^1$H NMR (CDCl$_3$, 500 MHz) δ 8.06-8.04 (m, 1H), 7.92 (dt, J=7.0, 2.0 Hz, 1H), 7.89 (d, J=1.5 Hz, 1H), 7.64 (d, J=1.5 Hz, 1H), 7.48-7.42 (m, 2H).

EXAMPLE 141 AND EXAMPLE 142

Methyl 2-(4-((2-(3-chlorophenyl)-6-(trifluoromethyl)pyridin-4-yl)methyl)phenyl)acetate and 2-(4-((2-(3-chlorophenyl)-6-(trifluoromethyl)pyridin-4-yl)methyl)phenyl)acetic acid

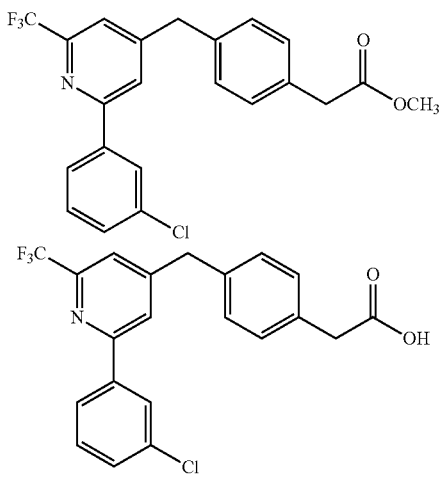

A 20-mL sealed tube, with stirrer bar, was charged with 4-chloro-2-(3-chlorophenyl)-6-(trifluoromethyl)pyridine (0.263 g, 0.90 mol), methyl 2-(4-((4,4,5,5-tetramethyl-1,3,2-dioxaborolan-2-yl)methyl)phenyl)acetate (0.261 g, 0.90 mmol), Pd(dppf)Cl$_2$ (0.073 g, 0.09 mmol), and powdered Na$_2$CO$_3$ (0.286 g, 2.70 mmol). Dioxane (8 mL) and water (4 mL) were added. The resulting mixture was stirred under Ar at 90° C. for 27 h. until the starting chloride was consumed. After cooling to room temperature, the reaction mixture was absorbed onto silica and purified by chromatography on silica using dichloromethane/methanol (10:0 to 9:1) as eluent to afford methyl 2-(4-((2-(3-chlorophenyl)-6-(trifluoromethyl)pyridin-4-yl)methyl)phenyl)acetate

EXAMPLE 141

(0.018 g, 4%) as a light brown solid. MW=419.82. M.p. 72-74° C. $^1$H NMR (CDCl$_3$, 500 MHz) δ 8.03-8.00 (m, 1H), 7.91-7.86 (m, 1H), 7.68 (s, 1H), 7.46-7.44 (m, 1H), 7.42-7.37 (m, 2H), 7.29-7.26 (m, 2H), 7.18-7.15 (m, 2H), 4.09 (s, 2H), 3.70 (s, 3H), 3.62 (s, 2H); APCI MS m/z 420 [M+H]$^+$.

EXAMPLE 142

(0.396 g). Prep HPLC of sample (0.055 g) afforded 2-(4-((2-(3-chlorophenyl)-6-(trifluoromethyl)pyridin-4-yl)methyl)phenyl)acetic acid (0.027 g, 7%) as a white solid. MW=405.80. M.p. 124-126° C. $^1$H NMR (CDCl$_3$, 500 MHz) δ 8.03-8.00 (m, 1H), 7.91-7.85 (m, 1H), 7.68 (s, 1H), 7.46-7.44 (m, 1H), 7.42-7.37 (m, 2H), 7.30-7.26 (m, 2H), 7.19-7.15 (m, 2H), 4.09 (s, 2H), 3.65 (s, 2H); APCI MS m/z 406 [M+H]$^+$.

EXAMPLE 143

2-(4-((2-(3-Chlorophenyl)-6-(trifluoromethyl)pyridin-4-yl)methyl)phenyl)ethanol

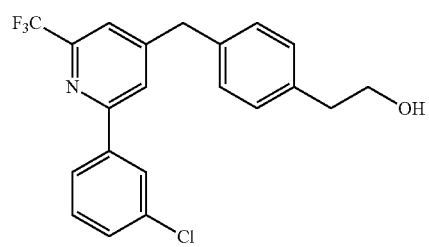

A 50-mL round bottom flask was charged with methyl 2-(4-((2-(3-chlorophenyl)-6-(trifluoromethyl)pyridin-4-yl)methyl)phenyl)acetate (0.165 g, 0.40 mmol) and THF (10 mL) at rt. Borane-dimethylsulfide complex (0.154 mL, 1.62 mmol) was added and the resulting solution was stirred at 55° C. for 3 h. After this time, the reaction was quenched with methanol then treated with 2N aqueous HCl (5 drops), and concentrated under reduced pressure. The residue was diluted with methanol and then concentrated under reduced pressure. The residue was purified by column chromatography on silica using hexanes/ethyl acetate (10:0 to 1:1) as the eluent followed by column chromatography on silica using hexanes/dichloromethane (10:0 to 0:10) as the eluent to afford the title compound (0.064 g, 18%) as a colorless gum. MW=391.81. $^1$H NMR (DMSO-d$_6$, 500 MHz) δ 8.33 (s, 1H), 8.17-8.15 (m, 1H), 8.11-8.06 (m, 1H), 7.77 (d, J=0.5 Hz, 1H), 7.60-7.54 (m, 2H), 7.28 (d, J=8.0 Hz, 2H), 7.16 (d, J=8.0 Hz, 2H), 4.58 (t, J=5.0 Hz, 1H), 4.12 (s, 2H), 3.59-3.54 (m, 2H), 2.67 (t, J=5.0 Hz, 2H); APCI MS m/z 392 [M+H]$^+$.

EXAMPLE 144

2-(4-((2-(3-Chlorophenyl)-6-(trifluoromethyl)pyridin-4-yl)methyl)phenyl)acetamide

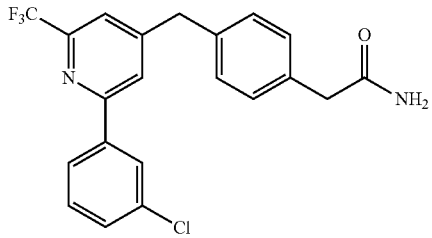

An 100-mL round bottom flask was charged with 2-(4-((2-(3-chlorophenyl)-6-(trifluoromethyl)pyridin-4-yl)methyl)phenyl)acetic acid (0.17 g, 0.42 mmol) in dichloromethane (10 ml). To this solution at 0° C. was added oxalyl chloride (0.18 mL, 2.10 mmol) followed by DMF (1 drop). After stirring for 5 h the volatile material was removed under reduced pressure to afford crude acid chloride. The residue was dissolved in dichloromethane (10 mL), cooled to 0° C., and 7N ammonia in methanol (10.0 mL, 70 mmol) was added. After stirring for 0.5 h, the volatile material was removed under reduced pressure. The residue was purified by chromatography on silica using hexanes/ethyl acetate (10:0 to 0:10) as eluent followed by chromatography on silica using dichloromethane/methanol (10:0 to 9:1) as eluent to afford the title compound (0.079 g, 21%) as an off-white solid. MW=404.81. M.p. 148-160° C. $^1$H NMR (DMSO-d$_6$, 500 MHz) δ 8.33 (s, 1H), 8.17-8.15 (m, 1H), 8.11-8.05 (m, 1H), 7.76 (d, J=0.5 Hz, 1H), 7.60-7.55 (m, 2H), 7.41 (br s, 1H), 7.31 (d, J=8.0 Hz, 2H), 7.21 (d, J=8.0 Hz, 2H), 6.82 (br s, 1H), 4.11 (s, 2H), 3.32 (s, 2H); APCI MS m/z 405 [M+H]$^+$.

EXAMPLE 145

2-(4-((2-(3-Chlorophenyl)-6-(trifluoromethyl)pyridin-4-yl)amino)phenyl)acetamide

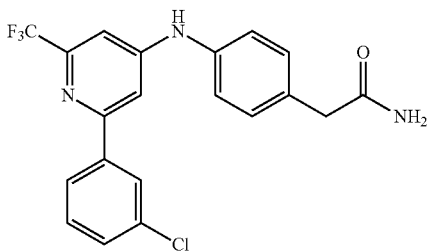 [SMILES: NC(=O)Cc1ccc(Nc2cc(-c3cccc(Cl)c3)nc(C(F)(F)F)c2)cc1]

Step 1. Preparation of ethyl 2-(4-((2-(3-chlorophenyl)-6-(trifluoromethyl)pyridin-4-yl)amino)phenyl) acetate

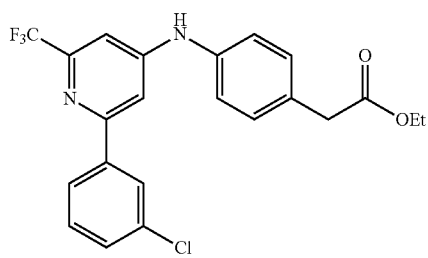 [SMILES: CCOC(=O)Cc1ccc(Nc2cc(-c3cccc(Cl)c3)nc(C(F)(F)F)c2)cc1]

A 10-mL microwave vial was charged with 4-chloro-2-(3-chlorophenyl)-6-(trifluoromethyl)pyridine (0.150 g, 0.51 mmol), 4-aminophenyl acetic acid ethyl ester (0.138 g, 0.77 mmol), palladium acetate (0.006 g, 0.026 mmol), rac-BINAP (0.024 g, 0.038 mmol) and cesium carbonate (0.418 g, 1.28 mmol) in dioxane (5 mL) under argon. The reaction mixture was heated to 120° C. under microwave irradiation for 2 h. After this time, the reaction mixture was cooled and absorbed onto silica (4 g). Purification by chromatography on silica using hexanes/ethyl acetate (10:0 to 0:10) as eluent followed by preparative HPLC (water/acetonitrile with 0.05% TFA) afforded the title compound (0.064 g, 28%) as a tacky solid. MW=434.84. $^1$H NMR (CDCl$_3$, 300 MHz) δ 9.39 (s, 1H), 8.00-7.97 (m, 1H), 7.93-7.86 (m, 1H), 7.57-7.52 (m, 3H), 7.35-7.25 (m, 4H), 7.21 (d, J=3.0 Hz, 1H), 4.09 (q, J=7.2 Hz, 2H), 3.67 (s, 3H), 1.20 (t, J=7.2 Hz, 3H); ESI MS ink 435 [M+H]$^+$.

EXAMPLE 145

2-(4-((2-(3-Chlorophenyl)-6-(trifluoromethyl)pyridin-4-yl)amino)phenyl)acetamide

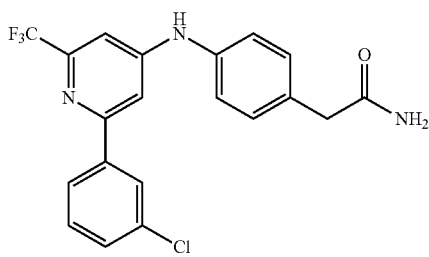 [SMILES: NC(=O)Cc1ccc(Nc2cc(-c3cccc(Cl)c3)nc(C(F)(F)F)c2)cc1]

A 10-mL vial was charged with ethyl 2-(4-((2-(3-chlorophenyl)-6-(trifluoromethyl)pyridin-4-yl)amino)phenyl)acetate (0.064 g, 0.15 mmol) and ammonium chloride (0.024 g, 0.44 mmol) in methanol (2 mL). To this mixture was added NH$_3$ (4.2 mL, 7N in methanol, 29.4 mmol). The vial was sealed and the resulting mixture was stirred at 100° C. for 42 h. After this time, the crude reaction solution concentrated under reduced pressure. The residue absorbed on silica (2 g) then purified by chromatography on silica using dichloromethane/methanol (10:0 to 9:1) as eluent to afford the title compound (0.027 g, 46%) as a light brown solid. MW=405.80. M.p. 97-99° C. $^1$H NMR (DMSO-d$_6$, 500 MHz) δ 9.39 (s, 1H), 7.99-7.97 (m, 1H), 7.91-7.86 (m, 1H), 7.57-7.51 (m, 3H), 7.46 (br s, 1H), 7.33-7.29 (m, 2H), 7.27-7.23 (m, 2H), 7.19 (d, J=2.0 Hz, 1H), 6.88 (br s, 1H), 3.37 (s, 2H); APCI MS m/z 406 [M+H]$^+$.

EXAMPLE 146

2-(4-((2-(3-Chlorophenyl)-6-(trifluoromethyl)pyridin-4-yl)amino)phenyl)ethanol

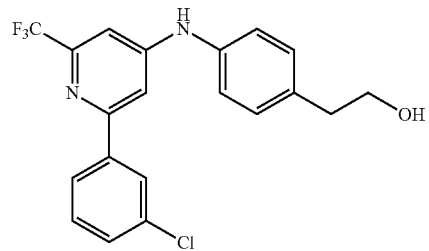 [SMILES: OCCc1ccc(Nc2cc(-c3cccc(Cl)c3)nc(C(F)(F)F)c2)cc1]

A 10-mL microwave vial was charged with 4-chloro-2-(3-chlorophenyl)-6-(trifluoromethyl)pyridine (0.140 g, 0.48 mmol), 4-aminophenethyl alcohol (0.099 g, 0.72 mmol), palladium acetate (0.005 g, 0.024 mmol), rac-BINAP (0.022 g, 0.036 mmol) and cesium carbonate (0.390 g, 1.20 mmol) in dioxane (5 mL) under argon. The reaction mixture was heated to 120° C. under microwave irradiation for 2 h. The reaction mixture was cooled, and absorbed onto silica (5 g). Purification by chromatography on silica using hexanes/ethyl acetate (10:0 to 0:10) as eluent followed by preparative HPLC (water/acetonitrile with 0.05% TFA) afforded the title compound (0.093 g, 50%) as a pale yellow solid. MW=392.80. M.p. 60-62° C. $^1$H NMR (DMSO-d$_6$, 500 MHz) δ 9.30 (s, 1H), 7.99-7.96 (m, 1H), 7.91-7.86 (m, 1H), 7.57-7.51 (m, 2H), 7.50 (d, J=2.0 Hz, 1H), 7.30-7.26 (m, 2H), 7.24-7.20 (m, 2H), 7.18 (d, J=2.0 Hz, 1H), 4.64 (t, J=5.0 Hz, 1H), 3.67-3.58 (m, 2H), 2.73 (t, J=7.0 Hz, 2H); ESI MS m/z 393 [M+H]$^+$.

EXAMPLE 147

3-(4-((2-(3-Chlorophenyl)-6-(trifluoromethyl)pyridin-4-yl)amino)phenyl)propan-1-ol

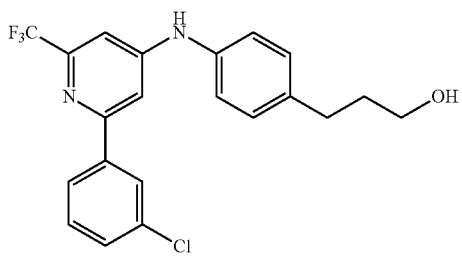 [SMILES: OCCCc1ccc(Nc2cc(-c3cccc(Cl)c3)nc(C(F)(F)F)c2)cc1]

A 10-mL microwave vial was charged with 4-chloro-2-(3-chlorophenyl)-6-(trifluoromethyl)pyridine (0.120 g, 0.41 mmol), 4-aminophenpropyl alcohol (0.093 g, 0.61 mmol), palladium acetate (0.005 g, 0.021 mmol), rac-BINAP (0.019 g, 0.031 mmol) and cesium carbonate (0.335 g, 1.02 mmol) in dioxane (5 mL) under argon. The reaction mixture was heated to 120° C. under microwave irradiation for 4 h. After this time, the reaction mixture was cooled and diluted with water (5 mL) and ethyl acetate (100 mL). The organic layer was washed with saturated sodium chloride (2×5 mL), dried over sodium sulfate, filtered, and the filtrate concentrated under reduced pressure. The residue was purified by chromatography on silica using hexanes/ethyl acetate (10:0 to 0:10) as eluent to afford the title compound (0.024 g, 15%) as an off-white solid. MW=406.83. M.p. 46-48° C. $^1$H NMR (DMSO-d$_6$, 500 MHz) δ 9.28 (s, 1H), 7.98-7.96 (m, 1H), 7.91-7.86 (m, 1H), 7.56-7.51 (m, 2H), 7.49 (d, J=2.0 Hz, 1H), 7.26 (d, J=8.5 Hz, 2H), 7.22 (d, J=8.5 Hz, 2H), 7.17 (d, J=2.0 Hz, 1H), 4.46 (t, J=5.0 Hz, 1H), 3.43 (q, J=6.0 Hz, 2H), 2.62 (t, J=7.5 Hz, 2H), 1.77-1.59 (m, 2H); APCI MS m/z 407 [M+H]$^+$.

EXAMPLE 148

2-(4-((2-(4-chlorophenyl)-6,7-dihydro-5H-cyclopenta[b]pyridin-4-yl)amino)phenyl)acetamide hydrochloride

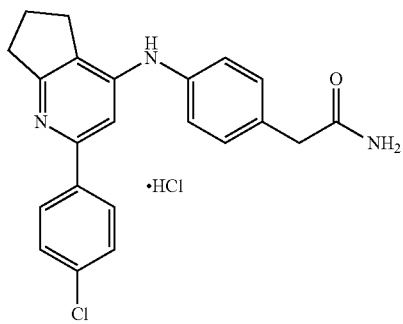 [SMILES: NC(=O)Cc1ccc(Nc2cc(-c3ccc(Cl)cc3)nc3c2CCC3)cc1 ; Cl]

Step 1. Preparation of 4-chloro-2-(4-chlorophenyl)-6,7-dihydro-5H-cyclopenta[b]pyridine

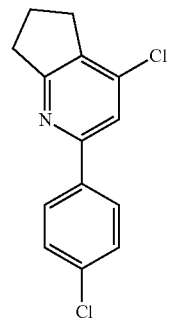 [SMILES: Clc1ccc(-c2cc(Cl)c3c(n2)CCC3)cc1]

Following General Procedure F, 2,4-dichloro-6,7-dihydro-5H-cyclopenta[b]pyridine (0.350 g, 1.86 mmol) was reacted with (4-chlorophenyl)boronic acid (0.378 g, 2.42 mmol) to afford the title compound (0.355 g, 78%). MW=264.15. $^1$H NMR (CD$_3$OD, 300 MHz) δ 7.96-7.83 (m, 2H), 7.61 (d, J=4.6 Hz, 1H), 7.51-7.39 (m, 2H), 3.13-2.99 (m, 4H), 2.25-2.14 (m, 2H); APCI MS m/z 264 [M+H]$^+$.

Step 2. Preparation of ethyl 2-(4-((2-(4-chlorophenyl)-6,7-dihydro-5H-cyclopenta[b]pyridin-4-yl)amino)phenyl)acetate

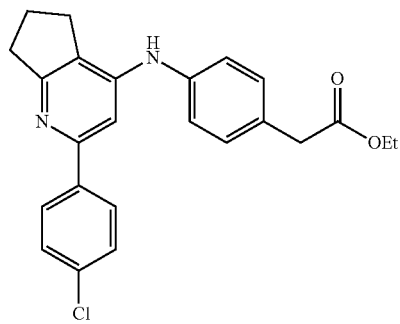 [SMILES: CCOC(=O)Cc1ccc(Nc2cc(-c3ccc(Cl)cc3)nc3c2CCC3)cc1]

Following General Procedure B2, 4-chloro-2-(4-chlorophenyl)-6,7-dihydro-5H-cyclopenta[b]pyridine (0.100 g, 0.38 mmol) was reacted with 4-aminophenylacetic acid ethyl ester (0.102 g, 0.57 mmol) to afford the title compound (0.075 g, 38%) as a yellow oil. MW=406.90. APCI MS m/z 407 [M+H]$^+$.

EXAMPLE 148

2-(4-((2-(4-Chlorophenyl)-6,7-dihydro-5H-cyclopenta[b]pyridin-4-yl)amino)phenyl)acetamide hydrochloride

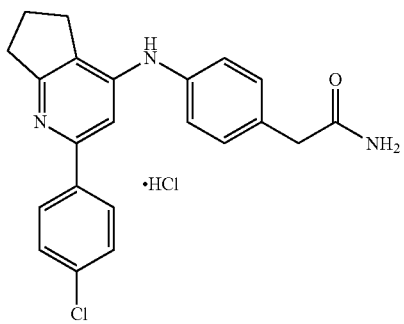 [SMILES: NC(=O)Cc1ccc(Nc2cc(-c3ccc(Cl)cc3)nc3c2CCC3)cc1 ; Cl]

Following General Procedure C, ethyl 2-(4-((2-(4-chlorophenyl)-6,7-dihydro-5H-cyclopenta[b]pyridine-4-yl)amino)phenyl)acetate (0.075 g, 0.18 mmol) was reacted with ammonia in methanol (7 M, 4 mL), followed by the formation of the hydrochloride salt to form the title compound (0.017 g, 22%) as an off-white solid. MW=414.33. $^1$H NMR (DMSO-$d_6$, 300 MHz) δ 14.03 (s, 1H), 9.80 (s, 1H), 7.83-7.75 (m, 2H), 7.70-7.63 (m, 2H), 7.54 (s, 1H), 7.42-7.30 (m, 4H), 6.98 (s, 1H), 6.94 (s, 1H), 3.42 (s, 2H), 3.16 (t, J=7.6 Hz, 2H), 2.92 (t, J=7.6 Hz, 2H), 2.31-2.18 (m, 2H); APCI MS m/z 378 [M+H]$^+$.

EXAMPLE 149

2-(4-((2-(4-Chlorophenyl)-6,7-dihydro-5H-cyclopenta[b]pyridin-4-yl)amino)phenyl)ethanol hydrochloride

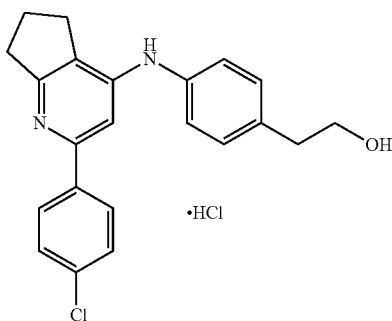 [SMILES: OCCc1ccc(Nc2cc(-c3ccc(Cl)cc3)nc3c2CCC3)cc1 ; Cl]

Following General Procedure B2, ethyl 2-(4-((2-(4-chlorophenyl)-6,7-dihydro-5H-cyclopenta[b]pyridine-4-yl)amino)phenyl)acetate (0.100 g, 0.38 mmol) was reacted with 4-aminophenethyl alcohol (0.078 g, 0.57 mmol) followed by the formation of the hydrochloride salt to afford the title compound (0.030 g, 30%) as a yellow solid. MW=401.33. $^1$H NMR (DMSO-$d_6$, 300 MHz) δ 13.99 (s, 1H), 9.77 (s, 1H), 7.82-7.73 (m, 2H), 7.70-7.62 (m, 2H), 7.39-7.27 (m, 4H), 6.95 (s, 1H), 3.64 (t, J=6.8 Hz, 2H), 3.15 (t, J=7.7 Hz, 2H), 2.91 (t, J=7.6 Hz, 2H), 2.76 (t, J=7.6 Hz, 2H), 2.30-2.15 (m, 2H); APCI MS m/z 365 [M+H]$^+$.

EXAMPLE 150

2-(4-((2-(3-Chloro-4-fluorophenyl)-6,7-dihydro-5H-cyclopenta[b]pyridin-4-yl)amino)phenyl)acetamide hydrochloride

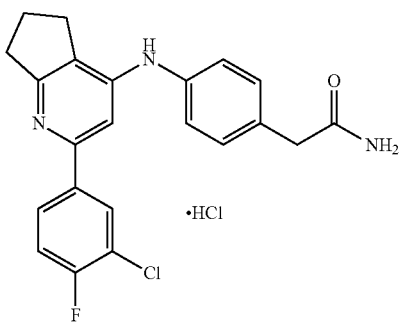 [SMILES: NC(=O)Cc1ccc(Nc2cc(-c3ccc(F)c(Cl)c3)nc3c2CCC3)cc1 ; Cl]

Step 1. Preparation of 4-chloro-2-(3-chloro-4-fluorophenyl)-6,7-dihydro-5H-cyclopenta[b]pyridine

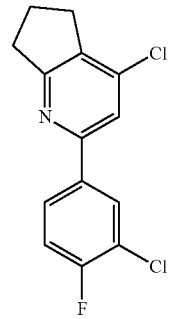 [SMILES: Fc1ccc(-c2cc(Cl)c3c(n2)CCC3)cc1Cl]

Following General Procedure F, 2,4-dichloro-6,7-dihydro-5H-cyclopenta[b]pyridine (0.300 g, 1.60 mmol) in toluene/ethanol/water (6 mL:3 mL:1 mL) was reacted with (3-chloro-4-fluorophenyl)boronic acid (0.362 g, 2.07 mmol) to afford the title compound (0.289 g, 96%) as a white solid. MW=282.14. $^1$H NMR (CD$_3$OD, 300 MHz) δ 8.15-8.07 (m, 1H), 7.94-7.86 (m, 1H), 7.66 (s, 1H), 7.33 (t, J=8.8 Hz, 1H), 3.12 (t, J=7.6 Hz, 2H), 3.04 (t, J=7.6 Hz, 2H), 2.21 (quin, J=7.6 Hz, 2H); APCI MS m/z 282 [M+H]$^+$.

Step 2. Preparation of ethyl 2-(4-((2-(3-chloro-4-fluorophenyl)-6,7-dihydro-5H-cyclopenta[b]pyridin-4-yl)amino)phenyl)acetate

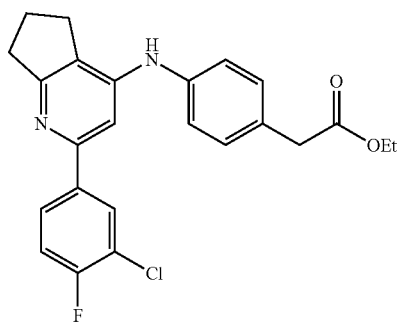 [SMILES: CCOC(=O)Cc1ccc(Nc2cc(-c3ccc(F)c(Cl)c3)nc3c2CCC3)cc1]

Following General Procedure B2, 4-chloro-2-(3-chloro4-fluorophenyl)-6,7-dihydro-5H-cyclopenta[b]pyridine (0.100 g, 0.35 mmol) was reacted with 4-aminophenylacetic acid ethyl ester (0.095 g, 0.53 mmol) to afford the title compound (0.142 g, 71%). MW=424.90. $^1$H NMR (CD$_3$OD, 300 MHz) δ 7.91-7.84 (m, 1H), 7.70-7.60 (m, 1H), 7.49-7.39 (m, 3H), 7.39-7.32 (m, 2H), 6.98 (s, 1H), 4.16 (q, J=7.1 Hz, 2H), 3.71 (s, 2H), 3.33-3.29 (m, 2H), 3.21 (t, J=7.6 Hz, 2H), 3.00 (t, J=7.6 Hz, 2H), 2.37 (quin, J=7.6 Hz, 3H); APCI MS m/z 425 [M+H]$^+$.

EXAMPLE 150

2-(4-((2-(3-Chloro-4-fluorophenyl)-6,7-dihydro-5H-cyclopenta[b]pyridin-4-yl)amino)phenyl)acetamide hydrochloride

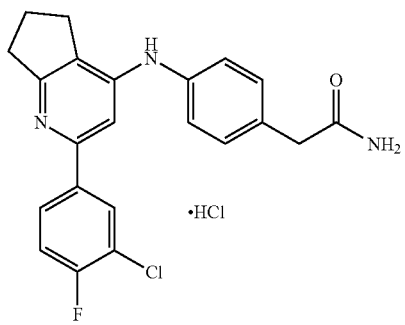 [SMILES: NC(=O)Cc1ccc(Nc2cc(-c3ccc(F)c(Cl)c3)nc3c2CCC3)cc1 ; Cl]

Following General Procedure C, ethyl 2-(4-((2-(3-chloro-4-fluorophenyl)-6,7-dihydro-5H-cyclopenta[b]pyridine-4-yl)amino)phenyl)acetate (0.075 g, 0.18 mmol) was reacted with ammonia in methanol (7 M, 4 mL), followed by the formation of the hydrochloride salt to afford the title compound (0.028 g, 37%) as a brown solid. MW=432.32. $^1$H NMR (DMSO-$d_6$, 300 MHz) δ 14.06 (s, 1H), 9.80 (s, 1H), 8.14-8.07 (m, 1H), 7.82-7.74 (m, 1H), 7.65 (t, J=8.9 Hz, 1H), 7.54 (s, 1H), 7.41-7.32 (m, 4H), 7.01 (s, 1H), 6.94 (s, 1H), 3.42 (s, 2H), 3.15 (t, J=7.6 Hz, 2H), 2.93 (t, J=7.6 Hz, 2H), 2.33-2.17 (m, 2H); APCI MS m/z 396 [M+H]$^+$.

EXAMPLE 151

2-(4-((2-(3-Chloro-4-fluorophenyl)-6,7-dihydro-5H-cyclopenta[b]pyridin-4-yl)amino)phenyl)ethanol hydrochloride

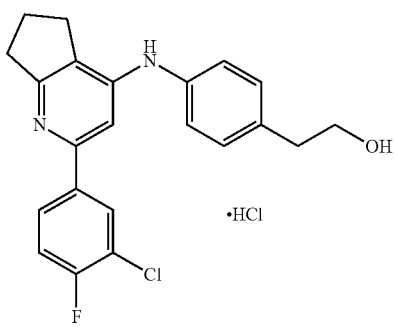 [SMILES: OCCc1ccc(Nc2cc(-c3ccc(F)c(Cl)c3)nc3c2CCC3)cc1 ; Cl]

Following General Procedure B2, ethyl 2-(4-((2-(3-chloro-4-fluorophenyl)-6,7-dihydro-5H-cyclopenta[b]pyridine-4-yl)amino)phenyl)acetate (0.110 g, 0.39 mmol) was reacted with 4-aminophenethyl alcohol (0.080 g, 0.58 mmol), followed by the formation of the hydrochloride salt to afford the title compound (0.011 g, 15%) as an off-white solid. MW=405.29. $^1$H NMR (DMSO-$d_6$, 300 MHz) δ 14.04 (s, 1H), 9.74 (s, 1H), 8.18-8.01 (m, 1H), 7.81-7.72 (m, 1H), 7.64 (t, J=8.9 Hz, 1H), 7.38-7.27 (m, 4H), 6.99 (s, 1H), 3.64 (t, J=6.8 Hz, 2H), 3.14 (t, J=7.6 Hz, 2H), 2.92 (t, J=7.6 Hz, 2H), 2.76 (t, J=6.8 Hz, 2H) 2.31-2.16 (m, 2H), 1.24 (s, 1H); APCI MS m/z 383 [M+H]$^+$.

EXAMPLE 152

2-(4-((2-(3-Chloro-5-fluorophenyl)-6,7-dihydro-5H-cyclopenta[b]pyridin-4-yl)amino)phenyl)acetamide hydrochloride

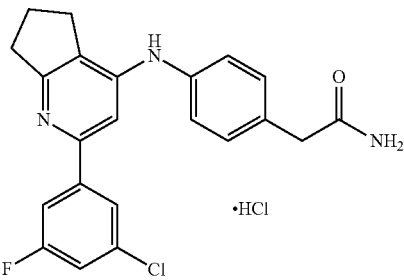 [SMILES: NC(=O)Cc1ccc(Nc2cc(-c3cc(F)cc(Cl)c3)nc3c2CCC3)cc1 ; Cl]

Step 1. Preparation of 4-chloro-2-(3-chloro-5-fluorophenyl)-6,7-dihydro-5H-cyclopenta[b]pyridine

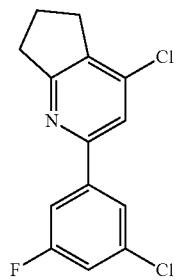

Following General Procedure F, 2,4-dichloro-6,7-dihydro-5H-cyclopenta[b]pyridine (0.250 g, 1.33 mmol) was reacted with (3-chloro-5-fluorophenyl)boronic acid (0.301 g, 2.07 mmol), to afford the title compound (0.224 g, 90%) as a white solid. MW=282.14. $^1$H NMR (CD$_3$OD, 300 MHz) δ 7.87-7.84 (m, 1H), 7.72-7.65 (m, 2H), 7.30-7.21 (m, 1H), 3.17-3.00 (m, 4H), 2.21 (quin, J=7.6 Hz, 2H); APCI MS m/z 282 [M+H]$^+$.

Step 2. Preparation of ethyl 2-(4-((2-(3-chloro-5-fluorophenyl)-6,7-dihydro-5H-cyclopenta[b]pyridin-4-yl)amino)phenyl)acetate

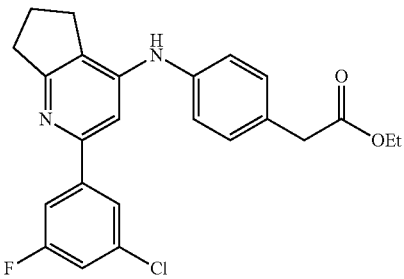 [SMILES: CCOC(=O)Cc1ccc(Nc2cc(-c3cc(F)cc(Cl)c3)nc3c2CCC3)cc1]

Following General Procedure B2, 4-chloro-2-(3-chloro-5-fluorophenyl)-6,7-dihydro-5H-cyclopenta[b]pyridine (0.100 g, 0.36 mmol) was reacted with 4-aminophenylacetic acid ethyl ester (0.096 g, 0.53 mmol) to afford the title compound (0.086 g, 87%) as a yellow oil. MW=424.90. $^1$H NMR (CD$_3$OD, 300 MHz) δ 7.54 (s, 1H), 7.43-7.34 (m, 1H), 7.31 (s, 1H), 7.28 (s, 1H), 7.25-7.13 (m, 3H), 7.10-7.06 (m, 1H), 5.48 (s, 1H), 4.21-4.07 (m, 2H), 3.69 (s, 2H), 2.98 (t, J=7.6 Hz, 2H), 2.86 (t, J=7.6 Hz, 2H), 2.17 (quin, J=7.6, 2H), 1.37-1.17 (m, 3H); APCI MS m/z 425 [M+H]$^+$.

EXAMPLE 152

2-(4-((2-(4-Chlorophenyl)-6,7-dihydro-5H-cyclopenta[b]pyridin-4-yl)amino)phenyl)acetamide hydrochloride

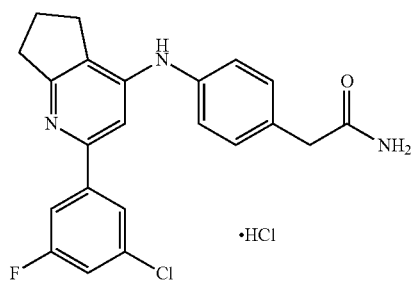 [SMILES: NC(=O)Cc1ccc(Nc2cc(-c3cc(F)cc(Cl)c3)nc3c2CCC3)cc1 ; Cl]

Following General Procedure C, ethyl 2-(4-((2-(3-chloro-5-fluorophenyl)-6,7-dihydro-5H-cyclopenta[b]pyridine-4-yl)amino)phenyl)acetate (0.086 g, 0.20 mmol) was reacted with ammonia in methanol (7 M, 4 mL), followed by the formation of the hydrochloride salt to afford the title compound (0.024 g, 29%) as a yellow solid. MW=432.32. $^1$H NMR (DMSO-d$_6$, 300 MHz) δ 14.19 (s, 1H), 9.79 (s, 1H), 7.82-7.77 (m, 1H), 7.77-7.67 (m, 2H), 7.54 (s, 1H), 7.36 (s, 4H), 7.08 (s, 1H), 6.93 (s, 1H), 3.42 (s, 2H), 3.15 (t, J=7.6 Hz, 2H), 2.93 (t, J=7.6 Hz, 2H), 2.31-2.16 (m, 2H); APCI MS m/z 396 [M+H]$^+$.

EXAMPLE 153

2-(4-((2-(3-Chloro-5-fluorophenyl)-6,7-dihydro-5H-cyclopenta[b]pyridin-4-yl)amino)phenyl)ethanol hydrochloride

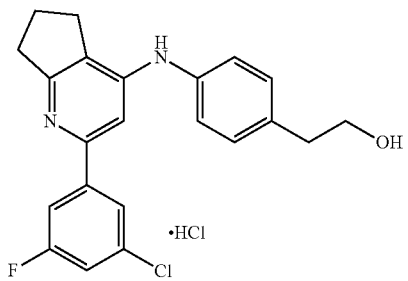 [SMILES: OCCc1ccc(Nc2cc(-c3cc(F)cc(Cl)c3)nc3c2CCC3)cc1 ; Cl]

Following General Procedure B2, ethyl 2-(4-((2-(3-chloro-5-fluorophenyl)-6,7-dihydro-5H-cyclopenta[b]pyridine-4-yl)amino)phenyl)acetate (0.075 g, 0.27 mmol) was reacted with 4-aminophenethyl alcohol (0.055 g, 0.40 mmol), followed by the formation of the hydrochloride salt to afford the title compound (0.017 g, 23%) as a yellow solid. MW=419.32. $^1$H NMR (DMSO-d$_6$, 300 MHz) δ 14.06 (s, 1H), 9.77 (s, 1H), 7.79-7.76 (m, 1H), 7.75-7.72 (m, 1H), 7.71-7.68 (m, 1H), 7.33 (s, 4H), 7.05 (s, 1H), 3.64 (t, J=6.9 Hz, 3H), 3.15 (t, J=7.6 Hz, 2H), 2.92 (t, J=7.6 Hz, 2H), 2.76 (t, J=6.9 Hz, 2H), 2.30-2.17 (m, 2H); APCI MS m/z 383 [M+H]$^+$.

EXAMPLE 154

2-(4-((2-(3,4-Dichlorophenyl)-6,7-dihydro-5H-cyclopenta[b]pyridin-4-yl)amino)phenyl)ethanol hydrochloride

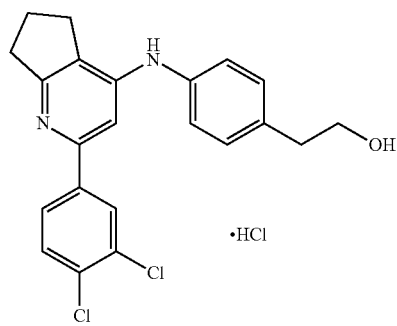 [SMILES: OCCc1ccc(Nc2cc(-c3ccc(Cl)c(Cl)c3)nc3c2CCC3)cc1 ; Cl]

Step 1. Preparation of 4-chloro-2-(3,4-dichlorophenyl)-6,7-dihydro-5H-cyclopenta[b]pyridine

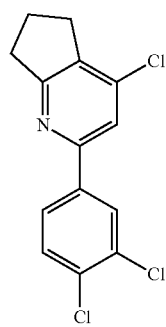 [SMILES: Clc1ccc(-c2cc(Cl)c3c(n2)CCC3)cc1Cl]

Following General Procedure F, 2,4-dichloro-6,7-dihydro-5H-cyclopenta[b]pyridine (0.150 g, 0.80 mmol) was reacted with (3,4-dichlorophenyl)boronic acid (0.198 g, 1.04 mmol) to afford the title compound (0.141 g, 94%). MW=298.59. $^1$H NMR (CD$_3$OD, 300 MHz) δ 8.16 (d, J=2.1 Hz, 1H), 7.90-7.84 (m, 1H), 7.69 (s, 1H), 7.61 (d, J=8.5 Hz, 1H), 3.12 (t, J=7.6 Hz, 2H), 3.05 (t, J=7.6 Hz, 2H), 2.21 (quin, J=7.6 Hz, 2H); APCI MS m/z 297 [M+H]$^+$.

EXAMPLE 154

2-(4-((2-(3,4-Dichlorophenyl)-6,7-dihydro-5H-cyclopenta[b]pyridin-4-yl)amino)phenyl)ethanol hydrochloride

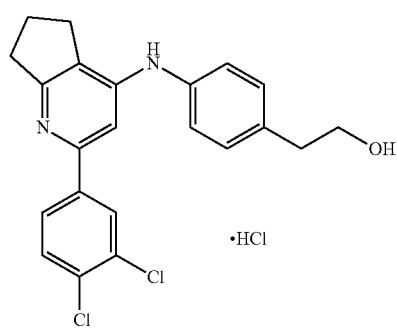 [SMILES: OCCc1ccc(Nc2cc(-c3ccc(Cl)c(Cl)c3)nc3c2CCC3)cc1 ; Cl]

Following General Procedure B2, ethyl 2-(4-((2-(3,4-dichlorophenyl)-6,7-dihydro-5H-cyclopenta[b]pyridine-4-yl)amino)phenyl)acetate (0.075 g, 0.25 mmol) was reacted with 4-aminophenethyl alcohol (0.052 g, 0.38 mmol), followed by the formation of the hydrochloride salt to afford the title compound (0.018 g, 25%) as an off-white solid. MW=435.77. $^1$H NMR (DMSO-$d_6$, 500 MHz) δ 14.40 (s, 1H), 9.77 (s, 1H), 8.15 (d, J=2.2 Hz, 1H), 7.82 (d, J=8.5 Hz, 1H), 7.77-7.73 (m, 1H), 7.32 (s, 4H), 7.04 (s, 1H), 4.67 (s, 1H), 3.63 (t, J=7.0 Hz, 2H), 3.14 (t, J=7.6 Hz, 2H), 2.91 (t, J=7.6 Hz, 2H), 2.76 (t, J=7.6 Hz, 2H), 2.26-2.14 (m, 2H); APCI MS m/z 399 [M+H]$^+$.

EXAMPLE 155

2-(4-((2-(2,5-Dichlorophenyl)-6,7-dihydro-5H-cyclopenta[b]pyridin-4-yl)amino)phenyl)acetamide hydrochloride

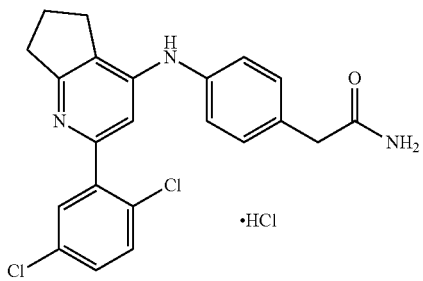 [SMILES: NC(=O)Cc1ccc(Nc2cc(-c3cc(Cl)ccc3Cl)nc3c2CCC3)cc1 ; Cl]

Step 1. Preparation of 4-chloro-2-(2,5-dichlorophenyl)-6,7-dihydro-5H-cyclopenta[b]pyridine hydrochloride

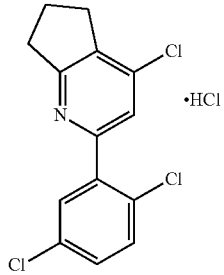 [SMILES: Clc1ccc(Cl)c(-c2cc(Cl)c3c(n2)CCC3)c1 ; Cl]

Following General Procedure F, 2,4-dichloro-6,7-dihydro-5H-cyclopenta[b]pyridine (0.300 g, 1.60 mmol) was reacted with (2,5-dichlorophenyl)boronic acid (0.396 g, 2.07 mmol), followed by the formation of the hydrochloride salt to afford the title compound (0.285 g, 95% yield) as a white solid. MW=335.06. $^1$H NMR (CDCl$_3$, 300 MHz) δ 13.09 (s, 1H), 7.56 (d, J=2.4 Hz, 1H), 7.45-7.37 (m, 2H), 7.33-7.29 (m, 1H), 3.16 (t, J=7.6 Hz, 2H), 3.06 (t, J=7.6 Hz, 2H), 2.21 (quin, J=7.6 Hz, 2H); APCI MS m/z 297 [M+H]$^+$.

EXAMPLE 155

2-(4-((2-(2,5-Dichlorophenyl)-6,7-dihydro-5H-cyclopenta[b]pyridin-4-yl)amino)phenyl)acetamide hydrochloride

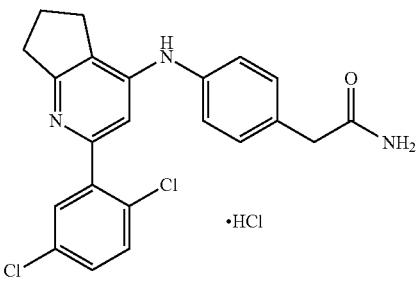 [SMILES: NC(=O)Cc1ccc(Nc2cc(-c3cc(Cl)ccc3Cl)nc3c2CCC3)cc1 ; Cl]

Following General Procedure A1, 4-chloro-2-(2,5-dichlorophenyl)-6,7-dihydro-5H-cyclopenta[b]pyridine hydrochloride (0.100 g, 0.33 mmol) was reacted with 2-(4-aminophenyl)acetamide (0.060 g, 0.40 mmol), followed by the formation of the hydrochloride salt to afford the title compound (0.009 g, 10%) as a tan solid. MW=448.77. $^1$H NMR (DMSO-$d_6$, 500 MHz) δ 14.18 (s, 1H), 10.16 (s, 1H), 7.79 (s, 1H), 7.71-7.64 (m, 2H), 7.50 (d, J=8.5 Hz, 1H), 7.42 (d, J=8.5 Hz, 1H), 7.31 (d, J=8.0 Hz, 1H), 7.16 (d, J=8.5 Hz, 1H), 6.91 (s, 1H), 3.66 (s, 2H), 3.30 (s, 2H), 3.15-3.06 (m, 2H), 3.0-2.89 (m, 2H), 2.31-2.19 (m, 2H); APCI MS m/z 412 [M+H]$^+$.

EXAMPLE 156

2-(4-((2-(2,5-Dichlorophenyl)-6,7-dihydro-5H-cyclopenta[b]pyridin-4-yl)amino)phenyl)ethanol hydrochloride

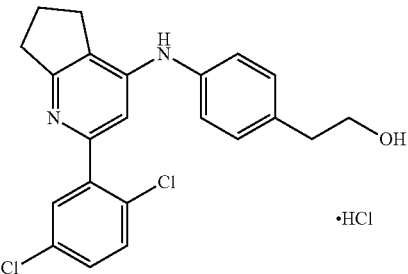 [SMILES: OCCc1ccc(Nc2cc(-c3cc(Cl)ccc3Cl)nc3c2CCC3)cc1 ; Cl]

Following General Procedure A1, 4-chloro-2-(2,5-dichlorophenyl)-6,7-dihydro-5H-cyclopenta[b]pyridine hydrochloride (0.100 g, 0.33 mmol) was reacted with 4-aminophenethyl alcohol (0.055 g, 0.40 mmol), followed by the formation of the hydrochloride salt to afford the title compound (0.068 g, 68%) as a light tan solid. MW=435.77. $^1$H NMR (DMSO-$d_6$, 300 MHz) δ 14.23 (s, 1H), 9.76 (s, 1H), 7.80-7.78 (m, 1H), 7.71-7.63 (m, 2H), 7.32 (d, J=8.4 Hz, 2H), 7.26 (d, J=8.4 Hz, 2H), 6.87 (s, 1H), 4.66 (s, 1H), 3.63 (t, J=6.9 Hz, 2H), 3.1 (t, J=7.6 Hz, 2H), 2.94 (t, J=7.6 Hz, 2H), 2.73 (t, J=6.9 Hz, 2H), 2.30-2.14 (m, 2H); APCI MS m/z 399 [M+H]$^+$.

EXAMPLE 157

2-(4-((2-(3,5-Dichlorophenyl)-6,7-dihydro-5H-cyclopenta[b]pyridin-4-yl)amino)phenyl)acetamide hydrochloride

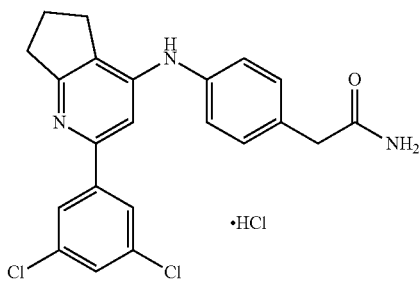 [SMILES: NC(=O)Cc1ccc(Nc2cc(-c3cc(Cl)cc(Cl)c3)nc3c2CCC3)cc1 ; Cl]

Step 1. Preparation of 4-chloro-2-(3,5-dichlorophenyl)-6,7-dihydro-5H-cyclopenta[b]pyridine hydrochloride

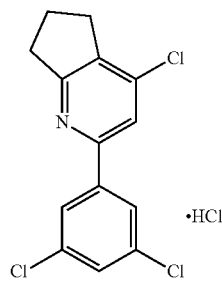 [SMILES: Clc1cc(Cl)cc(-c2cc(Cl)c3c(n2)CCC3)c1 ; Cl]

Following General Procedure F, 2,4-dichloro-6,7-dihydro-5H-cyclopenta[b]pyridine (0.300 g, 1.60 mmol) was reacted with (3,5-dichlorophenyl)boronic acid (0.396 g, 2.07 mmol), followed by the formation of the hydrochloride salt to afford the title compound (0.310 g, 100%) as a white solid. MW=335.06. $^1$H NMR (CD$_3$OD, 300 MHz) δ 14.06 (s, 1H), 8.02-7.93 (m, 2H), 7.71 (s, 1H), 7.50 (t, J=1.8 Hz, 1H), 3.17-3.01 (m, 4H), 2.27-2.17 (m, 2H); APCI MS m/z 297 [M+H]$^+$.

EXAMPLE 157

2-(4-((2-(3,4-Dichlorophenyl)-6,7-dihydro-5H-cyclopenta[b]pyridin-4-yl)amino)phenyl)ethanol hydrochloride

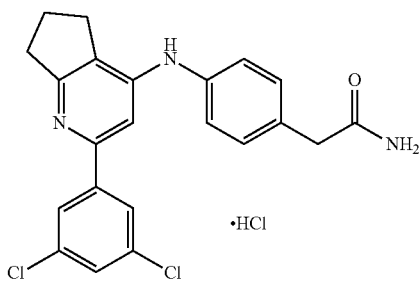 [SMILES: NC(=O)Cc1ccc(Nc2cc(-c3cc(Cl)cc(Cl)c3)nc3c2CCC3)cc1 ; Cl]

Following General Procedure A1, 4-chloro-2-(3,5-dichlorophenyl)-6,7-dihydro-5H-cyclopenta[b]pyridine hydrochloride (0.100 g, 0.33 mmol) was reacted with 2-(4-aminophenyl)acetamide (0.060 g, 0.40 mmol), followed by the formation of the hydrochloride salt to afford the title compound (0.024 g, 18%) as a tan solid. MW=448.77. $^1$H NMR (DMSO-d$_6$, 500 MHz) δ 14.12 (s, 1H), 9.53 (s, 1H), 7.89 (d, J=2.0 Hz, 2H), 7.81 (s, 1H), 7.36 (s, 4H), 7.13 (s, 1H), 3.73 (s, 2H), 3.63 (s, 2H), 3.11 (t, J=7.6 Hz, 2H), 2.91 (t, J=7.6 Hz, 2H), 2.30-2.14 (m, 2H); APCI MS m/z 412 [M+H]$^+$.

EXAMPLE 158

2-(4-((2-(3,5-Dichlorophenyl)-6,7-dihydro-5H-cyclopenta[b]pyridin-4-yl)amino)phenyl)ethanol hydrochloride

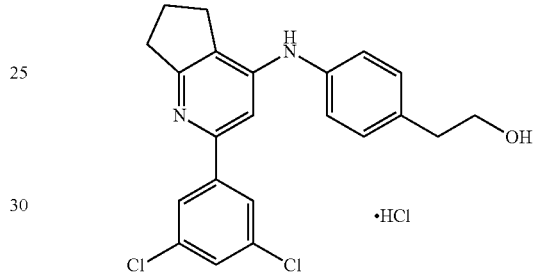

Following General Procedure A1, 4-chloro-2-(3,5-dichlorophenyl)-6,7-dihydro-5H-cyclopenta[b]pyridine hydrochloride (0.100 g, 0.33 mmol) was reacted with 4-aminophenethyl alcohol (0.055 g, 0.40 mmol), followed by the formation of the hydrochloride salt to afford the title compound (0.065 g, 65%) as a light yellow solid. MW=435.77. $^1$H NMR (DMSO-d$_6$, 300 MHz) δ 14.15 (s, 1H), 9.69 (s, 1H), 7.88 (d, J=1.8 Hz, 2H), 7.87-7.83 (m, 1H), 7.33 (s, 4H), 7.07 (s, 1H), 3.64 (t, J=6.9, 2H), 3.13 (t, J=7.6 Hz, 2H), 2.92 (t, J=7.6 Hz, 2H), 2.76 (t, J=6.9 Hz, 2H), 2.28-2.17 (m, 2H); APCI MS m/z 399 [M+H]$^+$.

EXAMPLE 159

2-(4-((2-(m-Tolyl)-6,7-dihydro-5H-cyclopenta[b]pyridin-4-yl)amino)phenyl)acetamide hydrochloride

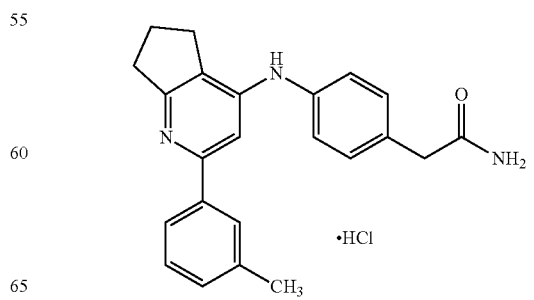

Step 1. Preparation of 4-chloro-2-(m-tolyl)-6,7-dihydro-5H-cyclopenta[b]pyridine hydrochloride

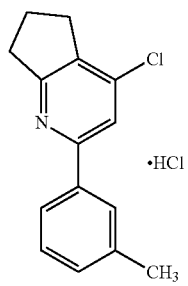 [SMILES: Cc1cccc(-c2cc(Cl)c3c(n2)CCC3)c1 ; Cl]

Following General Procedure F, 2,4-dichloro-6,7-dihydro-5H-cyclopenta[b]pyridine (0.300 g, 1.60 mmol) was reacted with 3-tolyboronic acid (0.282 g, 2.07 mmol), followed by the formation of the hydrochloride salt to afford the title compound (0.244 g, 82%) as a white solid. MW=280.19. $^1$H NMR (CDCl$_3$, 500 MHz) δ 13.97 (s, 1H), 7.97 (s, 1H), 7.91 (d, J=7.5 Hz, 1H), 7.74 (s, 1H), 7.49 (t, J=7.5 Hz, 1H), 7.41 (d, J=7.5 Hz, 1H), 3.84 (t, J=7.6 Hz, 2H), 3.15 (t, J=7.6 Hz, 2H), 2.49 (s, 3H), 2.41-2.37 (m, 2H); APCI MS m/z 244 [M+H]$^+$.

EXAMPLE 159

2-(4-((2-(m-Tolyl)-6,7-dihydro-5H-cyclopenta[b]pyridin-4-yl)amino)phenyl)acetamide hydrochloride

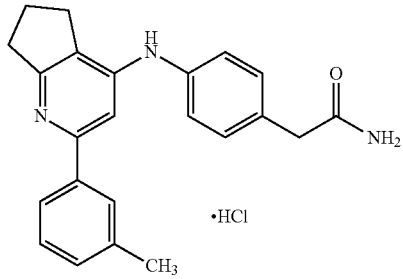 [SMILES: Cc1cccc(-c2cc(Nc3ccc(CC(N)=O)cc3)c3c(n2)CCC3)c1 ; Cl]

Following General Procedure A2, 4-chloro-2-(m-tolyl)-6,7-dihydro-5H-cyclopenta[b]pyridine hydrochloride (0.075 g, 0.27 mmol) was reacted with 2-(4-aminophenyl)acetamide (0.048 g, 0.32 mmol), followed by the formation of the hydrochloride salt to afford the title compound (0.075 g, 99%) as a tan solid. MW=393.91. $^1$H NMR (DMSO-d$_6$, 500 MHz) δ 13.93 (s, 1H), 9.79 (s, 1H), 7.57 (s, 1H), 7.51 (d, J=7.5 Hz, 2H), 7.46 (t, J=7.5 Hz, 1H), 7.41 (d, J=7.5 Hz, 1H), 7.39-7.33 (m, 4H), 6.96 (s, 1H), 6.91 (s, 1H), 3.42 (s, 2H), 3.16 (t, J=7.6 Hz, 2H), 2.92 (t, J=7.6 Hz, 2H), 2.39 (s, 3H), 2.24 (quin, J=7.6 Hz, 2H); APCI MS m/z 358 [M+H]$^+$.

EXAMPLE 160

2-(4-((2-(m-Tolyl)-6,7-dihydro-5H-cyclopenta[b]pyridin-4-yl)amino)phenyl)ethanol hydrochloride

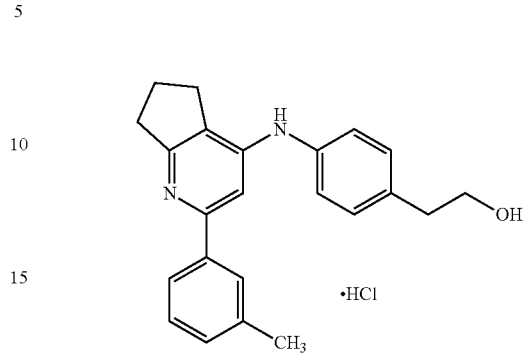

Following General Procedure A2, 4-chloro-2-(m-tolyl)-6,7-dihydro-5H-cyclopenta[b]pyridine hydrochloride (0.075 g, 0.27 mmol) was reacted with 4-aminophenethyl alcohol (0.044 g, 0.32 mmol), followed by the formation of the hydrochloride salt to afford the title compound (0.078 g, 100%) as a brown solid. MW=380.91. $^1$H NMR (DMSO-d$_6$, 500 MHz) δ 13.88 (s, 1H), 9.75 (s, 1H), 7.56 (s, 1H), 7.52-7.44 (m, 2H), 7.41 (d, J=7.5 Hz, 1H), 7.38-7.26 (m, 4H), 6.93 (s, 1H), 3.64 (t, J=6.9, 2H), 3.59 (t, J=6.9 Hz, 1H), 3.15 (t, J=7.6 Hz, 2H), 2.91 (t, J=7.6 Hz, 2H), 2.76 (t, J=6.9 Hz, 2H), 2.39 (m, 3H), 2.24 (quin, J=7.6, 2H); APCI MS m/z 345 [M+H]$^+$.

EXAMPLE 161

2-(4-((2-Cyclopentyl-6-(trifluoromethyl)pyridin-4-yl)amino)phenyl)acetic acid

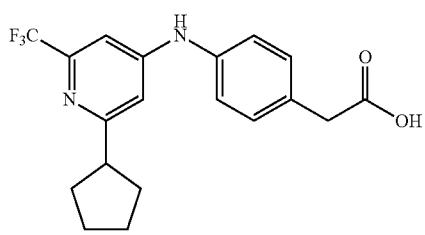 [SMILES: O=C(O)Cc1ccc(Nc2cc(C3CCCC3)nc(C(F)(F)F)c2)cc1]

Step 1. Preparation of ethyl 2-(4-((2-chloro-6-(trifluoromethyl)pyridin-4-yl)amino)phenyl)acetate

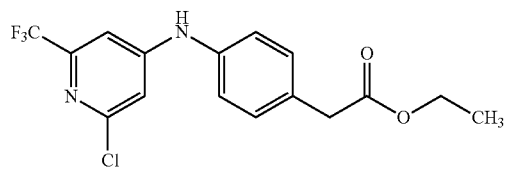 [SMILES: CCOC(=O)Cc1ccc(Nc2cc(Cl)nc(C(F)(F)F)c2)cc1]

Following General Procedure B1, 2-chloro-4-iodo-6-(trifluoromethyl)pyridine (0.244 g, 0.80 mmol) was reacted with ethyl 2-(4-aminophenyl)acetate (0.156 g, 0.87 mmol) to afford the title compound (0.066 g, 33%) as a colorless oil. MW=358.74. $^1$H NMR (CDCl$_3$, 500 MHz) δ 7.37-7.31 (m, 2H), 7.17-7.12 (m, 2H), 7.00 (d, J=2.0 Hz, 1H), 6.87 (d, J=2.0 Hz, 1H), 6.43 (s, 1H), 4.19 (q, J=7.2 Hz, 2H), 3.64 (s, 2H), 1.32-1.25 (m, 3H); APCI MS m/z 359 [M+H]+.

Step 2. Preparation of 2-(4-((2-(cyclopent-1-en-1-yl)-6-(trifluoromethyl)pyridin-4-yl)amino)phenyl)acetic acid

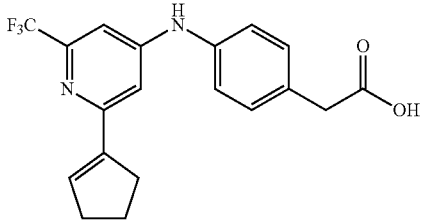 [SMILES: O=C(O)Cc1ccc(Nc2cc(C3=CCCC3)nc(C(F)(F)F)c2)cc1]

Following General Procedure F, ethyl 2-(4-((2-chloro-6-(trifluoromethyl)pyridin-4-yl)amino)phenyl)acetate (0.115 g, 0.32 mmol) was reacted with cyclopent-1-en-1-ylboronic acid (0.039 g, 0.35 mmol) to afford the title compound (0.028 g, 24%) as a yellow oil. MW=362.35. $^1$H NMR (CDCl$_3$, 500 MHz) δ. 7.35-7.28 (m, 2H), 7.18-7.11 (m, 2H), 7.02-6.95 (m, 1H), 6.89 (s, 1H), 6.69-6.63 (m, 1H), 6.18 (s, 1H), 3.65 (s, 3H), 2.05 (q, J=7.5 Hz, 4H), 1.30-1.22 (m, 2H); APCI MS m/z 363 [M+H]+.

EXAMPLE 161

2-(4-((2-Cyclopentyl-6-(trifluoromethyl)pyridin-4-yl)amino)phenyl)acetic acid

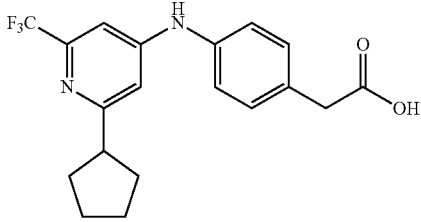 [SMILES: O=C(O)Cc1ccc(Nc2cc(C3CCCC3)nc(C(F)(F)F)c2)cc1]

To a solution of 2-(4-((2-(cyclopent-1-en-1-yl)-6-(trifluoromethyl)pyridin-4-yl)amino)phenyl)acetic acid (0.050 g, 0.14 mmol) in ethanol (5 mL) was added 10% Pd/C (0.002 g) and the mixture was stirred under an hydrogen atmosphere at rt for 48 h. After this time, the mixture was cooled and filtered through celite with ethanol washing. The filtrate was dried over sodium sulfate, filtered, and concentrated. The residue was purified by column chromatography (silica, hexane/ethyl acetate) to afford the title compound (0.021 g, 43%) as a light brown solid. MW=364.36. $^1$H NMR (DMSO-d$_6$, 500 MHz) δ 9.09 (s, 1H), 7.27 (d, J=8.0 Hz, 2H), 7.16 (d, J=8.0 Hz, 2H), 7.03 (s, 1H), 6.93 (s, 1H), 3.54 (s, 2H), 3.10-3.01 (m, 1H), 2.01-1.89 (m, 2H), 1.81-1.57 (m, 6H), 1.24 (s, 1H); APCI MS m/z 365 [M+H]+.

EXAMPLE 162

2-(4-((2-(3-Chlorophenyl)-6,7-dihydro-5H-cyclopenta[d]pyrimidin-4-yl)amino)phenyl)ethanol

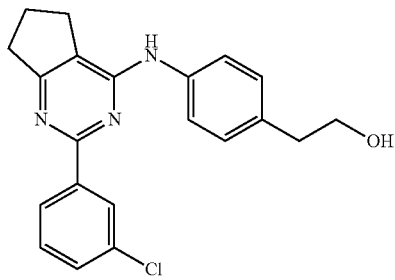 [SMILES: OCCc1ccc(Nc2nc(-c3cccc(Cl)c3)nc3c2CCC3)cc1]

Following general procedure B2, 4-chloro-2-(3-chlorophenyl)-6,7-dihydro-5H-cyclopenta[d]pyrimidine (0.208 g, 0.78 mmol) was reacted with 2-(4-aminophenyl)ethanol (0.118 g, 0.86 mmol) to afford the title compound (0.175 g, 61%) as a white solid. MW=365.86. $^1$H NMR (DMSO-d$_6$, 500 MHz) δ 8.78 (s, 1H), 8.28-8.22 (m, 2H), 7.70 (d, J=8.5 Hz, 2H), 7.53-7.49 (m, 2H), 7.22 (d, J=8.5 Hz, 2H), 4.62 (t, J=5.0 Hz, 1H), 3.65-3.59 (m, 2H), 2.29-2.84 (m, 4H), 2.72 (t, J=7.5 Hz, 2H), 2.10 (quin, J=7.5 Hz, 2H); APCI MS m/z 366 [M+H]+.

EXAMPLE 163

3-(4-((2-(3-Chlorophenyl)-6,7-dihydro-5H-cyclopenta[d]pyrimidin-4-yl)amino)phenyl)propan-1-ol

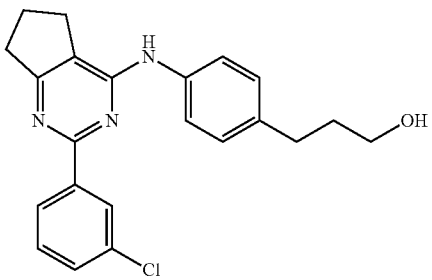 [SMILES: OCCCc1ccc(Nc2nc(-c3cccc(Cl)c3)nc3c2CCC3)cc1]

4-Chloro-2-(3-chlorophenyl)-6,7-dihydro-5H-cyclopenta[d]pyrimidine (0.090 g, 0.40 mmol) and 3-(4-aminophenyl)propan-1-ol (0.060 g, 0.40 mmol) were suspended in acetic acid (2 mL). The mixture was heated to 120° C. for 1 h. After this time, the reaction was cooled, diluted with saturated aqueous sodium bicarbonate, and extracted with ethyl acetate. The mixture was concentrated, redissolved in methanol (5 mL), and lithium hydroxide (4 equiv) was added. The mixture stirred for 1 h, diluted with water, and extracted with ethyl acetate. The combined organic layer was dried over anhydrous sodium sulfate, filtered, and the filtrate was concentrated. The residue was purified by column chromatography (silica, dichloromethane/ethyl acetate) to afford the title compound (0.061 g, 40%) as a white solid. MW=379.88. $^1$H NMR (DMSO-d$_6$, 500 MHz) δ 8.83 (s, 1H), 8.28-8.21 (m, 2H), 7.69 (d, J=8.5 Hz, 2H), 7.54-7.49 (m, 2H), 7.20 (d, J=8.5 Hz, 2H), 3.44 (t, J=6.5 Hz, 1H), 2.92-2.85 (m, 4H), 2.61 (t, J=7.5 Hz, 2H), 2.10 (quin, J=7.5 Hz, 2H), 1.76-1.74 (m, 2H); APCI MS m/z 380 [M+H]⁺.

EXAMPLE 164

1-(4-((2-(3-Chlorophenyl)-6,7-dihydro-5H-cyclopenta[d]pyrimidin-4-yl)amino)phenyl)propan-2-one

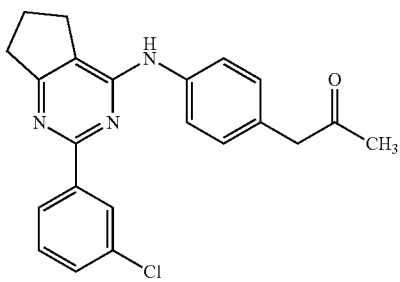 [SMILES: CC(=O)Cc1ccc(Nc2nc(-c3cccc(Cl)c3)nc3c2CCC3)cc1]

Step 1. Preparation of 1-(4-aminophenyl)propan-2-one

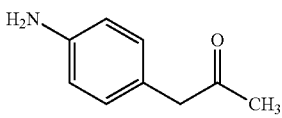

To a solution of 1-(4-nitrophenyl)propan-2-one (0.650 g, 3.63 mmol) in ethanol (20 mL) was added 10% palladium on carbon (0.060 g) and the mixture stirred at rt under 1 atm of H₂ for 1 h. After this time, the mixture was filtered over celite, concentrated, and the residue was purified by column chromatography (silica, hexanes/ethyl acetate) to afford the title compound (0.280 g, 51%) as an orange oil. MW=149.19. ¹H NMR (CDCl₃, 500 MHz) δ 7.00-6.96 (m, 2H), 6.68-6.63 (m, 2H), 3.63 (s, 2H), 3.56 (s, 2H), 2.11 (s, 3H); APCI MS m/z 150 [M+H]⁺.

EXAMPLE 164

1-(4-((2-(3-Chlorophenyl)-6,7-dihydro-5H-cyclopenta[d]pyrimidin-4-yl)amino)phenyl)propan-2-one

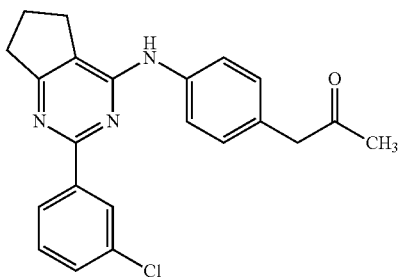 [SMILES: CC(=O)Cc1ccc(Nc2nc(-c3cccc(Cl)c3)nc3c2CCC3)cc1]

Following general procedure B1, 4-chloro-2-(3-chlorophenyl)-6,7-dihydro-5H-cyclopenta[d]pyrimidine (0.140 g, 0.53 mmol) was reacted with 1-(4-aminophenyl)propan-2-one (0.094 g, 0.63 mmol) to afford the title compound (0.119 g, 60%) as a light yellow solid. MW=377.87. ¹H NMR (DMSO-d₆, 500 MHz) δ 8.84 (s, 1H), 8.29-8.22 (m, 2H), 7.75 (d, J=8.5 Hz, 2H), 7.55-7.48 (m, 2H), 7.20 (d, J=8.5 Hz, 2H), 3.74 (s, 2H), 2.94-2.84 (m, 4H), 2.15 (s, 3H), 2.14-2.06 (m, 2H); APCI MS m/z 378 [M+H]⁺

EXAMPLE 165

1-(4-((2-(3-Chlorophenyl)-6,7-dihydro-5H-cyclopenta[d]pyrimidin-4-yl)amino)phenyl)propan-2-ol

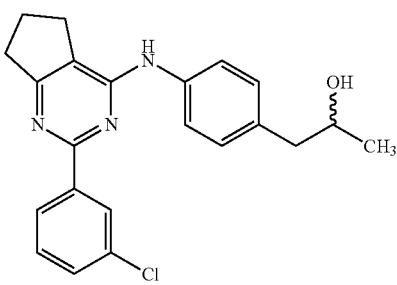 [SMILES: CC(O)Cc1ccc(Nc2nc(-c3cccc(Cl)c3)nc3c2CCC3)cc1]

To a solution of 1-(4-((2-(3-chlorophenyl)-6,7-dihydro-5H-cyclopenta[d]pyrimidin-4-yl)amino)phenyl)propan-2-one (0.072 g, 0.19 mmol) in methanol (5 mL) was added sodium borohydride (0.014 g, 0.38 mmol). The mixture stirred at rt for 10 min. After this time, the mixture was diluted with a saturated solution of NaHCO₃ and extracted with ethyl acetate. The organic layer were dried over anhydrous sodium sulfate, filtered, and the filtrate was concentrated. The residue was purified by column chromatography (silica, hexanes/ethyl acetate) to afford the title compound (0.069 g, 95%) as a white solid. MW=379.88. ¹H NMR (DMSO-d₆, 500 MHz) δ 8.27 (s, 1H), 8.29-8.16 (m, 2H), 7.69 (d, J=8.5 Hz, 2H), 7.54-7.49 (m, 2H), 7.20 (d, J=8.5 Hz, 2H), 4.54 (d, J=5.0 Hz, 1H), 3.87-3.80 (m, 1H), 2.93-2.84 (m, 4H), 2.72-2.66 (m, 1H), 2.58-2.53 (m, 1H), 2.10 (quin, J=7.5 Hz, 2H), 1.06 (d, J=6.0 Hz, 3H); APCI MS m/z 380 [M+H]⁺.

EXAMPLE 166

2-(3-Chlorophenyl)-N-phenyl-6,7-dihydro-5H-cyclopenta[d]pyrimidin-4-amine

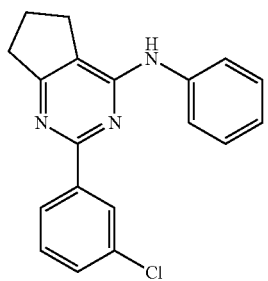 [SMILES: Clc1cccc(-c2nc3c(c(Nc4ccccc4)n2)CCC3)c1]

Following general procedure A1, 4-chloro-2-(3-chlorophenyl)-6,7-dihydro-5H-cyclopenta[d]pyrimidine (0.185 g, 0.70 mmol) was reacted with aniline (0.130 g, 1.4 mmol) to afford the title compound (0.215 g, 95%) as an orange solid. MW=321.80. $^1$H NMR (DMSO-$d_6$, 500 MHz) δ 8.25 (s, 1H), 8.30-8.22 (m, 2H), 7.79 (d, J=8.5 Hz, 2H), 7.55-7.49 (m, 2H), 7.41-7.35 (m, 2H), 7.10-7.05 (m, 1H), 2.93-2.86 (m, 4H), 2.10 (quin, J=7.5 Hz, 2H); APCI MS m/z 322 [M+H]$^+$.

EXAMPLE 167

3-(4-((2-(3-Chlorophenyl)-6,7-dihydro-5H-cyclopenta[d]pyrimidin-4-yl)amino)phenyl)propanamide

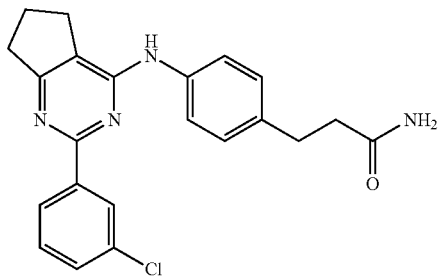 [SMILES: NC(=O)CCc1ccc(Nc2nc(-c3cccc(Cl)c3)nc3c2CCC3)cc1]

Following general procedure A1, 4-chloro-2-(3-chlorophenyl)-6,7-dihydro-5H-cyclopenta[d]pyrimidine (0.060 g, 0.23 mmol) was reacted with methyl 3-amino-2-(4-aminobenzyl)-3-oxopropanoate (0.050 g, 0.23 mmol) to afford the title compound (0.021 g, 23%) as a light brown solid. The intended product (methyl 3-amino-2-(4-((2-(3-chlorophenyl)-6,7-dihydro-5H-cyclopenta[d]pyrimidin-4-yl)amino)benzyl)-3-oxopropanoate) was very minor and not isolated. MW=392.88. $^1$H NMR (DMSO-$d_6$, 500 MHz) δ 8.78 (s, 1H), 8.30-8.21 (m, 2H), 7.70 (d, J=8.5 Hz, 2H), 7.55-7.49 (m, 2H), 7.29 (s, 1H), 7.21 (d, J=8.5 Hz, 2H), 6.75 (s, 1H), 2.94-2.84 (m, 4H), 2.80 (t, J=7.5 Hz, 2H), 2.37 (t, J=7.5 Hz, 2H), 2.10 (quin, J=7.5 Hz, 2H); APCI MS m/z 393 [M+H]$^+$.

EXAMPLE 168

2-(4-((2-(3-Chlorophenyl)-6,7-dihydro-5H-cyclopenta[d]pyrimidin-4-yl)amino)benzyl)-3-hydroxypropanamide

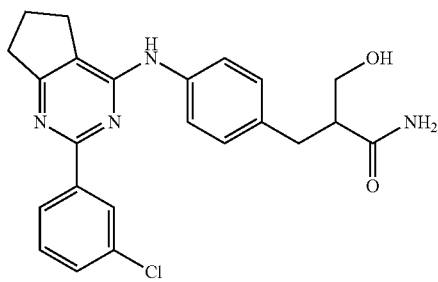 [SMILES: NC(=O)C(CO)Cc1ccc(Nc2nc(-c3cccc(Cl)c3)nc3c2CCC3)cc1]

Step 1. Preparation of isopropyl 3-amino-2-(4-((2-(3-chlorophenyl)-6,7-dihydro-5H-cyclopenta[d]pyrimidin-4-yl)amino)benzyl)-3-oxopropanoate

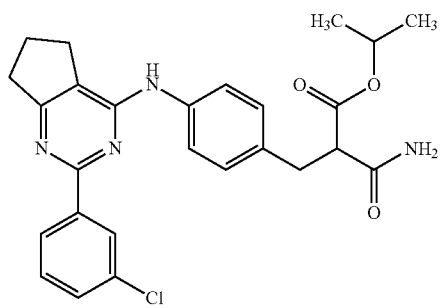 [SMILES: CC(C)OC(=O)C(Cc1ccc(Nc2nc(-c3cccc(Cl)c3)nc3c2CCC3)cc1)C(N)=O]

Following general procedure A1, 4-chloro-2-(3-chlorophenyl)-6,7-dihydro-5H-cyclopenta[d]pyrimidine (0.063 g, 0.24 mmol) was reacted with isopropyl 3-amino-2-(4-aminobenzyl)-3-oxopropanoate (0.060 g, 0.24 mmol) to afford the title compound (0.090 g, 78%) as a light brown foam. MW=478.97. APCI MS m/z 479 [M+H]$^+$.

EXAMPLE 168

2-(4-((2-(3-Chlorophenyl)-6,7-dihydro-5H-cyclopenta[d]pyrimidin-4-yl)amino)benzyl)-3-hydroxypropanamide

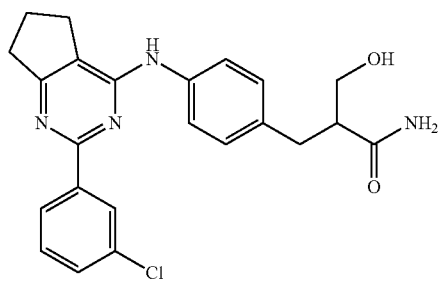 [SMILES: NC(=O)C(CO)Cc1ccc(Nc2nc(-c3cccc(Cl)c3)nc3c2CCC3)cc1]

To a solution of isopropyl 3-amino-2-(4-((2-(3-chlorophenyl)-6,7-dihydro-5H-cyclopenta[d]pyrimidin-4-yl)amino)benzyl)-3-oxopropanoate (0.090 g, 0.19 mmol) in THF (5 mL) was added lithium aluminum hydride (1.0 M, 0.38 mL, 0.38 mmol). The mixture stirred at 0° C. for 2 h. The mixture was quenched with water and sodium hydroxide (2M) and then extracted with ethyl acetate. The organic layer were dried over anhydrous sodium sulfate, filtered, and the filtrate was concentrated. The residue was purified by column chromatography (silica, dichloromethane/methanol) to afford the title compound (0.020 g, 25%) as a white solid. MW=422.91. $^1$H NMR (DMSO-$d_6$, 500 MHz) δ 8.77 (s, 1H), 8.30-8.21 (m, 2H), 7.70 (d, J=8.5 Hz, 2H), 7.55-7.49 (m, 2H), 7.23 (s, 1H), 7.18 (d, J=8.0 Hz, 2H), 6.73 (s, 1H), 4.67 (t, J=5.5 Hz, 1H), 3.59-3.52 (m, 1H), 3.43-3.36 (m, 1H), 2.94-2.84 (m, 4H), 2.79-2.56 (m, 3H), 2.10 (quin, J=7.5 Hz, 2H); APCI MS m/z 423 [M+H]$^+$.

EXAMPLE 169

2-(3-Chlorophenyl)-N-(4-(2-(dimethylamino)ethyl)phenyl)-6,7-dihydro-5H-cyclopenta[d]pyrimidin-4-amine hydrochloride

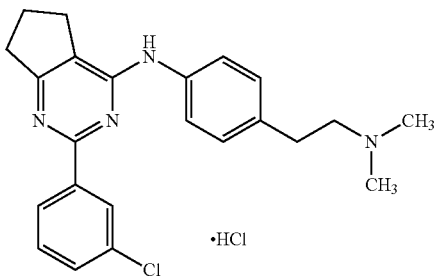 [SMILES: CN(C)CCc1ccc(Nc2nc(-c3cccc(Cl)c3)nc3c2CCC3)cc1 ; Cl]

Following general procedure B1, 4-chloro-2-(3-chlorophenyl)-6,7-dihydro-5H-cyclopenta[d]pyrimidine (0.093 g, 0.35 mmol) was reacted with 4-(2-(dimethylamino)ethyl)aniline (0.069 g, 0.42 mmol), followed by formation of the hydrochloride salt to afford the title compound (0.113 g, 75%) as a light yellow solid. MW=429.39. $^1$H NMR (DMSO-d$_6$, 500 MHz) δ 8.80 (s, 1H), 8.30-8.22 (m, 2H), 7.72 (d, J=8.5 Hz, 2H), 7.55-7.49 (m, 2H), 7.24 (d, J=8.5 Hz, 2H), 2.93-2.85 (m, 4H), 2.80-2.66 (m, 4H), 2.37 (s, 6H), 2.10 (quin, J=8.5 Hz, 2H); APCI MS m/z 393 [M+H]$^+$.

EXAMPLE 170

2-(3-Chlorophenyl)-N-(4-(2-(dimethylamino)ethyl)phenyl)-6-ethylpyrimidin-4-amine hydrochloride

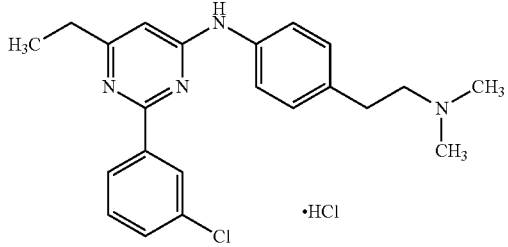 [SMILES: CCc1cc(Nc2ccc(CCN(C)C)cc2)nc(-c2cccc(Cl)c2)n1 ; Cl]

Following general procedure B1, 4-chloro-2-(3-chlorophenyl)-6-ethylpyrimidine (0.085 g, 0.33 mmol) was reacted with 4-(2-(dimethylamino)ethyl)aniline (0.066 g, 0.40 mmol), followed by formation of the hydrochloride salt to afford the title compound (0.101 g, 72%) as a light yellow solid. MW=417.37. $^1$H NMR (DMSO-d$_6$, 500 MHz) δ 9.60 (s, 1H), 8.35-8.27 (m, 2H), 7.66 (d, J=8.5 Hz, 2H), 7.59-7.52 (m, 2H), 7.26 (d, J=8.5 Hz, 2H), 6.60 (s, 1H), 2.91-2.78 (m, 4H), 2.67 (q, J=7.5 Hz, 2H), 1.26 (t, J=7.5 Hz, 3H); APCI MS m/z 381 [M+H]$^+$.

EXAMPLE 171

2-(4-((2-(3-Chlorophenyl)-6-ethylpyrimidin-4-yl)amino)phenyl)acetamide

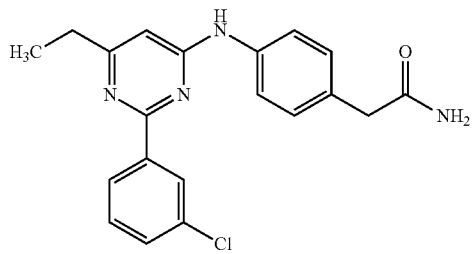

A mixture of 4-chloro-2-(3-chlorophenyl)-6-ethylpyrimidine (0.150 g, 0.59 mmol) and 2-(4-aminophenyl)acetamide (0.107 g, 0.71 mmol) and 4M HCl in dioxane (2 drops) in acetic acid (3 mL) was heated for 2 h at 108° C. After this time, the mixture was cooled to rt, neutralized with saturated NaHCO$_3$, extracted with EtOAc, dried (Na$_2$SO$_4$), filtered, and concentrated. The residue was purified by silica gel chromatography eluting with methylene chloride and methanol to afford the title compound (0.135 g, 62%) as a white solid. MW=366.84. $^1$H NMR (DMSO-d$_6$, 500 MHz) δ 9.57 (s, 1H), 8.33-8.29 (m, 2H), 7.64 (d, J=8.4 Hz, 2H), 7.58-7.54 (m, 2H), 7.43 (br s, 1H), 7.27 (d, J=8.5 Hz, 2H), 6.86 (br s, 1H), 6.59 (s, 1H), 3.35 (s, 2H), 2.67 (q, J=7.6 Hz, 2H), 1.26 (t, J=7.6 Hz, 3H); ESI MS m/z 367 [M+H]$^+$.

EXAMPLE 172

(R)-1-(4-((2-(3-Chlorophenyl)-6,7-dihydro-5H-cyclopenta[d]pyrimidin-4-yl)amino)phenyl)propan-2-ol

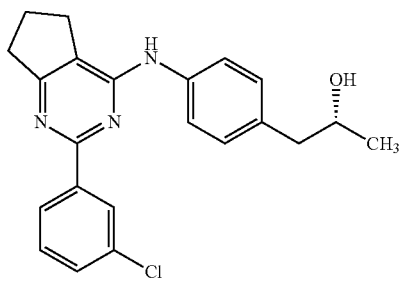 [SMILES: C[C@@H](O)Cc1ccc(Nc2nc(-c3cccc(Cl)c3)nc3c2CCC3)cc1]

Following general procedure B1, 4-chloro-2-(3-chlorophenyl)-6,7-dihydro-5H-cyclopenta[d]pyrimidine (0.075 g, 0.28 mmol) was reacted with (R)-1-(4-aminophenyl)propan-2-ol (0.050 g, 0.34 mmol) to afford the title compound (0.045 g, 42%) as a light yellow solid. MW=379.88. $^1$H NMR (DMSO-d$_6$, 500 MHz) δ 8.77 (s, 1H), 8.29-8.23 (m, 2H), 7.69 (d, J=8.5 Hz, 2H), 7.54-7.49 (m, 2H), 7.20 (d, J=8.5 Hz, 2H), 4.54 (d, J=5.0 Hz, 1H), 3.88-3.80 (m, 1H), 2.93-2.84 (m, 4H), 2.72-2.66 (m, 1H), 2.59-2.53 (m, 1H), 2.10 (quin, J=7.5 Hz, 2H), 1.06 (d, J=6.0 Hz, 3H); APCI MS m/z 380 [M+H]$^+$.

EXAMPLE 173

(S)-1-(4-((2-(3-Chlorophenyl)-6,7-dihydro-5H-cyclopenta[d]pyrimidin-4-yl)amino)phenyl)propan-2-ol

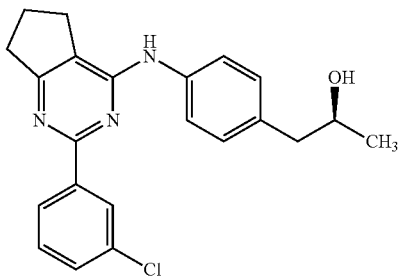 [SMILES: C[C@H](O)Cc1ccc(Nc2nc(-c3cccc(Cl)c3)nc3c2CCC3)cc1]

Following general procedure B1, 4-chloro-2-(3-chlorophenyl)-6,7-dihydro-5H-cyclopenta[d]pyrimidine (0.107 g, 0.40 mmol) was reacted with (S)-1-(4-aminophenyl)propan-2-ol (0.066 g, 0.44 mmol) to afford the title compound (0.123 g, 80%) as a light yellow solid. MW=379.88. $^1$H NMR (DMSO-$d_6$, 500 MHz) δ 8.77 (s, 1H), 8.29-8.16 (m, 2H), 7.69 (d, J=8.5 Hz, 2H), 7.54-7.49 (m, 2H), 7.20 (d, J=8.5 Hz, 2H), 4.54 (d, J=5.0 Hz, 1H), 3.87-3.80 (m, 1H), 2.93-2.84 (m, 4H), 2.72-2.66 (m, 1H), 2.58-2.53 (m, 1H), 2.10 (quin, J=7.5 Hz, 2H), 1.06 (d, J=6.0 Hz, 3H); APCI MS m/z 380 [M+H]$^+$.

EXAMPLE 174

2-(3-Chlorophenyl)-N-(4-vinylphenyl)-6,7-dihydro-5H-cyclopenta[d]pyrimidin-4-amine

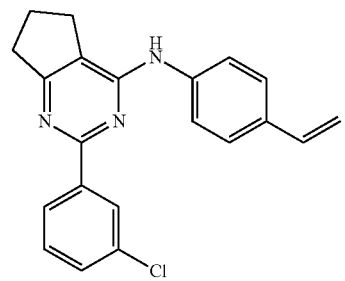 [SMILES: C=Cc1ccc(Nc2nc(-c3cccc(Cl)c3)nc3c2CCC3)cc1]

Following general procedure B1, 4-chloro-2-(3-chlorophenyl)-6,7-dihydro-5H-cyclopenta[d]pyrimidine (0.200 g, 0.75 mmol) was reacted with 4-vinylaniline (0.098 g, 0.83 mmol) to afford the title compound (0.160 g, 62%) as a light yellow solid. MW=347.84. $^1$H NMR (DMSO-$d_6$, 500 MHz) δ 8.82 (s, 1H), 8.31-8.23 (m, 2H), 7.81 (d, J=8.5 Hz, 2H), 7.55-7.47 (m, 4H), 6.77-6.68 (m, 1H), 5.77 (d, J=17.5 Hz, 1H), 5.19 (d, J=11.0 Hz, 1H), 2.96-2.87 (m, 4H), 2.10 (quin, J=7.5 Hz, 2H); APCI MS m/z 348 [M+H]$^+$.

EXAMPLE 175

1-(4-((2-(3-Chlorophenyl)-6,7-dihydro-5H-cyclopenta[d]pyrimidin-4-yl)amino)phenyl)ethane-1,2-diol

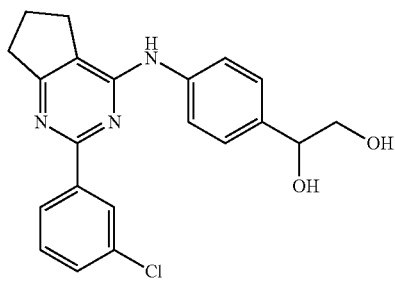 [SMILES: OCC(O)c1ccc(Nc2nc(-c3cccc(Cl)c3)nc3c2CCC3)cc1]

To a suspension of 2-(3-chlorophenyl)-N-(4-vinylphenyl)-6,7-dihydro-5H-cyclopenta[d]pyrimidin-4-amine (0.098 g, 0.28 mmol) in acetone (10 mL) and water (5 mL) was added 4-methylmorpholine N-oxide (0.183 g, 1.4 mmol) and potassium osmate dihydrate (0.002 g, 0.0056 mmol). The mixture was stirred at rt for 16 h. After this time, the reaction mixture was absorbed onto silica and purified by column chromatography (silica, hexanes/ethyl acetate) to afford the title compound (0.063 g, 58%) as a light brown solid. MW=381.86. $^1$H NMR (DMSO-$d_6$, 500 MHz) δ 8.82 (s, 1H), 8.30-8.22 (m, 2H), 7.74 (d, J=8.5 Hz, 2H), 7.54-7.49 (m, 2H), 7.33 (d, J=8.5 Hz, 2H), 5.16 (d, J=4.5 Hz, 1H), 4.68 (t, J=6.0 Hz, 1H), 4.55-4.51 (m, 1H), 3.46 (t, J=6.0 Hz, 2H), 2.95-2.85 (m, 4H), 2.10 (quin, J=7.5 Hz, 2H); APCI MS m/z 382 [M+H]$^+$.

EXAMPLE 176

3-(4-((2-(3-Chlorophenyl)-6,7-dihydro-5H-cyclopenta[d]pyrimidin-4-yl)amino)phenyl)-1,1,1-trifluoropropan-2-ol

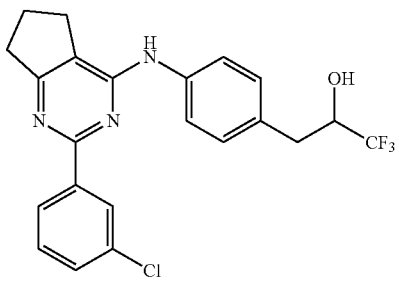 [SMILES: OC(Cc1ccc(Nc2nc(-c3cccc(Cl)c3)nc3c2CCC3)cc1)C(F)(F)F]

Step 1. Preparation of 2-(4-((2-(3-chlorophenyl)-6,7-dihydro-5H-cyclopenta[d]pyrimidin-4-yl)amino)phenyl)acetaldehyde

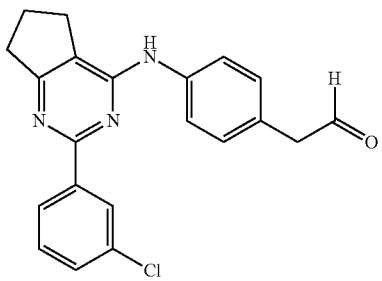 [SMILES: O=CCc1ccc(Nc2nc(-c3cccc(Cl)c3)nc3c2CCC3)cc1]

To a solution of 2-(4-((2-(3-chlorophenyl)-6,7-dihydro-5H-cyclopenta[d]pyrimidin-4-yl)amino)phenyl)ethanol (0.175 g, 0.48 mmol) in methylene chloride (10 mL) was added Dess-Martin periodinate (0.304 g, 0.72 mmol). The mixture stirred at rt for 16 h. After this time, the reaction was quenched with water and a saturated solution of $Na_2S_2O_3$ and then extracted with ethyl acetate. The organic layer were dried over anhydrous sodium sulfate, filtered, and the filtrate was concentrated. The residue was purified by column chromatography (silica, hexanes/ethyl acetate) to afford the title compound (0.114 g, 65%) as an orange oil. MW=363.84. $^1$H NMR (CDCl$_3$, 500 MHz) δ 9.78 (t, J=2.3 Hz, 1H), 8.40-8.37 (m, 1H), 8.29-8.25 (m, 1H), 7.71 (d, J=8.5 Hz, 2H), 7.41-7.36 (m, 2H), 7.27-7.23 (m, 2H), 6.33 (s, 1H), 3.71 (d, J=2.3 Hz, 2H), 3.04 (t, J=7.5 Hz, 2H), 2.81 (t, J=7.5 Hz, 2H), 2.21 (quin, J=7.5 Hz, 2H); APCI MS m/z 364 [M+H]$^+$.

EXAMPLE 176

3-(4-((2-(3-Chlorophenyl)-6,7-dihydro-5H-cyclopenta[d]pyrimidin-4-yl)amino)phenyl)-1,1,1-trifluoropropan-2-ol

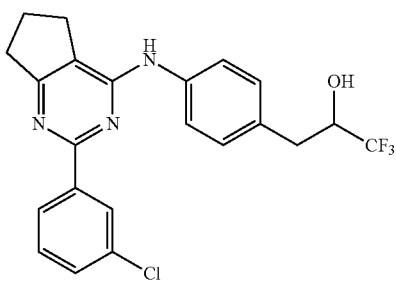 [SMILES: OC(Cc1ccc(Nc2nc(-c3cccc(Cl)c3)nc3c2CCC3)cc1)C(F)(F)F]

To a solution of 2-(4-((2-(3-chlorophenyl)-6,7-dihydro-5H-cyclopenta[d]pyrimidin-4-yl)amino)phenyl)acetaldehyde (0.114 g, 0.31 mmol) in THF (10 mL) was added trimethyl(trifluoromethyl)silane (0.053 g, 0.38 mmol). The mixture stirred at 0° C. for 1 h after which tributylammonium fluoride (1.0 M, 0.078 mL, 0.078 mmol) was added. The mixture stirred at rt for 16 h. After this time, the reaction was diluted with water and extracted with ethyl acetate. The organic layer was dried over anhydrous sodium sulfate, filtered, and the filtrate was concentrated. The residue was purified by preparative HPLC (water/acetonitrile with 0.05% TFA) to afford the title compound (0.010 g, 7%) as a light yellow solid. MW=433.85. $^1$H NMR (DMSO-d$_6$, 500 MHz) δ 8.82 (s, 1H), 8.30-8.22 (m, 2H), 7.75 (d, J=8.5 Hz, 2H), 7.56-7.49 (m, 2H), 7.31 (d, J=8.5 Hz, 2H), 6.20 (d, J=11.5 Hz, 1H), 4.23-4.12 (m, 1H), 2.95-2.85 (m, 4H), 2.76-2.68 (m, 1H), 2.10 (quin, J=7.5 Hz, 2H); APCI MS m/z 434 [M+H]$^+$.

EXAMPLE 177

2-(4-((2-(3-Chlorophenyl)-6,7-dihydro-5H-cyclopenta[d]pyrimidin-4-yl)amino)-2-methylphenyl)acetonitrile

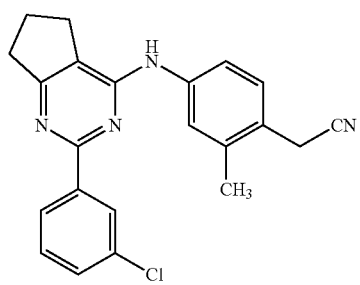 [SMILES: Cc1cc(Nc2nc(-c3cccc(Cl)c3)nc3c2CCC3)ccc1CC#N]

Following procedure A2, 4-chloro-2-(3-chlorophenyl)-6,7-dihydro-5H-cyclopenta[d]pyrimidine (0.120 g, 0.47 mmol) was reacted with 2-(4-amino-2-methylphenyl)acetonitrile (0.104 g, 0.71 mmol) to afford the title compound (0.054 g, 45%) as an off-white solid. MW=374.87. $^1$H NMR (DMSO-d$_6$, 500 MHz) δ 9.31 (s, 1H), 8.28 (s, 1H), 8.22 (d, J=7.0 Hz, 1H), 7.79 (s, 1H), 7.63-7.54 (m, 3H), 7.36 (d, J=8.2 Hz, 1H), 3.99 (s, 2H), 3.01-2.94 (m, 2H), 2.93-2.87 (m, 2H), 2.36 (s, 3H), 2.14 (t, J=7.6 Hz, 2H); APCI MS m/z 375 [M+H]$^+$.

EXAMPLE 178

4-((2-(3-Chlorophenyl)-6,7-dihydro-5H-cyclopenta[d]pyrimidin-4-yl)amino)butanamide

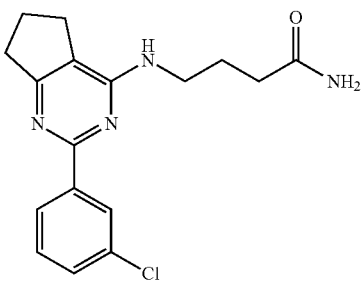 [SMILES: NC(=O)CCCNc1nc(-c2cccc(Cl)c2)nc2c1CCC2]

A solution of 4-chloro-2-(3-chlorophenyl)-6,7-dihydro-5H-cyclopenta[d]pyrimidine (0.032 g, 0.12 mmol), 4-aminobutanamide (0.061 g, 0.60 mmol), and N,N-diisopropylethylamine (0.031 g, 0.24 mmol) in NMP (3 mL) was heated at 90° C. overnight. After this time, the reaction mixture was cooled, diluted water, and extracted with ethyl acetate. The combined organic layer was dried over anhydrous sodium sulfate, filtered, and the filtrate was concentrated to afford the title compound (0.019 g, 61%) as a white solid.

MW=330.81. ¹H NMR (DMSO-d₆, 500 MHz) δ 8.31-8.26 (m, 2H), 7.51-7.46 (m, 2H), 7.27 (s, 1H), 7.03 (t, J=5.5 Hz, 1H), 6.73 (s, 1H), 3.48 (q, J=6.7 Hz, 2H), 2.81 (t, J=7.6 Hz, 2H), 2.68 (t, J=7.3 Hz, 2H), 2.16 (t, J=7.6 Hz, 2H), 2.03 (quin, J=7.6 Hz, 2H), 1.84 (quin, J=7.3 Hz, 2H); APCI MS m/z 331 [M+H]⁺.

EXAMPLE 179

2-(3-Chlorophenyl)-N-(4-(oxazol-2-ylmethyl)phenyl)-6,7-dihydro-5H-cyclopenta[d]pyrimidin-4-amine

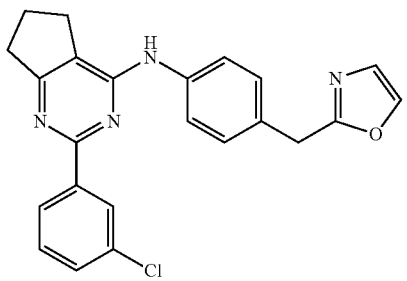 [SMILES: Clc1cccc(-c2nc3c(c(Nc4ccc(Cc5ncco5)cc4)n2)CCC3)c1]

Step 1. Preparation of 2-(4-nitrobenzyl)oxazole

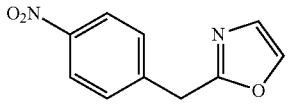 [SMILES: O=[N+]([O-])c1ccc(Cc2ncco2)cc1]

A mixture of 2-(4-nitrophenyl)acetamide (1.0 g, 5.55 mmol), 1,3-dioxol-2-one (0.955 g, 11.10 mmol), and Eaton's Reagent (9.9 g, 34.97 mmol) was heated to 100° C. overnight under a nitrogen atmosphere. After this time, the reaction was cooled, diluted with ice water, and extracted with ethyl acetate. The combined organic layer was dried over anhydrous sodium sulfate, filtered, and the filtrate was concentrated. The residue was purified by column chromatography (silica, dichloromethane/methanol) to afford the title compound (0.250 g, 25%). MW=204.18. ¹H NMR (DMSO-d₆, 500 MHz) δ 8.26-8.18 (m, 2H), 8.05 (d, J=0.8 Hz, 1H), 7.57 (d, J=8.8 Hz, 2H), 7.16 (s, 1H), 4.34 (s, 2H); APCI MS m/z 205 [M+H]⁺.

Step 2. Preparation of 4-(oxazol-2-ylmethyl)aniline

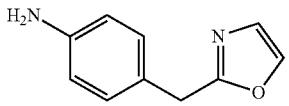

To a solution of 2-(4-nitrobenzyl)oxazole (0.108 g, 0.59 mmol) in ethanol (3 mL) was added tin chloride (0.531 g, 2.35 mmol) and the mixture was stirred at 50° C. for 3 h. After this time, the reaction mixture was cooled, diluted with 1M sodium hydroxide, and extracted with ethyl acetate. The combined organic layer was dried over anhydrous sodium sulfate, filtered, and the filtrate was concentrated to afford the title compound (0.076 g, 63%) as a yellow oil. MW=174.20. ¹H NMR (CD₃OD, 500 MHz) δ 7.78 (d, J=0.8 Hz, 1H), 7.05 (d, J=0.8 Hz, 1H), 7.02-6.97 (m, 2H), 6.69-6.65 (m, 2H), 3.97 (s, 2H); APCI MS m/z 175 [M+H]⁺.

EXAMPLE 179

2-(3-Chlorophenyl)-N-(4-(oxazol-2-ylmethyl)phenyl)-6,7-dihydro-5H-cyclopenta[d]pyrimidin-4-amine

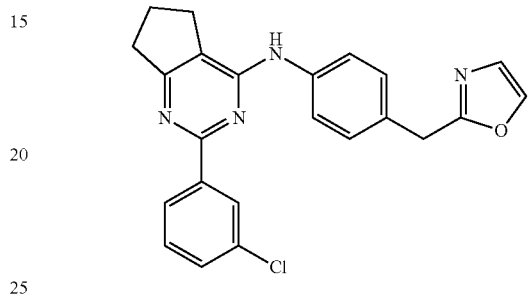

Following General Procedure B2, 4-chloro-2-(3-chlorophenyl)-6,7-dihydro-5H-cyclopenta[d]pyrimidine (0.075 g, 0.28 mmol) was reacted with 4-(oxazol-2-ylmethyl)aniline (0.074 g, 0.42 mmol) to afford the title compound (0.043 g, 58%) as an off-white solid. MW=402.88. ¹H NMR (DMSO-d₆, 300 MHz) δ 8.88 (s, 1H), 8.30-8.19 (m, 2H), 8.03 (d, J=0.8 Hz, 1H), 7.83-7.73 (m, 2H), 7.56-7.50 (m, 2H), 7.28 (d, J=8.6 Hz, 2H), 7.15 (d, J=0.8 Hz, 1H), 4.13 (s, 2H), 2.90 (q, J=7.6 Hz, 4H), 2.20-2.04 (m, 2H); APCI MS m/z 403 [M+H]⁺.

EXAMPLE 180

(4-((2-(3-Chlorophenyl)-6,7-dihydro-5H-cyclopenta[d]pyrimidin-4-yl)amino)phenyl)methanesulfonamide

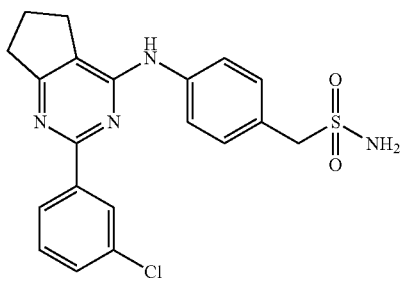 [SMILES: NS(=O)(=O)Cc1ccc(Nc2nc(-c3cccc(Cl)c3)nc3c2CCC3)cc1]

Following General Procedure A1, 4-chloro-2-(3-chlorophenyl)-6,7-dihydro-5H-cyclopenta[d]pyrimidine (0.075 g, 0.28 mmol) was reacted with (4-aminophenyl)methanesulfonamide (0.058 g, 0.31 mmol) to afford the title compound (0.043 g, 58%) as a white solid. MW=414.91. ¹H NMR (DMSO-d₆, 300 MHz) δ 8.93 (s, 1H), 8.32-8.21 (m, 2H), 7.85 (d, J=8.6 Hz, 2H), 7.57-7.50 (m, 2H), 7.36 (d, J=8.6 Hz, 2H), 6.85 (s, 2H), 4.25 (s, 2H), 2.99-2.86 (m, 4H), 2.18-2.05 (m, 2H); APCI MS m/z 415 [M+H]⁺.

EXAMPLE 181

2-(4-((2-(3-Chlorophenyl)-6-ethylpyrimidin-4-yl)oxy)phenyl)acetamide

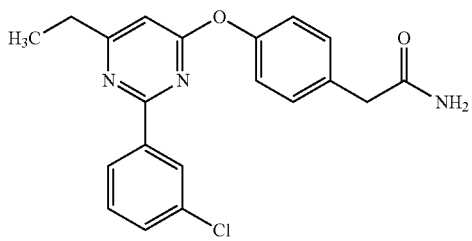 [SMILES: CCc1cc(Oc2ccc(CC(N)=O)cc2)nc(-c2cccc(Cl)c2)n1]

Step 1. Preparation of methyl 2-(4-((2-(3-chlorophenyl)-6-ethylpyrimidin-4-yl)oxy)phenyl)acetate

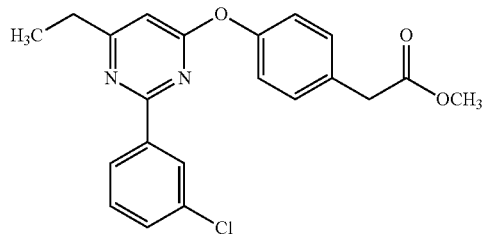 [SMILES: CCc1cc(Oc2ccc(CC(=O)OC)cc2)nc(-c2cccc(Cl)c2)n1]

A solution of 4-chloro-2-(3-chlorophenyl)-6-ethylpyrimidine (0.200 g, 0.79 mmol), methyl 2-(4-hydroxyphenyl)acetate (0.131 g, 0.79 mmol) and potassium carbonate (0.546 g, 3.95 mmol) in acetonitrile (5 mL) was heated to 85° C. for 7 h. The reaction mixture was diluted with water and extracted with ethyl acetate. The combined organic layer was dried over anhydrous sodium sulfate, filtered, and the filtrate was concentrated. The residue was purified by column chromatography (silica, hexanes/dichloromethane) to afford the title compound (0.130 g, 65%). MW=382.84. $^1$H NMR (CD$_3$OD, 500 MHz) δ 8.21 (t, J=1.8 Hz, 1H), 8.16-8.12 (m, 1H), 7.46-7.35 (m, 4H), 7.21-7.17 (m, 2H), 6.77 (s, 1H), 3.73 (s, 2H), 3.72 (s, 3H), 2.83 (q, J=7.6 Hz, 2H), 1.35 (t, J=6.4 Hz, 3H); APCI MS m/z 383 [M+H]$^+$.

EXAMPLE 181

2-(4-((2-(3-Chlorophenyl)-6-ethylpyrimidin-4-yl)oxy)phenyl)acetamide

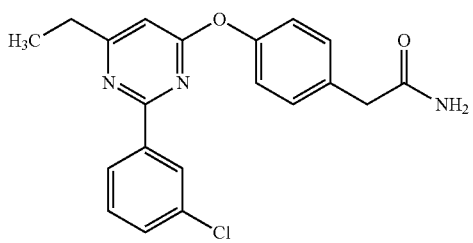 [SMILES: CCc1cc(Oc2ccc(CC(N)=O)cc2)nc(-c2cccc(Cl)c2)n1]

Methyl 2-(4-((2-(3-chlorophenyl)-6-ethylpyrimidin-4-yl)oxy)phenyl)acetate (0.075 g, 0.20 mmol) and ammonia in methanol (7 M, 3 mL) were heated at 100° C. for 72 h. After this time, the crude reaction solution was cooled, evaporated, and purified by column chromatography (silica, dichloromethane/methanol) to afford the title compound (0.048 g, 64%) as a white solid. MW=367.83. $^1$H NMR (DMSO-d$_6$, 500 MHz) δ 8.16-8.13 (m, 1H), 8.14-8.11 (m, 1H), 7.59-7.55 (m, 1H), 7.51 (t, J=7.9 Hz, 2H), 7.39-7.36 (m, 2H), 7.24-7.21 (m, 2H), 6.92 (s, 1H), 6.90 (s, 1H), 3.44 (s, 2H), 2.80 (q, J=7.6 Hz, 2H), 1.28 (t, J=7.6 Hz, 3H); APCI MS m/z 368 [M+H]$^+$.

EXAMPLE 182

2-(4-((2-(3-Chlorophenyl)-6-ethylpyrimidin-4-yl)oxy)phenyl)ethanol

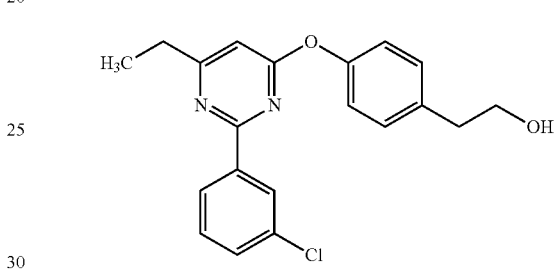

To a solution of methyl 2-(4-((2-(3-chlorophenyl)-6-ethylpyrimidin-4-yl)oxy)phenyl)acetate (0.075 g, 0.20 mmol) in THF (1.3 mL) at 0° C. was added BH$_3$.SMe$_2$ (0.031 g, 0.39 mmol). The mixture was warmed to rt and stirred overnight. After this time, the reaction was quenched with 0.5M HCl, diluted with saturated aqueous sodium bicarbonate, and extracted with ethyl acetate. The combined organic layer was dried over anhydrous sodium sulfate, filtered, and the filtrate was concentrated. The residue was purified by column chromatography (silica, methanol/dichloromethane) to afford the title compound as a white solid (0.052 g, 69%). MW=354.83. $^1$H NMR (DMSO-d$_6$, 500 MHz) δ 8.17-8.10 (m, 2H), 7.59-7.54 (m, 1H), 7.51 (t, J=7.9 Hz, 1H), 7.37-7.32 (m, 2H), 7.22-7.17 (m, 2H), 6.88 (s, 1H), 4.67 (t, J=5.2 Hz, 1H), 3.68-3.62 (m, 2H), 2.79 (q, J=7.3 Hz, 4H), 1.28 (t, J=7.6 Hz, 3H); APCI MS m/z 355 [M+H]$^+$.

EXAMPLE 183

2-(6-((2-(3-Chlorophenyl)-6-ethylpyrimidin-4-yl)oxy)pyridin-3-yl)acetamide

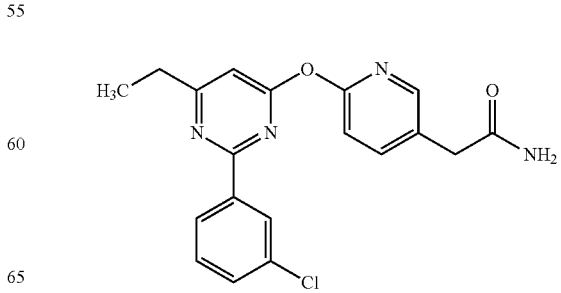

Step 1. Preparation of (6-methoxypyridin-3-yl)methanol

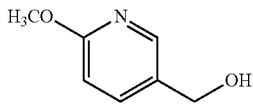

A solution of methyl 2-methoxypyridine-5-carboxylate (8.4 g, 50 mmol) in dixoane (70 mL) was treated with sodium borohydride (8.1 g, 244 mmol) at 0° C. The reaction mixture was warmed to 100° C. and heating continued overnight. After this time, the mixture was cooled, diluted with methanol, filtered through a fritted funnel with methanol washes, and the filtrate was concentrated. The residue was redissolved in water, 0.5 M sodium hydroxide was added dropwise, and the mixture extracted with ethyl acetate. The combined organic layer was dried over anhydrous sodium sulfate, filtered, and the filtrate was concentrated. The residue was purified by column chromatography (silica, dichloromethane/methanol) to afford the title compound (2.9 g, 35%) as a colorless oil. MW=139.15. $^1$H NMR (CD$_3$OD, 300 MHz) δ 8.11-8.05 (m, 1H), 7.67 (dd, J$_1$=10.9 Hz, J$_2$=2.43 Hz, 1H), 6.77 (d, J=8.5 Hz, 1H), 4.89 (s, 1H), 4.54 (s, 2H), 3.89 (s, 3H); APCI MS m/z 140 [M+H]$^+$.

Step 2. Preparation of (6-methoxypyridin-3-yl)methyl methanesulfonate

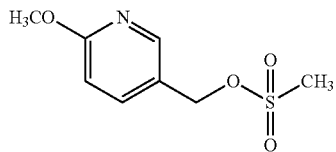

A solution of (6-methoxypyridin-3-yl)methanol (2.9 g, 20.93 mmol) and triethylamine (4.35 mL) in dichloromethane (20 mL) was treated with methanesulfonyl chloride (2.9 g, 25.1 mmol) dropwise and the reaction mixture stirred at rt overnight. After this time, the reaction was diluted with water and extracted with methylene chloride. The combined organic layer was dried over anhydrous sodium sulfate, filtered, and the filtrate was concentrated to afford the title compound (1.4 g, 49%) as a yellow oil. MW=217.24. $^1$H NMR (CDCl$_3$, 300 MHz) δ 8.16-8.14 (m, 1H), 7.68-7.59 (m, 1H), 6.76 (d, J=8.6 Hz, 1H), 4.55 (s, 2H), 3.94 (s, 3H), 3.19 (s, 3H).

Step 3. Preparation of 2-(6-methoxy-1,6-dihydropyridin-3-yl)acetonitrile

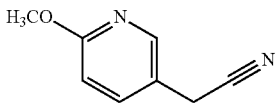 [SMILES: COc1ccc(CC#N)cn1]

A solution of (6-methoxypyridin-3-yl)methyl methanesulfonate (1.4 g, 6.14 mmol) in acetonitrile (13 mL) was treated with sodium cyanide (0.752 g, 15.3 mmol) dropwise and the reaction mixture was heated at reflux for 48 h. After this time, the reaction was cooled and concentrated. The residue was purified by column chromatography (silica, hexanes/ethyl acetate) to afford the title compound (0.800 g, 57%) as a white solid. MW=150.18. $^1$H NMR (CD$_3$OD, 300 MHz) δ 8.12-8.09 (m, 1H), 7.68 (dd, J$_1$=10.9 Hz, J$_2$=2.4 Hz, 1H), 6.82 (d, J=8.6 Hz, 1H), 4.86 (s, 1H), 3.90 (s, 3H), 3.85 (s, 2H); APCI MS m/z 151 [M+H]$^+$.

Step 4. Preparation of 2-(6-oxo-1,6-dihydropyridin-3-yl)acetonitrile

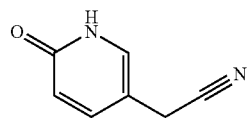

A solution of 2-(6-methoxy-1,6-dihydorpyridin-3-yl)acetonitrile (0.400 g, 2.7 mmol) and hydrogen bromide (4.1 g, 50.25 mmol) in ethanol (5 mL) was refluxed for 4 h. After this time, the reaction was cooled, diluted with saturated aqueous sodium bicarbonate, and extracted with ethyl acetate. The combined organic layer was dried over anhydrous sodium sulfate, filtered, and the filtrate was concentrated. The residue was purified by column chromatography (silica, hexanes/ethyl acetate) to afford the title compound (0.357 g, 89%) as a tan solid. MW=134.14. $^1$H NMR (DMSO-d$_6$, 300 MHz) δ 11.70 (s, 1H), 7.42-7.34 (m, 2H), 6.31 (d, J=9 Hz, 1H), 3.74 (s, 2H); APCI MS m/z 135 [M+H]$^+$.

Step 5. Preparation of 2-(6-((2-(3-chlorophenyl)-6-ethylpyrimidin-4-yl)oxy)pyridin-3-yl)acetonitrile

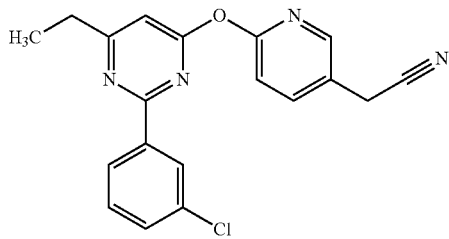 [SMILES: CCc1cc(Oc2ccc(CC#N)cn2)nc(-c2cccc(Cl)c2)n1]

A solution of 4-chloro-2-(3-chlorophenyl)-6-ethylpyrimidine (0.300 g, 1.19 mmol), 2-(6-oxo-1,6-dihydropyridin-3-yl)acetonitrile (0.239 g, 1.78 mmol), and potassium carbonate (0.246 g, 1.78 mmol) in DMF (3 mL) was heated with microwave irradiation to 120° C. for 1 h. After this time, the reaction was cooled and concentrated. The residue was purified by preparative HPLC (water/acetonitrile with 0.05% TFA) to afford the title compound (0.066 g, 22%). MW=350.80. $^1$H NMR (CD$_3$OD, 300 MHz) δ 8.51-8.41 (m, 2H), 8.32-8.28 (m, 1H), 7.89 (s, 1H), 7.64 (dd, J$_1$=12.1 Hz, J$_2$=2.6 Hz, 1H), 7.56-7.47 (m, 2H), 6.70 (d, J=9.5 Hz, 1H), 3.87-3.82 (m, 2H), 2.98 (q, J=7.6 Hz, 2H), 1.46-1.8 (m, 3H); APCI MS m/z 351 [M+H]$^+$.

EXAMPLE 183

2-(6-((2-(3-Chlorophenyl)-6-ethylpyrimidin-4-yl)oxy)pyridin-3-yl)acetamide

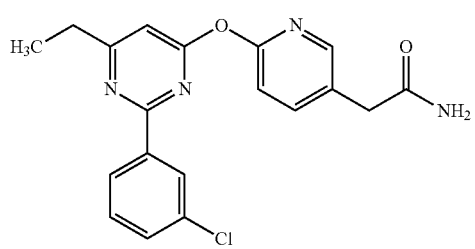 [SMILES: CCc1cc(Oc2ccc(CC(N)=O)cn2)nc(-c2cccc(Cl)c2)n1]

Sulfuric acid (2 mL) was added to 2-(6-((2-(3-chlorophenyl)-6-ethylpyrimidin-4-yl)oxy)pyridin-3-yl)acetonitrile (0.061 g, 0.18 mmol) at 0° C. and slowly warmed to rt. The mixture was stirred for 2 h, diluted with saturated aqueous sodium bicarbonate, and extracted with ethyl acetate. The combined organic layer was dried over anhydrous sodium sulfate, filtered, and the filtrate was concentrated. The residue was purified by column chromatography (silica, dichloromethane/methanol) to afford the title compound (0.020 g, 34%) as a white solid. MW=368.22. $^1$H NMR (DMSO-$d_6$, 300 MHz) δ 8.44-8.37 (m, 2H), 8.10-8.05 (m, 1H), 7.92 (s, 1H), 7.70-7.56 (m, 2H), 7.53-7.43 (m, 2H), 7.01 (s, 1H), 6.55 (d, J=9.4 Hz, 1H), 3.30 (d, 2H), 2.93 (q, J=7.6 Hz, 2H), 1.33 (t, J=7.6 Hz, 3H); APCI MS m/z 369 [M+H]$^+$.

EXAMPLE 184

2-(4-((2-(3-Chlorophenyl)-6-ethylpyrimidin-4-yl)amino)phenyl)-2-methylpropan-1-ol

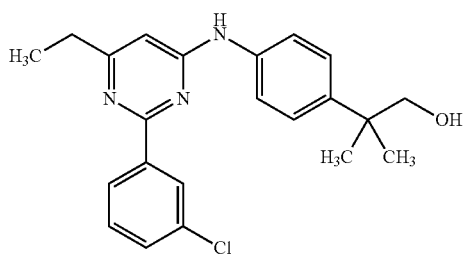 [SMILES: CCc1cc(Nc2ccc(C(C)(C)CO)cc2)nc(-c2cccc(Cl)c2)n1]

Following General Procedure A1, 4-chloro-2-(3-chlorophenyl)-6-ethylpyrimidine (0.075 g, 0.29 mmol) in NMP (3 mL) was reacted with 2-(4-aminophenyl)-2-methylpropan-1-ol (0.054 g, 0.33 mmol) to afford the title compound (0.066 g, 88%) as a light yellow solid. MW=381.91. $^1$H NMR (DMSO-$d_6$, 500 MHz) δ 9.54 (s, 1H), 8.35-8.28 (m, 2H), 7.63 (d, J=8.6 Hz, 2H), 7.58-7.55 (m, 2H), 7.42-7.32 (m, 2H), 6.59 (s, 1H), 4.64 (t, J=5.4 Hz, 1H), 3.42 (d, J=5.4 Hz, 2H), 2.66 (q, J=7.6 Hz, 2H), 1.32-1.18 (m, 9H); APCI MS m/z 382 [M+H]$^+$.

EXAMPLE 185

Ethyl 2-(4-((2-(3-chlorophenyl)-6-ethylpyrimidin-4-yl)amino)phenyl)acetate

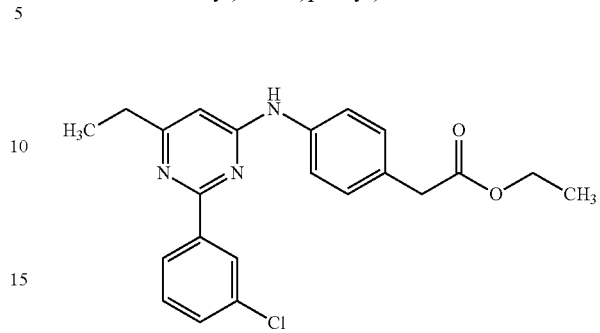

Step 1. Preparation of ethyl 2-(4-((2-(3-chlorophenyl)-6-ethylpyrimidin-4-yl)amino)phenyl)-3,3,3-trifluoropropanoate

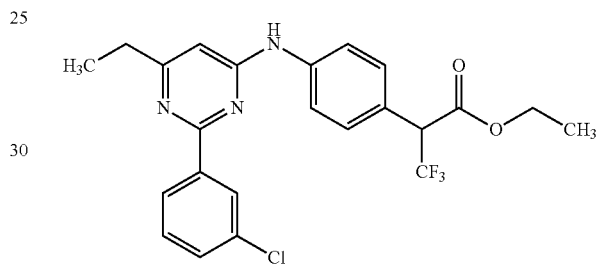

Following General Procedure A1, 4-chloro-2-(3-chlorophenyl)-6-ethylpyrimidine (0.055 g, 0.22 mmol) was reacted with ethyl 2-(4-aminophenyl)-3,3,3-trifluoropropanoate (0.080 g, 0.33 mmol) to afford the title compound (0.100 g, 100%) as an amber oil. MW=463.88. $^1$H NMR (CDCl$_3$, 300 MHz) δ 8.44-8.39 (m, 1H), 8.34-8.27 (m, 1H), 7.57-7.46 (m, 4H), 7.44-7.36 (m, 2H), 6.87 (s, 1H), 6.54 (s, 1H), 4.38-4.11 (m, 3H), 2.74 (q, J=7.6 Hz, 2H), 1.40-1.21 (m, 6H); APCI MS m/z 464 [M+H]$^+$.

EXAMPLE 185

Ethyl 2-(4-((2-(3-chlorophenyl)-6-ethylpyrimidin-4-yl)amino)phenyl)acetate

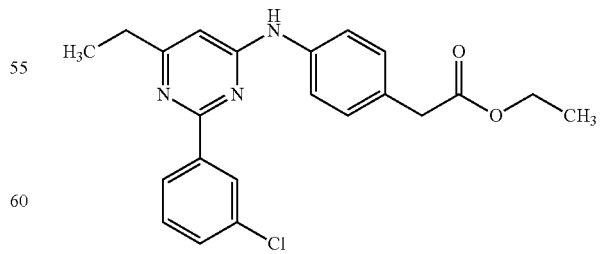

To a solution of ethyl 2-(4-((2-(3-chlorophenyl)-6-ethylpyrimidin-4-yl)amino)phenyl)-3,3,3-trifluoropropanoate (0.130 g, 0.28 mmol) in dioxane (11 mL) and water (7 mL) was added LiOH.H$_2$O (0.035 g, 0.84 mmol) and the mixture was stirred at rt for 12 h. After this time, the mixture was diluted with water and extracted with ethyl acetate. The combined organic layer was dried over anhydrous sodium sulfate, filtered, and the filtrate was concentrated. The residue was purified by column chromatography (silica, hexanes/ethyl acetate) to afford the title compound (0.053 g, 53%) as a white solid. MW=395.88. $^1$H NMR (DMSO-$d_6$, 500 MHz) δ 9.60 (s, 1H), 8.34-8.27 (m, 2H), 7.67 (d, J=8.5 Hz, 2H), 7.59-7.52 (m, 2H), 7.27 (d, J=8.5 Hz, 2H), 6.60 (s, 1H), 4.09 (q, J=7.1 Hz, 2H), 3.64 (s, 2H), 2.67 (q, J=7.6 Hz, 2H), 1.26 (t, J=7.6 Hz, 3H), 1.20 (t, J=7.1 Hz, 3H); APCI MS m/z 396 [M+H]$^+$.

EXAMPLE 186

2-(4-((2-(3-Chlorophenyl)-6-ethylpyrimidin-4-yl)amino)phenyl)-3,3,3-trifluoropropan-1-ol

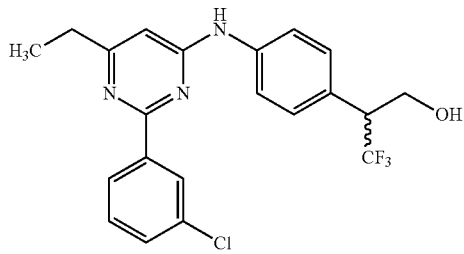 [SMILES: CCc1cc(Nc2ccc(C(CO)C(F)(F)F)cc2)nc(-c2cccc(Cl)c2)n1]

A solution of ethyl 2-(4-((2-(3-chlorophenyl)-6-ethylpyrimidin-4-yl)amino)phenyl)-3,3,3-trifluoropropanoate (0.070 g, 0.15 mmol) in dichloromethane (3 mL) at 0° C. was slowly treated with DIBAL (0.064 g, 0.45 mmol) dropwise and the resulting mixture was stirred for 2 h and then warmed to rt for 2 h. After this time, the reaction was quenched with methanol, 2M HCl, and water and then extracted with ethyl acetate. The combined organic layer was dried over anhydrous sodium sulfate, filtered, and the filtrate was concentrated. The residue was purified by column chromatography (silica, hexanes/ethyl acetate) to afford the title compound (0.035 g, 51%) as a white solid. MW=421.84. $^1$H NMR (DMSO-$d_6$, 300 MHz) δ 9.71 (s, 1H), 8.38-8.27 (m, 2H), 7.75 (d, J=8.4 Hz, 2H), 7.61-7.52 (m, 2H), 7.39 (d, J=8.4 Hz, 2H), 6.63 (s, 1H), 5.10 (t, J=5.4 Hz, 1H), 4.02-3.91 (m, 1H), 3.90-3.80 (m, 1H), 3.77-3.61 (m, 1H), 2.69 (q, J=7.6 Hz, 2H), 1.27 (t, J=7.6 Hz, 3H); APCI MS m/z 422 [M+H]$^+$.

EXAMPLE 187

2-(4-((2-(3-Chlorophenyl)-6-ethylpyrimidin-4-yl)amino)phenyl)-2-methylpropanamide

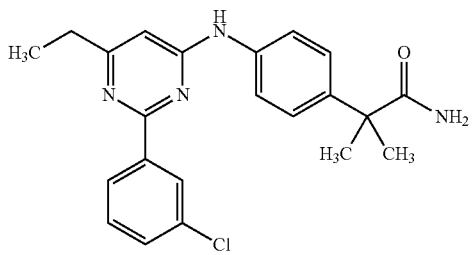 [SMILES: CCc1cc(Nc2ccc(C(C)(C)C(N)=O)cc2)nc(-c2cccc(Cl)c2)n1]

Step 1. Preparation of methyl 2-(4-((2-(3-chlorophenyl)-6-ethylpyrimidin-4-yl)amino)phenyl)-2-methylpropanoate

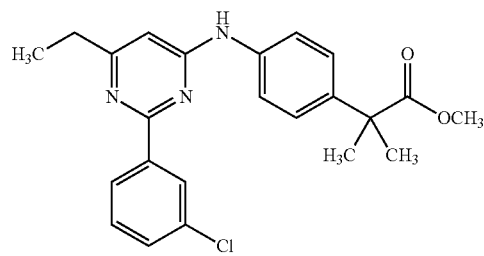 [SMILES: CCc1cc(Nc2ccc(C(C)(C)C(=O)OC)cc2)nc(-c2cccc(Cl)c2)n1]

Following General Procedure A1, 4-chloro-2-(3-chlorophenyl)-6-ethylpyrimidine (0.075 g, 0.29 mmol) in NMP (3 mL) was reacted with 2-(4-aminophenyl)-2-methylpropanamide (0.069 g, 0.36 mmol) to afford the title compound (0.105 g, 100%) as an amber oil. MW=409.91. $^1$H NMR (CDCl$_3$, 300 MHz) δ 8.44-8.39 (m, 1H), 8.33-8.26 (m, 1H), 7.43-7.40 (m, 1H), 7.40-7.35 (m, 4H), 6.77 (s, 1H), 6.52 (s, 1H), 4.12 (q, J=7.1 Hz, 1H), 3.69 (s, 3H), 2.71 (q, J=7.6 Hz, 2H), 2.61 (s, 6H), 1.59 (s, 3H); APCI MS m/z 410 [M+H]$^+$.

Step 2. Preparation of 2-(4-((2-(3-chlorophenyl)-6-ethylpyrimidin-4-yl)amino)phenyl)-2-methylpropanoic acid

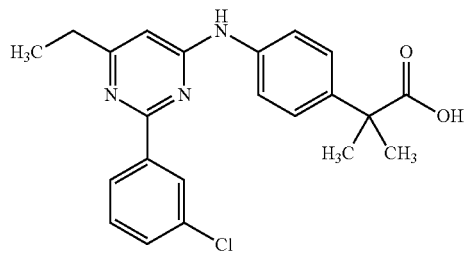 [SMILES: CCc1cc(Nc2ccc(C(C)(C)C(=O)O)cc2)nc(-c2cccc(Cl)c2)n1]

To a solution of methyl 2-(4-((2-(3-chlorophenyl)-6-ethylpyrimidin-4-yl)amino)phenyl)-2-methylpropanoate (0.100 g, 0.24 mmol) in dioxane (9 mL) and water (6 mL) was added LiOH.H$_2$O (0.031 g, 0.73 mmol) and the reaction mixture stirred under a nitrogen atmosphere at 50° C. for 16 h. After this time, the reaction mixture was cooled and treated with 1M HCl to pH 3.0 and concentrated to afford the title compound (0.167 g, 100%) as a yellow oil. MW=395.88. $^1$H NMR (CDCl$_3$, 300 MHz) δ 9.79 (s, 1H), 8.86 (s, 1H), 8.44-8.39 (m, 1H), 8.33-8.26 (m, 1H), 7.43-7.40 (m, 1H), 7.40-7.35 (m, 4H), 6.77 (s, 1H), 6.52 (s, 1H), 2.89 (q, J=7.6 Hz, 2H), 2.42-2.38 (m, 3H), 2.08-2.00 (m, 3H), 1.65-1.57 (m, 3H); APCI MS m/z 396 [M+H]$^+$.

EXAMPLE 187

2-(4-((2-(3-Chlorophenyl)-6-ethylpyrimidin-4-yl)amino)phenyl)-2-methylpropanamide

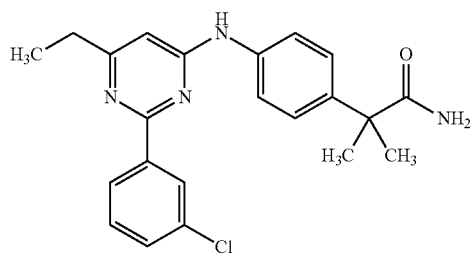 [SMILES: CCc1cc(Nc2ccc(C(C)(C)C(N)=O)cc2)nc(-c2cccc(Cl)c2)n1]

A suspension of 2-(4-((2-(3-chlorophenyl)-6-ethylpyrimidin-4-yl)amino)phenyl)-2-methylpropanoic acid (0.150 g, 0.38 mmol) in methylene chloride (5 mL) and dioxane (5 mL) under a nitrogen atmosphere was treated with oxalyl chloride (0.241 g, 1.89 mmol), followed by the addition of DMF (1 drop). The reaction mixture was stirred at rt for 4 h. After this time, the mixture was concentrated and the residue was treated with ammonia (7.0 N in methanol, 4 mL). The reaction mixture was stirred for 2 h, then concentrated and the residue was purified by preparative HPLC (water/acetonitrile with 0.05% TFA) to afford the title compound (0.065 g, 44%) as a white solid. MW=394.90. $^1$H NMR (DMSO-$d_6$, 500 MHz) δ 9.60 (s, 1H), 8.35-8.27 (m, 2H), 7.68 (d, J=9.0 Hz, 2H), 7.59-7.54 (m, 2H), 7.37-7.32 (m, 2H), 6.86 (d, J=9.0 Hz, 2H), 6.60 (s, 1H), 2.67 (q, J=7.6 Hz, 2H), 1.45 (s, 6H), 1.26 (t, J=7.6 Hz, 3H); APCI MS m/z 395 [M+H]$^+$.

EXAMPLE 188

N-(4-((4-chloro-1H-pyrazol-1-yl)methyl)phenyl)-2-(3-chlorophenyl)-6-ethylpyrimidin-4-amine

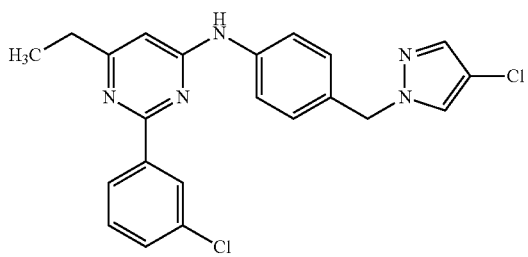 [SMILES: CCc1cc(Nc2ccc(Cn3cc(Cl)cn3)cc2)nc(-c2cccc(Cl)c2)n1]

Step 1. Preparation of 4-chloro-1-(4-nitrobenzyl)-1H-pyrazole

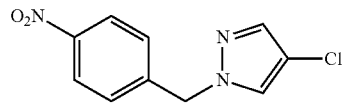 [SMILES: O=[N+]([O-])c1ccc(Cn2cc(Cl)cn2)cc1]

A mixture of 4-chloro-2-(3-chlorophenyl)-6-ethylpyrimidine (0.458 g, 2.12 mmol), 4-chloro-1H-pyrazole (0.500 g, 4.88 mmol), and potassium carbonate (0.645 g, 4.67 mmol) in acetonitrile (27 mL) was stirred at rt overnight. After this time, the mixture was diluted with water and extracted with ethyl acetate. The combined organic layer was dried over anhydrous sodium sulfate, filtered, and the filtrate was concentrated to afford the title compound (0.759 g, crude) as a white solid. MW=237.64. $^1$H NMR (CDCl$_3$, 500 MHz) δ 8.24-8.19 (m, 2H), 7.51 (s, 1H), 7.44 (s, 1H) 7.36-7.31 (m, 2H), 5.36 (s, 2H); APCI MS m/z 238 [M+H]$^+$.

Step 2. 4-((4-chloro-1H-pyrazol-1-yl)methyl)aniline

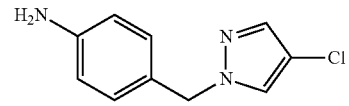

To a solution of 4-chloro-1-(4-nitrobenzyl)-1H-pyrazole (0.750 g, 3.16 mmol) in ethyl acetate (30 mL) was added Pt/C (0.038 g, 0.19 mmol). The mixture was stirred at rt for 48 h, filtered through celite, washed with ethyl acetate, and the filtrate was concentrated. The residue was purified by column chromatography (silica, hexanes/ethyl acetate) to afford the title compound (0.357 g, 43%) as a peach solid. MW=207.66. $^1$H NMR (CDCl$_3$, 500 MHz) δ 7.41 (s, 1H), 7.26 (s, 1H), 7.07-7.01 (m, 2H), 6.65-6.59 (m, 2H), 5.09 (s, 2H), 3.74 (s, 2H); APCI MS m/z 207 [M+H]$^+$.

EXAMPLE 188

N-(4-((4-Chloro-1H-pyrazol-1-yl)methyl)phenyl)-2-(3-chlorophenyl)-6-ethylpyrimidin-4-amine

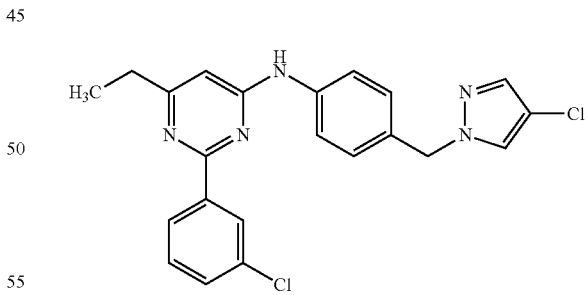

Following General Procedure A1, 4-chloro-2-(3-chlorophenyl)-6-ethylpyrimidine (0.100 g, 0.39 mmol) in NMP (3 mL) was reacted with 4-((4-chloro-1H-pyrazol-1-yl)methyl)aniline (0.098 g, 0.47 mmol) to afford the title compound (0.078 g, 78%) as a light brown solid. MW=424.33. $^1$H NMR (DMSO-$d_6$, 500 MHz) δ 9.67 (s, 1H), 8.34-8.26 (m, 2H), 8.09 (s, 1H), 7.71 (d, J=8.5 Hz, 2H), 7.60-7.52 (m, 3H), 7.32-7.27 (m, 2H), 6.61 (s, 1H), 5.26 (s, 2H), 2.67 (q, J=7.6 Hz, 2H), 1.29-1.24 (m, 3H); APCI MS m/z 424 [M+H]$^+$.

EXAMPLE 189

N-(4-((1H-Pyrazol-1-yl)methyl)phenyl)-2-(3-chloro-phenyl)-6-ethylpyrimidin-4-amine

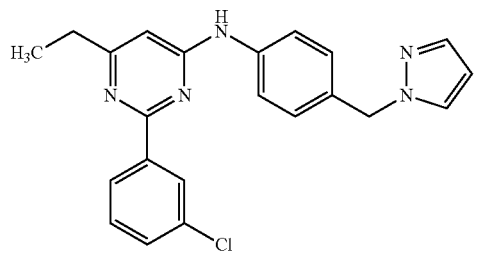 [SMILES: CCc1cc(Nc2ccc(Cn3cccn3)cc2)nc(-c2cccc(Cl)c2)n1]

Step 1. Preparation of 1-(4-nitrobenzyl)-1H-pyrazole

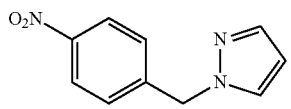 [SMILES: O=[N+]([O-])c1ccc(Cn2cccn2)cc1]

A mixture of 4-nitrobenzyl bromide (0.500 g, 2.31 mmol), 1H-pyrazole (0.362 g, 5.23 mmol), and potassium carbonate (0.704 g, 5.09 mmol) in acetonitrile (30 mL) was stirred at rt overnight. After this time, the mixture was diluted with water and extracted with ethyl acetate. The combined organic layer was dried over anhydrous sodium sulfate, filtered, and the filtrate was concentrated. The residue was purified by column chromatography (silica, hexanes/ethyl acetate) to afford the title compound (0.380 g, 76%) as a white solid. MW=203.20. $^1$H NMR (CDCl$_3$, 500 MHz) δ 8.21-8.19 (m, 1H), 8.19-8.16 (m, 1H), 7.61-7.57 (m, 1H), 7.48-7.44 (m, 1H), 7.32-7.28 (m, 2H), 6.35 (t, J=2.1 Hz, 1H), 5.44 (s, 2H); APCI MS m/z 204 [M+H]$^+$.

Step 2. Preparation of 4-((1H-pyrazol-1-yl)methyl)aniline

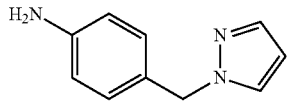

A solution of 1-(4-nitrobenzyl)-1H-pyrazole (0.375 g, 1.85 mmol) in ethyl acetate (15 mL) was treated with Pt/C (0.018 g, 0.09 mmol) and the mixture stirred at rt for 16 h under a hydrogen atmosphere. After this time, the mixture was filtered through celite, washed with ethyl acetate, and the filtrate was concentrated. The residue was purified by column chromatography (silica, hexanes/ethyl acetate) to afford the title compound (0.213 g, 57%) as a yellow solid. MW=173.21. $^1$H NMR (CDCl$_3$, 300 MHz) δ 7.58-7.47 (m, 1H), 7.32 (d, J=2.1 Hz, 1H), 7.09-7.01 (m, 2H), 6.68-6.59 (m, 2H), 6.24 (t, J=2.1 Hz, 1H), 5.19 (s, 2H), 3.69 (s, 2H); APCI MS m/z 174 [M+H]$^+$.

EXAMPLE 189

N-(4-((1H-Pyrazol-1-yl)methyl)phenyl)-2-(3-chloro-phenyl)-6-ethylpyrimidin-4-amine

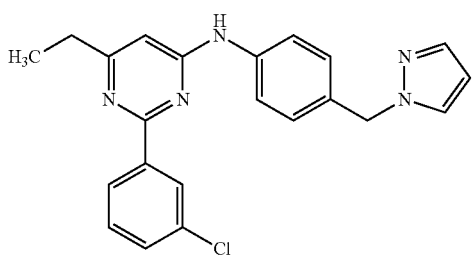 [SMILES: CCc1cc(Nc2ccc(Cn3cccn3)cc2)nc(-c2cccc(Cl)c2)n1]

Following General Procedure A1, 4-chloro-2-(3-chloro-phenyl)-6-ethylpyrimidine (0.100 g, 0.39 mmol) was reacted with 4-((1H-pyrazol-1-yl)methyl)aniline (0.082 g, 0.47 mmol) to afford the title compound (0.067 g, 67%) as a yellow solid. MW=389.88. $^1$H NMR (DMSO-d$_6$, 500 MHz) δ 9.64 (s, 1H), 8.35-8.25 (m, 2H), 7.82 (d, J=2.1 Hz, 1H), 7.69 (d, J=8.4 Hz, 2H), 7.59-7.52 (m, 2H), 7.48-7.44 (m, 1H), 7.30-7.23 (m, 2H), 6.00 (s, 1H), 6.27 (t, J=2.1 Hz, 1H), 5.30 (s, 2H), 2.67 (q, J=7.6 Hz, 2H), 1.26 (t, J=7.6 Hz, 3H); APCI MS m/z 390 [M+H]$^+$.

EXAMPLE 190

4-(4-((4-Chloro-1H-pyrazol-1-yl)methyl)benzyl)-2-(3-chlorophenyl)-6-ethylpyrimidine

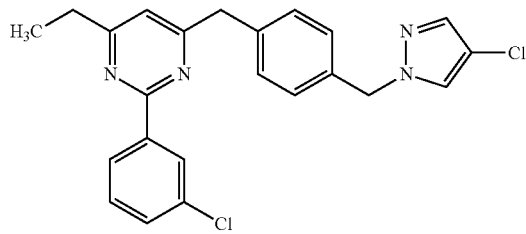 [SMILES: CCc1cc(Cc2ccc(Cn3cc(Cl)cn3)cc2)nc(-c2cccc(Cl)c2)n1]

Step 1. Preparation of (4-((4-chloro-1H-pyrazol-1-yl)methyl)phenyl)methanol

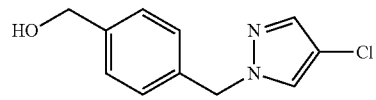 [SMILES: OCc1ccc(Cn2cc(Cl)cn2)cc1]

A mixture of 4-(chloromethyl)benzyl alcohol (0.500 g, 3.19 mmol), 4-chloro-1H-pyrazole (0.753 g, 7.34 mmol), and potassium carbonate (0.908 g, 7.02 mmol) in acetonitrile (40 mL) was stirred at rt overnight. After this time, the mixture was diluted with water and extracted with ethyl acetate. The combined organic layer was dried over anhydrous sodium sulfate, filtered and the filtrate was concentrated. The residue was purified by column chromatography (silica, hexanes/ethyl acetate) to afford the title compound (0.375 g, 75%) as a white solid. MW=222.67. ¹H NMR (CDCl₃, 500 MHz) δ 7.45 (s, 1H), 7.37 (s, 1H), 7.35 (s, 1H), 7.33 (s, 1H), 7.23 (s, 1H), 7.22 (s, 1H), 5.24 (s, 2H), 4.70 (d, J=5.9 Hz, 2H), 1.68 (t, J=5.9 Hz, 1H).

Step 2. Preparation of 1-(4-(bromomethyl)benzyl)-4-chloro-1H-pyrazole

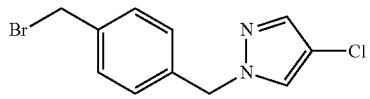 [SMILES: Clc1cnn(Cc2ccc(CBr)cc2)c1]

A solution of (4-((4-chloro-1H-pyrazol-1-yl)methyl)phenyl)methanol (0.375 g, 1.68 mmol) in methylene chloride (7 mL) at 0° C. under a nitrogen atmosphere was treated with PBr₃ (0.456 g, 1.68 mmol) and the mixture was warmed to rt and stirred for 1 h. After this time, the mixture was diluted with saturated aqueous sodium bicarbonate and ice and then extracted with dichloromethane. The combined organic layer was dried over anhydrous sodium sulfate, filtered, and the filtrate was concentrated. The residue was purified by column chromatography (silica, hexanes/dichloromethane) to afford the title compound (0.342 g, 91%) as a white solid. MW=285.57. ¹H NMR (CDCl₃, 500 MHz) δ 7.46 (s, 1H), 7.38 (d, J=8.1 Hz, 2H), 7.35 (s, 1H), 7.19 (d, J=8.1 Hz, 2H), 5.24 (s, 2H), 4.47 (s, 2H).

Step 3. Preparation of 4-chloro-1-(4-((4,4,5,5-tetramethyl-1,3,2-dioxaborolan-2-yl)methyl)benzyl)-1H-pyrazole

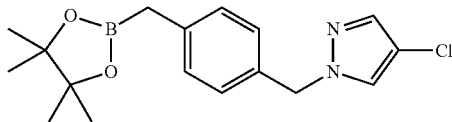 [SMILES: CC1(C)OB(Cc2ccc(Cn3cc(Cl)cn3)cc2)OC1(C)C]

A mixture of 1-(4-(bromomethyl)benzyl)-4-chloro-1H-pyrazole (0.340 g, 1.19 mmol), pinacol diborane (0.363 g, 1.43 mmol), tetrakis(triphenylphosphine)palladium(0) (0.137 g, 0.12 mmol) and K₂CO₃ (0.793 g, 3.57 mmol) in dioxane (10 mL) was stirred under an argon atmosphere at 80° C. for 18 h. After this time, the mixture was cooled, diluted with ethyl acetate (40 mL), and filtered through celite. The filtrate was washed with saturated sodium chloride (3×5 mL), dried over sodium sulfate, filtered, and concentrated. The residue was purified by column chromatography (silica, hexanes/dichloromethane) to afford the title compound (0.240 g, crude) as a dark yellow oil. MW=332.63. ¹H NMR (CDCl₃, 500 MHz) δ 10.01 (s, 1H), 7.89-7.84 (m, 2H), 7.49 (s, 1H), 7.46-7.43 (m, 1H), 7.41 (s, 1H), 7.36-7.29 (m, 3H), 7.19-7.06 (m, 3H), 5.33 (s, 2H), 5.21-5.18 (m, 2H), 2.89 (s, 1H), 1.61 (s, 2H), 1.23 (s, 3H).

EXAMPLE 190

4-(4-((4-Chloro-1H-pyrazol-1-yl)methyl)benzyl)-2-(3-chlorophenyl)-6-ethylpyrimidine

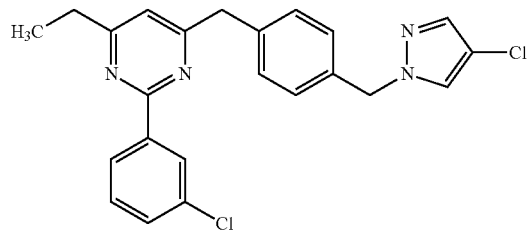 [SMILES: CCc1cc(Cc2ccc(Cn3cc(Cl)cn3)cc2)nc(-c2cccc(Cl)c2)n1]

A mixture of 4-chloro-2-(3-chlorophenyl)-6-ethylpyrimidine (0.100 g, 0.40 mmol), 4-chloro-1-(4-((4,4,5,5-tetramethyl-1,3,2-dioxaborolan-2-yl)methyl)benzyl)-1H-pyrazole (0.197 g, 0.59 mmol), Pd(dppf)Cl₂ (0.032 g, 0.04 mmol), and powdered Na₂CO₃ (0.126 g, 1.19 mmol) in dioxane (2.4 mL) and water (1.6 mL) was stirred under an argon atmosphere at 90° C. for 6 h, cooled, and filtered through celite with ethyl acetate washing. The filtrate was washed with saturated sodium chloride (3×25 mL), dried over anhydrous sodium sulfate, filtered, and concentrated. The residue was purified by column chromatography (silica, hexane/dichloromethane) to afford the title compound (0.043 g, 43%) as a yellow oil. MW=423.34. ¹H NMR (DMSO-d₆, 500 MHz) δ 8.38-8.32 (m, 2H), 8.05 (s, 1H), 7.62-7.50 (m, 3H), 7.35 (d, J=8.1 Hz, 2H), 7.25 (s, 1H), 7.20 (d, J=8.1 Hz, 2H), 5.25 (s, 2H), 4.11 (s, 2H), 2.77 (q, J=7.6 Hz, 2H), 1.26 (t, J=7.6 Hz, 3H); APCI MS m/z 423 [M+H]⁺.

EXAMPLE 191

2-(4-((2-(3-chlorophenyl)-6-ethylpyrimidin-4-yl)amino)phenyl)ethanol

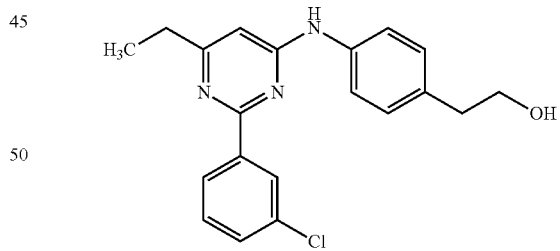

A mixture of 4-chloro-2-(3-chlorophenyl)-6-ethylpyrimidine (0.150 g, 0.59 mmol) and 2-(4-aminophenyl)ethanol (0.134 g, 0.89 mmol) and 4M HCl in dioxane (0.222 mL, 0.89 mmol) in EtOH was heated for 2.5 h at 85° C. After this time, the mixture was neutralized with NaHCO₃ at 0° C. and purified by silica gel chromatography eluting with methylene chloride and methanol to afford the title compound (0.145 g, 70%) as a yellow solid. MW=353.85. ¹H NMR (DMSO-d₆, 500 MHz) δ 9.53 (s, 1H), 8.33-8.28 (m, 2H), 7.62-7.55 (m, 4H), 7.22 (d, J=8.4 Hz, 2H), 6.58 (s, 1H), 4.62 (t, J=5.2 Hz, 1H), 3.63-3.59 (m, 2H), 2.72-2.64 (m, 4H), 1.26 (t, J=7.6 Hz, 3H); ESI MS m/z 354 [M+H]⁺.

EXAMPLE 192

2-(2-((2-(3-Chlorophenyl)-6-ethylpyrimidin-4-yl)imino)-2,3-dihydrooxazol-5-yl)acetamide

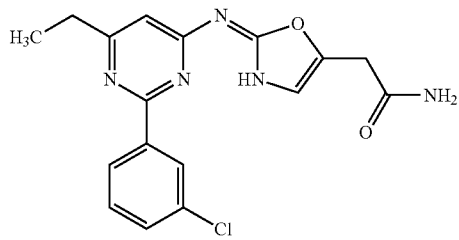 [SMILES: CCc1cc(/N=c2\[nH]cc(CC(N)=O)o2)nc(-c2cccc(Cl)c2)n1]

Step 1. Preparation of methyl 4-oxobutanoate

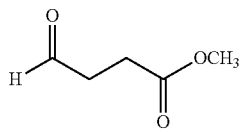

A 500-mL Parr bottle was charged with methyl 4-chloro-4-oxobutyrate (20.0 g, 133 mmol), 2,6-lutidine (15.6 mL, 134 mmol) and 10% palladium on carbon (1.4 g) in tetrahydrofuran (250 mL). This mixture was vigorously shaken under $H_2$ (40 psi) for 6 h. The mixture was then filtered through celite and the filtrate concentrated under reduced pressure. The residue was distilled under vacuum (130° C./10 mm) to afford the title compound (8.52 g, 55%) as a colorless oil. MW=116.12. $^1$H NMR (CDCl$_3$, 300 MHz) δ 9.82 (s, 1H), 3.70 (s, 3H), 2.81 (t, J=6.6 Hz, 2H), 2.64 (t, J=6.3 Hz, 2H).

Step 2. Preparation of methyl 3-bromo-4-oxobutanoate

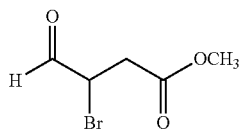

A 500-mL round bottom flask was charged with methyl 4-oxobutanoate (8.52 g, 73.3 mmol), dioxane (0.7 mL) in diethyl ether (70 mL). Bromine (3.94 mL, 77.0 mmol) was added at room temperature over 1.5 h. After this time, the mixture was diluted with dichloromethane (250 mL) and solid sodium bicarbonate (13.6 g, 161 mmol) was added. After stirring for 2 h the mixture was filtered and the filtrate concentrated under reduced pressure to afford the title compound (15.3 g, 100%) as a colorless oil. MW=195.01. $^1$H NMR (CDCl$_3$, 300 MHz) δ 9.54 (s, 1H), 4.68 (dd, J=6.9, 6.6 Hz, 1H), 3.74 (s, 3H), 3.25 (dd, J=17.4, 7.2 Hz, 1H), 2.94 (dd, J=17.1, 6.6 Hz, 1H).

Step 3. Preparation of methyl 2-(2-aminooxazol-5-yl)acetate

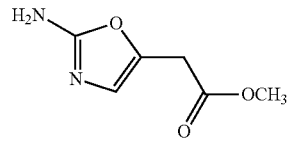 [SMILES: COC(=O)Cc1cnc(N)o1]

A 250-mL round bottom flask was charged with methyl 3-bromo-4-oxobutanoate (5.00 g, 25.6 mmol) and urea (2.08 g, 34.6 mmol) in DMF (15 mL) and heated to 110° C. for 30 minutes. After this time, the mixture was cooled to room temperature and concentrated under reduced pressure. The residue was absorbed onto silica and purified by chromatography on silica using dichloromethane/(89:9:1 dichloromethane/methane/conc. NH$_4$OH) (10:0 to 0:10) as eluent, to afford the title compound (0.72 g, 18%) as a red oil. MW=156.14. $^1$H NMR (DMSO-d$_6$, 300 MHz) δ 9.54 (s, 1H), 6.48 (s, 2H), 6.45 (s, 1H), 3.64 (s, 2H), 3.62 (s, 3H).

Step 4. Methyl 2-(2-((2-(3-chlorophenyl)-6-ethylpyrimidin-4-yl)amino)oxazol-5-yl)acetate

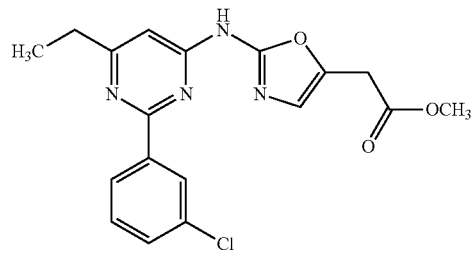 [SMILES: CCc1cc(Nc2ncc(CC(=O)OC)o2)nc(-c2cccc(Cl)c2)n1]

A 10-mL microwave vial was charged with 4-chloro-2-(3-chlorophenyl)-6-ethylpyrimidine (0.150 g, 0.59 mmol), methyl 2-(2-aminooxazol-5-yl)acetate (0.138 g, 0.89 mmol), palladium acetate (0.006 g, 0.029 mmol), rac-BINAP (0.028 g, 0.044 mmol) and cesium carbonate (0.482 g, 1.48 mmol) in dioxane (5 mL) under argon. The reaction mixture was heated to 120° C. under microwave irradiation for 2 h until the starting material was consumed (monitored by LCMS analysis). The reaction mixture was cooled and filtered through celite. The filtrate was diluted with ethyl acetate (50 mL), washed with saturated sodium bicarbonate (10 mL), dried over anhydrous sodium sulfate, filtered, and the filtrate was concentrated under reduced pressure. The residue was purified by chromatography on silica using hexanes/ethyl acetate (10:0 to 0:10) to afford the title compound (0.075 g, 34%) as an off-white solid. MW=372.81. $^1$H NMR (CDCl$_3$, 300 MHz) δ 8.65 (s, 1H), 8.37-8.33 (m, 1H), 8.25 (dt, J=7.2, 1.5 Hz, 1H), 8.02 (s, 1H), 7.49-7.38 (m, 2H), 6.40-6.35 (m, 1H), 4.08 (s, 2H), 3.41 (s, 3H), 2.91 (q, J=7.5 Hz, 2H), 1.41 (t, J=7.5 Hz, 3H); ESI MS m/z 373 [M+H]$^+$.

EXAMPLE 192

2-(2-((2-(3-Chlorophenyl)-6-ethylpyrimidin-4-yl)imino)-2,3-dihydrooxazol-5-yl)acetamide

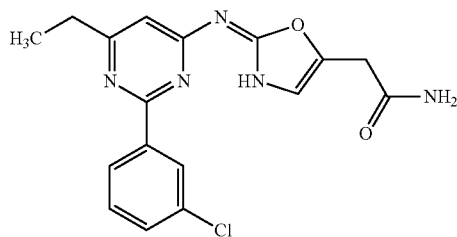

A 20-mL vial was charged with methyl 2-(2-((2-(3-chlorophenyl)-6-ethylpyrimidin-4-yl)amino)oxazol-5-yl)acetate (0.073 g, 0.20 mmol) and ammonium chloride (0.031 g, 0.59 mmol). To this was added methanol (4 mL) followed by NH$_3$ (5.6 mL, 7N in methanol, 39 mmol). The vial was sealed and the resulting mixture was stirred at 100° C. for 65 h. The crude reaction solution concentrated under reduced pressure. The residue was adsorbed onto silica then purified by chromatography on silica using dichloromethane/methanol (10:0 to 8:2) as eluent to afford 2-(2-((2-(3-chlorophenyl)-6-ethylpyrimidin-4-yl)imino)-2,3-dihydrooxazol-5-yl)acetamide (0.051 g, 72%) as an off-white solid. MW=357.79. M.p.>260° C. $^1$H NMR (DMSO-d$_6$, 300 MHz) δ 8.68 (s, 1H), 8.61 (s, 1H), 8.37-8.32 (m, 2H), 8.00 (s, 1H), 7.63-7.52 (m, 2H), 5.34 (d, J=8.1 Hz, 1H), 5.19 (ddd, J=8.1, 8.1, 3.3 Hz, 1H), 2.99 (dd, J=18.0, 8.4 Hz, 1H), 2.76 (q, J=7.5 Hz, 2H), 2.44 (dd, J=18.3, 3.6 Hz, 1H), 1.27 (t, J=7.5 Hz, 3H); APCI MS m/z 358 [M+H]$^+$.

EXAMPLE 193

2-(4-((2-(3-Chlorophenyl)-6-ethylpyrimidin-4-yl)methyl)phenyl)-N-propylacetamide

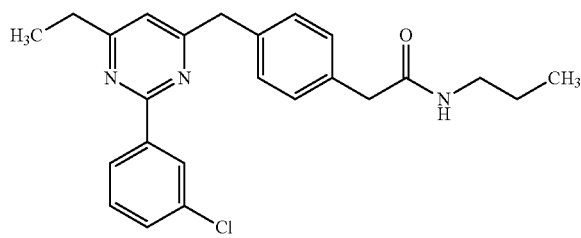 [SMILES: CCCNC(=O)Cc1ccc(Cc2cc(CC)nc(-c3cccc(Cl)c3)n2)cc1]

Step 1. Preparation of 2-(4-((2-(3-Chlorophenyl)-6-ethylpyrimidin-4-yl)methyl)phenyl)acetyl chloride

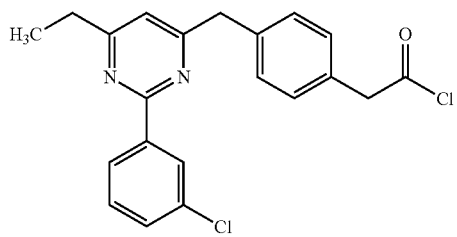 [SMILES: CCc1cc(Cc2ccc(CC(=O)Cl)cc2)nc(-c2cccc(Cl)c2)n1]

An 250-mL round bottom flask was charged with 2-(4-((2-(3-chlorophenyl)-6-ethylpyrimidin-4-yl)methyl)phenyl)acetic acid (0.22 g, 0.60 mmol) in dichloromethane (15 ml). To this solution at 0° C. was added oxalyl chloride (0.25 mL, 3.00 mmol) followed by DMF (1 drop). After stirring for 4 h, the volatile material was removed under reduced pressure to afford crude acid chloride as a red oil. MW=385.29.

EXAMPLE 193

2-(4-((2-(3-Chlorophenyl)-6-ethylpyrimidin-4-yl)methyl)phenyl)-N-propylacetamide

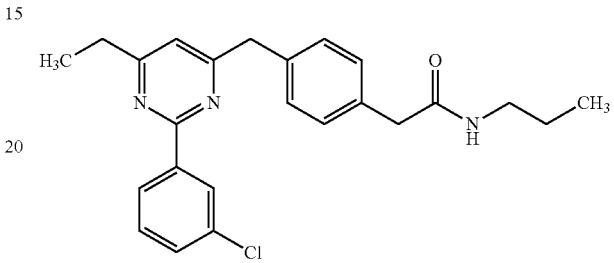

To a stirred solution of crude 2-(4-((2-(3-chlorophenyl)-6-ethylpyrimidin-4-yl)methyl)phenyl)acetyl chloride (~0.20 mmol) in dichloromethane (8 mL) at 0° C. was added n-propylamine (0.082 mL, 1.00 mmol) followed by diisopropylethylamine (0.17 mL, 1.00 mmol). After stirring for 2.5 h, the reaction mixture was diluted with dichloromethane (50 mL) and water (5 mL). The mixture was acidified with 2N aqueous HCl until pH~5. The organic layer was washed with saturated sodium chloride (5 mL), dried over sodium sulfate, filtered, and concentrated under reduced pressure. The residue was purified by chromatography on silica using hexanes/ethyl acetate (10:0 to 1:1) as eluent followed by preparative HPLC (water/acetonitrile with 0.05% TFA) to afford the title compound (0.044 g, 55%) as a white solid. MW=407.94. M.p. 123-125° C. $^1$H NMR (DMSO-d$_6$, 500 MHz) δ 8.37-8.31 (m, 2H), 7.98-7.93 (m, 1H), 7.60 (dt, J=8.5, 2.0 Hz, 1H), 7.55 (t, J=7.5 Hz, 1H), 7.28 (d, J=8.0 Hz, 2H), 7.24 (s, 1H), 7.20 (d, J=8.0 Hz, 2H), 4.09 (s, 2H), 3.34 (s, 2H), 2.97 (q, J=6.0 Hz, 2H), 2.77 (t, J=7.5 Hz, 2H), 1.43-1.34 (m, 2H), 1.26 (t, J=7.5 Hz, 3H), 0.81 (t, J=7.5 Hz, 3H); APCI MS m/z 408 [M+H]$^+$.

EXAMPLE 194

2-(4-((2-(3-Chlorophenyl)-6-ethylpyrimidin-4-yl)methyl)phenyl)-N-methyl-N-propylacetamide

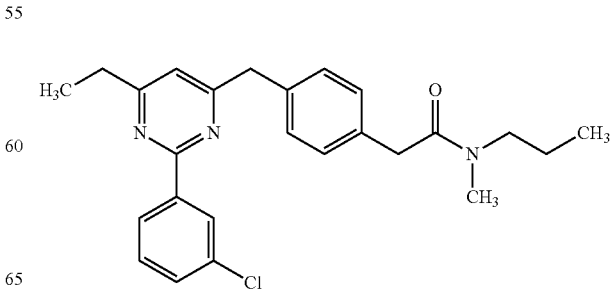

To a stirred solution of crude 2-(4-((2-(3-chlorophenyl)-6-ethylpyrimidin-4-yl)methyl)phenyl)acetyl chloride (~0.20 mmol) in dichloromethane (8 mL) at 0° C. was added N-methyl-n-propylamine (0.10 mL, 1.00 mmol) followed by diisopropylethylamine (0.17 mL, 1.00 mmol). After stirring for 3 h the reaction mixture was diluted with dichloromethane (50 mL) and water (5 mL). The mixture was acidified with 2N aqueous HCl until pH~5. The organic layer was washed with saturated sodium chloride (5 mL), dried over sodium sulfate, filtered, and concentrated under reduced pressure. The residue was purified by chromatography on silica using hexanes/ethyl acetate (10:0 to 1:1) as eluent followed by preparative HPLC (water/acetonitrile with 0.05% TFA) to afford the title compound (0.040 g, 48%) as a colorless oil. MW=421.96. $^1$H NMR (DMSO-$d_6$, 500 MHz) δ 8.37-8.33 (m, 2H), 7.59 (dt, J=7.5, 2.0 Hz, 1H), 7.55 (t, J=7.5 Hz, 1H), 7.29 (d, J=8.0 Hz, 2H), 7.25 (d, J=5.5 Hz, 1H), 7.18 (t, J=8.0 Hz, 2H), 4.10 (s, 2H), 3.63 (d, J=4.0 Hz, 2H), 3.27-3.19 (m, 2H), 2.94 (s, 1.6H), 2.81-2.79 (m, 3.4H), 1.47-1.37 (m, 2H), 1.26 (t, J=7.5 Hz, 3H), 0.80-0.73 (m, 3H); APCI MS m/z 422 [M+H]$^+$.

EXAMPLE 195

2-(4-((2-(3-chlorophenyl)-6-ethylpyrimidin-4-yl)methyl)phenyl)-N-(2-hydroxyethyl)acetamide

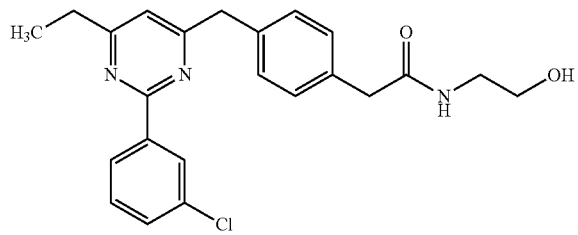 [SMILES: CCc1cc(Cc2ccc(CC(=O)NCCO)cc2)nc(-c2cccc(Cl)c2)n1]

To a stirred solution of crude 2-(4-((2-(3-chlorophenyl)-6-ethylpyrimidin-4-yl)methyl)phenyl)acetyl chloride (~0.20 mmol) in dichloromethane (8 mL) at 0° C. was added ethanolamine (0.060 mL, 1.00 mmol) followed by diisopropylethylamine (0.17 mL, 1.00 mmol). After stirring for 3 h, the reaction mixture was diluted with dichloromethane (50 mL) and water (5 mL). The mixture was acidified with 2N aqueous HCl until pH~5. The organic layer was washed with saturated sodium chloride (5 mL), dried over sodium sulfate, filtered, and concentrated under reduced pressure. The residue was purified by chromatography on silica using hexanes/ethyl acetate (10:0 to 0:10) as eluent followed by preparative HPLC (water/acetonitrile with 0.05% TFA) to afford the title compound (0.036 g, 45%) as a white solid. MW=409.91. M.p. 136-138° C. $^1$H NMR (DMSO-$d_6$, 500 MHz) δ 8.37-8.31 (m, 2H), 8.02-7.96 (m, 1H), 7.59 (dt, J=6.5, 2.0 Hz, 1H), 7.55 (t, J=8.0 Hz, 1H), 7.28 (d, J=8.0 Hz, 2H), 7.25 (s, 1H), 7.20 (d, J=8.0 Hz, 2H), 4.63 (t, J=5.0 Hz, 1H), 4.09 (s, 2H), 3.40-3.35 (m, 4H), 3.90 (q, J=6.0 Hz, 2H), 2.77 (q, J=7.5 Hz, 2H), 1.26 (t, J=7.5 Hz, 3H); APCI MS m/z 410 [M+H]$^+$.

EXAMPLE 196

2-(4-((2-(3-Chlorophenyl)-6-ethylpyrimidin-4-yl)methyl)phenyl)-2-methylpropanamide

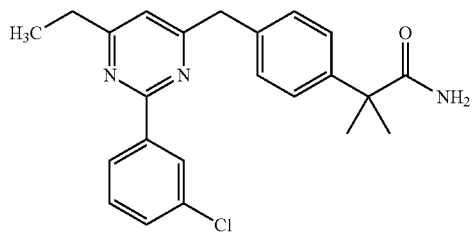 [SMILES: CCc1cc(Cc2ccc(C(C)(C)C(N)=O)cc2)nc(-c2cccc(Cl)c2)n1]

Step 1. Preparation of methyl 2-(p-tolyl)acetate

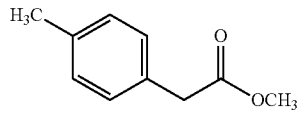

A 500-mL round bottom flask, with stirrer bar, was charged with p-tolylacetic acid (10.0 g, 66.5 mmol) and methanol (240 mL). Concentrated sulfuric acid (0.1 mL) was added at room temperature. The resulting solution was stirred at 65° C. for 18 h. After this time, the mixture was concentrated in vacuo, and the residue was diluted with ethyl acetate (100 mL) and saturated sodium bicarbonate (50 mL). The organic layer was washed with saturated sodium chloride (2×20 mL), dried over sodium sulfate, filtered, and concentrated under reduced pressure to afford the title compound (11.8 g, 100%) as a colorless oil. MW=164.20. $^1$H NMR (CDCl$_3$, 300 MHz) δ 7.20-7.10 (m, 4H), 3.68 (s, 3H), 3.59 (s, 2H), 2.33 (s, 3H).

Step 2: Preparation of methyl 2-methyl-2-(p-tolyl)propanoate

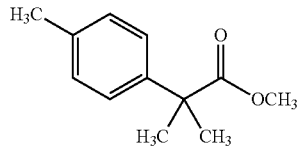

A 500-mL round bottom flask, with stirrer bar, was charged with 2-(p-tolyl)acetate (11.8 g, 66.5 mmol), dimethylformamide (24 mL) and tetrahydrofuran (240 mL) then cooled to 0° C. Sodium hydride (2.92 g, 60% suspension, 73.0 mmol) was added portionwise over 3 minutes. After stirring for 30 minutes, iodomethane (4.55 mL, 73.0 mmol) was added dropwise over 5 minutes and the mixture stirred for 1 hour. After this time, additional sodium hydride (2.92 g, 60% suspension, 73.0 mmol, 1.1 eq.) was added portionwise over 8 minutes to the suspension and the mixture stirred an additional 30 minutes. After this time, iodomethane (4.55 mL, 73.0 mmol) was added dropwise over 5 minutes. The resulting mixture was allowed to slowly warm to room temperature and stirred for 48 h. The reaction was then quenched with water (250 mL) and diluted with MTBE (300 mL). The aqueous layer was separated and extracted with MTBE (3×100 mL). The combined extract was washed with saturated sodium chloride (3×50 mL), then dried over sodium sulfate, filtered, and concentrated under reduced pressure to afford the title compound (13.5 g, 100%) as a colorless oil. MW=192.25. ¹H NMR (CDCl₃, 300 MHz) δ 7.25-7.10 (m, 4H), 3.64 (s, 3H), 2.32 (s, 3H), 1.57 (s, 6H).

Step 3. Preparation of methyl 2-(4-(bromomethyl)phenyl)-2-methylpropanoate

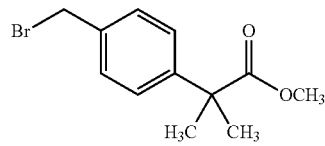

A 500-mL round bottom flask, with stirrer bar, was charged with methyl 2-methyl-2-(p-tolyl)propanoate (2.50 g, 13.0 mmol), NBS (2.31 g, 13.0 mmol), and carbon tetrachloride (240 mL). The resulting solution was heated at reflux and AIBN (0.043 g, 0.26 mmol) was added. After stirring for 3.5 h, the reaction was cooled to room temperature and the solids removed by filtration. The filtrate was concentrated under reduced pressure. The residue was purified by chromatography on silica using hexane/ethyl acetate (100:0 to 80:20) as eluent as eluent to afford the title compound (2.20 g, 62%.) as a colorless oil. MW=271.15. ¹H NMR (CDCl₃, 300 MHz) δ 7.39-7.28 (m, 4H), 4.48 (s, 2H), 3.65 (s, 3H), 1.57 (s, 6H).

Step 4: Preparation of ethyl 2-methyl-2-(4-((4,4,5,5-tetramethyl-1,3,2-dioxaborolan-2-yl)methyl)phenyl)propanoate

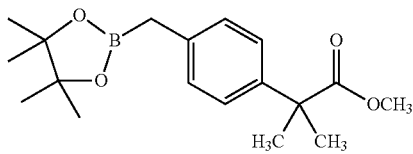 [SMILES: COC(=O)C(C)(C)c1ccc(CB2OC(C)(C)C(C)(C)O2)cc1]

A 500-mL round bottom flask, with stirrer bar, was charged with methyl 2-(4-(bromomethyl)phenyl)-2-methylpropanoate (2.06 g, 7.59 mmol), pinacol diborane (2.31 g, 9.11 mmol), tetrakis(triphenylphosphine)palladium(0) (0.88 g, 0.76 mmol), and K₂CO₃ (3.15 g, 22.8 mmol). Dioxane (60 mL) was added and the resulting mixture was stirred under Ar at 80° C. for 20 h. After this time, the mixture was cooled to room temperature, diluted with ethyl acetate (200 mL), and filtered through celite. The filtrate was washed with brine (4×50 mL), dried over sodium sulfate, filtered, and concentrated under reduced pressure. The residue (4.4 g) was purified by chromatography on silica using hexane/ethyl acetate (100:0 to 50:50) as eluent to afford the title compound (1.07 g, 44%) as a colorless oil. MW=318.22. ¹H NMR (CDCl₃, 500 MHz) δ 7.22-7.11 (m, 4H), 3.64 (s, 3H), 2.26 (s, 2H), 1.55 (s, 6H), 1.24 (s, 12H).

Step 5: Preparation of methyl 2-(4-((2-(3-chlorophenyl)-6-ethylpyrimidin-4-yl)methyl)phenyl)-2-methylpropanoate

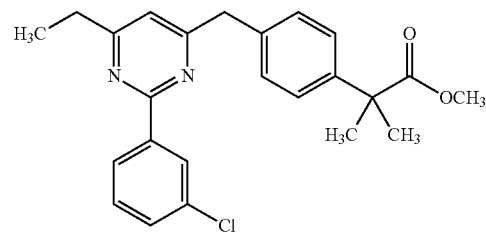 [SMILES: CCc1cc(Cc2ccc(C(C)(C)C(=O)OC)cc2)nc(-c2cccc(Cl)c2)n1]

A 20-mL sealed tube, with stirrer bar, was charged with 4-chloro-2-(3-chlorophenyl)-6-ethylpyrimidine (0.303 g, 1.20 mol), methyl 2-methyl-2-(4-((4,4,5,5-tetramethyl-1,3,2-dioxaborolan-2-yl)methyl)phenyl)propanoate (0.420 g, 1.32 mmol), Pd(dppf)Cl₂ (0.098 g, 0.12 mmol), and powdered Na₂CO₃ (0.380 g, 3.60 mmol). Dioxane (6 mL) and water (3 mL) were added. The resulting mixture was stirred under Ar at 90° C. for 2 h. After this time, the mixture was cooled to room temperature and filtered through celite washing with ethyl acetate until the filtrate was colorless. The filtrate was washed with saturated sodium chloride (3×25 mL) then dried over sodium sulfate, filtered, and concentrated under reduced pressure. The residue (0.87 g) was purified by chromatography on silica using hexane/dichloromethane (10:0 to 8:2) as eluent to afford the title compound (0.47 g, 96%) as a colorless oil. MW=408.92. ¹H NMR (CDCl₃, 300 MHz) δ 8.50-8.47 (m, 1H), 8.40-8.35 (m, 1H), 7.46-7.37 (m, 2H), 7.31-7.24 (m, 4H), 6.87 (s, 1H), 4.10 (s, 2H), 3.65 (s, 3H), 2.77 (q, J=7.8 Hz, 2H), 1.57 (s, 6H), 1.32 (t, J=7.5 Hz, 3H).; ESI MS m/z 409 [M+H]⁺.

Step 6. Preparation of 2-(4-((2-(3-Chlorophenyl)-6-ethylpyrimidin-4-yl)methyl)phenyl)-2-methylpropanoic acid

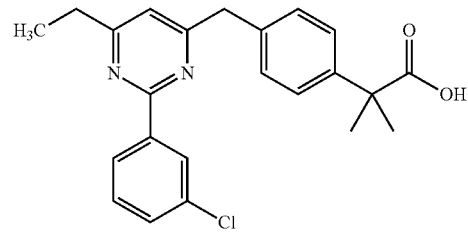 [SMILES: CCc1cc(Cc2ccc(C(C)(C)C(=O)O)cc2)nc(-c2cccc(Cl)c2)n1]

An 250-mL round bottom flask was charged with methyl 2-(4-((2-(3-chlorophenyl)-6-ethylpyrimidin-4-yl)methyl)phenyl)-2-methylpropanoate (0.472 g, 1.15 mmol), dioxane (24 ml) and water (12 ml). To this solution was then added lithium hydroxide monohydrate (0.242 g, 5.77 mmol). The resulting mixture was stirred at 50° C. for 7 h. After this time the reaction mixture was cooled and treated with 2M aqueous HCl until pH~5. The volatile materials were removed under reduced pressure to afford the title compound (0.70 g, >100%) as a white solid. MW=394.89. ¹H NMR (DMSO-d₆, 500 MHz) δ 12.26 (br s, 1H), 8.38-8.34 (m, 2H), 7.61-7.53 (m, 2H), 7.35-7.27 (m, 5H), 4.09 (s, 2H), 2.78 (q, J=8.0 Hz, 2H), 1.44 (s, 6H), 1.27 (t, J=7.5 Hz, 3H). ESI MS m/z 395 [M+H]⁺.

EXAMPLE 196

2-(4-((2-(3-Chlorophenyl)-6-ethylpyrimidin-4-yl)methyl)phenyl)-2-methylpropanamide

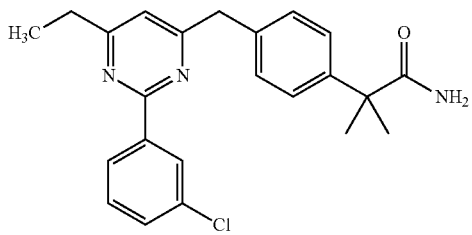 [SMILES: CCc1cc(Cc2ccc(C(C)(C)C(N)=O)cc2)nc(-c2cccc(Cl)c2)n1]

An 250-mL round bottom flask was charged with 2-(4-((2-(3-chlorophenyl)-6-ethylpyrimidin-4-yl)methyl)phenyl)-2-methylpropanoic acid (0.35 g, ~0.57 mmol) in dichloromethane (10 ml) and dioxane (10 mL). To this mixture at 0° C. was added oxalyl chloride (0.24 mL, 2.87 mmol) followed by DMF (1 drop). After stirring for 6 h, the volatile material was removed under reduced pressure to afford crude acid chloride. The residue was dissolved in dichloromethane (24 mL), cooled to 0° C. and 7N ammonia in methanol (10.0 mL, 70 mmol) was added.

After stirring for 15 h the volatile material was removed under reduced pressure. The residue was diluted with dichloromethane (125 mL) and washed with saturated sodium chloride (3×15 mL), dried over sodium sulfate, filtered and concentrated under reduced pressure. The residue was purified by chromatography on silica using hexanes/ethyl acetate as eluent followed by preparative HPLC (water/acetonitrile with 0.05% TFA) to afford the title compound (0.057 g, 24%) as a yellow-orange solid. MW=393.91. M.p. 35-37° C. $^1$H NMR (DMSO-$d_6$, 500 MHz) δ 8.38-8.34 (m, 2H), 7.61-7.54 (m, 2H), 7.34-7.27 (m, 5H), 6.82 (br s, 2H), 4.09 (s, 2H), 2.78 (q, J=7.5 Hz, 2H), 1.40 (s, 6H), 1.27 (t, J=7.5 Hz, 3H). APCI MS m/z 394 [M+H]$^+$.

EXAMPLE 197

2-(4-((2-(3-Chlorophenyl)-6-ethylpyrimidin-4-yl)methyl)phenyl)-2-methylpropan-1-ol

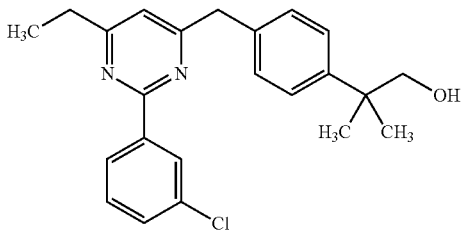 [SMILES: CCc1cc(Cc2ccc(C(C)(C)CO)cc2)nc(-c2cccc(Cl)c2)n1]

A 25-mL round bottom flask was charged with methyl 2-(4-((2-(3-chlorophenyl)-6-ethylpyrimidin-4-yl)methyl)phenyl)-2-methylpropanoate (0.259 g, 0.57 mmol) and THF (6 mL) at rt. Borane-dimethylsulfide complex (0.158 mL, 1.67 mmol) was added and the resulting solution was stirred at 55° C. for 2.5 h. LCMS analysis indicated only partial reduction. Borane-dimethylsulfide complex (0.100 mL, 1.05 mmol) was added and the resulting solution was stirred at 55° C. for a further 19 h until the starting material was consumed (monitored by LCMS analysis). The reaction was quenched with methanol then treated with 2N aqueous HCl (0.1 mL) and concentrated under reduced pressure. The residue was diluted with methanol and then concentrated under reduced pressure. The residue absorbed onto silica (2 g) then purified by column chromatography on silica using hexanes/ethyl acetate (10:0 to 0:10) as the eluent to afford the title compound (0.078 g, 36%) as a colorless oil. MW=380.91. $^1$H NMR (DMSO-$d_6$, 500 MHz) δ 8.38-8.34 (m, 2H), 7.61-7.54 (m, 2H), 7.33-7.26 (m, 5H), 4.60 (t, J=5.5 Hz, 1H), 4.07 (s, 2H), 3.38 (d, J=5.5 Hz, 2H), 2.78 (q, J=7.5 Hz, 2H), 1.27 (t, J=7.5 Hz, 3H), 1.18 (s, 6H); APCI MS m/z 381 [M+H]$^+$.

EXAMPLE 198

2-(4-((2-(Cyclopentyloxy)-6-(trifluoromethyl)pyrimidin-4-yl)amino)phenyl)acetamide

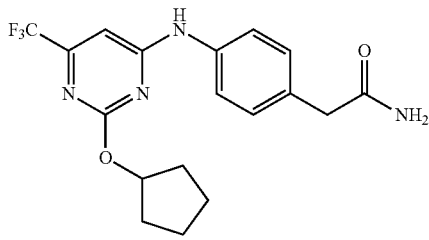 [SMILES: NC(=O)Cc1ccc(Nc2cc(C(F)(F)F)nc(OC3CCCC3)n2)cc1]

Step 1. Preparation of 4-chloro-2-(methylsulfonyl)-6-(trifluoromethyl)pyrimidine

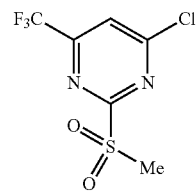 [SMILES: CS(=O)(=O)c1nc(Cl)cc(C(F)(F)F)n1]

A 250-mL round bottom flask was charged with 4-chloro-2-(methylthio)-6-(trifluoromethyl)pyrimidine (2.50 g, 10.9 mmol) in dichloromethane (20 mL). To this solution at 0° C. was added a solution of m-CPBA in dichloromethane (40 mL) over 7 minutes. After stirring for 7 h, the reaction mixture diluted with dichloromethane and washed with saturated sodium thiosulfate (25 mL), saturated sodium carbonate (2×10 mL), and saturated sodium chloride (2×10 mL). The organic layer was dried over sodium sulfate, filtered, and concentrated under reduced pressure to afford the title compound (2.89 g, 100%) as a white solid. MW=260.62. $^1$H NMR (CDCl$_3$, 300 MHz) δ 7.90 (s, 1H), 3.44 (s, 3H).

Step 2. Preparation of 4-chloro-2-(cyclopentyloxy)-6-(trifluoromethyl)pyrimidine

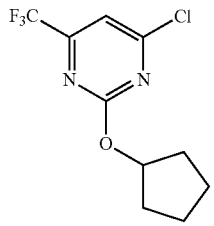 [SMILES: FC(F)(F)c1cc(Cl)nc(OC2CCCC2)n1]

To a stirred solution of cyclopentanol (0.61 mL, 6.75 mmol) in tetrahydrofuran (24 mL) at 0° C. was added potassium tert-butoxide (0.76 g, 6.75 mmol). The resulting yellow solution was added dropwise to a stirred solution of 4-chloro-2-(methylsulfonyl)-6-(trifluoromethyl)pyrimidine (1.76 g, 6.75 mmol) in tetrahydrofuran (24 mL) at −78° C. over 15 minutes. The reaction was then stirred at −78° C. for 2 h then allowed to warm to rt. After stirring for 15 h at room temperature, the reaction was quenched with water (20 mL) and diluted with ethyl acetate (200 mL). The aqueous layer was extracted with ethyl acetate (2×74 mL). The combined organic extract was washed with saturated sodium chloride (2×20 mL), dried over sodium sulfate, filtered, and concentrated under reduced pressure. The residue was purified by chromatography on silica using hexanes/ethyl acetate (10:0 to 0:10) as eluent to afford the title compound (0.60 g, 33%) as a colorless oil. MW=266.65. $^1$H NMR (CDCl$_3$, 500 MHz) δ 7.26 (s, 1H), 5.48 (sept, J=3.0 Hz, 1H), 2.08-1.76 (m, 6H), 1.75-1.58 (m, 2H).

EXAMPLE 198

2-(4-((2-(Cyclopentyloxy)-6-(trifluoromethyl)pyrimidin-4-yl)amino)phenyl)acetamide

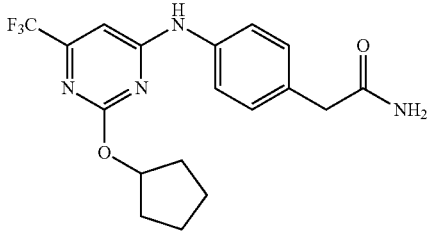 [SMILES: NC(=O)Cc1ccc(Nc2cc(C(F)(F)F)nc(OC3CCCC3)n2)cc1]

A 10-mL microwave vial was charged with 4-chloro-2-(cyclopentyloxy)-6-(trifluoromethyl)pyrimidine (0.090 g, 0.34 mmol) and (4-aminophenyl)acetamide (0.076 g, 0.51 mmol) in NMP (3 mL). The resulting mixture was heated at 120° C. under microwave irradiation for 1 h. The reaction mixture was cooled, diluted with water (50 mL) affording a solid. The solid was isolated by filtration and chromatography on silica using hexanes/ethyl acetate (10:0 to 0:10) as eluent to afford the title compound (0.067 g, 52%) as a white solid. MW=380.36. M.p. 208-210° C. $^1$H NMR (DMSO-d$_6$, 500 MHz) δ 10.05 (s, 1H), 7.58 (br d, J=7.5 Hz, 2H), 7.42 (s, 1H), 7.25 (d, J=7.5 Hz, 2H), 6.85 (s, 1H), 6.74 (s, 1H), 5.31 (septet, J=3.0 Hz, 1H), 2.01-1.90 (m, 2H), 1.80-1.66 (m, 4H), 1.65-1.55 (m, 2H); APCI MS m/z 381 [M+H]$^+$.

EXAMPLE 199

2-(4-((2-(Cyclopentyloxy)-6-(trifluoromethyl)pyrimidin-4-yl)amino)phenyl)ethanol

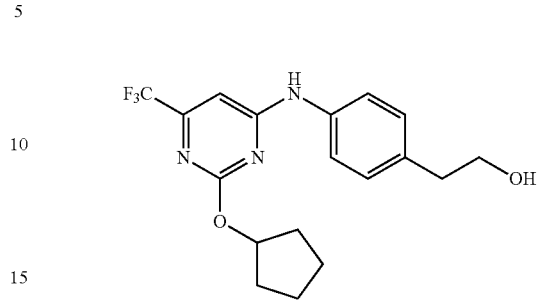

A 10-mL microwave vial was charged with 4-chloro-2-(cyclopentyloxy)-6-(trifluoromethyl)pyrimidine (0.090 g, 0.34 mmol) and (4-aminophenyl)ethyl alcohol (0.069 g, 0.51 mmol) in NMP (3 mL). The resulting mixture was heated at 120° C. under microwave irradiation for 1 h. After this time, the reaction mixture was cooled and diluted with water (50 mL) affording a solid. The solid was isolated by filtration and chromatography on silica using hexanes/ethyl acetate (10:0 to 0:10) as eluent to afford the title compound (0.087 g, 70%) as a white solid. MW=367.37. M.p. 173-175° C. $^1$H NMR (DMSO-d$_6$, 500 MHz) δ 10.01 (s, 1H), 7.56 (br d, J=7.0 Hz, 2H), 7.22 (d, J=8.5 Hz, 2H), 6.73 (s, 1H), 5.30 (septet, J=3.0 Hz, 1H), 4.61 (t, J=5.0 Hz, 1H), 3.62-3.57 (m, 2H), 2.70 (t, J=7.0 Hz, 2H), 2.00-1.90 (m, 2H), 1.80-1.66 (m, 4H), 1.65-1.55 (m, 2H); APCI MS m/z 368 [M+H]$^+$.

EXAMPLE 200

2-(4-((2-(Cyclopentyloxy)-6-(trifluoromethyl)pyrimidin-4-yl)methyl)phenyl)acetic acid

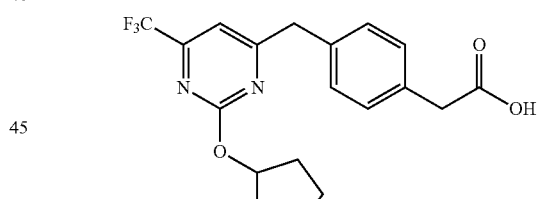

Step 1. Preparation of methyl 2-(4-((2-(cyclopentyloxy)-6-(trifluoromethyl)pyrimidin-4-yl)methyl)phenyl)acetate

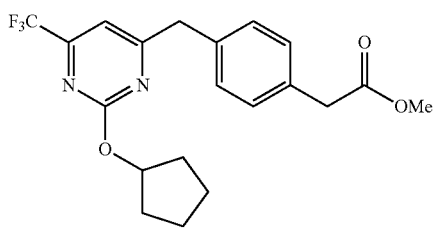 [SMILES: COC(=O)Cc1ccc(Cc2cc(C(F)(F)F)nc(OC3CCCC3)n2)cc1]

A 20-mL sealed tube, with stirrer bar, was charged with 4-chloro-2-(cyclopentyloxy)-6-(trifluoromethyl)pyrimidine (0.400 g, 1.50 mol), methyl 2-(4-((4,4,5,5-tetramethyl-1,3,2-dioxaborolan-2-yl)methyl)phenyl)acetate (0.478 g, 1.65 mmol), Pd(dppf)Cl$_2$ (0.122 g, 0.15 mmol), and powdered Na$_2$CO$_3$ (0.477 g, 4.50 mmol). Dioxane (8 mL) and water (4 mL) were added. The resulting mixture was stirred under Ar at 90° C. for 2.5 h. After this time, the mixture was cooled to room temperature and filtered through celite washing with ethyl acetate until the filtrate was colorless. The aqueous layer was separated and the organic layer was washed with saturated sodium chloride (2×10 mL) then dried over sodium sulfate, filtered and concentrated under reduced pressure. The residue was purified by chromatography on silica using hexane/ethyl acetate (10:0 to 3:1) as eluent to afford the title compound (0.40 g, 67%) as a yellow oil. MW=394.39. $^1$H NMR (CDCl$_3$, 300 MHz) δ 7.25 (s, 4H), 7.14 (s, 1H), 5.46 (septet, J=3.0 Hz, 1H), 4.08 (s, 2H), 3.69 (s, 3H), 3.62 (s, 2H), 2.04-1.73 (m, 6H), 1.72-1.56 (m, 2H); ESI MS m/z 327 [M-C$_5$H$_9$+2H]$^+$.

EXAMPLE 200

2-(4-((2-(Cyclopentyloxy)-6-(trifluoromethyl)pyrimidin-4-yl)methyl)phenyl)acetic acid

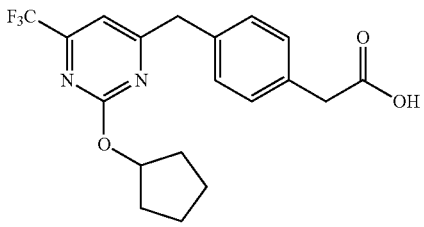 [SMILES: O=C(O)Cc1ccc(Cc2cc(C(F)(F)F)nc(OC3CCCC3)n2)cc1]

An 100-mL round bottom flask was charged with methyl 2-(4-((2-(cyclopentyloxy)-6-(trifluoromethyl)pyrimidin-4-yl)methyl)phenyl)acetate (0.100 g, 0.25 mmol), dioxane (6 ml) and water (3 ml). To this solution was then added lithium hydroxide monohydrate (0.053 g, 1.26 mmol). The resulting mixture was stirred at 50° C. for 1.5 h. The cooled reaction mixture was treated with 2N aqueous HCl until pH~5, then diluted with ethyl acetate (75 mL). The organic layer was washed with saturated sodium chloride (5 mL), dried over sodium sulfate, filtered, and concentrated under reduced pressure. The residue was purified by chromatography on silica using hexane/ethyl acetate (10:0 to 0:10) as the eluent, followed by preparative HPLC (water/acetonitrile with 0.05% TFA) to afford the title compound (0.051 g, 53%) as an off-white solid. MW=380.36. M.p. 97-99° C. $^1$H NMR (DMSO-d$_6$, 500 MHz) δ 12.28 (br s, 1H), 7.52 (s, 1H), 7.28 (d, J=8.0 Hz, 2H), 7.20 (d, J=8.0 Hz, 2H), 5.35 (septet, J=3.0 Hz, 1H), 4.11 (s, 2H), 3.52 (s, 2H), 2.00-1.89 (m, 2H), 1.77-1.65 (m, 4H), 1.65-1.55 (m, 2H); APCI MS m/z 381 [M+H]$^+$.

EXAMPLE 201

2-(4-((2-(Cyclopentyloxy)-6-(trifluoromethyl)pyrimidin-4-yl)methyl)phenyl)acetamide

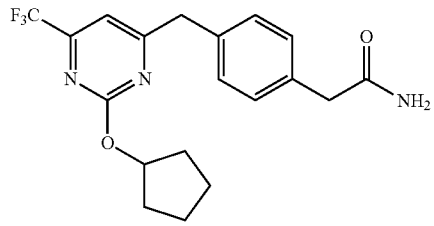 [SMILES: NC(=O)Cc1ccc(Cc2cc(C(F)(F)F)nc(OC3CCCC3)n2)cc1]

A 20-mL vial was charged with methyl 2-(4-((2-(cyclopentyloxy)-6-(trifluoromethyl)pyrimidin-4-yl)methyl)phenyl)acetate (0.150 g, 0.38 mmol) in methanol (2 mL). To this mixture was added NH$_3$ (10.8 mL, 7N in methanol, 76.0 mmol). The vial was sealed and the resulting mixture was stirred at 100° C. for 23 h. The crude reaction solution concentrated under reduced pressure. The residue was purified by chromatography on silica using hexanes/ethyl acetate (10:0 to 0:10) as eluent followed by chromatography on silica using dichloromethane/methanol (10:0 to 96:4) as eluent to afford the title compound (0.066 g, 46%) as a white solid. MW=379.38. M.p. 130-132° C. $^1$H NMR (DMSO-d$_6$, 500 MHz) δ 7.51 (s, 1H), 7.41 (br s, 1H), 7.26 (d, J=8.0 Hz, 2H), 7.20 (d, J=8.0 Hz, 2H), 6.83 (br s, 1H), 5.35 (septet, J=3.0 Hz, 1H), 4.10 (s, 2H), 3.33 (s, 2H), 2.00-1.90 (m, 2H), 1.77-1.66 (m, 4H), 1.65-1.55 (m, 2H); ESI MS m/z 380 [M+H]$^+$.

EXAMPLE 202

2-(4-((2-(Cyclopentyloxy)-6-(trifluoromethyl)pyrimidin-4-yl)methyl)phenyl)ethanol

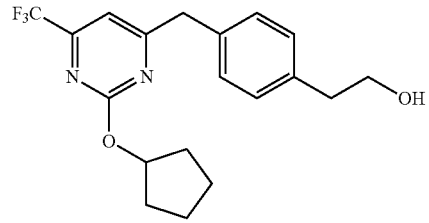 [SMILES: OCCc1ccc(Cc2cc(C(F)(F)F)nc(OC3CCCC3)n2)cc1]

A 25-mL round bottom flask was charged with methyl 2-(4-((2-(cyclopentyloxy)-6-(trifluoromethyl)pyrimidin-4-yl)methyl)phenyl)acetate (0.069 g, 0.17 mmol) and dichloromethane (6 mL) at 0° C. A 1M solution of DIBAL-H in THF (0.70 mL, 0.70 mmol) was added and the resulting solution was stirred at 0° C. for 1 h until the starting material was consumed (monitored by LCMS analysis). The reaction was quenched with methanol then absorbed onto silica (2 g) and concentrated under reduced pressure. Purification by column chromatography on silica using hexanes/ethyl acetate (10:0 to 1:1) as the eluent afforded the title compound (0.055 g, 87%) as a white solid. MW=366.38. M.p. 48-50° C. $^1$H NMR (DMSO-d$_6$, 500 MHz) δ 7.51 (s, 1H), 7.23 (d, J=7.5 Hz, 2H), 7.16 (d, J=8.0 Hz, 2H), 5.38-5.32 (m, 1H), 4.58 (t, J=5.5 Hz, 1H), 4.09 (s, 2H), 3.56 (q, J=6.0 Hz, 2H), 2.68 (t, J=7.0 Hz, 2H), 2.00-1.89 (m, 2H), 1.77-1.66 (m, 4H), 1.66-1.55 (m, 2H); APCI MS m/z 367 [M+H]+.

EXAMPLE 203

Methyl 2-(4-((2-(3-chlorophenyl)-6-(trifluoromethyl)pyrimidin-4-yl)methyl)phenyl)acetate

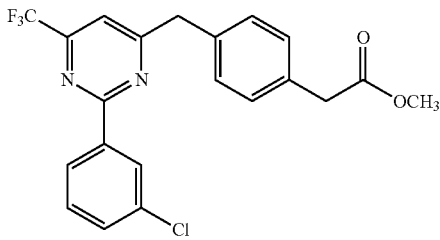 [SMILES: COC(=O)Cc1ccc(Cc2cc(C(F)(F)F)nc(-c3cccc(Cl)c3)n2)cc1]

Step 1. Preparation of 2-(3-chlorophenyl)-6-(trifluoromethyl)pyrimidin-4(3H)-one

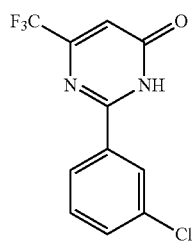 [SMILES: O=c1cc(C(F)(F)F)nc(-c2cccc(Cl)c2)[nH]1]

A 500-mL round bottomed flask was charged with 3-chlorobenzimidamide (4.81 g, 25.3 mmol), ethyl 4,4,4-trifluoro-3-oxobutanoate (5.00 g, 27.1 mmol), and ethanol (90 mL) and cooled to 0° C. A 25% sodium methoxide solution in methanol (13.0 mL, 55.3 mmol) was added to the mixture. The resulting mixture was stirred at reflux for 20 h. After this time, the mixture was cooled to room temperature and concentrated under reduced pressure to 25 mL. The residual slurry was cautiously treated with 2N HCl (50 mL) forming a solid. The solid was collected by filtration and washed with water followed by ether to afford the title compound (3.60 g, 48%) as a white solid, which was carried forward into the next step without further purification. MW=274.63. $^1$H NMR (DMSO-$d_6$, 500 MHz) δ 13.39 (s, 1H), 8.18 (s, 1H), 8.10 (d, J=7.5 Hz, 1H), 7.73-7.69 (m, 1H), 7.60 (t, J=8.0 Hz, 1H), 6.94 (s, 1H).

Step 2. Preparation of 4-chloro-2-(3-chlorophenyl)-6-(trifluoromethyl)pyrimidine

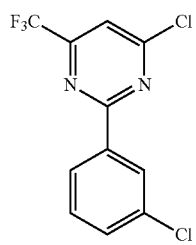 [SMILES: FC(F)(F)c1cc(Cl)nc(-c2cccc(Cl)c2)n1]

A 250-mL round bottom flask was charged with 2-(3-chlorophenyl)-6-(trifluoromethyl)pyrimidin-4(3H)-one (3.60 g, 13.1 mmol). POCl$_3$ (14.4 mL, 157 mmol) was cautiously added at 0° C. The resulting mixture was stirred at 100° C. for 3.5 h. After cooling to room temperature, the mixture was concentrated under reduced pressure. The residue was dissolved in dichloromethane (50 mL) and treated with aqueous sodium bicarbonate until the pH~8. The aqueous layer was extracted with dichloromethane (4×25 mL). The combined organic extract was washed the saturated sodium chloride (20 mL), dried over sodium sulfate, filtered, and concentrated under reduced pressure. The residue was purified by silica chromatography using hexanes/dichloromethane (3:1) as eluent to afford the title compound (3.36 g, 87%) as a white solid. MW=293.07. $^1$H NMR (CDCl$_3$, 500 MHz) δ 8.49 (t, J=1.5 Hz, 1H), 8.39 (dt, J=8.0, 1.5 Hz, 1H), 7.57 (s, 1H), 7.53 (ddd, J=8.0, 2.0, 1.0 Hz, 1H), 7.45 (t, J=8.0 Hz, 1H).

EXAMPLE 203

Methyl 2-(4-((2-(3-chlorophenyl)-6-(trifluoromethyl)pyrimidin-4-yl)methyl)phenyl)acetate

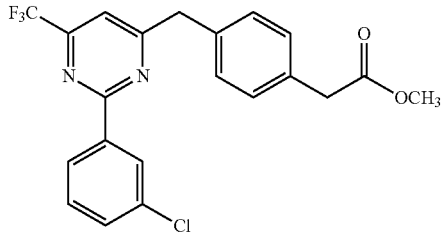 [SMILES: COC(=O)Cc1ccc(Cc2cc(C(F)(F)F)nc(-c3cccc(Cl)c3)n2)cc1]

A 20-mL sealed tube, with stirrer bar, was charged with 4-chloro-2-(3-chlorophenyl)-6-(trifluoromethyl)pyrimidine (0.404 g, 1.38 mol), methyl 2-(4-((4,4,5,5-tetramethyl-1,3,2-dioxaborolan-2-yl)methyl)phenyl)acetate (0.400 g, 1.38 mmol), Pd(dppf)Cl$_2$ (0.113 g, 0.14 mmol), and powdered Na$_2$CO$_3$ (0.438 g, 4.14 mmol). Dioxane (6 mL) and water (3 mL) were added. The resulting mixture was stirred under Ar at 90° C. for 1.25 h. After this time, the mixture was cooled to room temperature and filtered through celite washing with ethyl acetate until the filtrate was colorless. The aqueous layer was separated and the organic layer was washed with saturated sodium chloride (2×5 mL) then dried over sodium sulfate, filtered, and concentrated under reduced pressure. The residue was purified by chromatography on silica using hexane/ethyl acetate (95:5 to 2:1) as eluent to afford the title compound (0.284 g, 49%) as a light orange solid. MW=420.81. M.p. 70-72° C. $^1$H NMR (DMSO-$d_6$, 500 MHz) δ 8.36-8.33 (m, 2H), 7.68 (ddd, J=8.0, 2.0, 1.0 Hz, 1H), 7.62 (t, J=8.0 Hz, 1H), 7.37 (d, J=7.0 Hz, 2H), 7.24 (d, J=8.0 Hz, 2H), 4.31 (s, 2H), 3.64 (s, 2H), 3.59 (s, 3H); ESI MS m/z 421 [M+H]+.

EXAMPLE 204

2-(4-((2-(3-Chlorophenyl)-6-(trifluoromethyl)pyrimidin-4-yl)methyl)phenyl)acetamide

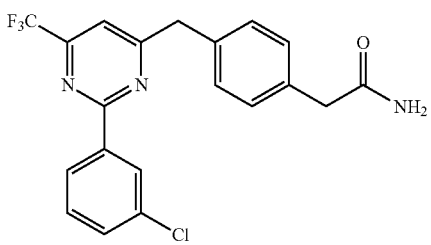 [SMILES: NC(=O)Cc1ccc(Cc2cc(C(F)(F)F)nc(-c3cccc(Cl)c3)n2)cc1]

A 20-mL vial was charged with methyl 2-(4-((2-(3-chlorophenyl)-6-(trifluoromethyl)pyrimidin-4-yl)methyl)phenyl)acetate (0.136 g, 0.32 mmol) and ammonium chloride (0.052 g, 0.97 mmol, 3.0 eq.) in methanol (4 mL). To this mixture was added $NH_3$ (8.0 mL, 7N in methanol, 56.0 mmol). The vial was sealed and the resulting mixture was stirred at 100° C. for 70 h. After this time, the crude reaction was concentrated under reduced pressure and the residue absorbed on silica (2 g) then purified by chromatography on silica using hexanes/ethyl acetate (10:0 to 0:10) as eluent followed by preparative HPLC (water/acetonitrile with 0.05% TFA) to afford the title compound (0.088 g, 67%) as a white solid. MW=405.80. M.p. 170-172° C. $^1$H NMR (DMSO-$d_6$, 500 MHz) δ 8.37-8.33 (m, 2H), 7.93 (s, 1H), 7.68 (ddd, J=8.0, 2.0, 1.0 Hz, 1H), 7.62 (t, J=8.0 Hz, 1H), 7.43 (br s, 1H), 7.34 (d, J=8.0 Hz, 2H), 7.23 (d, J=8.0 Hz, 2H), 6.82 (br s, 1H), 4.30 (s, 2H), 3.33 (s, 2H); APCI MS m/z 406 [M+H]$^+$.

EXAMPLE 205

2-(4-((2-(3-Chlorophenyl)-6-(trifluoromethyl)pyrimidin-4-yl)methyl)phenyl)ethanol

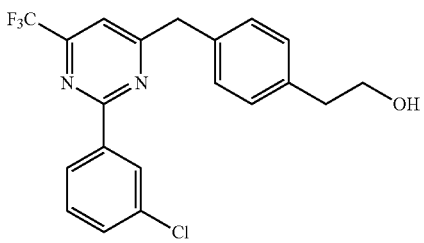 [SMILES: OCCc1ccc(Cc2cc(C(F)(F)F)nc(-c3cccc(Cl)c3)n2)cc1]

A 25-mL round bottom flask was charged with methyl 2-(4-((2-(3-chlorophenyl)-6-(trifluoromethyl)pyrimidin-4-yl)methyl)phenyl)acetate (0.126 g, 0.30 mmol) and THF (4 mL) at rt. Borane-dimethylsulfide complex (0.085 mL, 0.90 mmol) was added and the resulting solution was stirred at 55° C. for 2 h. LCMS analysis indicated only partial reduction. Borane-dimethylsulfide complex (0.045 mL, 0.47 mmol) was added and the resulting solution was stirred at 55° C. for a further 2.5 h until the starting material was consumed (monitored by LCMS analysis). The reaction was quenched with methanol then treated with 2N aqueous HCl (5 drops) and concentrated under reduced pressure. The residue was diluted with methanol and then concentrated under reduced pressure. The residue absorbed onto silica (2 g) then purified by column chromatography on silica using hexanes/ethyl acetate (10:0 to 3:1) as the eluent to afford the title compound (0.086 g, 73%) as an orange solid. MW=392.80. M.p. 78-80° C. $^1$H NMR (DMSO-$d_6$, 500 MHz) δ 8.37-8.33 (m, 2H), 7.93 (s, 1H), 7.68 (ddd, J=8.0, 2.0, 1.0 Hz, 1H), 7.62 (t, J=8.0 Hz, 1H), 7.32 (d, J=8.0 Hz, 2H), 7.18 (d, J=8.0 Hz, 2H), 4.59 (br s, 1H), 4.28 (s, 2H), 3.57 (d, J=7.0 Hz, 2H), 2.68 (d, J=7.0 Hz, 2H); APCI MS m/z 393 [M+H]$^+$.

EXAMPLE 206

2-(4-((2-(3-Chlorophenyl)-6-cyclopropylpyrimidin-4-yl)amino)phenyl)ethanol

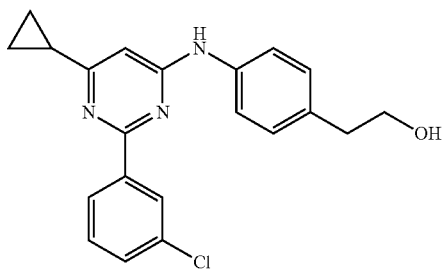 [SMILES: OCCc1ccc(Nc2cc(C3CC3)nc(-c3cccc(Cl)c3)n2)cc1]

Step 1. Preparation of 2-(3-chlorophenyl)-6-cyclopropylpyrimidin-4(3H)-one

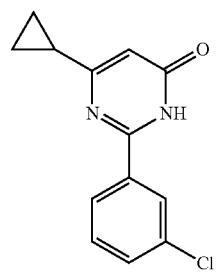 [SMILES: O=c1cc(C2CC2)nc(-c2cccc(Cl)c2)[nH]1]

A 500-mL round bottomed flask was charged with 3-chlorobenzimidamide (5.75 g, 30.1 mmol), ethyl 3-cyclopropyl-3-oxopropanoate (5.00 g, 32.0 mmol), and ethanol (100 mL) and the mixture cooled to 0° C. To the stirred mixture was added 25% sodium methoxide in methanol (15.0 mL, 64.0 mmol). The resulting mixture was stirred at reflux for 20 h. After cooling to room temperature, the mixture was evaporated under reduced pressure to 25 mL. The residual slurry was cautiously treated with 2N HCl (50 mL) forming a solid. The solid was collected by filtration and washed with water followed by ether to afford the title compound (2.46 g, 31%) as a white solid, which was carried forward into the next step without further purification. MW=246.69. $^1$H NMR (DMSO-$d_6$, 500 MHz) δ 12.55 (s, 1H), 8.13 (s, 1H), 8.06 (d, J=7.5 Hz, 1H), 7.64-7.60 (m, 1H), 7.54 (t, J=8.0 Hz, 1H), 6.34 (s, 1H), 2.00-1.93 (m, 1H), 1.08-1.02 (m, 2H), 0.99-0.91 (m, 2H).

Step 2. Preparation of 4-chloro-2-(3-chlorophenyl)-6-cyclopropylpyrimidine

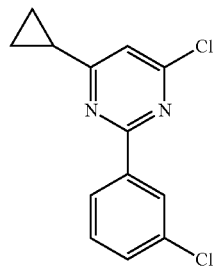 [SMILES: Clc1cccc(-c2nc(Cl)cc(C3CC3)n2)c1]

A 250-mL round bottom flask was charged with 2-(3-chlorophenyl)-6-cyclopropylpyrimidin-4(3H)-one (2.46 g, 9.97 mmol). POCl$_3$ (11.0 mL, 120 mmol) was cautiously added at 0° C. The resulting mixture was stirred at 100° C. for 1.5 h. After cooling to room temperature, the mixture was concentrated under reduced pressure. The residue was dissolved in dichloromethane (50 mL) treated with aqueous sodium bicarbonate until the pH~8. The aqueous layer was extracted with dichloromethane (4×25 mL). The combined organic extract was washed the saturated sodium chloride (20 mL), dried over sodium sulfate, filtered, and concentrated under reduced pressure. The residue was purified by silica chromatography using hexanes/dichloromethane (3:1) as eluent to afford the title compound (2.55 g, 96%) as a white solid. MW=265.14. $^1$H NMR (CDCl$_3$, 500 MHz) δ 8.38 (t, J=1.5 Hz, 1H), 8.28 (dt, J=8.0, 1.5 Hz, 1H), 7.44 (ddd, J=8.0, 2.0, 1.0 Hz, 1H), 7.38 (t, J=8.0 Hz, 1H), 7.12 (s, 1H), 2.04-1.97 (m, 1H), 1.33-1.27 (m, 2H), 1.18-1.13 (m, 2H).

EXAMPLE 206

2-(4-((2-(3-Chlorophenyl)-6-cyclopropylpyrimidin-4-yl)amino)phenyl)ethanol

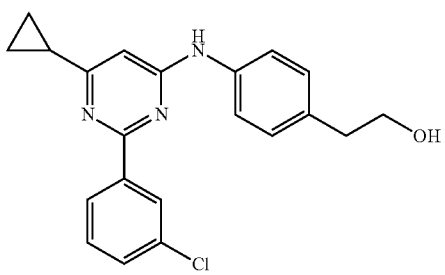 [SMILES: OCCc1ccc(Nc2cc(C3CC3)nc(-c3cccc(Cl)c3)n2)cc1]

A 10-mL microwave vial was charged with 4-chloro-2-(3-chlorophenyl)-6-cyclopropylpyrimidine (0.100 g, 0.38 mmol) and 4-aminophenethyl alcohol (0.103 g, 0.75 mmol) in NMP (3 mL). The resulting mixture was heated at 120° C. under microwave irradiation for 1 h. The reaction mixture was cooled, diluted with water (20 mL) affording a solid. The solid was isolated by filtration and purified by chromatography on silica using hexanes/ethyl acetate (10:0 to 1:1) as eluent to afford the title compound (0.101 g, 73%) as a white solid. MW=365.86. M.p. 124-126° C. $^1$H NMR (DMSO-d$_6$, 500 MHz) δ 9.46 (s, 1H), 8.27-8.21 (m, 2H), 7.62-7.51 (m, 4H), 7.21 (d, J=8.5 Hz, 2H), 6.62 (s, 1H), 4.61 (br s, 1H), 3.60 (t, J=7.0 Hz, 2H), 2.70 (t, J=7.0 Hz, 2H), 2.06-1.99 (m, 1H), 1.11-1.06 (m, 2H), 1.02-0.95 (m, 2H); ESI MS m/z 366 [M+H]$^+$.

EXAMPLE 207

2-(4-((2-(3-Chlorophenyl)-6-cyclopropylpyrimidin-4-yl)amino)phenyl)acetamide

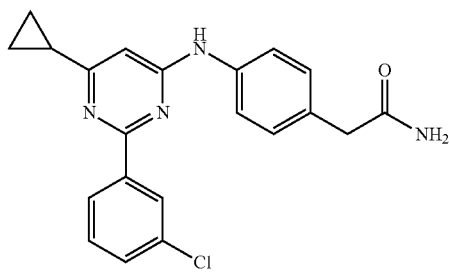 [SMILES: NC(=O)Cc1ccc(Nc2cc(C3CC3)nc(-c3cccc(Cl)c3)n2)cc1]

A 10-mL microwave vial was charged with 4-chloro-2-(3-chlorophenyl)-6-cyclopropylpyrimidine (0.100 g, 0.38 mmol) and (4-aminophenyl)acetamide (0.113 g, 0.75 mmol) in NMP (3 mL). The resulting mixture was heated at 120° C. under microwave irradiation for 2 h. The reaction mixture was cooled, diluted with water (50 mL) affording a solid. The solid was isolated by filtration and purified by chromatography on silica using hexanes/ethyl acetate (10:0 to 0:10) as eluent to afford the title compound (0.107 g, 78%) as a white solid. MW=378.85. M.p. 174-176° C. $^1$H NMR (DMSO-d$_6$, 500 MHz) δ 9.51 (s, 1H), 8.27-8.22 (m, 2H), 7.61 (d, J=8.0 Hz, 2H), 7.57-7.52 (m, 2H), 7.43 (br s, 1H), 7.25 (d, J=8.5 Hz, 2H), 6.85 (br s, 1H), 6.63 (s, 1H), 3.35 (s, 2H), 2.07-2.00 (m, 1H), 1.12-1.06 (m, 2H), 1.03-0.95 (m, 2H); ESI MS m/z 379 [M+H]$^+$.

EXAMPLE 208

Methyl 2-(4-((2-(3-chlorophenyl)-6-cyclopropylpyrimidin-4-yl)methyl)phenyl)acetate

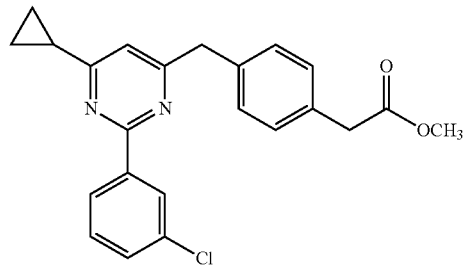 [SMILES: COC(=O)Cc1ccc(Cc2cc(C3CC3)nc(-c3cccc(Cl)c3)n2)cc1]

A 20-mL sealed tube, with stirrer bar, was charged with 4-chloro-2-(3-chlorophenyl)-6-cyclopropylpyrimidine (0.365 g, 1.38 mol), methyl 2-(4-((4,4,5,5-tetramethyl-1,3,2-dioxaborolan-2-yl)methyl)phenyl)acetate (0.400 g, 1.38 mmol), Pd(dppf)Cl$_2$ (0.113 g, 0.14 mmol), and powdered Na$_2$CO$_3$ (0.438 g, 4.14 mmol). Dioxane (6 mL) and water (3 mL) were added. The resulting mixture was stirred under Ar at 90° C. for 1.5 h until the starting chloride was consumed. After cooling to room temperature, the reaction mixture was filtered through celite washing with ethyl acetate until the filtrate was colorless. The aqueous layer was separated and the organic layer was washed with saturated sodium chloride (2×5 mL) then dried over sodium sulfate, filtered, and concentrated under reduced pressure. The residue was purified by chromatography on silica using hexane/ethyl acetate (95:5 to 1:2) as eluent to afford the title compound (0.285 g, 52%) as a colorless oil. MW=392.88. $^1$H NMR (DMSO-d$_6$, 500 MHz) δ 8.30-8.27 (m, 2H), 7.59-7.51 (m, 2H), 7.31 (d, J=8.0 Hz, 2H), 7.28 (s, 1H), 7.21 (d, J=8.0 Hz, 2H), 4.07 (s, 2H), 3.64 (s, 2H), 3.59 (s, 3H), 2.16-2.09 (m, 1H), 1.16-1.05 (m, 4H); ESI MS m/z 393 [M+H]$^+$.

EXAMPLE 209

2-(4-((2-(3-chlorophenyl)-6-cyclopropylpyrimidin-4-yl)methyl)phenyl)acetamide

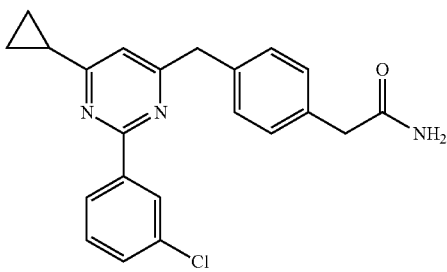 [SMILES: NC(=O)Cc1ccc(Cc2cc(C3CC3)nc(-c3cccc(Cl)c3)n2)cc1]

A 20-mL vial was charged with methyl 2-(4-((2-(3-chlorophenyl)-6-(trifluoromethyl)pyrimidin-4-yl)methyl)phenyl)acetate (0.125 g, 0.32 mmol) and ammonium chloride (0.051 g, 0.95 mmol) in methanol (4 mL). To this mixture was added NH$_3$ (6.0 mL, 7N in methanol, 42.0 mmol). The vial was sealed and the resulting mixture was stirred at 100° C. for 69 h. After this time, the reaction mixture was concentrated under reduced pressure, the residue was absorbed on silica (2 g), and then purified by chromatography on silica using hexanes/ethyl acetate (10:0 to 0:10) as eluent to afford the title compound (0.095 g, 79%) as a white solid. MW=377.87. M.p. 161-163° C. $^1$H NMR (DMSO-d$_6$, 500 MHz) δ 8.31-8.27 (m, 2H), 7.59-7.51 (m, 2H), 7.41 (br s, 1H), 7.30-7.25 (m, 3H), 7.21 (d, J=8.0 Hz, 2H), 6.82 (br s, 1H), 4.06 (s, 2H), 3.33 (s, 2H), 2.17-2.09 (m, 1H), 1.16-1.05 (m, 4H); ESI MS m/z 378 [M+H]$^+$.

EXAMPLE 210

2-(4-((2-(3-Chlorophenyl)-6-cyclopropylpyrimidin-4-yl)methyl)phenyl)ethanol

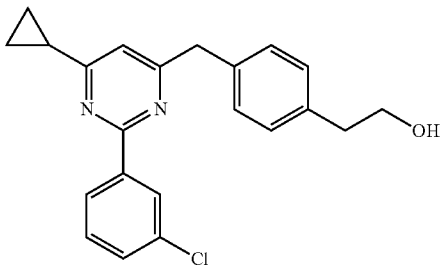 [SMILES: OCCc1ccc(Cc2cc(C3CC3)nc(-c3cccc(Cl)c3)n2)cc1]

A 25-mL round bottom flask was charged with methyl 2-(4-((2-(3-chlorophenyl)-6-cyclopropylpyrimidin-4-yl)methyl)phenyl)acetate (0.149 g, 0.38 mmol) and THF (5 mL) at rt. Borane-dimethylsulfide complex (0.108 mL, 1.13 mmol) was added and the resulting solution was stirred at 55° C. for 2.5 h until the starting material was consumed (monitored by LCMS analysis). The reaction was quenched with methanol then treated with 2N aqueous HCl (5 drops) and concentrated under reduced pressure. The residue was diluted with methanol and then concentrated under reduced pressure. The residue was absorbed onto silica (2 g) and purified by column chromatography on silica using hexanes/ethyl acetate (10:0 to 3:1) as the eluent to afford the title compound (0.113 g, 82%) as a colorless oil. MW=364.87. $^1$H NMR (DMSO-d$_6$, 500 MHz) δ 8.31-8.27 (m, 2H), 7.59-7.51 (m, 2H), 7.27 (s, 1H), 7.26 (d, J=8.0 Hz, 2H), 7.16 (d, J=8.0 Hz, 2H), 4.58 (t, J=5.0 Hz, 1H), 4.04 (s, 2H), 3.59-3.52 (m, 2H), 2.68 (t, J=7.0 Hz, 2H), 2.16-2.09 (m, 1H), 1.16-1.05 (m, 4H); APCI MS m/z 365 [M+H]$^+$.

EXAMPLE 211

Ethyl 2-(6-((2-(3-chlorophenyl)-6-cyclopropylpyrimidin-4-yl)amino)pyridin-3-yl)acetate

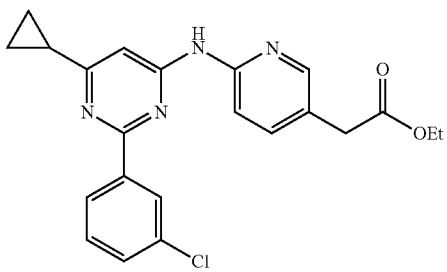 [SMILES: CCOC(=O)Cc1ccc(Nc2cc(C3CC3)nc(-c3cccc(Cl)c3)n2)nc1]

A 20-mL vial was charged with 4-chloro-2-(3-chlorophenyl)-6-cyclopropylpyrimidine (0.380 g, 1.43 mmol), ethyl 2-(6-aminopyridin-3-yl)acetate (0.410 g, 2.27 mmol), palladium acetate (0.016 g, 0.071 mmol), rac-BINAP (0.069 g, 0.11 mmol) and cesium carbonate (1.17 g, 3.58 mmol) in dioxane (10 mL) under argon. The reaction mixture was heated to 110° C. under microwave irradiation for 1.25 h. The reaction mixture was cooled, and diluted with ethyl acetate and filtered through celite. The filtrate was washed with saturated sodium chloride (2×10 mL), dried over sodium sulfate, filtered, and the filtrate concentrated under reduced pressure. The residue was purified by chromatography on silica using hexanes/ethyl acetate (10:0 to 0:10) as eluent to afford the title compound (0.504 g, 86%) as an off-white solid. MW=408.88. M.p. 133-135° C. $^1$H NMR (DMSO-d$_6$, 500 MHz) δ 10.13 (s, 1H), 8.31-8.29 (m, 1H), 8.27 (dt, J=7.0, 1.5 Hz, 1H), 8.22 (d, J=2.0 Hz, 1H), 7.75-7.68 (m, 2H), 7.62 (br s, 1H), 7.59-7.52 (m, 2H), 4.10 (q, J=7.5 Hz, 2H), 3.68 (s, 2H), 2.07 (septet, J=4.5 Hz, 1H), 1.21 (t, J=7.0 Hz, 3H), 1.14-1.10 (m, 2H), 1.06-1.00 (m, 2H); APCI MS m/z 409 [M+H]$^+$.

EXAMPLE 212

2-(6-((2-(3-Chlorophenyl)-6-cyclopropylpyrimidin-4-yl)amino)pyridin-3-yl)acetamide

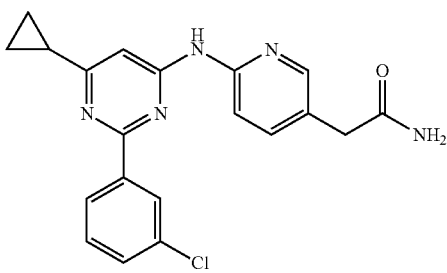 [SMILES: NC(=O)Cc1ccc(Nc2cc(C3CC3)nc(-c3cccc(Cl)c3)n2)nc1]

A 10-mL vial was charged with ethyl 2-(6-((2-(3-chlorophenyl)-6-cyclopropylpyrimidin-4-yl)amino)pyridin-3-yl)acetate (0.070 g, 0.17 mmol) and NH$_3$ (4.9 mL, 7N in methanol, 34.2 mmol). The vial was sealed and the resulting mixture was stirred at 100° C. for 23 h. The crude reaction solution concentrated under reduced pressure. The residue was absorbed on silica (2 g) then purified by chromatography on silica using dichloromethane/methanol (10:0 to 9:1) as eluent to afford the title compound (0.029 g, 45%) as a white solid. M.p. 232-235° C. $^1$H NMR (DMSO-d$_6$, 500 MHz) δ 10.10 (s, 1H), 8.31-8.29 (m, 1H), 8.27 (dt, J=7.5, 2.0 Hz, 1H), 8.19 (d, J=2.0 Hz, 1H), 7.75-7.69 (m, 1H), 7.67 (dd, J=8.5, 2.0 Hz, 1H), 7.60 (br s, 1H), 7.58-7.52 (m, 2H), 7.50 (br s, 1H), 6.93 (br s, 1H), 3.37 (s, 2H), 2.07 (septet, J=4.5 Hz, 1H), 1.14-1.09 (m, 2H), 1.06-1.00 (m, 2H); APCI MS m/z 380 [M+H]$^+$.

EXAMPLE 213

2-(6-((2-(3-Chlorophenyl)-6-cyclopropylpyrimidin-4-yl)amino)pyridin-3-yl)acetic acid

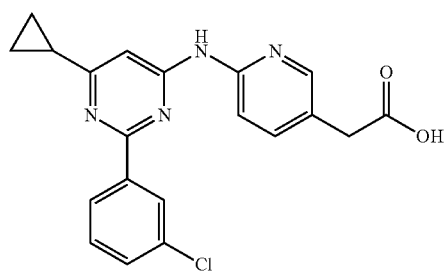 [SMILES: O=C(O)Cc1ccc(Nc2cc(C3CC3)nc(-c3cccc(Cl)c3)n2)nc1]

An 250-mL round bottom flask was charged with ethyl 2-(6-((2-(3-chlorophenyl)-6-cyclopropylpyrimidin-4-yl)amino)pyridin-3-yl)acetate (0.417 g, 1.02 mmol), dioxane (20 ml) and water (10 ml). To this solution was then added lithium hydroxide monohydrate (0.214 g, 5.10 mmol). The resulting mixture was stirred at 50° C. for 1.5 h. The cooled reaction mixture was treated with 2N aqueous HCl until pH~4 affording a solid. The solid was isolated by filtration and dried under reduced pressure at 55° C. to afford the title compound (0.408 g, 100%) as a white solid. MW=380.83. M.p.>260° C. $^1$H NMR (DMSO-d$_6$, 500 MHz) δ 12.33 (br s, 1H), 10.41 (s, 1H), 8.32-8.24 (m, 3H), 7.80-7.70 (m, 2H), 7.60-7.52 (m, 3H), 3.62 (s, 2H), 2.10 (septet, J=4.5 Hz, 1H), 1.16-1.10 (m, 2H), 1.10-1.02 (m, 2H); ESI MS m/z 381 [M+H]$^+$.

EXAMPLE 214

2-(6-((2-(3-Chlorophenyl)-6-cyclopropylpyrimidin-4-yl)amino)pyridin-3-yl)acetic acid

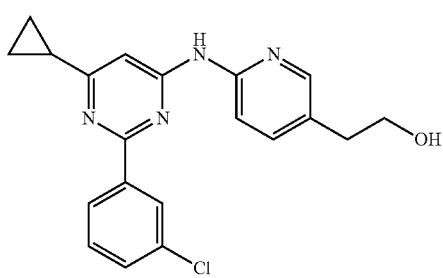 [SMILES: OCCc1ccc(Nc2cc(C3CC3)nc(-c3cccc(Cl)c3)n2)nc1]

A 25-mL round bottom flask was charged with 2-(6-((2-(3-chlorophenyl)-6-cyclopropylpyrimidin-4-yl)amino)pyridin-3-yl)acetic acid (0.100 g, 0.26 mmol) and THF (8 mL) at rt. Borane-dimethylsulfide complex (124 mL, 1.31 mmol) was added and the resulting solution was stirred at 55° C. for 1 h until the starting material was consumed (monitored by LCMS analysis). The reaction was quenched with methanol then treated with 2N aqueous HCl (5 drops) and concentrated under reduced pressure. The residue was diluted with methanol and then concentrated under reduced pressure. The residue was absorbed onto silica (2 g) and purified by column chromatography on silica using dichloromethane/methanol (10:0 to 9:1) as the eluent, followed by preparative HPLC (water/acetonitrile with 0.05% TFA) to afford the title compound (0.031 g, 32%) as a white solid. M.p. 146-148° C. $^1$H NMR (DMSO-d$_6$, 500 MHz) δ 10.05 (s, 1H), 8.31-8.29 (m, 1H), 8.27 (dt, J=7.0, 1.5 Hz, 1H), 8.20-8.18 (m, 1H), 7.70-7.64 (m, 2H), 7.62 (br s, 1H), 7.58-7.52 (m, 2H), 4.67 (br s, 1H), 3.61 (t, J=7.0 Hz, 2H), 3.13 (s, 3H), 2.70 (t, J=7.0 Hz, 2H), 2.06 (septet, J=4.5 Hz, 1H), 1.13-1.09 (m, 2H), 1.05-1.00 (m, 2H); APCI MS m/z 367 [M+H]$^+$.

EXAMPLE 215

2-(6-((2-(3-Chlorophenyl)-6-cyclopropylpyrimidin-4-yl)amino)pyridin-3-yl)-N-(2-hydroxyethyl)acetamide

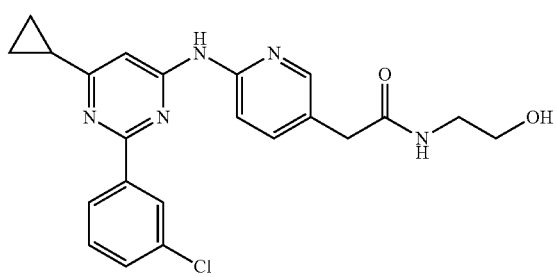 [SMILES: O=C(Cc1ccc(Nc2cc(C3CC3)nc(-c3cccc(Cl)c3)n2)nc1)NCCO]

To a stirred suspension of 2-(6-((2-(3-chlorophenyl)-6-cyclopropylpyrimidin-4-yl)amino)pyridin-3-yl)acetic acid (0.185 g, 0.48 mmol) in dimethylformaminde (7 mL) at 0°

C. was added ethanolamine (0.044 mL, 0.72 mmol, 1.5 eq.) followed by diisopropylethylamine (0.34 mL, 1.94 mmol, 4.0 eq.) and HATU (0.221 g, 0.58 mmol). After stirring for 2 h, the reaction mixture was diluted with water (100 mL) and the resulting white solid isolated by filtration. The solid was purified by chromatography on silica using dichloromethane/methanol (10:0 to 9:1) as eluent followed by preparative HPLC (water/acetonitrile with 0.05% TFA) to afford 2-(6-((2-(3-chlorophenyl)-6-cyclopropylpyrimidin-4-yl)amino)pyridin-3-yl)-N-(2-hydroxyethyl)acetamide (67 mg, 33%) as a white solid. M.p. 131-133° C. $^1$H NMR (DMSO-d$_6$, 500 MHz) δ 10.10 (s, 1H), 8.31-8.29 (m, 1H), 8.27 (dt, J=7.0, 1.5 Hz, 1H), 8.19 (d, J=1.5 Hz, 1H), 8.08 (t, J=5.5 Hz, 1H), 7.74-7.69 (m, 1H), 7.67 (dd, J=8.5, 2.0 Hz, 1H), 7.60 (br s, 1H), 7.58-7.52 (m, 2H), 4.68 (t, J=5.5 Hz, 1H), 3.44-3.39 (m, 4H), 3.13 (q, J=6.0 Hz, 2H), 2.07 (septet, J=4.5 Hz, 1H), 1.14-1.09 (m, 2H), 1.06-1.00 (m, 2H); APCI MS m/z 424 [M+H]$^+$.

EXAMPLE 216

2-(4-((2-Cyclopentyl-6,7-dihydro-5H-cyclopenta[d]pyrimidin-4-yl)amino)phenyl)acetamide

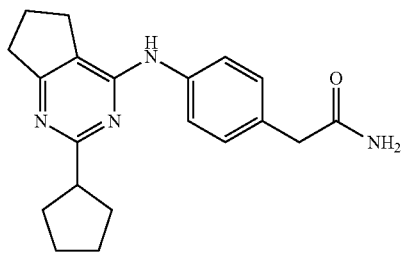 [SMILES: NC(=O)Cc1ccc(Nc2nc(C3CCCC3)nc3c2CCC3)cc1]

Step 1. Preparation of 2-cyclopentyl-6,7-dihydro-3H-cyclopenta[d]pyrimidin-4(5H)-one

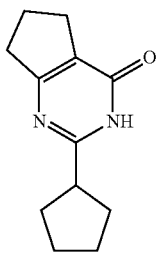 [SMILES: O=c1[nH]c(C2CCCC2)nc2c1CCC2]

A 250-mL round bottomed flask was charged with cyclopentanecarboximidamide hydrochloride (5.38 g, 36.2 mmol), ethyl 2-oxocyclopentanecarboxylate (5.14 g, 38.7 mmol), and ethanol (100 mL). To the stirred mixture at rt was added sodium methoxide (3.91 g, 72.4 mmol). The resulting mixture was stirred under reflux for 22 h. After cooling to room temperature, the mixture was evaporated under reduced pressure to 25 mL. The residual slurry was cautiously treated with 2N HCl (50 mL). The solution was extracted with ethyl acetate (4×50 mL). The combined extract was washed with saturated sodium chloride (2×25 mL), dried over sodium sulfate, filtered, and concentrated under reduced pressure to afford the title compound which was carried forward into the next step without further purification.

Step 2. Preparation of 4-chloro-2-cyclopentyl-6,7-dihydro-5H-cyclopenta[d]pyrimidine

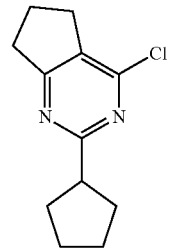 [SMILES: Clc1nc(C2CCCC2)nc2c1CCC2]

A 250-mL round bottom flask was charged with crude 2-cyclopentyl-6,7-dihydro-3H-cyclopenta[d]pyrimidin-4(5H)-one (4.05 g) and POCl$_3$ (22 mL, 23.8 mmol). The resulting mixture was stirred at 100° C. for 5 h. After cooling to room temperature, the mixture was concentrated under reduced pressure. The residue was poured into water (250 mL) and dichloromethane (50 mL) then treated with aqueous sodium hydroxide until the pH~8. The aqueous layer was extracted with dichloromethane (2×50 mL). The combined organic extract was washed the saturated sodium chloride (2×20 mL), dried over sodium sulfate, filtered, and concentrated under reduced pressure. The residue was purified by silica on chromatography using dichloromethane/methanol (10:0 to 9:1) as eluent to afford the title compound (0.095 g, 3% over 2 steps) as a brown oil. MW=222.71. $^1$H NMR (CDCl$_3$, 300 MHz) δ 3.31 (quin, J=2.4 Hz, 1H), 3.07 (t, J=7.8 Hz, 2H), 2.97 (t, J=7.5 Hz, 2H), 2.22-2.00 (m, 4H), 1.98-1.76 (m, 4H), 1.75-1.60 (m, 2H).

EXAMPLE 216

2-(4-((2-Cyclopentyl-6,7-dihydro-5H-cyclopenta[d]pyrimidin-4-yl)amino)phenyl)acetamide

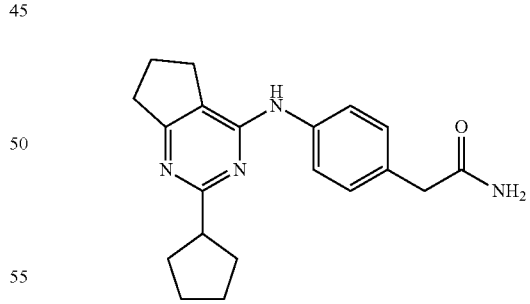

A 10-mL microwave vial was charged with 4-chloro-2-cyclopentyl-6,7-dihydro-5H-cyclopenta[d]pyrimidine (0.132 g, 0.59 mmol) and (4-aminophenyl)acetamide (0.178 g, 1.18 mmol) in NMP (4 mL). The resulting mixture was heated at 120° C. under microwave irradiation for 2 h. The reaction mixture was cooled, diluted with water (40 mL), then extracted with 3:1 chloroform/isopropanol (3×25 mL). The combined extract was washed with saturated sodium chloride (5 mL), dried over sodium sulfate, filtered, and concentrated under reduced pressure. The residue was purified by chromatography on silica using dichloromethane/methanol (9:1) as eluent followed by chromatography on silica using dichloromethane/methanol (10:0 to 9:1) as eluent to afford the title compound (0.112 g, 56%) as a light brown solid. MW=336.43. M.p. 228-230° C. $^1$H NMR (DMSO-d$_6$, 500 MHz) δ 8.51 (s, 1H), 7.72 (d, J=8.5 Hz, 2H), 7.39 (s, 1H), 7.16 (d, J=8.5 Hz, 2H), 6.82 (s, 1H), 3.10 (quin, J=8.0 Hz, 1H), 2.77 (q, J=9.0 Hz, 4H), 2.01 (quin, J=7.5 Hz, 2H), 1.98-1.90 (m, 2H), 1.87-1.78 (m, 2H), 1.78-1.68 (m, 2H), 1.65-1.55 (m, 2H); APCI MS m/z 337 [M+H]$^+$.

EXAMPLE 217

2-(4-((2-Cyclopentyl-6,7-dihydro-5H-cyclopenta[d]pyrimidin-4-yl)amino)phenyl)ethanol

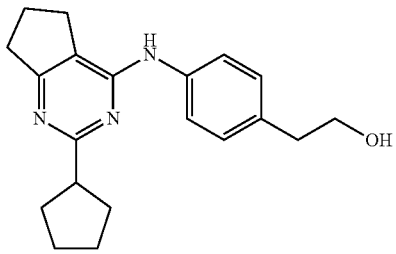 [SMILES: OCCc1ccc(Nc2nc(C3CCCC3)nc3c2CCC3)cc1]

A 10-mL microwave vial was charged with 4-chloro-2-cyclopentyl-6,7-dihydro-5H-cyclopenta[d]pyrimidine (0.132 g, 0.59 mmol) and 4-aminophenethyl alcohol (0.162 g, 1.18 mmol) in NMP (4 mL). The resulting mixture was heated at 120° C. under microwave irradiation for 2 h. The reaction mixture was cooled, diluted with water (40 mL) to afford a solid. The solid was isolated by filtration then purified by chromatography on silica using hexanes/ethyl acetate (10:0 to 0:10) as eluent to afford the title compound (0.098 g, 51%) as a light brown solid. MW=323.43. M.p. 178-180° C. $^1$H NMR (DMSO-d$_6$, 500 MHz) δ 8.47 (s, 1H), 7.70 (d, J=8.5 Hz, 2H), 7.12 (d, J=8.5 Hz, 2H), 4.59 (t, J=5.0 Hz, 1H), 3.61-3.55 (m, 2H), 3.09 (quin, J=8.0 Hz, 1H), 2.77 (q, J=7.5 Hz, 4H), 2.67 (t, J=7.0 Hz, 2H), 2.01 (quin, J=7.5 Hz, 2H), 1.97-1.90 (m, 2H), 1.87-1.78 (m, 2H), 1.78-1.68 (m, 2H), 1.65-1.55 (m, 2H); APCI MS m/z 324 [M+H]$^+$.

EXAMPLE 218

4-(4-((4-Chloro-1H-pyrazol-1-yl)methyl)benzyl)-2-(3-chlorophenyl)-6-(trifluoromethyl)pyrimidine

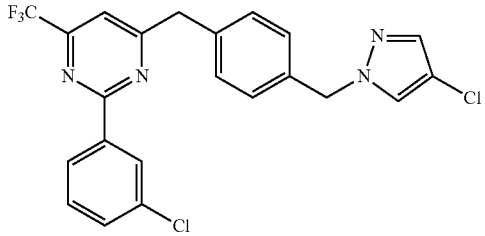 [SMILES: FC(F)(F)c1cc(Cc2ccc(Cn3cc(Cl)cn3)cc2)nc(-c2cccc(Cl)c2)n1]

A mixture of 4-chloro-2-(3-chlorophenyl)-6-(trifluoromethyl)pyrimidine (0.076 g, 0.26 mmol), 4-chloro-1-((4,4,5,5-tetramethyl-1,3,2-dioxaborolan-2-yl)methyl)benzyl)-1H-pyrazole (0.129 g, 0.39 mmol), Pd(dppf)Cl$_2$ (0.021 g, 0.03 mmol), and powdered Na$_2$CO$_3$ (0.082 g, 0.77 mmol) in dioxane (2 mL) and water (1 mL) was stirred under an argon atmosphere at 90° C. for 3 h. After this time, the mixture was cooled and filtered through celite with ethyl acetate washes. The filtrate was washed with brine (3×15 mL), dried over sodium sulfate, filtered, and concentrated. The residue was purified by column chromatography (silica, hexane/ethyl acetate) to afford the title compound (0.073 g, 98%) as an off-white solid. MW=463.28. $^1$H NMR (DMSO-d$_6$, 300 MHz) δ 8.37-8.30 (m, 2H), 8.07 (s, 1H), 7.96 (s, 1H), 7.72-7.66 (m, 1H), 7.65-7.58 (m, 1H), 7.54 (s, 1H), 7.40 (d, J=8.1 Hz, 2H), 7.22 (d, J=8.1 Hz, 2H), 5.26 (s, 2H), 4.31 (s, 2H); APCI MS m/z 463 [M+H]$^+$.

EXAMPLE 219

2-(4-((2-(3-Chlorophenyl)-6-(trifluoromethyl)pyrimidin-4-yl)amino)phenyl)ethanol

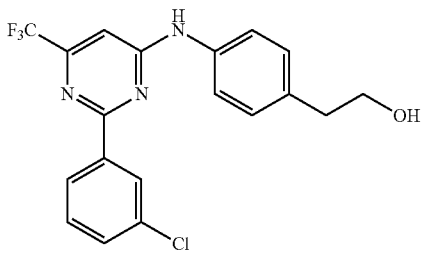 [SMILES: OCCc1ccc(Nc2cc(C(F)(F)F)nc(-c3cccc(Cl)c3)n2)cc1]

Following General Procedure A2, 4-chloro-2-(3-chlorophenyl)-6-(trifluoromethyl)pyrimidine (0.100 g, 0.34 mmol) in NMP (3 mL) was reacted with 4-aminophenethyl alcohol (0.094 g, 0.68 mmol) to afford the title compound (0.044 g, 44%) as an off-white solid. MW=393.79. $^1$H NMR (DMSO-d$_6$, 500 MHz) δ 10.20 (s, 1H), 8.30-8.25 (m, 2H), 7.78-7.56 (m, 4H), 7.29 (d, J=8.5 Hz, 2H), 7.07 (s, 1H), 4.64 (t, J=5.2 Hz, 1H), 3.66-3.60 (m, 2H), 2.74 (t, J=7.0 Hz, 2H); APCI MS m/z 394 [M+H]$^+$.

EXAMPLE 220

2-(4-((2-(3-Chlorophenyl)-6-(trifluoromethyl)pyrimidin-4-yl)amino)phenyl)acetamide

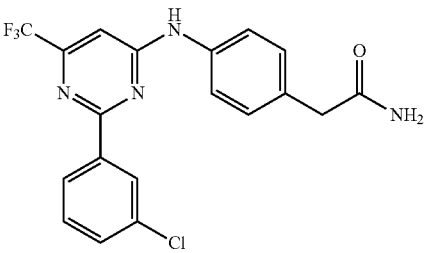 [SMILES: NC(=O)Cc1ccc(Nc2cc(C(F)(F)F)nc(-c3cccc(Cl)c3)n2)cc1]

Following General Procedure A2, 4-chloro-2-(3-chlorophenyl)-6-(trifluoromethyl)pyrimidine (0.100 g, 0.34 mmol) was reacted with 2-(4-aminophenyl)acetamide (0.103 g, 0.68 mmol) to afford the title compound (0.042 g, 56%) as an off-white solid. MW=406.79. $^1$H NMR (DMSO-d$_6$, 500 MHz) δ 10.24 (s, 1H), 8.33-8.25 (m, 2H), 7.74-7.58 (m, 4H), 7.33 (d, J=8.5 Hz, 2H), 7.09 (s, 1H), 6.88 (s, 1H), 3.39 (s, 2H), 2.70 (s, 1H); APCI MS m/z 407 [M+H]⁺.

EXAMPLE 221

2-(4-((2-Cyclopentyl-6-ethylpyrimidin-4-yl)amino)phenyl)acetamide

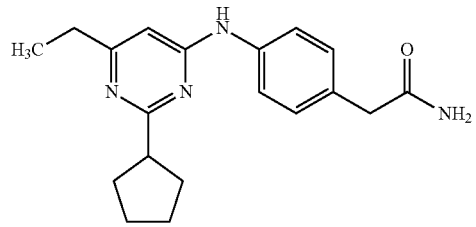 [SMILES: CCc1cc(Nc2ccc(CC(N)=O)cc2)nc(C2CCCC2)n1]

Step 1. Preparation of ethyl cyclopentanecarbimidate

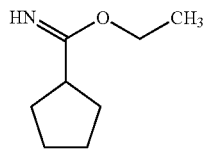

A solution of cyclopentanecarbonitrile (10.0 g, 105.1 mmol) in EtOH (7 mL) was treated with HCl (4.0 M in dioxane, 105 mL, 3.02 mol) and the mixture stirred at rt overnight. After this time, nitrogen gas was passed through the mixture and the mixture was concentrated. The residue was treated with ether and reconcentrated. The residue was again suspended in ether and filtered to afford the title compound (16.0 g, crude) as a white solid. MW=141.21. $^1$H NMR (CDCl$_3$, 500 MHz) δ 4.79-4.46 (m, 2H), 3.43-3.23 (m, 1H), 2.76 (s, 1H), 2.20-2.00 (m, 2H), 1.86-1.63 (m, 6H), 1.55-1.40 (m, 3H); APCI MS m/z 142 [M+H]⁺.

Step 2. Preparation of cyclopentanecarboximidamide

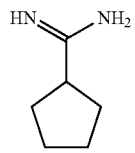

A solution of ethyl cyclopentanecarbimidate (16.0 g, 113.4 mmol) in ammonia (7.0 N in methanol, 125 mL) was stirred at rt for 48 h. After this time, nitrogen gas was passed through the mixture and the reaction was concentrated to afford the title compound (14.4 g, crude) as an off-white gum. MW=112.17. $^1$H NMR (CD$_3$OD, 500 MHz) δ 2.94-2.80 (m, 1H), 2.16-1.99 (m, 2H), 1.91-1.79 (m, 2H), 1.78-1.64 (m, 4H); APCI MS m/z 113 [M+H]⁺.

Step 3. Preparation of 2-cyclopentyl-6-ethylpyrimidin-4(3H)-one

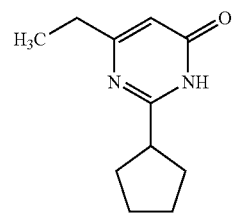

A solution of cyclopentanecarboximidamide (8.5 g, 75.8 mmol) in ethanol (150 mL) was treated with ethyl propionaylacetate (13.7 g, 94.7 mmol), followed by the addition of sodium methoxide (4.9 g, 90.9 mmol). The mixture was then heated to 85° C. overnight. After this time, the mixture was cooled and concentrated to a volume of approximately 50 mL. Then, 2M HCl in EtOH (68 mL) was added slowly. The resulting precipitate was filtered, washed with water and ether, and the residue was dried on a high vacuum overnight to afford the title compound (8.9 g, crude) as a pink solid. MW=192.26. $^1$H NMR (DMSO-d$_6$, 500 MHz) δ 12.00 (s, 1H), 6.14 (s, 1H), 3.01 (quin, J=8.0 Hz, 1H), 2.55 (q, J=7.5 Hz, 2H), 2.13-2.01 (m, 2H), 1.94-1.77 (m, 4H), 1.74-1.63 (m, 2H), 1.22 (t, J=7.5 Hz, 3H); APCI MS m/z 193 [M+H]⁺.

Step 4. Preparation of 4-chloro-2-cyclopentyl-6-ethylpyrimidine

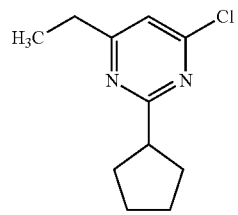

Phosphorus(V) oxychloride (150 g, 99.0 mmol) was slowly added to 2-cyclopentyl-6-ethylpyrimidin-4(3H)-one (18.9 g, 98.3 mmol) at 0° C. Then, the reaction mixture was warmed to 100° C. for 3 h. After this time, the mixture was cooled, diluted with sodium hydroxide, and extracted with ethyl acetate. The combined organic layer was dried over anhydrous sodium sulfate, filtered, and the filtrate was concentrated. The residue was purified by column chromatography (silica, hexanes/dichloromethane) to afford the title compound (5.1 g, 57%) as yellow oil. MW=210.70. $^1$H NMR (CDCl$_3$, 300 MHz) δ 7.01 (s, 1H), 3.36-3.20 (m, 1H), 2.74 (q, J=7.5 Hz, 2H), 2.14-1.99 (m, 2H), 1.98-1.76 (m, 4H), 1.75-1.63 (m, 2H), 1.29 (t, J=7.5 Hz, 3H); APCI MS m/z 211 [M+H]⁺.

EXAMPLE 221

2-(4-((2-Cyclopentyl-6-ethylpyrimidin-4-yl)amino)phenyl)acetamide

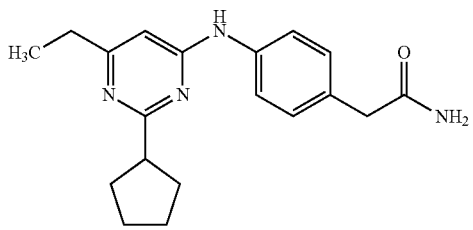 [SMILES: CCc1cc(Nc2ccc(CC(N)=O)cc2)nc(C2CCCC2)n1]

Following General Procedure A2,4-chloro-2-cyclopentyl-6-ethylpyrimidine (0.100 g, 0.47 mmol) was reacted with 2-(4-aminophenyl)acetamide (0.086 g, 0.57 mmol) to afford the title compound (0.097 g, 97%) as a tan solid. MW=324.42. $^1$H NMR (DMSO-$d_6$, 500 MHz) δ 14.18 (s, 1H), 11.23 (s, 1H), 7.64 (s, 1H), 7.49 (s, 1H), 7.36-7.25 (m, 2H), 6.88 (s, 1H), 6.76 (s, 1H), 3.37 (d, J=7.5 Hz, 3H), 2.82-2.66 (m, 2H), 2.13-1.98 (m, 2H), 1.94-1.73 (m, 4H), 1.72-1.59 (m, 2H), 1.25 (s, 3H); APCI MS m/z 325 [M+H]$^+$.

EXAMPLE 222

2-(4-((2-Cyclopentyl-6-ethylpyrimidin-4-yl)amino)phenyl)ethanol

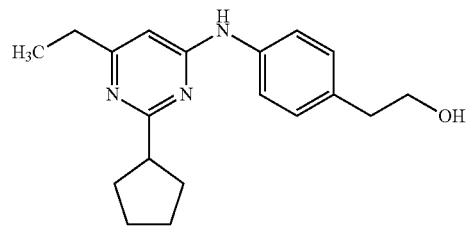 [SMILES: CCc1cc(Nc2ccc(CCO)cc2)nc(C2CCCC2)n1]

Following General Procedure A2,4-chloro-2-cyclopentyl-6-ethylpyrimidine (0.100 g, 0.47 mmol) was reacted with 4-aminophenethyl alcohol (0.078 g, 0.57 mmol) to afford the title compound (0.092 g, 92%) as an off-white solid. MW=311.42. $^1$H NMR (DMSO-$d_6$, 500 MHz) δ 14.15 (s, 1H), 11.14 (s, 1H), 7.62 (s, 1H), 7.34-7.17 (m, 2H), 6.75 (s, 1H), 4.63 (s, 1H), 3.61 (t, J=6.9 Hz, 2H), 2.80-2.67 (m, 4H), 2.12-2.00 (m, 2H), 1.93-1.73 (m, 4H), 1.71-1.58 (m, 2H), 1.24 (s, 3H); APCI MS m/z 312 [M+H]$^+$.

EXAMPLE 223

Methyl 2-(4-((2-cyclopentyl-6-ethylpyrimidin-4-yl)methyl)phenyl)acetate

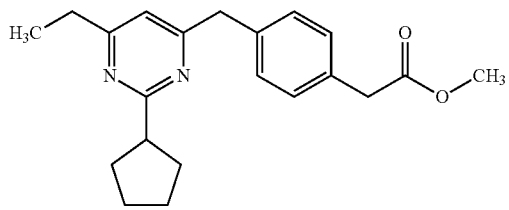 [SMILES: CCc1cc(Cc2ccc(CC(=O)OC)cc2)nc(C2CCCC2)n1]

A mixture of 4-chloro-2-cyclopentyl-6-ethylpyrimidine (0.275 g, 0.95 mmol), methyl 2-(4-((4,4,5,5-tetramethyl-1,3,2-dioxaborolan-2-yl)methyl)phenyl)acetate (0.200 g, 0.95 mmol), Pd(dppf)Cl$_2$ (0.078 g, 0.095 mmol), and powdered Na$_2$CO$_3$ (0.302 g, 2.85 mmol) in dioxane (5 mL) and water (3 mL) was stirred under an argon atmosphere at 90° C. for 48 h. After this time, the mixture was cooled and filtered through celite washing with ethyl acetate. The filtrate was washed with brine (3×15 mL), dried over sodium sulfate, filtered, and concentrated. The residue was purified by column chromatography (silica, hexane/ethyl acetate) to afford the title compound (0.027 g, 14%) as a brown oil. MW=338.44. $^1$H NMR (DMSO-$d_6$, 500 MHz) δ 7.28-7.22 (m, 2H), 7.21-7.17 (m, 2H), 7.01 (s, 1H), 3.96 (s, 2H), 3.63 (s, 2H), 3.59 (s, 3H), 3.21 (quin, J=8.1 Hz, 1H), 2.63 (q, J=7.6 Hz, 2H), 2.01-1.90 (m, 2H), 1.88-1.79 (m, 2H), 1.78-1.70 (m, 2H), 1.69-1.57 (m, 2H), 1.17 (t, J=7.6 Hz, 3H); APCI MS m/z 339 [M+H]$^+$.

EXAMPLE 224

2-(4-((2-Cyclopentyl-6-ethylpyrimidin-4-yl)methyl)phenyl)acetic acid

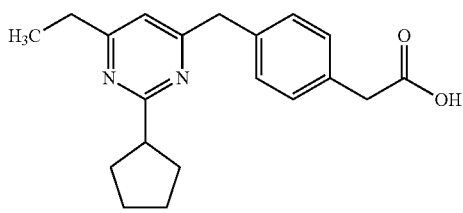 [SMILES: CCc1cc(Cc2ccc(CC(=O)O)cc2)nc(C2CCCC2)n1]

A mixture of 4-chloro-2-cyclopentyl-6-ethylpyrimidine (0.200 g, 0.95 mmol), methyl 2-(4-((4,4,5,5-tetramethyl-1,3,2-dioxaborolan-2-yl)methyl)phenyl)acetate 0. (275 g, 0.95 mmol), Pd(dppf)Cl$_2$ (0.078 g, 0.095 mmol), and powdered Na$_2$CO$_3$ (0.302 g, 2.85 mmol) in dioxane (5 mL) and water (3 mL) was stirred under argon at 90° C. for 24 h. After this time, the mixture was cooled and filtered through celite washing with ethyl acetate. The filtrate was washed with brieme (3×15 mL), dried over sodium sulfate, filtered, and concentrated. The residue was purified by column chromatography (silica, dichloromethane/methanol) to afford the title compound (0.121 g, 61%) as a brown oil. MW=324.42. $^1$H NMR (DMSO-$d_6$, 500 MHz) δ 12.26 (s, 1H), 7.25-7.18 (m, 4H), 7.01 (s, 1H), 3.95 (s, 2H), 3.51 (s, 2H), 3.22 (t, J=8.1 Hz, 1H), 2.67-2.59 (m, 2H), 2.01-1.92 (m, 2H), 1.88-1.71 (m, 4H), 1.67-1.58 (m, 2H) 1.17 (t, J=7.6 Hz, 3H); APCI MS m/z 325 [M+H]$^+$.

EXAMPLE 225

2-(4-((2-Cyclopentyl-6-ethylpyrimidin-4-yl)methyl)phenyl)ethanol

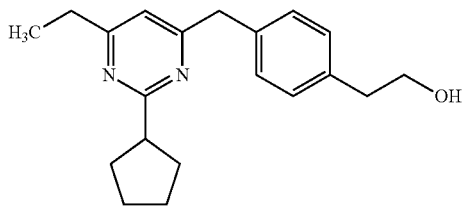 [SMILES: CCc1cc(Cc2ccc(CCO)cc2)nc(C2CCCC2)n1]

A solution of 2-(4-((2-cyclopentyl-6-ethylpyrimidin-4-yl)methyl)phenyl)acetic acid (0.050 g, 0.15 mmol) in THF (5 mL) at rt under a nitrogen atmosphere was treated with BH$_3$.SMe$_2$ (0.047 g, 0.62 mmol) and the mixture was heated at 55° C. for 4 h. After this time, the mixture was cooled, diluted with methanol, and concentrated. The residue was purified by column chromatography (silica, hexanes/ethyl acetate) to afford the title compound (0.013 g, 30%) as a yellow oil. MW=310.43. $^1$H NMR (DMSO-d$_6$, 500 MHz) δ 7.22-7.17 (m, 2H), 7.16-7.11 (m, 2H), 7.00 (s, 1H), 4.58 (t, J=5.2 Hz, 1H), 3.93 (s, 2H), 3.60-3.53 (m, 2H), 3.21 (quin, J=8.1 Hz, 1H), 2.71-2.58 (m, 4H), 2.01-1.91 (m, 2H), 1.88-1.79 (m, 2H), 1.78-1.69 (m, 2H), 1.67-1.57 (m, 2H), 1.16 (t, J=7.6 Hz, 3H); APCI MS m/z 311 [M+H]$^+$.

EXAMPLE 226

2-(4-((2-Cyclopentyl-6-ethylpyrimidin-4-yl)methyl)phenyl)acetamide

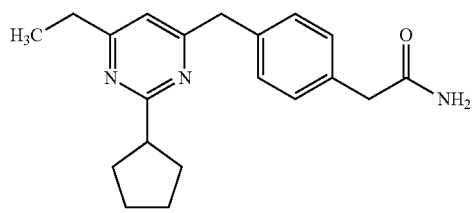 [SMILES: CCc1cc(Cc2ccc(CC(N)=O)cc2)nc(C2CCCC2)n1]

A mixture of ammonia (7.0 N in methanol, 4 mL) and methyl 2-(4-((2-cyclopentyl-6-ethylpyrimidin-4-yl)methyl)phenyl)acetate (0.067 g, 0.20 mmol) and heated at 100° C. for 48 h. After this time, the mixture was cooled and filtered through celite with ethyl acetate washings. The filtrate was washed with brine (3×15 mL), dried over sodium sulfate, filtered, and concentrated. The residue was purified by column chromatography (silica, hexanes/ethyl acetate) to afford the title compound (0.039 g, 59%) as a white solid. MW=323.43. $^1$H NMR (DMSO-d$_6$, 500 MHz) δ 7.44 (s, 1H), 7.27-7.11 (m, 4H), 7.01 (s, 1H), 6.86 (s, 1H), 3.95 (s, 2H) 3.31 (s, 2H), 3.29-3.14 (m, 1H), 2.62 (q, J=7.6 Hz, 2H), 2.06-1.91 (m, 2H), 1.90-1.67 (m, 4H), 1.66-1.53 (m, 2H), 1.16 (t, J=7.6 Hz, 3H); APCI MS m/z 324 [M+H]$^+$.

EXAMPLE 227

2-(4-((2-Cyclopentyl-6-(trifluoromethyl)pyrimidin-4-yl)amino)phenyl)ethanol

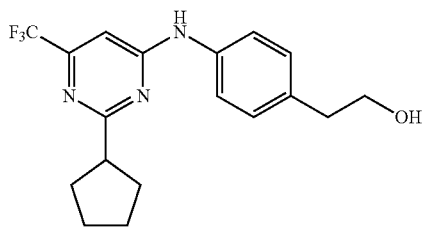 [SMILES: OCCc1ccc(Nc2cc(C(F)(F)F)nc(C3CCCC3)n2)cc1]

Step 1. Preparation of 2-cyclopentyl-6-(trifluoromethyl)pyrimidin-4-ol

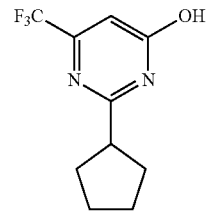 [SMILES: Oc1cc(C(F)(F)F)nc(C2CCCC2)n1]

To a solution of cyclopentanecarboximidamide (3.0 g, 27.1 mmol) in ethanol (100 mL) was added ethyl 4,4,4-trifluoro-3-oxobutanoate (5.0 g, 27.1 mmol) and sodium methoxide (1.76 g, 32.5 mmol). The mixture was stirred at 85° C. for 16 h. After this time, the mixture was concentrated, diluted with ethanol (10 mL), and the suspension was chilled to 0° C. HCl (2M, 50 mL) was added and the suspension was filtered and washed with water. The solid was dried under heat and vacuum to afford the title compound (2.24 g, 36%) as a white solid. MW=232.20. $^1$H NMR (DMSO-d$_6$, 500 MHz) δ 12.96 (s, 1H), 6.67 (s, 1H), 3.03 (quin, J=8.2 Hz, 1H), 2.00-1.92 (m, 2H), 1.83-1.67 (m, 4H), 1.64-1.53 (m, 2H); APCI MS m/z 233 [M+H]$^+$.

Step 2. Preparation of 4-chloro-2-cyclopentyl-6-(trifluoromethyl)pyrimidine

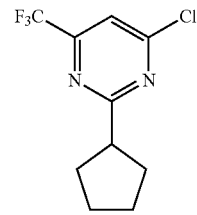 [SMILES: FC(F)(F)c1cc(Cl)nc(C2CCCC2)n1]

2-Cyclopentyl-6-(trifluoromethyl)pyrimidin-4-ol (2.2 g, 9.47 mmol) was suspended in POCl$_3$ (8.8 ml, 94.7 mmol) and heated to 75° C. for 2 h. After this time, the mixture was added to a chilled sodium hydroxide solution (1 M) and then extracted with ethyl acetate. The organic layer were dried over anhydrous sodium sulfate, filtered, and the filtrate was concentrated. The residue was purified by column chromatography (silica, hexanes/ethyl acetate) to afford the title compound (2.1 g, 90%) as a clear oil. MW=250.65. $^1$H NMR (CDCl$_3$, 500 MHz) δ 7.46 (s, 1H), 3.42 (quin, J=8.2 Hz, 1H), 2.18-2.07 (m, 2H), 1.99-1.80 (m, 4H), 1.76-1.66 (m, 2H); APCI MS m/z 251 [M+H]$^+$.

EXAMPLE 227

2-(4-((2-Cyclopentyl-6-(trifluoromethyl)pyrimidin-4-yl)amino)phenyl)ethanol

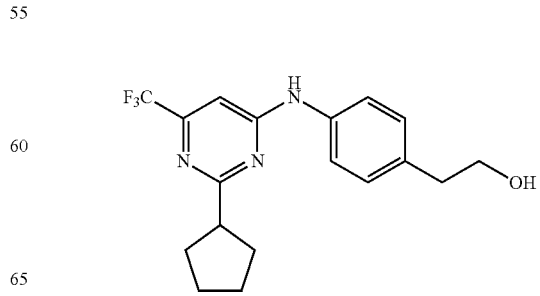

Following general procedure A1, 4-chloro-2-cyclopentyl-6-(trifluoromethyl)pyrimidine (0.100 g, 0.40 mmol) was reacted with 2-(4-aminophenyl)ethanol (0.066 g, 0.48 mmol) to afford the title compound (0.097 g, 69%) as a white solid. MW=351.37. ¹H NMR (DMSO-$d_6$, 500 MHz) δ 9.93 (s, 1H), 7.68-7.54 (m, 2H), 7.21 (d, J=8.5 Hz, 2H), 6.92 (s, 1H), 4.61 (t, J=5.0 Hz, 1H), 3.63-3.56 (m, 2H), 3.19 (quin, J=8.0 Hz, 1H), 2.70 (t, J=7.0 Hz, 2H), 2.05-1.96 (m, 2H), 1.89-1.60 (m, 6H); APCI MS m/z 352 [M+H]⁺.

EXAMPLE 228

2-(4-((2-Cyclopentyl-6-(trifluoromethyl)pyrimidin-4-yl)amino)phenyl)acetamide

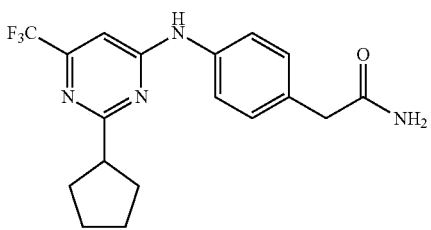 [SMILES: NC(=O)Cc1ccc(Nc2cc(C(F)(F)F)nc(C3CCCC3)n2)cc1]

Following general procedure A1, 4-chloro-2-cyclopentyl-6-(trifluoromethyl)pyrimidine (0.100 g, 0.40 mmol) was reacted with 2-(4-aminophenyl)acetamide (0.072 g, 0.48 mmol) to afford the title compound (0.095 g, 65%) as a white solid. MW=364.36. ¹H NMR (DMSO-$d_6$, 500 MHz) δ 9.97 (s, 1H), 7.69-7.57 (m, 2H), 7.42 (s, 1H), 7.25 (d, J=8.0 Hz, 2H), 6.93 (s, 1H), 6.85 (s, 1H), 3.34 (s, 2H), 3.20 (quin, J=8.0 Hz, 1H), 2.05-1.97 (m, 2H), 1.89-1.59 (m, 6H); APCI MS m/z 365 [M+H]⁺.

EXAMPLE 229

2-(4-((2-Cyclopentyl-6-(trifluoromethyl)pyrimidin-4-yl)methyl)phenyl)acetic acid

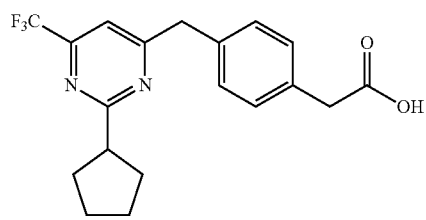 [SMILES: O=C(O)Cc1ccc(Cc2cc(C(F)(F)F)nc(C3CCCC3)n2)cc1]

Step 1. Preparation of methyl 2-(4-((2-cyclopentyl-6-(trifluoromethyl)pyrimidin-4-yl)methyl)phenyl)acetate

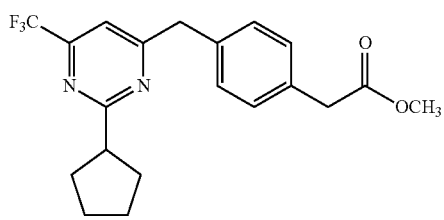 [SMILES: COC(=O)Cc1ccc(Cc2cc(C(F)(F)F)nc(C3CCCC3)n2)cc1]

Following general procedure G, 4-chloro-2-cyclopentyl-6-(trifluoromethyl)pyrimidine (0.245 g, 0.98 mmol) was reacted with methyl 2-(4-((4,4,5,5-tetramethyl-1,3,2-dioxaborolan-2-yl)methyl)phenyl)acetate (0.284 g, 0.98 mmol) to afford crude product (0.179 g) as an oil. MW=378.39. ¹H NMR (CDCl₃, 500 MHz) δ 7.26-7.22 (m, 4H), 7.16 (s, 1H), 4.13 (s, 2H), 3.70 (s, 3H), 3.62 (s, 2H), 3.42 (quin, J=8.2 Hz, 1H), 2.15-2.07 (m, 2H), 2.00-1.80 (m, 4H), 1.76-1.65 (m, 2H); APCI MS m/z 379 [M+H]⁺.

EXAMPLE 229

2-(4-((2-Cyclopentyl-6-(trifluoromethyl)pyrimidin-4-yl)methyl)phenyl)acetic acid

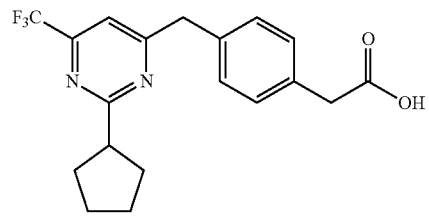 [SMILES: O=C(O)Cc1ccc(Cc2cc(C(F)(F)F)nc(C3CCCC3)n2)cc1]

Following general procedure D, methyl 2-(4-((2-cyclopentyl-6-(trifluoromethyl)pyrimidin-4-yl)methyl)phenyl)acetate (0.55 mmol) was reacted with lithium hydroxide (0.055 g) to afford the title compound (0.051 g, 25% over two steps) as a light yellow oil. MW=364.36. ¹H NMR (DMSO-$d_6$, 500 MHz) δ 12.27 (s, 1H), 7.72 (s, 1H), 7.28 (d, J=8.0 Hz, 2H), 7.20 (d, J=8.0 Hz, 2H), 4.17 (s, 2H), 3.52 (s, 2H), 3.41-3.33 (m, 1H), 2.08-1.99 (m, 2H), 1.89-1.60 (m, 6H); APCI MS m/z 365 [M+H]⁺.

EXAMPLE 230

2-(4-((2-Cyclopentyl-6-(trifluoromethyl)pyrimidin-4-yl)methyl)phenyl)acetamide

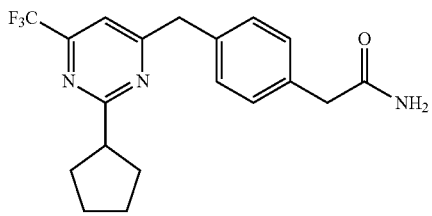 [SMILES: NC(=O)Cc1ccc(Cc2cc(C(F)(F)F)nc(C3CCCC3)n2)cc1]

To a solution of 2-(4-((2-cyclopentyl-6-(trifluoromethyl)pyrimidin-4-yl)methyl)phenyl)acetic acid (0.045 g, 0.12 mmol) in DMF (2 mL) was added EDC (0.047 g, 0.24 mmol), HOBT (0.033 g, 0.24 mmol) and 7N ammonia in methanol (0.17 mL, 1.2 mmol). The mixture was sealed and stirred at 85° C. for 3 h. After this time, the mixture was diluted with ethyl acetate and then washed with water. The organic layer were dried over anhydrous sodium sulfate, filtered, and the filtrate was concentrated. The residue was purified by column chromatography (silica, hexanes/ethyl acetate) to afford the title compound (0.034 g, 79%) as a white solid. MW=363.38. ¹H NMR (DMSO-$d_6$, 500 MHz) δ 7.71 (s, 1H), 7.41 (s, 1H), 7.26 (d, J=8.0 Hz, 2H), 7.20 (d, J=8.0 Hz, 2H), 6.83 (s, 1H), 4.16 (s, 2H), 3.41-3.33 (m, 1H), 3.33 (s, 2H), 2.09-1.99 (m, 2H), 1.89-1.61 (m, 6H); APCI MS m/z 364 [M+H]+.

EXAMPLE 231

2-(4-((2-Cyclopentyl-6-(trifluoromethyl)pyrimidin-4-yl)methyl)phenyl)ethanol

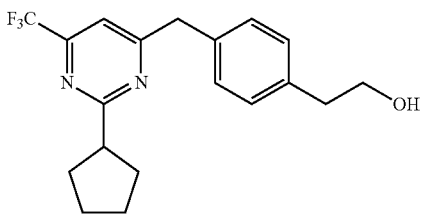 [SMILES: OCCc1ccc(Cc2cc(C(F)(F)F)nc(C3CCCC3)n2)cc1]

Following general procedure E1, methyl 2-(4-((2-cyclopentyl-6-(trifluoromethyl)pyrimidin-4-yl)methyl)phenyl)acetate (0.079 g, 0.21 mmol) was reacted with DIBAL (1.0 M, 1.0 mL, 1.0 mmol) to afford the title compound (0.061 g, 83%) as a light yellow oil. MW=350.38. $^1$H NMR (DMSO-d$_6$, 500 MHz) δ 7.70 (s, 1H), 7.23 (d, J=8.0 Hz, 2H), 7.16 (d, J=8.0 Hz, 2H), 4.58 (t, J=5.5 Hz, 1H), 4.15 (s, 2H), 3.41-3.33 (m, 1H), 2.68 (t, J=7.0 Hz, 2H), 2.09-1.99 (m, 2H), 1.90-1.61 (m, 6H); APCI MS m/z 351 [M+H]+.

EXAMPLE 232

2-(4-((2-(Cyclopentyloxy)-6,7-dihydro-5H-cyclopenta[d]pyrimidin-4-yl)amino)phenyl)acetamide

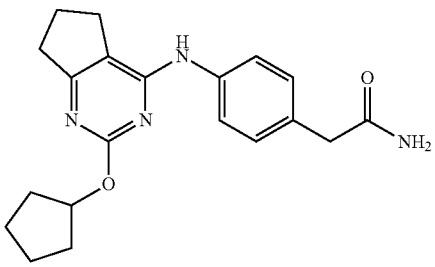 [SMILES: NC(=O)Cc1ccc(Nc2nc(OC3CCCC3)nc3c2CCC3)cc1]

Step 1. Preparation of 4-chloro-2-(methylthio)-6,7-dihydro-5H-cyclopenta[d]pyrimidine

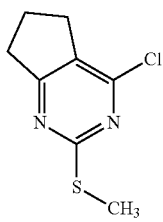

A mixture of 2,4-dichloro-6,7-dihydro-5H-cyclopenta[d]pyrimidine (0.250 g, 1.32 mmol) and sodium thiomethoxide (0.093 g, 1.32 mmol) in THF (10 mL) was stirred at rt for 6 h. After this time, the mixture was diluted with saturated aqueous sodium bicarbonate and extracted with ethyl acetate. The combined organic layer was dried over anhydrous sodium sulfate, filtered and the filtrate was concentrated. The residue was purified by column chromatography (silica, hexanes/ethyl acetate) to afford the title compound (0.210 g, 84%) as an off-white solid. MW=200.69. $^1$H NMR (DMSO-d$_6$, 300 MHz) δ 2.90 (t, J=7.6 Hz, 2H), 2.71 (t, J=7.6 Hz, 2H), 2.56 (s, 3H), 2.10 (quin, J=7.6 Hz, 2H); APCI MS m/z 201 [M+H]+.

Step 2. Preparation of 4-chloro-2-(methylsulfonyl)-6,7-dihydro-5H-cyclopenta[d]pyrimidine

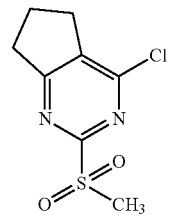

To a solution of 4-chloro-2-(methylthio)-6,7-dihydro-5H-cyclopenta[d]pyrimidine (0.208 g, 1.04 mmol) in methylene chloride (4 mL) was added m-CPBA (0.805 g, 4.66 mmol) in portions over a 15 min period at 0° C. and then the mixture was slowly warmed to rt and stirred overnight. After this time, the reaction mixture was diluted with water and extracted with ethyl acetate. The combined organic layer was dried over anhydrous sodium sulfate, filtered, and the filtrate was concentrated to afford the title compound (0.157 g, 75%). MW=232.69. $^1$H NMR (CDCl$_3$, 300 MHz) δ 3.39-3.28 (m, 5H), 3.11 (t, J=7.6 Hz, 2H), 2.27 (t, J=7.6 Hz, 2H); APCI MS m/z 233 [M+H]+.

Step 3. Preparation of 4-chloro-2-(cyclopentyloxy)-6,7-dihydro-5H-cyclopenta[d]pyrimidine

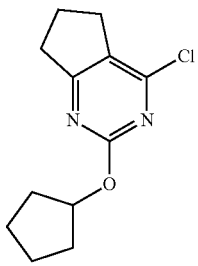 [SMILES: Clc1nc(OC2CCCC2)nc2c1CCC2]

To a solution of cyclopentanol (0.287 g, 3.33 mmol) in THF (5 mL) was added sodium hydride (0.016 g, 0.67 mmol) and the mixture stirred at rt under a nitrogen atmosphere for 30 min. Then, the mixture was added treated with a solution of 4-chloro-2-(methylsulfonyl)-6,7-dihydro-5H-cyclopenta[d]pyrimidine (0.155 g, 0.67 mmol) dropwise in THF (2 mL) and the resulting mixture stirred at rt for 2 h. After this time, the reaction mixture was diluted with water and extracted with ethyl acetate. The combined organic layer was dried over anhydrous sodium sulfate, filtered, and the filtrate was concentrated. The residue was purified by column chromatography (silica, hexanes/dichloromethane) to afford the title compound (0.080 g, 52%). MW=238.71. ¹H NMR (CD₃OD, 300 MHz) δ 5.64-5.40 (m, 1H), 2.90 (t, J=7.6 Hz, 2H), 2.78 (t, J=7.6 Hz, 2H), 2.21-2.08 (m, 2H), 1.90-1.71 (m, 4H), 1.71-1.59 (m, 2H), 1.38-1.18 (m, 2H); APCI MS m/z 239 [M+H]⁺.

Step 4. Preparation of ethyl 2-(4-((2-(cyclopentyloxy)-6,7-dihydro-5H-cyclopenta[d]pyrimidin-4-yl)amino)phenyl)acetate

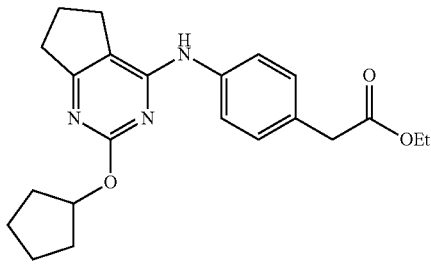 [SMILES: CCOC(=O)Cc1ccc(Nc2nc(OC3CCCC3)nc3c2CCC3)cc1]

Following General Procedure B2, 4-chloro-2-(cyclopentyloxy)-6,7-dihydro-5H-cyclopenta[d]pyrimidine (0.075 g, 0.31 mmol) was reacted with 4-aminophenylacetic acid ethyl ester (0.084 g, 0.47 mmol) to afford the title compound (0.110 g, crude) as a white solid. MW=381.47. ¹H NMR (CD₃OD, 300 MHz) δ 7.61 (d, J=8.6 Hz, 2H), 7.18 (d, J=8.6 Hz, 2H), 5.55-5.45 (m, 1H), 4.13 (q, J=7.6 Hz, 2H), 3.57 (s, 2H), 2.79 (t, J=7.6 Hz, 2H), 2.71 (t, J=7.6 Hz, 2H), 2.14-1.95 (m, 4H), 1.89 (s, 1H), 1.87-1.76 (m, 4H), 1.72-1.61 (m, 2H), 1.24 (t, J=7.1 Hz, 1H); APCI MS m/z 382 [M+H]⁺.

EXAMPLE 232

2-(4-((2-(Cyclopentyloxy)-6,7-dihydro-5H-cyclopenta[d]pyrimidin-4-yl)amino)phenyl)acetamide

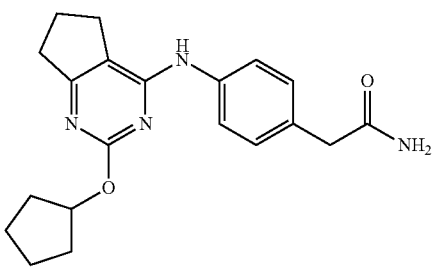 [SMILES: NC(=O)Cc1ccc(Nc2nc(OC3CCCC3)nc3c2CCC3)cc1]

Following General Procedure C, ethyl 2-(4-((2-(cyclopentyloxy)-6,7-dihydro-5H-cyclopenta[d]pyrimidin-4-yl)amino)phenyl)acetate (0.100 g, 0.26 mmol) was reacted with ammonia in methanol (7.0 M, 4 mL) to afford the title compound (0.030 g, 30%) as a brown solid. MW=352.43. ¹H NMR (DMSO-d₆, 300 MHz) δ 9.28 (s, 1H), 7.66 (d, J=8.6 Hz, 2H), 7.37 (s, 1H), 7.13 (d, J=8.6 Hz, 2H), 6.83 (s, 1H), 5.56-540 (m, 1H), 3.28 (s, 2H), 2.74 (t, J=7.6 Hz, 2H), 2.64 (t, J=7.6 Hz, 2H), 2.07-1.91 (m, 4H), 1.82-1.69 (m, 4H), 1.69-1.56 (m, 2H); APCI MS m/z 353 [M+H]⁺.

EXAMPLE 233

2 2-(4-((2-(Cyclopentyloxy)-6,7-dihydro-5H-cyclopenta[d]pyrimidin-4-yl)amino)phenyl)ethanol

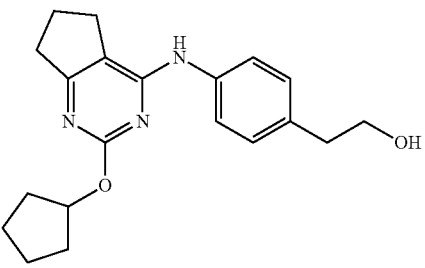 [SMILES: OCCc1ccc(Nc2nc(OC3CCCC3)nc3c2CCC3)cc1]

Following General Procedure B1, 4-chloro-2-(cyclopentyloxy)-6,7-dihydro-5H-cyclopenta[d]pyrimidine (0.200 g, 0.84 mmol), dioxane (3 mL) was reacted with 4-aminophenethyl alcohol (0.172 g, 1.26 mmol) to afford the title compound (0.044 g, 22%) as a white solid. MW=339.43. ¹H NMR (DMSO-d₆, 300 MHz) δ 9.23 (s, 1H), 7.64 (d, J=8.4 Hz, 2H), 7.08 (d, J=8.4 Hz, 2H), 5.49-5.40 (m, 1H), 3.65-3.50 (m, 2H), 2.73 (t, J=7.6 Hz, 2H) 2.69-5.59 (m, 5H), 2.09-1.90 (m, 4H), 1.80-1.53 (m, 6H); APCI MS m/z 340 [M+H]⁺.

EXAMPLE 234

2-(4-((2-(3-Chlorophenyl)-5,6,7,8-tetrahydroquinazolin-4-yl)amino)phenyl)acetamide

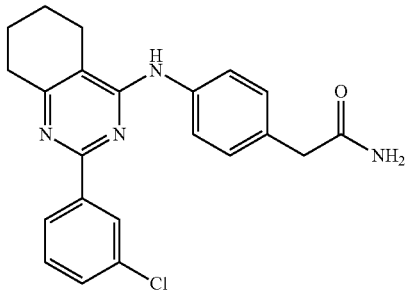

Step 1. Preparation of 2-(3-chlorophenyl)-5,6,7,8-tetrahydroquinazolin-4(3H)-one

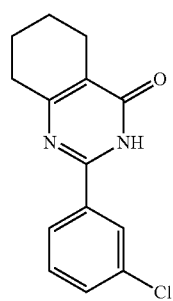 [SMILES: O=c1[nH]c(-c2cccc(Cl)c2)nc2c1CCCC2]

A solution of 3-chlorobenzimidamide (5 g, 32.34 mmol) in ethanol (90 mL) was treated with ethyl-2-cyclohexaneonecarboxylate (6.3 g, 40.43 mmol) and sodium methoxide (2.1 g, 38.81 mmol). The reaction mixture was heated at 85° C. for 18 h. After this time, the reaction mixture was cooled and concentrated to a volume of approximately 50 mL. Then, 2.0 M HCl (68 mL) was added slowly. The resulting precipitate was filtered, washed with water and ether, and the residue was dried on a high vacuum overnight to afford the title compound (2.2 g, crude) as a light yellow solid. MW=260.72. $^1$H NMR (DMSO-$d_6$, 300 MHz) δ 12.64 (s, 1H), 8.16-8.10 (m, 1H), 8.08-7.99 (m, 1H), 7.66-7.57 (m, 1H), 7.54 (t, J=7.9 Hz, 1H), 2.66-2.55 (m, 2H), 2.44-2.33 (m, 2H), 1.84-1.61 (m, 4H); APCI MS m/z 261 [M+H]$^+$.

Step 2. Preparation of 4-chloro-2-(3-chlorophenyl)-5,6,7,8-tetrahydroquinazoline

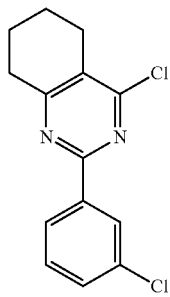 [SMILES: Clc1cccc(-c2nc(Cl)c3c(n2)CCCC3)c1]

Phosphorus(V) oxychloride (17.6 g, 114.7 mmol) was slowly added to 2-(3-chlorophenyl)-5,6,7,8-tetrahydroquinazolin-4(3H)-one (2.2 g, 8.5 mmol) at 0° C. The reaction mixture was warmed to 100° C. and held at that temperature for 2 h. After this time, the mixture was cooled, quenched with saturated sodium hydroxide, and extracted with ethyl acetate. The combined organic layer was dried over anhydrous sodium sulfate, filtered, and the filtrate was concentrated. The residue was purified by column chromatography (silica, hexanes/dichloromethane) to afford the title compound (2.1 g, 23%) as a white solid. MW=279.16. $^1$H NMR (CDCl$_3$, 300 MHz) δ 8.43-8.37 (m, 1H), 8.32-8.24 (m, 1H), 7.49-7.33 (m, 2H), 3.03-2.87 (m, 2H), 2.86-2.70 (m, 2H), 1.98-1.83 (m, 4H); APCI MS m/z 279 [M+H]$^+$.

EXAMPLE 234

2-(4-((2-(Cyclopent-1-en-1-yl)-6-(trifluoromethyl)pyridin-4-yl)amino)phenyl)acetic acid

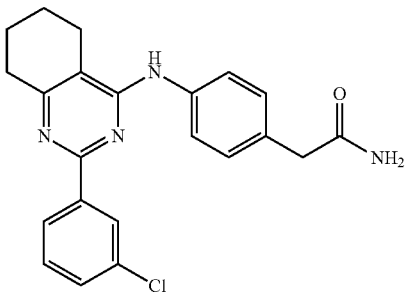

Following General Procedure A1, 4-chloro-2-(3-chlorophenyl)-5,6,7,8-tetrahydroquinazoline (0.100 g, 0.36 mmol) was reacted with 2-(4-aminophenyl)acetamide (0.065 g, 0.43 mmol) and the reaction mixture was stirred at 80° C. for 18 h. After this time, the reaction mixture was cooled, diluted with water, and extracted with ethyl acetate. The combined organic layer was dried over anhydrous sodium sulfate, filtered, and the filtrate was concentrated. The residue was purified by column chromatography (silica, dichloromethane/methanol) to afford the title compound (0.103 g, 100%) as a white solid. MW=392.88. $^1$H NMR (DMSO-$d_6$, 300 MHz) δ 8.42 (s, 1H), 8.27-8.16 (m, 2H), 7.73-7.64 (m, 2H), 7.55-7.45 (m, 3H), 7.26 (d, J=8.5 Hz, 2H), 6.90 (s, 1H), 3.36 (s, 2H) 2.79-2.70 (m, 2H), 2.66-2.56 (m, 2H), 1.83 (s, 4H); APCI MS m/z 393 [M+H]$^+$.

EXAMPLE 235

2-(4-((2-(3-Chlorophenyl)-5,6,7,8-tetrahydroquinazolin-4-yl)amino)phenyl)ethanol

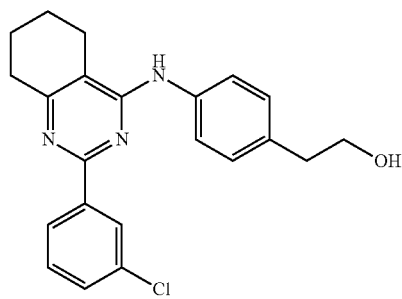 [SMILES: OCCc1ccc(Nc2nc(-c3cccc(Cl)c3)nc3c2CCCC3)cc1]

Following General Procedure A1, 4-chloro-2-(3-chlorophenyl)-5,6,7,8-tetrahydroquinazoline (0.100 g, 0.36 mmol) was reacted with 4-aminophenethyl alcohol (0.059 g, 0.43 mmol) to afford the title compound (0.101 g, 100%) as a yellow solid. MW=379.88. $^1$H NMR (DMSO-$d_6$, 300 MHz) δ 8.35 (s, 1H), 8.25-8.16 (m, 2H), 7.69-7.64 (m, 2H), 7.52-7.47 (m, 2H), 7.22 (d, J=8.5 Hz, 2H), 4.63 (t, J=5.2 Hz, 1H), 3.66-3.58 (m, 2H), 2.78-2.68 (m, 4H), 2.63-2.57 (m, 2H), 1.89-1.77 (m, 4H); APCI MS m/z 380 [M+H]$^+$.

EXAMPLE 236

2-(4-((2-(Pyrrolidin-1-yl)-6,7-dihydro-5H-cyclopenta[b]pyridin-4-yl)amino)phenyl)acetamide hydrochloride

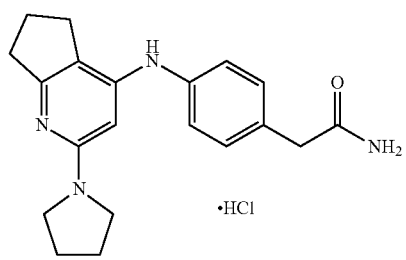 [SMILES: NC(=O)Cc1ccc(Nc2cc(N3CCCC3)nc3c2CCC3)cc1 ; Cl]

Step 1. Preparation of 4-chloro-2-(pyrrolidin-1-yl)-6,7-dihydro-5H-cyclopenta[b]pyridine

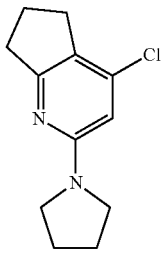 [SMILES: Clc1cc(N2CCCC2)nc2c1CCC2]

Following general procedure B1, 2,4-dichloro-6,7-dihydro-5H-cyclopenta[b]pyridine (0.150 g, 0.80 mmol) was reacted with pyrrolidine (0.085 g, 1.2 mmol) to afford the title compound (0.069 g, 38%) as a light yellow solid. MW=222.71. $^1$H NMR (CDCl$_3$, 300 MHz) δ 6.13 (s, 1H), 3.46-3.36 (m, 4H), 2.97-2.81 (m, 4H), 2.13-1.94 (6H); APCI MS m/z 223 [M+H]$^+$.

Step 2. Preparation of ethyl 2-(4-((2-(pyrrolidin-1-yl)-6,7-dihydro-5H-cyclopenta[b]pyridin-4-yl)amino)phenyl)acetate

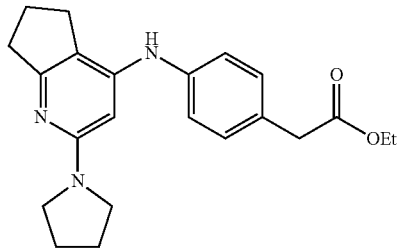 [SMILES: CCOC(=O)Cc1ccc(Nc2cc(N3CCCC3)nc3c2CCC3)cc1]

Following general procedure B1, 4-chloro-2-(pyrrolidin-1-yl)-6,7-dihydro-5H-cyclopenta[b]pyridine (0.068 g, 0.30 mmol) was reacted with ethyl 2-(4-aminophenyl)acetate (0.080 g, 0.45 mmol) to afford the title compound (0.100 g, 90%) as a brown oil. MW=365.47. APCI MS m/z 366 [M+H]$^+$.

EXAMPLE 236

2-(4-((2-(Pyrrolidin-1-yl)-6,7-dihydro-5H-cyclopenta[b]pyridin-4-yl)amino)phenyl)acetamide hydrochloride

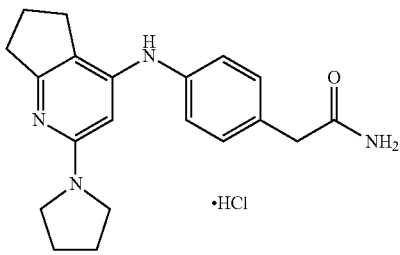 [SMILES: NC(=O)Cc1ccc(Nc2cc(N3CCCC3)nc3c2CCC3)cc1 ; Cl]

Following general procedure C, ethyl 2-(4-((2-(pyrrolidin-1-yl)-6,7-dihydro-5H-cyclopenta[b]pyridin-4-yl)amino)phenyl)acetate (0.100 g, 0.27 mmol) was reacted with ammonia in methanol (7.0 M, 3 mL), followed by formation of the hydrochloride salt to afford the title compound (0.039 g, 39%) as a light yellow solid. MW=372.89. $^1$H NMR (DMSO-d$_6$, 500 MHz) δ 12.00 (s, 1H), 8.97 (s, 1H), 7.52 (s, 1H), 7.32 (d, J=8.5 Hz, 2H), 7.28 (d, J=8.5 Hz, 2H), 6.90 (s, 1H), 5.77-5.75 (m, 1H), 3.40 (s, 2H), 3.37-3.31 (m, 4H), 2.97 (t, J=7.5 Hz, 2H), 2.77 (t, J=7.5 Hz, 2H), 2.13 (quin, J=7.5 Hz, 2H), 1.98-1.91 (m, 4H); APCI MS m/z 337 [M+H]$^+$.

EXAMPLE 237

Methyl 2-(4-((2-(pyrrolidin-1-yl)-6,7-dihydro-5H-cyclopenta[b]pyridin-4-yl)amino)phenyl)acetate hydrochloride

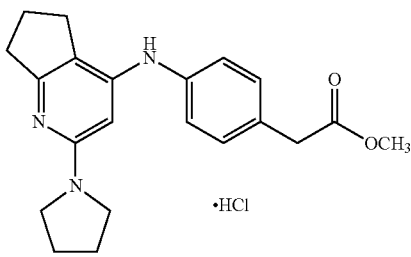 [SMILES: COC(=O)Cc1ccc(Nc2cc(N3CCCC3)nc3c2CCC3)cc1 ; Cl]

Following general procedure C, ethyl 2-(4-((2-(pyrrolidin-1-yl)-6,7-dihydro-5H-cyclopenta[b]pyridin-4-yl)amino)phenyl)acetate (0.100 g, 0.27 mmol) was reacted with ammonia in methanol (7.0 M, 3 mL). Formation of the amide[2-(4-((2-(pyrrolidin-1-yl)-6,7-dihydro-5H-cyclopenta[b]pyridin-4-yl)amino)phenyl)acetamide] was the major product and formation of the ester[methyl 2-(4-((2-(pyrrolidin-1-yl)-6,7-dihydro-5H-cyclopenta[b]pyridin-4-yl)amino)phenyl)acetate] was minor Chromatography, followed by formation of the hydrochloride salt, gave the methyl ester product (0.020 g, 19%) as a light yellow solid. MW=387.90. $^1$H NMR (DMSO-d$_6$, 500 MHz) δ 12.04 (s, 1H), 8.98 (s, 1H), 7.37-7.29 (m, 4H), 5.77 (s, 1H), 3.71 (s, 2H), 3.63 (s, 3H), 3.38-3.33 (m, 4H), 2.98 (t, J=7.5 Hz, 2H), 2.77 (t, J=7.5 Hz, 2H), 2.13 (quin, J=7.5 Hz, 2H), 1.98-1.92 (m, 4H); APCI MS m/z 352 [M+H]$^+$.

EXAMPLE 238

2-(4-((2-(Piperazin-1-yl)-6,7-dihydro-5H-cyclopenta[b]pyridin-4-yl)amino)phenyl)ethanol hydrochloride

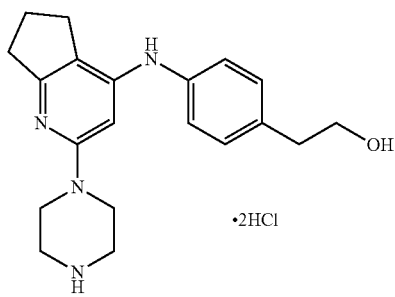 [SMILES: OCCc1ccc(Nc2cc(N3CCNCC3)nc3c2CCC3)cc1 ; "·2HCl"]

Step 1. Preparation of tert-butyl 4-(4-chloro-6,7-dihydro-5H-cyclopenta[b]pyridin-2-yl)piperazine-1-carboxylate

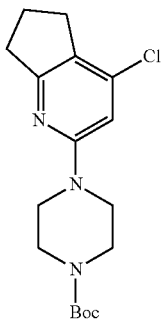 [SMILES: CC(C)(C)OC(=O)N1CCN(c2cc(Cl)c3c(n2)CCC3)CC1]

Following general procedure B1, 2,4-dichloro-6,7-dihydro-5H-cyclopenta[b]pyridine (0.150 g, 0.80 mmol) was reacted with tert-butyl piperazine-1-carboxylate (0.223 g, 1.2 mmol) to afford the title compound (0.052 g, 19%) as a yellow solid. MW=337.84. $^1$H NMR (CDCl$_3$, 500 MHz) δ 6.39 (s, 1H), 3.56-3.50 (m, 4H), 3.49-3.44 (m, 4H), 2.92 (t, J=7.5 Hz, 2H), 2.87 (t, J=7.5 Hz, 2H), 2.08 (quin, J=7.5 Hz, 2 H), 1.48 (s, 9H); APCI MS m/z 338[M+H]$^+$.

Step 2. Preparation of tert-butyl 4-(4-((4-(2-hydroxyethyl)phenyl)amino)-6,7-dihydro-5H-cyclopenta[b]pyridin-2-yl)piperazine-1-carboxylate

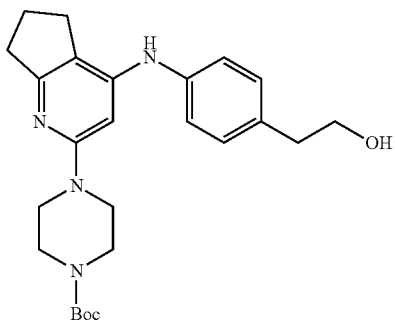 [SMILES: CC(C)(C)OC(=O)N1CCN(c2cc(Nc3ccc(CCO)cc3)c3c(n2)CCC3)CC1]

Following general procedure B1, tert-butyl 4-(4-chloro-6,7-dihydro-5H-cyclopenta[b]pyridin-2-yl)piperazine-1-carboxylate (0.050 g, 0.15 mmol) was reacted with 2-(4-aminophenyl)ethanol (0.030 g, 0.22 mmol) to afford the title compound (0.026 g, 40%) as an orange oil. MW=438.56. APCI MS m/z 439 [M+H]$^+$.

EXAMPLE 238

2-(4-((2-(Piperazin-1-yl)-6,7-dihydro-5H-cyclopenta[b]pyridin-4-yl)amino)phenyl)ethanol hydrochloride

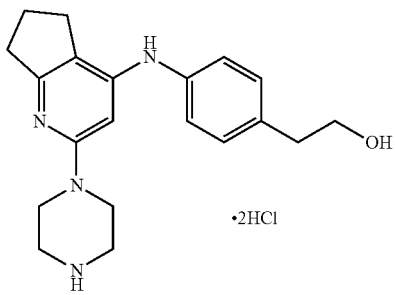 [SMILES: OCCc1ccc(Nc2cc(N3CCNCC3)nc3c2CCC3)cc1 ; "·2HCl"]

To a solution of tert-butyl 4-(4-((4-(2-hydroxyethyl)phenyl)amino)-6,7-dihydro-5H-cyclopenta[b]pyridin-2-yl)piperazine-1-carboxylate (0.026 g, 0.059 mmol) in methylene chloride (5 mL) was added TFA (0.1 mL). The mixture stirred at rt for 16 h and purified by preparative HPLC (water/acetonitrile with 0.05% TFA), followed by formation of the hydrochloride salt to afford the title compound (0.010 g, 41%) as a yellow-brown solid. MW 32 411.37. $^1$H NMR (DMSO-d$_6$, 500 MHz) δ 13.21 (s, 1H), 9.46-9.19 (m, 3H), 7.31 (d, J=8.0 Hz, 2H), 7.25 (d, J=8.0 Hz, 2H), 6.04 (s, 1H), 3.68-3.56 (m, 6H), 3.20 (br s, 4H), 3.05-2.96 (m, 2H), 2.81-2.72 (m, 4H), 2.19-2.10 (m, 2H); APCI MS m/z 339 [M+H]$^+$.

EXAMPLE 239

2-(4-((2-(furan-2-yl)-6,7-dihydro-5H-cyclopenta[b]pyridin-4-yl)amino)phenyl)ethanol hydrochloride

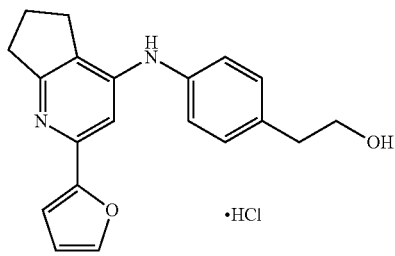 [SMILES: OCCc1ccc(Nc2cc(-c3ccco3)nc3c2CCC3)cc1 ; Cl]

Step 1. Preparation of 4-chloro-2-(furan-2-yl)-6,7-dihydro-5H-cyclopenta[b]pyridine

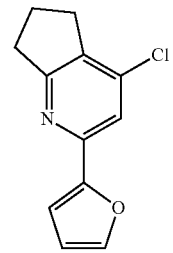 [SMILES: Clc1cc(-c2ccco2)nc2c1CCC2]

To a solution of 2,4-dichloro-6,7-dihydro-5H-cyclopenta[b]pyridine (0.130 g, 0.69 mmol) in dioxane (3 mL) was added tributyl(furan-2-yl)stannane (0.271 g, 0.76 mmol) and tetrakis(triphenylphosphine)palladium (0.039 g, 0.035 mmol). The mixture was purged with nitrogen and then heated to 110° C. under sealed conditions for 2 h. After this time, the mixture was diluted with water and extracted with ethyl acetate. The organic layer were dried over anhydrous sodium sulfate, filtered, and the filtrate was concentrated. The residue was purified by column chromatography (silica, hexanes/ethyl acetate) to afford the title compound (0.140 g, 92%) as a white solid. MW=219.67. $^1$H NMR (CDCl$_3$, 500 MHz) δ 7.52-7.48 (m, 1H), 7.45 (s, 1H), 7.02-6.98 (m, 1H), 6.52-6.48 (m, 1H), 3.10 (t, J=7.5 Hz, 2H), 2.99 (t, J=7.5 Hz, 2H), 2.15 (quin, J=7.5 Hz, 2H); APCI MS m/z 220 [M+H]$^+$.

EXAMPLE 239

2-(4-((2-(Furan-2-yl)-6,7-dihydro-5H-cyclopenta[b]pyridin-4-yl)amino)phenyl)ethanol hydrochloride

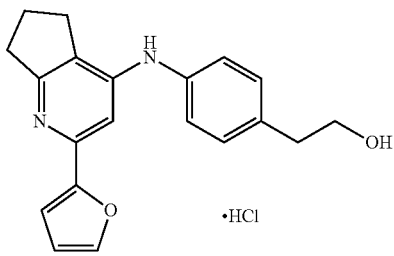 [SMILES: OCCc1ccc(Nc2cc(-c3ccco3)nc3c2CCC3)cc1 ; Cl]

Following general procedure B1, 4-chloro-2-(furan-2-yl)-6,7-dihydro-5H-cyclopenta[b]pyridine (0.064 g, 0.29 mmol) was reacted with 2-(4-aminophenyl)ethanol (0.048 g, 0.35 mmol), followed by formation of the hydrochloride salt to afford the title compound (0.038 g, 37%) as a white solid. MW=356.85. $^1$H NMR (DMSO-$d_6$, 500 MHz) δ 14.14 (s, 1H), 9.57 (s, 1H), 7.95 (s, 1H), 7.52 (s, 1H), 7.35 (d, J=8.5 Hz, 2H), 7.27 (d, J=8.5 Hz, 2H), 7.01 (s, 1H), 6.77-6.72 (m, 1H), 4.68 (s, 1H), 3.66 (t, J=7.0 Hz, 2H), 3.11 (t, J=7.5 Hz, 2H), 2.88 (t, J=7.0 Hz, 2H), 2.78 (t, J=7.0 Hz, 2H), 2.20 (quin, J=7.5 Hz, 2H); APCI MS m/z 321 [M+H]$^+$.

EXAMPLE 240

2-(4-((2-(Furan-2-yl)-6,7-dihydro-5H-cyclopenta[b]pyridin-4-yl)amino)phenyl)acetamide hydrochloride

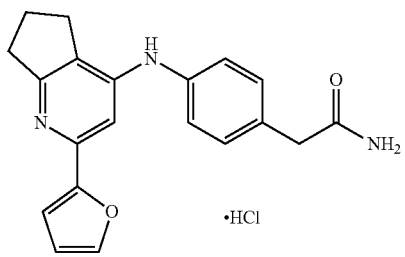 [SMILES: NC(=O)Cc1ccc(Nc2cc(-c3ccco3)nc3c2CCC3)cc1 ; Cl]

Step 1. Preparation of ethyl 2-(4-((2-(furan-2-yl)-6,7-dihydro-5H-cyclopenta[b]pyridin-4-yl)amino)phenyl)acetate

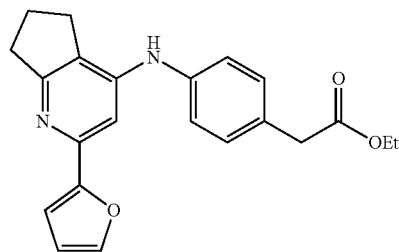 [SMILES: CCOC(=O)Cc1ccc(Nc2cc(-c3ccco3)nc3c2CCC3)cc1]

Following general procedure B1, 4-chloro-2-(furan-2-yl)-6,7-dihydro-5H-cyclopenta[b]pyridine (0.064 g, 0.29 mmol) was reacted with ethyl 2-(4-aminophenyl)acetate (0.073 g, 0.41 mmol) to afford the title compound (0.075 g, 61%) as a white foam. MW=362.42. $^1$H NMR (CDCl$_3$, 500 MHz) δ 7.45-4.43 (m, 1H), 7.30 (d, J=8.5 Hz, 2H), 7.24 (s, 1H), 7.18 (d, J=8.5 Hz, 2H), 6.93-6.89 (m, 1H), 6.48-6.44 (m, 1H), 5.73 (s, 1H), 4.18 (q, J=7.0 Hz, 2H), 3.62 (s, 2H), 3.05 (t, J=7.5 Hz, 2H), 2.80 (t, J=7.5 Hz, 2H), 2.18 (quin, J=7.5 Hz, 2H), 1.28 (t, J=7.0 Hz, 3H); APCI MS m/z 363 [M+H]$^+$.

EXAMPLE 240

2-(4-((2-(Furan-2-yl)-6,7-dihydro-5H-cyclopenta[b]pyridin-4-yl)amino)phenyl)acetamide hydrochloride

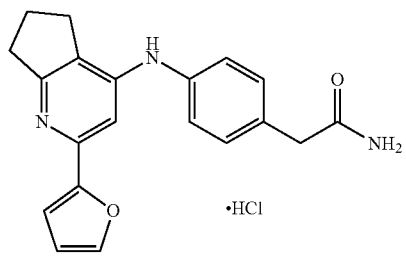 [SMILES: NC(=O)Cc1ccc(Nc2cc(-c3ccco3)nc3c2CCC3)cc1 ; Cl]

Following general procedure C, ethyl 2-(4-((2-(furan-2-yl)-6,7-dihydro-5H-cyclopenta[b]pyridin-4-yl)amino)phenyl)acetate (0.075 g, 0.21 mmol) was reacted with ammonia in methanol (7.0 M, 5 mL), followed by formation of the hydrochloride salt to afford the title compound (0.039 g, 51%) as a light yellow solid. MW=369.85. $^1$H NMR (DMSO-$d_6$, 500 MHz) δ 14.21 (s, 1H), 9.78 (s, 1H), 8.01-7.98 (m, 1H), 7.64 (d, J=3.5 Hz, 1H), 7.56 (s, 1H), 7.40 (d, J=8.5 Hz, 2H), 7.32 (d, J=8.5 Hz, 2H), 7.02 (s, 1H), 6.93 (s, 1H), 6.79-6.75 (m, 1H), 3.45 (s, 2H), 3.15 (t, J=7.5 Hz, 2H), 2.89 (t, J=7.5 Hz, 2H), 2.22 (quin, J=7.5 Hz, 2H); APCI MS m/z 334 [M+H]$^+$.

EXAMPLE 241

2-(4-((2-(Oxazol-2-yl)-6,7-dihydro-5H-cyclopenta[b]pyridin-4-yl)amino)phenyl)ethanol

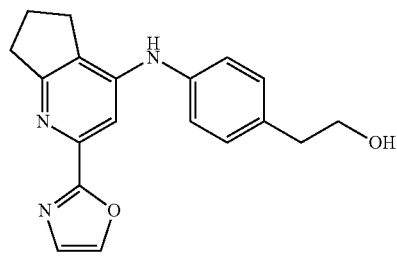 [SMILES: OCCc1ccc(Nc2cc(-c3ncco3)nc3c2CCC3)cc1]

Step 1. Preparation of 2-(4-chloro-6,7-dihydro-5H-cyclopenta[b]pyridin-2-yl)oxazole

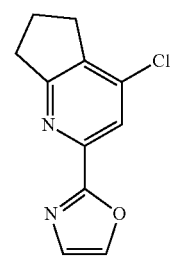 [SMILES: Clc1cc(-c2ncco2)nc2c1CCC2]

To a solution of 2,4-dichloro-6,7-dihydro-5H-cyclopenta[b]pyridine (0.152 g, 0.81 mmol) in dioxane (3 mL) was added 2-(tributylstannyl)oxazole (0.318 g, 0.89 mmol) and tetrakis(triphenylphosphine)palladium (0.046 g, 0.040 mmol). The mixture was purged with nitrogen and then heated to 110° C. under sealed conditions for 16 h. After this time, the mixture was diluted with water and extracted with ethyl acetate. The organic layer were dried over anhydrous sodium sulfate, filtered, and the filtrate was concentrated. The residue was purified by column chromatography (silica, hexanes/ethyl acetate) to afford the title compound (0.061 g, 34%) as a white solid. MW=220.66. $^1$H NMR (CDCl$_3$, 500 MHz) δ 7.94 (s, 1H), 7.78 (s, 1H), 7.29 (s, 1H), 3.19 (t, J=7.5 Hz, 2H), 3.06 (t, J=7.5 Hz, 2H), 2.22 (quin, J=7.5 Hz, 2H); APCI MS m/z 221 [M+H]$^+$.

EXAMPLE 241

2-(4-((2-(Oxazol-2-yl)-6,7-dihydro-5H-cyclopenta[b]pyridin-4-yl)amino)phenyl)ethanol

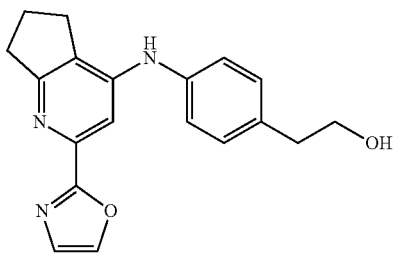 [SMILES: OCCc1ccc(Nc2cc(-c3ncco3)nc3c2CCC3)cc1]

Following general procedure B1, 2-(4-chloro-6,7-dihydro-5H-cyclopenta[b]pyridin-2-yl)oxazole (0.059 g, 0.27 mmol) was reacted with 2-(4-aminophenyl)ethanol (0.044 g, 0.32 mmol) to afford the title compound (0.049 g, 57%) as a light yellow solid. MW=321.37. $^1$H NMR (DMSO-d$_6$, 500 MHz) δ 8.19-8.14 (m, 2H), 7.45 (s, 1H), 7.30-7.28 (m, 1H), 7.24 (d, J=8.5 Hz, 2H), 7.15 (d, J=8.5 Hz, 2H), 4.64 (s, 1H), 3.66-3.59 (m, 2H), 2.90 (t, J=7.5 Hz, 2H), 2.84 (t, J=7.0 Hz, 2H), 2.72 (t, J=7.0 Hz, 2H), 2.09 (quin, J=7.5 Hz, 2H); APCI MS m/z 322 [M+H]$^+$.

EXAMPLE 242

2-(4-((2-(Oxazol-2-yl)-6,7-dihydro-5H-cyclopenta[b]pyridin-4-yl)amino)phenyl)acetamide

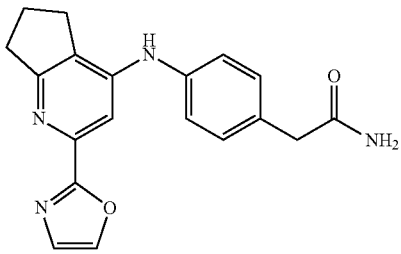 [SMILES: NC(=O)Cc1ccc(Nc2cc(-c3ncco3)nc3c2CCC3)cc1]

Step 1. Preparation of ethyl 2-(4-((2-(oxazol-2-yl)-6,7-dihydro-5H-cyclopenta[b]pyridin-4-yl)amino)phenyl)acetate

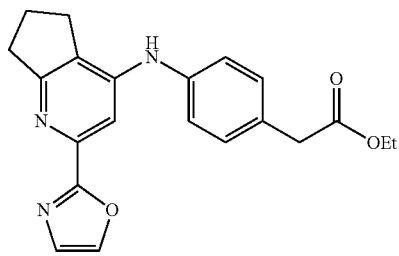 [SMILES: CCOC(=O)Cc1ccc(Nc2cc(-c3ncco3)nc3c2CCC3)cc1]

Following general procedure B1, 2-(4-chloro-6,7-dihydro-5H-cyclopenta[b]pyridin-2-yl)oxazole (0.040 g, 0.18 mmol) was reacted with ethyl 2-(4-aminophenyl)acetate (0.039 g, 0.22 mmol) to afford the title compound (0.047 g, 71%) as a white foam. MW=363.41. $^1$H NMR (CDCl$_3$, 500 MHz) δ 7.72 (s, 1H), 7.66 (s, 1H), 7.31 (d, J=8.5 Hz, 2H), 7.22-7.17 (m, 3H), 5.80 (s, 1H), 4.18 (q, J=7.0 Hz, 2H), 3.61 (s, 2H), 3.11 (t, J=7.5 Hz, 2H), 2.84 (t, J=7.5 Hz, 2H), 2.22 (quin, J=7.5 Hz, 2H), 1.28 (t, J=7.0 Hz, 3H); APCI MS m/z 364 [M+H]$^+$.

EXAMPLE 242

2-(4-((2-(Oxazol-2-yl)-6,7-dihydro-5H-cyclopenta[b]pyridin-4-yl)amino)phenyl)acetamide

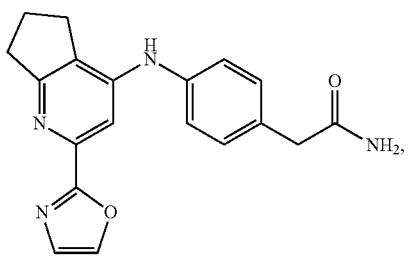 [SMILES: NC(=O)Cc1ccc(Nc2cc(-c3ncco3)nc3c2CCC3)cc1]

Following general procedure C, ethyl 2-(4-((2-(oxazol-2-yl)-6,7-dihydro-5H-cyclopenta[b]pyridin-4-yl)amino)phenyl)acetate (0.047 g, 0.13 mmol) was reacted with ammonia in methanol (7.0 M, 5 mL) to afford the title compound (0.027 g, 63%) as a white solid. MW=334.37. $^1$H NMR (DMSO-d$_6$, 500 MHz) δ 8.24 (s, 1H), 8.16 (s, 1H), 7.49-7.43 (m, 2H), 7.32-7.25 (m, 3H), 7.17 (d, J=8.5 Hz, 2H), 6.87 (s, 1H), 3.37 (s, 2H), 2.90 (t, J=7.5 Hz, 2H), 2.85 (t, J=7.5 Hz, 2H), 2.09 (quin, J=7.5 Hz, 2H); APCI MS m/z 335 [M+H]$^+$.

EXAMPLE 243

2 2-(4-((2-(Thiophen-3-yl)-6,7-dihydro-5H-cyclopenta[b]pyridin-4-yl)amino)phenyl)ethanol

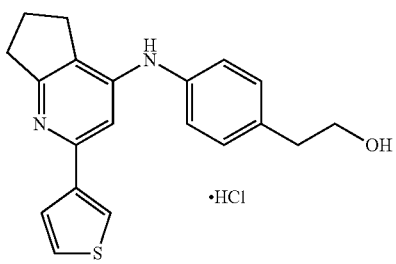 [SMILES: OCCc1ccc(Nc2cc(-c3ccsc3)nc3c2CCC3)cc1 ; Cl]

Step 1. Preparation of 4-chloro-2-(thiophen-3-yl)-6,7-dihydro-5H-cyclopenta[b]pyridine

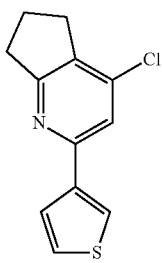

Following general procedure F, 2,4-dichloro-6,7-dihydro-5H-cyclopenta[b]pyridine (0.150 g, 0.80 mmol) was reacted with thiophen-3-ylboronic acid (0.112 g, 0.88 mmol) to afford the title compound (0.132 g, 70%) as a white solid. MW=235.73. $^1$H NMR (CDCl$_3$, 500 MHz) δ 7.88-7.82 (m, 1H), 7.61-7.56 (m, 1H), 7.40-7.34 (m, 1H), 3.11 (t, J=7.5 Hz, 2H), 3.00 (t, J=7.5 Hz, 2H), 2.16 (quin, J=7.5 Hz, 2H); APCI MS m/z 236 [M+H]$^+$.

EXAMPLE 243

2 2-(4-((2-(Thiophen-3-yl)-6,7-dihydro-5H-cyclopenta[b]pyridin-4-yl)amino)phenyl)ethanol

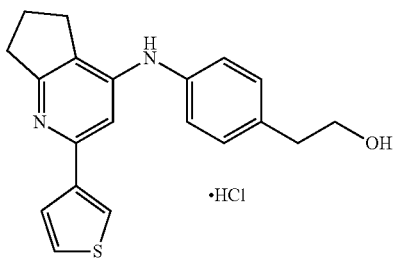 [SMILES: OCCc1ccc(Nc2cc(-c3ccsc3)nc3c2CCC3)cc1 ; Cl]

Following general procedure B1, 4-chloro-2-(thiophen-3-yl)-6,7-dihydro-5H-cyclopenta[b]pyridine (0.060 g, 0.25 mmol) was reacted with 2-(4-aminophenyl)ethanol (0.041 g, 0.30 mmol), followed by formation of the hydrochloride salt to afford the title compound (0.025 g, 27%) as a white solid. MW=356.85. MW=372.91. $^1$H NMR (DMSO-d$_6$, 500 MHz) δ 13.91 (s, 1H), 9.68 (s, 1H), 8.37-8.32 (m, 1H), 7.80-7.76 (m, 1H), 7.59-7.55 (m, 1H), 7.34 (d, J=8.5 Hz, 2H), 7.30 (d, J=8.5 Hz, 2H), 7.03 (s, 1H), 4.67 (s, 1H), 3.65 (t, J=7.0 Hz, 2H), 3.15 (t, J=7.5 Hz, 2H), 2.88 (t, J=7.0 Hz, 2H), 2.77 (t, J=7.0 Hz, 2H), 2.20 (quin, J=7.5 Hz, 2H); APCI MS m/z 337 [M+H]$^+$.

EXAMPLE 244

2-(4-((2-(Thiophen-3-yl)-6,7-dihydro-5H-cyclopenta[b]pyridin-4-yl)amino)phenyl)acetamide

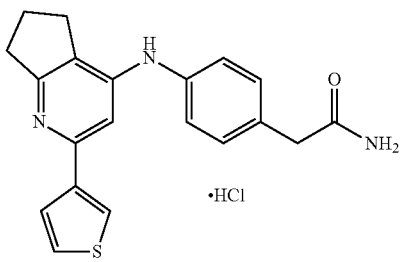 [SMILES: NC(=O)Cc1ccc(Nc2cc(-c3ccsc3)nc3c2CCC3)cc1 ; Cl]

Step 1. Preparation of ethyl 2-(4-((2-(thiophen-3-yl)-6,7-dihydro-5H-cyclopenta[b]pyridin-4-yl)amino)phenyl)acetate

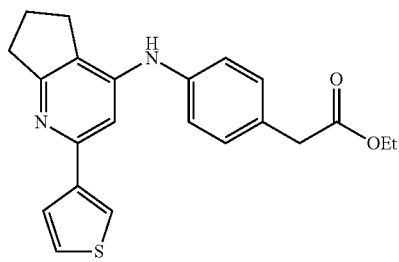 [SMILES: CCOC(=O)Cc1ccc(Nc2cc(-c3ccsc3)nc3c2CCC3)cc1]

Following general procedure B1, 4-chloro-2-(thiophen-3-yl)-6,7-dihydro-5H-cyclopenta[b]pyridine (0.070 g, 0.30 mmol) was reacted with ethyl 2-(4-aminophenyl)acetate (0.064 g, 0.36 mmol) to afford the title compound (0.065 g, 57%) as an orange-brown oil. MW=378.49. APCI MS m/z 379 [M+H]$^+$.

EXAMPLE 244

2-(4-((2-(Thiophen-3-yl)-6,7-dihydro-5H-cyclopenta[b]pyridin-4-yl)amino)phenyl)acetamide

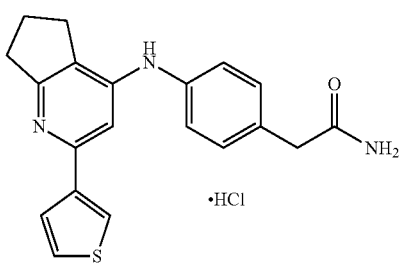 [SMILES: NC(=O)Cc1ccc(Nc2cc(-c3ccsc3)nc3c2CCC3)cc1 ; Cl]

Following general procedure C, ethyl 2-(4-((2-(thiophen-3-yl)-6,7-dihydro-5H-cyclopenta[b]pyridin-4-yl)amino)phenyl)acetate (0.065 g, 0.17 mmol) was reacted with ammonia in methanol (7.0 M, 5 mL), followed by formation of the hydrochloride salt to afford the title compound (0.033 g, 50%) as a light yellow solid. MW=385.91. $^1$H NMR (DMSO-$d_6$, 500 MHz) δ 13.84 (s, 1H), 9.69 (s, 1H), 8.35-8.31 (m, 1H), 7.81-7.76 (m, 1H), 7.59-7.56 (m, 1H), 7.51 (s, 1H), 7.38 (d, J=8.5 Hz, 2H), 7.33 (d, J=8.5 Hz, 2H), 7.05 (s, 1H), 6.92 (s, 1H), 3.43 (s, 2H), 3.15 (t, J=7.5 Hz, 2H), 2.89 (t, J=7.5 Hz, 2H), 2.23 (quin, J=7.5 Hz, 2H); APCI MS m/z 350 [M+H]$^+$.

EXAMPLE 245

2-(4-((2-(5-Chlorothiophen-2-yl)-6,7-dihydro-5H-cyclopenta[b]pyridin-4-yl)amino)phenyl)acetamide hydrochloride

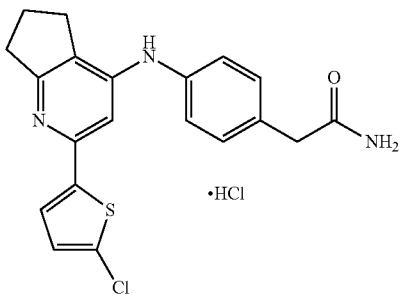 [SMILES: NC(=O)Cc1ccc(Nc2cc(-c3ccc(Cl)s3)nc3c2CCC3)cc1 ; Cl]

Step 1. Preparation 4-chloro-2-(5-chlorothiophen-2-yl)-6,7-dihydro-5H-cyclopenta[b]pyridine

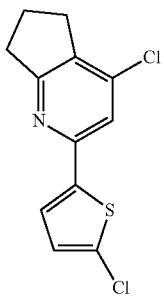

Following general procedure F, 2,4-dichloro-6,7-dihydro-5H-cyclopenta[b]pyridine (0.150 g, 0.80 mmol) was reacted with (5-chlorothiophen-2-yl)boronic acid (0.142 g, 0.88 mmol) to afford the title compound (0.031 g, 14%) as a white solid. MW=270.18. $^1$H NMR (CDCl$_3$, 500 MHz) δ 7.32 (s, 1H), 7.27 (d, J=4.0 Hz, 1H), 6.89 (d, J=4.0 Hz, 1H), 3.08 (t, J=7.5 Hz, 2H), 2.98 (t, J=7.5 Hz, 2H), 2.16 (quin, J=7.5 Hz, 2H); APCI MS m/z 270 [M+H]$^+$.

Step 2. Preparation of ethyl 2-(4-((2-(5-chlorothiophen-2-yl)-6,7-dihydro-5H-cyclopenta[b]pyridin-4-yl)amino)phenyl)acetate

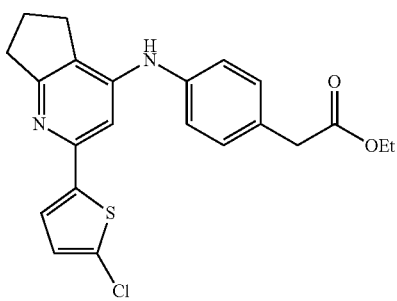 [SMILES: CCOC(=O)Cc1ccc(Nc2cc(-c3ccc(Cl)s3)nc3c2CCC3)cc1]

Following general procedure B1, 4-chloro-2-(5-chlorothiophen-2-yl)-6,7-dihydro-5H-cyclopenta[b]pyridine (0.030 g, 0.11 mmol) was reacted with ethyl 2-(4-aminophenyl)acetate (0.024 g, 0.13 mmol) to afford crude product (0.023 g) as an orange oil. MW=412.93. APCI MS m/z 413 [M+H]$^+$.

EXAMPLE 245

2-(4-((2-(5-Chlorothiophen-2-yl)-6,7-dihydro-5H-cyclopenta[b]pyridin-4-yl)amino)phenyl)acetamide hydrochloride

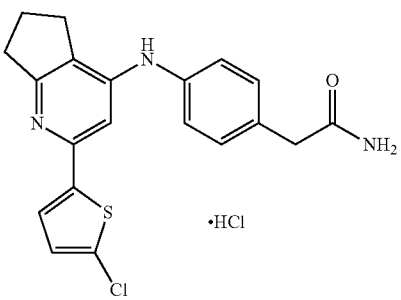 [SMILES: NC(=O)Cc1ccc(Nc2cc(-c3ccc(Cl)s3)nc3c2CCC3)cc1 ; Cl]

Following general procedure C, ethyl 2-(4-((2-(5-chlorothiophen-2-yl)-6,7-dihydro-5H-cyclopenta[b]pyridin-4-yl)amino)phenyl)acetate (0.11 mmol) was reacted with ammonia in methanol (7.0 M, 5 mL), followed by formation of the hydrochloride salt to afford the title compound (0.011 g, 24% over two steps) as a light yellow solid. MW=420.36. $^1$H NMR (DMSO-$d_6$, 500 MHz) δ 14.09 (s, 1H), 9.64 (s, 1H), 7.74 (s, 1H), 7.51 (s, 1H), 7.36 (d, J=8.5 Hz, 2H), 7.30-7.27 (m, 3H), 6.96-6.86 (m, 2H), 3.42 (s, 2H), 3.14-3.05 (m, 2H), 2.89-2.82 (m, 2H), 2.23-2.13 (m, 2H); APCI MS m/z 384 [M+H]$^+$.

EXAMPLE 246

2-(4-((2-(Cyclopent-1-en-1-yl)-6,7-dihydro-5H-cyclopenta[b]pyridin-4-yl)amino)phenyl)acetamide hydrochloride

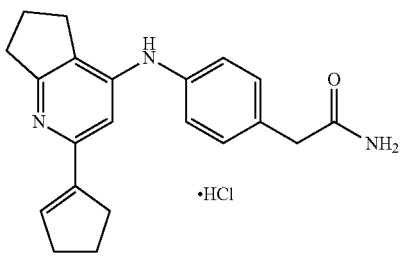 [SMILES: NC(=O)Cc1ccc(Nc2cc(C3=CCCC3)nc3c2CCC3)cc1 ; Cl]

Step 1. Preparation of 4-chloro-2-(cyclopent-1-en-1-yl)-6,7-dihydro-5H-cyclopenta[b]pyridine

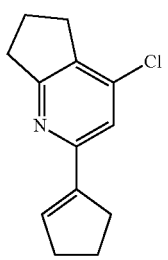 [SMILES: Clc1cc(C2=CCCC2)nc2c1CCC2]

Following general procedure F except the reaction was heated to 140° C. under microwave irradiation for 2 h, 2,4-dichloro-6,7-dihydro-5H-cyclopenta[b]pyridine (0.157 g, 0.84 mmol) was reacted with cyclopent-1-en-1-ylboronic acid (0.112 g, 1.0 mmol) to afford the title compound (0.120 g, 65%) as a white solid. MW=219.71. $^1$H NMR (CDCl$_3$, 500 MHz) δ 7.06 (s, 1H), 6.62-6.57 (m, 1H), 3.06 (t, J=7.5 Hz, 2H), 2.97 (t, J=7.5 Hz, 2H), 2.77-2.70 (m, 2H), 2.58-2.52 (m, 2H), 2.13 (quin, J=7.5 Hz, 2H), 2.08-2.00 (m, 2H); APCI MS m/z 220 [M+H]$^+$.

EXAMPLE 246

2-(4-((2-(Cyclopent-1-en-1-yl)-6,7-dihydro-5H-cyclopenta[b]pyridin-4-yl)amino)phenyl)acetamide hydrochloride

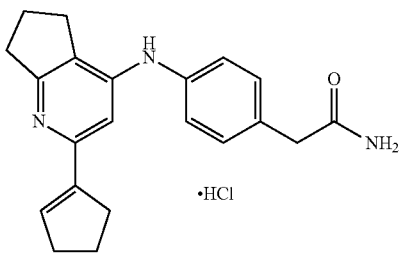 [SMILES: NC(=O)Cc1ccc(Nc2cc(C3=CCCC3)nc3c2CCC3)cc1 ; Cl]

Following general procedure A2, 4-chloro-2-(cyclopent-1-en-1-yl)-6,7-dihydro-5H-cyclopenta[b]pyridine (0.100 g, 0.45 mmol) was reacted with 2-(4-aminophenyl)acetamide (0.081 g, 0.54 mmol), followed by formation of the hydrochloride salt to afford the title compound (0.048 g, 29%) as a light yellow solid. MW=420.38. $^1$H NMR (DMSO-d$_6$, 500 MHz) δ 13.47 (s, 1H), 9.69 (s, 1H), 7.52 (s, 1H), 7.37 (d, J=8.5 Hz, 2H), 7.29 (d, J=8.5 Hz, 2H), 6.92-6.88 (m, 1H), 6.71-6.68 (m, 1H), 3.42 (s, 2H), 3.12 (t, J=7.5 Hz, 2H), 2.85 (t, J=7.5 Hz, 2H), 2.61-2.54 (m, 4H), 2.19 (quin, J=7.5 Hz, 2H), 1.95 (quin, J=7.5 Hz, 2H); APCI MS m/z 384 [M+H]$^+$.

EXAMPLE 247

2-(4-((2-Cyclopentyl-6,7-dihydro-5H-cyclopenta[b]pyridin-4-yl)amino)phenyl)acetamide hydrochloride

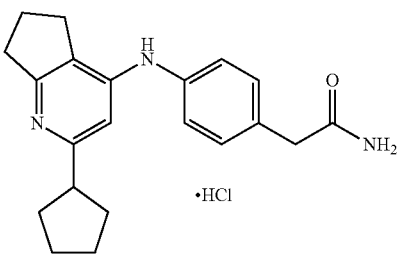 [SMILES: NC(=O)Cc1ccc(Nc2cc(C3CCCC3)nc3c2CCC3)cc1 ; Cl]

To a solution of 2-(4-((2-(cyclopent-1-en-1-yl)-6,7-dihydro-5H-cyclopenta[b]pyridin-4-yl)amino)phenyl)acetamide hydrochloride (0.042 g, 0.11 mmol) in ethanol (10 mL) was added 10% palladium on carbon (0.005 g). The mixture stirred at rt for 2 h under an atmosphere of hydrogen. After this time, the mixture was filtered over celite, concentrated, and the residue converted to the hydrochloride salt to afford the title compound (0.040 g, 95%) as a white solid. MW=420.38. $^1$H NMR (DMSO-d$_6$, 500 MHz) δ 13.60 (s, 1H), 9.59 (s, 1H), 7.52 (s, 1H), 7.36 (d, J=8.0 Hz, 1H), 7.26 (d, J=8.0 Hz, 2H), 6.92 (s, 1H), 6.69-6.66 (m, 1H), 3.42 (s, 1H), 3.18-3.04 (m, 3H), 2.83 (t, J=7.5 Hz, 2H), 2.18 (quin, J=7.5 Hz, 2H), 2.07-1.96 (m, 2H), 1.77-1.69 (m, 2H), 1.68-1.52 (m, 4H), 1.37-1.22 (m, 2H); APCI MS m/z 384 [M+H]$^+$.

EXAMPLE 248

2-(4-((2-(Cyclopent-1-en-1-yl)-6,7-dihydro-5H-cyclopenta[b]pyridin-4-yl)amino)phenyl)ethanol hydrochloride

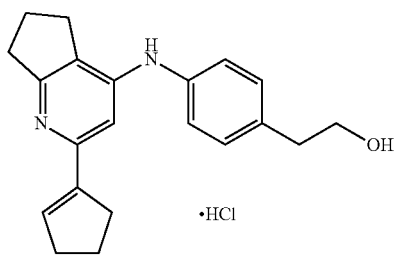 [SMILES: OCCc1ccc(Nc2cc(C3=CCCC3)nc3c2CCC3)cc1 ; Cl]

Following general procedure B1, 4-chloro-2-(cyclopent-1-en-1-yl)-6,7-dihydro-5H-cyclopenta[b]pyridine (0.095 g, 0.43 mmol) was reacted with 2-(4-aminophenyl)ethanol (0.089 g, 0.65 mmol), followed by formation of the hydrochloride salt to afford the title compound (0.110 g, 79%) as a yellow solid. MW=356.89. ¹H NMR (DMSO-d₆, 500 MHz) δ 13.67 (s, 1H), 9.71 (s, 1H), 7.33 (d, J=8.5 Hz, 2H), 7.26 (d, J=8.5 Hz, 2H), 6.99 (s, 1H), 6.66 (s, 1H), 3.64 (t, J=7.0 Hz, 2H), 3.13 (t, J=7.5 Hz, 2H), 2.84 (t, J=7.5 Hz, 2H), 2.76 (t, J=7.0 Hz, 2H), 2.56 (t, J=7.5 Hz, 4H), 2.18 (quin, J=7.5 Hz, 2H) 1.94 (quin, J=7.5 Hz, 2H); APCI MS m/z 321 [M+H]⁺.

EXAMPLE 249

2-(4-((2-cyclopentyl-6,7-dihydro-5H-cyclopenta[b]pyridin-4-yl)amino)phenyl)ethanol hydrochloride

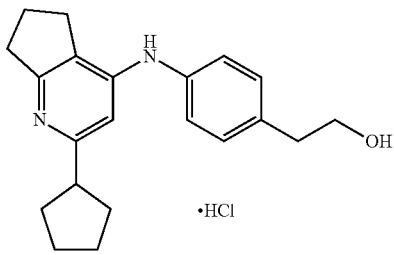 [SMILES: OCCc1ccc(Nc2cc(C3CCCC3)nc3c2CCC3)cc1 ; Cl]

To a solution of 2-(4-((2-(cyclopent-1-en-1-yl)-6,7-dihydro-5H-cyclopenta[b]pyridin-4-yl)amino)phenyl)ethanol (0.070 g, 0.22 mmol) in ethanol (10 mL) was added 10% palladium on carbon (0.010 g) and the mixture was stirred at under an atmosphere of hydrogen at rt for 3 h. After this time, the mixture was filtered over celite, concentrated, purified by column chromatography (silica, dichloromethane/methanol) and followed by formation of the hydrochloride salt to afford the title compound (0.053 g, 68%) as a white solid. MW=358.91. ¹H NMR (DMSO-d₆, 500 MHz) δ 13.66 (s, 1H), 9.58 (s, 1H), 7.33 (d, J=8.5 Hz, 2H), 7.23 (d, J=8.5 Hz, 2H), 6.65 (s, 1H), 4.67 (br s, 1H), 3.65-3.63 (m, 2H), 3.15-3.04 (m, 3H), 2.82 (t, J=7.5 Hz, 2H), 2.76 (t, J=7.0 Hz, 2H), 2.18 (quin, J=7.5 Hz, 2H), 2.06-1.96 (m, 2H), 1.78-1.54 (m, 6H); APCI MS m/z 323 [M+H]⁺.

EXAMPLE 250

2-(4-((2-Cyclohexyl-6,7-dihydro-5H-cyclopenta[b]pyridin-4-yl)amino)phenyl)acetamide hydrochloride

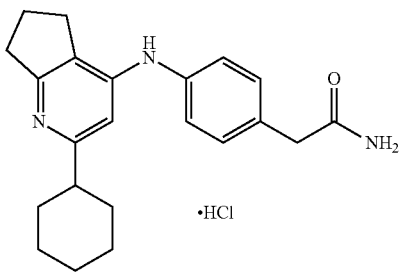 [SMILES: NC(=O)Cc1ccc(Nc2cc(C3CCCCC3)nc3c2CCC3)cc1 ; Cl]

Step 1. Preparation of 4-chloro-2-(cyclohex-1-en-1-yl)-6,7-dihydro-5H-cyclopenta[b]pyridine

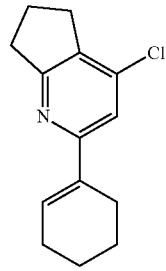 [SMILES: Clc1cc(C2=CCCCC2)nc2c1CCC2]

Following general procedure F, 2,4-dichloro-6,7-dihydro-5H-cyclopenta[b]pyridine (0.157 g, 0.84 mmol) was reacted with cyclohex-1-en-1-ylboronic acid (0.142 g, 1.13 mmol) to afford crude product (0.130 g) as an oil. MW=233.74. ¹H NMR (CDCl₃, 500 MHz) δ 7.13 (s, 1H), 7.08 (s, 1H), 6.70-6.66 (m, 1H), 3.06 (t, J=7.5 Hz, 2H), 2.96 (t, J=7.5 Hz, 2H), 2.47-2.42 (m, 2H), 2.27-2.22 (m, 2H), 2.17-2.09 (m, 2H), 1.82-1.75 (m, 2H), 1.69-1.63 (m, 2H); APCI MS m/z 234 [M+H]⁺.

Step 2. Preparation of ethyl 2-(4-((2-(cyclohex-1-en-1-yl)-6,7-dihydro-5H-cyclopenta[b]pyridin-4-yl)amino)phenyl)acetate

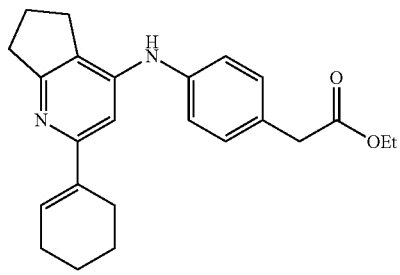 [SMILES: CCOC(=O)Cc1ccc(Nc2cc(C3=CCCCC3)nc3c2CCC3)cc1]

Following general procedure B1, 4-chloro-2-(cyclohex-1-en-1-yl)-6,7-dihydro-5H-cyclopenta[b]pyridine (1.03 mmol) was reacted with ethyl 2-(4-aminophenyl)acetate (0.150 g, 0.84 mmol) to afford the title compound (0.121 g, 31% over two steps) as an orange oil. MW=376.49. APCI MS m/z 377 [M+H]⁺.

Step 3. Preparation of ethyl 2-(4-((2-cyclohexyl-6,7-dihydro-5H-cyclopenta[b]pyridin-4-yl)amino)phenyl)acetate

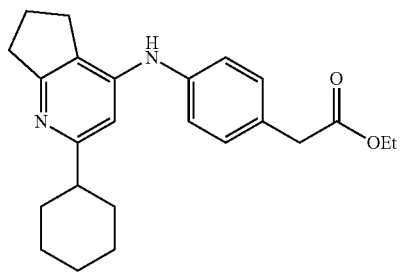 [SMILES: CCOC(=O)Cc1ccc(Nc2cc(C3CCCCC3)nc3c2CCC3)cc1]

To a solution of ethyl 2-(4-((2-(cyclohex-1-en-1-yl)-6,7-dihydro-5H-cyclopenta[b]pyridin-4-yl)amino)phenyl)acetate (0.120 g, 0.32 mmol) in ethanol (10 mL) was added 10% palladium on carbon (0.020 g) and the mixture stirred at under an atmosphere of hydrogen at rt for 16 h. After this time, the mixture was filtered over celite, concentrated, and purified by column chromatography (silica, dichloromethane/methanol) to afford the title compound (0.130 g, 100%) as an off-white solid. MW=378.51. $^1$H NMR (CD$_3$OD, 500 MHz) δ 7.17 (d, J=8.3 Hz, 2H), 7.06 (d, J=8.3 Hz, 2H), 6.57-6.54 (m, 1H), 4.06 (q, J=7.0 Hz, 2H), 3.53 (s, 2H), 2.80 (t, J=7.5 Hz, 2H), 2.69 (t, J=7.5 Hz, 2H), 2.45-2.36 (m, 1H), 2.02 (quin, J=7.5 Hz, 2H), 1.78-1.58 (m, 5H), 1.33-1.13 (m, 8H); APCI MS m/z 379 [M+H]$^+$.

EXAMPLE 250

2-(4-((2-Cyclohexyl-6,7-dihydro-5H-cyclopenta[b]pyridin-4-yl)amino)phenyl)acetamide hydrochloride

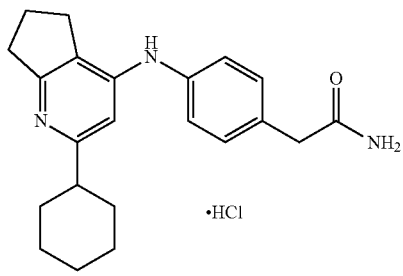 [SMILES: NC(=O)Cc1ccc(Nc2cc(C3CCCCC3)nc3c2CCC3)cc1 ; Cl]

Following general procedure C, ethyl 2-(4-((2-cyclohexyl-6,7-dihydro-5H-cyclopenta[b]pyridin-4-yl)amino)phenyl)acetate (0.065 g, 0.17 mmol) was reacted with ammonia in methanol (7.0 M, 3 mL), followed by formation of the hydrochloride salt to afford the title compound (0.023 g, 35%) as a white solid. MW=385.93. $^1$H NMR (DMSO-d$_6$, 300 MHz) δ 13.73 (s, 1H), 9.62 (s, 1H), 7.56 (s, 1H), 7.37 (d, J=8.4 Hz, 2H), 7.26 (d, J=8.4 Hz, 2H), 6.94 (s, 1H), 6.65 (s, 1H), 3.42 (s, 2H), 3.07 (t, J=7.5 Hz, 2H), 2.83 (t, J=7.5 Hz, 2H), 2.78-2.66 (m, 1H), 2.18 (quin, J=7.5 Hz, 2H), 1.87-1.60 (m, 5H), 1.52-1.13 (m, 5H); APCI MS m/z 350 [M+H]$^+$.

EXAMPLE 251

2-(4-((2-cyclohexyl-6,7-dihydro-5H-cyclopenta[b]pyridin-4-yl)amino)phenyl)ethanol hydrochloride

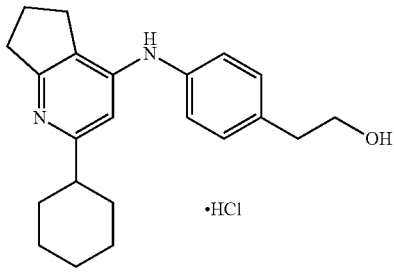 [SMILES: OCCc1ccc(Nc2cc(C3CCCCC3)nc3c2CCC3)cc1 ; Cl]

Following general procedure E2, ethyl 2-(4-((2-cyclohexyl-6,7-dihydro-5H-cyclopenta[b]pyridin-4-yl)amino)phenyl)acetate (0.065 g, 0.17 mmol) was reacted with BH$_3$.DMS (10.0 M, 0.10 mL, 1.0 mmol), followed by formation of the hydrochloride salt to afford the title compound (0.035 g, 55%) as a white solid. MW=372.93. $^1$H NMR (DMSO-d$_6$, 300 MHz) δ 13.59 (s, 1H), 9.57 (s, 1H), 7.34 (d, J=8.5 Hz, 2H), 7.23 (d, J=8.5 Hz, 2H), 6.63 (s, 1H), 4.73-4.63 (m, 1H), 3.71-3.59 (m, 2H), 3.06 (t, J=7.5 Hz, 2H), 2.88-2.63 (m, 5H), 2.18 (quin, J=7.5 Hz, 2H) 1.85-1.61 (m, 5H), 1.52-1.11 (m, 5H); APCI MS m/z 337 [M+H]$^+$.

EXAMPLE 252

2-(4-((2-(Piperazin-1-yl)-6,7-dihydro-5H-cyclopenta[b]pyridin-4-yl)amino)phenyl)acetamide hydrochloride

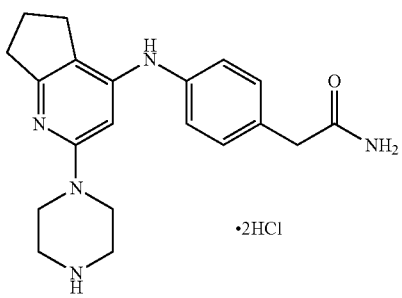 [SMILES: NC(=O)Cc1ccc(Nc2cc(N3CCNCC3)nc3c2CCC3)cc1 ; "·2HCl"]

Step 1. Preparation of ethyl 2-(4-((2-chloro-6,7-dihydro-5H-cyclopenta[b]pyridin-4-yl)amino)phenyl)acetate

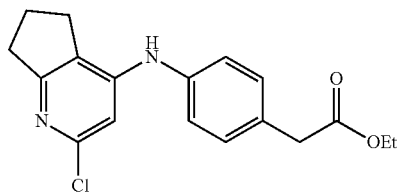 [SMILES: CCOC(=O)Cc1ccc(Nc2cc(Cl)nc3c2CCC3)cc1]

A microwave vessel was charged with a solution of 2,4-dichloro-6,7-dihydro-5H-cyclopenta[b]pyridine (0.165 g, 0.88 mmol) in ethanol (3 mL). p-Toluenesulfonic acid (0.167 g, 0.88 mmol) and ethyl 2-(4-aminophenyl)acetate (0.157 g, 0.88 mmol) were added and the vessel was sealed with an aluminum cap. The mixture was heated to 120° C. for 2 d, cooled, diluted with satd. aq. sodium bicarbonate, and extracted with ethyl acetate. The combined organic layer was dried over anhydrous sodium sulfate, filtered, and the filtrate was concentrated. The residue was purified by column chromatography (silica, hexanes/ethyl acetate) to afford the title compound (0.160 g, 55%) as an orange oil. MW=330.81. $^1$H NMR (CDCl$_3$, 500 MHz) δ 7.33-7.28 (m, 2H) 7.16-7.12 (m, 2H), 6.74 (s, 1H), 5.73 (s, 1H), 4.18 (q, J=7.0 Hz, 2H), 3.62 (s, 2H), 2.98 (t, J=7.5 Hz, 2H), 2.76 (t, J=7.5 Hz, 2H), 2.18 (quin, J=7.5 Hz, 2H), 1.28 (t, J=7.0 Hz, 3H); APCI MS m/z 331 [M+H]⁺.

Step 2. Preparation of tert-butyl 4-(4-((4-(2-ethoxy-2-oxoethyl)phenyl)amino)-6,7-dihydro-5H-cyclopenta[b]pyridin-2-yl)piperazine-1-carboxylate

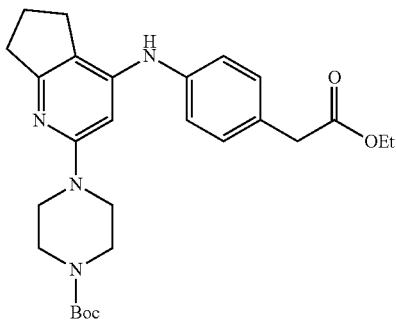 [SMILES: CCOC(=O)Cc1ccc(Nc2cc(N3CCN(C(=O)OC(C)(C)C)CC3)nc3c2CCC3)cc1]

Following general procedure B1, ethyl 2-(4-((2-chloro-6,7-dihydro-5H-cyclopenta[b]pyridin-4-yl)amino)phenyl)acetate (0.110 g, 0.33 mmol) was reacted with tert-butyl piperazine-1-carboxylate (0.073 g, 0.40 mmol) to afford the title compound (0.034 g, 21%) as an orange foam. MW=480.59. ¹H NMR (CDCl₃, 500 MHz) δ 7.27 (d, J=8.3 Hz, 2H), 7.13 (d, J=8.3 Hz, 2H), 6.17 (s, 1H), 5.59 (s, 1H), 4.17 (q, J=7.0 Hz, 2H), 3.60 (s, 2H), 3.54-3.48 (m, 4H), 3.40-3.34 (m, 4H), 2.89 (t, J=7.5 Hz, 2H), 2.70 (t, J=7.5 Hz, 2H), 2.12 (quin, J=7.5 Hz, 2H), 1.47 (s, 9H), 1.27 (t, J=7.0 Hz, 3H); APCI MS m/z 481 [M+H]⁺.

Step 3. Preparation of tert-butyl 4-(4-((4-(2-amino-2-oxoethyl)phenyl)amino)-6,7-dihydro-5H-cyclopenta[b]pyridin-2-yl)piperazine-1-carboxylate

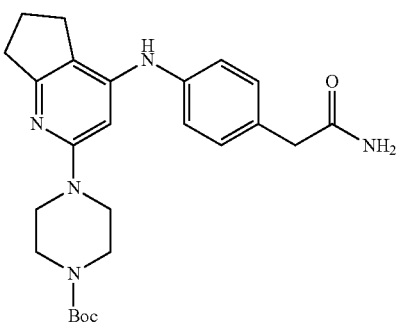 [SMILES: CC(C)(C)OC(=O)N1CCN(c2cc(Nc3ccc(CC(N)=O)cc3)c3c(n2)CCC3)CC1]

Following general procedure C, tert-butyl 4-(4-((4-(2-ethoxy-2-oxoethyl)phenyl)amino)-6,7-dihydro-5H-cyclopenta[b]pyridin-2-yl)piperazine-1-carboxylate (0.034 g, 0.071 mmol) was reacted with ammonia in methanol (7.0 M, 5 mL) to afford crude product (0.031 g) as an orange oil. MW=451.56. APCI MS m/z 452 [M+H]⁺.

EXAMPLE 252

2-(4-((2-(Piperazin-1-yl)-6,7-dihydro-5H-cyclopenta[b]pyridin-4-yl)amino)phenyl)acetamide hydrochloride

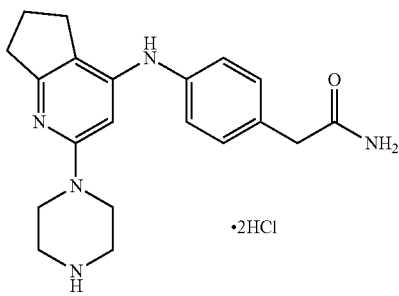 [SMILES: NC(=O)Cc1ccc(Nc2cc(N3CCNCC3)nc3c2CCC3)cc1 ; "·2HCl"]

To a solution of tert-butyl 4-(4-((4-(2-amino-2-oxoethyl)phenyl)amino)-6,7-dihydro-5H-cyclopenta[b]pyridin-2-yl)piperazine-1-carboxylate in methanol (3 mL) was added HCl (6 M, 0.1 mL). The mixture was heated to 65° C. for 16 h. The Boc group was removed, however, the amide function was replaced with a methyl ester group. The mixture was concentrated and following general procedure C, desired product was obtained after forming the hydrochloride salt (0.015 g, 50%) as an orange-brown solid. MW=424.37. ¹H NMR (DMSO-d₆, 500 MHz) δ 13.26 (s, 1H), 9.40-9.28 (m, 3H), 7.53 (s, 1H), 7.34 (d, J=8.5 Hz, 2H), 7.29 (d, J=8.5 Hz, 2H), 6.91 (s, 1H), 6.07 (s, 1H), 3.64-3.57 (m, 4H), 3.41 (s, 2H), 3.20 (br s, 4H), 3.02 (t, J=7.5 Hz, 2H), 2.78 (t, J=7.5 Hz, 2H), 2.15 (quin, J=7.5 Hz, 2H); APCI MS m/z 352 [M+H]⁺.

EXAMPLE 253

2-(4-((2-(4-methylpiperazin-1-yl)-6,7-dihydro-5H-cyclopenta[b]pyridin-4-yl)amino)phenyl)acetamide hydrochloride

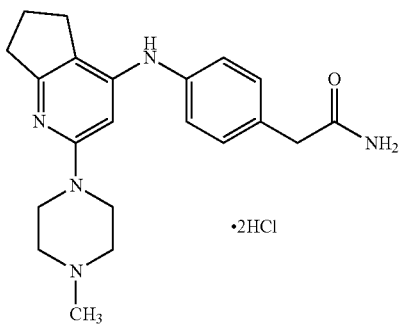 [SMILES: CN1CCN(c2cc(Nc3ccc(CC(N)=O)cc3)c3c(n2)CCC3)CC1 ; "·2HCl"]

Step 1. Preparation of ethyl 2-(4-((2-(4-methylpiperazin-1-yl)-6,7-dihydro-5H-cyclopenta[b]pyridin-4-yl)amino)phenyl)acetate

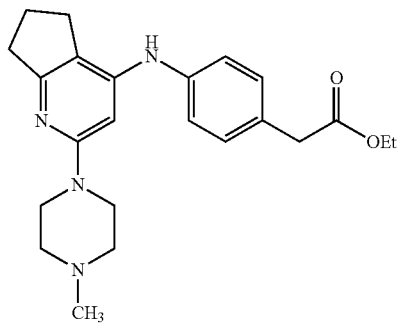 [SMILES: CCOC(=O)Cc1ccc(Nc2cc(N3CCN(C)CC3)nc3c2CCC3)cc1]

Following general procedure B1, ethyl 2-(4-((2-chloro-6,7-dihydro-5H-cyclopenta[b]pyridin-4-yl)amino)phenyl)acetate (0.095 g, 0.29 mmol) was reacted with 1-methylpiperazine (0.043 g, 0.44 mmol) to afford the title compound (0.017 g, 15%) as an orange oil. MW=394.51. $^1$H NMR (CD$_3$OD, 500 MHz) δ 7.15 (d, J=8.3 Hz, 2H), 7.07 (d, J=8.3 Hz, 2H), 6.07 (s, 1H), 4.05 (q, J=7.0 Hz, 2H), 3.51 (s, 2H), 2.72 (t, J=7.5 Hz, 2H), 2.64 (t, J=7.5 Hz, 2H), 2.46-2.38 (m, 4H), 2.21 (s, 3H), 1.99 (quin, J=7.5 Hz, 2H), 1.15 (t, J=7.0 Hz, 3H); APCI MS m/z 395 [M+H]$^+$.

EXAMPLE 253

2-(4-((2-(4-Methylpiperazin-1-yl)-6,7-dihydro-5H-cyclopenta[b]pyridin-4-yl)amino)phenyl)acetamide hydrochloride

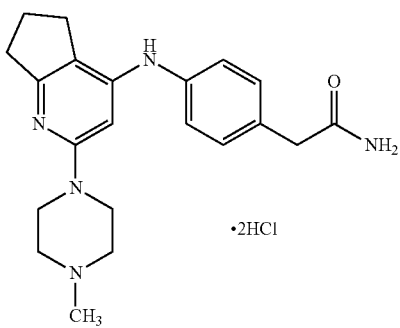 [SMILES: CN1CCN(c2cc(Nc3ccc(CC(N)=O)cc3)c3c(n2)CCC3)CC1 ; "·2HCl"]

Following general procedure C, ethyl 2-(4-((2-(4-methylpiperazin-1-yl)-6,7-dihydro-5H-cyclopenta[b]pyridin-4-yl)amino)phenyl)acetate (0.017 g, 0.043 mmol) was reacted with ammonia in methanol (7.0 M, 5 mL), followed by formation of the hydrochloride salt to afford the title compound (0.012 g, 66%) as an orange-brown solid. MW=438.39. $^1$H NMR (DMSO-d$_6$, 500 MHz) δ 13.38 (s, 1H), 11.19 (s, 1H), 9.32 (s, 1H), 7.53 (s, 1H), 7.35 (d, J=8.0 Hz, 2H), 7.30 (d, J=8.0 Hz, 2H), 6.91 (s, 1H), 6.09 (s, 1H), 4.03 (d, J=12.5 Hz, 2H), 3.48 (d, J=12.5 Hz, 2H), 3.43-3.13 (m, 4H), 3.16-2.98 (m, 4H), 2.81-2.74 (m, 5H), 2.20-2.10 (m, 2H); APCI MS m/z 366 [M+H]$^+$.

EXAMPLE 254

2-(4-((2-Morpholino-6,7-dihydro-5H-cyclopenta[b]pyridin-4-yl)amino)phenyl)acetamide hydrochloride

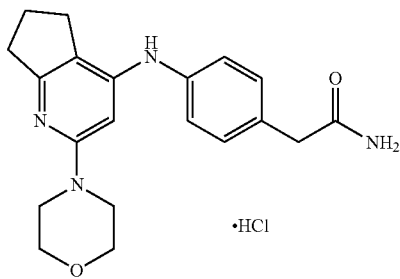 [SMILES: NC(=O)Cc1ccc(Nc2cc(N3CCOCC3)nc3c2CCC3)cc1 ; Cl]

Step 1. Preparation of ethyl 2-(4-((2-morpholino-6,7-dihydro-5H-cyclopenta[b]pyridin-4-yl)amino)phenyl)acetate

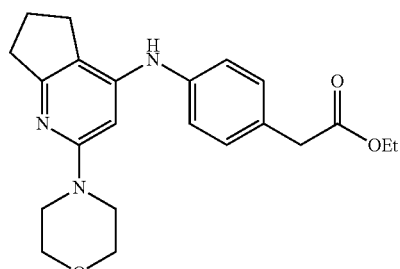

Following general procedure B1, ethyl 2-(4-((2-chloro-6,7-dihydro-5H-cyclopenta[b]pyridin-4-yl)amino)phenyl)acetate (0.120 g, 0.36 mmol) was reacted with morpholine (0.063 g, 0.73 mmol) to afford the title compound (0.034 g, 15%) as an orange foam. MW=381.47. APCI MS m/z 382 [M+H]$^+$.

EXAMPLE 254

2-(4-((2-Morpholino-6,7-dihydro-5H-cyclopenta[b]pyridin-4-yl)amino)phenyl)acetamide hydrochloride

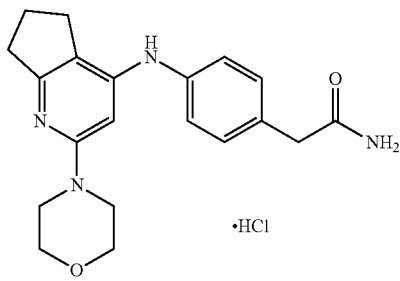 [SMILES: NC(=O)Cc1ccc(Nc2cc(N3CCOCC3)nc3c2CCC3)cc1 ; Cl]

Following general procedure C, ethyl 2-(4-((2-morpholino-6,7-dihydro-5H-cyclopenta[b]pyridin-4-yl)amino)phenyl)acetate (0.034 g, 0.089 mmol) was reacted with ammonia in methanol (7.0 M, 4 mL), followed by formation

EXAMPLE 255

(R)-2-(4-((2-(3-Methylpiperazin-1-yl)-6,7-dihydro-5H-cyclopenta[b]pyridin-4-yl)amino)phenyl)acetamide hydrochloride

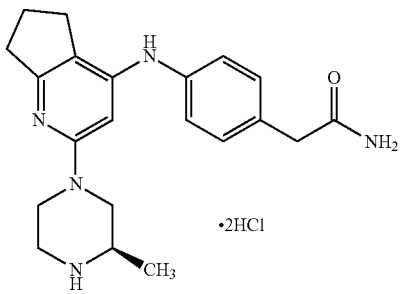 [SMILES: C[C@@H]1CN(c2cc(Nc3ccc(CC(N)=O)cc3)c3c(n2)CCC3)CCN1 ; "·2HCl"]

Step 1. Preparation of (R)-tert-butyl 4-(4-((4-(2-ethoxy-2-oxoethyl)phenyl)amino)-6,7-dihydro-5H-cyclopenta[b]pyridin-2-yl)-2-methylpiperazine-1-carboxylate

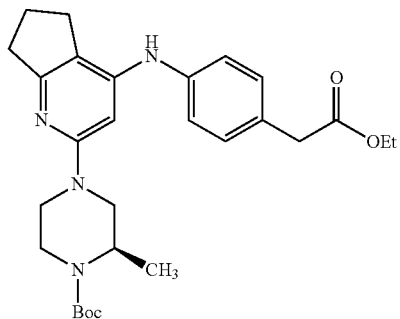 [SMILES: CCOC(=O)Cc1ccc(Nc2cc(N3CCN(C(=O)OC(C)(C)C)[C@H](C)C3)nc3c2CCC3)cc1]

Following general procedure B1, ethyl 2-(4-((2-chloro-6,7-dihydro-5H-cyclopenta[b]pyridin-4-yl)amino)phenyl)acetate (0.094 g, 0.28 mmol) was reacted with (R)-tert-butyl 2-methylpiperazine-1-carboxylate (0.112 g, 0.56 mmol) to afford the title compound (0.038 g, 27%) as an orange foam. MW=494.63. $^1$H NMR (CDCl$_3$, 500 MHz) δ 7.26 (d, J=8.3 Hz, 2H), 7.13 (d, J=8.3 Hz, 2H), 6.14 (s, 1H), 5.58 (s, 1H), 4.27 (br s, 1H), 4.17 (q, J=7.0 Hz, 2H), 4.04-3.97 (m, 1H), 3.91-3.84 (m, 1H), 3.79-3.73 (m, 1H), 3.60 (s, 2H), 2.88 (t, J=7.5 Hz, 2H), 2.86-2.78 (m, 1H), 2.70 (t, J=7.5 Hz, 2H), 2.11 (quin, J=7.5 Hz, 2H), 1.47 (s, 9H), 1.27 (t, J=7.0 Hz, 3H), 1.20 (d, J=6.6 Hz, 3H); APCI MS m/z 495 [M+H]$^+$.

of the hydrochloride salt to afford the title compound (0.025 g, 73%) as a white solid. MW=388.89. $^1$H NMR (DMSO-d$_6$, 500 MHz) δ 12.68 (s, 1H), 9.16 (s, 1H), 7.51 (s, 1H), 7.33 (d, J=8.5 Hz, 2H), 7.27 (d, J=8.5 Hz, 2H), 6.90 (s, 1H), 6.04 (s, 1H), 3.74-3.66 (m, 4H), 3.40 (s, 2H), 3.35-3.28 (m, 4H), 2.98 (t, J=7.5 Hz, 2H), 2.77 (t, J=7.5 Hz, 2H), 2.14 (quin, J=7.5 Hz, 2H); APCI MS m/z 353 [M+H]$^+$.

Step 2. Preparation of (R)-methyl 2-(4-((2-(3-methylpiperazin-1-yl)-6,7-dihydro-5H-cyclopenta[b]pyridin-4-yl)amino)phenyl)acetate

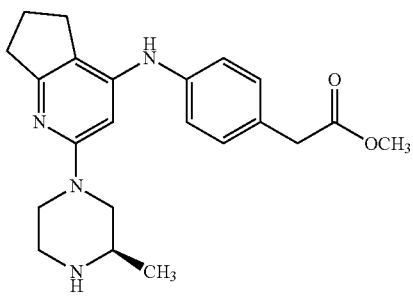 [SMILES: COC(=O)Cc1ccc(Nc2cc(N3CCN[C@H](C)C3)nc3c2CCC3)cc1]

A solution of (R)-tert-butyl 4-(4-((4-(2-ethoxy-2-oxoethyl)phenyl)amino)-6,7-dihydro-5H-cyclopenta[b]pyridin-2-yl)-2-methylpiperazine-1-carboxylate (0.038 g, 0.077 mmol) in HCl in methanol (1.25 M, 2 mL) was heated to 65° C. for 2 h. The mixture was cooled and concentrated to afford crude product. MW=380.45. APCI MS m/z 381 [M+H]$^+$.

EXAMPLE 255

(R)-2-(4-((2-(3-Methylpiperazin-1-yl)-6,7-dihydro-5H-cyclopenta[b]pyridin-4-yl)amino)phenyl)acetamide hydrochloride

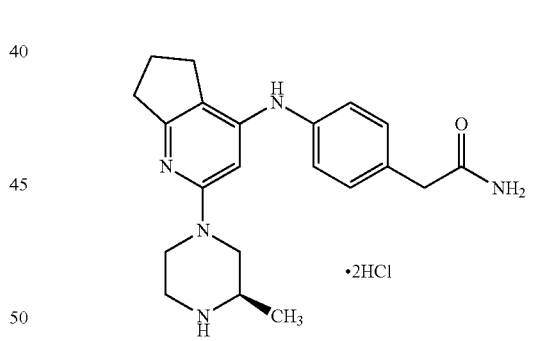

Following general procedure C, (R)-methyl 2-(4-((2-(3-methylpiperazin-1-yl)-6,7-dihydro-5H-cyclopenta[b]pyridin-4-yl)amino)phenyl)acetate (0.077 mmol) was reacted with ammonia in methanol (7.0 M, 4 mL), followed by formation of the hydrochloride salt to afford the title compound (0.006 g, 18% over two steps) as a yellow solid. MW=438.39. $^1$H NMR (DMSO-d$_6$, 500 MHz) δ 13.14 (s, 1H), 9.56-9.15 (m, 3H), 7.51 (s, 1H), 7.34 (d, J=8.0 Hz, 2H), 7.28 (d, J=8.0 Hz, 2H), 6.91 (s, 1H), 6.10 (s, 1H), 4.03 (d, J=13.5 Hz, 2H), 3.84 (d, J=13.5 Hz, 2H), 3.43-3.21 (m, 5H), 3.15-2.96 (m, 4H), 2.77 (t, J=7.5 Hz, 2H), 2.20-2.10 (m, 2H), 1.26 (d, J=6.5 Hz, 3H); APCI MS m/z 366 [M+H]$^+$.

EXAMPLE 256

2-(4-((2-(Cyclopentyloxy)-6,7-dihydro-5H-cyclopenta[b]pyridin-4-yl)amino)phenyl)acetamide hydrochloride

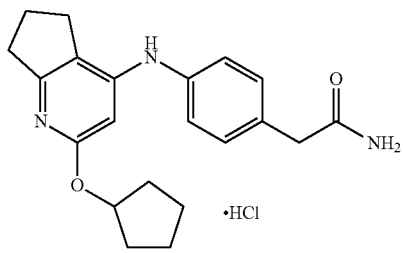 [SMILES: NC(=O)Cc1ccc(Nc2cc(OC3CCCC3)nc3c2CCC3)cc1 ; Cl]

Step 1. Preparation of 2,4-dichloro-6,7-dihydro-5H-cyclopenta[b]pyridine 1-oxide

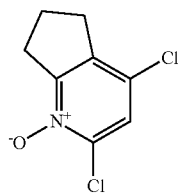

To a solution of 2,4-dichloro-6,7-dihydro-5H-cyclopenta[b]pyridine (0.165 g, 0.87 mmol) in methylene chloride (10 mL) was added MCBPA (77%, 0.236 g, 1.0 mmol). The reaction stirred at rt for 16 h. After this time, the mixture was diluted with methylene chloride and washed sequentially with water, a saturated solution of $Na_2S_2O_3$, a saturated solution of $NaHCO_3$, and brine. The organic layers were dried over anhydrous sodium sulfate, filtered, and the filtrate was concentrated. The residue was purified by column chromatography (silica, hexanes/ethyl acetate) to afford the title compound (0.106 g, 60%) as a white solid. MW=204.05. $^1$H NMR (CDCl$_3$, 300 MHz) δ 7.34 (s, 1H), 3.27 (t, J=7.5 Hz, 2H), 3.06 (t, J=7.5 Hz, 2H), 2.25 (quin, J=7.5 Hz, 2H); APCI MS m/z 204 [M+H]$^+$.

Step 2. Preparation of 4-chloro-2-(cyclopentyloxy)-6,7-dihydro-5H-cyclopenta[b]pyridine 1-oxide

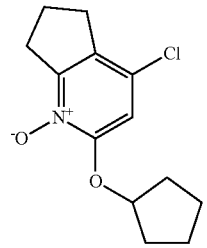

To a solution of cyclopentanol (0.050 g, 0.59 mmol) in NMP (3 mL) at rt was added potassium tert-butoxide (0.060 g, 0.54 mmol). The mixture was stirred at rt for 1 h. 2,4-Dichloro-6,7-dihydro-5H-cyclopenta[b]pyridine 1-oxide (0.100 g, 0.49 mmol) in NMP (1 mL) was added and the mixture was heated to 80° C. for 1 h. The mixture was diluted with methylene chloride and washed with water. The organic layer were dried over anhydrous sodium sulfate, filtered, and the filtrate was concentrated. The residue was purified by column chromatography (silica, dichloromethane/methanol) to afford crude product (0.140 g) as a brown oil. MW=253.72. $^1$H NMR (CDCl$_3$, 300 MHz) δ 6.69 (s, 1H), 5.04 (s, 1H), 3.23 (t, J=7.6 Hz, 2H), 2.99 (t, J=7.6 Hz, 2H), 2.20 (quin, J=7.6 Hz, 2H), 2.00-1.56 (m, 8H); APCI MS m/z 254 [M+H]$^+$.

Step 3. Preparation of 4-chloro-2-(cyclopentyloxy)-6,7-dihydro-5H-cyclopenta[b]pyridine

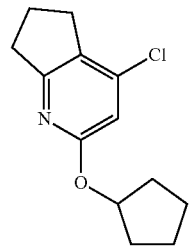 [SMILES: Clc1cc(OC2CCCC2)nc2c1CCC2]

To a solution of crude 4-chloro-2-(cyclopentyloxy)-6,7-dihydro-5H-cyclopenta[b]pyridine 1-oxide (0.49 mmol) in methylene chloride (5 mL) was added phophorous trichloride (0.100 g, 0.74 mmol). The mixture stirred at rt for 2 h. After this time, the mixture was quenched with a saturated solution of NaHCO$_3$ and extracted with methylene chloride. The organic layer was dried over anhydrous sodium sulfate, filtered, and the filtrate was concentrated. The residue was purified by column chromatography (silica, hexanes/ethyl acetate) to afford the title compound (0.029 g, 25% over two steps) as a clear oil. MW=237.73. $^1$H NMR (CDCl$_3$, 300 MHz) δ 6.45 (s, 1H), 5.34-5.26 (m, 1H), 3.01-2.84 (m, 4H), 2.11 (quin, J=7.5 Hz, 2H), 2.00-1.57 (m, 8H); APCI MS m/z 238 [M+H]$^+$.

Step 4. Preparation of ethyl 2-(4-((2-(cyclopentyloxy)-6,7-dihydro-5H-cyclopenta[b]pyridin-4-yl)amino)phenyl)acetate

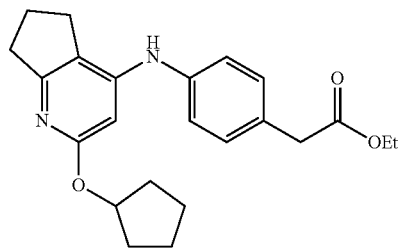 [SMILES: CCOC(=O)Cc1ccc(Nc2cc(OC3CCCC3)nc3c2CCC3)cc1]

Following general procedure B2, 4-chloro-2-(cyclopentyloxy)-6,7-dihydro-5H-cyclopenta[b]pyridine (0.070 g, 0.29 mmol) was reacted with ethyl 2-(4-aminophenyl)acetate (0.080 g, 0.44 mmol) to afford the title compound (0.088 g, 78%) as a yellow foam. MW=380.48. APCI MS m/z 381 [M+H]$^+$.

EXAMPLE 256

2-(4-((2-(Cyclopentyloxy)-6,7-dihydro-5H-cyclo-penta[b]pyridin-4-yl)amino)phenyl)acetamide hydrochloride

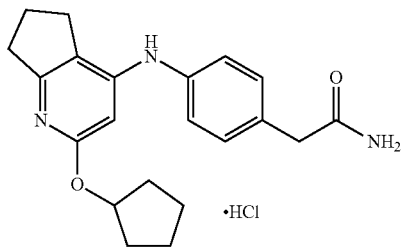 [SMILES: NC(=O)Cc1ccc(Nc2cc(OC3CCCC3)nc3c2CCC3)cc1 ; Cl]

·HCl

Following general procedure C, ethyl 2-(4-((2-(cyclopentyloxy)-6,7-dihydro-5H-cyclopenta[b]pyridin-4-yl)amino)phenyl)acetate (0.088 g, 0.23 mmol) was reacted with ammonia in methanol (7.0 M, 3 mL), followed by formation of the hydrochloride salt to afford the title compound (0.029 g, 32%) as a white solid. MW=387.90. $^1$H NMR (DMSO-$d_6$, 500 MHz) δ 13.83 (s, 1H), 9.57 (s, 1H), 7.53 (s, 1H), 7.37 (d, J=8.0 Hz, 2H), 7.29 (d, J=8.0 Hz, 2H), 6.91 (s, 1H), 6.14 (s, 1H), 4.98-4.93 (m, 1H), 3.42 (s, 2H), 2.94 (t, J=7.5 Hz, 2H), 2.79 (t, J=7.5 Hz, 2H), 2.15 (quin, J=7.5 Hz, 2H), 1.89-1.58 (m, 8H); APCI MS m/z 352 [M+H]$^+$.

EXAMPLE 257

2-(4-((2-(Cyclopentyloxy)-6,7-dihydro-5H-cyclo-penta[b]pyridin-4-yl)amino)phenyl)ethanol hydrochloride

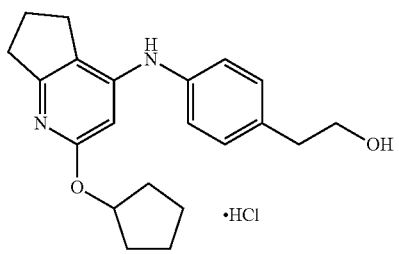 [SMILES: OCCc1ccc(Nc2cc(OC3CCCC3)nc3c2CCC3)cc1 ; Cl]

·HCl

Following general procedure B1, 4-chloro-2-(cyclopentyloxy)-6,7-dihydro-5H-cyclopenta[b]pyridine (0.045 g, 0.19 mmol) was reacted with 2-(4-aminophenyl)ethanol (0.039 g, 0.28 mmol), followed by formation of the hydrochloride salt to afford the title compound (0.050 g, 70%) as a white solid. MW=374.90. $^1$H NMR (DMSO-$d_6$, 300 MHz) δ 13.82 (s, 1H), 9.52 (s, 1H), 7.33 (d, J=8.5 Hz, 2H), 7.25 (d, J=8.5 Hz, 2H), 6.11 (s, 1H), 5.00-4.89 (m, 1H), 3.63 (t, J=7.0 Hz, 2H), 2.93 (t, J=7.5 Hz, 2H), 2.84-2.69 (m, 4H), 2.15 (quin, J=7.5 Hz, 2H), 1.91-1.52 (m, 8H); APCI MS m/z 339 [M+H]$^+$.

EXAMPLE 258

2-(4-((2-(Cyclopentylthio)-6,7-dihydro-5H-cyclo-penta[b]pyridin-4-yl)amino)phenyl)acetamide

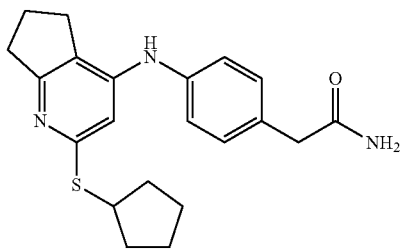 [SMILES: NC(=O)Cc1ccc(Nc2cc(SC3CCCC3)nc3c2CCC3)cc1]

Step 1. Preparation of 4-chloro-2-(cyclopentylthio)-6,7-dihydro-5H-cyclopenta[b]pyridine 1-oxide

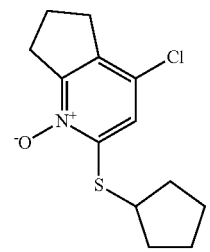

To a solution of cyclopentyl mercaptan (0.112 g, 1.10 mmol) in dioxane (4 mL) at rt was added potassium tert-butoxide (0.100 g, 0.88 mmol). The mixture was stirred at rt for 1 h. After this time, 2,4-dichloro-6,7-dihydro-5H-cyclopenta[b]pyridine 1-oxide (0.150 g, 0.74 mmol) in dioxane (1 mL) was added and the mixture was heated to 100° C. for 1 h. Then, the mixture was diluted with methylene chloride and washed with water. The organic layer were dried over anhydrous sodium sulfate, filtered, and the filtrate was concentrated. The residue was purified by column chromatography (silica, dichloromethane/methanol) to afford the title compound (0.170 g, 86%) as a brown oil. MW=269.79. $^1$H NMR (CDCl$_3$, 500 MHz) δ 6.99 (s, 1H) 3.60-3.52 (m, 1H), 3.22 (t, J=7.5 Hz, 2H), 3.01 (t, J=7.5 Hz, 2H), 2.26-2.15 (m, 4H), 1.88-1.79 (m, 2H), 1.77-1.64 (m, 4H); APCI MS m/z 270 [M+H]$^+$.

Step 2. Preparation of 4-chloro-2-(cyclopentylthio)-6,7-dihydro-5H-cyclopenta[b]pyridine

To a solution of 4-chloro-2-(cyclopentylthio)-6,7-dihydro-5H-cyclopenta[b]pyridine 1-oxide (0.160 g, 0.59 mmol) in methylene chloride (10 mL) was added phophorous trichloride (0.1 mL, 0.89 mmol). The mixture stirred at rt for 2 h. After this time, the mixture was quenched with a saturated solution of NaHCO₃ and extracted with methylene chloride. The organic layer was dried over anhydrous sodium sulfate, filtered, and the filtrate was concentrated. The residue was purified by column chromatography (silica, hexanes/ethyl acetate) to afford the title compound (0.137 g, 91%) as a clear oil. MW=253.79. $^1$H NMR (CDCl₃, 500 MHz) δ 6.96 (s, 1H) 3.98-3.90 (m, 1H), 3.02 (t, J=7.5 Hz, 2H), 2.93 (t, J=7.5 Hz, 2H), 2.22-2.08 (m, 4H), 1.83-1.72 (m, 2H), 1.68-1.58 (4H); APCI MS m/z 254 [M+H]⁺.

Step 3. Preparation of ethyl 2-(4-((2-(cyclopentylthio)-6,7-dihydro-5H-cyclopenta[b]pyridin-4-yl)amino)phenyl)acetate

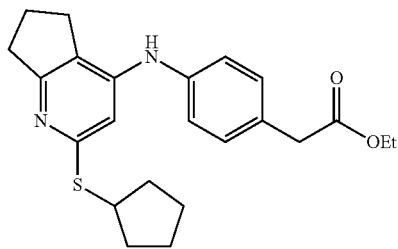 [SMILES: CCOC(=O)Cc1ccc(Nc2cc(SC3CCCC3)nc3c2CCC3)cc1]

Following general procedure B1, 4-chloro-2-(cyclopentylthio)-6,7-dihydro-5H-cyclopenta[b]pyridine (0.130 g, 0.51 mmol) was reacted with ethyl 2-(4-aminophenyl)acetate (0.137 g, 0.77 mmol) to afford crude product (0.220 g) as a colorless gum. MW=396.55. $^1$H NMR (CDCl₃, 300 MHz) δ 7.27 (d, J=8.5 Hz, 2H), 7.12 (d, J=8.5 Hz, 2H), 6.74 (s, 1H), 5.62 (s, 1H), 4.17 (q, J=7.0 Hz, 2H), 3.93-3.79 (m, 1H), 3.60 (s, 2H), 3.52-3.46 (m, 2H), 2.97 (t, J=7.5 Hz, 2H), 2.74 (t, J=7.5 Hz, 2H), 2.22-2.02 (m, 4H), 1.83-1.51 (m, 6H), 1.27 (t, J=7.0 Hz, 3H); APCI MS m/z 397 [M+H]⁺.

EXAMPLE 258

2-(4-((2-(Cyclopentylthio)-6,7-dihydro-5H-cyclopenta[b]pyridin-4-yl)amino)phenyl)acetamide

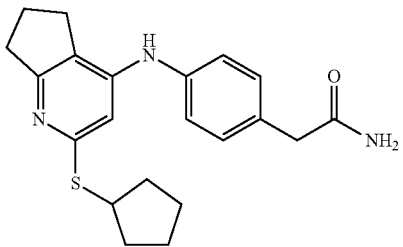 [SMILES: NC(=O)Cc1ccc(Nc2cc(SC3CCCC3)nc3c2CCC3)cc1]

Following general procedure C, ethyl 2-(4-((2-(cyclopentylthio)-6,7-dihydro-5H-cyclopenta[b]pyridin-4-yl)amino)phenyl)acetate (0.51 mmol) was reacted with ammonia in methanol (7.0 M, 5 mL) to afford the title compound (0.130 g, 69% over two steps) as an off-white solid. MW=367.51. $^1$H NMR (DMSO-d₆, 300 MHz) δ 8.00 (s, 1H), 7.44 (s, 1H), 7.23 (d, J=8.5 Hz, 2H), 7.10 (d, J=8.5 Hz, 2H), 6.87 (s, 1H), 6.52 (s, 1H), 3.82 (quin, J=7.0 Hz, 1H), 3.33 (s, 2H), 2.84-2.67 (m, 4H), 2.12-1.95 (m, 4H), 1.73-1.39 (m, 6H); APCI MS m/z 368 [M+H]⁺.

EXAMPLE 259

2-(4-((2-(Cyclopentylsulfonyl)-6,7-dihydro-5H-cyclopenta[b]pyridin-4-yl)amino)phenyl)acetamide

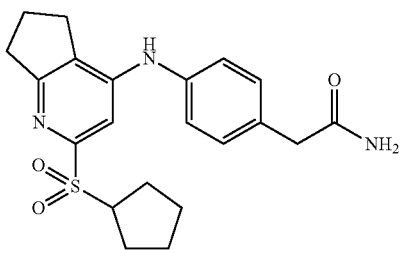 [SMILES: NC(=O)Cc1ccc(Nc2cc(S(=O)(=O)C3CCCC3)nc3c2CCC3)cc1]

To a solution of 2-(4-((2-(cyclopentylthio)-6,7-dihydro-5H-cyclopenta[b]pyridin-4-yl)amino)phenyl)acetamide (0.095 g, 0.26 mmol) in methylene chloride (5 mL) at rt was added MCPBA (77%, 0.127 g, 0.52 mmol). The mixture stirred at rt for 1 h. After this time, the mixture was diluted with methylene chloride and washed sequentially with water, a saturated solution of Na₂S₂O₃, a saturated solution of NaHCO₃, and brine. The organic layers were dried over anhydrous sodium sulfate, filtered, and the filtrate was concentrated. The residue was purified by column chromatography (silica, dichloromethane/methanol) to afford the title compound (0.083 g, 81%) as a white solid. MW=399.51. $^1$H NMR (DMSO-d₆, 500 MHz) δ 8.53 (s, 1H), 7.47 (s, 1H), 7.30 (d, J=8.5 Hz, 2H), 7.26 (s, 1H), 7.16 (d, J=8.5 Hz, 2H), 6.87 (s, 1H), 3.99-3.89 (m, 1H), 3.38 (s, 2H), 2.90 (t, J=7.5 Hz, 2H), 2.85 (t, J=7.5 Hz, 2H), 2.11 (quin, J=7.5 Hz, 2H), 1.87-1.74 (m, 4H), 1.65-1.49 (m, 4H); APCI MS m/z 400 [M+H]⁺.

EXAMPLE 260

2-(4-((2-Isopropoxy-6,7-dihydro-5H-cyclopenta[b]pyridin-4-yl)amino)phenyl)ethanol hydrochloride

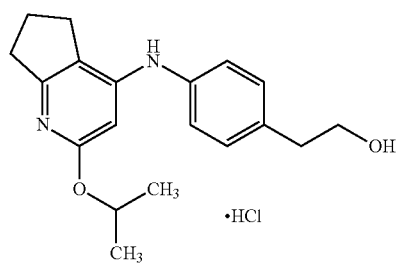 [SMILES: CC(C)Oc1cc(Nc2ccc(CCO)cc2)c2c(n1)CCC2 ; Cl]

321

Step 1. Preparation of 4-chloro-2-isopropoxy-6,7-dihydro-5H-cyclopenta[b]pyridine 1-oxide

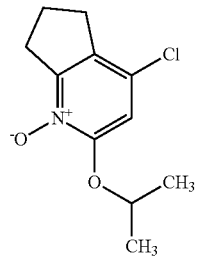

To a solution of iso-propanol (0.047 g, 0.79 mmol) in dioxane (3 mL) at rt was added potassium tert-butoxide (0.053 g, 0.47 mmol). The mixture was stirred at rt for 30 min. Then, 2,4-dichloro-6,7-dihydro-5H-cyclopenta[b]pyridine 1-oxide (0.100 g, 0.39 mmol) in dioxane (1 mL) was added and the mixture was heated under microwave irradiation to 100° C. for 30 min After this time, the mixture was diluted with methylene chloride and washed with water. The organic layer were dried over anhydrous sodium sulfate, filtered, and the filtrate was concentrated. The residue was purified by column chromatography (silica, dichloromethane/methanol) to afford the title compound (0.079 g, 88%) as a white solid. MW=227.69. $^1$H NMR (CDCl$_3$, 300 MHz) δ 6.73 (s, 1H), 4.90-4.85 (m, 1H), 3.23 (t, J=7.5 Hz, 2H), 3.00 (t, J=7.5 Hz, 2H), 2.20 (quin, J=7.5 Hz, 2H), 1.44 (d, J=6.0 Hz, 6H); APCI MS m/z 228 [M+H]$^+$.

Step 2. Preparation of 4-chloro-2-isopropoxy-6,7-dihydro-5H-cyclopenta[b]pyridine

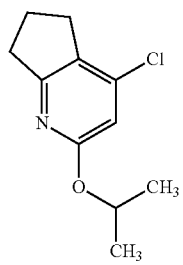

To a solution of 4-chloro-2-isopropoxy-6,7-dihydro-5H-cyclopenta[b]pyridine 1-oxide (0.079 g, 0.35 mmol) in methylene chloride (5 mL) was added phosphorous trichloride (0.096 g, 0.70 mmol). The mixture stirred at rt for 30 min After this time, the mixture was quenched with a saturated solution of NaHCO$_3$ and extracted with methylene chloride. The organic layer were dried over anhydrous sodium sulfate, filtered, and the filtrate was concentrated. The residue was purified by column chromatography (silica, hexanes/ethyl acetate) to afford the title compound (0.057 g, 77%) as a clear oil. MW=211.69. $^1$H NMR (CDCl$_3$, 300 MHz) δ 6.47 (s, 1H), 5.27-5.18 (m, 1H), 3.01-2.84 (m, 4H), 2.11 (quin, J=7.5 Hz, 2H), 1.31 (d, J=6.0 Hz, 6H); APCI MS m/z 212 [M+H]$^+$.

322

EXAMPLE 260

2-(4-((2-Isopropoxy-6,7-dihydro-5H-cyclopenta[b]pyridin-4-yl)amino)phenyl)ethanol hydrochloride

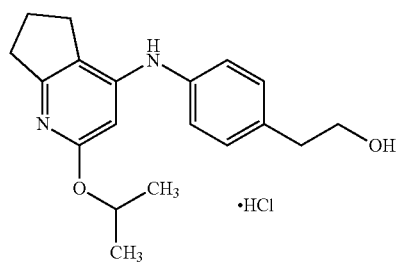 [SMILES: CC(C)Oc1cc(Nc2ccc(CCO)cc2)c2c(n1)CCC2 ; Cl]

Following general procedure B1, 4-chloro-2-isopropoxy-6,7-dihydro-5H-cyclopenta[b]pyridine (0.057 g, 0.27 mmol) was reacted with 2-(4-aminophenyl)ethanol (0.056 g, 0.40 mmol), followed by formation of the hydrochloride salt to afford the title compound (0.033 g, 35%) as a white solid. MW=348.87. $^1$H NMR (DMSO-d$_6$, 300 MHz) δ 13.84 (s, 1H), 9.50 (s, 1H), 7.33 (d, J=8.5 Hz, 2H), 7.25 (d, J=8.5 Hz, 2H), 6.12 (s, 1H), 4.82-4.67 (m, 1H), 3.64 (t, J=7.0 Hz, 2H), 2.93 (t, J=7.5 Hz, 2H), 2.83-2.69 (m, 4H), 2.15 (quin, J=7.5 Hz, 2H), 1.28 (d, J=6.0 Hz, 6H); APCI MS m/z 313 [M+H]$^+$.

EXAMPLE 261

2-(4-((2-Isopropoxy-6,7-dihydro-5H-cyclopenta[b]pyridin-4-yl)amino)phenyl)acetamide hydrochloride

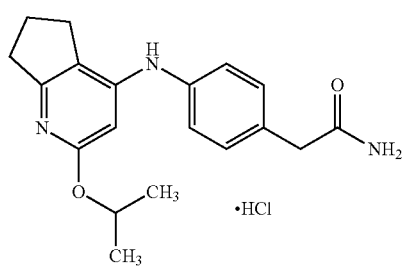 [SMILES: CC(C)Oc1cc(Nc2ccc(CC(N)=O)cc2)c2c(n1)CCC2 ; Cl]

Step 1. Preparation of ethyl 2-(4-((2-isopropoxy-6,7-dihydro-5H-cyclopenta[b]pyridin-4-yl)amino)phenyl)acetate

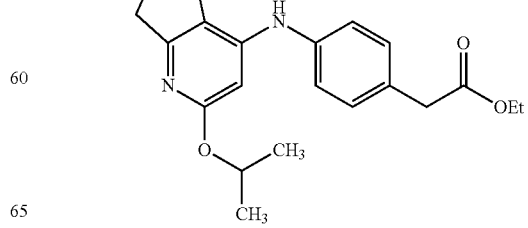

Following general procedure B1, 4-chloro-2-isopropoxy-6,7-dihydro-5H-cyclopenta[b]pyridine (0.090 g, 0.43 mmol) was reacted with ethyl 2-(4-aminophenyl)acetate (0.114 g, 0.64 mmol) to afford the title compound (0.130 g, 86%) as a yellow gel. MW=354.44. APCI MS m/z 355 [M+H]$^+$.

EXAMPLE 261

2-(4-((2-Isopropoxy-6,7-dihydro-5H-cyclopenta[b]pyridin-4-yl)amino)phenyl)acetamide hydrochloride

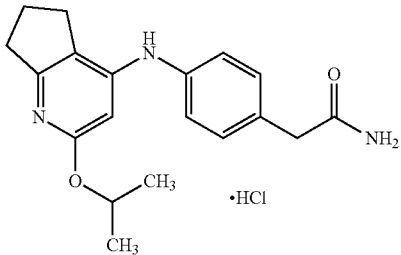 [SMILES: CC(C)Oc1cc(Nc2ccc(CC(N)=O)cc2)c2c(n1)CCC2 ; Cl]

Following general procedure C, ethyl 2-(4-((2-isopropoxy-6,7-dihydro-5H-cyclopenta[b]pyridin-4-yl)amino)phenyl)acetate (0.130 g, 0.37 mmol) was reacted with ammonia in methanol (7.0 M, 4 mL), followed by formation of the hydrochloride salt to afford the title compound (0.112 g, 84%) as a white solid. MW=361.87. $^1$H NMR (DMSO-d$_6$, 500 MHz) δ 13.89 (s, 1H), 9.60 (s, 1H), 7.55 (s, 1H), 7.37 (d, J=8.0 Hz, 2H), 7.29 (d, J=8.0 Hz, 2H), 6.91 (s, 1H), 6.16 (s, 1H), 4.75 (quin, J=6.0 Hz, 1H), 3.42 (s, 2H), 2.95 (t, J=7.5 Hz, 2H), 2.80 (t, J=7.5 Hz, 2H), 2.16 (quin, J=7.5 Hz, 2H), 1.29 (d, J=6.0 Hz, 6H); APCI MS m/z 326 [M+H]$^+$.

EXAMPLE 262

2-(4-((2-(3-Chlorophenyl)-6,7-dihydro-5H-cyclopenta[b]pyridin-4-yl)(hydroxy)methyl)phenyl)acetamide hydrochloride

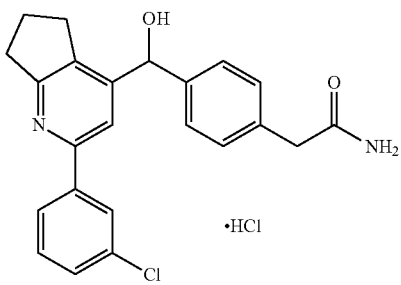 [SMILES: NC(=O)Cc1ccc(C(O)c2cc(-c3cccc(Cl)c3)nc3c2CCC3)cc1 ; Cl]

Step 1. Preparation of 2-(3-chlorophenyl)-6,7-dihydro-5H-cyclopenta[b]pyridine-4-carbonitrile

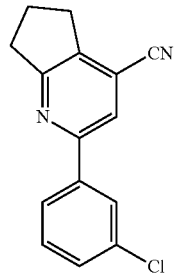

To a suspension of 4-chloro-2-(3-chlorophenyl)-6,7-dihydro-5H-cyclopenta[b]pyridine hydrochloride (0.250 g, 0.83 mmol) in dioxane (5 mL) was added tetrakis(triphenylphosphine)palladium (0.096 g, 0.083 mmol) and zinc cyanide (0.292 g, 2.5 mmol). The suspension was purged with nitrogen gas and then heated with microwave irradiation to 160° C. for h. After this time, the mixture was diluted with a saturated solution of NaHCO$_3$ and extracted with ethyl acetate. The organic layer were dried over anhydrous sodium sulfate, filtered, and the filtrate was concentrated. The residue was purified by column chromatography (silica, hexanes/ethyl acetate) to afford the title compound (0.157 g, 74%) as a white solid. MW=254.7. $^1$H NMR (CDCl$_3$, 300 MHz) δ 8.01-7.96 (m, 1H), 7.85-7.77 (m, 1H), 7.64 (s, 1H), 7.44-7.38 (m, 2H), 3.21-3.14 (m, 4H), 2.27 (quin, J=7.5 Hz, 2H); APCI MS m/z 255 [M+H]$^+$.

Step 2. Preparation of 2-(3-chlorophenyl)-6,7-dihydro-5H-cyclopenta[b]pyridine-4-carbaldehyde

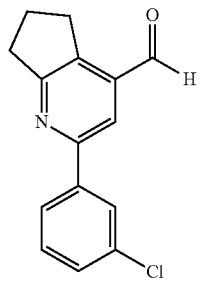 [SMILES: O=Cc1cc(-c2cccc(Cl)c2)nc2c1CCC2]

To a solution of 2-(3-chlorophenyl)-6,7-dihydro-5H-cyclopenta[b]pyridine-4-carbonitrile (0.275 g, 1.08 mmol) in methylene chloride (15 mL) was added DIBAL (1.0 M, 2.2 mL, 2.2 mmol) at −78° C. The solution was stirred at 0° C. for 4 h. The reaction was quenched with methanol and HCl. The mixture was diluted with a saturated solution of NaHCO$_3$ and extracted with ethyl acetate. The organic layer were dried over anhydrous sodium sulfate, filtered, and the filtrate was concentrated. The residue was purified by column chromatography (silica, hexanes/ethyl acetate) to afford the title compound (0.150 g, 48%) as a colorless oil. MW=257.71. $^1$H NMR (CDCl$_3$, 500 MHz) δ 10.27 (s, 1H), 7.83 (s, 1H), 8.06-8.03 (m, 1H), 7.91-7.87 (m, 1H), 7.45-7.37 (m, 2H), 3.33 (t, J=7.5 Hz, 2H), 3.15 (t, J=7.5 Hz, 2H), 2.27 (quin, J=7.5 Hz, 2H); APCI MS m/z 258 [M+H]$^+$.

Step 3. Preparation of ethyl 2-(4-((2-(3-chlorophenyl)-6,7-dihydro-5H-cyclopenta[b]pyridin-4-yl)(hydroxy)methyl)phenyl)acetate

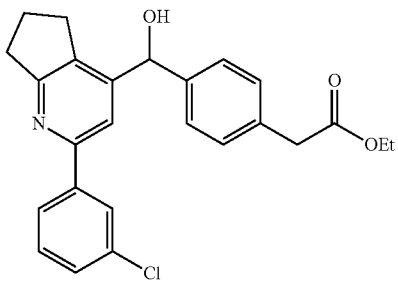 [SMILES: CCOC(=O)Cc1ccc(C(O)c2cc(-c3cccc(Cl)c3)nc3c2CCC3)cc1]

To a suspension of 2-(3-chlorophenyl)-6,7-dihydro-5H-cyclopenta[b]pyridine-4-carbaldehyde (0.210 g, 0.81 mmol) in dioxane (10 mL) was added palladium chloride (0.007 g, 0.040 mmol), trinaphthyl phosphine (0.017 g, 0.040 mmol), potassium carbonate 0. (336 g, 2.43 mmol), and methyl 2-(4-(4,4,5,5-tetramethyl-1,3,2-dioxaborolan-2-yl)phenyl)acetate (0.200 g, 0.97 mmol). The mixture was purged with nitrogen and then heated to 100° C. under sealed conditions for 16 h. After this time, the mixture was diluted with water and extracted with ethyl acetate. The organic layer were dried over anhydrous sodium sulfate, filtered, and the filtrate was concentrated. The residue was purified by column chromatography (silica, hexanes/ethyl acetate) to afford the title compound (0.250 g, 75%) as a white foam. MW=421.9. $^1$H NMR (CDCl$_3$, 500 MHz) δ 8.01-7.97 (m, 1H), 7.87-7.83 (m, 1H), 7.76 (s, 1H), 7.40-7.23 (m, 6H), 5.81 (s, 1H), 4.13 (q, J=7.0 Hz, 2H), 3.59 (s, 2H), 3.07-2.98 (m, 2H), 2.87-2.79 (m, 1H), 2.64-2.49 (m, 1H), 2.08 (quin, J=7.5 Hz, 2H), 1.30-1.21 (m, 3H); APCI MS m/z 422 [M+H]$^+$.

EXAMPLE 262

2-(4-((2-(3-Chlorophenyl)-6,7-dihydro-5H-cyclopenta[b]pyridin-4-yl)(hydroxy)methyl)phenyl)acetamide hydrochloride

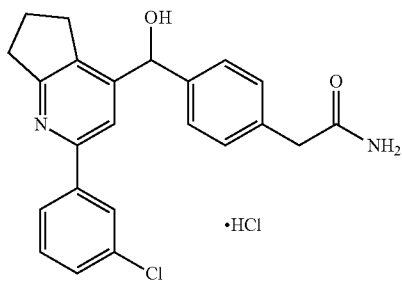 [SMILES: NC(=O)Cc1ccc(C(O)c2cc(-c3cccc(Cl)c3)nc3c2CCC3)cc1 ; Cl]

Following general procedure C, ethyl 2-(4-((2-(3-chlorophenyl)-6,7-dihydro-5H-cyclopenta[b]pyridin-4-yl)(hydroxy)methyl)phenyl)acetate (0.018 g, 0.043 mmol) was reacted with ammonia in methanol (7.0 M, 4 mL), followed by formation of the hydrochloride salt to afford the title compound (0.010 g, 55%) as a white solid. MW=429.34. $^1$H NMR (DMSO-d$_6$, 500 MHz) δ 8.11-8.09 (m, 1H), 8.06 (s, 1H), 8.01-7.97 (m, 1H), 7.60-7.54 (m, 2H), 7.43 (s, 1H), 7.34 (d, J=8.0 Hz, 2H), 7.21 (d, J=8.0 Hz, 2H), 6.82 (s, 1H), 5.80 (s, 1H), 3.33 (s, 2H), 3.06-2.93 (m, 3H), 2.71-2.61 (m, 2H), 2.11-2.01 (m, 2H); APCI MS m/z 393 [M+H]$^+$.

EXAMPLE 263

2-(4-((2-(3-Chlorophenyl)-6,7-dihydro-5H-cyclopenta[b]pyridin-4-yl)(hydroxy)methyl)phenyl)ethanol

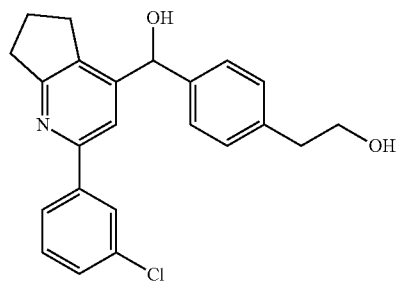 [SMILES: OCCc1ccc(C(O)c2cc(-c3cccc(Cl)c3)nc3c2CCC3)cc1]

Following general procedure E1, ethyl 2-(4-((2-(3-chlorophenyl)-6,7-dihydro-5H-cyclopenta[b]pyridin-4-yl)(hydroxy)methyl)phenyl)acetate (0.065 g, 0.15 mmol) was reacted with DIBAL (1.0 M, 0.46 mL, 0.46 mmol), followed by formation of the hydrochloride salt to afford the title compound (0.047 g, 73%) as a white solid. MW=379.88. $^1$H NMR (DMSO-d$_6$, 500 MHz) δ 8.10-8.07 (m, 1H), 8.03 (s, 1H), 8.00-7.97 (m, 1H), 7.59-7.52 (m, 2H), 7.31 (d, J=8.0 Hz, 2H), 7.16 (d, J=8.0 Hz, 2H), 5.78 (s, 1H), 3.56 (t, J=7.0 Hz, 2H), 3.03-2.90 (m, 3H), 2.71-2.60 (m, 3H), 2.09-2.00 (m, 2H); APCI MS m/z 380 [M+H]$^+$.

EXAMPLE 264

2-(4-((6-(3-Chlorophenyl)-2-ethylpyrimidin-4-yl)amino)phenyl)ethanol

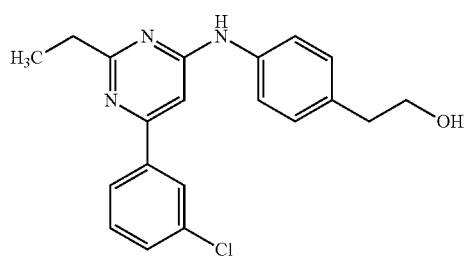 [SMILES: CCc1nc(Nc2ccc(CCO)cc2)cc(-c2cccc(Cl)c2)n1]

Step 1. Preparation of 6-(3-chlorophenyl)-2-ethylpyrimidin-4(3H)-one

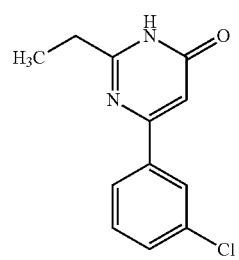 [SMILES: CCc1nc(-c2cccc(Cl)c2)cc(=O)[nH]1]

To a solution of ammonium hydroxide (3 mL) and ammonia in methanol (7.0 N, 10 mL) in ethanol (6 mL) was added 1,1,1-triethoxypropane (6.2 g, 35.3 mmol) and ethyl 3-(3-chlorophenyl)-3-oxopropanoate (4.0 g, 17.6 mmol) dropwise as a solution in ethanol (10 mL). Once the addition was complete, ammonium hydroxide (10 mL) was added. The mixture was heated with stirring in a sealed flask at 60° C. overnight. After this time, the mixture was cooled to rt and concentrated. The residue was purified by column chromatography (silica, hexanes/DCM) to afford the title compound (0.250 g, 6%) as a white solid. MW=234.68. $^1$H NMR (CDCl$_3$, 500 MHz) δ 8.03 (t, J=1.9 Hz, 1H), 7.86-7.82 (m, 1H), 7.46-7.38 (m, 2H), 6.73 (s, 1H), 2.80 (q, J=7.6 Hz, 2H), 1.42 (t, J=7.6 Hz, 3H); APCI MS m/z 235 [M+H]$^+$.

Step 2. Preparation of
4-chloro-6-(3-chlorophenyl)-2-ethylpyrimidine

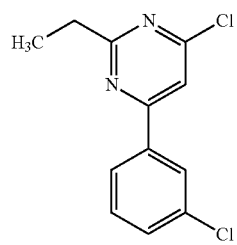 [SMILES: CCc1nc(Cl)cc(-c2cccc(Cl)c2)n1]

A mixture of 6-(3-chlorophenyl)-2-ethylpyrimidin-4(3H)-one (0.240 g, 1.0 mmol) and POCl$_3$ (5 mL) was heated to 85° C. for 6 h. After this time, the reaction was cooled, neutralized with saturated aqueous sodium bicarbonate, and extracted with methylene chloride. The combined organic layer was dried over anhydrous sodium sulfate, filtered, and the filtrate was concentrated. The residue was purified by column chromatography (silica, hexanes/ethyl acetate) to afford the title compound as an off-white solid (0.210 g, 81%). MW=253.13. $^1$H NMR (CDCl$_3$, 500 MHz) δ 8.10 (t, J=1.9 Hz, 1H), 7.96-7.92 (m, 1H), 7.55-7.41 (m, 3H), 3.03 (q, J=7.6 Hz, 2H), 1.55 (s, 1H), 1.42 (t, J=7.6 Hz, 3H); APCI MS m/z 254 [M+H]$^+$.

EXAMPLE 264

2-(4-((6-(3-Chlorophenyl)-2-ethylpyrimidin-4-yl)amino)phenyl)ethanol

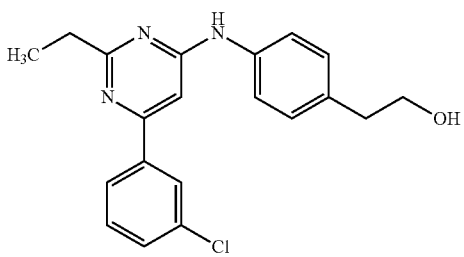 [SMILES: CCc1nc(Nc2ccc(CCO)cc2)cc(-c2cccc(Cl)c2)n1]

A solution of 4-chloro-6-(3-chlorophenyl)-2-ethylpyrimidine (0.100 g, 0.39 mmol), 4-aminophenethyl alcohol (0.081 g, 0.59 mmol) and HCl in dioxane (4.0 M, 0.023 mL, 0.59 mmol) in ethanol (2 mL) was heated to 85° C. for 3 h. After this time, the reaction was cooled, neutralized with saturated aqueous sodium bicarbonate, and extracted with ethyl acetate. The combined organic layers were dried over anhydrous sodium sulfate, filtered and the filtrate was concentrated. The residue was purified by preparative HPLC (water/acetonitrile with 0.05% TFA) to afford the title compound (0.027 g, 27%) as a light yellow solid. MW=353.85. $^1$H NMR (DMSO-d$_6$, 500 MHz) δ 8.01 (t, J=1.8 Hz, 1H), 7.88 (d, J=7.6 Hz, 1H), 7.69-7.57 (m, 4H), 7.25 (d, J=8.3 Hz, 2H), 7.04 (s, 1H), 3.61 (t, J=7.0 Hz, 2H), 2.87 (q, J=7.6 Hz, 2H), 2.72 (t, J=7.0 Hz, 2H), 1.33 (t, J=7.6 Hz, 3H); APCI MS m/z 354 [M+H]$^+$.

EXAMPLE 265

2-(4-((6-(3-chlorophenyl)-2-ethylpyrimidin-4-yl)amino)phenyl)acetamide

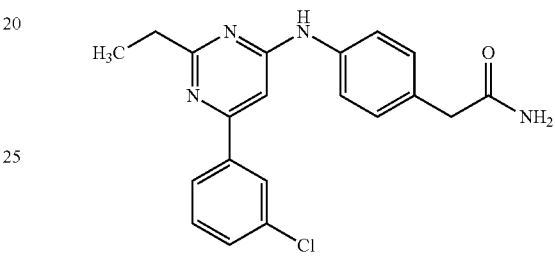

A mixture of 4-chloro-6-(3-chlorophenyl)-2-ethylpyrimidine (0.080 g, 0.32 mmol) and 2-(4-aminophenyl)acetamide (0.057 g, 0.38 mmol) and 4M HCl in dioxane (2 drops) in acetic acid (2.5 mL) was heated for 2.5 h at 85° C. After this time, the mixture was cooled to 0° C., neutralized with NaHCO$_3$, extracted with CH$_2$Cl$_2$ (2×30 mL) and EtOAc, dried (Na$_2$SO$_4$), filtered, and concentrated. The residue was purified by silica gel chromatography eluting with methylene chloride and methanol to afford the title compound (0.045 g, 40%) as a white solid. MW=366.84. $^1$H NMR (DMSO-d$_6$, 500 MHz) δ 9.60 (s, 1H), 8.05 (d, J=2.0 Hz, 1H), 7.95-7.93 (m, 1H), 7.64 (d, J=8.4 Hz, 2H), 7.58-7.54 (m, 2H), 7.42 (br s, 1H), 7.23 (d, J=8.4 Hz, 2H), 7.05 (s, 1H), 6.85 (br s, 1H), 2.81 (q, J=7.6 Hz, 2H), 1.32 (t, J=7.6 Hz, 3H); ESI MS m/z 367 [M+H]$^+$.

EXAMPLE 266

3-(3-(2-(3-chlorophenyl)-6,7-dihydro-5H-cyclopenta[b]pyridin-4-yl)phenyl)propan-1-ol hydrochloride

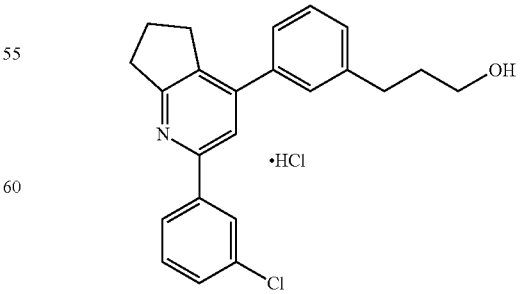

A mixture of 4-chloro-2-(3-chlorophenyl)-6,7-dihydro-5H-cyclopenta[b]pyridine hydrochloride (0.070 g, 0.23 mmol), (3-(3-hydroxypropyl)phenyl)boronic acid (0.054 g, 0.30 mmol), 2M Na₂CO₃ (0.5 mL), and Pd(PPh₃)₄ (0.013 g, 0.012 mmol) in dioxane (50 mL) was heated at reflux under nitrogen for 2.5 h. After this time, the mixture was diluted with ethyl acetate (100 mL), washed with water (100 mL), dried (Na₂SO₄), filtered, and concentrated. The resulting residue was purified by silica gel chromatography eluting with 20% ethyl acetate/hexanes to 100% ethyl acetate to afford the free base of title compound (0.028 g, 34%) as a white foam. This material was redissolved in Et₂O (20 mL) and 4N HCl in dioxane (0.1 mL) added. The mixture was concentrated, triturated with Et₂O, and lyophilized with a water/acetonitrile/methanol mixture to afford the title compound as a white solid. MW=363.88. $^1$H NMR (DMSO-$d_6$, 300 MHz) δ 8.21 (s, 1H), 8.12-8.08 (m, 1H), 7.92 (s, 1H), 7.58-7.33 (m, 6H), 3.45 (t, J=6.4 Hz, 2H), 3.16-3.01 (m, 4H), 2.74-2.69 (m, 2H), 2.19-2.08 (m, 2H), 1.83-0.83 (m, 2H); APCI MS m/z 364 [M+H]$^+$.

EXAMPLE 267

2-(4-((2-(3-chlorophenyl)-6,7-dihydro-5H-cyclopenta[b]pyridin-4-yl)sulfonyl)phenyl)acetamide

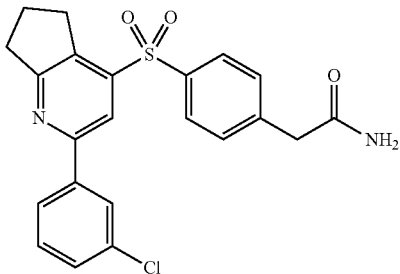 [SMILES: NC(=O)Cc1ccc(S(=O)(=O)c2cc(-c3cccc(Cl)c3)nc3c2CCC3)cc1]

Step 1. Preparation of methyl 2-(4-((2-(3-chlorophenyl)-6,7-dihydro-5H-cyclopenta[b]pyridin-4-yl)thio)phenyl)acetate

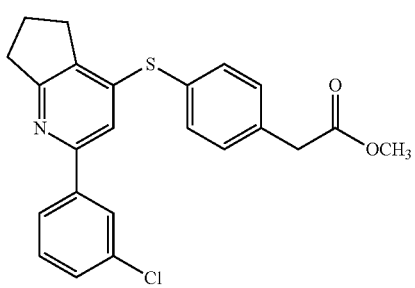 [SMILES: COC(=O)Cc1ccc(Sc2cc(-c3cccc(Cl)c3)nc3c2CCC3)cc1]

A mixture of 4-chloro-2-(3-chlorophenyl)-6,7-dihydro-5H-cyclopenta[b]pyridine hydrochloride (0.120 g, 0.40 mmol), methyl 2-(4-mercaptophenyl)acetate (0.100 g, 0.55 mmol), and Et₃N (0.145 g, 1.3 mmol) in DMF was heated at 110° C. for 24 h. After this time, the mixture was concentrated, diluted with EtOAc (100 mL), washed with 10% aqueous LiCl (2×100 mL), dried (Na₂SO₄), filtered, and concentrated. The residue was purified by silica gel chromatography eluting with 100% hexanes to 1:1 ethyl acetate/hexanes to afford the title compound (0.164 g, 100%) as a white solid. MW=409.93. $^1$H NMR (CDCl₃, 300 MHz) δ 7.78-7.77 (m, 1H), 7.61-7.46 (m, 3H), 7.37 (d, J=8.2 Hz, 2H), 7.30-7.28 (m, 3H), 6.89 (s, 1H), 3.73 (s, 3H), 3.70 (s, 2H), 3.09 (t, J=7.7 Hz, 2H), 2.90 (t, J=7.4 Hz, 2H), 2.24-2.05 (m, 4H); APCI MS m/z 410 [M+H]$^+$.

Step 2. Preparation of methyl 2-(4-((2-(3-chlorophenyl)-6,7-dihydro-5H-cyclopenta[b]pyridin-4-yl)sulfonyl)phenyl)acetate

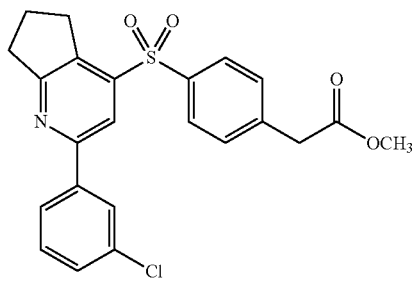 [SMILES: COC(=O)Cc1ccc(S(=O)(=O)c2cc(-c3cccc(Cl)c3)nc3c2CCC3)cc1]

A solution of methyl 2-(4-((2-(3-chlorophenyl)-6,7-dihydro-5H-cyclopenta[b]pyridin-4-yl)thio)phenyl)acetate (0.164 g, 0.40 mmol) and m-CPBA (0.269 g, 1.2 mmol) in CH₂Cl₂ (15 mL) was stirred at room temperature for 2 h. After this time, the mixture was diluted with CH₂Cl₂ (100 mL), washed with water (100 mL) and saturated NaHCO₃ (100 mL), dried (MgSO₄), filtered, and concentrated. The residue was purified by silica gel chromatography eluting with 100% hexanes to 1:1 ethyl acetate/hexanes to afford the title compound (0.109 g, 62%) as a white solid. MW=441.93. $^1$H NMR (CDCl₃, 300 MHz) δ 8.09-8.0 (m, 2H), 7.97-7.85 (m, 3H), 7.57-7.39 (m, 4H), 3.75-3.68 (m, 5H), 3.18-3.07 (m, 4H), 2.22-2.05 (m, 2H); APCI MS m/z 442 [M+H]$^+$.

EXAMPLE 267

2-(4-((2-(3-chlorophenyl)-6,7-dihydro-5H-cyclopenta[b]pyridin-4-yl)sulfonyl)phenyl)acetamide

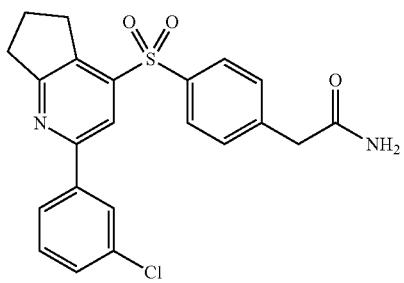 [SMILES: NC(=O)Cc1ccc(S(=O)(=O)c2cc(-c3cccc(Cl)c3)nc3c2CCC3)cc1]

A suspension of methyl 2-(4-((2-(3-chlorophenyl)-6,7-dihydro-5H-cyclopenta[b]pyridin-4-yl)sulfonyl)phenyl)acetate (0.109 g, 0.25 mmol) in 7N NH₃ in MeOH was heated at 100° C. in a sealed tube. After 24 h, the mixture was concentrated and purified by silica gel chromatography eluting with 100% methylene chloride to 1:1 methylene chloride/89:9:1 (methylene chloride/methanol/concentrated ammonium hydroxide) to afford the title compound (0.055 g, 53%) as a white solid. MW=426.92. ¹H NMR (DMSO-d₆, 300 MHz) δ 8.20-8.18 (m, 2H), 8.10-8.08 (m, 1H), 8.03 (d, J=8.4 Hz, 2H), 7.56-7.51 (m, 5H), 6.98 (s, 1H), 3.50 (s, 2H), 3.12 (t, J=7.6 Hz, 2H), 3.03 (t, J=7.8 Hz, 2H), 2.13-2.08 (m, 2H); APCI MS m/z 427 [M+H]⁺.

EXAMPLE 268

4-((4-(2-hydroxyethyl)phenyl)amino)-2-phenyl-7,8-dihydro-6H-thiopyrano[3,2-d]pyrimidine 5,5-dioxide

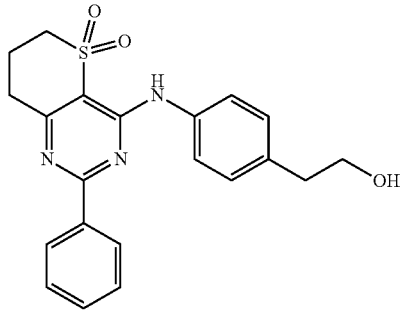 [SMILES: O=S1(=O)CCCc2nc(-c3ccccc3)nc(Nc3ccc(CCO)cc3)c21]

Following general procedure G, 5,5-dioxido-2-phenyl-7,8-dihydro-6H-thiopyrano[3,2-d]pyrimidin-4-yl trifluoromethanesulfonate (0.123 g, 0.30 mmol) was reacted with 2-(4-aminophenyl)ethanol (0.045 g, 0.33 mmol) to afford the desired product (0.081 g, 68%) as a light yellow solid. MW=395.47. ¹H NMR (DMSO-d₆, 500 MHz) δ 8.72 (s, 1H), 8.29-8.25 (m, 2H), 7.61-7.49 (m, 5H), 7.30 (d, J=8.5 Hz, 2H), 4.65 (t, J=5.5 Hz, 1H), 3.76-3.71 (m, 2H), 3.67-3.61 (m, 2H), 3.07 (t, J=6.5 Hz, 2H), 2.75 (t, J=7.0 Hz, 2H), 2.43-2.35 (m, 2H); APCI MS m/z 396 [M+H]⁺.

EXAMPLE 269

2-(4-((5,5-dioxido-2-phenyl-7,8-dihydro-6H-thiopyrano[3,2-d]pyrimidin-4-yl)amino)phenyl)acetamide

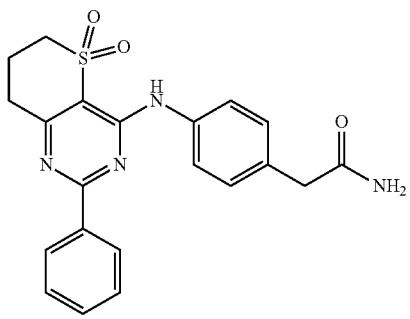 [SMILES: NC(=O)Cc1ccc(Nc2nc(-c3ccccc3)nc3c2S(=O)(=O)CCC3)cc1]

Following general procedure G, 5,5-dioxido-2-phenyl-7,8-dihydro-6H-thiopyrano[3,2-d]pyrimidin-4-yl trifluoromethanesulfonate (0.125 g, 0.31 mmol) was reacted with 2-(4-aminophenyl)acetamide (0.051 g, 0.34 mmol) to afford the desired product (0.077 g, 61%) as a white solid. MW=408.47. ¹H NMR (DMSO-d₆, 500 MHz) δ 8.74 (s, 1H), 8.30-8.25 (m, 2H), 7.61 (d, J=8.5 Hz, 2H), 7.59-7.50 (m, 3H), 7.48 (s, 1H), 7.33 (d, J=8.5 Hz, 2H), 6.89 (s, 1H), 3.77-3.71 (m, 2H), 3.40 (s, 2H), 3.08 (t, J=6.5 Hz, 2H), 2.43-2.35 (m, 2H); APCI MS m/z 409 [M+H]+.

EXAMPLE 270

2-(4-((5,5-dioxido-2-phenyl-7,8-dihydro-6H-thiopyrano[3,2-d]pyrimidin-4-yl)amino)phenyl)-N-propylacetamide

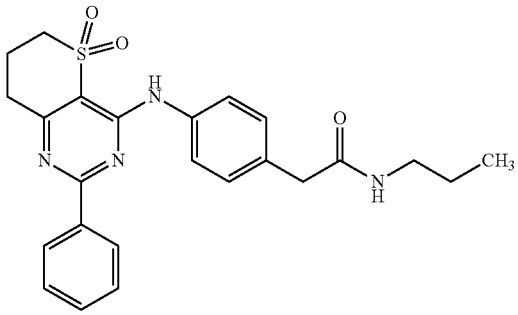 [SMILES: CCCNC(=O)Cc1ccc(Nc2nc(-c3ccccc3)nc3c2S(=O)(=O)CCC3)cc1]

Step 1. ethyl 2-(4-((5,5-dioxido-2-phenyl-7,8-dihydro-6H-thiopyrano[3,2-d]pyrimidin-4-yl)amino)phenyl)acetate

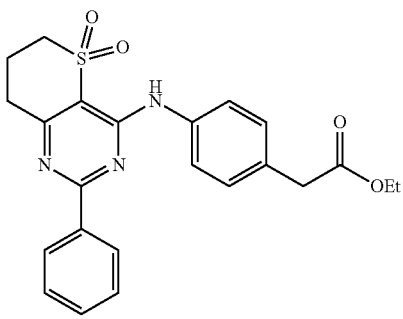 [SMILES: CCOC(=O)Cc1ccc(Nc2nc(-c3ccccc3)nc3c2S(=O)(=O)CCC3)cc1]

Following general procedure G, 5,5-dioxido-2-phenyl-7,8-dihydro-6H-thiopyrano[3,2-d]pyrimidin-4-yl trifluoromethanesulfonate (1.0 g, 2.46 mmol) was reacted with ethyl 2-(4-aminophenyl)acetate (0.527 g, 2.94 mmol) to afford the desired product (0.83 g, 77%) as a light yellow solid. MW=437.51. ¹H NMR (DMSO-d₆, 500 MHz) δ 8.77 (s, 1H), 8.28-8.24 (m, 2H), 7.64-7.49 (m, 5H), 7.34 (d, J=8.5 Hz, 2H), 4.10 (q, J=7.0 Hz, 2H), 3.76-3.72 (m, 2H), 3.70 (s, 2H), 3.08 (t, J=6.5 Hz, 2H), 2.43-2.35 (m, 2H), 1.20 (t, J=7.0 Hz, 3H); APCI MS m/z 438 [M+H]+.

Step 2. 2-(4-((5,5-dioxido-2-phenyl-7,8-dihydro-6H-thiopyrano[3,2-d]pyrimidin-4-yl)amino)phenyl)acetic acid

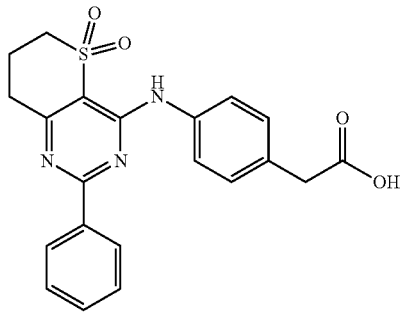 [SMILES: O=C(O)Cc1ccc(Nc2nc(-c3ccccc3)nc3c2S(=O)(=O)CCC3)cc1]

Following general procedure D, ethyl 2-(4-((5,5-dioxido-2-phenyl-7,8-dihydro-6H-thiopyrano[3,2-d]pyrimidin-4-yl)amino)phenyl)acetate (0.80 g, 1.83 mmol) was reacted with lithium hydroxide (0.380 g, 9.15 mmol) to afford the desired product (0.650 g, 86%) as a light yellow solid. MW=409.46. $^1$H NMR (DMSO-d$_6$, 500 MHz) δ 12.34 (s, 1H), 8.76 (s, 1H), 8.29-8.25 (m, 2H), 7.62 (d, J=8.5 Hz, 2H), 7.59-7.49 (m, 3H), 7.33 (d, J=8.5 Hz, 2H), 3.76-3.72 (m, 2H), 3.60 (s, 2H), 3.08 (t, J=6.5 Hz, 2H), 2.43-2.35 (m, 2H); APCI MS m/z 410 [M+H]+.

Step 3. 2-(4-((5,5-dioxido-2-phenyl-7,8-dihydro-6H-thiopyrano[3,2-d]pyrimidin-4-yl)amino)phenyl)-N-propylacetamide

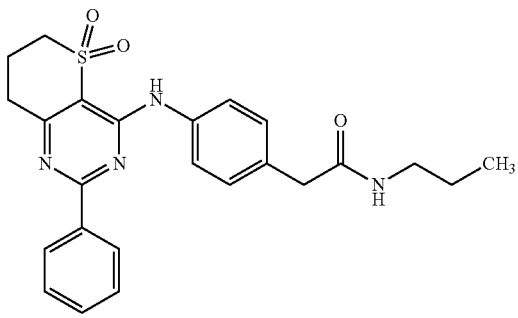 [SMILES: CCCNC(=O)Cc1ccc(Nc2nc(-c3ccccc3)nc3c2S(=O)(=O)CCC3)cc1]

To a solution of 2-(4-((5,5-dioxido-2-phenyl-7,8-dihydro-6H-thiopyrano[3,2-d]pyrimidin-4-yl)amino)phenyl)acetic acid (0.115 g, 0.28 mmol) in DMF (4 mL) was added EDC (0.107 g, 0.56 mmol), HOBT (0.076 g, 0.56 mmol) and n-propylamine (0.12 mL, 1.4 mmol). The mixture was stirred at rt for 16 h. The mixture was diluted with ethyl acetate and then washed with water. The organic layer were dried over anhydrous sodium sulfate, filtered and the filtrate was concentrated. The residue was purified by column chromatography (silica, dichloromethane/methanol) to afford the desired product (0.110 g, 87%) as a white solid. MW=450.55. $^1$H NMR (DMSO-d$_6$, 500 MHz) δ 8.74 (s, 1H), 8.29-8.25 (m, 2H), 8.05-7.99 (m, 1H), 7.63-7.49 (m, 5H), 7.33 (d, J=8.5 Hz, 2H), 3.76-3.71 (m, 2H), 3.42 (s, 2H), 3.10-2.99 (m, 4H), 2.42-2.35 (m, 2H), 1.45-1.38 (m, 2H), 0.85 (t, J=7.5 Hz, 3H); APCI MS m/z 451 [M+H]+.

EXAMPLE 271

2-(4-((2-(3-chlorophenyl)-7,8-dihydro-6H-thiopyrano[3,2-d]pyrimidin-4-yl)amino)phenyl)acetamide

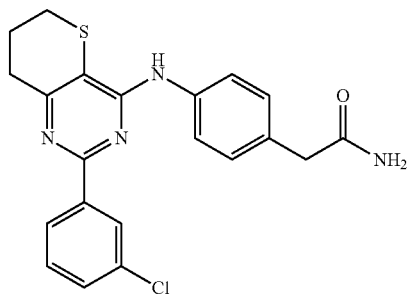 [SMILES: NC(=O)Cc1ccc(Nc2nc(-c3cccc(Cl)c3)nc3c2SCCC3)cc1]

Step 1. Preparation of 2-(3-chlorophenyl)-7,8-dihydro-6H-thiopyrano[3,2-d]pyrimidin-4-ol

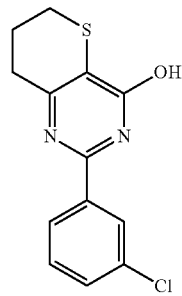 [SMILES: Oc1nc(-c2cccc(Cl)c2)nc2c1SCCC2]

To a solution of 3-chlorobenzimidamide (4.3 g, 27.7 mmol) in ethanol (120 mL) was added methyl 3-oxotetrahydro-2H-thiopyran-2-carboxylate (4.82 g, 27.7 mmol) and sodium methoxide (1.8 g, 33.2 mmol). The mixture was stirred at 85° C. for 16 h. After this time, the mixture was concentrated after which ethanol (10 mL) was added and the suspension was chilled to 0° C. HCl (2 M, 50 mL) was added and the suspension was filtered and washed with water. The solid was dried under heat and vacuum to afford the title compound (5.2 g, 67%) as a light yellow solid. MW=278.75. $^1$H NMR (DMSO-d$_6$, 500 MHz) δ 12.81 (s, 1H), 8.12 (s, 1H), 8.03 (d, J=7.5 Hz, 1H), 7.63-7.58 (m, 1H), 7.56-7.51 (m, 1H), 3.01-2.95 (m, 2H), 2.74 (t, J=6.0 Hz, 2H), 2.12-2.04 (m, 2H); APCI MS m/z 279 [M+H]$^+$.

Step 2. Preparation of 2-(3-chlorophenyl)-7,8-dihydro-6H-thiopyrano[3,2-d]pyrimidin-4-yl trifluoromethanesulfonate

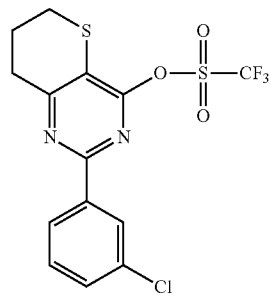 [SMILES: O=S(=O)(Oc1nc(-c2cccc(Cl)c2)nc2c1SCCC2)C(F)(F)F]

To a suspension of 2-(3-chlorophenyl)-7,8-dihydro-6H-thiopyrano[3,2-d]pyrimidin-4-ol (5.2 g, 18.6 mmol) in methylene chloride (200 mL) at 0° C. was added N,N-dimethylaminopyridine (0.020 g, cat.), triethylamine (5.2 mL, 37.3 mmol) and trifluoromethanesulfonic acid (3.7 mL, 22.4 mmol). The suspension was warmed to rt and stirred for 3 h. The mixture was cooled to 0° C. and the reaction was quenched with a saturated solution of NaHCO$_3$. The organic layer was washed a saturated solution of NaHCO$_3$ and brine. The organic layers were dried over anhydrous sodium sulfate, filtered and the filtrate was concentrated. The residue was purified by column chromatography (silica, methylene chloride) to afford title compound (6.6 g, 86%) as a white solid. MW=410.82. $^1$H NMR (CDCl$_3$, 300 MHz) δ 8.35-8.31 (m, 1H), 8.25-8.18 (m, 1H), 7.48-7.36 (m, 2H), 3.18-3.05 (m, 4H), 2.38-2.27 (m, 2H); APCI MS m/z 411 [M+H]$^+$.

EXAMPLE 271

2-(4-((2-(3-Chlorophenyl)-7,8-dihydro-6H-thiopyrano[3,2-d]pyrimidin-4-yl)amino)phenyl)acetamide

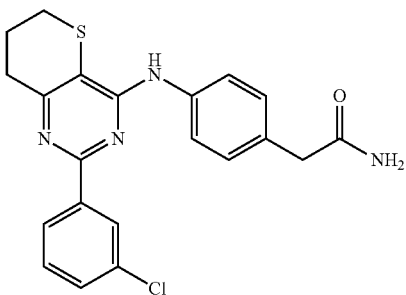 [SMILES: NC(=O)Cc1ccc(Nc2nc(-c3cccc(Cl)c3)nc3c2SCCC3)cc1]

Following general procedure H, 2-(3-chlorophenyl)-7,8-dihydro-6H-thiopyrano[3,2-d]pyrimidin-4-yl trifluoromethanesulfonate (0.125 g, 0.30 mmol) was reacted with 2-(4-aminophenyl)acetamide (0.050 g, 0.33 mmol) to afford the title compound (0.101 g, 82%) as a white solid. MW=410.92. $^1$H NMR (DMSO-d$_6$, 500 MHz) δ 8.25-8.21 (m, 1H), 8.19 (s, 1H), 8.17-8.13 (m, 1H), 7.61 (d, J=8.5 Hz, 2H), 7.52-7.41 (m, 3H), 7.25 (d, J=8.5 Hz, 2H), 3.37 (s, 2H), 3.22-3.16 (m, 2H), 2.90 (t, J=6.5 Hz, 2H), 2.22-2.16 (m, 2H); APCI MS m/z 411 [M+H]$^+$.

EXAMPLE 272

2-(4-((2-(3-chlorophenyl)-7,8-dihydro-6H-thiopyrano[3,2-d]pyrimidin-4-yl)amino)phenyl)ethanol

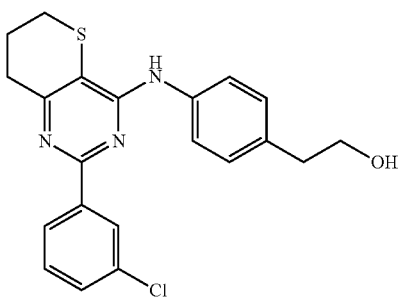 [SMILES: OCCc1ccc(Nc2nc(-c3cccc(Cl)c3)nc3c2SCCC3)cc1]

Following general procedure H, 2-(3-chlorophenyl)-7,8-dihydro-6H-thiopyrano[3,2-d]pyrimidin-4-yl trifluoromethanesulfonate (0.120 g, 0.29 mmol) was reacted with 2-(4-aminophenyl)ethanol (0.044 g, 0.32 mmol) to afford the title compound (0.101 g, 87%) as a white solid. MW=397.92. $^1$H NMR (DMSO-d$_6$, 500 MHz) δ 8.20-8.17 (m, 2H), 8.16-8.12 (m, 1H), 7.58 (d, J=8.5 Hz, 2H), 7.51-7.46 (m, 2H), 7.21 (d, J=8.5 Hz, 2H), 4.63 (t, J=5.5 Hz, 1H), 3.65-3.59 (m, 2H), 3.20-3.16 (m, 2H), 2.90 (t, J=6.0 Hz, 2H), 2.73 (t, J=7.0 Hz, 2H), 2.22-2.15 (m, 2H); APCI MS m/z 398 [M+H]$^+$.

EXAMPLE 273

2-(3-Chlorophenyl)-4-((4-(2-hydroxyethyl)phenyl)amino)-7,8-dihydro-6H-thiopyrano[3,2-d]pyrimidine 5,5-dioxide

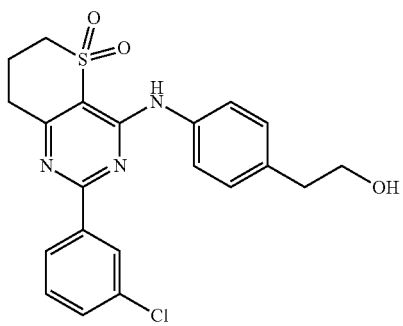 [SMILES: O=S1(=O)CCCc2nc(-c3cccc(Cl)c3)nc(Nc3ccc(CCO)cc3)c21]

Step 1. Preparation of 2-(3-chlorophenyl)-5,5-dioxido-7,8-dihydro-6H-thiopyrano[3,2-d]pyrimidin-4-yl trifluoromethanesulfonate

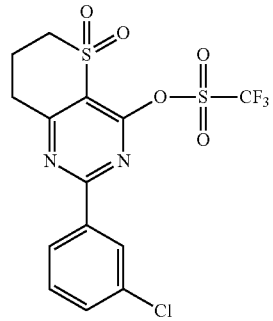 [SMILES: O=S1(=O)CCCc2nc(-c3cccc(Cl)c3)nc(OS(=O)(=O)C(F)(F)F)c21]

To a solution of 2-(3-chlorophenyl)-7,8-dihydro-6H-thiopyrano[3,2-d]pyrimidin-4-yl trifluoromethanesulfonate (4.2 g, 10.2 mmol) in methylene chloride (150 mL) was added MCBPA (77%, 6.87 g, 30.7 mmol). The reaction stirred at rt for 4 h. The mixture was diluted with methylene chloride and washed with water, a saturated solution of Na$_2$S$_2$O$_3$, a saturated solution of NaHCO$_3$, and brine. The organic layers were dried over anhydrous sodium sulfate, filtered and the filtrate was concentrated to afford the title compound (4.48 g, 98%) as a white solid. MW=442.82. $^1$H NMR (CDCl$_3$, 500 MHz) δ 8.41-8.39 (m, 1H), 8.32-8.28 (m, 1H), 7.59-7.54 (m, 1H), 7.49-7.44 (m, 1H), 3.53-3.47 (m, 2H), 3.26 (t, J=6.0 Hz, 2H), 2.62-2.54 (m, 2H); APCI MS m/z 443 [M+H]$^+$.

EXAMPLE 273

2-(3-Chlorophenyl)-4-((4-(2-hydroxyethyl)phenyl)amino)-7,8-dihydro-6H-thiopyrano[3,2-d]pyrimidine 5,5-dioxide

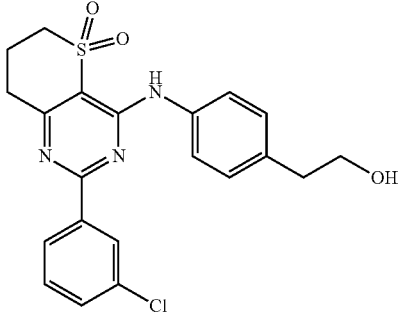 [SMILES: O=S1(=O)CCCc2nc(-c3cccc(Cl)c3)nc(Nc3ccc(CCO)cc3)c21]

Following general procedure H, 2-(3-chlorophenyl)-5,5-dioxido-7,8-dihydro-6H-thiopyrano[3,2-d]pyrimidin-4-yl trifluoromethanesulfonate (0.124 g, 0.28 mmol) was reacted with 2-(4-aminophenyl)ethanol (0.042 g, 0.31 mmol) to afford the title compound (0.105 g, 87%) as a white solid. MW=429.92. $^1$H NMR (DMSO-$d_6$, 500 MHz) δ 8.77 (s, 1H), 8.22-8.17 (m, 2H), 7.65-7.61 (m, 1H), 7.58-7.52 (m, 3H), 7.29 (d, J=8.5 Hz, 2H), 4.65 (t, J=5.5 Hz, 1H), 3.77-3.71 (m, 2H), 3.67-3.61 (m, 2H), 3.08 (t, J=6.5 Hz, 2H), 2.76 (t, J=7.0 Hz, 2H), 2.43-2.35 (m, 2H); APCI MS m/z 430 [M+H]$^+$.

EXAMPLE 274

2-(4-((2-(3-chlorophenyl)-5,5-dioxido-7,8-dihydro-6H-thiopyrano[3,2-d]pyrimidin-4-yl)amino)phenyl)acetamide

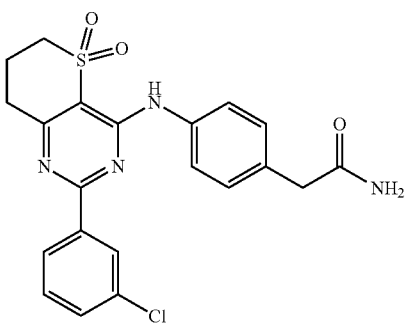 [SMILES: NC(=O)Cc1ccc(Nc2nc(-c3cccc(Cl)c3)nc3c2S(=O)(=O)CCC3)cc1]

Following general procedure H, 2-(3-chlorophenyl)-5,5-dioxido-7,8-dihydro-6H-thiopyrano[3,2-d]pyrimidin-4-yl trifluoromethanesulfonate (0.127 g, 0.29 mmol) was reacted with 2-(4-aminophenyl)acetamide (0.047 g, 0.32 mmol) to afford the title compound (0.074 g, 61%) as a light yellow solid. MW=442.92. $^1$H NMR (DMSO-$d_6$, 500 MHz) δ 8.79 (s, 1H), 8.24-8.17 (m, 2H), 7.65-7.54 (m, 4H), 7.48 (s, 1H), 7.33 (d, J=8.5 Hz, 2H), 6.89 (s, 1H), 3.77-3.71 (m, 2H), 3.41 (s, 2H), 3.08 (t, J=6.5 Hz, 2H), 2.43-2.35 (m, 2H); APCI MS m/z 443 [M+H]$^+$.

EXAMPLE 275

2-(4-((2-(3-chlorophenyl)-5,5-dioxido-7,8-dihydro-6H-thiopyrano[3,2-d]pyrimidin-4-yl)amino)phenyl)acetic acid

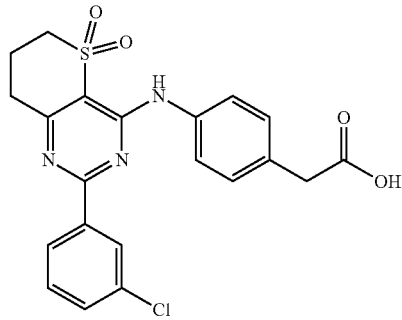 [SMILES: O=C(O)Cc1ccc(Nc2nc(-c3cccc(Cl)c3)nc3c2S(=O)(=O)CCC3)cc1]

Step 1. Preparation of ethyl 2-(4-((2-(3-chlorophenyl)-5,5-dioxido-7,8-dihydro-6H-thiopyrano[3,2-d]pyrimidin-4-yl)amino)phenyl)acetate

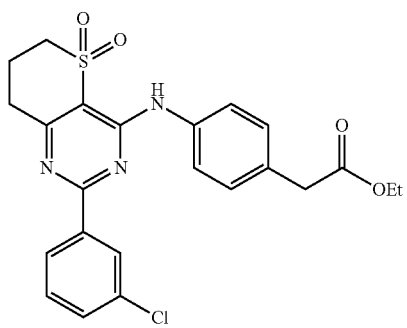 [SMILES: CCOC(=O)Cc1ccc(Nc2nc(-c3cccc(Cl)c3)nc3c2S(=O)(=O)CCC3)cc1]

Following general procedure H, 2-(3-chlorophenyl)-5,5-dioxido-7,8-dihydro-6H-thiopyrano[3,2-d]pyrimidin-4-yl trifluoromethanesulfonate (1.0 g, 2.26 mmol) was reacted with ethyl 2-(4-aminophenyl)acetate (0.445 g, 2.49 mmol) to afford the title compound (0.827 g, 78%) as a light yellow solid. MW=471.96. APCI MS m/z 472 [M+H]$^+$.

EXAMPLE 275

2-(4-((2-(3-Chlorophenyl)-5,5-dioxido-7,8-dihydro-6H-thiopyrano[3,2-d]pyrimidin-4-yl)amino)phenyl)acetic acid

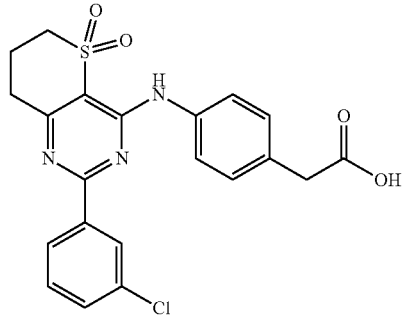 [SMILES: O=C(O)Cc1ccc(Nc2nc(-c3cccc(Cl)c3)nc3c2S(=O)(=O)CCC3)cc1]

Following general procedure D, ethyl 2-(4-((2-(3-chlorophenyl)-5,5-dioxido-7,8-dihydro-6H-thiopyrano[3,2-d]pyrimidin-4-yl)amino)phenyl)acetate (0.82 g, 1.74 mmol) was reacted with lithium hydroxide (0.365 g, 8.7 mmol) to afford the desired product (0.675 g, 87%) as a light yellow solid. MW=443.90. $^1$H NMR (DMSO-d$_6$, 500 MHz) δ 12.33 (s, 1H), 8.81 (s, 1H), 8.23-8.16 (m, 2H), 7.66-7.53 (m, 4H), 7.33 (d, J=8.5 Hz, 2H), 3.77-3.71 (m, 2H), 3.61 (s, 2H), 3.09 (t, J=6.5 Hz, 2H), 2.43-2.35 (m, 2H); APCI MS m/z 444 [M+H]$^+$.

EXAMPLE 276

2-(4-((2-(3-Chlorophenyl)-5,5-dioxido-7,8-dihydro-6H-thiopyrano[3,2-d]pyrimidin-4-yl)amino)phenyl)-N-propylacetamide

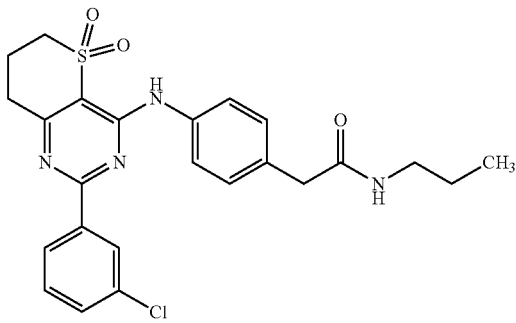 [SMILES: CCCNC(=O)Cc1ccc(Nc2nc(-c3cccc(Cl)c3)nc3c2S(=O)(=O)CCC3)cc1]

To a solution of 2-(4-((2-(3-chlorophenyl)-5,5-dioxido-7,8-dihydro-6H-thiopyrano[3,2-d]pyrimidin-4-yl)amino)phenyl)acetic acid (0.125 g, 0.28 mmol) in DMF (5 mL) was added EDC (0.108 g, 0.56 mmol), HOBT (0.076 g, 0.56 mmol) and n-propylamine (0.12 mL, 1.4 mmol). The mixture was stirred at rt for 2 d. After this time, the mixture was diluted with ethyl acetate and then washed with water. The organic layer were dried over anhydrous sodium sulfate, filtered, and the filtrate was concentrated. The residue was purified by column chromatography (silica, dichloromethane/methanol) to afford the title compound (0.113 g, 83%) as a light yellow solid. MW=485.00. $^1$H NMR (DMSO-d$_6$, 500 MHz) δ 8.79 (s, 1H), 8.22-8.16 (m, 2H), 8.06-8.00 (m, 1H), 7.65-7.61 (m, 1H), 7.59-7.53 (m, 3H), 7.33 (d, J=8.5 Hz, 2H), 3.77-3.71 (m, 2H), 3.43 (s, 2H), 3.08 (t, J=6.5 Hz, 2H), 3.05-2.99 (m, 2H), 2.43-2.35 (m, 2H), 1.45-1.38 (m, 2H), 0.84 (t, J=7.5 Hz, 3H); APCI MS m/z 485 [M+H]$^+$.

EXAMPLE 277

2-(4-((2-(3-Chlorophenyl)-5,5-dioxido-7,8-dihydro-6H-thiopyrano[3,2-d]pyrimidin-4-yl)methyl)phenyl)acetamide

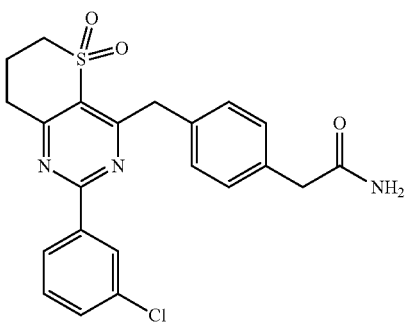 [SMILES: NC(=O)Cc1ccc(Cc2nc(-c3cccc(Cl)c3)nc3c2S(=O)(=O)CCC3)cc1]

Step 1. Preparation of methyl 2-(4-((2-(3-chlorophenyl)-5,5-dioxido-7,8-dihydro-6H-thiopyrano[3,2-d]pyrimidin-4-yl)methyl)phenyl)acetate Following general procedure H, 2-(3-chlorophenyl)-5,5-dioxido-7,8-dihydro-6H-thiopyrano[3,2-d]pyrimidin-4-yl trifluoromethanesulfonate (0.250 g, 0.56 mmol) was reacted with methyl 2-(4-((4,4,5,5-tetramethyl-1,3,2-dioxaborolan-2-yl)methyl)phenyl)acetate (0.160 g, 0.56 mmol) to afford the title compound (0.058 g, 22%) as a white solid. MW=456.9. $^1$H NMR (CDCl$_3$, 500 MHz) δ 8.28 (t, J=1.2 Hz, 1H), 8.30-8.26 (m, 1H), 7.52-7.45 (m, 3H), 7.42-7.37 (m, 1H), 7.23 (d, J=8.0 Hz, 2H), 4.60 (s, 2H), 3.67 (s, 3H), 3.60 (s, 2H), 3.50-3.45 (m, 2H), 3.18 (t, J=6.5 Hz, 2H), 2.54-2.48 (m, 2H); APCI MS m/z 457 [M+H]$^+$.

Step 2. Preparation of 2-(4-((2-(3-chlorophenyl)-5,5-dioxido-7,8-dihydro-6H-thiopyrano[3,2-d]pyrimidin-4-yl)methyl)phenyl)acetic acid Following general procedure D, methyl 2-(4-((2-(3-chlorophenyl)-5,5-dioxido-7,8-dihydro-6H-thiopyrano[3,2-d]pyrimidin-4-yl)methyl)phenyl)acetate (0.058 g, 0.13 mmol) was reacted with lithium hydroxide (0.026 g, 0.64 mmol) to afford the title compound (0.042 g, 75%) as a yellow-brown solid. MW=442.92. $^1$H NMR (DMSO-d$_6$, 300 MHz) δ 12.29 (s, 1H), 8.32-8.24 (m, 2H), 7.71-7.53 (m, 2H), 7.38 (d, J=8.0 Hz, 2H), 7.20 (d, J=8.0 Hz, 2H), 4.53 (s, 2H), 3.80-3.70 (m, 2H), 3.52 (s, 2H), 3.21 (t, J=6.0 Hz, 2H), 2.42-2.31 (m, 2H); APCI MS m/z 443 [M+H]$^+$.

EXAMPLE 277

2-(4-((2-(3-Chlorophenyl)-5,5-dioxido-7,8-dihydro-6H-thiopyrano[3,2-d]pyrimidin-4-yl)methyl)phenyl)acetamide

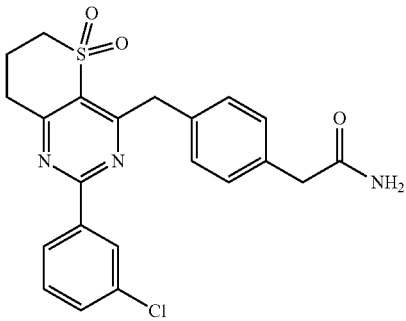 [SMILES: NC(=O)Cc1ccc(Cc2nc(-c3cccc(Cl)c3)nc3c2S(=O)(=O)CCC3)cc1]

To a solution of 2-(4-((2-(3-chlorophenyl)-5,5-dioxido-7,8-dihydro-6H-thiopyrano[3,2-d]pyrimidin-4-yl)methyl)phenyl)acetic acid (0.040 g, 0.090 mmol) in DMF (2 mL) was added EDC (0.034 g, 0.18 mmol), HOBT (0.024 g, 0.18 mmol) and ammonia in methanol (0.13 mL, 0.90 mmol). The mixture was sealed and stirred at 85° C. for 16 h. The mixture was diluted with ethyl acetate and then washed with water. The organic layer were dried over anhydrous sodium sulfate, filtered, and the filtrate was concentrated. The residue was purified by column chromatography (silica, dichloromethane/ethyl acetate) to afford the title compound (0.025 g, 62%) as a white solid. MW=441.93. $^1$H NMR (DMSO-d$_6$, 500 MHz) δ 8.30-8.26 (m, 2H), 7.69-7.64 (m, 1H), 7.61-7.56 (m, 1H), 7.40 (s, 1H), 7.37 (d, J=8.0 Hz, 2H), 7.19 (d, J=8.0 Hz, 2H), 6.82 (s, 1H), 4.52 (s, 2H), 3.77-3.71 (m, 2H), 3.32 (s, 2H), 3.21 (t, J=6.5 Hz, 2H), 2.40-2.38 (m, 2H); APCI MS m/z 442 [M+H]$^+$.

EXAMPLE 278

2-(3-chlorophenyl)-4-(4-(2-hydroxyethyl)benzyl)-7,8-dihydro-6H-thiopyrano[3,2-d]pyrimidine 5,5-dioxide

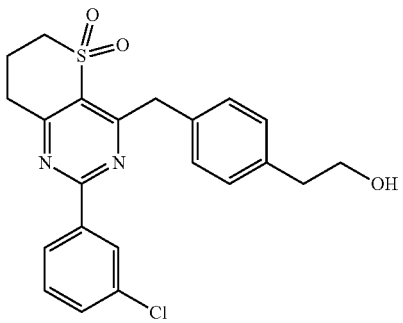 [SMILES: O=S1(=O)CCCc2nc(-c3cccc(Cl)c3)nc(Cc3ccc(CCO)cc3)c21]

Following general procedure E1, methyl 2-(4-((2-(3-chlorophenyl)-5,5-dioxido-7,8-dihydro-6H-thiopyrano[3,2-d]pyrimidin-4-yl)methyl)phenyl)acetate (0.060 g, 0.13 mmol) was reacted with DIBAL (1.0 M, 0.65 mL, 0.65 mmol) to afford the title compound (0.045 g, 81%) as a white solid. MW=428.93. $^1$H NMR (DMSO-d$_6$, 500 MHz) δ 8.29-8.25 (m, 2H), 7.67-7.64 (m, 1H), 7.61-7.56 (m, 1H), 7.34 (d, J=8.5 Hz, 2H), 7.15 (d, J=8.5 Hz, 2H), 4.58 (t, J=5.5 Hz, 1H), 4.51 (s, 2H), 3.76-3.71 (m, 2H), 3.59-3.53 (m, 2H), 2.68 (t, J=7.5 Hz, 2H), 2.40-2.32 (m, 2H); APCI MS m/z 429 [M+H]$^+$.

EXAMPLE 279

2-(4-((2-(3-Chlorophenyl)-6,7-dihydrothieno[3,2-d]pyrimidin-4-yl)amino)phenyl)ethanol

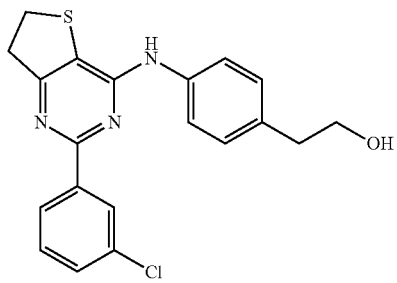 [SMILES: OCCc1ccc(Nc2nc(-c3cccc(Cl)c3)nc3c2SCC3)cc1]

Step 1. Preparation of 2-(3-chlorophenyl)-6,7-dihydrothieno[3,2-d]pyrimidin-4-ol

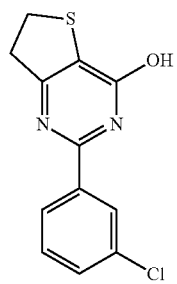

To a solution of 3-chlorobenzimidamide (4.8 g, 31.2 mmol) in ethanol (150 mL) was added methyl 3-oxotetrahydrothiophene-2-carboxylate (5.0 g, 31.2 mmol) and sodium methoxide (1.7 g, 31.2 mmol). The mixture was stirred at 85° C. for 16 h. The mixture was concentrated after which ethanol (10 mL) was added and the suspension was chilled to 0° C. HCl (2 M, 50 mL) was added and the suspension was filtered and washed with water. The solid was purified by column chromatography (silica, dichloromethane/methanol) to afford the title compound (1.9 g, 23%) as a brown solid. MW=264.73. $^1$H NMR (DMSO-d$_6$, 500 MHz) δ 12.85 (s, 1H), 8.13 (s, 1H), 8.07-8.01 (m, 1H), 7.63-7.59 (m, 1H), 7.56-7.51 (m, 1H), 3.41-3.24 (m, 4H); APCI MS m/z 265 [M+H]$^+$.

343
Step 2. Preparation of 2-(3-chlorophenyl)-6,7-dihydrothieno[3,2-d]pyrimidin-4-yl trifluoromethanesulfonate

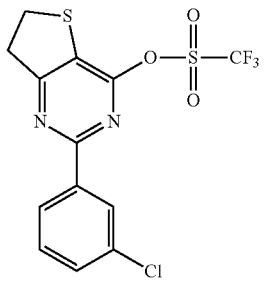 [SMILES: O=S(=O)(Oc1nc(-c2cccc(Cl)c2)nc2c1SCC2)C(F)(F)F]

To a suspension of 2-(3-chlorophenyl)-6,7-dihydrothieno[3,2-d]pyrimidin-4-ol (1.9 g, 7.2 mmol) in methylene chloride (50 mL) at 0° C. was added N,N-dimethylaminopyridine (0.020 g, cat.), triethylamine (2.0 mL, 14.4 mmol) and trifluoromethanesulfonic acid (1.3 mL, 7.9 mmol). The suspension was warmed to rt and stirred for 3 h. The mixture was cooled to 0° C. and the reaction was quenched with a saturated solution of NaHCO$_3$. The organic layer was washed a saturated solution of NaHCO$_3$ and brine. The organic layers were dried over anhydrous sodium sulfate, filtered, and the filtrate was concentrated. The residue was purified by column chromatography (silica, hexanes/ethyl acetate) to afford the title compound (1.23 g, 44%) as a light yellow solid. MW=396.79. $^1$H NMR (CDCl$_3$, 500 MHz) δ 8.35-8.32 (m, 1H), 8.24-8.20 (m, 1H), 7.48-7.38 (m, 2H), 3.59-3.49 (m, 4H); APCI MS m/z 397 [M+H]$^+$.

EXAMPLE 279

2-(4-((2-(3-Chlorophenyl)-6,7-dihydrothieno[3,2-d]pyrimidin-4-yl)amino)phenyl)ethanol

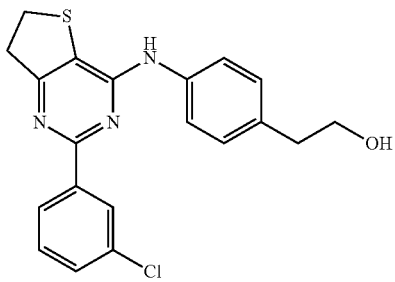 [SMILES: OCCc1ccc(Nc2nc(-c3cccc(Cl)c3)nc3c2SCC3)cc1]

Following general procedure H, 2-(3-chlorophenyl)-6,7-dihydrothieno[3,2-d]pyrimidin-4-yl trifluoromethanesulfonate (0.094 g, 0.24 mmol) was reacted with 2-(4-aminophenyl)ethanol (0.033 g, 0.24 mmol) to afford the title compound (0.062 g, 68%) as a white solid. MW=383.89. $^1$H NMR (DMSO-d$_6$, 500 MHz) δ 8.81 (s, 1H), 8.24-8.15 (m, 2H), 7.60 (d, J=8.5 Hz, 2H), 7.53-7.48 (m, 2H), 7.21 (d, J=8.5 Hz, 2H), 4.63 (t, J=5.5 Hz, 1H), 3.66-3.59 (m, 2H), 3.46-3.40 (m, 2H), 3.35-3.32 (m, 2H), 2.72 (t, J=7.0 Hz, 2H); APCI MS m/z 384 [M+H]$^+$.

EXAMPLE 280

2-(4-((2-(3-chlorophenyl)-6,7-dihydrothieno[3,2-d]pyrimidin-4-yl)amino)phenyl)acetamide

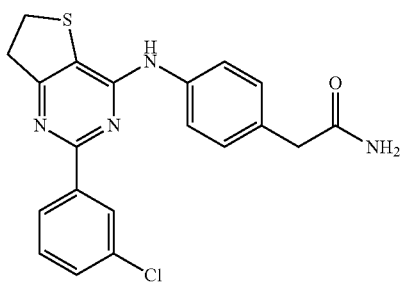 [SMILES: NC(=O)Cc1ccc(Nc2nc(-c3cccc(Cl)c3)nc3c2SCC3)cc1]

Following general procedure H, 2-(3-chlorophenyl)-6,7-dihydrothieno[3,2-d]pyrimidin-4-yl trifluoromethanesulfonate (0.100 g, 0.25 mmol) was reacted with 2-(4-aminophenyl)acetamide (0.038 g, 0.25 mmol) to afford the title compound (0.057 g, 57%) as a white solid. MW=396.89. $^1$H NMR (DMSO-d$_6$, 500 MHz) δ 8.85 (s, 1H), 8.25-8.17 (m, 2H), 7.63 (d, J=8.5 Hz, 2H), 7.53-7.49 (m, 2H), 7.44 (s, 1H), 7.25 (d, J=8.5 Hz, 2H), 6.86 (s, 1H), 3.47-3.40 (m, 2H), 3.38-3.32 (m, 4H); APCI MS m/z 397 [M+H]$^+$.

EXAMPLE 281

2-(3-Chlorophenyl)-4-((4-(2-hydroxyethyl)phenyl)amino)-6,7-dihydrothieno[3,2-d]pyrimidine 5,5-dioxide

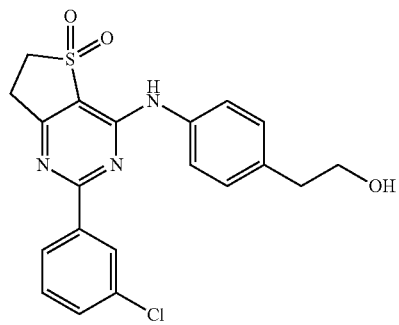 [SMILES: O=S1(=O)CCc2nc(-c3cccc(Cl)c3)nc(Nc3ccc(CCO)cc3)c21]

Step 1. Preparation of 2-(3-chlorophenyl)-5,5-dioxido-6,7-dihydrothieno[3,2-d]pyrimidin-4-yl trifluoromethanesulfonate

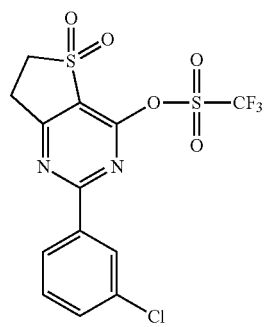 [SMILES: O=S1(=O)CCc2nc(-c3cccc(Cl)c3)nc(OS(=O)(=O)C(F)(F)F)c21]

To a solution of 2-(3-chlorophenyl)-6,7-dihydrothieno[3,2-d]pyrimidin-4-yl trifluoromethanesulfonate (1.0 g, 2.52 mmol) in methylene chloride (25 mL) was added MCBPA (77%, 1.69 g, 7.56 mmol). The reaction stirred at rt for 16 h. The mixture was diluted with methylene chloride and washed with water, a saturated solution of $Na_2S_2O_3$, a saturated solution of $NaHCO_3$, and brine. The organic layers were dried over anhydrous sodium sulfate, filtered, and the filtrate was concentrated to afford the title compound (1.0 g, 92%) as a white solid. MW=428.79. $^1$H NMR (CDCl$_3$, 500 MHz) δ 8.44 (s, 1H), 8.36-8.32 (m, 1H), 7.62-7.55 (m, 1H), 7.51-7.45 (m, 1H), 3.75-3.61 (m, 4H); APCI MS m/z 429 [M+H]$^+$.

EXAMPLE 281

2-(3-Chlorophenyl)-4-((4-(2-hydroxyethyl)phenyl)amino)-6,7-dihydrothieno[3,2-d]pyrimidine 5,5-dioxide

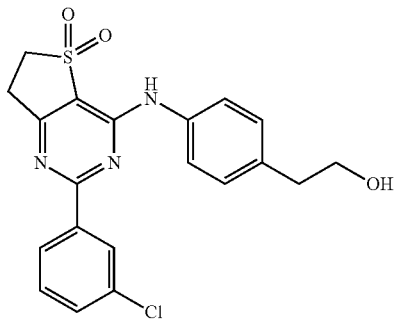 [SMILES: O=S1(=O)CCc2nc(-c3cccc(Cl)c3)nc(Nc3ccc(CCO)cc3)c21]

Following general procedure H, 2-(3-chlorophenyl)-5,5-dioxido-6,7-dihydrothieno[3,2-d]pyrimidin-4-yl trifluoromethanesulfonate (0.095 g, 0.22 mmol) was reacted with 2-(4-aminophenyl)ethanol (0.036 g, 0.26 mmol) to afford the title compound (0.060 g, 65%) as a white solid. MW=415.89. $^1$H NMR (DMSO-d$_6$, 500 MHz) δ 9.51 (s, 1H), 8.24-8.17 (m, 2H), 7.64-7.60 (m, 1H), 7.58-7.53 (m, 3H), 7.27 (d, J=8.5 Hz, 2H), 4.65 (t, J=5.5 Hz, 1H), 3.72 (t, J=7.0 Hz, 2H), 3.67-3.62 (m, 2H), 3.44-3.38 (m, 2H), 2.76 (t, J=7.0 Hz, 2H); APCI MS m/z 416 [M+H]$^+$.

EXAMPLE 282

2-(4-((2-(3-chlorophenyl)-5,5-dioxido-6,7-dihydrothieno[3,2-d]pyrimidin-4-yl)amino)phenyl)acetamide

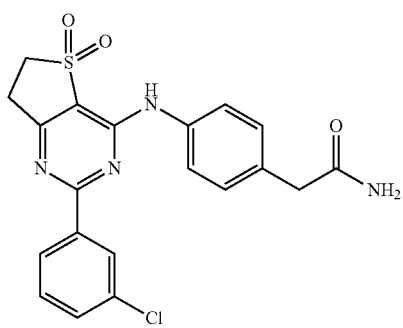 [SMILES: NC(=O)Cc1ccc(Nc2nc(-c3cccc(Cl)c3)nc3c2S(=O)(=O)CC3)cc1]

Following general procedure H, 2-(3-chlorophenyl)-5,5-dioxido-6,7-dihydrothieno[3,2-d]pyrimidin-4-yl trifluoromethanesulfonate (0.100 g, 0.23 mmol) was reacted with 2-(4-aminophenyl)acetamide (0.042 g, 0.28 mmol) to afford the title compound (0.070 g, 70%) as a white solid. MW=428.89. $^1$H NMR (DMSO-d$_6$, 500 MHz) δ 9.55 (s, 1H), 8.24-8.18 (m, 2H), 7.65-7.52 (m, 4H), 7.48 (s, 1H), 7.30 (d, J=8.0 Hz, 2H), 6.89 (s, 1H), 3.72 (t, J=7.0 Hz, 2H), 3.46-3.39 (m, 4H); APCI MS m/z 429 [M+H]$^+$.

EXAMPLE 283

2-(4-((2-Cyclopentyl-7,8-dihydro-6H-thiopyrano[3,2-d]pyrimidin-4-yl)amino)phenyl)ethanol

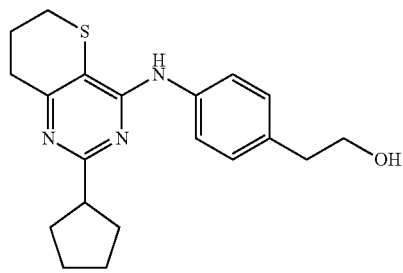 [SMILES: OCCc1ccc(Nc2nc(C3CCCC3)nc3c2SCCC3)cc1]

Step 1. Preparation of 2-cyclopentyl-7,8-dihydro-6H-thiopyrano[3,2-d]pyrimidin-4-ol

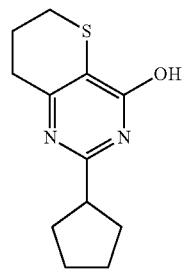 [SMILES: Oc1nc(C2CCCC2)nc2c1SCCC2]

To a solution of cyclopentanecarboximidamide (3.2 g, 28.0 mmol) in ethanol (150 mL) was added methyl 3-oxotetrahydro-2H-thiopyran-2-carboxylate (4.95 g, 28.0 mmol) and sodium methoxide (1.5 g, 28.0 mmol). The mixture was stirred at 85° C. for 16 h. The ethanol was removed under vacuum and the residue was diluted with water and extracted with methylene chloride. The organic layers were dried over anhydrous sodium sulfate, filtered and the filtrate was concentrated. The residue was diluted with hexanes and the solid was filtered to afford the title compound (2.9 g, 44%) as a white solid. MW=236.33. $^1$H NMR (CDCl$_3$, 500 MHz) δ 11.41 (s, 1H), 3.13-2.99 (m, 1H), 2.99-2.94 (m, 2H), 2.81-2.70 (m, 2H), 2.21-2.14 (m, 2H), 2.14-2.04 (m, 2H), 1.92-1.79 (m, 4H), 1.73-1.64 (m, 2H); APCI MS m/z 237 [M+H]$^+$.

Step 2. Preparation of 2-cyclopentyl-7,8-dihydro-6H-thiopyrano[3,2-d]pyrimidin-4-yl trifluoromethanesulfonate

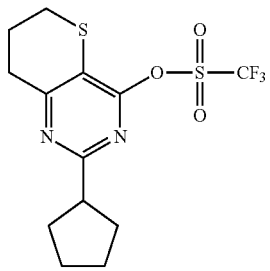 [SMILES: O=S(=O)(Oc1nc(C2CCCC2)nc2c1SCCC2)C(F)(F)F]

To a suspension of 2-cyclopentyl-7,8-dihydro-6H-thiopyrano[3,2-d]pyrimidin-4-ol (2.9 g, 12.3 mmol) in methylene chloride (100 mL) at 0° C. was added N,N-dimethylaminopyridine (0.020 g, cat.), triethylamine (3.5 mL, 24.6 mmol) and trifluoromethanesulfonic acid (2.3 mL, 13.5 mmol). The suspension was warmed to rt and stirred for 3 h. The mixture was cooled to 0° C. and the reaction was quenched with a saturated solution of NaHCO$_3$. The organic layer was washed a saturated solution of NaHCO$_3$ and brine. The organic layers were dried over anhydrous sodium sulfate, filtered, and the filtrate was concentrated. The residue was purified by column chromatography (silica, hexanes/ethyl acetate) to afford the title compound (3.40 g, 75%) as a yellow solid. MW=368.40. $^1$H NMR (CDCl$_3$, 500 MHz) δ 3.28-3.20 (m, 1H), 3.10-3.05 (m, 1H), 2.98 (t, J=6.5 Hz, 2H), 2.31-2.24 (m, 2H), 2.09-1.99 (m, 2H), 1.89-1.76 (m, 4H), 1.70-1.62 (m, 2H); APCI MS m/z 369 [M+H]$^+$.

EXAMPLE 283

2-(4-((2-Cyclopentyl-7,8-dihydro-6H-thiopyrano[3,2-d]pyrimidin-4-yl)amino)phenyl)ethanol

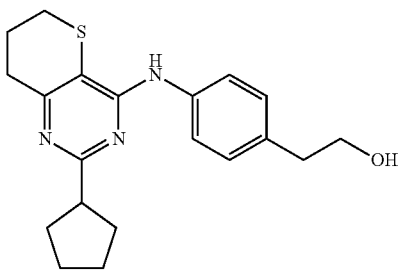 [SMILES: OCCc1ccc(Nc2nc(C3CCCC3)nc3c2SCCC3)cc1]

Following general procedure H, 2-cyclopentyl-7,8-dihydro-6H-thiopyrano[3,2-d]pyrimidin-4-yl trifluoromethanesulfonate (0.200 g, 0.54 mmol) was reacted with 2-(4-aminophenyl)ethanol (0.088 g, 0.65 mmol) to afford the desired product (0.081 g, 42%) as a white solid. MW=355.50. $^1$H NMR (DMSO-d$_6$, 500 MHz) δ 7.81 (s, 1H), 7.57 (d, J=8.5 Hz, 2H), 7.12 (d, J=8.5 Hz, 2H), 4.59 (t, J=5.5 Hz, 1H), 3.62-3.55 (m, 2H), 3.12-3.07 (m, 2H), 3.00 (quin, J=8.0 Hz, 1H), 2.75 (t, J=6.5 Hz, 2H), 2.68 (t, J=7.0 Hz, 2H), 2.15-2.08 (m, 2H), 1.94-1.86 (m, 2H), 1.81-1.65 (m, 4H), 1.62-1.53 (m, 2H); APCI MS m/z 356 [M+H]$^+$.

EXAMPLE 284

2-(4-((2-cyclopentyl-7,8-dihydro-6H-thiopyrano[3,2-d]pyrimidin-4-yl)amino)phenyl)acetamide

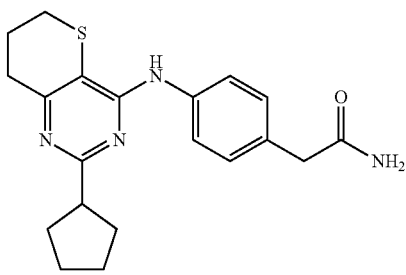 [SMILES: NC(=O)Cc1ccc(Nc2nc(C3CCCC3)nc3c2SCCC3)cc1]

Following general procedure H, 2-cyclopentyl-7,8-dihydro-6H-thiopyrano[3,2-d]pyrimidin-4-yl trifluoromethanesulfonate (0.133 g, 0.36 mmol) was reacted with 2-(4-aminophenyl)acetamide (0.063 g, 0.43 mmol) to afford the title compound (0.072 g, 54%) as an off-white solid. MW=368.50. $^1$H NMR (DMSO-d$_6$, 300 MHz) δ 7.91 (s, 1H), 7.59 (d, J=8.5 Hz, 2H), 7.44 (s, 1H), 7.16 (d, J=8.5 Hz, 2H), 3.31 (s, 2H), 3.13-3.07 (m, 2H), 3.00 (quin, J=8.0 Hz, 1H), 2.75 (t, J=6.5 Hz, 2H), 2.17-2.06 (m, 2H), 1.97-1.48 (m, 8H); APCI MS m/z 369 [M+H]$^+$.

EXAMPLE 285

2-Cyclopentyl-4-((4-(2-hydroxyethyl)phenyl)amino)-7,8-dihydro-6H-thiopyrano[3,2-d]pyrimidine 5,5-dioxide

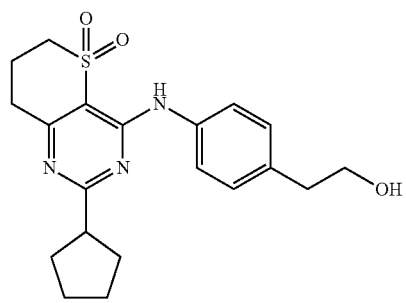 [SMILES: O=S1(=O)CCCc2nc(C3CCCC3)nc(Nc3ccc(CCO)cc3)c21]

Step 1. Preparation of 2-cyclopentyl-5,5-dioxido-7,8-dihydro-6H-thiopyrano[3,2-d]pyrimidin-4-yl trifluoromethanesulfonate

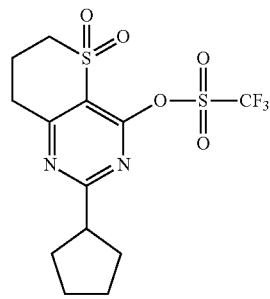 [SMILES: O=S1(=O)CCCc2nc(C3CCCC3)nc(OS(=O)(=O)C(F)(F)F)c21]

To a solution of 2-cyclopentyl-7,8-dihydro-6H-thiopyrano[3,2-d]pyrimidin-4-yl trifluoromethanesulfonate (2.9 g, 7.88 mmol) in methylene chloride (100 mL) was added MCBPA (77%, 5.3 g, 23.6 mmol). The reaction stirred at rt for 16 h. The mixture was diluted with methylene chloride and washed with water, a saturated solution of Na$_2$S$_2$O$_3$, a saturated solution of NaHCO$_3$, and brine. The organic layers were dried over anhydrous sodium sulfate, filtered, and the filtrate was concentrated to afford crude product (1.9 g) as a light brown gum. Crude product was contaminated with the hydrolyzed material (2-cyclopentyl-4-hydroxy-7,8-dihydro-6H-thiopyrano[3,2-d]pyrimidine 5,5-dioxide). MW=400.39. APCI MS m/z 401 [M+H]$^+$.

EXAMPLE 285

2-Cyclopentyl-4-((4-(2-hydroxyethyl)phenyl)amino)-7,8-dihydro-6H-thiopyrano[3,2-d]pyrimidine 5,5-dioxide

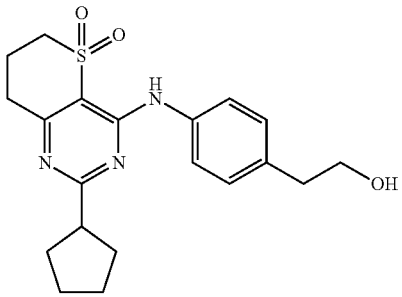 [SMILES: O=S1(=O)CCCc2nc(C3CCCC3)nc(Nc3ccc(CCO)cc3)c21]

Following general procedure H, 2-cyclopentyl-5,5-dioxido-7,8-dihydro-6H-thiopyrano[3,2-d]pyrimidin-4-yl trifluoromethanesulfonate (0.200 g, crude) was reacted with 2-(4-aminophenyl)ethanol (0.034 g, 0.25 mmol) to afford the title compound (0.040 g, 20%) as a white solid. MW=387.50. $^1$H NMR (DMSO-d$_6$, 500 MHz) δ 8.57 (s, 1H), 7.52 (d, J=8.5 Hz, 2H), 7.21 (d, J=8.5 Hz, 2H), 4.62 (t, J=5.5 Hz, 1H), 3.70-3.65 (m, 2H), 3.63-3.57 (m, 2H), 3.09 (quin, J=8.0 Hz, 1H), 2.93 (t, J=6.5 Hz, 2H), 2.71 (t, J=7.0 Hz, 2H), 2.37-2.29 (m, 2H), 1.99-1.90 (m, 2H), 1.83-1.54 (m, 6H); APCI MS m/z 388 [M+H]$^+$.

EXAMPLE 286

2-(4-((2-cyclopentyl-5,5-dioxido-7,8-dihydro-6H-thiopyrano[3,2-d]pyrimidin-4-yl)amino)phenyl)acetamide

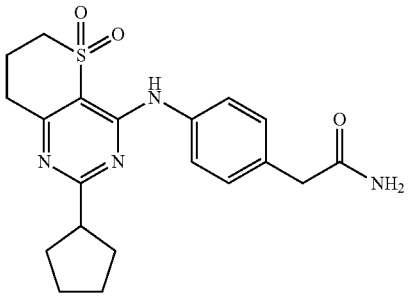 [SMILES: NC(=O)Cc1ccc(Nc2nc(C3CCCC3)nc3c2S(=O)(=O)CCC3)cc1]

Following general procedure H, 2-cyclopentyl-5,5-dioxido-7,8-dihydro-6H-thiopyrano[3,2-d]pyrimidin-4-yl trifluoromethanesulfonate (0.200 g, crude) was reacted with 2-(4-aminophenyl)acetamide (0.038 g, 0.25 mmol) to afford the title compound (0.055 g, 27%) as a white solid. MW=400.49. $^1$H NMR (DMSO-d$_6$, 500 MHz) δ 8.60 (s, 1H), 7.55 (d, J=8.5 Hz, 2H), 7.44 (s, 1H), 7.25 (d, J=8.5 Hz, 2H), 6.87 (s, 1H), 3.71-3.64 (m, 2H), 3.36 (s, 2H), 3.10 (quin, J=8.0 Hz, 1H), 2.94 (t, J=6.5 Hz, 2H), 2.38-2.29 (m, 2H), 1.99-1.91 (m, 2H), 1.84-1.55 (m, 6H); APCI MS m/z 401 [M+H]$^+$.

EXAMPLE 287

2-Cyclopentyl-4-((4-(3-hydroxypropyl)phenyl)amino)-7,8-dihydro-6H-thiopyrano[3,2-d]pyrimidine 5,5-dioxide

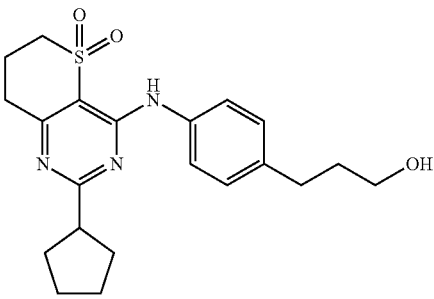 [SMILES: O=S1(=O)CCCc2nc(C3CCCC3)nc(Nc3ccc(CCCO)cc3)c21]

Following general procedure H, 2-cyclopentyl-5,5-dioxido-7,8-dihydro-6H-thiopyrano[3,2-d]pyrimidin-4-yl trifluoromethanesulfonate (0.215 g, crude) was reacted with 3-(4-aminophenyl)propan-1-ol (0.040 g, 0.26 mmol) to afford the title compound (0.018 g, 17%) as a white solid. MW=401.52. $^1$H NMR (DMSO-d$_6$, 500 MHz) δ 8.56 (s, 1H), 7.51 (d, J=8.5 Hz, 2H), 7.19 (d, J=8.5 Hz, 2H), 4.44 (t, J=5.5 Hz, 1H), 3.70-3.65 (m, 2H), 3.45-3.38 (m, 2H), 3.09 (quin, J=8.0 Hz, 1H), 2.93 (t, J=6.5 Hz, 2H), 2.63-2.57 (m, 2H), 2.36-2.28 (m, 2H), 1.99-1.90 (m, 2H), 1.83-1.55 (m, 8H); APCI MS m/z 402 [M+H]$^+$.

EXAMPLE 288

2-Cyclopentyl-4-(4-(2-hydroxyethyl)benzyl)-7,8-dihydro-6H-thiopyrano[3,2-d]pyrimidine 5,5-dioxide

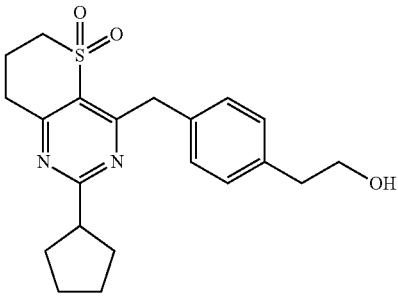 [SMILES: O=S1(=O)CCCc2nc(C3CCCC3)nc(Cc3ccc(CCO)cc3)c21]

Step 1. Preparation of 4-chloro-2-cyclopentyl-7,8-dihydro-6H-thiopyrano[3,2-d]pyrimidine 5,5-dioxide

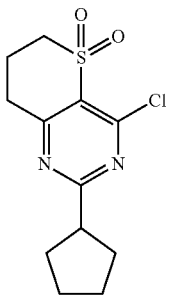 [SMILES: O=S1(=O)CCCc2nc(C3CCCC3)nc(Cl)c21]

To mixture of 2-cyclopentyl-4-hydroxy-7,8-dihydro-6H-thiopyrano[3,2-d]pyrimidine 5,5-dioxide (0.650 g, 2.42 mmol) in dichloroethane (10 mL) was added phosphorous trichloride (1.35 mL, 14.5 mmol). The mixture was stirred at 65° C. for 24 h. The reaction was quenched into a mixture of methlyene chloride and a saturated solution of NaHCO$_3$ and extracted with methylene chloride. The organic layers were dried over anhydrous sodium sulfate, filtered, and the filtrate was concentrated. The residue was purified by column chromatography (silica, hexanes/ethyl acetate) to afford the title compound (0.150 g, 22%) as a tan solid. MW=286.78. $^1$H NMR (CDCl$_3$, 500 MHz) δ 3.49-3.42 (m, 2H), 3.31 (p, J=8.0 Hz, 1H), 3.11 (t, J=6.2 Hz, 2H), 2.53-2.45 (m, 2H), 2.13-2.04 (m, 2H), 1.94-1.78 (m, 4H), 1.75-1.65 (m, 2H); APCI MS m/z 287 [M+H]$^+$.

Step 2. Preparation of methyl 2-(4-((2-cyclopentyl-5,5-dioxido-7,8-dihydro-6H-thiopyrano[3,2-d]pyrimidin-4-yl)methyl)phenyl)acetate

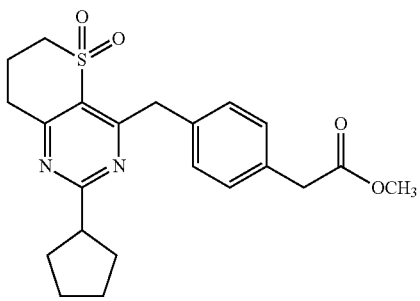 [SMILES: COC(=O)Cc1ccc(Cc2nc(C3CCCC3)nc3c2S(=O)(=O)CCC3)cc1]

Following general procedure H, 4-chloro-2-cyclopentyl-7,8-dihydro-6H-thiopyrano[3,2-d]pyrimidine 5,5-dioxide (0.150 g, 0.52 mmol) was reacted with methyl 2-(4-((4,4,5,5-tetramethyl-1,3,2-dioxaborolan-2-yl)methyl)phenyl)acetate (0.152 g, 0.52 mmol) to afford the title compound (0.099 g, 46%) as a light yellow oil. MW=414.52. $^1$H NMR (CDCl$_3$, 500 MHz) δ 7.45 (d, J=8.0 Hz, 2H), 7.20 (d, J=8.0 Hz, 2H), 4.50 (s, 2H), 3.67 (s, 3H), 3.58 (s, 2H), 3.44-3.40 (m, 2H), 3.27 (quin, J=8.0 Hz, 1H), 3.06 (t, J=6.2 Hz, 2H), 2.48-2.42 (m, 2H), 2.04-1.97 (m, 2H), 1.88-1.73 (m, 4H), 1.70-1.62 (m, 2H); APCI MS m/z 415 [M+H]$^+$.

EXAMPLE 288

2-Cyclopentyl-4-(4-(2-hydroxyethyl)benzyl)-7,8-dihydro-6H-thiopyrano[3,2-d]pyrimidine 5,5-dioxide

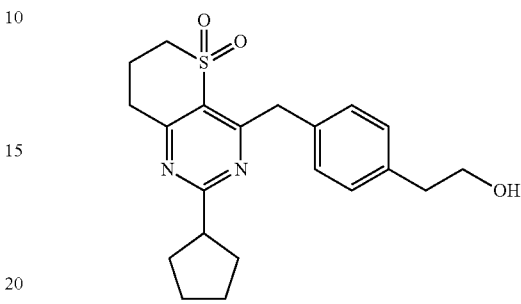

Following general procedure E1, methyl 2-(4-((2-cyclopentyl-5,5-dioxido-7,8-dihydro-6H-thiopyrano[3,2-d]pyrimidin-4-yl)methyl)phenyl)acetate (0.060 g, 0.14 mmol) was reacted with DIBAL (1.0 M, 0.58 mL, 0.58 mmol) to afford the title compound (0.040 g, 71%) as a white solid. MW=386.51. $^1$H NMR (DMSO-d$_6$, 500 MHz) δ 7.26 (d, J=8.5 Hz, 2H), 7.11 (d, J=8.5 Hz, 2H), 4.58 (t, J=5.5 Hz, 1H), 4.38 (s, 2H), 3.69-3.62 (m, 2H), 3.59-3.52 (m, 2H), 3.23 (quin, J=8.0 Hz, 1H), 3.06 (t, J=6.5 Hz, 2H), 2.66 (t, J=7.0 Hz, 2H), 2.33-2.25 (m, 2H), 2.00-1.91 (m, 2H), 1.81-1.56 (m, 6H); APCI MS m/z 387 [M+H]$^+$.

EXAMPLE 289

2-(3-Chlorophenyl)-4-(4-methylbenzyl)-6,7-dihydro-5H-cyclopenta[b]pyridine hydrochloride

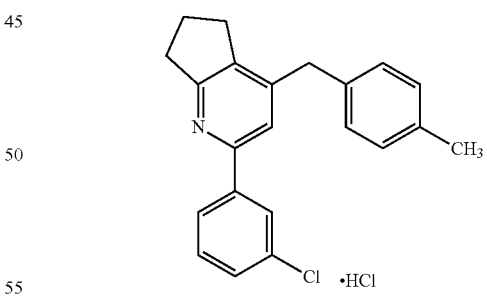

A 20-mL vial, with stirrer bar, was charged with 4-chloro-2-(3-chlorophenyl)-6,7-dihydro-5H-cyclopenta[b]pyridine (0.200 g, 1.20 mmol), Pd(dppf)Cl$_2$ (0.062 g, 0.076 mmol) and THF (4.0 mL) at rt under nitrogen. A solution of 4-methylbenzylzinc chloride (2.3 mL, 0.5M in THF, 1.14 mmol) was added. The reaction mixture was placed under argon and stirred at 80° C. for 23 h. until the starting chloride was consumed. The cooled reaction was absorbed onto silica and purified by chromatography on silica gel using hexanes/ethyl acetate as the eluent followed by chromatography on silica gel using hexanes/dichloromethane as the eluent, to afford the free base of the title compound (0.104 g, 41% yield) as an oil. MW=333.85. ¹H NMR (CDCl₃, 500 MHz) δ 7.93-7.91 (m, 1H), 7.76 (dt, J=7.0, 1.5 Hz, 1H), 7.36-7.30 (m, 2H), 7.24 (s, 1H), 7.11 (d, J=8.0 Hz, 2H), 7.06 (d, J=8.0 Hz, 2H), 3.91 (s, 2H), 3.07 (t, J=7.5 Hz, 2H), 2.87 (t, J=7.5 Hz, 2H), 2.33 (s, 3H), 2.13 (quin, J=7.5 Hz, 2H). Treatment with 1.25M HCl in methanol (0.38 mL, 0.47 mmol) afforded 2-(3-chlorophenyl)-4-(4-methylbenzyl)-6,7-dihydro-5H-cyclopenta[b]pyridine hydrochloride (0.108 g, 38%) as a white solid. MW=370.31. M.p. 44-46° C. ¹H NMR (DMSO-d₆, 500 MHz) δ 8.10-8.07 (m, 1H), 7.98-7.93 (m, 1H), 7.81 (s, 1H), 7.57-7.50 (m, 2H), 7.17 (d, J=8.0 Hz, 2H), 7.11 (d, J=8.0 Hz, 2H), 4.60 (br s, 1H), 4.01 (s, 2H), 3.04 (t, J=7.5 Hz, 2H), 2.87 (t, J=7.5 Hz, 2H), 2.25 (s, 3H), 2.09 (quin, J=7.5 Hz, 2H); ESI MS m/z 334 [M+H]⁺.

EXAMPLE 290

2-(3-Chlorophenyl)-N-(4-fluorophenyl)-6,7-dihydro-5H-cyclopenta[b]pyridin-4-amine hydrochloride

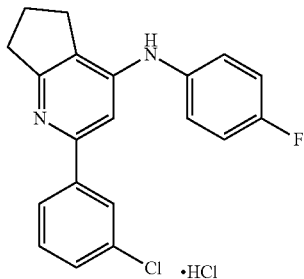 [SMILES: Fc1ccc(Nc2cc(-c3cccc(Cl)c3)nc3c2CCC3)cc1 ; Cl]

A 10-mL microwave vial was charged with 4-chloro-2-(3-chlorophenyl)-6,7-dihydro-5H-cyclopenta[b]pyridine (0.072 g, 0.27 mmol), 4-fluoroaniline (0.052 mL, 0.54 mmol) and conc. HCl (1 drop) in NMP (2 mL). The resulting mixture was heated at 120° C. under microwave irradiation for 3 h. After this time, the reaction mixture was cooled, diluted with water (25 mL) then treated with saturated sodium bicarbonate until pH~8 and extracted with ethyl acetate. The combined extract was washed with saturated sodium chloride, dried over sodium sulfate, filtered, and concentrated under reduced pressure. The residue was purified by chromatography on silica using hexanes/ethyl acetate (10:0 to 1:1) as the eluent to afford the free base of the title compound (0.064 g, 70%) as an oil. MW=338.81. ¹H NMR (DMSO-d₆, 500 MHz) δ 8.14 (s, 1H), 7.93-7.90 (m, 1H), 7.76 (dt, J=7.0, 2.0 Hz, 1H), 7.45-7.39 (m, 2H), 7.31-7.26 (m, 2H), 7.24-7.18 (m, 2H), 7.13 (s, 1H), 2.91 (t, J=7.5 Hz, 2H), 2.82 (t, J=7.5 Hz, 2H), 2.09 (quin, J=7.5 Hz, 2H). Treatment with 1.25M HCl in methanol (0.15 mL, 0.19 mmol, 1.0 eq.) afforded the title compound (0.064 g, 91%) as a white solid. MW=375.27. M.p. 103-106° C. ¹H NMR (DMSO-d₆, 500 MHz) δ 13.99 (br s, 1H), 9.05 (br s, 1H), 7.92-7.89 (m, 1H), 7.75-7.70 (m, 1H), 7.57-7.49 (m, 2H), 7.41-7.35 (m, 2H), 7.31-7.25 (m, 2H), 7.04 (s, 1H), 3.04 (t, J=7.5 Hz, 2H), 2.87 (t, J=7.5 Hz, 2H), 2.17 (quin, J=7.5 Hz, 2H); ESI MS m/z 339 [M+H]⁺.

EXAMPLE 291

2-(4-((3-Chloro-2-(3-chlorophenyl)-6,7-dihydro-5H-cyclopenta[b]pyridin-4-yl)amino)phenyl)acetonitrile hydrochloride

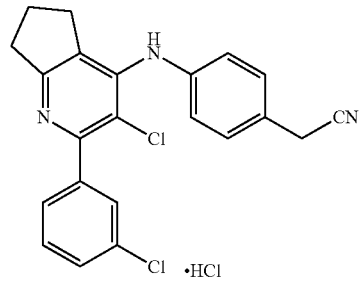 [SMILES: N#CCc1ccc(Nc2c(Cl)c(-c3cccc(Cl)c3)nc3c2CCC3)cc1 ; Cl]

Step 1. Preparation of 2-(3-chlorophenyl)-N-(diphenylmethylene)-6,7-dihydro-5H-cyclopenta[b]pyridin-4-amine

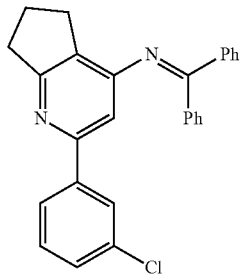 [SMILES: Clc1cccc(-c2cc(N=C(c3ccccc3)c3ccccc3)c3c(n2)CCC3)c1]

A 20-mL vial, with stirrer bar, was charged with 4-chloro-2-(3-chlorophenyl)-6,7-dihydro-5H-cyclopenta[b]pyridine hydrochloride (1.00 g, 3.33 mmol), benzophenone imine (0.56 mL, 3.66 mmol), Pd(dba)₂ (0.057 g, 0.10 mmol, 0.03 eq.), 1,3-bis(2,6-di-iso-propylphenyl)imidazolium chloride (0.042 g, 0.10 mmol) and potassium tert-butoxide (0.93 g, 8.32 mmol) in dioxane (12 mL) at rt. The reaction mixture was placed under argon and stirred at 100° C. for 24 h. The cooled reaction was diluted with ethyl acetate (150 mL) and washed with saturated sodium chloride (2×25 mL). The organic layer was dried over sodium sulfate, filtered, and concentrated under reduced pressure. The residue was purified by chromatography on silica gel using hexanes/ethyl acetate (10:0 to 8:2) as the eluent to afford the title compound (0.47 g, 34%) as a yellow solid. MW=408.92. ¹H NMR (CDCl₃, 500 MHz) δ 7.85-7.70 (m, 3H), 7.69-7.63 (m, 1H), 7.56-7.39 (m, 3H), 7.36-7.26 (m, 5H), 7.22-7.10 (m, 2H), 6.81 (s, 1H), 2.97 (t, J=7.5 Hz, 2H), 2.62 (t, J=7.5 Hz, 2H), 2.07-1.98 (m, 2H); ESI MS m/z 409 [M+H]⁺.

Step 2. Preparation of 2-(3-chlorophenyl)-6,7-dihydro-5H-cyclopenta[b]pyridin-4-amine

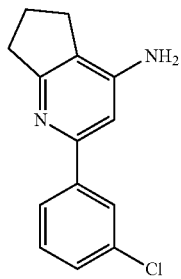 [SMILES: Nc1cc(-c2cccc(Cl)c2)nc2c1CCC2]

A 250-mL round bottom flask was charged with 2-(3-chlorophenyl)-N-(diphenylmethylene)-6,7-dihydro-5H-cyclopenta[b]pyridin-4-amine (0.47 g, 1.15 mmol) and 2N aqueous HCl (12 mL, 24 mmol) in THF (50 mL). After 18 h at rt, the resultant solution was concentrated under reduced pressure. The solid residue was washed with 2N aqueous HCl (10 mL) then diethyl ether. The solid and aqueous layers were combined diluted with ethyl acetate then treated with 2N aqueous NaOH. The aqueous layer was extracted with ethyl acetate. The combined ethyl acetate extract was washed with saturated sodium chloride (5 mL), dried over sodium sulfate, filtered and concentrated under reduced pressure to afford the title compound (0.25 g, 89%) as a white solid. MW=244.72. $^1$H NMR (DMSO-$d_6$, 500 MHz) δ 7.92 (t, J=7.0 Hz, 1H), 7.81 (dt, J=7.5, 1.5 Hz, 1H), 7.44 (t, J=8.0 Hz, 1H), 7.41-7.38 (m, 1H), 6.86 (s, 1H), 5.86 (s, 2H), 2.82 (t, J=7.5 Hz, 2H), 2.68 (t, J=7.5 Hz, 2H), 2.02 (quin, J=7.5 Hz, 2H).

Step 3. Preparation of 3-chloro-2-(3-chlorophenyl)-6,7-dihydro-5H-cyclopenta[b]pyridin-4-amine

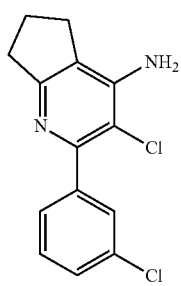 [SMILES: Nc1c(Cl)c(-c2cccc(Cl)c2)nc2c1CCC2]

A 25-mL round bottom flask was charged with 2-(3-chlorophenyl)-6,7-dihydro-5H-cyclopenta[b]pyridin-4-amine (0.250 g, 1.02 mmol) in DMF (6 mL). N-Chlorosuccinimide (0.136 g, 1.02 mmol) was added at rt and the resultant solution was stirred for 3 h. Further N-chlorosuccinimde (0.036 g, 0.27 mmol) was added and the reaction was stirred for 2 h. The reaction was diluted with water (100 mL) and ethyl acetate (50 mL). The layers were separated and the aqueous layer extracted with ethyl acetate (2×25 mL). The combined extract acetate extract was washed with saturated sodium chloride (2×10 mL), dried over sodium sulfate, filtered and concentrated under reduced pressure. The residue was purified by chromatography on silica gel using hexanes/ethyl acetate (10:0 to 9:1) as the eluent to afford the title compound (0.110 g, 38%) as a white solid. MW=279.16. $^1$H NMR (CD$_3$, 500 MHz) δ 7.62-7.59 (m, 1H), 7.52-7.48 (m, 1H), 7.37-7.32 (m, 2H), 4.54 (s, 2H), 2.99 (t, J=7.5 Hz, 2H), 2.80 (t, J=7.5 Hz, 2H), 2.21 (quin, J=7.5 Hz, 2H); ESI MS m/z 279 [M+H]$^+$.

EXAMPLE 291

2-(4-((3-Chloro-2-(3-chlorophenyl)-6,7-dihydro-5H-cyclopenta[b]pyridin-4-yl)amino)phenyl)acetonitrile hydrochloride

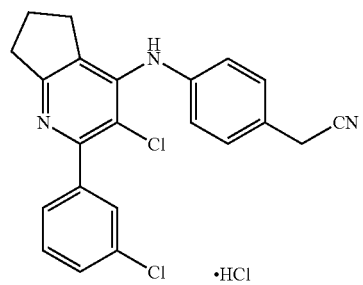 [SMILES: N#CCc1ccc(Nc2c(Cl)c(-c3cccc(Cl)c3)nc3c2CCC3)cc1 ; Cl]

A 20-mL vial, with stirrer bar, was charged with 3-chloro-2-(3-chlorophenyl)-6,7-dihydro-5H-cyclopenta[b]pyridin-4-amine (0.110 g, 0.39 mmol), (4-bromophenyl)acetonitrile (0.085 g, 0.43 mmol), Pd$_2$(dba)$_3$ (0.011 g, 12 mmol), X-Phos (0.021 g, 0.043 mmol) and potassium phosphate (0.125 g, 0.49 mmol) in toluene (4 mL) at rt. The reaction mixture was placed under argon and stirred at 100° C. for 30 h. After this time, additional (4-bromophenyl)acetonitrile (0.085 g, 0.43 mmol), Pd$_2$(dba)$_3$ (0.011 g, 0.012 mmol) and X-Phos (0.021 g, 43 mmol) in toluene (1 mL) were added. After a further 16 h, an additional solution of (4-bromophenyl)acetonitrile (0.085 g, 0.43 mmol), Pd$_2$(dba)$_3$ (0.011 g, 0.012 mmol) and X-Phos (0.021 g, 43 mmol) in toluene (1 mL) was added and the reaction stirred for 23 h. The cooled reaction was filtered through celite and concentrated under reduced pressure. The residue was purified by chromatography on silica using hexanes/ethyl acetate (10:0 to 0:10) as the eluent followed by chromatography on silica using hexanes/ethyl acetate (10:0 to 1:1) as the eluent to afford the free base of the title compound (0.041 g, 26%) as an oil. MW=394.30. ESI MS m/z 394 [M+H]$^+$. Treatment with 1.25M HCl in methanol (0.12 mL, 0.15 mmol, 1.5 eq.) followed by recrystallization from acetonitrile/water afforded the title compound (0.016 g, 38%) as an off-white solid. MW=430.76. M.p. 206-208° C. $^1$H NMR (DMSO-$d_6$, 500 MHz) δ 8.70 (br s, 1H), 7.67 (s, 1H), 7.65-7.52 (m, 3H), 7.36-7.26 (m, 2H), 7.15-7.01 (m, 2H), 4.04 (s, 2H), 2.89 (t, J=7.5 Hz, 2H), 2.34-2.25 (m, 2H), 1.96 (quin, J=7.5 Hz, 2H); ESI MS m/z 395 [M+H]$^+$.

EXAMPLE 292

[4-[[2-(5-Chloro-2-thienyl)-5-ethyl-6-methyl-pyrimidin-4-yl]amino]phenyl]boronic acid

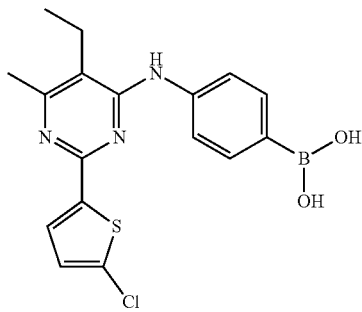 [SMILES: CCc1c(C)nc(-c2ccc(Cl)s2)nc1Nc1ccc(B(O)O)cc1]

Step 1. [2-(5-Chloro-2-thienyl)-5-ethyl-6-methyl-pyrimidin-4-yl]trifluoromethanesulfonate

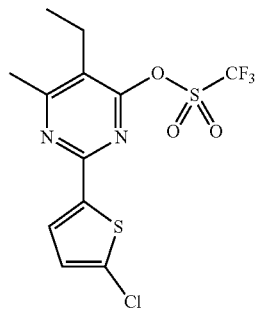 [SMILES: CCc1c(C)nc(-c2ccc(Cl)s2)nc1OS(=O)(=O)C(F)(F)F]

A 18-mL vial was charged with 2-(5-chloro-2-thienyl)-5-ethyl-4-methyl-1H-pyrimidin-6-one (254 mg, 1 mmol, 1 eq., preparation described in EXAMPLE 71) and N,N-diisopropylethylamine (440 mg, 3.4 mmol, 3.4 eq.). Dichloromethane (6 ml, DCM) was added. To the mixture at 0° C. was added a solution of triflic anhydride in dichloromethane (1M, 1.5 ml, 1.5 eq.) dropwise by a syringe. After the addition was complete, the mixture was stirred at 0° C.~rt for 1 hr. The mixture was then poured into NaHCO$_3$ aq. (20 ml). The organic layer was separated and the aqueous layer was extracted with dichloromethane (15 ml). The organics were combined and dried over Na$_2$SO$_4$. The volatile material was removed and the crude material was purified by chromatography on silica gel using hexane/DCM (9:1 then 4:1) as eluent to afford the title compound as white solid (337 mg, 87% yield).

Step 2. 2-(5-Chloro-2-thienyl)-5-ethyl-6-methyl-N-[4-(4,4,5,5-tetramethyl-1,3,2-dioxaborolan-2-yl)phenyl]pyrimidin-4-amine

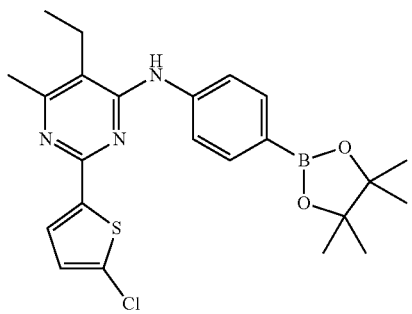

A 18-mL vial was charged with [2-(5-chloro-2-thienyl)-5-ethyl-6-methyl-pyrimidin-4-yl]trifluoromethanesulfonate (39 mg, 0.1 mmole) and 4-(4,4,5,5-tetramethyl-1,3,2-dioxaborolan-2-yl)aniline (22 mg, 0.1 mmol) and DMSO (0.5 ml). The resulting mixture was stirred under Ar for 3.5 hr. After cooling to room temperature, water was added to the mixture (5 ml). The precipitate was collected by filtration and the crude product was purified by chromatography on silica gel using hexane/DCM (4:1) followed by 2% of methanol in DCM as eluent to afford the title compound, containing impurities, which was forward to the next step without any further purification (10.3 mg, 23% yield).

Step 3. [4-[[2-(5-Chloro-2-thienyl)-5-ethyl-6-methyl-pyrimidin-4-yl]amino]phenyl]boronic acid

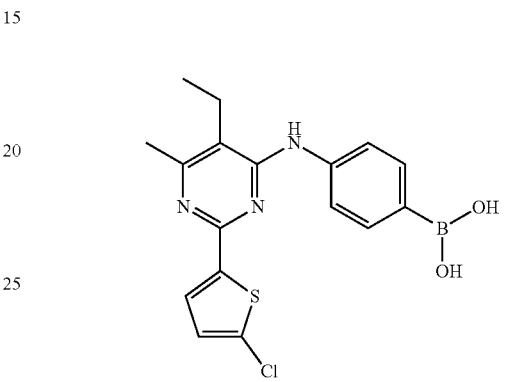

A 18-mL vial was charged with 2-(5-chloro-2-thienyl)-5-ethyl-6-methyl-N-[4-(4,4,5,5-tetramethyl-1,3,2-dioxaborolan-2-yl)phenyl]pyrimidin-4-amine (10.3 mg, 0.023 mmol) and potassium hydrogen difluoride (40 mg, 0.5 mmol). Water (0.2 ml) and MeOH (1 ml) were added respectively. The resulting mixture was stirred at rt for 1 hr. Then the volatile material was removed under reduced pressure. The residue was treated with trimethylsilyl chloride (0.1 ml) in a mixture of acetonitrile (1 ml) and water (0.2 ml). After the mixture was stirred at rt for 1 hr, the volatile material was removed the residue was treated with NaHCO$_3$ aq. (5 ml). The precipitate was collected and purified by Preparative TLC plate using 5% of acetone in DCM as mobile phase to give the title compound (2 mg, 23% yield). MW=373.66. $^1$H NMR (Methanol-d$_4$, 400 MHz) δ 7.87 (d, J=8.4 Hz, 2H), 7.74 (d, J=8.4 Hz, 2H), 7.67 (d, J=4.0 Hz, 1H), 6.93 (d, J=4.0 Hz, 1H), 2.67 (q, J=7.6 Hz, 2H), 2.54 (s, 3H), 1.21 (t, J=7.6 Hz, 3H).

EXAMPLE 293

2-(5-Chloro-2-thienyl)-N-(1-hydroxy-3H-2,1-benzoxaborol-5-yl)-6,7-dihydro-5H-cyclopenta[d]pyrimidin-4-amine

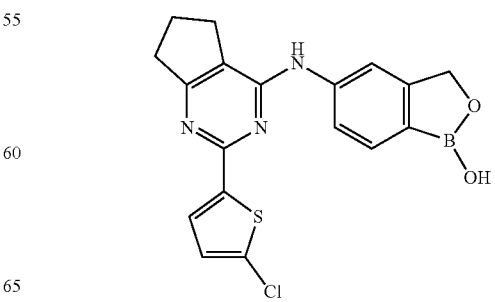

The title compound was prepared in a similar manner to those described herein, with modifications within the skill of one skilled in the art (5 mg, 34% yield). MW=383.66. $^1$H NMR (400 MHz, CDCl$_3$) δ 8.00 (s, 1H), 7.72 (m, 2H), 7.48 (d, J=8.0 Hz, 1H), 6.96 (d, J=4.0 Hz, 1H), 6.40 (br, 1H), 5.18 (s, 2H), 3.03 (t, J=7.2 Hz, 2H), 2.84 (t, J=7.2 Hz, 2H), 2.23 (m, 2H).

EXAMPLE 294

2-(3-Chlorophenyl)-N-(1-hydroxy-3H-2,1-benzoxaborol-5-yl)-6,7-dihydro-5H-cyclopenta[d]pyrimidin-4-amine

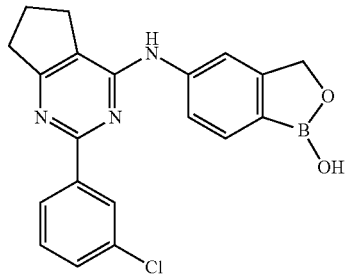 [SMILES: OB1OCc2cc(Nc3nc(-c4cccc(Cl)c4)nc4c3CCC4)ccc21]

The title compound was prepared in a similar manner to those described herein, with modifications within the skill of one skilled in the art (10 mg, 69% yield). MW=377.63. $^1$H NMR (400 MHz, CDCl$_3$) δ 8.43 (s, 1H), 8.31 (d, J=8.4 Hz, 1H), 8.06 (s, 1H), 7.76 (d, J=8.0 Hz, 1H), 7.50 (d, J=8.0 Hz, 1H), 7.43 (m, 2H), 6.46 (br, 1H), 5.18 (s, 2H), 3.09 (t, J=7.2 Hz, 2H), 2.89 (t, J=7.2 Hz, 2H), 2.26 (m, 2H).

EXAMPLE 295

2-(4-Chlorophenyl)-N-(1-hydroxy-3H-2,1-benzoxaborol-5-yl)-6,7-dihydro-5H-cyclopenta[d]pyrimidin-4-amine

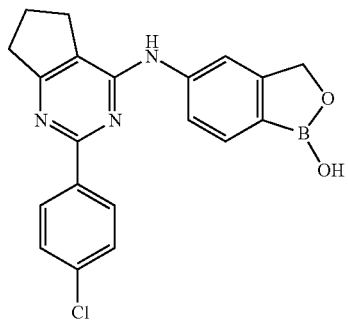 [SMILES: OB1OCc2cc(Nc3nc(-c4ccc(Cl)cc4)nc4c3CCC4)ccc21]

The title compound was prepared in a similar manner to those described herein, with modifications within the skill of one skilled in the art (6 mg, 41% yield). MW=377.63. $^1$H NMR (400 MHz, DMSO-D$_6$) δ 9.01 (brs, 1H), 8.31 (d, J=8.8 Hz, 2H), 7.94 (s, 1H), 7.71 (brs, 2H), 7.56 (d, J=8.8 Hz, 2H), 5.04 (s, 2H), 2.92 (m, 4H), 2.11 (m, 2H).

EXAMPLE 296

2-[4-[[2-(5-Chloro-2-thienyl)-6-(trifluoromethyl)pyrimidin-4-yl]amino]phenyl]acetic acid

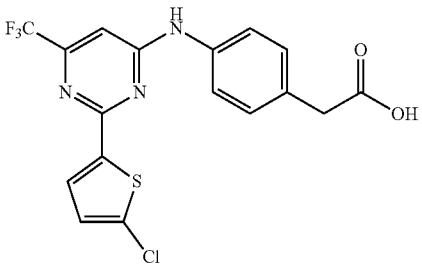 [SMILES: O=C(O)Cc1ccc(Nc2cc(C(F)(F)F)nc(-c3ccc(Cl)s3)n2)cc1]

The title compound was prepared in a similar manner to those described herein, with modifications within the skill of one skilled in the art (1 mg, 3.5% yield). MW=410.80. $^1$H NMR (400 MHz, Methanol-D$_4$) δ 7.81 (d, J=4.0 Hz, 1H), 7.70 (brs, 2H), 7.35 (d, J=8.4 Hz, 2H), 7.07 (d, J=4.0 Hz, 1H), 6.89 (s, 1H), 3.64 (s, 2H).

EXAMPLE 297

2-[4-[[2-(5-Chloro-2-thienyl)-6-cyclopropyl-pyrimidin-4-yl]amino]phenyl]acetic acid

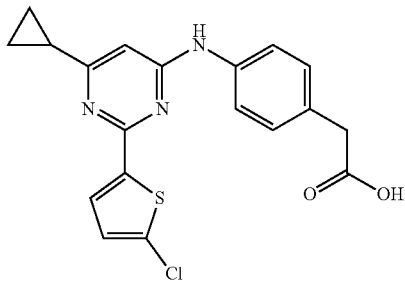 [SMILES: O=C(O)Cc1ccc(Nc2cc(C3CC3)nc(-c3ccc(Cl)s3)n2)cc1]

The title compound was prepared in a similar manner to those described herein, with modifications within the skill of one skilled in the art (9 mg, 14% yield). MW=385.87. $^1$H NMR (400 MHz, DMSO-D$_6$) δ 12.3 (brs, 1H), 9.55 (brs, 1H), 7.65-7.20 (m, 3H), 7.25 (d, J=8.4 Hz, 2H), 7.18 (d, J=4.0 Hz, 1H), 6.54 (s, 1H), 3.53 (s, 2H), 1.98 (m, 1H), 1.01-0.97 (m, 4H).

EXAMPLE 298

2-(5-Chloro-2-thienyl)-6-cyclopropyl-N-[4-(1H-tetrazol-5-ylmethyl)phenyl]pyrimidin-4-amine

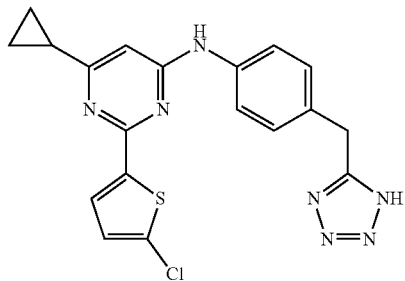 [SMILES: Clc1ccc(-c2nc(Nc3ccc(Cc4nnn[nH]4)cc3)cc(C3CC3)n2)s1]

The title compound was prepared in a similar manner to those described herein, with modifications within the skill of one skilled in the art (16 mg, 84% yield, HCl salt). MW/HCl=446.40. $^1$H NMR (400 MHz, DMSO-D$_6$) δ 9.69 (brs, 1H), 7.66 (m, 3H), 7.27 (d, J=8.8 Hz, 2H), 7.19 (d, J=4.0 Hz, 1H), 4.26 (s, 2H), 2.0 (m, 1H), 1.00 (m, 4H).

EXAMPLE 299

2-(5-Chloro-2-thienyl)-5-ethyl-6-methyl-N-[4-(pyrazol-1-ylmethyl)phenyl]pyrimidin-4-amine

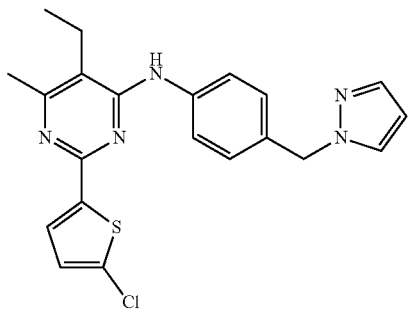 [SMILES: CCc1c(C)nc(-c2ccc(Cl)s2)nc1Nc1ccc(Cn2cccn2)cc1]

The title compound was prepared in a similar manner to those described herein, with modifications within the skill of one skilled in the art (12 mg, 27% yield, HCl salt). MW=446.60. $^1$H NMR (400 MHz, DMSO-D$_6$) δ 7.9 (brs, 1H), 7.68 (d, J=4.0 Hz, 1H), 7.62 (d, J=8.4 Hz, 2H), 7.48 (d, J=4.0 Hz, 1H), 7.27 (m, 3H), 6.29 (m, 1H), 5.35 (s, 2H), 2.72 (q, J=7.2 Hz, 2H), 2.52 (s, 3H), 1.11 (t, J=7.2 Hz, 3H).

EXAMPLE 300

2-(5-Chloro-2-thienyl)-N-[4-(1,3-dihydrotriazol-2-ylmethyl)phenyl]-5-ethyl-6-methyl-pyrimidin-4-amine

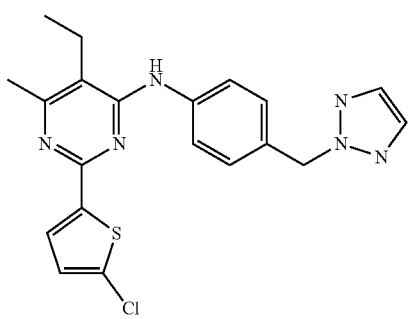 [SMILES: CCc1c(C)nc(-c2ccc(Cl)s2)nc1Nc1ccc(CN2NC=CN2)cc1]

Step 1: 2-[(4-Nitrophenyl)methyl]triazole

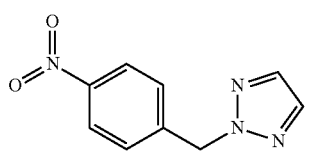 [SMILES: O=[N+]([O-])c1ccc(Cn2nccn2)cc1]

A 18-mL vial was charged with 1-(chloromethyl)-4-nitrobenzene (500 mg, 3 mmol, 1 eq.), triazole (310 mg, 4.5 mmol, 1.5 eq.), potassium carbonate (1.24 g, 9 mmol, 3 eq.) and DMF (5 ml). After the resulting mixture was stirred at rt overnight, water (20 ml) was added. The precipitate was collected by filtration and washed with small amount of water. After drying, 340 mg of the title compound was obtained as a mixture of two regioisomers (340 mg, 55% yield).

Step 2: 4-(Triazol-2-ylmethyl)aniline

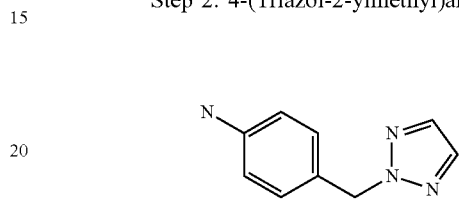

A 25-mL round bottomed flask was charged with 2-[(4-nitrophenyl)methyl]triazole (195 mg, 0.95 mmol, 1 eq.), palladium on carbon (206 mg, 10 wt. % loading, 0.2 eq.) and ethanol (3 ml). The resulting mixture was stirred under H$_2$ over night. The mixture was passed through a plug of celite and washed with methanol (5 ml). Removal of solvent under reduced pressure gave the crude product (160 mg, two regioisomers, 97% yield). The product thus obtained was forwarded to the next step without any further purification.

Step 3: 2-(5-Chloro-2-thienyl)-N-[4-(1,3-dihydrotriazol-2-ylmethyl)phenyl]-5-ethyl-6-methyl-pyrimidin-4-amine

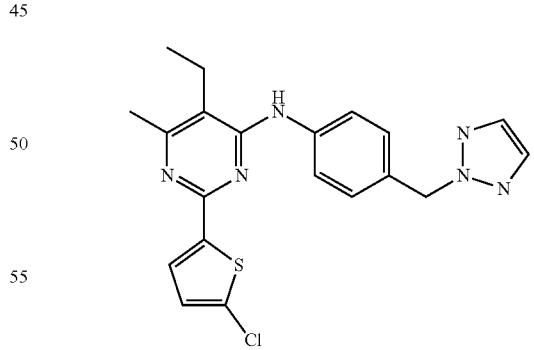

The title compound was prepared in a similar manner to those described herein, with modifications within the skill of one skilled in the art (12 mg, 20% yield, only one isomer was isolated). MW=412.94. $^1$H NMR (400 MHz, CDCl$_3$) δ 7.70-7.61 (m, 5H), 7.38 (d, J=8.8 Hz, 2H), 6.93 (d, J=4.0 Hz, 1H), 6.58 (brs, 1H), 5.63 (s, 2H), 2.62 (q, J=7.6 Hz, 2H), 2.49 (s, 3H), 1.21 (t, J=7.6 Hz, 3H).

EXAMPLE 301

2-[4-[[2-(5-Chloro-2-thienyl)-5-ethyl-6-methyl-pyrimidin-4-yl]amino]phenyl]-N-cyano-acetamide

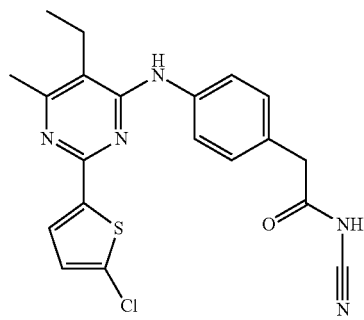 [SMILES: CCc1c(C)nc(-c2ccc(Cl)s2)nc1Nc1ccc(CC(=O)NC#N)cc1]

Step 1: 2-[4-[[2-(5-Chloro-2-thienyl)-5-ethyl-6-methyl-pyrimidin-4-yl]amino]phenyl]acetic acid

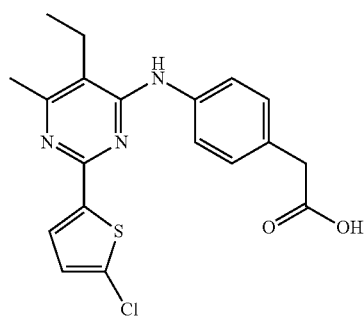 [SMILES: CCc1c(C)nc(-c2ccc(Cl)s2)nc1Nc1ccc(CC(=O)O)cc1]

The title compound was prepared in a similar manner to those described herein, with modifications within the skill of one skilled in the art (271 mg, 37% yield).

Step 2: 2-[4-[[2-(5-Chloro-2-thienyl)-5-ethyl-6-methyl-pyrimidin-4-yl]amino]phenyl]-N-cyano-acetamide

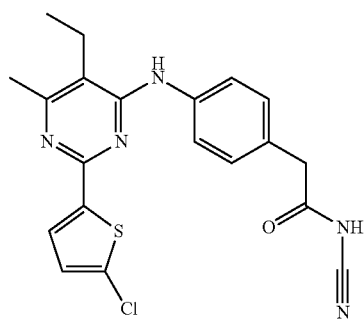 [SMILES: CCc1c(C)nc(-c2ccc(Cl)s2)nc1Nc1ccc(CC(=O)NC#N)cc1]

A 8-mL vial was charged with 2-[4-[[2-(5-chloro-2-thienyl)-5-ethyl-6-methyl-pyrimidin-4-yl]amino]phenyl]acetic acid (30 mg, 0.077 mmol, 1 eq.), cyamide (30 mg, 0.71 mmol, 9 eq.), HATU (44 mg, 0.16 mmol, 1.5 eq.), diisopropylethylamine (35 mg, 0.27 mmol, 3.5 eq.) and DMF (0.5 ml). The resulting mixture was stirred at rt overnight until the starting acid was consumed. The mixture was added to NaHCO$_3$ aq. (5 ml) and extracted with ethyl acetate (5 ml×3). The organic layers were combined and dried over Na$_2$SO$_4$. Removal of solvent gave a residue, which was purified by chromatography on silica gel using 0.5~3% of MeOH in DCM as eluent to give the title compound as a white solid (16 mg, 50% yield). MW=411.91. $^1$H NMR (400 MHz, DMSO-d$_6$) δ 8.54 (brs, 1H), 7.67 (d, J=8.8 Hz, 2H), 7.55 (d, J=4.0 Hz, 1H), 7.24 (d, J=8.8 Hz, 2H), 7.15 (d, J=4.0 Hz, 1H), 5.77 (s, 2H), 2.74 (q, J=7.6 Hz, 2H), 2.40 (s, 3H), 1.20 (t, J=7.6 Hz, 3H).

EXAMPLE 302

3-[[4-[[2-(5-Chloro-2-thienyl)-5-ethyl-6-methyl-pyrimidin-4-yl]amino]phenyl]methyl]-4H-1,2,4-oxadiazol-5-one

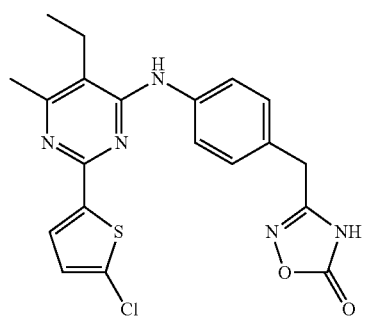 [SMILES: CCc1c(C)nc(-c2ccc(Cl)s2)nc1Nc1ccc(Cc2noc(=O)[nH]2)cc1]

Step 1: 2-[4-[[2-(5-Chloro-2-thienyl)-5-ethyl-6-methyl-pyrimidin-4-yl]amino]phenyl]-N-hydroxy-acetamidine

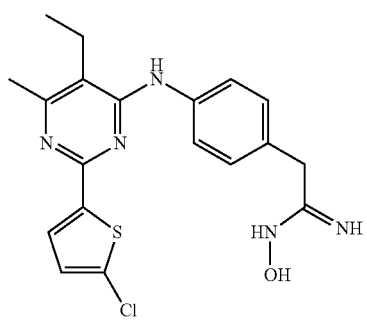 [SMILES: CCc1c(C)nc(-c2ccc(Cl)s2)nc1Nc1ccc(CC(=N)NO)cc1]

A 50-mL round bottomed flask was charged with 2-[4-[[2-(5-Chloro-2-thienyl)-5-ethyl-6-methyl-pyrimidin-4-yl]amino]phenyl]acetonitrile (120 mg, 0.325 mmol, 1 eq.), NH$_2$OH/HCl (160 mg, 2.3 mmol, 7 eq), K$_2$CO$_3$ (320 mg, 2.3 mol, 7 eq.), EtOH (10 ml) and water (1 ml). The mixture was stirred under reflux overnight. After cooling to room temperature, the volatile material was removed under reduced pressure. The residue was purified by chromatography on silica gel using 1.5~4% of methanol in dichloromethane as eluent to give the title compound (61 mg, 47% yield).

Step 2: Phenyl (NE)-N-[2-[4-[[2-(5-chloro-2-thienyl)-5-ethyl-6-methyl-pyrimidin-4-yl]amino]phenyl]-1-(hydroxyamino)ethylidene]carbamate

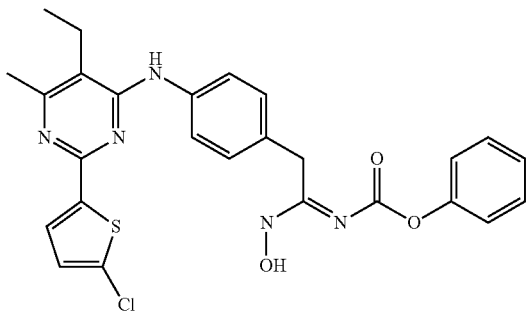 [SMILES: CCc1c(C)nc(-c2ccc(Cl)s2)nc1Nc1ccc(C/C(=N\C(=O)Oc2ccccc2)NO)cc1]

A 18-mL vial was charged with 2-[4-[[2-(5-Chloro-2-thienyl)-5-ethyl-6-methyl-pyrimidin-4-yl]amino]phenyl]-N-hydroxy-acetamidine (61 mg, 0.15 mmol), phenyl chloroformate (29 mg, 0.18 mmol, 1.2 eq.), Et₃N (20 mg, 0.2 mmol, 1.3 eq.) and dichloromethane (5 ml). The mixture was stirred at OC rt until starting material was consumed (4 hr). The mixture was poured into saturated sodium bicarbonate solution (10 ml) and extracted with dichloromethane (3×5 ml). The organic layers were combined and dried over Na2SO4. Removal of solvent under reduced pressure gave the title compound (80 mg, 100% yield). The product thus obtained was forwarded to the next step without any purification.

Step 3: 3-[[4-[[2-(5-Chloro-2-thienyl)-5-ethyl-6-methyl-pyrimidin-4-yl]amino]phenyl]methyl]-4H-1,2,4-oxadiazol-5-one

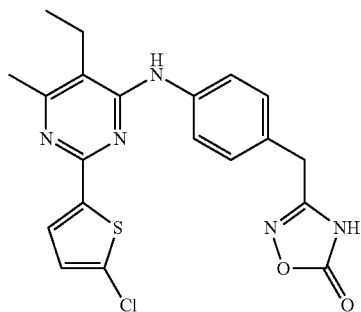 [SMILES: CCc1c(C)nc(-c2ccc(Cl)s2)nc1Nc1ccc(Cc2noc(=O)[nH]2)cc1]

A 50-mL round bottomed flask was charged with Phenyl (NE)-N-[2-[4-[[2-(5-chloro-2-thienyl)-5-ethyl-6-methyl-pyrimidin-4-yl]amino]phenyl]-1-(hydroxyamino)ethylidene]carbamate (80 mg, 0.15 mmol) and toluene (10 ml). The mixture was stirred under reflux overnight. After cooling to room temperature, the volatile material was removed under reduced pressure and the residue was purified by chromatography on silica gel using 1~2% methanol in dichloromethane as eluent to give the title compound as a white solid (16 mg, 25% yield over two steps). MW=427.91. ¹H NMR (400 MHz, DMSO-d₆) δ 12.4 (brs, 1H), 8.57 (brs, 1H), 7.73 (d, J=8.4 Hz, 2H), 7.56 (d, J=3.6 Hz, 1H), 7.29 (d, J=8.4 Hz, 2H), 7.15 (d, J=3.6 Hz, 1H), 3.86 (s, 2H), 2.73 (q, J=7.6 Hz, 2H), 2.40 (s, 3H), 1.10 (t, J=7.6 Hz, 3H).

EXAMPLE 303

2-[4-[[2-(5-Chloro-2-thienyl)-5-ethyl-6-methyl-pyrimidin-4-yl]amino]phenyl]-3-hydroxy-cyclopent-2-en-1-one

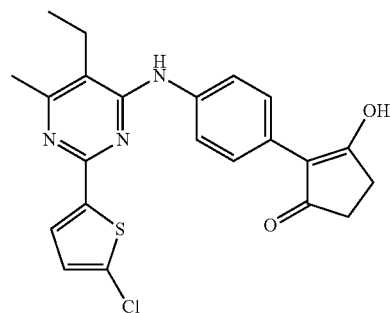 [SMILES: CCc1c(C)nc(-c2ccc(Cl)s2)nc1Nc1ccc(C2=C(O)CCC2=O)cc1]

Step 1: 4-[[2-(5-Chloro-2-thienyl)-5-ethyl-6-methyl-pyrimidin-4-yl]amino]benzaldehyde

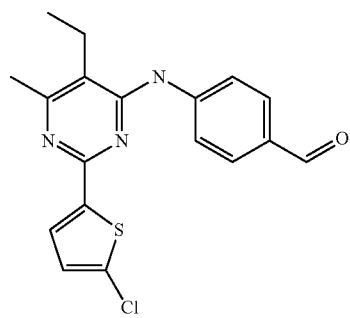 [SMILES: CCc1c(C)nc(-c2ccc(Cl)s2)nc1Nc1ccc(C=O)cc1]

A 50-mL round bottomed flask was charged with 4-[[2-(5-chloro-2-thienyl)-5ethyl-6-methyl-pyrimidin-4-yl]amino]benzonitrile (130 mg, 0.366 mmol), toluene (6 ml) and dichloromethane (12 ml). The mixture was added DIBAL-H (1 ml, 1M in DCM, 1 mmol, 2.73 eq.) dropwise by a syringe at 0° C. After the addition was complete, the mixture was allowed to warm to room temperature overnight. Then the mixture was added 2N HCl aq. (2 ml). The volatile material was removed under reduced pressure and the residue was partitioned between ethyl acetate (10 ml) and sodium bicarbonate (10 ml). The organic layer was separated and dried over Na₂SO₄. Removal of solvent gave the title compound as a solid (165 mg, 100% yield). The product thus obtained was forwarded to the next step without any further purification.

Step 2: 2-[4-[[2-(5-Chloro-2-thienyl)-5-ethyl-6-methyl-pyrimidin-4-yl]amino]phenyl]-3-hydroxy-cyclopent-2-en-1-one

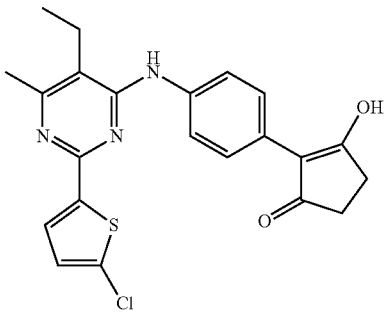 [SMILES: CCc1c(C)nc(-c2ccc(Cl)s2)nc1Nc1ccc(C2=C(O)CCC2=O)cc1]

A 18-mL vial was charged with 4-[[2-(5-Chloro-2-thie-nyl)-5-ethyl-6-methyl-pyrimidin-4-yl]amino]benzaldehyde (139 mg, 0.39 mmol, 1 eq.), trimethyl-(2-trimethylsilyloxy-cyclobuten-1-yl)oxy-silane (140 mg, 0.6 mmol, 1.53 eq.), and dichloromethane (2 ml). To the mixture was added $BF_3/Et_2O$ (80 µL, 0.63 mmol, 1.6 eq.). The mixture was stirred at room temperature overnight and then added to sodium bicarbonate solution (10 ml). The mixture was extracted with ethyl acetate (3×5 ml). The organic layers were combined and dried over $Na_2SO_4$. Removal of solvent gave a residue, which was purified by chromatography on silica gel using 2~3% of methanol in dichloromethane as eluent to give the title compound as a solid (22 mg, 13% yield). MW=425.93. $^1$H NMR (400 MHz, DMSO-$d_6$) δ 12.4 (brs, 1H), 8.52 (brs, 1H), 7.92 (d, J=8.8 Hz, 2H), 7.67 (d, J=8.8 Hz, 2H), 7.56 (d, J=4.0 Hz, 1H), 7.15 (d, J=4.0 Hz, 1H), 3.34 (m, 4H), 2.73 (q, J=7.2 Hz, 2H), 2.40 (s, 3H), 1.11 (t, J=7.2 Hz, 3H).

EXAMPLE 304

N-[4-[(4-Chloropyrazol-1-yl)methyl]phenyl]-2-(5-chloro-2-thienyl)-5-ethyl-6-methyl-pyrimidin-4-amine

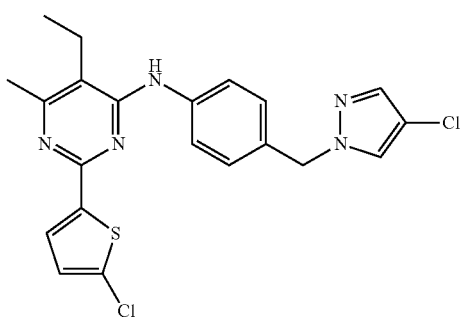 [SMILES: CCc1c(C)nc(-c2ccc(Cl)s2)nc1Nc1ccc(Cn2cc(Cl)cn2)cc1]

The title compound was prepared in a similar manner to those described herein, with modifications within the skill of one skilled in the art (12 mg, 23% yield). MW=444.38. $^1$H NMR (400 MHz, CDCl$_3$) δ 7.71 (d, J=8.8 Hz, 2H), 7.66 (d, J=4.0 Hz, 1H), 7.49 (s, 1H), 7.39 (s, 1H), 7.30 (d, J=8.8 Hz, 2H), 6.93 (d, J=4.0 Hz, 1H), 6.55 (brs, 1H), 5.27 (s, 2H), 2.65 (q, J=7.6 Hz, 2H), 2.49 (s, 3H), 1.25 (t, J=7.6 Hz, 3H).

EXAMPLE 305

Methyl 2-[[4-[[2-(5-chloro-2-thienyl)-5-ethyl-6-methyl-pyrimidin-4-yl]amino]phenyl]methyl]-1H-imidazole-4-carboxylate

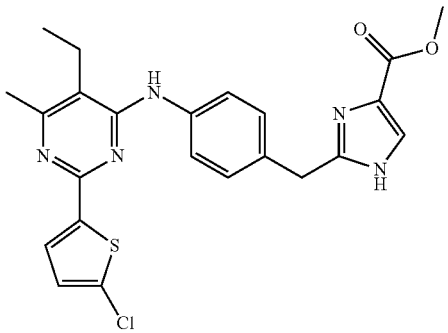

Step 1: N-Hydroxy-2-(4-nitrophenyl)acetamidine

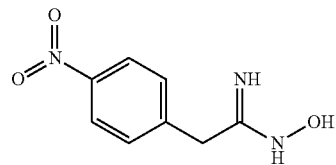 [SMILES: N=C(Cc1ccc([N+](=O)[O-])cc1)NO]

A 250-mL round bottomed flask was charged with 2-(4-nitrophenyl)acetonitrile (2.5 g, 15.4 mmol, 1 eq.), $NH_2OH/HCl$ (2.12 g, 31 mmol, 2 eq), $NaHCO_3$ (2.82 g, 2.3 mol, 7 eq.), MeOH (100 ml) and water (16 ml). The mixture was stirred under reflux overnight. After cooling to room temperature, the volatile material was removed under reduced pressure. The residue was treated with water (100 ml). Solid was collected by filtration and washed with water (3×20 ml) followed by dichloromethane (3×10 ml). After drying, the title compound was obtained as yellowish solid (2.46 g, 84% yield).

Step 2: Methyl 2-[(4-nitrophenyl)methyl]-1H-imidazole-4-carboxylate

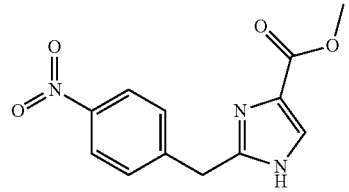 [SMILES: COC(=O)c1c[nH]c(Cc2ccc([N+](=O)[O-])cc2)n1]

A 250-mL round bottomed flask was charged with N-hydroxy-2-(4-nitrophenyl)acetamidine (1 g, 5 mmol, 1 eq.), methyl propiolate (500 mg, 6 mmol, 1.2 eq.) and EtOH (24 ml). The resulting mixture was stirred under reflux for 7 hrs. After cooling to room temperature, the volatile material was removed under reduced pressure and the residue was added phenyl ether (200 ml). The mixture was stirred at 190° C. for 30 minutes. After cooling to room temperature, the mixture was poured into hexane (1 L). Solid was collected and washed with hexane. The crude product thus obtained (964 mg) was purified by chromatography on silica gel using 10~20% acetone in dichloromethane as eluent to afford the title compound as a gray solid (220 mg, 17% yield over two steps).

Step 3: Methyl 2-[(4-aminophenyl)methyl]-1H-imidazole-4-carboxylate

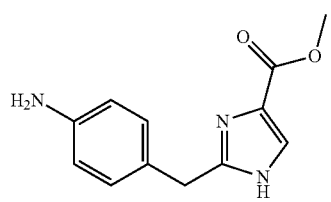 [SMILES: COC(=O)c1c[nH]c(Cc2ccc(N)cc2)n1]

A 100-mL round bottomed flask was charged with methyl 2-[(4-nitrophenyl)methyl]-1H-imidazole-4-carboxylate (220 mg, 0.84 mmol), Pd/C (270 mg, 10 wt %, 0.255 mmol, 0.3 eq.) and EtOH (24 ml). The mixture was stirred under 1 atmosphere of hydrogen overnight. The insoluble material was removed by filtration and the organics was evaporated under reduced pressure to dryness to afford the title compound (177 mg, 91% yield). The product thus obtained was forwarded to the next step without any further purification.

Step 4: Methyl 2-[[4-[[2-(5-chloro-2-thienyl)-5-ethyl-6-methyl-pyrimidin-4-yl]amino]phenyl]methyl]-1H-imidazole-4-carboxylate

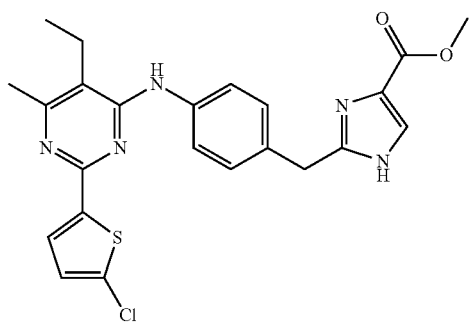

A 8-mL vial was charged with 4-chloro-2-(5-chloro-2-thienyl)-5-ethyl-6-methyl-pyrimidine (100 mg, 0.366 mmol, 1.05 eq.), methyl 2-[(4-aminophenyl)methyl]-1H-imidazole-4-carboxylate (81 mg, 0.348 mmol, 1 eq.), AcOH (0.8 ml). To the mixture was added 4N HCl in dioxane (4 drops using 1 ml of a syringe). The resulting mixture was stirred under 110° C. for 2 hrs. After cooling to room temperature, the mixture was added to sodium bicarbonate solution (20 ml). The precipitate was collected by filtration and washed with water then purified by chromatography on silica gel using 1~1.5% of methanol in dichloromethane as eluent to give the title compound as a foam (79 mg, 48% yield).). MW=467.97. $^1$H NMR (400 MHz, CDCl$_3$) δ 7.65 (m, 4H), 7.30 (m, 2H), 6.93 (d, J=3.6 Hz, 1H), 6.54 (brs, 1H), 4.18 (s, 2H), 3.90 (s, 3H), 2.64 (q, J=6.8 Hz, 2H), 2.49 (s, 3H), 1.26 (t, J=6.8 Hz, 3H).

EXAMPLE 306

2-[[4-[[2-(5-Chloro-2-thienyl)-5-ethyl-6-methyl-pyrimidin-4-yl]amino]phenyl]methyl]-1H-imidazole-4-carboxylic acid

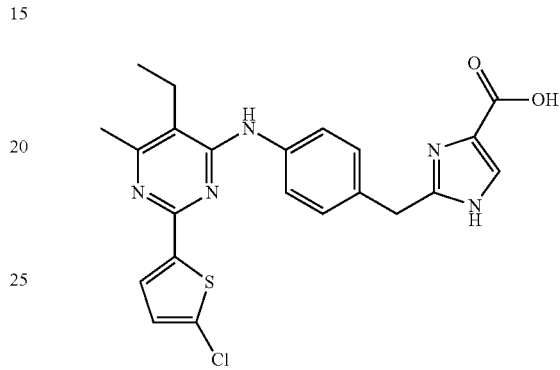

A 8-mL vial was charged with methyl 2-[[4-[[2-(5-chloro-2-thienyl)-5-ethyl-6-methyl-pyrimidin-4-yl]amino]phenyl]methyl]-1H-imidazole-4-carboxylate (8 mg, 0.017 mmol, 1 eq.), LiOH/H$_2$O (19 mg, 0.44 mmol, 26 eq.), THF (1 ml), MeOH (0.2 ml) and water (0.2 ml). The resulting mixture was stirred at 55° C. overnight. After cooling to room temperature, the mixture was added 2N HCl aq. to pH 6~7. The precipitate was collected by filtration and washed with water. After drying, the title compound was obtained as a solid (4.8 mg, 62% yield). MW=453.94. $^1$H NMR (400 MHz, DMSO-d$_6$) δ 8.52 (brs, 1H), 7.65 (m, 3H), 7.55 (d, J=4.0 Hz, 1H), 7.25 (d, J=8.0 Hz, 2H), 7.16 (d, J=4.0 Hz, 1H), 3.97 (s, 2H), 2.73 (q, J=7.2 Hz, 2H), 2.49 (s, 3H), 1.09 (t, J=7.2 Hz, 3H).

EXAMPLE 307

2-[4-[[2-(5-Chloro-2-thienyl)-5-ethyl-6-methyl-pyrimidin-4-yl]amino]phenyl]-N-propyl-acetamide

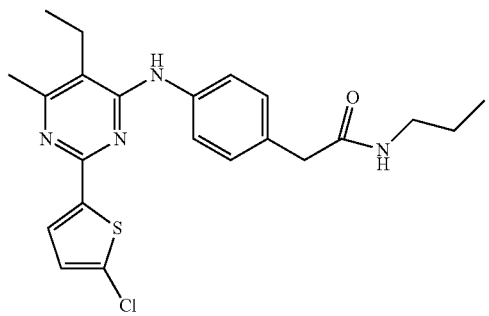 [SMILES: CCCNC(=O)Cc1ccc(Nc2nc(-c3ccc(Cl)s3)nc(C)c2CC)cc1]

The title compound was prepared in a similar manner to those described herein, with modifications within the skill of one skilled in the art (8 mg, 36% yield). MW=428.98. $^1$H NMR (400 MHz, CDCl$_3$) δ 7.70 (d, J=8.8 Hz, 2H), 7.67 (d, J=4.0 Hz, 1H), 7.31 (d, J=8.8 Hz, 2H), 6.93 (d, J=4.0 Hz, 1H), 6.55 (brs, 1H), 5.45 (brs, 1H), 3.61 (s, 2H), 3.21 (q, J=6.4 Hz, 2H), 2.65 (q, J=7.6 Hz, 2H), 2.50 (s, 3H), 1.49 (m, 2H), 1.26 (t, J=7.6 Hz, 3H), 0.88 (t, J=7.2 Hz, 3H).

EXAMPLE 308

2-[4-[[2-(5-Chloro-2-thienyl)-5-ethyl-6-methyl-pyrimidin-4-yl]amino]phenyl]-N-methyl-acetamide

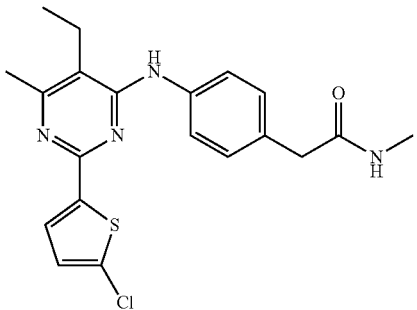

The title compound was prepared in a similar manner to those described herein, with modifications within the skill of one skilled in the art (14 mg, 67% yield). MW=400.92. $^1$H NMR (400 MHz, CDCl$_3$) δ 7.85 (brs, 1H), 7.69 (d, J=8.4 Hz, 2H), 7.31 (d, J=8.4 Hz, 2H), 6.95 (d, J=4.0 Hz, 1H), 6.65 (brs, 1H), 5.45 (brs, 1H), 3.62 (s, 2H), 2.81 (d, J=4.8 Hz, 3H), 2.66 (q, J=7.6 Hz, 2H), 2.56 (s, 3H), 1.49 (m, 2H), 1.27 (t, J=7.6 Hz, 3H).

EXAMPLE 309

2-[4-[[2-(5-Chloro-2-thienyl)-5-ethyl-6-methyl-pyrimidin-4-yl]amino]phenyl]-N-ethyl-acetamide

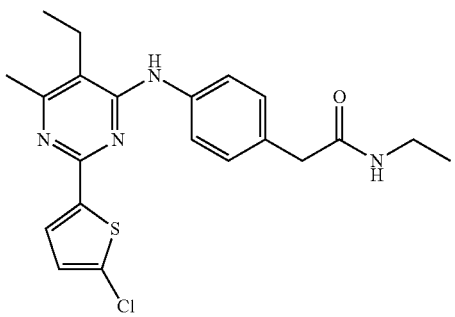 [SMILES: CCNC(=O)Cc1ccc(Nc2nc(-c3ccc(Cl)s3)nc(C)c2CC)cc1]

The title compound was prepared in a similar manner to those described herein, with modifications within the skill of one skilled in the art (7 mg, 36% yield). MW=414.95. $^1$H NMR (400 MHz, CDCl$_3$) δ 7.85 (brs, 1H), 7.68 (d, J=8.0 Hz, 2H), 7.32 (d, J=8.0 Hz, 2H), 6.96 (d, J=4.0 Hz, 1H), 5.45 (brs, 1H), 3.60 (s, 2H), 3.30 (m, 2H), 2.66 (m, 2H), 2.56 (s, 3H), 1.27 (t, J=7.2 Hz, 3H), 1.11 (t, J=7.6 Hz, 3H).

EXAMPLE 310

2-[[4-[[2-(5-Chloro-2-thienyl)-5-ethyl-6-methyl-pyrimidin-4-yl]amino]phenyl]methyl]-1H-imidazole-4-carboxamide

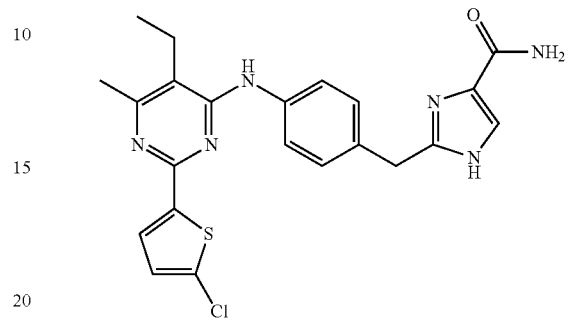

A 25-mL round bottomed flask was charged with methyl 2-[[4-[[2-(5-chloro-2-thienyl)-5-ethyl-6-methyl-pyrimidin-4-yl]amino]phenyl]methyl]-1H-imidazole-4-carboxylate (18 mg, 0.038 mmol) and 2N NH$_3$ in ethanol (10 ml). The mixture was stirred under reflux overnight. After cooling to room temperature, the volatile material was removed under reduced pressure and the residue was purified by chromatography on silica gel using 10% acetone in dichloromethane as eluent to afford the title compound (5.5 mg, 32% yield). MW=452.96. $^1$H NMR (400 MHz, CDCl$_3$) δ 7.68~7.65 (m, 4H), 7.30 (d, J=8.0 Hz, 2H), 6.93 (d, J=4.0 Hz, 1H), 6.54 (brs, 1H), 4.45 (brs, 2H), 4.19 (s, 2H), 2.65 (q, J=7.6 Hz, 2H), 2.49 (s, 3H), 1.26 (t, J=7.6 Hz, 3H).

EXAMPLE 311

[4-[[[2-(5-Chloro-2-thienyl)-5-ethyl-6-methyl-pyrimidin-4-yl]amino]methyl]phenyl]boronic acid

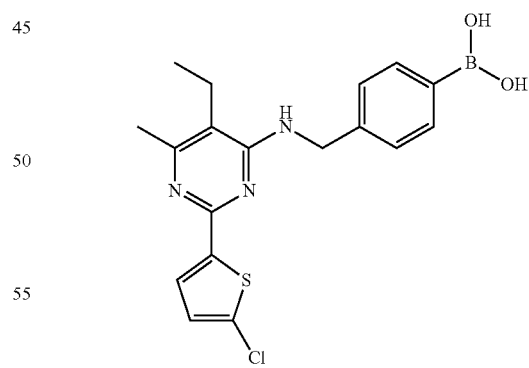

The title compound was prepared in a similar manner to those described herein, with modifications within the skill of one skilled in the art (7.2 mg, 53% yield). MW=387.69. $^1$H NMR (400 MHz, DMSO-d$_6$) δ 7.94 (s, 2H), 7.71 (d, J=8.0 Hz, 2H), 7.61 (t, J=6.0 Hz, 1H), 7.51 (d, J=4.0 Hz, 1H), 7.33 (d, J=8.0 Hz, 2H), 7.10 (d, J=4.0 Hz, 1H), 4.61 (d, J=6.0 Hz, 2H), 2.55 (q, J=7.2 Hz, 2H), 2.29 (s, 3H), 1.06 (t, J=7.2 Hz, 3H).

EXAMPLE 312

2-(5-Chloro-2-thienyl)-N-(2,2-dioxo-1,3-dihydro-2-benzothiophen-5-yl)-5-ethyl-6-methyl-pyrimidin-4-amine

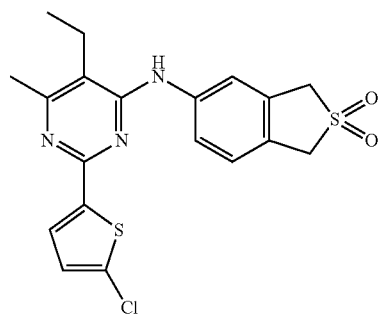 [SMILES: CCc1c(C)nc(-c2ccc(Cl)s2)nc1Nc1ccc2c(c1)CS(=O)(=O)C2]

The title compound was prepared in a similar manner to those described herein, with modifications within the skill of one skilled in the art (2.5 mg, 15% yield). MW=419.95. $^1$H NMR (400 MHz, CDCl$_3$) δ 7.88 (s, 1H), 7.65 (d, J=4.0 Hz, 1H), 7.55 (d, J=8.0 Hz, 1H), 7.33 (d, J=8.0 Hz, 1H), 6.94 (d, J=4.0 Hz, 1H), 6.57 (s, 1H), 4.46 (s, 2H), 4.41 (s, 2H), 2.66 (q, J=7.2 Hz, 2H), 2.51 (s, 3H), 1.26 (t, J=7.2 Hz, 3H).

EXAMPLE 313

2-(3-Chlorophenyl)-N-[4-(2H-tetrazol-5-ylmethyl)phenyl]-7,8-dihydro-6H-thiopyrano[3,2-d]pyrimidin-4-amine

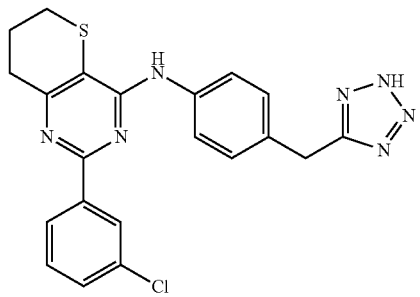 [SMILES: Clc1cccc(-c2nc3c(c(Nc4ccc(Cc5nn[nH]n5)cc4)n2)SCCC3)c1]

Step 1: Methyl 4-(2-methoxy-2-oxo-ethyl)thiobutanoate

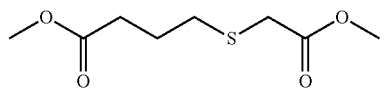

A 250-mL round bottomed flask was charged with methyl sulfanylacetate (15 g, 141 mmol, 1 eq.), methyl 4-chlorobutanoate (20.5 g, 150 mmol, 1.06 eq.), sodium methoxide (32.5 g, 25 w % in methanol, 150 mmol, 1.06 eq.), sodium iodide (160 mg, 1.06 mmol, 0.0075 eq.) and methanol (75 ml). The resulting mixture was stirred under reflux under Ar overnight. After cooling to room temperature, the solvent was removed under reduced pressure, then the residue was dissolved in CH$_2$Cl$_2$ (100 mL). The solution was washed with H$_2$O (30 mL), brine (30 mL), and dried with Na$_2$SO$_4$. Removal of solvent under reduced pressure gave the title compound as an oil (26.12 g, 90% yield). The product thus obtained was forwarded to the next step without any further purification.

Step 2: Methyl 3-oxotetrahydrothiopyran-2-carboxylate

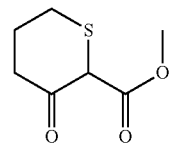

A 250-mL round bottomed flask was charged with methyl 4-(2-methoxy-2-oxo-ethyl)thiobutanoate (26 g, 126 mmol, 1 eq.), sodium methoxide (30 g, 25 w % in methanol, 139 mmol, 1.1 eq.) and toluene (100 ml). The resulting mixture was stirred at 80° C. overnight and then methanol was removed by distillation until the temperature of the reaction mixture rose to 106° C. After cooling to room temperature, the mixture was poured into a mixture of ice (100 g) and 12N HCl (20 mL). The organic layer was separated and the aqueous layer was extracted with dichloromethane (3×20 ml) and the combined organic layers were dried over Na$_2$SO$_4$. Removal of solvent under reduced pressure gave the title compound as art oil (19.3 g, 88% yield). The product thus obtained was forwarded to the next step without any further purification.

Step 3: 2-(3-chlorophenyl)-7,8-dihydro-6H-thiopyrano[3,2-d]pyrimidin-4-ol

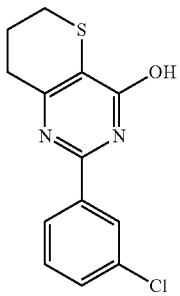 [SMILES: Oc1nc(-c2cccc(Cl)c2)nc2c1SCCC2]

A 100-mL round bottomed flask was charged with methyl 3-oxotetrahydrothiopyran-2-carboxylate (1.5 g, 8.6 mmol, 1.47 eq.), 3-chlorobenzamidine (HCl salt, 1.1 g, 5.75 mmol, 1 eq.) and ethanol (20 ml). The resulting mixture was stirred under reflux for 48 hrs. After cooling to room temperature, the volatile material was removed under reduced pressure and the residue was treated with hydrochloric acid (2N, 10 ml) and water (20 ml). The precipitate was collected by filtration and washed with water (3×10 ml) followed by ether (3×10 ml). After drying, the title compound was obtained as white solid (1.15 g, 72% yield).

Step 4: [2-(3-Chlorophenyl)-7,8-dihydro-6H-thiopyrano[3,2-d]pyrimidin-4-yl]trifluoromethanesulfonate

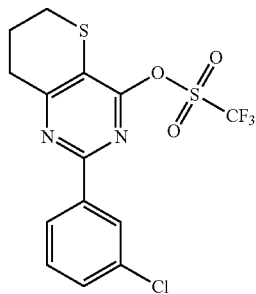 [SMILES: O=S(=O)(Oc1nc(-c2cccc(Cl)c2)nc2c1SCCC2)C(F)(F)F]

A 100-mL round bottomed flask was charged with 2-(3-chlorophenyl)-7,8-dihydro-6H-thiopyrano[3,2-d]pyrimidin-4-ol (840 mg, 3 mmol, 1 eq.), N,N- diisopropylethylamine (1.16 g, 9 mmol, 3 eq.) and dichloromethane (30 ml). To the mixture at 0° C. was added a solution of triflic anhydride in dichloromethane (1M, 4 ml, 1.3 eq.) dropwise by a syringe. After the addition was complete, the mixture was stirred at 0° C.~rt for 1 hr. The mixture was then poured into NaHCO$_3$ aq. (20 ml). The organic layer was separated and the aqueous layer was extracted with dichloromethane (20 ml). The organics were combined and dried over Na$_2$SO$_4$. The volatile material was removed and the crude material was purified by chromatography on silica gel using hexane/DCM (9:1 then 0:1) as eluent to afford the title compound as white solid (997 mg, 81% yield).

Step 5: 2-[4-[[2-(3-Chlorophenyl)-7,8-dihydro-6H-thiopyrano[3,2-d]pyrimidin-4-yl]amino]phenyl]acetonitrile

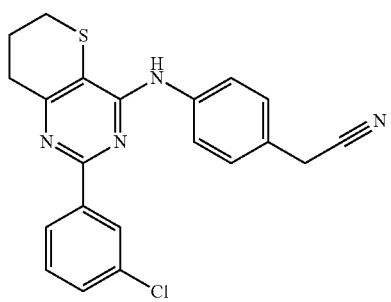 [SMILES: N#CCc1ccc(Nc2nc(-c3cccc(Cl)c3)nc3c2SCCC3)cc1]

A 8-mL vial was charged with 2-(4-aminophenyl)acetonitrile (40 mg, 0.3 mmol, 1.25 eq.), [2-(3-chlorophenyl)-7,8-dihydro-6H-thiopyrano[3,2-d]pyrimidin-4-yl]trifluoromethanesulfonate (100 mg, 0.24 mmol, 1. eq.) and DMF (1 ml). The resulting mixture was stirred at 70° C. overnight. After cooling to room temperature, water was added to the mixture (5 ml). The precipitate was collected by filtration and washed with water (20 ml). After drying, the crude product was purified by chromatography on silica gel using hexane/dichloromethane (1:1, 1:1.5 then 1:2) as eluent to give the title compound (35 mg, 37% yield).

Step 6: 2-(3-Chlorophenyl)-N-[4-(2H-tetrazol-5-ylmethyl)phenyl]-7,8-dihydro-6H-thiopyrano[3,2-d]pyrimidin-4-amine

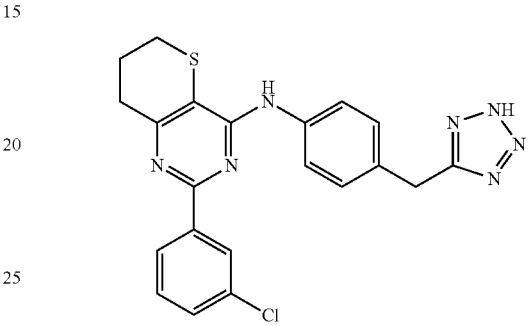

A 8-mL vial was charged with 2-[4-[[2-(3-chlorophenyl)-7,8-dihydro-6H-thiopyrano[3,2-d]pyrimidin-4-yl]amino]phenyl]acetonitrile (32 mg, 0.081 mmol, 1 eq.), azido(trimethyl)silane (0.2 ml, excess) and tetrabutylammonium fluoride hydrate (50 mg, 0.19 mmol, 2.3 eq.). The mixture was stirred at 110° C. overnight. After cooling to room temperature, the mixture was partitioned between dichloromethane (4 ml) and 2N HCl (4 ml). The solid was collected by filtration and washed with water (10 ml) followed dichloromethane (10 ml). After drying, the title compound was obtained as HCl salt (25 mg, 65% yield).). MW/HCl=472.39. $^1$H NMR (400 MHz, DMSO-D$_6$) δ 8.6 (brs, 1H), 8.16 (s, 1H), 8.11 (d, J=7.2 Hz, 1H), 7.64 (d, J=8.4 Hz, 2H), 7.53 (m, 2H), 7.29 (d, J=8.4 Hz, 2H), 4.31 (s, 2H), 3.21 (d, J=5.6 Hz, 2H), 2.94 (d, J=6.4 Hz, 2H), 2.19 (m, 2H).

EXAMPLE 314

2-[4-[[2-(3-Chlorophenyl)-7,8-dihydro-6H-thiopyrano[3,2-d]pyrimidin-4-yl]amino]phenyl]-N-cyanoacetamide

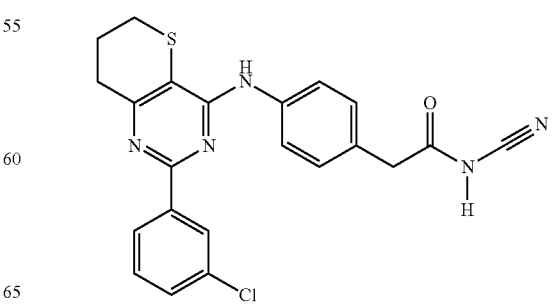

377

Step 1: 2-[4-[[2-(3-Chlorophenyl)-7,8-dihydro-6H-thiopyrano[3,2-d]pyrimidin-4-yl]amino]phenyl]acetic acid

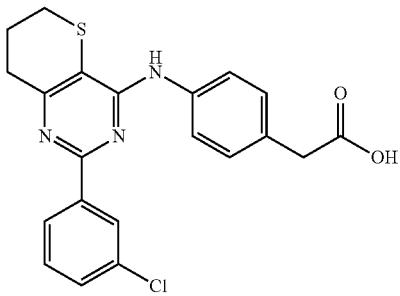 [SMILES: O=C(O)Cc1ccc(Nc2nc(-c3cccc(Cl)c3)nc3c2SCCC3)cc1]

A 8-mL vial was charged with [2-(3-chlorophenyl)-7,8-dihydro-6H-thiopyrano[3,2-d]pyrimidin-4-yl]trifluoromethanesulfonate (100 mg, 0.243 mmol, 1 eq.), 2-(4-aminophenyl)acetic acid (37 mg, 0.245 mmol, 1 eq.) and DMSO (1 ml). The resulting mixture was stirred at 110° C. under Ar for 6 hr. After cooling to room temperature, water was added to the mixture (15 ml). The precipitate was collected by filtration and washed with water (15 ml). After drying, the title compound was obtained (97.5 mg, 97% yield). The product thus obtained was forwarded to the next step without any further purification.

Step 2: 2-[4-[[2-(3-Chlorophenyl)-7,8-dihydro-6H-thiopyrano[3,2-d]pyrimidin-4-yl]amino]phenyl]-N-cyano-acetamide

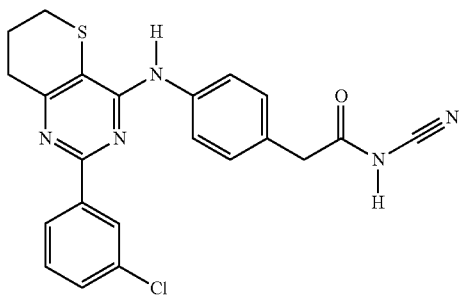 [SMILES: N#CNC(=O)Cc1ccc(Nc2nc(-c3cccc(Cl)c3)nc3c2SCCC3)cc1]

A 8-mL vial was charged with 2-[4-[[2-(3-Chlorophenyl)-7,8-dihydro-6H-thiopyrano[3,2-d]pyrimidin-4-yl]amino]phenyl]acetic acid (95 mg, 0.23 mmol, 1 eq.), cyamide (15 mg, 0.36 mmol, 1.5 eq.), HATU (130 mg, 0.36 mmol, 1.5 eq.), diisopropylethylamine (90 mg, 0.69 mmol, 3 eq.) and DMF (1 ml). The resulting mixture was stirred at rt overnight until the starting acid was consumed. The mixture was added to NaHCO$_3$ aq. (5 ml) and extracted with ethyl acetate (3×5 ml). The organic layers were combined and dried over Na$_2$SO$_4$. Removal of solvent gave a residue, which was purified by chromatography on silica gel using a preparation TLC plate and 2% of MeOH in DCM as mobile phase to give the title compound as a white solid (20 mg, 20% yield). MW=435.93. $^1$H NMR (400 MHz, methanol-d$_4$) δ 8.19 (s, 1H),), 8.11 (d, J=7.2 Hz, 1H), 7.65 (d, J=8.4 Hz, 2H), 7.43 (m, 2H), 7.32 (d, J=8.4 Hz, 2H), 3.69 (s, 2H), 3.18 (t, J=5.6 Hz, 2H), 2.94 (d, J=6.4 Hz, 2H), 2.27 (m, 2H).

EXAMPLE 315

2-[4-[[2-(3-Chlorophenyl)-5,5-dioxo-7,8-dihydro-6H-thiopyrano[3,2-d]pyrimidin-4-yl]amino]phenyl]-N-cyano-acetamide

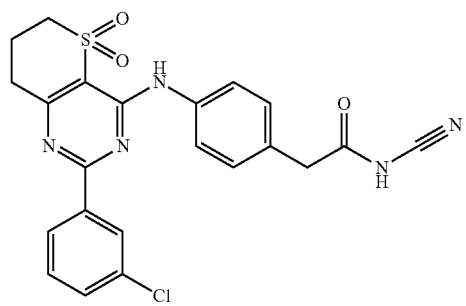 [SMILES: N#CNC(=O)Cc1ccc(Nc2nc(-c3cccc(Cl)c3)nc3c2S(=O)(=O)CCC3)cc1]

A 18-mL vial was charged with 2-[4-[[2-(3-Chlorophenyl)-7,8-dihydro-6H-thiopyrano[3,2-d]pyrimidin-4-yl]amino]phenyl]-N-cyano-acetamide (19 mg, 0.044 mmol, 1 eq.), oxone (55 mg, 0.18 mmol, 4 eq.), THF (3 ml) and water (3 ml). The clear solution was stirred at room temperature overnight. The volatile material was removed under reduced pressure and the residue was treated with sodium bicarbonate solution. Solid was collected by filtration and washed with water. After drying, the title compound was obtained as a white solid (11 mg, 53% yield). MW=467.93. $^1$H NMR (400 MHz, methanol-d$_4$) δ 8.34 (s, 1H),), 8.25 (d, J=7.6 Hz, 1H), 7.60 (d, J=8.0 Hz, 2H), 7.49 (m, 2H), 7.39 (d, J=8.0 Hz, 2H), 3.61 (t, J=4.8 Hz, 2H), 3.56 (s, 2H), 3.13 (t, J=6.4 Hz, 2H), 2.54 (m, 2H).

EXAMPLE 316

2-(3-Chlorophenyl)-5,5-dioxo-N-[4-(2H-tetrazol-5-ylmethyl)phenyl]-7,8-dihydro-6H-thiopyrano[3,2-d]pyrimidin-4-amine

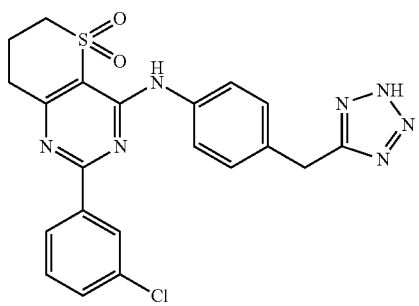 [SMILES: O=S1(=O)CCCc2nc(-c3cccc(Cl)c3)nc(Nc3ccc(Cc4nn[nH]n4)cc3)c21]

Step 1: [2-(3-Chlorophenyl)-5,5-dioxo-7,8-dihydro-6H-thiopyrano[3,2-d]pyrimidin-4-yl]trifluoromethanesulfonate

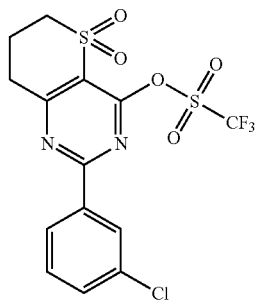 [SMILES: O=S1(=O)CCCc2nc(-c3cccc(Cl)c3)nc(OS(=O)(=O)C(F)(F)F)c21]

A 25-mL round bottomed flask was charged with [2-(3-Chlorophenyl)-7,8-dihydro-6H-thiopyrano[3,2-d]pyrimidin-4-yl]trifluoromethanesulfonate (200 mg, 0.487 mmol, 1 eq.), 3-chloroperbenzoic acid (450 mg, 2 mmol, 4 eq.) and dichloromethane (10 ml). The resulting mixture was stirred at room temperature until the starting sulfide was consumed. The mixture was then poured into sodium bicarbonate solution (20 ml). The organic layer was separated and washed with sodium bicarbonate solution (10 ml). After drying over Na$_2$SO$_4$, solvent was removed under reduced pressure. The residue was purified by chromatography on silica gel using dichloromethane/hexane (1:1, 1.5:1, and 2:1) as eluent to give the title compound as a white solid (137 mg, 64% yield).

Step 2: 2-[4-[[2-(3-Chlorophenyl)-5,5-dioxo-7,8-dihydro-6H-thiopyrano[3,2-d]pyrimidin-4-yl]amino]phenyl]acetonitrile

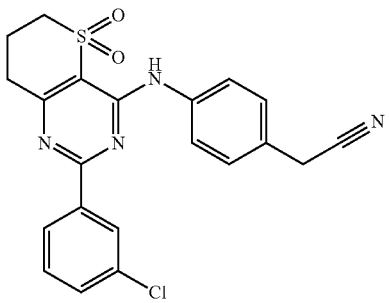 [SMILES: N#CCc1ccc(Nc2nc(-c3cccc(Cl)c3)nc3c2S(=O)(=O)CCC3)cc1]

An 8-mL vial was charged with 2-(4-aminophenyl)acetonitrile (30 mg, 0.23 mmol, 2 eq.), [2-(3-Chlorophenyl)-5,5-dioxo-7,8-dihydro-6H-thiopyrano[3,2-d]pyrimidin-4-yl]trifluoromethanesulfonate (50 mg, 0.112 mmol, 1. eq.) and DMF (0.5 ml). The resulting mixture was stirred at 70° C. overnight. After cooling to room temperature, water was added to the mixture (5 ml). The precipitate was collected by filtration and washed with water (10 ml). After drying, the crude product was purified by chromatography on silica gel using dichloromethane as eluent to give the title compound (18 mg, 38% yield).

Step 3: 2-(3-Chlorophenyl)-5,5-dioxo-N-[4-(2H-tetrazol-5-ylmethyl)phenyl]-7,8-dihydro-6H-thiopyrano[3,2-d]pyrimidin-4-amine

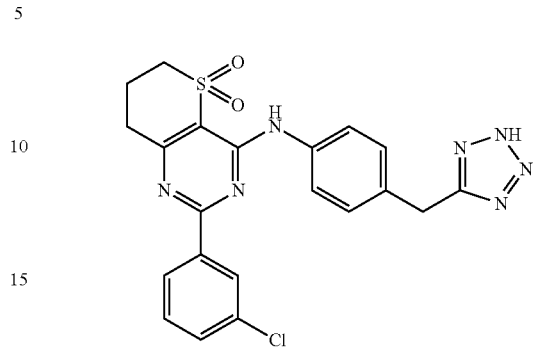

A 8-mL vial was charged with 2-[4-[[2-(3-Chlorophenyl)-5,5-dioxo-7,8-dihydro-6H-thiopyrano[3,2-d]pyrimidin-4-yl]amino]phenyl]acetonitrile (17 mg, 0.04 mmol, 1 eq.), azido(trimethyl)silane (0.2 ml, excess) and tetrabutylammonium fluoride hydrate (50 mg, 0.19 mmol, 4.6 eq.). The mixture was stirred at 110° C. overnight. After cooling to room temperature, the mixture was partitioned between dichloromethane (8 ml) and 2N HCl (4 ml). The organic layer was separated and washed with sodium bicarbonate solution (5 ml) and dried over Na$_2$SO$_4$. Removal of solvent under reduced pressure gave a residue, which was purified using a preparation TLC plate and 3% of methanol in dichloromethane as mobile to give the title compound as white solid (13 mg, 70% yield). MW=467.93. $^1$H NMR (400 MHz, methanol-d$_4$) δ 8.32 (s, 1H), 8.24 (d, J=7.2 Hz, 1H), 7.67 (d, J=8.4 Hz, 2H), 7.46 (m, 2H), 7.38 (d, J=8.4 Hz, 2H), 4.38 (s, 2H), 3.63 (d, J=5.6 Hz, 2H), 3.14 (d, J=6.4 Hz, 2H), 2.54 (m, 2H).

EXAMPLE 317

2-(5-chloro-2-thienyl)-5-ethyl-6-methyl-N-[4-(methylsulfonylmethyl)phenyl]pyrimidin-4-amine

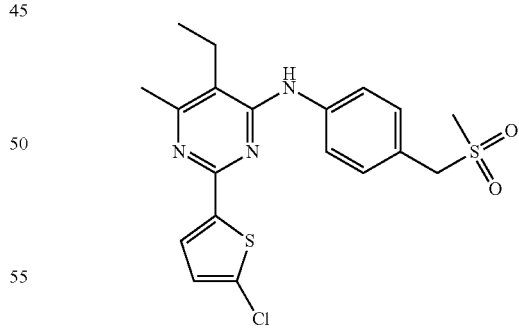

The title compound was prepared in a similar manner to those described herein, with modifications within the skill of one skilled in the art (5.6 mg, 13% yield). MW=421.96. $^1$H NMR (400 MHz, CDCl$_3$) δ 7.80 (d, J=8.8 Hz, 2H), 7.68 (d, J=4.0 Hz, 1H), 7.46 (d, J=8.8 Hz, 2H), 6.94 (d, J=4.0 Hz, 1H), 6.61 (s, 1H), 4.28 (s, 2H), 2.82 (s, 3H), 2.66 (q, J=7.2 Hz, 2H), 2.51 (s, 3H), 1.26 (t, J=7.2 Hz, 3H).

The following compounds may be synthesized using methods analogous to those described herein and known in the art, using appropriate starting materials. These compounds may not yet have been made or tested:
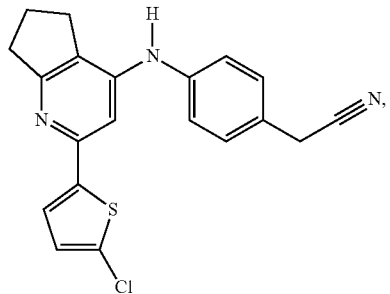
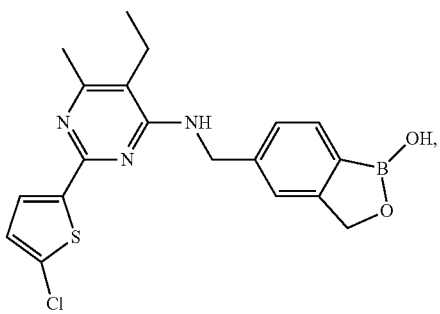
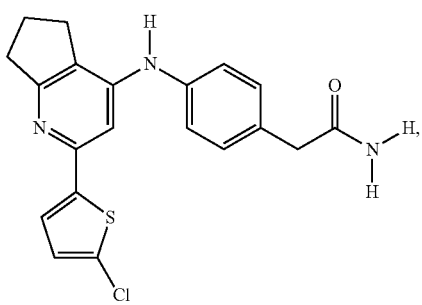
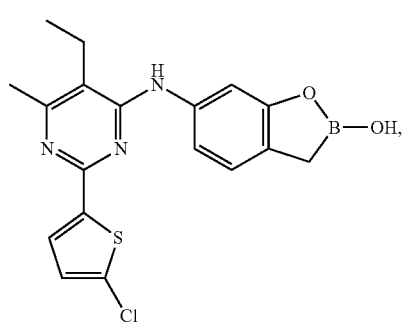
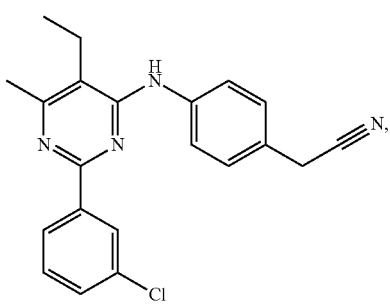
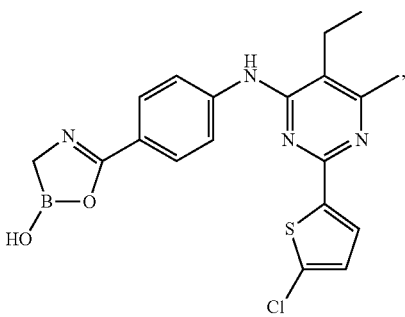
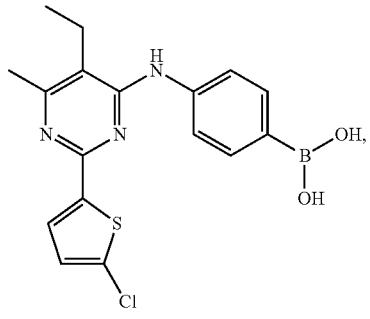
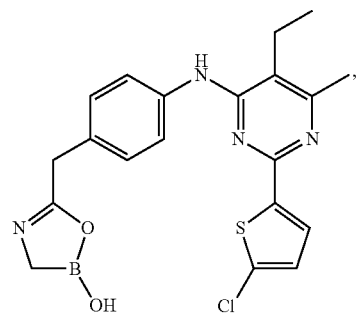
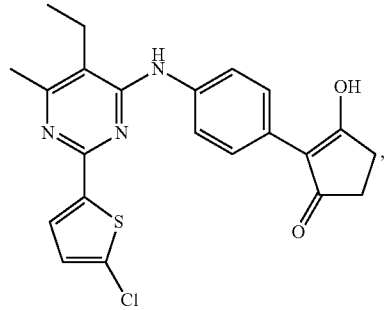
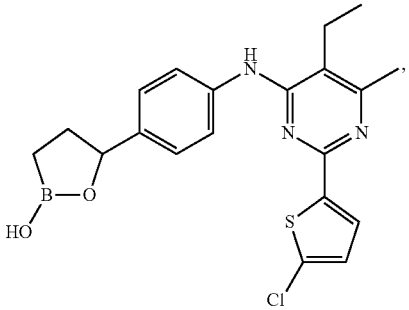

383
-continued
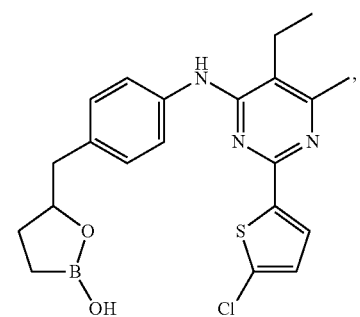
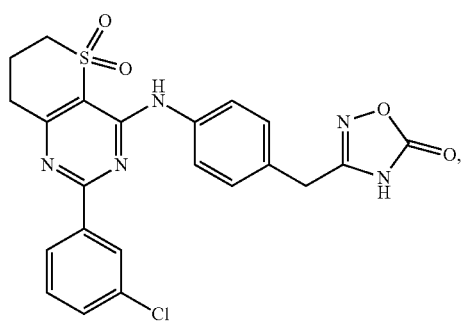
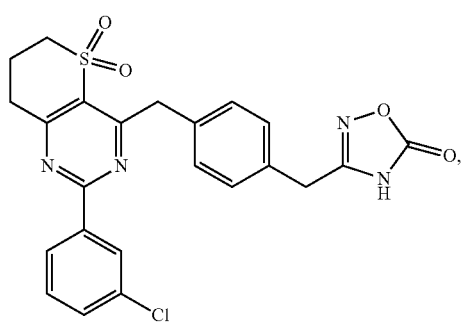
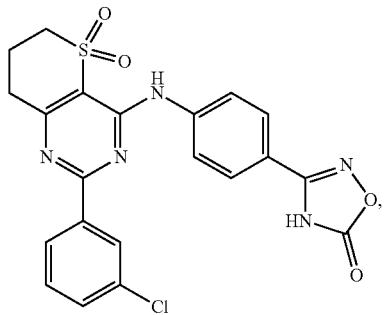
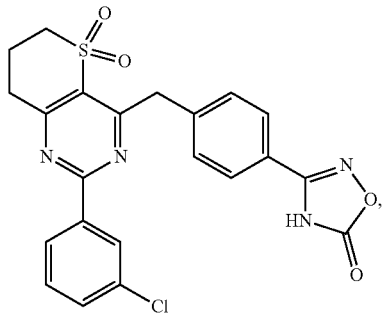
384
-continued
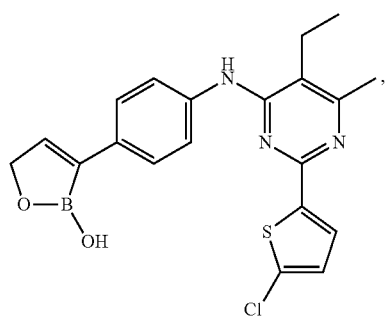
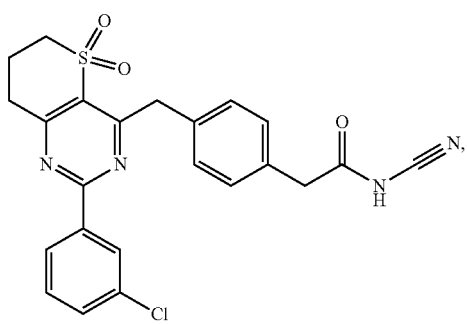
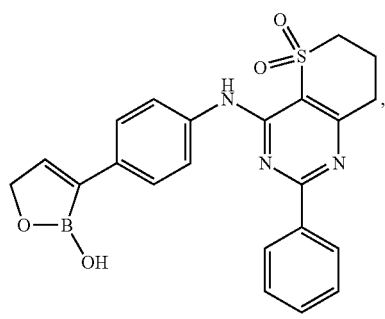
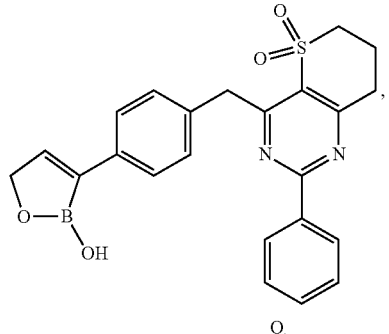
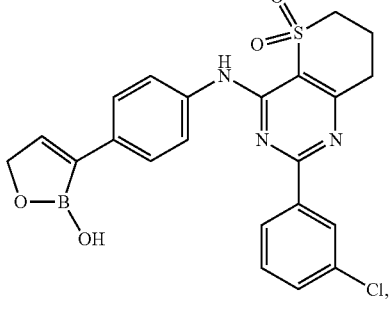

385
-continued
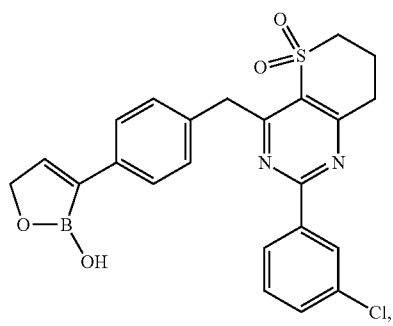
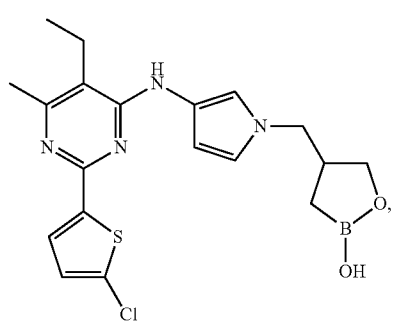
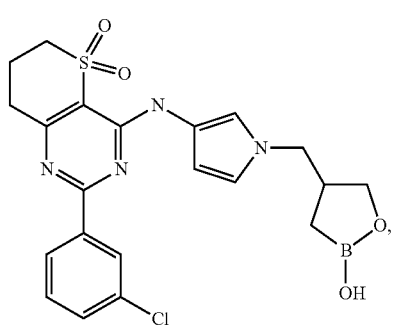
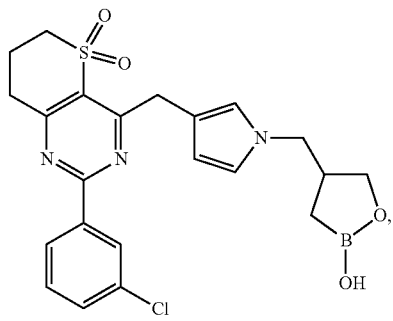
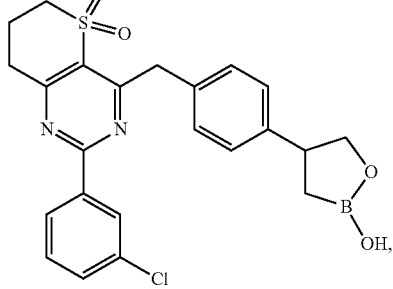
386
-continued
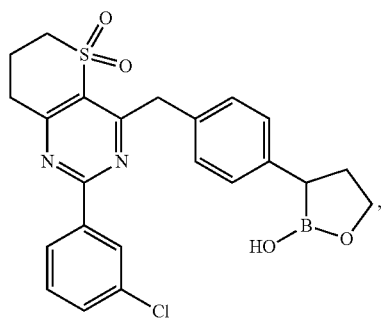
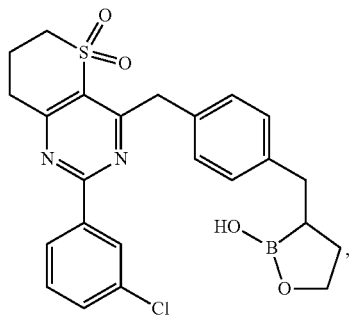
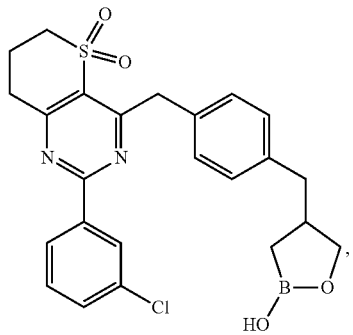 [SMILES: O=S1(=O)CCCc2nc(-c3cccc(Cl)c3)nc(Cc3ccc(CC4CCB(O)O4)cc3)c21]
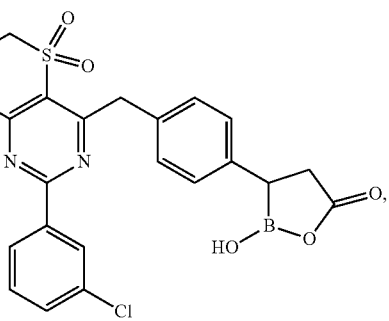
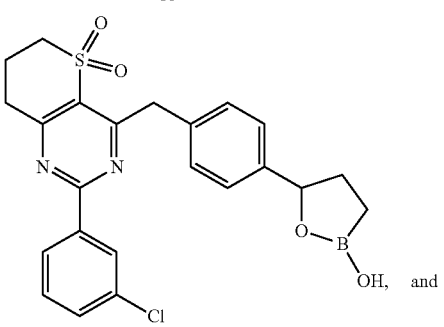
and -continued

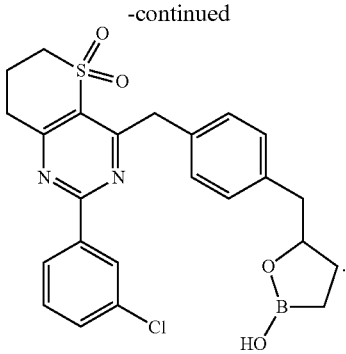

Biological Assays

The activity of many of the compounds in Examples 1-41 and 43-317 as PDE4 inhibitors is illustrated in the following assay. Certain compounds listed above, which have not yet been made and/or tested, are predicted to have activity in this assay as well.

Kinetic Assay of PDE4 Activity

PDE4 activity may be measured by any method known in the art. Here, a kinetic assay of cAMP hydrolysis by purified PDE4 was used, in which PDE4 activity was measured by coupling the formation of the PDE4 reaction product, 5'-adenosine monophosphate, to the oxidation of reduced nicotinamide adenine dinucleotide (NADH) by the use of three coupling enzymes (myokinase, pyruvate kinase and lactate dehydrogenase), which allows fluorescent determination of reaction rates. Assays are performed in 96-well plates in a total volume of 200 µl/well. Compounds are dissolved in dimethylsulfoxide (DMSO) and added to plates in a volume of 10 µl followed by addition of 165 µl of assay mix. Plates are pre-incubated at 25° C. for 15 min and the reactions are initiated by the addition of 25 µl of cAMP followed by thorough mixing. Reaction rates are measured by monitoring the decrease in fluorescence using excitation at 355 nm and emission at 460 nm for a period of 10 min in a fluorescence plate reader. Initial rates (slopes) are determined from linear portions of the progress curves. Final concentrations of assay components are as follows: 50 mM Tris, pH 8, 10 mM $MgCl_2$, 50 mM KCl, 2% DMSO, 5 mM tris(2-carboxyethyl)phosphine (TCEP), 0.4 mM phosphenolpyruvate (PEP), 0.01 mM NADH, 0.04 mM adenosine triphosphate (ATP), 0.004 mM cAMP, 7.5 units myokinase from yeast, 1.6 units pyruvate kinase, 2 units lactate dehydrogenase, and either 0.5 nM human PDE4D7 or 10 nM human PDE4B1. All data are percent normalized relative to controls and are presented as percent inhibition. An inhibitory concentration 50% ($IC_{50}$) value is calculated by fitting of a sigmoidal dose response curve. Human PDE4D7 contained a mutation of serine 54 to aspartic acid to mimic activation by cAMP-dependent protein kinase A (PKA). Human PDE4B1 contained a corresponding mutation of serine 133 to aspartic acid to also mimic PKA activation. These methods were adapted from Burgin, A. B. et al., "Design of Phosphodiesterase Type 4D (PDE4D) Allosteric Modulators for Cognition with Improved Safety," *Nature Biotechnology* 28, 63-70 (2010).

Results are shown below in Table 1, in which + indicates <1 µM and − indicates >1 µM. A − does not mean that the compound is undesirable. "ND" indicates no data; these compounds may not yet have been tested. It is expected that these compounds when tested will be active and will have utility similar to those that have been tested ("NT"). Also, the asterisk (*) indicates that the PDE4 isoform contains a UCR1 activating mutation: PDE4B1*=PDE4B1 containing a UCR1 activating mutation S133D. PDE4D7*=PDE4D7 containing a UCR1 activating mutation S54D.

TABLE 1

| | Activity: Inhibition of PDE4 | | |
|---|---|---|---|
| Ex. No. | PDE4B1* $IC_{50}$ | PDE4D7* $IC_{50}$ | PDE4D7 $IC_{50}$ |
| 1 | + | + | ND |
| 2 | − | − | ND |
| 3 | + | + | − |
| 4 | − | − | − |
| 5 | + | + | − |
| 6 | − | + | − |
| 7 | − | − | − |
| 8 | − | NT | − |
| 9 | + | + | − |
| 10 | + | − | − |
| 11 | − | − | − |
| 12 | − | − | − |
| 13 | ND | ND | ND |
| 14 | ND | ND | ND |
| 15 | + | + | − |
| 16 | + | + | − |
| 17 | ND | ND | ND |
| 18 | ND | ND | ND |
| 19 | − | − | − |
| 20 | + | + | + |
| 21 | + | + | − |
| 22 | − | NT | − |
| 23 | − | NT | − |
| 24 | − | − | − |
| 25 | − | − | − |
| 26 | − | + | − |
| 27 | + | + | − |
| 28 | − | + | − |
| 29 | + | + | + |
| 30 | + | + | + |
| 31 | − | NT | − |
| 32 | − | NT | − |
| 33 | − | NT | − |
| 34 | + | − | − |
| 35 | − | − | − |
| 36 | + | − | − |
| 37 | − | − | − |
| 38 | + | + | + |
| 39 | + | + | − |
| 40 | + | + | + |
| 41 | + | + | + |
| 43 | − | − | − |
| 44 | − | − | NT |
| 45 | − | + | NT |
| 46 | + | + | NT |
| 47 | − | − | NT |
| 48 | − | + | NT |
| 49 | − | − | NT |
| 50 | − | NT | NT |
| 51 | + | + | + |
| 52 | + | + | + |
| 53 | − | − | NT |
| 54 | + | + | NT |
| 55 | + | + | NT |
| 56 | + | + | NT |
| 57 | + | + | + |
| 58 | + | + | + |
| 59 | − | + | NT |
| 60 | − | + | NT |
| 61 | − | + | − |
| 62 | + | + | + |
| 63 | − | − | NT |
| 64 | − | − | ND |
| 65 | + | + | + |
| 66 | − | + | − |

TABLE 1-continued

Activity: Inhibition of PDE4

| Ex. No. | PDE4B1* IC$_{50}$ | PDE4D7* IC$_{50}$ | PDE4D7 IC$_{50}$ |
|---|---|---|---|
| 67 | + | + | + |
| 68 | + | + | − |
| 69 | − | + | − |
| 70 | − | − | − |
| 71 | + | + | + |
| 72 | − | − | ND |
| 73 | + | + | ND |
| 74 | + | + | ND |
| 75 | + | + | ND |
| 76 | + | + | ND |
| 77 | + | + | ND |
| 78 | + | + | ND |
| 79 | + | + | ND |
| 80 | + | ND | + |
| 81 | + | ND | + |
| 82 | + | ND | + |
| 83 | − | ND | − |
| 84 | − | ND | − |
| 85 | + | ND | + |
| 86 | − | ND | − |
| 87 | − | ND | − |
| 88 | + | ND | − |
| 89 | − | ND | − |
| 90 | − | ND | − |
| 91 | ND | ND | ND |
| 92 | − | ND | − |
| 93 | + | ND | − |
| 94 | + | ND | − |
| 95 | − | ND | ND |
| 96 | − | ND | − |
| 97 | − | ND | − |
| 98, 99 | − | ND | − |
| 100 | − | ND | − |
| 101 | − | ND | − |
| 102 | − | ND | − |
| 103 | − | ND | − |
| 104 | − | ND | − |
| 105 | − | ND | − |
| 106 | − | ND | − |
| 107 | − | ND | − |
| 108 | + | ND | + |
| 109 | + | ND | − |
| 110 | − | ND | − |
| 111 | + | ND | − |
| 112 | + | ND | − |
| 113 | + | ND | − |
| 114 | − | ND | − |
| 115 | + | + | − |
| 116 | + | ND | − |
| 117 | − | ND | − |
| 118 | − | ND | − |
| 119 | + | ND | − |
| 120 | + | ND | − |
| 121 | + | ND | + |
| 122 | + | ND | − |
| 123 | ND | ND | ND |
| 124 | + | ND | − |
| 125 | + | ND | − |
| 126 | − | ND | − |
| 127 | − | ND | − |
| 128 | − | ND | − |
| 129 | + | ND | − |
| 130 | + | ND | − |
| 131 | + | ND | − |
| 132 | − | ND | − |
| 133 | − | ND | − |
| 134 | − | ND | − |
| 135, 136 | − | ND | ND |
| 137 | − | ND | ND |
| 138 | + | ND | − |
| 139 | + | ND | + |
| 140 | + | ND | − |
| 141 | − | ND | − |
| 142 | − | ND | − |
| 143 | + | ND | − |
| 144 | + | ND | − |
| 145 | + | ND | + |
| 146 | + | ND | + |
| 147 | + | ND | + |
| 148 | + | ND | − |
| 149 | + | ND | − |
| 150 | + | ND | − |
| 151 | − | ND | − |
| 152 | + | ND | − |
| 153 | − | ND | − |
| 154 | − | ND | − |
| 155 | − | ND | − |
| 156 | + | ND | − |
| 157 | − | ND | − |
| 158 | − | ND | − |
| 159 | − | ND | − |
| 160 | − | ND | − |
| 161 | + | ND | − |
| 162 | + | ND | + |
| 163 | + | ND | + |
| 164 | − | ND | − |
| 165 | + | ND | − |
| 166 | − | ND | − |
| 167 | + | ND | − |
| 168 | + | ND | − |
| 169 | − | ND | − |
| 170 | − | ND | − |
| 171 | + | ND | + |
| 172 | + | ND | − |
| 173 | + | ND | − |
| 174 | − | ND | − |
| 175 | + | ND | − |
| 176 | − | ND | − |
| 177 | − | ND | − |
| 178 | − | ND | − |
| 179 | − | ND | − |
| 180 | − | ND | − |
| 181 | + | ND | − |
| 182 | + | ND | + |
| 183 | − | ND | − |
| 184 | − | ND | − |
| 185 | − | ND | − |
| 186 | − | ND | − |
| 187 | − | ND | − |
| 188 | − | ND | − |
| 189 | + | ND | + |
| 190 | + | ND | + |
| 191 | + | ND | + |
| 192 | − | ND | − |
| 193 | + | ND | − |
| 194 | + | ND | + |
| 195 | + | ND | + |
| 196 | − | ND | − |
| 197 | − | ND | − |
| 198 | − | ND | − |
| 199 | − | ND | + |
| 200 | − | ND | − |
| 201 | − | ND | − |
| 202 | − | ND | − |
| 203 | − | ND | − |
| 204 | − | ND | − |
| 205 | − | ND | − |
| 206 | + | ND | + |
| 207 | + | ND | + |
| 208 | − | ND | − |
| 209 | − | ND | − |
| 210 | − | ND | − |
| 211 | − | ND | − |
| 212 | − | − | − |
| 213 | − | − | − |
| 214 | − | + | − |
| 215 | + | + | + |
| 216 | + | ND | + |
| 217 | + | ND | − |
| 218 | − | + | − |

TABLE 1-continued

Activity: Inhibition of PDE4

| Ex. No. | PDE4B1* IC$_{50}$ | PDE4D7* IC$_{50}$ | PDE4D7 IC$_{50}$ |
|---|---|---|---|
| 219 | + | ND | − |
| 220 | + | ND | + |
| 221 | + | ND | + |
| 222 | + | ND | + |
| 223 | − | ND | − |
| 224 | − | ND | − |
| 225 | − | ND | − |
| 226 | − | ND | + |
| 227 | + | ND | + |
| 228 | + | ND | + |
| 229 | − | ND | − |
| 230 | + | ND | − |
| 231 | − | ND | − |
| 232 | − | ND | − |
| 233 | − | ND | − |
| 234 | + | + | + |
| 235 | + | + | + |
| 236 | − | ND | − |
| 237 | − | ND | − |
| 238 | − | ND | − |
| 239 | − | ND | − |
| 240 | + | ND | − |
| 241 | − | ND | − |
| 242 | − | ND | − |
| 243 | − | ND | − |
| 244 | − | ND | − |
| 245 | + | ND | − |
| 246 | − | ND | − |
| 247 | + | ND | − |
| 248 | − | ND | − |
| 249 | − | ND | − |
| 250 | + | ND | − |
| 251 | − | ND | − |
| 252 | − | ND | ND |
| 253 | − | ND | − |
| 254 | − | ND | ND |
| 255 | − | ND | − |
| 256 | + | ND | − |
| 257 | + | ND | − |
| 258 | − | ND | − |
| 259 | − | ND | − |
| 260 | + | ND | − |
| 261 | + | ND | − |
| 262 | − | ND | − |
| 263 | − | ND | − |
| 264 | + | ND | + |
| 265 | + | ND | + |
| 266 | − | ND | − |
| 267 | − | ND | − |
| 268 | + | ND | + |
| 269 | + | ND | + |
| 270 | + | ND | + |
| 271 | + | ND | + |
| 272 | + | ND | + |
| 273 | + | ND | + |
| 274 | + | ND | + |
| 275 | + | ND | + |
| 276 | + | ND | − |
| 277 | + | ND | + |
| 278 | + | ND | + |
| 279 | + | ND | + |
| 280 | + | ND | + |
| 281 | + | ND | + |
| 282 | + | ND | − |
| 283 | + | + | + |
| 284 | + | + | + |
| 285 | + | + | + |
| 286 | + | + | + |
| 287 | + | + | + |
| 288 | + | + | + |
| 289 | − | ND | − |
| 290 | + | ND | − |
| 291 | − | ND | − |
| 292 | + | + | + |
| 293 | + | + | + |
| 294 | + | − | − |
| 295 | + | + | − |
| 296 | + | − | − |
| 297 | + | − | − |
| 298 | + | + | − |
| 299 | − | ND | − |
| 300 | + | + | − |
| 301 | + | + | − |
| 302 | + | − | − |
| 303 | − | − | − |
| 304 | + | ND | − |
| 305 | + | + | − |
| 306 | + | − | − |
| 307 | + | + | + |
| 308 | + | + | − |
| 309 | + | + | + |
| 310 | − | − | − |
| 311 | + | − | − |
| 312 | + | + | − |
| 313 | + | + | + |
| 314 | + | + | + |
| 315 | + | + | + |
| 316 | + | + | + |
| 317 | + | + | − |

Table 2 shows the selectivity of certain compounds disclosed herein. In Table 2, + indicates a selectivity of the given ratio of isoforms of >10×, and − indicates a selectivity of ≤10×. A − does not mean that the compound is undesirable. "ND" indicates no data; these compounds may not yet have been tested. It is expected that these compounds when tested will be active and will have utility similar to those that have been tested. Again, the asterisk (*) indicates that the PDE4 isoform contains a UCR1 activating mutation: PDE4B1*=PDE4B1 containing a UCR1 activating mutation S133D. PDE4D7*=PDE4D7 containing a UCR1 activating mutation S54D.

TABLE 2

Selectivity Against PDE4 Isoforms

| Example No. | D*/B* | B*/D* | D/B* | D/D* |
|---|---|---|---|---|
| 1 | ND | − | ND | ND |
| 2 | ND | − | ND | ND |
| 3 | ND | − | ND | + |
| 4 | ND | + | ND | ND |
| 5 | − | ND | + | + |
| 6 | ND | + | ND | − |
| 7 | ND | − | ND | − |
| 9 | + | ND | + | ND |
| 10 | + | ND | + | ND |
| 20 | − | ND | ND | + |
| 21 | − | ND | ND | + |
| 24 | − | − | − | − |
| 25 | − | ND | − | − |
| 26 | ND | − | ND | ND |
| 27 | − | ND | − | − |
| 28 | ND | − | − | − |
| 29 | − | − | − | − |
| 30 | − | − | − | − |
| 34 | − | ND | ND | ND |
| 36 | − | − | ND | ND |
| 37 | − | − | − | − |
| 38 | − | ND | − | − |
| 39 | − | − | − | − |
| 40 | − | − | − | − |
| 41 | ND | ND | − | ND |
| 43 | − | − | − | − |
| 44 | − | − | ND | ND |

TABLE 2-continued

Selectivity Against PDE4 Isoforms

| Example No. | D*/B* | B*/D* | D/B* | D/D* |
|---|---|---|---|---|
| 47 | − | − | ND | ND |
| 48 | ND | − | ND | ND |
| 51 | − | − | + | + |
| 52 | ND | + | − | + |
| 54 | − | − | ND | ND |
| 55 | − | ND | ND | ND |
| 56 | ND | − | ND | ND |
| 57 | ND | + | − | + |
| 58 | ND | + | − | + |
| 59 | ND | + | ND | ND |
| 60 | ND | − | ND | ND |
| 61 | ND | + | − | + |
| 62 | ND | − | − | + |
| 63 | ND | − | ND | ND |
| 64 | − | ND | ND | ND |

In Vivo Assays

PDE4 inhibitors may be shown to be effective in an animal model of depression (such as forced swimming test) and animal models of memory (such as maze test and novel object recognition test). See Saccomano, N. A. et al., *J. Med. Chem.* 34, p 291-298, 1991; O'Donnell, J. M. and Zhang, H. T., *Trends Pharmacol. Sci.*, 25, p 158-163 (2004; Zhang, H. T. and O'Donnell, J. M, *Psychopharmacology*, 150, p 311-316, 2000. Since these improvements are hypothesized to be caused by activation of the central nerve system as a result of increase of the intracellular cAMP level, compounds disclosed herein are expected to be effective in diseases that are improved by activation of the central nervous system. Examples of such diseases include depression, anxiety, degradation of learning and memory ability, Alzheimer's disease, arteriosclerotic dementia, Parkinson's disease, Huntington's disease and late motor disorders.

Depression

The forced-swim test (FST) is the most widely used test of antidepressant drug action. In the FST, a rat is placed in an inescapable cylinder of water. (See Krishnan V and Nestler E J, "Animal models of depression: molecular perspectives," *Current topics in behavioral neurosciences* 2011; 7:121-47; and Bergner C L et al., "Mouse models for studying depression-like states and antidepressant drugs," *Methods Mol Biol* 2010; 602:267-82.) This causes stress to the animal and following an initial period of swimming and climbing, the rat eventually displays a floating or immobile posture. The rat is removed from the water after 15 minutes Immobility has been interpreted as an expression of behavioral despair or entrapment and is reversed by the single dose administration of almost all available antidepressants.

Intact, adult male or female rats are used for the FST. Either outbred or inbred strains of rats may be used for the study. The rats are group housed and allowed to acclimate for 7 days after arrival. All rats will be housed on standard bedding, kept under a reversed 12:12 hr light:dark (lights on ~6 pm:6 am), and will receive food and water ad lib.

Comparison is made between a group of 10 rats that is dosed with vehicle only versus groups of 10 rats that are dosed with varying amounts of the test compound. Typically, test compounds are dosed at 0.1, 0.3, 1, 3, and 10 mg/kg by oral gavage. The dosing volume will be 10 ml/Kg for PO. The vehicle for dosing will be chosen based on the solubility of the compound. For oral dosing, the compound may be dosed in solution or may be dosed in suspension depending upon solubility. PO dosing is performed by oral gavage while the rat is restrained by hand using a flexible tube appropriate for rat.

For the FST, rats are placed in a cylindrical 5 gallon tank so the animals can swim or float without touching the bottom with their tails. The test is recorded via video camera for analysis offline or scored in real time by an observer. Behavior is scored by categorizing behavior as active escape (swimming, climbing), passive (floating immobile) or neutral (quiet paddling or grooming behaviors). For each rat, onset to the first 5 second bout of immobility, the number of bouts of immobility, and total time spent immobile is recorded Immobility may be compared during the first 5 min of the FST or during the last 5 min of the FST. Comparison of data between groups is by ANOVA.

Compounds disclosed herein are expected to demonstrate activity in the models disclosed above, and to have utility in the treatment of diseases disclosed herein, including disorders of the central nervous system, psychological disorders, and disorders of cognition.

Cognition and Memory

PDE4 inhibitors, for example PDE4D inhibitors, are expected to have utility as memory enhancers and cognitive adjuvants. One test for the efficacy of compounds disclosed herein may be carried out as described by Li, Y F et al., "Phosphodiesterase-4D knock-out and RNA interference-mediated knock-down enhance memory and increase hippocampal neurogenesis via increased cAMP signaling," *J Neurosci.* 2011 Jan. 5; 31(1): 172-183.

Compounds disclosed herein are expected to demonstrate activity in the models disclosed above, and to have utility in the treatment of diseases disclosed herein, including disorders of the central nervous system, psychological disorders, and disorders of cognition.

Solubility Protocol

To measure compound solubility in aqueous buffer, about 5 mg of a compound may be mixed with 500 μL of pH 7.4, 0.1 M sodium phosphate buffer. The mixture is adjusted to the original pH of 7.4 and then mixed overnight or longer via rotary mixing. The sample is checked for pH and then filtered through a 0.45 μm filter. If the pH drifted away, the sample is adjusted to its original pH and mixed for at least 15 minutes before filtration. The filtrate is analyzed using HPLC. Generally, solubility ≥1 mg/mL is considered to be better than solubility of <1 mg/mL, as it is generally easier to formulate for oral delivery. Certain compounds disclosed herein are expected to have solubility of ≥1 mg/mL. However, ideal solubility may vary; for example, an aqueous formulation may benefit from an even higher solubility. Conversely, a formulation containing hydrophilic carriers and one or more surfactants may be used to deliver a compound of low aqueous solubility.

Stability Protocol

To provide a measure of compound stability, about 3 mg of a compound may be dissolved in 3 mL of acetonitrile/water mixture (50/50). 100 μL of the stock solution is added to 20 mL each of 0.025 M pH 5.0 sodium acetate buffer (A5.0), 0.025 M pH 5.0 citrate buffer (C5.0) and 0.025 M pH 7.4 sodium phosphate buffer (P7.4). A two mL aliquot of each solution is kept in a glass vial equipped a cap lined with Teflon. Two vials containing the solution may be stored at 4° C. or −20° C. as control. Other aliquots may be stressed at RT, 45° C. or 75° C. for specified time check points, e.g. 1 day, 1 week, 2 weeks, 4 weeks, 8 weeks, or 12 weeks. The stressed samples in duplicate are assayed against the control using HPLC. The results are reported in % degradation. Preliminary shelf life (T90) is estimated assuming the rate of chemical degradation is double when the temperature is up 10° C.

It is expected that certain compounds disclosed herein, when tested, will be sufficiently shelf-stable.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treatment of Alzheimer's disease in a subject in need thereof, comprising the administration to the subject of a therapeutically effective amount of a compound of structural Formula XI:

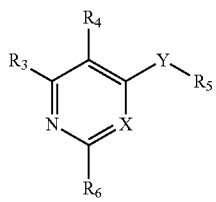

(XI)

or a salt thereof, wherein:
Y is C(R$_2$)$_2$;
X is chosen from CH and N;
n is an integer chosen from 0, 1 or 2;
each R$_2$ is independently chosen from hydrogen and lower alkyl;
R$_3$ is chosen from methyl, ethyl, trifluoromethyl, and cyclopropyl;
R$_4$ is chosen from hydrogen and ethyl;
R$_5$ is either benzoxaborole, or is chosen from phenyl and pyridinyl, either of which is para-substituted with a substituent of the form R$_8$—R$_9$—(R$_{10}$)$_a$(R$_{10}$)$_b$, and is optionally substituted with a substituent R$_{13}$;
R$_8$ is chosen from a bond and lower alkyl;
R$_9$ is chosen from halogen, lower alkyl, lower haloalkyl, lower hydroxyalkyl, lower alkoxy, lower haloalkoxy, cyano, —C(O)N—, S(O)$_2$—, B(OH)$_2$, 5-6 membered monocyclic heterocycloalkyl, and 5-6 membered monocyclic heteroaryl;
(R$_{10}$)$_a$ and (R$_{10}$)$_b$ are each independently chosen from null, hydrogen, halogen, trifluoromethyl, trifluoromethoxy, hydroxyl, lower hydroxyalkyl, cyano, oxo, lower alkyl, C(O)OH, and C(O)O lower alkyl;
R$_{13}$ is chosen from halogen, hydroxy, lower alkyl, trifluoromethyl, lower alkoxy, trifluoromethoxy, NH$_2$, and cyano;
R$_6$ is chosen from 3-chlorophenyl, 5-chloro-2-thienyl, cyclopentyl optionally substituted with one or two R$_{14}$, and cyclopentoxy optionally substituted with one or two R$_{14}$; and
each R$_{14}$ is independently chosen from halogen, hydroxy, lower alkyl, trifluoromethyl, lower alkoxy, trifluoromethoxy, NH$_2$, and cyano.

2. The method as recited in claim 1, wherein the compound is of any one of structural Formulas XIII, XIV, XV, and XVI:

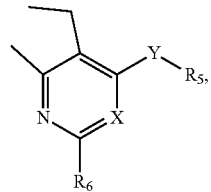

(XIII)

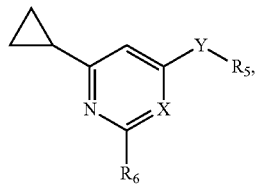

(XIV)

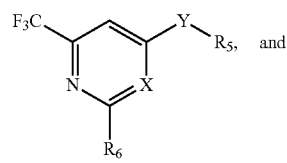

(XV)

and

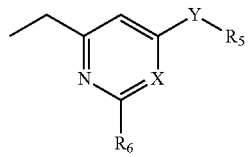

(XVI)

or a salt thereof, wherein:
Y is CH$_2$;
X is chosen from CH and N;
R$_5$ is either benzoxaborole, or is chosen from phenyl and pyridinyl, either of which is para-substituted with a substituent of the form R$_8$—R$_9$—(R$_{10}$)$_a$(R$_{10}$)$_b$, and is optionally
R$_8$ is chosen from a bond and lower alkyl;
R$_9$ is chosen from halogen, lower alkyl, lower haloalkyl, lower hydroxyalkyl, lower alkoxy, lower haloalkoxy, cyano, —C(O)N—, S(O)$_2$—, B(OH)$_2$, 5-6 membered monocyclic heterocycloalkyl, and 5-6 membered monocyclic heteroaryl;
(R$_{10}$)$_a$ and (R$_{10}$)$_b$ are each independently chosen from null, hydrogen, halogen, trifluoromethyl, trifluoromethoxy, hydroxyl, lower hydroxyalkyl, cyano, oxo, lower alkyl, C(O)OH, and C(O)O lower alkyl;
R$_{13}$ is chosen from halogen, hydroxy, lower alkyl, trifluoromethyl, lower alkoxy, trifluoromethoxy, NH$_2$, and cyano;
R$_6$ is chosen from 3-chlorophenyl, 5-chloro-2-thienyl, cyclopentyl optionally substituted with one or two R$_{14}$, and cyclopentoxy optionally substituted with one or two R$_{14}$; and
each R$_{14}$ is independently chosen from halogen, hydroxy, lower alkyl, trifluoromethyl, lower alkoxy, trifluoromethoxy, NH$_2$, and cyano.

3. The method as recited in claim 2, wherein R$_5$ is either benzoxaborole, or is phenyl which is para-substituted with a substituent of the form R$_8$—R$_9$—(R$_{10}$)$_a$(R$_{10}$)$_b$, and is optionally substituted with a substituent R$_{13}$.

4. The method as recited in claim 3, wherein R$_5$ is phenyl which is para-substituted with a substituent of the form R$_8$—R$_9$—(R$_{10}$)$_a$(R$_{10}$)$_b$.

5. The method as recited in claim 4, wherein
$R_9$ is —C(O)N—;
$R_{10a}$ is chosen from lower hydroxyalkyl and hydrogen; and
$R_{10b}$ is hydrogen.

6. The method as recited in claim 4, wherein
$R_9$ is lower alkyl;
$R_{10a}$ is C(O)OH; and
$R_{10b}$ is null.

7. The method as recited in claim 4, wherein $R_9$ is lower hydroxyalkyl.

8. The method as recited in claim 7, wherein $R_9$ is chosen from methanol, ethanol, isopropanol, N-propanol, and t-butanol.

9. The method as recited in claim 8, wherein $R_9$ is chosen from ethanol and N-propanol.

10. The method as recited in claim 4, wherein $R_9$ is chosen from 5-6 membered monocyclic heterocycloalkyl, and 5-6 membered monocyclic heteroaryl.

11. The method as recited in claim 10, wherein —$R_9$—$(R_{10})_a(R_{10})_b$ is chosen from:

[structures]

12. The method as recited in claim 11, wherein —$R_9$—$(R_{10})_a(R_{10})_b$ is chosen from:

[structures]

13. The method as recited in claim 4, wherein $R_8$ is a bond.

14. The method as recited in claim 4, wherein $R_8$ is lower alkyl.

15. The method as recited in claim 14, wherein $R_8$ is methyl.

16. The method as recited in claim 10, wherein $R_5$ is benzoxaborole.

17. The method as recited in claim 14, wherein X is N.

18. The method as recited in claim 13, wherein X is CH.

19. The method as recited in claim 17, wherein $R_6$ is chosen from 3-chlorophenyl and 5-chloro-2-thienyl.

20. The method as recited in claim 19, wherein $R_6$ is 3-chlorophenyl.

21. The method as recited in claim 19, wherein $R_6$ is 5-chloro-2-thienyl.

22. The method as recited in claim 18, wherein $R_6$ is chosen from 3-chlorophenyl and 5-chloro-2-thienyl.

23. The method as recited in claim 22, wherein $R_6$ is 3-chlorophenyl.

24. The method as recited in claim 23, wherein $R_6$ is 5-chloro-2-thienyl.

25. The method as recited in claim 2, wherein $R_6$ is chosen from cyclopentyl optionally substituted with one or two $R_{14}$, and cyclopentoxy optionally substituted with one or two $R_{14}$.

26. A method of treatment of Alzheimer's disease in a subject in need thereof, comprising the administration to the subject of a therapeutically effective amount of a compound selected from the group consisting of:

[structure]

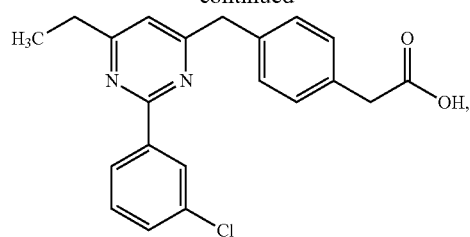
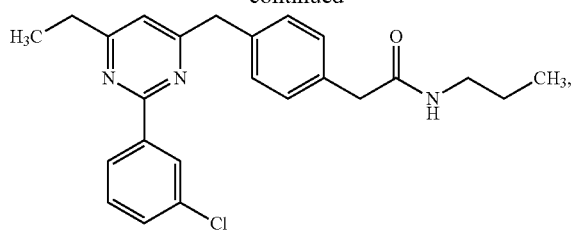
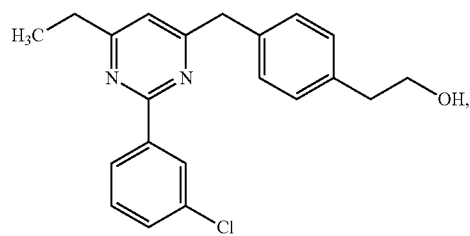
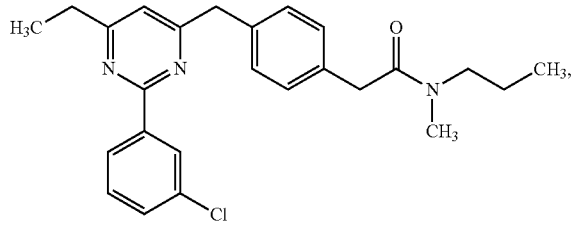
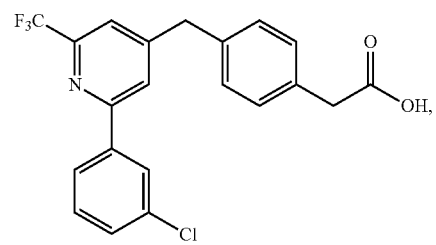
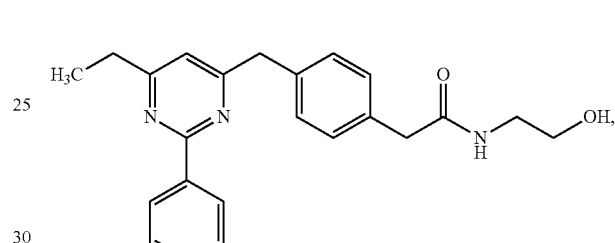
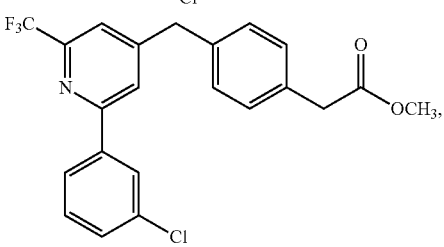
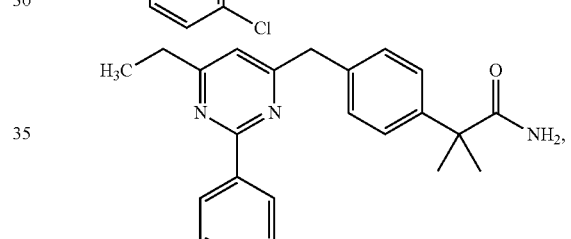
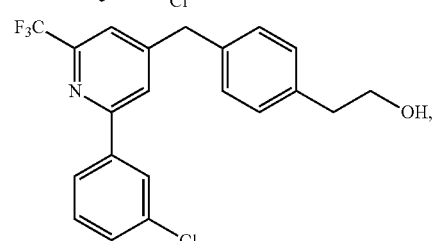
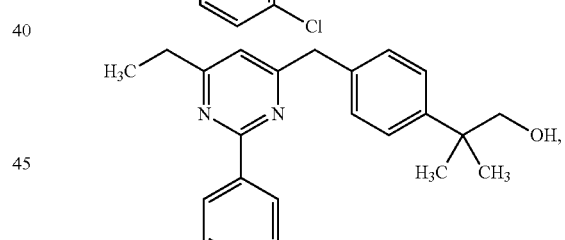
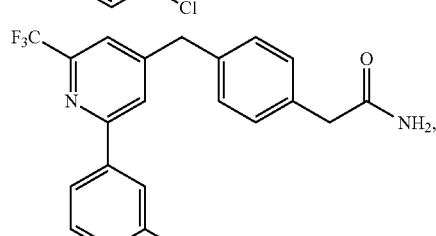
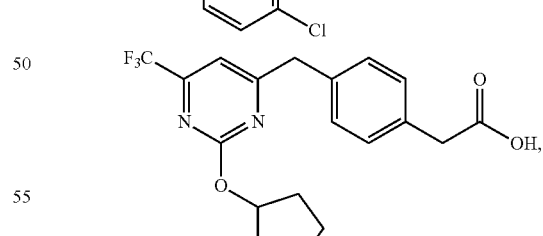
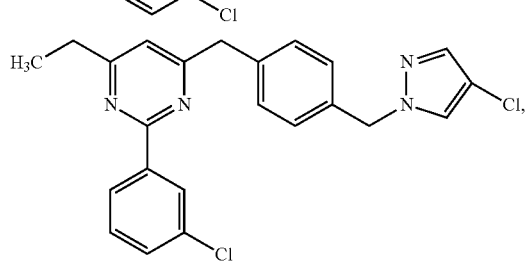

401
-continued
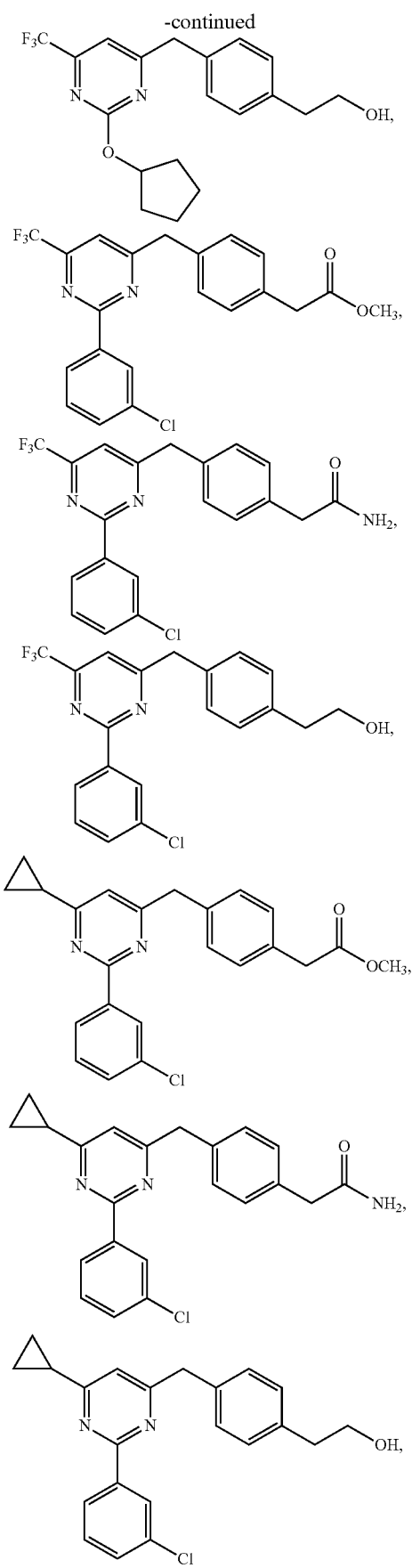
402
-continued
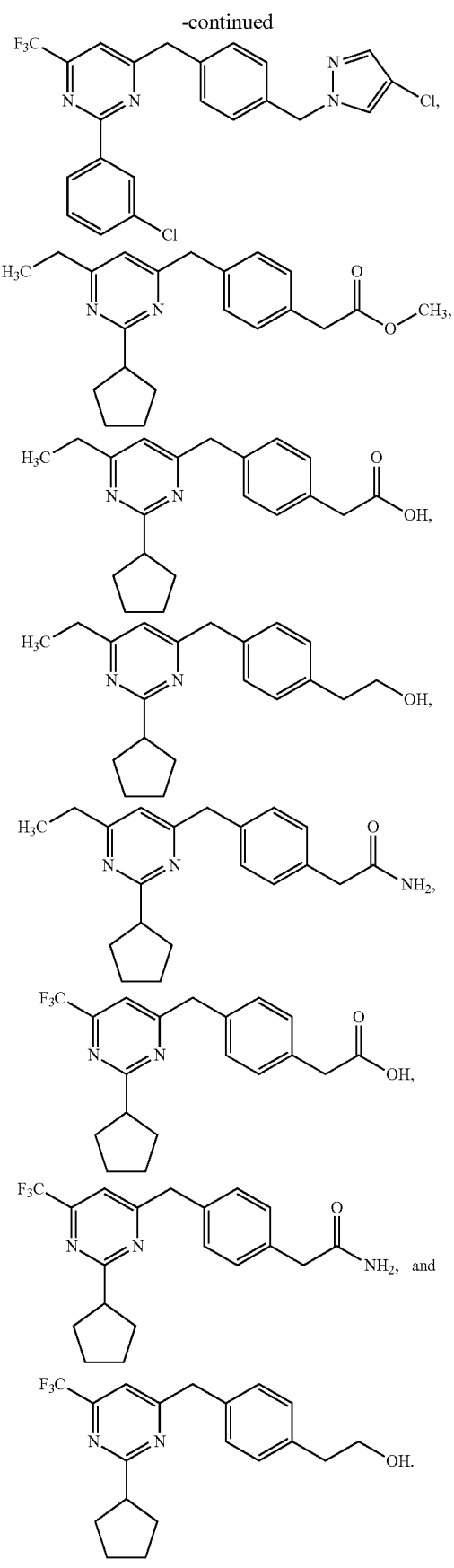

27. The method as recited in claim 1 wherein the compound is formulated as a pharmaceutical composition comprising a pharmaceutically acceptable carrier.

28. The method as recited in claim 27, wherein the pharmaceutical composition additionally comprises another therapeutic agent.

29. The method as recited in claim 28, wherein the additional therapeutic agent is an antidepressant.

30. The method as recited in claim 27, wherein the pharmaceutical composition is formulated as a tablet or capsule.

31. The method as recited in claim 26, wherein the compound is selected from the group consisting of

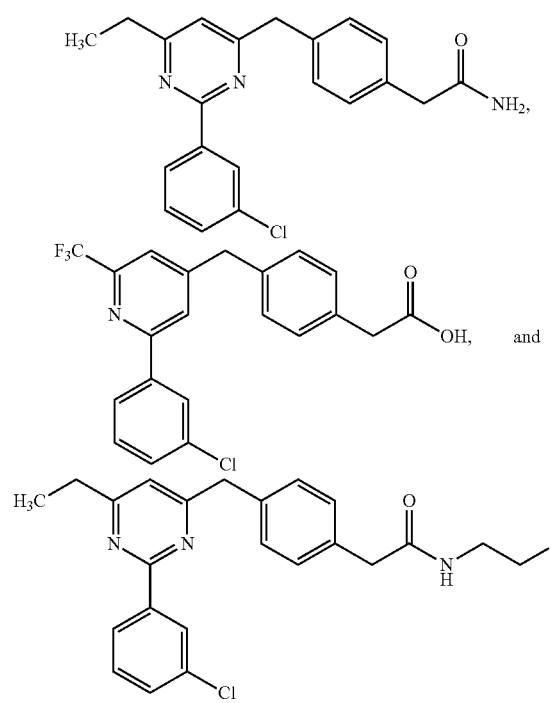

or a salt thereof.

32. The method as recited in claim 31, wherein the compound is

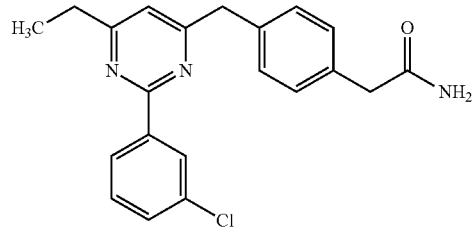 [SMILES: CCc1cc(Cc2ccc(CC(N)=O)cc2)nc(-c2cccc(Cl)c2)n1]

or a salt thereof.

33. The method as recited in claim 31, wherein the compound is

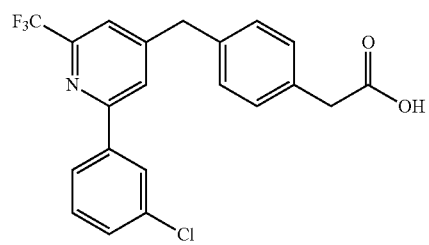 [SMILES: O=C(O)Cc1ccc(Cc2cc(-c3cccc(Cl)c3)nc(C(F)(F)F)c2)cc1]

or a salt thereof.

34. The method as recited in claim 31, wherein the compound is

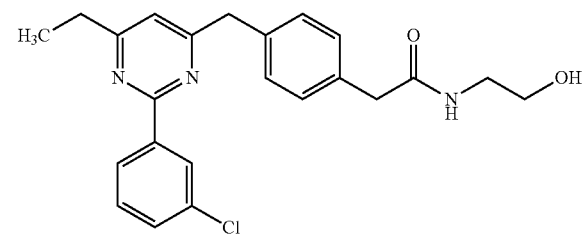 [SMILES: CCc1cc(Cc2ccc(CC(=O)NCCO)cc2)nc(-c2cccc(Cl)c2)n1]

or a salt thereof.

* * * * *

UNITED STATES PATENT AND TRADEMARK OFFICE
CERTIFICATE OF CORRECTION

PATENT NO. : 9,777,024 B2
APPLICATION NO. : 14/938544
DATED : October 3, 2017
INVENTOR(S) : Mark Gurney et al.

Page 1 of 5

It is certified that error appears in the above-identified patent and that said Letters Patent is hereby corrected as shown below:

In the Specification (1) At Column 1, Line 12, please insert between paragraphs 1 and 2 the following paragraph:
--Inventions disclosed herein were made with government support under R43MH091791 and U01NS078034 awarded by the National Institutes of Health. The government has certain rights in these inventions.--
(2) At Column 7, Line 38, replace "embodiment above in paragraphs [017]–[077] above may" with --embodiment above may--
(3) At Column 10, Line 21, replace "embodiment above in paragraphs [079]–[0114] above may" with --embodiment above may--
(4) At Column 12, Line 33, replace "embodiment above in paragraphs [0116]–[0152] above may" with --embodiment above may--
(5) At Column 16, Line 9, replace "embodiment above in paragraphs [0154]–[0188] above may" with --embodiment above may--
(6) At Column 19, Line 22, replace "embodiment above in paragraphs [0190]–[0224] above may" with --embodiment above may--
(7) At Column 22, Line 29, replace "embodiment above in paragraphs [0226]–[0257] above may" with --embodiment above may--
(8) At Column 24, Line 17, replace "embodiment above in paragraphs [0259]–[0285] above may" with --embodiment above may--
(9) At Column 26, Line 62, replace "embodiment above in paragraphs [0287]–[0310] above may" with --embodiment above may--
(10) At Column 31, Line 50, replace "embodiment above in paragraphs [0312]–[0337] above may" with --embodiment above may--

(11) At Column 70, Line 20, replace " 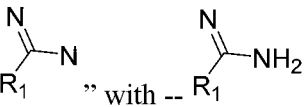 --

Signed and Sealed this
Nineteenth Day of June, 2018

Andrei Iancu
*Director of the United States Patent and Trademark Office*

CERTIFICATE OF CORRECTION (continued)
U.S. Pat. No. 9,777,024 B2

(12) At Column 70, Line 25, replace " 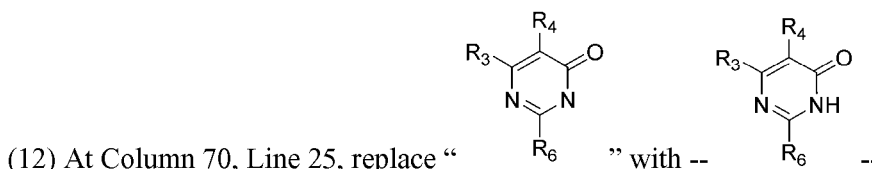 " with -- --

(13) At Column 70, Line 55, replace " 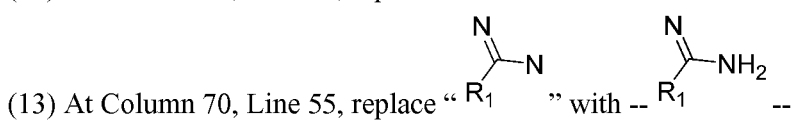 " with -- --

(14) At Column 70, Line 60, replace " 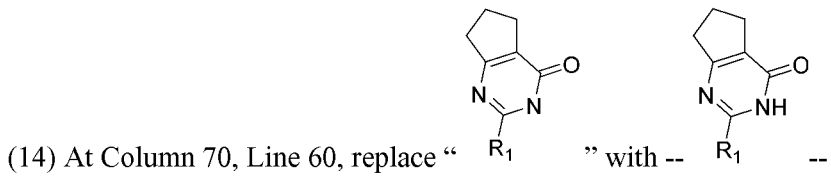 " with -- --

(15) At Column 71, Line 5, replace " 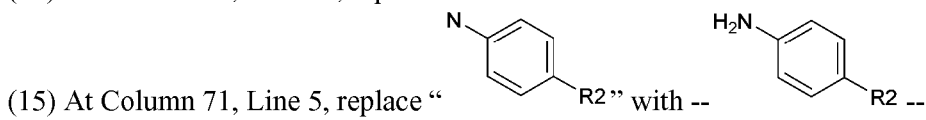 " with -- --

(16) At Column 71, Line 15, replace " 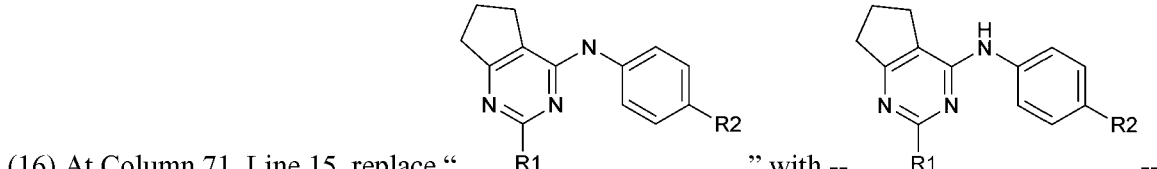 " with -- --

(17) At Column 71, Line 25, replace " 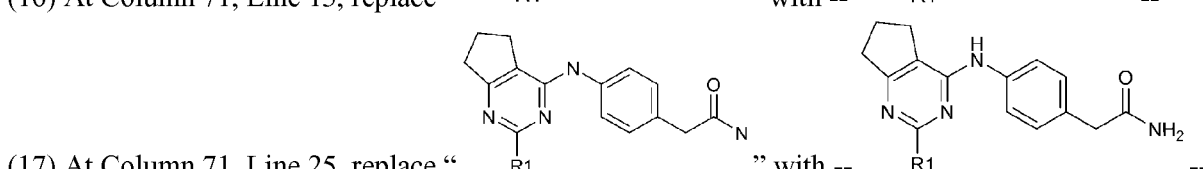 " with -- --

(18) At Column 77, Line 40, replace " 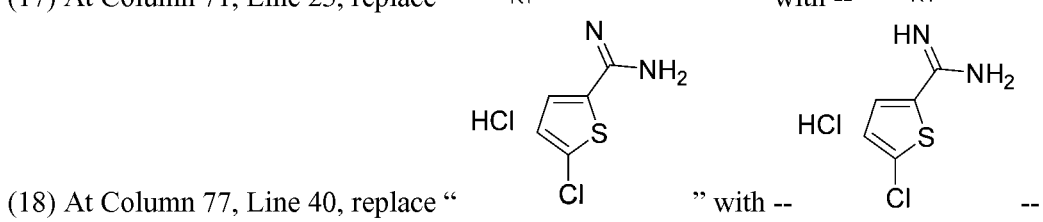 " with -- --

(19) At Column 78, Line 35, replace " 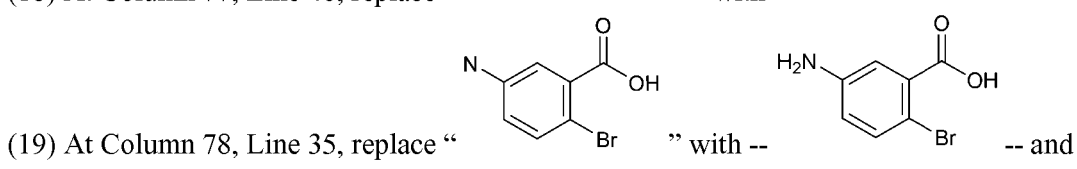 " with -- -- and "110C" with --110 °C--
(20) At Column 79, Line 26, replace "95 C" with --95 °C--
(21) At Column 86, Line 35, replace "at OC" with --at 0 °C--
(22) At Column 99, Line 26, replace "at 90 C" with --at 90 °C--

(23) At Column 122, Line 50, replace " 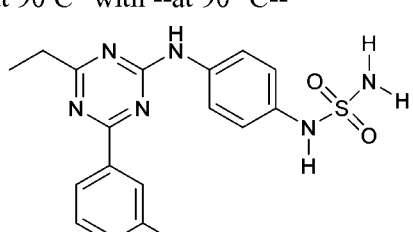 " with 

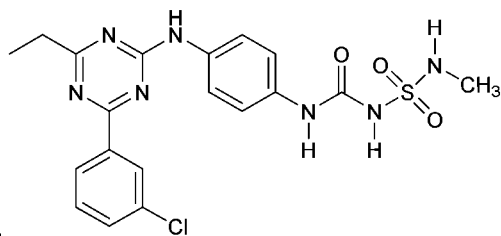

-- --

(24) At Column 130, Lines 51-52, replace "2-(4-((2-(3-Chlorophenyl)-6,7-dihydro-5H-cyclopenta[d]pyrimidin-4-yl)methyl)phenyl)acetamide" with --2-(3-chlorophenyl)-4-(4-methylbenzyl)-6,7-dihydro-5H-cyclopenta[d]pyrimidine--

(25) At Column 136, Lines 35-36, replace "2-[4-[[2-(5-chloro-2-thienyl)-6,7-dihydro-5H-cyclopenta[d]pyrimidin-4-yl]amino]phenyl]acetic acid" with --2-(5-chloro-2-thienyl)-5-ethyl-N-(1-hyrdoxy-3H-2,1-benzoxaborol-5-yl)-6-methyl-pyrimidin-4-amine--

(26) At Column 137, Line 32, replace "Step 1,5-Chlorothiophene-2-carboxamidinie HCl salt" with --Step 1, 5-Chlorothiophene-2-carboxamidinie HCl salt--

(27) At Column 137, Line 43, replace "EXAMPLE 18" with --EXAMPLE 9--

(28) At Column 154, Lines 21-22, replace "Trans-2-4-((2-(3-chlorophenyl)-6,7-dihydro-SH-cyclopenta[b]pyridine-4-yl)amino)cyclohexyl)acetonitrile" with --Trans-2-4-((2-(3-chlorophenyl)-6,7-dihydro-5H-cyclopenta[b]pyridine-4-yl)amino)cyclohexyl)acetonitrile--

(29) At Column 191, Line 61, replace "5-chloro3-pyridinyl" with --5-chloro-3-pyridinyl--

(30) At Column 210, Lines 57-58, replace "4-chloro-2-(3-chloro4-fluorophenyl)-6,7-dihydro-5H-cyclopenta[b]pyridine" with --4-chloro-2-(3-chloro-4-fluorophenyl)-6,7-dihydro-5H-cyclopenta[b]pyridine--

(31) At Column 289, Lines 50-51, replace "2-(4-((2-(Cyclopent-1-en-1-yl)-6-(trifluoromethyl)pyridin-4-yl)amino)phenyl)acetic acid" with --2-(4-((2-(3-chlorophenyl)-6-(trifluoromethyl)pyridin-4-yl)amino)phenyl)acetamide--

(32) At Column 294, Line 8, replace "MW 32 411.37" with --MW = 411.37--

(33) At Column 308, Line 12, replace "2H) 1.85" with --2H), 1.85--

(34) At Column 309, Line 1, replace "2H) 7.16" with --2H), 7.16--

(35) At Column 361, Line 45, replace " 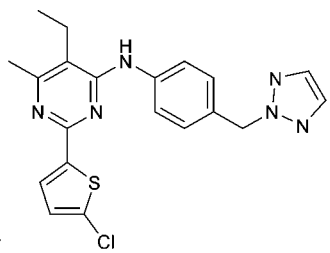 " with

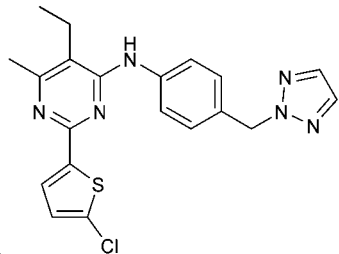

-- --

(36) At Column 362, Line 20, replace " 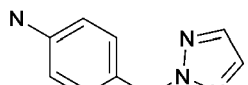 " with -- 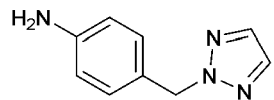 --

(37) At Column 362, Line 50, replace " 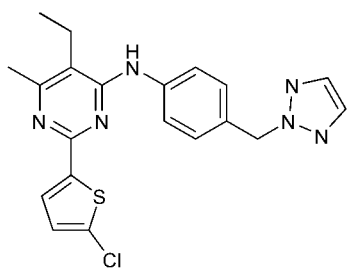 " with
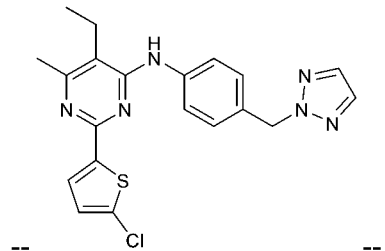
-- --
(38) At Column 365, Line 10, replace " 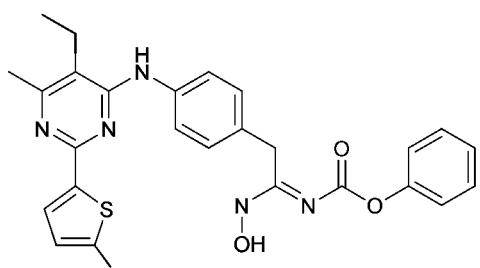 " with
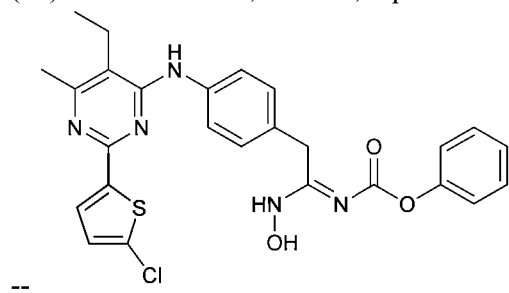
-- --
(39) At Column 366, Line 40, replace " 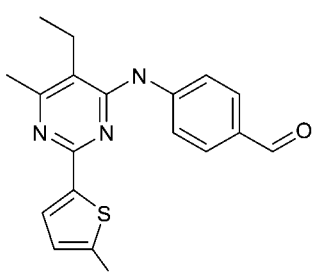 " with

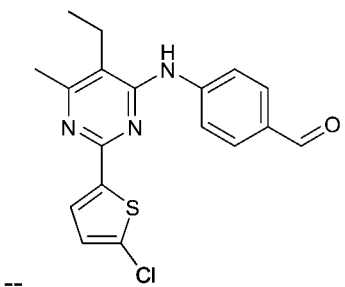

(40) At Column 366, Lines 50-52, replace "4-[[2-(5-chloro-2-thienyl)-5ethyl-6-methyl-pyrimidin-4-yl]amino]benzonitrile" with --4-[[2-(5-chloro-2-thienyl)-5-ethyl-6-methyl-pyrimidin-4-yl]amino]benzonitrile--

In the Claims

(41) At Column 396, Lines 38-39 in Claim 2, replace "with a substituent of the form $R_8$-$R_9$-$(R_{10})_a(R_{10})_b$, and is optionally $R_8$ is chosen from a bond and lower alkyl;" with --with a substituent of the form $R_8$-$R_9$-$(R_{10})_a(R_{10})_b$, and is optionally substituted with a substituent $R_{13}$; $R_8$ is chosen from a bond and lower alkyl;--

(42) At Column 398, Lines 46-47 in Claim 24, replace "The method as recited in claim 23" with --The method as recited in claim 22--